US012465653B2

(12) United States Patent
Kudirka et al.

(10) Patent No.: US 12,465,653 B2
(45) **Date of Patent: *Nov. 11, 2025**

(54) THIENOAZEPINE IMMUNOCONJUGATES, AND USES THEREOF

(71) Applicant: BOLT BIOTHERAPEUTICS, INC., Redwood City, CA (US)

(72) Inventors: Romas Kudirka, Redwood City, CA (US); Brian Safina, Redwood City, CA (US)

(73) Assignee: BOLT BIOTHERAPEUTICS, INC., Redwood City, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/118,105

(22) Filed: Mar. 6, 2023

(65) Prior Publication Data

US 2023/0338571 A1 Oct. 26, 2023

Related U.S. Application Data

(62) Division of application No. 17/078,467, filed on Oct. 23, 2020, now Pat. No. 11,654,199.

(60) Provisional application No. 62/984,184, filed on Mar. 2, 2020, provisional application No. 62/926,333, filed on Oct. 25, 2019.

(51) Int. Cl.
*A61K 47/68* (2017.01)
*C07K 16/28* (2006.01)

(52) U.S. Cl.
CPC ...... *A61K 47/6803* (2017.08); *A61K 47/6849* (2017.08); *A61K 47/6889* (2017.08); *C07K 16/2827* (2013.01)

(58) Field of Classification Search
None
See application file for complete search history.

(56) References Cited

U.S. PATENT DOCUMENTS 11,654,199 B2 5/2023 Kudirka et al.

FOREIGN PATENT DOCUMENTS

| | | | |
|---|---|---|---|
| WO | 2011022508 | A2 | 2/2011 |
| WO | 2018140831 | A2 | 8/2018 |
| WO | 2019222676 | A1 | 11/2019 |
| WO | 2020252254 | A1 | 12/2020 |
| WO | 2020252294 | A1 | 12/2020 |
| WO | 2021081402 | A1 | 4/2021 |

OTHER PUBLICATIONS

Migianu, E , et al., "Synthesis of New Thieno[b]azepinediones from alpha-Methylene Ketones", Synthesis 2002(8), 1096-1100 (2002).

(Continued)

*Primary Examiner* — Karl J Puttlitz

(74) *Attorney, Agent, or Firm* — Viksnins Harris Padys Malen LLP

(57) ABSTRACT

The invention provides immunoconjugates of Formula I comprising an antibody linked by conjugation to one or more thienoazepine derivatives. The invention also provides thienoazepine derivative intermediate compositions comprising a reactive functional group. Such intermediate compositions are suitable substrates for formation of the immunoconjugates through a linker or linking moiety. The invention further provides methods of treating cancer with the immunoconjugates.

30 Claims, 29 Drawing Sheets

Specification includes a Sequence Listing.

| Binding agent | SEQ ID NO: | HCDR1 | SEQ ID NO: | HCDR2 | SEQ ID NO: | HCDR3 | SEQ ID NO: | LCDR1 | SEQ ID NO: | LCDR2 | SEQ ID NO: | LCDR3 |
|---|---|---|---|---|---|---|---|---|---|---|---|---|
| 1 | 1 | SYAIS | 24 | VINPSAGST DYAQKFQG | 58 | DLYPYVVVVAAGS YGMDV | 96 | RASQGIDSYLA | 129 | AASSLQS | 152 | QQSYSTPIT |
| 2 | 2 | SYYMH | 25 | WMNPNSDI AGYAQKFQ G | 59 | PSIVGAYDAFDI | 97 | RASQSISSWLA | 129 | AASSLQS | 153 | QQSYTTPIT |
| 3 | 3 | RHLLH | 26 | WISPQHGV RNYAQKFQ G | 60 | ESVEGYFDL | 98 | RASQSISSYLN | 129 | AASSLQS | 154 | QQIFSTPLT |
| 4 | 4 | SHHMH | 27 | WVSPSHGL TGYAQKFQ G | 61 | DNWNVHDAFDI | 99 | RASQGISSYLA | 130 | GASNLQS | 155 | QQSYSTPLT |
| 5 | 5 | RFMH | 28 | WMSLNSGL TGYAQKFQ G | 62 | GTYNDAFDI | 100 | RASQTISNYLN | 129 | AASSLQS | 153 | QQSYTTPIT |
| 6 | 6 | SYYIH | 29 | WMKPSSGT TGYAQKFQ G | 63 | EQWLVNDAFDI | 101 | RASQSVDRNYVT | 131 | GASTRAT | 156 | QQSYTTPYT |
| 7 | 7 | NYYIH | 30 | WMNPNGD VAGYAQKF QG | 64 | DSSGWMRNDAFDI | 102 | RASQGISQYLA | 132 | GASNLHS | 157 | QQTFTTPLT |
| 8 | 2 | SYYMH | 31 | GIDPNSGGT NYAQKFQG | 65 | SMFPTIFGDNAFDI | 103 | QASQDIGNYLN | 133 | AASSLES | 155 | QQSYSTPLT |
| 9 | 8 | HYYMH | 32 | WMNPDSGS TGYAQKFQ G | 66 | ALFPYPFYYYYMD V | 104 | RASQGIRNDLG | 134 | SASNLQS | 158 | QQANSFPFT |
| 10 | 9 | GYYMH | 33 | WMSLNSGL TGYAQKFQ G | 67 | DRGWFDP | 97 | RASQSISSWLA | 135 | AASTLES | 159 | QQSYTTPYS |

(56) References Cited

OTHER PUBLICATIONS

Patent Cooperation Treaty , International Searching Authority, Search Report and Written Opinion for PCT/US2020/057162, 17 pages, dated Feb. 1, 2021.
Patent Cooperation Treaty , International Searching Authority, Search Report and Written Opinion for PCT/US2020/057167, 17 pages, Feb. 1, 2021.

| Binding agent | SEQ ID NO: | HCDR1 | SEQ ID NO: | HCDR2 | SEQ ID NO: | HCDR3 | SEQ ID NO: | LCDR1 | SEQ ID NO: | LCDR2 | SEQ ID NO: | LCDR3 |
|---|---|---|---|---|---|---|---|---|---|---|---|---|
| 1 | 1 | SYAIS | 24 | VINPSAGSTDYAQKFQG | 58 | DLYPYVVVVAAGSYGMDV | 96 | RASQGIDSYLA | 129 | AASSLQS | 152 | QQSYSTPIT |
| 2 | 2 | SYYMH | 25 | WMNPNSDIAGYAQKFQG | 59 | PSIVGAYDAFDI | 97 | RASQSISSWLA | 129 | AASSLQS | 153 | QQSYTTPIT |
| 3 | 3 | RHLLH | 26 | WISPQHGVRNYAQKFQG | 60 | ESVEGYFDL | 98 | RASQSISSYLN | 129 | AASSLQS | 154 | QQIFSTPLT |
| 4 | 4 | SHHMH | 27 | WVSPSHGLTGYAQKFQG | 61 | DNWNVHDAFDI | 99 | RASQGISSYLA | 130 | GASNLQS | 155 | QQSYSTPLT |
| 5 | 5 | RFMH | 28 | WMSLNSGLTGYAQKFQG | 62 | GTYNDAFDI | 100 | RASQTISNYLN | 129 | AASSLQS | 153 | QQSYTTPIT |
| 6 | 6 | SYYIH | 29 | WMKPSSGTTGYAQKFQG | 63 | EQWLVNDAFDI | 101 | RASQSVDRNYVT | 131 | GASTRAT | 156 | QQSYTTPYT |
| 7 | 7 | NYYIH | 30 | WMNPNGDVAGYAQKFQG | 64 | DSSGWMRNDAFDI | 102 | RASQGISQYLA | 132 | GASNLHS | 157 | QQTFTTPLT |
| 8 | 2 | SYYMH | 31 | GIDPNSGGTNYAQKFQG | 65 | SMFPTIFGDNAFDI | 103 | QASQDIGNYLN | 133 | AASSLES | 155 | QQSYSTPLT |
| 9 | 8 | HYYMH | 32 | WMNPDSGSTGYAQKFQG | 66 | ALFPYPFYYYYMDV | 104 | RASQGIRNDLG | 134 | SASNLQS | 158 | QQANSFPFT |
| 10 | 9 | GYYMH | 33 | WMSLNSGLTGYAQKFQG | 67 | DRGWFDP | 97 | RASQSISSWLA | 135 | AASTLES | 159 | QQSYTTPYS |

*Fig. 1A*

| | | | | | | | | | | | | |
|---|---|---|---|---|---|---|---|---|---|---|---|---|
| 11 | 7 | NYYIH | 34 | WMNPNGDV AGYADSFQG | 64 | DSSGWMRNDAFDI | 102 | RASQGISQYLA | 132 | GASNLHS | 160 | QQTFITPLT |
| 12 | 10 | NYMYH | 35 | WISTYHGST NYAQKFQG | 68 | DARGYSGYDL | 105 | RASQIIGNYLA | 136 | HASILET | 161 | QQSYSTPT |
| 13 | 2 | SYYMH | 25 | WMNPNSDIA GYAQKFQG | 69 | EGRHGEYLY | 106 | RASQIISSYLN | 129 | AASSLQS | 162 | QQGFSTPFT |
| 14 | 11 | TYYVH | 36 | WMNPNTVY TGSAQKFQG | 70 | EGWGSSGYFDY | 107 | QASQDISNYLN | 129 | AASSLQS | 163 | QQSFTNPVT |
| 15 | 12 | SYALS | 37 | RIIPAVGSVT YAQKFQG | 71 | HLFPTVFDDYYGM DV | 108 | RASQGISNYLA | 137 | AASTLQS | 164 | QQSYSAPYT |
| 16 | 1 | SYAIS | 38 | GIIPIFGTAN YAQKFQG | 72 | GGYSYGSFQH | 109 | RASQGISNNLN | 138 | AATTLQS | 165 | QQSYSTPYT |
| 17 | 13 | RHYVH | 39 | WMSPSSGIT GYAQKFQG | 73 | VRWSSDAFDI | 98 | RASQSISSYLN | 129 | AASSLQS | 155 | QQSYSTPLT |
| 18 | 2 | SYYMH | 40 | WMTPSTGN AGYAQKFQ G | 74 | EEWLGHFQH | 110 | RASQGISNGLS | 137 | AASTLQS | 166 | QQSHSTPLT |
| 19 | 14 | SHYMH | 41 | WMNPNSGN TGYAQKFQ G | 75 | ERFLGGMDV | 111 | RASQSITGWLA | 129 | AASSLQS | 165 | QQSYSTPYT |
| 20 | 15 | DYYMH | 42 | WMHPNSGH TGYAQKFQ G | 74 | EEWLGHFQH | 97 | RASQSISSWLA | 139 | DATHLET | 152 | QQSYSTPIT |
| 21 | 14 | SHYMH | 43 | WMNPNSGH TGNAQKFQ G | 76 | GNWVDAFDI | 112 | RASQGIRNDLA | 137 | AASTLQS | 155 | QQSYSTPLT |
| 22 | 16 | GYTLH | 44 | WIDPNSGVT SSAQKFQG | 77 | ESEVMMAYFQH | 113 | QASQDISSYLN | 140 | AASSLQT | 165 | QQSYSTPYT |
| 23 | 9 | GYYMH | 45 | WISPNSGVT DFTQKFQG | 78 | ESWSGEFDY | 114 | RASQSITTYLN | 141 | AASSLQG | 165 | QQSYSTPYT |

*Fig. 1B*

| | | | | | | | | | | | | |
|---|---|---|---|---|---|---|---|---|---|---|---|---|
| 24 | 17 | NHYMH | 46 | WMNPNSGH TGYAQRFQG | 79 | EAVAGPMDV | SEQ ID NO: | LCDR1 | SEQ ID NO: | LCDR2 | SEQ ID NO: | LCDR3 |
| 25 | 9 | GYYMH | 25 | WMNPNSDIA GYAQKFQG | 80 | DAWELLAFDI | 98 | RASQSISSYLN | 129 | AASSLQS | 155 | QQSYSTPLT |
| 26 | 17 | NHYMH | 41 | WMNPNSGN TGYAQKFQ G | 81 | DRWDGDYYSA | 115 | RASQSVSTWLA | 142 | AASNLES | 165 | QQSYSTPYT |
| 27 | 7 | NYYIH | 47 | WMSPNGGN TGYAQKFQ G | 82 | ESWELTGFDY | 116 | RASQSISNWLA | 143 | DVSHLES | 167 | QQSYSTPFT |
| 28 | 2 | SYYMH | 41 | WMNPNSGN TGYAQKFQ G | 83 | ERFAGGMDA | 117 | QASQGISNYLA | 144 | DASSLQS | 155 | QQSYSTPLT |
| 29 | 18 | NSYMH | 48 | WMDPSSGY TGSAHKFQG | 84 | DSGGAFDI | 118 | RASQSLSSSSLA | 131 | GASTRAT | 168 | QQYGSSPFT |
| 30 | 19 | TYYMH | 49 | WMNPHSAD TGYAEKFQG | 85 | EVFEGGMDV | 119 | RASEHIANWLA | 145 | GVSSLES | 165 | QQSYSTPYT |
| 31 | 2 | SYYMH | 50 | WLTPSTGHA GYAQKFQG | 86 | EGYGGNYGN | 120 | RASQSVGSWVA | 146 | PASTLQS | 155 | QQSYSTPLT |
| 32 | 2 | SYYMH | 51 | WMNPNSGH TGYAQKFQ G | 87 | EDFYGDFDY | 121 | RASQSISPWLA | 147 | DASNLET | 169 | QQTYSTPIT |
| 33 | 20 | RHFIH | 44 | WIDPNSGVT SSAQKFQG | 88 | ELSRWGFDY | 122 | RASQGISRYLA | 137 | AASTLQS | 155 | QQSYSTPLT |
| 34 | 3 | RHLLH | 52 | WISPQHGVR NYAHKFQG | 60 | ESVEGYFDL | 123 | RASQTVSSNYLA | 148 | GASTRAS | 170 | QQYYTTPLT |

*Fig. 1C*

| | | | | | | | | | | | | | |
|---|---|---|---|---|---|---|---|---|---|---|---|---|---|
| 35 | 2 | SYYMH | 53 | MINPSGGSTS YAQKFQG | 89 | DIFPTMIAGGGFDL | 98 | RASQSISSYLN | 129 | AASSLQS | 171 | QQSFSTPLT |
| 36 | 21 | TFGIS | 38 | GIIPIFGTANY AQKFQG | 90 | GGYSYGSFDY | 97 | RASQSISSWLA | 147 | DASNLET | 172 | QQSYSTPPT |
| 37 | 22 | SYGIN | 41 | WMNPNSGNT GYAQKFQG | 91 | GSFPLVFTIFGVGD V | 109 | RASQGISNNLN | 150 | ATSTLQS | 165 | QQSYSTPYT |
| 38 | 2 | SYYMH | 54 | WISPRSGVTS YAQKFQG | 92 | DLDYVRAFDI | 124 | RSSQGIRNDLS | 151 | LASNSHS | 173 | LQHNSYPLT |
| 39 | 2 | SYYMH | 55 | WMDPNSGNT GYAQKFQG | 93 | ESWGGYFDL | 126 | RASQSISRWLA | 129 | AASSLQS | 165 | QQSYSTPYT |
| 40 | 23 | NHYVH | 56 | WMNPTGGIT GYAQKFQG | 94 | DRTTYAFDI | 97 | RASQSISSWLA | 149 | DSSSLQT | 174 | QQSYSTPVT |
| 41 | 14 | SHYMH | 43 | WMNPNSGHT GNAQKFQG | 76 | GNWVDAFDI | 125 | RDSHSITTWLA | 142 | AASNLES | 175 | QHFYNTQYT |
| 42 | 3 | RHLLH | 57 | WVSPIHGLTG YAPRFQG | 95 | VHGSGSDGMDV | 127 | RASQVIRNDLA | 137 | AASTLQS | 176 | QQSLQYPSHF |

*Fig. 1D*

| Binding Agent | SEQ ID NO: | HFW1 | SEQ ID NO: | HFW2 | SEQ ID NO: | HFW3 | SEQ ID NO: | HFW4 |
|---|---|---|---|---|---|---|---|---|
| 1 | 177 | QVQLVQSGAEVKKPGASVK VSCKASGGTFS | 192 | WVRQAPGQG LEWMG | 196 | RVTMTRDTSTSTVYMELSSLR SEDTAVYYCAR | 202 | WGQGTLVT VSS |
| 2 | 178 | QVQLVQSGAEVKKPGASVK VSCKASGYTFT | 192 | WVRQAPGQG LEWMG | 197 | RVTMTRDTSTSTVYMELSSLR SEDTAVYYCAI | 202 | WGQGTLVT VSS |
| 3 | 178 | QVQLVQSGAEVKKPGASVK VSCKASGYTFT | 192 | WVRQAPGQG LEWMG | 196 | RVTMTRDTSTSTVYMELSSLR SEDTAVYYCAR | 202 | WGQGTLVT VSS |
| 4 | 178 | QVQLVQSGAEVKKPGASVK VSCKASGYTFT | 192 | WVRQAPGQG LEWMG | 196 | RVTMTRDTSTSTVYMELSSLR SEDTAVYYCAR | 202 | WGQGTLVT VSS |
| 5 | 179 | QVQLVQSGAEVKKPGASVK VSCKASGYTFN | 192 | WVRQAPGQG LEWMG | 198 | RVTMTRDTSTSTVYMELSSLR SEDTAVYYCTR | 202 | WGQGTLVT VSS |
| 6 | 178 | QVQLVQSGAEVKKPGASVK VSCKASGYTFT | 192 | WVRQAPGQG LEWMG | 196 | RVTMTRDTSTSTVYMELSSLR SEDTAVYYCAR | 202 | WGQGTLVT VSS |
| 7 | 178 | QVQLVQSGAEVKKPGASVK VSCKASGYTFT | 193 | WVRQAPGQG LEWLG | 197 | RVTMTRDTSTSTVYMELSSLR SEDTAVYYCAI | 202 | WGQGTLVT VSS |
| 8 | 180 | QVQLVQSGAEVKKPGASVK VSCKASGNTFT | 192 | WVRQAPGQG LEWMG | 196 | RVTMTRDTSTSTVYMELSSLR SEDTAVYYCAR | 202 | WGQGTLVT VSS |
| 9 | 181 | QVQLVQSGAEVKKPGASVK VSCKASGHSFT | 192 | WVRQAPGQG LEWMG | 196 | RVTMTRDTSTSTVYMELSSLR SEDTAVYYCAR | 202 | WGQGTLVT VSS |
| 10 | 178 | QVQLVQSGAEVKKPGASVK VSCKASGYTFT | 194 | WVRQAPGQG LEWIG | 196 | RVTMTRDTSTSTVYMELSSLR SEDTAVYYCAR | 202 | WGQGTLVT VSS |

*Fig. 2A*

| | | | | | | | | |
|---|---|---|---|---|---|---|---|---|
| 11 | 178 | QVQLVQSGAEVKKPGASVK VSCKASGYTFT | 193 | WVRQAPGQG LEWLG | 197 | RVTMTRDTSTSTVYMELSSLR SEDTAVYYCAI | 202 | WGQGTLVT VSS |
| 12 | 177 | QVQLVQSGAEVKKPGASVK VSCKASGGTFS | 192 | WVRQAPGQG LEWMG | 196 | RVTMTRDTSTSTVYMELSSLR SEDTAVYYCAR | 202 | WGQGTLVT VSS |
| 13 | 182 | QVQLVQSGAEVKKPGASVK VSCKASGYPFT | 192 | WVRQAPGQG LEWMG | 196 | RVTMTRDTSTSTVYMELSSLR SEDTAVYYCAR | 202 | WGQGTLVT VSS |
| 14 | 183 | QVQLVQSGAEVKKPGASVK VSCKASGYRFT | 192 | WVRQAPGQG LEWMG | 196 | RVTMTRDTSTSTVYMELSSLR SEDTAVYYCAR | 202 | WGQGTLVT VSS |
| 15 | 184 | QVQLVQSGAEVKKPGSSVK VSCKASGGTFS | 192 | WVRQAPGQG LEWMG | 199 | RVTITADESTSTAYMELSSLRS EDTAVYYCAR | 202 | WGQGTLVT VSS |
| 16 | 184 | QVQLVQSGAEVKKPGSSVK VSCKASGGTFS | 192 | WVRQAPGQG LEWMG | 199 | RVTITADESTSTAYMELSSLRS EDTAVYYCAR | 202 | WGQGTLVT VSS |
| 17 | 185 | QVQLVQSGAEVKKPGASVK VSCKASGDTFT | 192 | WVRQAPGQG LEWMG | 196 | RVTMTRDTSTSTVYMELSSLR SEDTAVYYCAR | 202 | WGQGTLVT VSS |
| 18 | 178 | QVQLVQSGAEVKKPGASVK VSCKASGYTFT | 195 | WVRQAPGQG LEWVG | 196 | RVTMTRDTSTSTVYMELSSLR SEDTAVYYCAR | 202 | WGQGTLVT VSS |
| 19 | 178 | QVQLVQSGAEVKKPGASVK VSCKASGYTFT | 192 | WVRQAPGQG LEWMG | 196 | RVTMTRDTSTSTVYMELSSLR SEDTAVYYCAR | 203 | WGQGTTVT VSS |
| 20 | 178 | QVQLVQSGAEVKKPGASVK VSCKASGYTFT | 192 | WVRQAPGQG LEWMG | 200 | RVTMTRDTSTSTVNMELSSLR SEDTAVYYCAR | 202 | WGQGTLVT VSS |
| 21 | 178 | QVQLVQSGAEVKKPGASVK VSCKASGYTFT | 192 | WVRQAPGQG LEWMG | 196 | RVTMTRDTSTSTVYMELSSLR SEDTAVYYCAR | 204 | WGQGTMVT VSS |
| 22 | 178 | QVQLVQSGAEVKKPGASVK VSCKASGYTFT | 192 | WVRQAPGQG LEWMG | 196 | RVTMTRDTSTSTVYMELSSLR SEDTAVYYCAR | 202 | WGQGTLVT VSS |

*Fig. 2B*

| | | | | | | | | |
|---|---|---|---|---|---|---|---|---|
| 23 | 178 | QVQLVQSGAEVKKPGASVK VSCKASGYTFT | 192 | WVRQAPGQG LEWMG | 196 | RVTMTRDTSTSTVYMELSSLR SEDTAVYYCAR | 202 | WGQGTLVT VSS |
| 24 | 185 | QVQLVQSGAEVKKPGASVK VSCKASGDTFT | 192 | WVRQAPGQG LEWMG | 196 | RVTMTRDTSTSTVYMELSSLR SEDTAVYYCAR | 203 | WGQGTTVT VSS |
| 25 | 178 | QVQLVQSGAEVKKPGASVK VSCKASGYTFT | 192 | WVRQAPGQG LEWMG | 196 | RVTMTRDTSTSTVYMELSSLR SEDTAVYYCAR | 202 | WGQGTLVT VSS |
| 26 | 186 | QVQLAQSGAEVKKPGASVK VSCKASGYTFT | 192 | WVRQAPGQG LEWMG | 196 | RVTMTRDTSTSTVYMELSSLR SEDTAVYYCAR | 202 | WGQGTLVT VSS |
| 27 | 178 | QVQLVQSGAEVKKPGASVK VSCKASGYTFT | 192 | WVRQAPGQG LEWMG | 196 | RVTMTRDTSTSTVYMELSSLR SEDTAVYYCAR | 202 | WGQGTLVT VSS |
| 28 | 178 | QVQLVQSGAEVKKPGASVK VSCKASGYTFT | 192 | WVRQAPGQG LEWMG | 196 | RVTMTRDTSTSTVYMELSSLR SEDTAVYYCAR | 203 | WGQGTTVT VSS |
| 29 | 187 | QVQLVQSGAEVKKPGASVK VSCKASGYTFS | 192 | WVRQAPGQG LEWMG | 201 | RVTMTRDTSTSTVYMELSSLR SEDTAVYYCAE | 204 | WGQGTMVT VSS |
| 30 | 188 | QVQLVQSGAEVKKPGASVK VSCKASGYPFS | 192 | WVRQAPGQG LEWMG | 196 | RVTMTRDTSTSTVYMELSSLR SEDTAVYYCAR | 203 | WGQGTTVT VSS |
| 31 | 178 | QVQLVQSGAEVKKPGASVK VSCKASGYTFT | 192 | WVRQAPGQG LEWMG | 196 | RVTMTRDTSTSTVYMELSSLR SEDTAVYYCAR | 202 | WGQGTLVT VSS |
| 32 | 178 | QVQLVQSGAEVKKPGASVK VSCKASGYTFT | 192 | WVRQAPGQG LEWMG | 196 | RVTMTRDTSTSTVYMELSSLR SEDTAVYYCAR | 202 | WGQGTLVT VSS |
| 33 | 178 | QVQLVQSGAEVKKPGASVK VSCKASGYTFT | 192 | WVRQAPGQG LEWMG | 196 | RVTMTRDTSTSTVYMELSSLR SEDTAVYYCAR | 205 | WGPGTMVT VSS |
| 34 | 178 | QVQLVQSGAEVKKPGASVK VSCKASGYTFT | 192 | WVRQAPGQG LEWMG | 196 | RVTMTRDTSTSTVYMELSSLR SEDTAVYYCAR | 206 | WGRGTLVT VSS |

*Fig. 2C*

| | | | | | | | | |
|---|---|---|---|---|---|---|---|---|
| 35 | 188 | QVQLVQSGAEVKKPGASVK VSCKASGYPFS | 192 | WVRQAPGQG LEWMG | 196 | RVTMTRDTSTSTVYMELSSLR SEDTAVYYCAR | 206 | WGRGTLVT VSS |
| 36 | 184 | QVQLVQSGAEVKKPGSSVK VSCKASGGTFS | 192 | WVRQAPGQG LEWMG | 199 | RVTITADESTSTAYMELSSLRS EDTAVYYCAR | 202 | WGQGTLVT VSS |
| 37 | 178 | QVQLVQSGAEVKKPGASVK VSCKASGYTFT | 192 | WVRQAPGQG LEWMG | 196 | RVTMTRDTSTSTVYMELSSLR SEDTAVYYCAR | 204 | WGQGTMVT VSS |
| 38 | 178 | QVQLVQSGAEVKKPGASVK VSCKASGYTFT | 192 | WVRQAPGQG LEWMG | 196 | RVTMTRDTSTSTVYMELSSLR SEDTAVYYCAR | 203 | WGQGTTVT VSS |
| 39 | 189 | QVQLVQSGAEVKKPGASVK VSCKASGYSFT | 192 | WVRQAPGQG LEWMG | 196 | RVTMTRDTSTSTVYMELSSLR SEDTAVYYCAR | 206 | WGRGTLVT VSS |
| 40 | 190 | QVQLVQSGAEVKKPGASVK VSCKASGYTFI | 192 | WVRQAPGQG LEWMG | 196 | RVTMTRDTSTSTVYMELSSLR SEDTAVYYCAR | 204 | WGQGTMVT VSS |
| 41 | 178 | QVQLVQSGAEVKKPGASVK VSCKASGYTFT | 192 | WVRQAPGQG LEWMG | 196 | RVTMTRDTSTSTVYMELSSLR SEDTAVYYCAR | 204 | WGQGTMVT VSS |
| 42 | 191 | QVQLVQSGAEVKKPGSSVK VSCKASGYTFT | 192 | WVRQAPGQG LEWMG | 199 | RVTITADESTSTAYMELSSLRS EDTAVYYCAR | 203 | WGQGTTVT VSS |

*Fig. 2D*

| Binding agent | SEQ ID NO: | LFW1 | SEQ ID NO: | LFW2 | SEQ ID NO: | LFW3 | SEQ ID NO: | LFW4 |
|---|---|---|---|---|---|---|---|---|
| 1 | 207 | DIQMTQSPSSLSASVGDRVTITC | 210 | WYQQKPGKAPKLLIY | 213 | GVPSRFSGSGSGTDFTLTISSLQPEDFATYYC | 217 | FGGGTKVEIK |
| 2 | 207 | DIQMTQSPSSLSASVGDRVTITC | 210 | WYQQKPGKAPKLLIY | 213 | GVPSRFSGSGSGTDFTLTISSLQPEDFATYYC | 217 | FGGGTKVEIK |
| 3 | 207 | DIQMTQSPSSLSASVGDRVTITC | 210 | WYQQKPGKAPKLLIY | 213 | GVPSRFSGSGSGTDFTLTISSLQPEDFATYYC | 217 | FGGGTKVEIK |
| 4 | 207 | DIQMTQSPSSLSASVGDRVTITC | 210 | WYQQKPGKAPKLLIY | 213 | GVPSRFSGSGSGTDFTLTISSLQPEDFATYYC | 217 | FGGGTKVEIK |
| 5 | 207 | DIQMTQSPSSLSASVGDRVTITC | 210 | WYQQKPGKAPKLLIY | 213 | GVPSRFSGSGSGTDFTLTISSLQPEDFATYYC | 217 | FGGGTKVEIK |
| 6 | 208 | EIVMTQSPATLSVSPGERATLSC | 211 | WYQQKPGQAPRLLIY | 214 | GIPARFSGSGSGTEFTLTISSLQSEDFAVYYC | 218 | FGQGTKVEIK |
| 7 | 207 | DIQMTQSPSSLSASVGDRVTITC | 210 | WYQQKPGKAPKLLIY | 213 | GVPSRFSGSGSGTDFTLTISSLQPEDFATYYC | 217 | FGGGTKVEIK |
| 8 | 207 | DIQMTQSPSSLSASVGDRVTITC | 210 | WYQQKPGKAPKLLIY | 213 | GVPSRFSGSGSGTDFTLTISSLQPEDFATYYC | 217 | FGGGTKVEIK |
| 9 | 207 | DIQMTQSPSSLSASVGDRVTITC | 210 | WYQQKPGKAPKLLIY | 213 | GVPSRFSGSGSGTDFTLTISSLQPEDFATYYC | 217 | FGGGTKVEIK |
| 10 | 207 | DIQMTQSPSSLSASVGDRVTITC | 210 | WYQQKPGKAPKLLIY | 213 | GVPSRFSGSGSGTDFTLTISSLQPEDFATYYC | 217 | FGGGTKVEIK |

*Fig. 3A*

| | | | | | | | | |
|---|---|---|---|---|---|---|---|---|
| 11 | 207 | DIQMTQSPSSLSASVGDRVTITC | 210 | WYQQKPGKAPKLLIY | 213 | GVPSRFSGSGSGTDFTLTISSLQPEDFATYYC | 217 | FGGGTKVEIK |
| 12 | 207 | DIQMTQSPSSLSASVGDRVTITC | 210 | WYQQKPGKAPKLLIY | 213 | GVPSRFSGSGSGTDFTLTISSLQPEDFATYYC | 217 | FGGGTKVEIK |
| 13 | 207 | DIQMTQSPSSLSASVGDRVTITC | 210 | WYQQKPGKAPKLLIY | 213 | GVPSRFSGSGSGTDFTLTISSLQPEDFATYYC | 217 | FGGGTKVEIK |
| 14 | 207 | DIQMTQSPSSLSASVGDRVTITC | 210 | WYQQKPGKAPKLLIY | 213 | GVPSRFSGSGSGTDFTLTISSLQPEDFATYYC | 217 | FGGGTKVEIK |
| 15 | 207 | DIQMTQSPSSLSASVGDRVTITC | 210 | WYQQKPGKAPKLLIY | 213 | GVPSRFSGSGSGTDFTLTISSLQPEDFATYYC | 217 | FGGGTKVEIK |
| 16 | 207 | DIQMTQSPSSLSASVGDRVTITC | 210 | WYQQKPGKAPKLLIY | 213 | GVPSRFSGSGSGTDFTLTISSLQPEDFATYYC | 217 | FGGGTKVEIK |
| 17 | 207 | DIQMTQSPSSLSASVGDRVTITC | 210 | WYQQKPGKAPKLLIY | 213 | GVPSRFSGSGSGTDFTLTISSLQPEDFATYYC | 217 | FGGGTKVEIK |
| 18 | 207 | DIQMTQSPSSLSASVGDRVTITC | 210 | WYQQKPGKAPKLLIY | 213 | GVPSRFSGSGSGTDFTLTISSLQPEDFATYYC | 217 | FGGGTKVEIK |
| 19 | 207 | DIQMTQSPSSLSASVGDRVTITC | 210 | WYQQKPGKAPKLLIY | 213 | GVPSRFSGSGSGTDFTLTISSLQPEDFATYYC | 218 | FGQGTKVEIK |
| 20 | 207 | DIQMTQSPSSLSASVGDRVTITC | 210 | WYQQKPGKAPKLLIY | 213 | GVPSRFSGSGSGTDFTLTISSLQPEDFATYYC | 219 | FGQGTRLEIK |
| 21 | 207 | DIQMTQSPSSLSASVGDRVTITC | 210 | WYQQKPGKAPKLLIY | 213 | GVPSRFSGSGSGTDFTLTISSLQPEDFATYYC | 217 | FGGGTKVEIK |
| 22 | 207 | DIQMTQSPSSLSASVGDRVTITC | 210 | WYQQKPGKAPKLLIY | 213 | GVPSRFSGSGSGTDFTLTISSLQPEDFATYYC | 221 | FGQGTKLEIK |

*Fig. 3B*

| | | | | | | | |
|---|---|---|---|---|---|---|---|
| 23 | 207 | DIQMTQSPSSLSASVGDRVTITC | 210 | WYQQKPGKAPKLLIY | 213 | GVPSRFSGSGSGTDFTLTISSLQPEDFATYYC | 218 | FGQGTKVEIK |
| 24 | 207 | DIQMTQSPSSLSASVGDRVTITC | 210 | WYQQKPGKAPKLLIY | 213 | GVPSRFSGSGSGTDFTLTISSLQPEDFATYYC | 220 | FGGGTKLEIK |
| 25 | 207 | DIQMTQSPSSLSASVGDRVTITC | 210 | WYQQKPGKAPKLLIY | 213 | GVPSRFSGSGSGTDFTLTISSLQPEDFATYYC | 221 | FGQGTKLEIK |
| 26 | 207 | DIQMTQSPSSLSASVGDRVTITC | 210 | WYQQKPGKAPKLLIY | 213 | GVPSRFSGSGSGTDFTLTISSLQPEDFATYYC | 222 | FGPGTKVDIK |
| 27 | 207 | DIQMTQSPSSLSASVGDRVTITC | 210 | WYQQKPGKAPKLLIY | 213 | GVPSRFSGSGSGTDFTLTISSLQPEDFATYYC | 217 | FGGGTKVEIK |
| 28 | 208 | EIVMTQSPATLSVSPGERATLSC | 211 | WYQQKPGQAPRLLIY | 214 | GIPARFSGSGSGTEFTLTISSLQSEDFAVYYC | 222 | FGPGTKVDIK |
| 29 | 207 | DIQMTQSPSSLSASVGDRVTITC | 210 | WYQQKPGKAPKLLIY | 213 | GVPSRFSGSGSGTDFTLTISSLQPEDFATYYC | 221 | FGQGTKLEIK |
| 30 | 207 | DIQMTQSPSSLSASVGDRVTITC | 210 | WYQQKPGKAPKLLIY | 213 | GVPSRFSGSGSGTDFTLTISSLQPEDFATYYC | 217 | FGGGTKVEIK |
| 31 | 207 | DIQMTQSPSSLSASVGDRVTITC | 210 | WYQQKPGKAPKLLIY | 213 | GVPSRFSGSGSGTDFTLTISSLQPEDFATYYC | 219 | FGQGTRLEIK |
| 32 | 207 | DIQMTQSPSSLSASVGDRVTITC | 210 | WYQQKPGKAPKLLIY | 213 | GVPSRFSGSGSGTDFTLTISSLQPEDFATYYC | 218 | FGQGTKVEIK |
| 33 | 208 | EIVMTQSPATLSVSPGERATLSC | 211 | WYQQKPGQAPRLLIY | 214 | GIPARFSGSGSGTEFTLTISSLQSEDFAVYYC | 217 | FGGGTKVEIK |
| 34 | 207 | DIQMTQSPSSLSASVGDRVTITC | 210 | WYQQKPGKAPKLLIY | 213 | GVPSRFSGSGSGTDFTLTISSLQPEDFATYYC | 219 | FGQGTRLEIK |

*Fig. 3C*

| | | | | | | | | |
|---|---|---|---|---|---|---|---|---|
| 35 | 207 | DIQMTQSPSSLSASVGDRVTITC | 210 | WYQQKPGKAPKLLIY | 213 | GVPSRFSGSGSGTDFTLTISSLQPEDFATYYC | 218 | FGQGTKVEIK |
| 36 | 207 | DIQMTQSPSSLSASVGDRVTITC | 210 | WYQQKPGKAPKLLIY | 213 | GVPSRFSGSGSGTDFTLTISSLQPEDFATYYC | 218 | FGQGTKVEIK |
| 37 | 207 | DIQMTQSPSSLSASVGDRVTITC | 210 | WYQQKPGKAPKLLIY | 213 | GVPSRFSGSGSGTDFTLTISSLQPEDFATYYC | 217 | FGGGTKVEIK |
| 38 | 207 | DIQMTQSPSSLSASVGDRVTITC | 210 | WYQQKPGKAPKLLIY | 213 | GVPSRFSGSGSGTDFTLTISSLQPEDFATYYC | 221 | FGQGTKLEIK |
| 39 | 207 | DIQMTQSPSSLSASVGDRVTITC | 210 | WYQQKPGKAPKLLIY | 213 | GVPSRFSGSGSGTDFTLTISSLQPEDFATYYC | 218 | FGQGTKVEIK |
| 40 | 209 | DIQITHSPSSLSASVGYRLTITC | 212 | WYHQKPWNAPKLMIY | 215 | GVPSRFSGSGSGTYFTLTISSLQPEDFATYYC | 218 | FGQGTKVEIK |
| 41 | 207 | DIQMTQSPSSLSASVGDRVTITC | 210 | WYQQKPGKAPKLLIY | 213 | GVPSRFSGSGSGTDFTLTISSLQPEDFATYYC | 218 | FGQGTKVEIK |
| 42 | 207 | DIQMTQSPSSLSASVGDRVTITC | 210 | WYQQKPGKAPKLLIY | 216 | GVPSRFSGSGSGTDFTLTISSLQPEDFAPYYC | 222 | FGPGTKVDIK |

*Fig. 3D*

| Binding agent | SEQ ID NO: | VH |
|---|---|---|
| 1 | 223 | QVQLVQSGAEVKKPGASVKVSCKASGGTFSSYAISWVRQAPGQGLEWMGVINPSAGSTDYAQKFQGRVTMTRDTSTSTV YMELSSLRSEDTAVYYCARDLYPYVVVVAAGSYGMDVWGQGTLVTVSS |
| 2 | 224 | QVQLVQSGAEVKKPGASVKVSCKASGYTFTSYYMHWVRQAPGQGLEWMGWMNPNSDIAGYAQKFQGRVTMTRDTSTS TVYMELSSLRSEDTAVYYCAIPSIVGAYDAFDIWGQGTLVTVSS |
| 3 | 225 | QVQLVQSGAEVKKPGASVKVSCKASGYTFTRHLLHWVRQAPGQGLEWMGWISPQHGVRNYAQKFQGRVTMTRDTSTST VYMELSSLRSEDTAVYYCARESVEGYFDLWGQGTLVTVSS |
| 4 | 226 | QVQLVQSGAEVKKPGASVKVSCKASGYTFTSHHMHWVRQAPGQGLEWMGWVSPSHGLTGYAQKFQGRVTMTRDTSTST VYMELSSLRSEDTAVYYCARDNWNVHDAFDIWGQGTLVTVSS |
| 5 | 227 | QVQLVQSGAEVKKPGASVKVSCKASGYTFNRFMHWVRQAPGQGLEWMGWMSLNSGLTGYAQKFQGRVTMTRDTSTST VYMELSSLRSEDTAVYYCTRGTYNDAFDIWGQGTLVTVSS |
| 6 | 228 | QVQLVQSGAEVKKPGASVKVSCKASGYTFTSYYIHWVRQAPGQGLEWMGWMKPSSGTTGYAQKFQGRVTMTRDTSTST VYMELSSLRSEDTAVYYCAREQWLVNDAFDIWGQGTLVTVSS |
| 7 | 229 | QVQLVQSGAEVKKPGASVKVSCKASGYTFTSYYIHWVRQAPGQGLEWMGWMKPSSGTTGYAQKFQGRVTMTRDTSTST VYMELSSLRSEDTAVYYCAREQWLVNDAFDIWGQGTLVTVSS |
| 8 | 230 | QVQLVQSGAEVKKPGASVKVSCKASGNTFTSYYMHWVRQAPGQGLEWMGGIDPNSGGTNYAQKFQGRVTMTRDTSTST VYMELSSLRSEDTAVYYCARSMFPTIFGDNAFDIWGQGTLVTVSS |
| 9 | 231 | QVQLVQSGAEVKKPGASVKVSCKASGHSFTHYYMHWVRQAPGQGLEWMGWMNPDSGSTGYAQKFQGRVTMTRDTSTS TVYMELSSLRSEDTAVYYCARALFPYPFYYYYMDVWGQGTLVTVSS |
| 10 | 232 | QVQLVQSGAEVKKPGASVKVSCKASGYTFTGYYMHWVRQAPGQGLEWIGWMSLNSGLTGYAQKFQGRVTMTRDTSTST VYMELSSLRSEDTAVYYCARDRGWFDPWGQGTLVTVSS |
| 11 | 233 | QVQLVQSGAEVKKPGASVKVSCKASGYTFTNYYIHWVRQAPGQGLEWLGWMNPNGDVAGYADSFQGRVTMTRDTSTST VYMELSSLRSEDTAVYYCAIDSSGWMRNDAFDIWGQGTLVTVSS |

*Fig. 4A*

| | | |
|---|---|---|
| 12 | 234 | QVQLVQSGAEVKKPGASVKVSCKASGGTFSNYMYHWVRQAPGQGLEWMGWISTYHGSTNYAQKFQGRVTMTRDTSTST<br>VYMELSSLRSEDTAVYYCARDARGYSGYDLWGQGTLVTVSS |
| 13 | 235 | QVQLVQSGAEVKKPGASVKVSCKASGYPFTSYYMHWVRQAPGQGLEWMGWMNPNSDIAGYAQKFQGRVTMTRDTSTS<br>TVYMELSSLRSEDTAVYYCAREGRHGEYLYWGQGTLVTVSS |
| 14 | 236 | QVQLVQSGAEVKKPGASVKVSCKASGYRFTTYYVHWVRQAPGQGLEWMGWMNPNTVYTGSAQKFQGRVTMTRDTSTS<br>TVYMELSSLRSEDTAVYYCAREGWGSSGYFDYWGQGTLVTVSS |
| 15 | 237 | QVQLVQSGAEVKKPGSSVKVSCKASGGTFSSYALSWVRQAPGQGLEWMGRIIPAVGSVTYAQKFQGRVTITADESTSTAY<br>MELSSLRSEDTAVYYCARHLFPTVFDDYYGMDVWGQGTLVTVSS |
| 16 | 238 | QVQLVQSGAEVKKPGSSVKVSCKASGGTFSSYAISWVRQAPGQGLEWMGGIIPIFGTANYAQKFQGRVTITADESTSTAYM<br>ELSSLRSEDTAVYYCARGGYSYGSFQHWGQGTLVTVSS |
| 17 | 239 | QVQLVQSGAEVKKPGASVKVSCKASGDTFTRHYVHWVRQAPGQGLEWMGWMSPSSGITGYAQKFQGRVTMTRDTSTST<br>VYMELSSLRSEDTAVYYCARVRWSSDAFDIWGQGTLVTVSS |
| 18 | 240 | QVQLVQSGAEVKKPGASVKVSCKASGYTFTSYYMHWVRQAPGQGLEWVGWMTPSTGNAGYAQKFQGRVTMTRDTSTS<br>TVYMELSSLRSEDTAVYYCAREEWLGHFQHWGQGTLVTVSS |
| 19 | 241 | QVQLVQSGAEVKKPGASVKVSCKASGYTFTSHYMHWVRQAPGQGLEWMGWMNPNSGNTGYAQKFQGRVTMTRDTSTS<br>TVYMELSSLRSEDTAVYYCARERFLGGMDVWGQGTTVTVSS |
| 20 | 242 | QVQLVQSGAEVKKPGASVKVSCKASGYTFTDYYMHWVRQAPGQGLEWMGWMHPNSGHTGYAQKFQGRVTMTRDTSTS<br>TVNMELSSLRSEDTAVYYCAREEWLGHFQHWGQGTLVTVSS |
| 21 | 243 | QVQLVQSGAEVKKPGASVKVSCKASGYTFTSHYMHWVRQAPGQGLEWMGWMNPNSGHTGNAQKFQGRVTMTRDTSTS<br>TVYMELSSLRSEDTAVYYCARGNWVDAFDIWGQGTMVTVSS |
| 22 | 244 | QVQLVQSGAEVKKPGASVKVSCKASGYTFTGYTLHWVRQAPGQGLEWMGWIDPNSGVTSSAQKFQGRVTMTRDTSTSTV<br>YMELSSLRSEDTAVYYCARESEVMMAYFQHWGQGTLVTVSS |
| 23 | 245 | QVQLVQSGAEVKKPGASVKVSCKASGYTFTGYYMHWVRQAPGQGLEWMGWISPNSGVTDFTQKFQGRVTMTRDTSTST<br>VYMELSSLRSEDTAVYYCARESWSGEFDYWGQGTLVTVSS |

*Fig. 4B*

| | | |
|---|---|---|
| 24 | 246 | QVQLVQSGAEVKKPGASVKVSCKASGDTFTNHYMHWVRQAPGQGLEWMGWMNPNSGHTGYAQRFQGRVTMTRDTSTSTVYMELSSLRSEDTAVYYCAREAVAGPMDVWGQGTTVTVSS |
| 25 | 247 | QVQLVQSGAEVKKPGASVKVSCKASGYTFTGYYMHWVRQAPGQGLEWMGWMNPNSDIAGYAQKFQGRVTMTRDTSTSTVYMELSSLRSEDTAVYYCARDAWELLAFDIWGQGTLVTVSS |
| 26 | 248 | QVQLAQSGAEVKKPGASVKVSCKASGYTFTNHYMHWVRQAPGQGLEWMGWMNPNSGNTGYAQKFQGRVTMTRDTSTSTVYMELSSLRSEDTAVYYCARDRWDGDYYSAWGQGTLVTVSS |
| 27 | 249 | QVQLVQSGAEVKKPGASVKVSCKASGYTFTNYYIHWVRQAPGQGLEWMGWMSPNGGNTGYAQKFQGRVTMTRDTSTSTVYMELSSLRSEDTAVYYCARESWELTGFDYWGQGTLVTVSS |
| 28 | 250 | QVQLVQSGAEVKKPGASVKVSCKASGYTFTSYYMHWVRQAPGQGLEWMGWMNPNSGNTGYAQKFQGRVTMTRDTSTSTVYMELSSLRSEDTAVYYCARERFAGGMDAWGQGTTVTVSS |
| 29 | 251 | QVQLVQSGAEVKKPGASVKVSCKASGYTFSNSYMHWVRQAPGQGLEWMGWMDPSSGYTGSAHKFQGRVTMTRDTSTSTVYMELSSLRSEDTAVYYCAEDSGGAFDIWGQGTMVTVSS |
| 30 | 252 | QVQLVQSGAEVKKPGASVKVSCKASGYPFSTYYMHWVRQAPGQGLEWMGWMNPHSADTGYAEKFQGRVTMTRDTSTSTVYMELSSLRSEDTAVYYCAREVFEGGMDVWGQGTTVTVSS |
| 31 | 253 | QVQLVQSGAEVKKPGASVKVSCKASGYTFTSYYMHWVRQAPGQGLEWMGWLTPSTGHAGYAQKFQGRVTMTRDTSTSTVYMELSSLRSEDTAVYYCAREGYGGNYGNWGQGTLVTVSS |
| 32 | 254 | QVQLVQSGAEVKKPGASVKVSCKASGYTFTSYYMHWVRQAPGQGLEWMGWMNPNSGHTGYAQKFQGRVTMTRDTSTSTVYMELSSLRSEDTAVYYCAREDFYGDFDYWGQGTLVTVSS |
| 33 | 255 | QVQLVQSGAEVKKPGASVKVSCKASGYTFTRHFIHWVRQAPGQGLEWMGWIDPNSGVTSSAQKFQGRVTMTRDTSTSTVYMELSSLRSEDTAVYYCARELSRWGFDYWGPGTMVTVSS |
| 34 | 256 | QVQLVQSGAEVKKPGASVKVSCKASGYTFTRHLLHWVRQAPGQGLEWMGWISPQHGVRNYAHKFQGRVTMTRDTSTSTVYMELSSLRSEDTAVYYCARESVEGYFDLWGRGTLVTVSS |
| 35 | 257 | QVQLVQSGAEVKKPGASVKVSCKASGYPFSSYYMHWVRQAPGQGLEWMGMINPSGGSTSYAQKFQGRVTMTRDTSTSTVYMELSSLRSEDTAVYYCARDIFPTMIAGGGFDLWGRGTLVTVSS |

*Fig. 4C*

| | | |
|---|---|---|
| 36 | 258 | QVQLVQSGAEVKKPGSSVKVSCKASGGTFSTFGISWVRQAPGQGLEWMGGIIPIFGTANYAQKFQGRVTITADESTSTAYMELSSLRSEDTAVYYCARGGYSYGSFDYWGQGTLVTVSS |
| 37 | 259 | QVQLVQSGAEVKKPGASVKVSCKASGYTFTSYGINWVRQAPGQGLEWMGWMNPNSGNTGYAQKFQGRVTMTRDTSTSTVYMELSSLRSEDTAVYYCARGSFPLVFTIFGVGDVWGQGTMVTVSS |
| 38 | 260 | QVQLVQSGAEVKKPGASVKVSCKASGYTFTSYYMHWVRQAPGQGLEWMGWISPRSGVTSYAQKFQGRVTMTRDTSTSTVYMELSSLRSEDTAVYYCARDLDYVRAFDIWGQGTTVTVSS |
| 39 | 261 | QVQLVQSGAEVKKPGASVKVSCKASGYSFTSYYMHWVRQAPGQGLEWMGWMDPNSGNTGYAQKFQGRVTMTRDTSTSTVYMELSSLRSEDTAVYYCARESWGGYFDLWGRGTLVTVSS |
| 40 | 262 | QVQLVQSGAEVKKPGASVKVSCKASGYTFINHYVHWVRQAPGQGLEWMGWMNPTGGITGYAQKFQGRVTMTRDTSTSTVYMELSSLRSEDTAVYYCARDRTTYAFDIWGQGTMVTVSS |
| 41 | 263 | QVQLVQSGAEVKKPGASVKVSCKASGYTFTSHYMHWVRQAPGQGLEWMGWMNPNSGHTGNAQKFQGRVTMTRDTSTSTVYMELSSLRSEDTAVYYCARGNWVDAFDIWGQGTMVTVSS |
| 42 | 264 | QVQLVQSGAEVKKPGSSVKVSCKASGYTFTRHLLHWVRQAPGQGLEWMGWVSPIHGLTGYAPRFQGRVTITADESTSTAYMELSSLRSEDTAVYYCARVHGSGSDGMDVWGQGTTVTVSS |

*Fig. 4D*

| Binding agent | SEQ ID NO: | VL |
|---|---|---|
| 1 | 265 | DIQMTQSPSSLSASVGDRVTITCRASQGIDSYLAWYQQKPGKAPKLLIYAASSLQSGVPSRFSGSGSGTDFTLTISSLQPEDFATYYCQQSYSTPITFGGGTKVEIK |
| 2 | 266 | DIQMTQSPSSLSASVGDRVTITCRASQSISSWLAWYQQKPGKAPKLLIYAASSLQSGVPSRFSGSGSGTDFTLTISSLQPEDFATYYCQQSYTTPITFGGGTKVEIK |
| 3 | 267 | DIQMTQSPSSLSASVGDRVTITCRASQSISSYLNWYQQKPGKAPKLLIYAASSLQSGVPSRFSGSGSGTDFTLTISSLQPEDFATYYCQQIFSTPLTFGGGTKVEIK |
| 4 | 268 | DIQMTQSPSSLSASVGDRVTITCRASQGISSYLAWYQQKPGKAPKLLIYGASNLQSGVPSRFSGSGSGTDFTLTISSLQPEDFATYYCQQSYSTPLTFGGGTKVEIK |
| 5 | 269 | DIQMTQSPSSLSASVGDRVTITCRASQTISNYLNWYQQKPGKAPKLLIYAASSLQSGVPSRFSGSGSGTDFTLTISSLQPEDFATYYCQQSYTTPITFGGGTKVEIK |
| 6 | 270 | EIVMTQSPATLSVSPGERATLSCRASQSVDRNYVTWYQQKPGQAPRLLIYGASTRATGIPARFSGSGSGTEFTLTISSLQSEDFAVYYCQQSYTTPYTFGQGTKVEIK |
| 7 | 271 | DIQMTQSPSSLSASVGDRVTITCRASQGISQYLAWYQQKPGKAPKLLIYGASNLHSGVPSRFSGSGSGTDFTLTISSLQPEDFATYYCQQTFTTPLTFGGGTKVEIK |
| 8 | 272 | DIQMTQSPSSLSASVGDRVTITCQASQDIGNYLNWYQQKPGKAPKLLIYAASSLESGVPSRFSGSGSGTDFTLTISSLQPEDFATYYCQQSYSTPLTFGGGTKVEIK |
| 9 | 273 | DIQMTQSPSSLSASVGDRVTITCRASQGIRNDLGWYQQKPGKAPKLLIYSASNLQSGVPSRFSGSGSGTDFTLTISSLQPEDFATYYCQQANSFPFTFGGGTKVEIK |
| 10 | 274 | DIQMTQSPSSLSASVGDRVTITCRASQSISSWLAWYQQKPGKAPKLLIYAASTLESGVPSRFSGSGSGTDFTLTISSLQPEDFATYYCQQSYTTPYSFGGGTKVEIK |
| 11 | 275 | DIQMTQSPSSLSASVGDRVTITCRASQGISQYLAWYQQKPGKAPKLLIYGASNLHSGVPSRFSGSGSGTDFTLTISSLQPEDFATYYCQQTFITPLTFGGGTKVEIK |
| 12 | 276 | DIQMTQSPSSLSASVGDRVTITCRASQIIGNYLAWYQQKPGKAPKLLIYHASILETGVPSRFSGSGSGTDFTLTISSLQPEDFATYYCQQSYSTPTFGGGTKVEIK |
| 13 | 277 | DIQMTQSPSSLSASVGDRVTITCRASQIISSYLNWYQQKPGKAPKLLIYAASSLQSGVPSRFSGSGSGTDFTLTISSLQPEDFATYYCQQGFSTPFTFGGGTKVEIK |
| 14 | 278 | DIQMTQSPSSLSASVGDRVTITCQASQDISNYLNWYQQKPGKAPKLLIYAASSLQSGVPSRFSGSGSGTDFTLTISSLQPEDFATYYCQQSFTNPVTFGGGTKVEIK |
| 15 | 279 | DIQMTQSPSSLSASVGDRVTITCRASQGISNYLAWYQQKPGKAPKLLIYAASTLQSGVPSRFSGSGSGTDFTLTISSLQPEDFATYYCQQSYSAPYTFGGGTKVEIK |
| 16 | 280 | DIQMTQSPSSLSASVGDRVTITCRASQGISNNLNWYQQKPGKAPKLLIYAATTLQSGVPSRFSGSGSGTDFTLTISSLQPEDFATYYCQQSYSTPYTFGGGTKVEIK |

*Fig. 4E*

| | | |
|---|---|---|
| 17 | 281 | DIQMTQSPSSLSASVGDRVTITCRASQSISSYLNWYQQKPGKAPKLLIYAASSLQSGVPSRFSGSGSGTDFTLTISSLQPEDFATYYCQQSYSTPLTFGGGTKVEIK |
| 18 | 282 | DIQMTQSPSSLSASVGDRVTITCRASQGISNGLSWYQQKPGKAPKLLIYAASTLQSGVPSRFSGSGSGTDFTLTISSLQPEDFATYYCQQSHSTPLTFGGGTKVEIK |
| 19 | 283 | DIQMTQSPSSLSASVGDRVTITCRASQSITGWLAWYQQKPGKAPKLLIYAASSLQSGVPSRFSGSGSGTDFTLTISSLQPEDFATYYCQQSYSTPYTFGQGTKVEIK |
| 20 | 284 | DIQMTQSPSSLSASVGDRVTITCRASQSISSWLAWYQQKPGKAPKLLIYDATHLETGVPSRFSGSGSGTDFTLTISSLQPEDFATYYCQQSYSTPITFGQGTRLEIK |
| 21 | 285 | DIQMTQSPSSLSASVGDRVTITCRASQGIRNDLAWYQQKPGKAPKLLIYAASTLQSGVPSRFSGSGSGTDFTLTISSLQPEDFATYYCQQSYSTPLTFGGGTKVEIK |
| 22 | 286 | DIQMTQSPSSLSASVGDRVTITCQASQDISSYLNWYQQKPGKAPKLLIYAASSLQTGVPSRFSGSGSGTDFTLTISSLQPEDFATYYCQQSYSTPYTFGQGTKLEIK |
| 23 | 287 | DIQMTQSPSSLSASVGDRVTITCRASQSITTYLNWYQQKPGKAPKLLIYAASSLQGGVPSRFSGSGSGTDFTLTISSLQPEDFATYYCQQSYSTPYTFGQGTKVEIK |
| 24 | 288 | DIQMTQSPSSLSASVGDRVTITCRASQSISSYLNWYQQKPGKAPKLLIYAASSLQSGVPSRFSGSGSGTDFTLTISSLQPEDFATYYCQQSYSTPLTFGGGTKLEIK |
| 25 | 289 | DIQMTQSPSSLSASVGDRVTITCRASQSVSTWLAWYQQKPGKAPKLLIYAASNLESGVPSRFSGSGSGTDFTLTISSLQPEDFATYYCQQSYSTPYTFGQGTKLEIK |
| 26 | 290 | DIQMTQSPSSLSASVGDRVTITCRASQSISNWLAWYQQKPGKAPKLLIYDVSHLESGVPSRFSGSGSGTDFTLTISSLQPEDFATYYCQQSYSTPFTFGPGTKVDIK |
| 27 | 291 | DIQMTQSPSSLSASVGDRVTITCQASQGISNYLAWYQQKPGKAPKLLIYDASSLQSGVPSRFSGSGSGTDFTLTISSLQPEDFATYYCQQSYSTPLTFGGGTKVEIK |
| 28 | 292 | EIVMTQSPATLSVSPGERATLSCRASQSLSSSSLAWYQQKPGQAPRLLIYGASTRATGIPARFSGSGSGTEFTLTISSLQSEDFAVYYCQQYGSSPFTFGPGTKVDIK |
| 29 | 293 | DIQMTQSPSSLSASVGDRVTITCRASEHIANWLAWYQQKPGKAPKLLIYGVSSLESGVPSRFSGSGSGTDFTLTISSLQPEDFATYYCQQSYSTPYTFGQGTKLEIK |
| 30 | 294 | DIQMTQSPSSLSASVGDRVTITCRASQSVGSWVAWYQQKPGKAPKLLIYPASTLQSGVPSRFSGSGSGTDFTLTISSLQPEDFATYYCQQSYSTPLTFGGGTKVEIK |
| 31 | 295 | DIQMTQSPSSLSASVGDRVTITCRASQSISPWLAWYQQKPGKAPKLLIYDASNLETGVPSRFSGSGSGTDFTLTISSLQPEDFATYYCQQTYSTPITFGQGTRLEIK |
| 32 | 296 | DIQMTQSPSSLSASVGDRVTITCRASQGISRYLAWYQQKPGKAPKLLIYAASTLQSGVPSRFSGSGSGTDFTLTISSLQPEDFATYYCQQSYSTPLTFGQGTKVEIK |
| 33 | 297 | EIVMTQSPATLSVSPGERATLSCRASQTVSSNYLAWYQQKPGQAPRLLIYGASTRASGIPARFSGSGSGTEFTLTISSLQSEDFAVYYCQQYYTTPLTFGGGTKVEIK |
| 34 | 298 | DIQMTQSPSSLSASVGDRVTITCRASQSISSYLNWYQQKPGKAPKLLIYAASSLQSGVPSRFSGSGSGTDFTLTISSLQPEDFATYYCQQSFSTPLTFGQGTRLEIK |

*Fig. 4F*

| | | |
|---|---|---|
| 35 | 299 | DIQMTQSPSSLSASVGDRVTITCRASQSISSWLAWYQQKPGKAPKLLIYDASNLETGVPSRFSGSGSGTDFTLTISSLQPEDFATYYCQQSYSTPPTFGQGTKVEIK |
| 36 | 300 | DIQMTQSPSSLSASVGDRVTITCRASQGISNNLNWYQQKPGKAPKLLIYATSTLQSGVPSRFSGSGSGTDFTLTISSLQPEDFATYYCQQSYSTPYTFGQGTKVEIK |
| 37 | 301 | DIQMTQSPSSLSASVGDRVTITCRSSQGIRNDLSWYQQKPGKAPKLLIYLASNSHSGVPSRFSGSGSGTDFTLTISSLQPEDFATYYCLQHNSYPLTFGGGTKVEIK |
| 38 | 302 | DIQMTQSPSSLSASVGDRVTITCRASQSISRWLAWYQQKPGKAPKLLIYAASSLQSGVPSRFSGSGSGTDFTLTISSLQPEDFATYYCQQSYSTPYTFGQGTKLEIK |
| 39 | 303 | DIQMTQSPSSLSASVGDRVTITCRASQSISSWLAWYQQKPGKAPKLLIYDSSSLQTGVPSRFSGSGSGTDFTLTISSLQPEDFATYYCQQSYSTPVTFGQGTKVEIK |
| 40 | 304 | DIQITHSPSSLSASVGYRLTITCRDSHSITTWLAWYHQKPWNAPKLMIYAASNLESGVPSRFSGSGSGTYFTLTISSLQPEDFATYYCQHFYNTQYTFGQGTKVEIK |
| 41 | 305 | DIQMTQSPSSLSASVGDRVTITCRASQVIRNDLAWYQQKPGKAPKLLIYAASTLQSGVPSRFSGSGSGTDFTLTISSLQPEDFATYYCQQSLQYPSHFFGQGTKVEIK |
| 42 | 306 | DIQMTQSPSSLSASVGDRVTITCRASQSISRYLNWYQQKPGKAPKLLIYAASTLQSGVPSRFSGSGSGTDFTLTISSLQPEDFAPYYCQQSYSTPLTFGPGTKVDIK |

*Fig. 4G*

| Binding agent | SEQ ID NO: | HCDR1 | SEQ ID NO: | HCDR2 | SEQ ID NO: | HCDR3 | SEQ ID NO: | LCDR1 | SEQ ID NO: | LCDR2 | SEQ ID NO: | LCDR3 |
|---|---|---|---|---|---|---|---|---|---|---|---|---|
| 1 | 308 | SDYMH | 322 | WMSPYNGIT GYAQKFQG | 339 | DRFSGSYDY | 360 | RASQSISSWLA | 375 | AASSLQS | 387 | QQSYSTPYT |
| 2 | 309 | GYYMH | 323 | WMSPSSGITG YAQKFQG | 340 | DRGWFDP | 361 | RASQSVGTWLA | 376 | AASTLEN | 388 | QQSFSTPYT |
| 3 | 310 | SYYMH | 324 | WMTTNSGIT GYAQKFQG | 341 | EGYSSGLDY | 360 | RASQSISSWLA | 375 | AASSLQS | 387 | QQSYSTPYT |
| 4 | 311 | GYYIH | 325 | GIIPIFGTASY AQKFQG | 342 | DGRFWSGYPDY | 362 | RASQGISNYLA | 377 | RASNLES | 389 | QQSYSTPLT |
| 5 | 312 | THYMH | 326 | WMNPNSGH AGSAQKFQG | 343 | ESIAVAGYDY | 360 | RASQSISSWLA | 378 | AASTLQR | 387 | QQSYSTPYT |
| 6 | 313 | SHDIN | 327 | WMNPNSGNT GYAQKFQG | 344 | DRWYMGSADY | 363 | RASQSISTWLA | 379 | AASTLQS | 390 | QQSYSTPFT |
| 7 | 310 | SYYMH | 327 | WMNPNSGNT GYAQKFQG | 345 | DDWGGDWFDP | 364 | QASQDISNHLN | 380 | GASNLQR | 391 | QQSYSTPIT |
| 8 | 312 | THYMH | 328 | WMNPNSGNT GYSQKFQG | 346 | ERLSVAGFDY | 365 | RASQGISSWLA | 375 | AASSLQS | 387 | QQSYSTPYT |
| 9 | 314 | DHYLH | 329 | WMNPNIGNT GYAQKFQG | 347 | EPLQLGGFDY | 366 | RASESISSWLA | 375 | AASSLQS | 389 | QQSYSTPLT |
| 10 | 309 | GYYMH | 330 | WMNPNGGTT GYAQNFQG | 348 | EGFGPNAFDI | 360 | RASQSISSWLA | 381 | AASNLQS | 392 | QQYYSTPYT |
| 11 | 309 | GYYMH | 327 | WMNPNSGNT GYAQKFQG | 349 | DSWYGDWFDP | 367 | RASQSVGSWLA | 382 | GASSLQS | 389 | QQSYSTPLT |
| 12 | 309 | GYYMH | 322 | WMSPYNGIT GYAQKFQG | 350 | EVIEVGMDV | 360 | RASQSISSWLA | 383 | AASHLQS | 387 | QQSYSTPYT |
| 13 | 315 | NYYMH | 323 | WMSPSSGITG YAQKFQG | 351 | EAWFGELST | 368 | RASQNISNFLN | 375 | AASSLQS | 393 | QQSYSLPYT |
| 14 | 316 | AYYVH | 331 | WMNPNRGIT DSAQKFQG | 352 | EAYVAAFDI | 365 | RASQGISSWLA | 375 | AASSLQS | 389 | QQSYSTPLT |
| 15 | 317 | RHYVH | 332 | WMNPNSGSA GYAQKFQG | 353 | ERGYNAFDY | 369 | RASQSLSSSYLA | 131 | GASTRAT | 394 | HQYFTTPLT |
| 16 | 318 | NYIH | 333 | WIHPRSGAT GYAPKFQG | 354 | DSVFGLDY | 370 | RASQSISSYLN | 379 | AASTLQS | 395 | QQSYSMPYT |
| 17 | 310 | SYYMH | 334 | WISPRSGVTS YAQKFQG | 355 | DLDYVRAFDI | 371 | RASQSISRWLA | 375 | AASSLQS | 387 | QQSYSTPYT |

*Fig. 5A*

| | | | | | | | | | | | | |
|---|---|---|---|---|---|---|---|---|---|---|---|---|
| 18 | 310 | SYYMH | 335 | WMDPNSGNT GYAQKFQG | 356 | ESWGGYFDL | 360 | RASQSISSWLA | 385 | DSSSLQT | 396 | QQSYSTPVT |
| 19 | 319 | NHYVH | 336 | WMNPTGGIT GYAQKFQG | 357 | DRTTYAFDI | 372 | RDSHSITTWLA | 386 | AASNLES | 397 | QHFYNTQYT |
| 20 | 320 | SHYMH | 337 | WMNPNSGHT GNAQKFQG | 358 | GNWVDAFDI | 373 | RASQVIRNDLA | 379 | AASTLQS | 398 | QQSLQYPSHF |
| 21 | 321 | RHLLH | 338 | WVSPIHGLTG YAPRFQG | 359 | VHGSGSDGMDV | 374 | RASQSISRYLN | 379 | AASTLQS | 389 | QQSYSTPLT |

*Fig. 5B*

| Binding agent | SEQ ID NO: | HFW1 | SEQ ID NO: | HFW2 | SEQ ID NO: | HFW3 | SEQ ID NO: | HFW4 |
|---|---|---|---|---|---|---|---|---|
| 1 | 399 | QVQLVQSGAEVKKPGASVKV SCKASGYTFS | 407 | WVRQAPGQGLEW MG | 409 | RVTMTRDTSTSTVYMELSSLRSED TAVYYCAR | 411 | WGQGTLVTV SS |
| 2 | 400 | QVQLVQSGAEVKKPGASVKV SCKASGYTFT | 407 | WVRQAPGQGLEW MG | 409 | RVTMTRDTSTSTVYMELSSLRSED TAVYYCAR | 411 | WGQGTLVTV SS |
| 3 | 399 | QVQLVQSGAEVKKPGASVKV SCKASGYTFS | 407 | WVRQAPGQGLEW MG | 409 | RVTMTRDTSTSTVYMELSSLRSED TAVYYCAR | 411 | WGQGTLVTV SS |
| 4 | 401 | QVQLVQSGAEVKKPGSSVKV SCKASGYTFT | 407 | WVRQAPGQGLEW MG | 410 | RVTITADESTSTAYMELSSLRSEDT AVYYCAR | 411 | WGQGTLVTV SS |
| 5 | 399 | QVQLVQSGAEVKKPGASVKV SCKASGYTFS | 407 | WVRQAPGQGLEW MG | 409 | RVTMTRDTSTSTVYMELSSLRSED TAVYYCAR | 411 | WGQGTLVTV SS |
| 6 | 400 | QVQLVQSGAEVKKPGASVKV SCKASGYTFT | 407 | WVRQAPGQGLEW MG | 409 | RVTMTRDTSTSTVYMELSSLRSED TAVYYCAR | 411 | WGQGTLVTV SS |
| 7 | 400 | QVQLVQSGAEVKKPGASVKV SCKASGYTFT | 407 | WVRQAPGQGLEW MG | 409 | RVTMTRDTSTSTVYMELSSLRSED TAVYYCAR | 411 | WGQGTLVTV SS |
| 8 | 399 | QVQLVQSGAEVKKPGASVKV SCKASGYTFS | 407 | WVRQAPGQGLEW MG | 409 | RVTMTRDTSTSTVYMELSSLRSED TAVYYCAR | 411 | WGQGTLVTV SS |
| 9 | 402 | QVQLVQSGAEVKEPGASVKV SCKASGYTFT | 407 | WVRQAPGQGLEW MG | 409 | RVTMTRDTSTSTVYMELSSLRSED TAVYYCAR | 411 | WGQGTLVTV SS |
| 10 | 400 | QVQLVQSGAEVKKPGASVKV SCKASGYTFT | 407 | WVRQAPGQGLEW MG | 409 | RVTMTRDTSTSTVYMELSSLRSED TAVYYCAR | 412 | WGQGTTVTV SS |
| 11 | 400 | QVQLVQSGAEVKKPGASVKV SCKASGYTFT | 407 | WVRQAPGQGLEW MG | 409 | RVTMTRDTSTSTVYMELSSLRSED TAVYYCAR | 411 | WGQGTLVTV SS |
| 12 | 400 | QVQLVQSGAEVKKPGASVKV SCKASGYTFT | 408 | WMRQAPGQGLEW IG | 409 | RVTMTRDTSTSTVYMELSSLRSED TAVYYCAR | 412 | WGQGTTVTV SS |
| 13 | 400 | QVQLVQSGAEVKKPGASVKV SCKASGYTFT | 407 | WVRQAPGQGLEW MG | 409 | RVTMTRDTSTSTVYMELSSLRSED TAVYYCAR | 411 | WGQGTLVTV SS |
| 14 | 403 | QVQLVQSGAEVKKPGASVKV SCKASGYNFS | 407 | WVRQAPGQGLEW MG | 409 | RVTMTRDTSTSTVYMELSSLRSED TAVYYCAR | 412 | WGQGTTVTV SS |
| 15 | 400 | QVQLVQSGAEVKKPGASVKV SCKASGYTFT | 407 | WVRQAPGQGLEW MG | 409 | RVTMTRDTSTSTVYMELSSLRSED TAVYYCAR | 411 | WGQGTLVTV SS |
| 16 | 607 | QVQLVQSGAEVKKPGASVKV SCKASGYTLP | 407 | WVRQAPGQGLEW MG | 409 | RVTMTRDTSTSTVYMELSSLRSED TAVYYCAR | 411 | WGQGTLVTV SS |
| 17 | 400 | QVQLVQSGAEVKKPGASVKV SCKASGYTFT | 407 | WVRQAPGQGLEW MG | 409 | RVTMTRDTSTSTVYMELSSLRSED TAVYYCAR | 412 | WGQGTTVTV SS |

*Fig. 6A*

| | | | | | | | | |
|---|---|---|---|---|---|---|---|---|
| 18 | 405 | QVQLVQSGAEVKKPGASVKV SCKASGYSFT | 407 | WVRQAPGQGLEW MG | 409 | RVTMTRDTSTSTVYMELSSLRSED TAVYYCAR | 413 | WGRGTLVTV SS |
| 19 | 406 | QVQLVQSGAEVKKPGASVKV SCKASGYTFI | 407 | WVRQAPGQGLEW MG | 409 | RVTMTRDTSTSTVYMELSSLRSED TAVYYCAR | 414 | WGQGTMVTV SS |
| 20 | 400 | QVQLVQSGAEVKKPGASVKV SCKASGYTFT | 407 | WVRQAPGQGLEW MG | 409 | RVTMTRDTSTSTVYMELSSLRSED TAVYYCAR | 414 | WGQGTMVTV SS |
| 21 | 401 | QVQLVQSGAEVKKPGSSVKV SCKASGYTFT | 407 | WVRQAPGQGLEW MG | 410 | RVTITADESTSTAYMELSSLRSEDT AVYYCAR | 412 | WGQGTTVTV SS |

*Fig. 6B*

| Binding agent | SEQ ID NO: | LFW1 | SEQ ID NO: | LFW2 | SEQ ID NO: | LFW3 | SEQ ID NO: | LFW4 |
|---|---|---|---|---|---|---|---|---|
| 1 | 415 | DIQMTQSPSSLSASVGDR VTITC | 418 | WYQQKPGKAPKLLIY | 421 | GVPSRFSGSGSGTDFTLTISSLQPE DFATYYC | 425 | FGGGTKVEIK |
| 2 | 415 | DIQMTQSPSSLSASVGDR VTITC | 418 | WYQQKPGKAPKLLIY | 421 | GVPSRFSGSGSGTDFTLTISSLQPE DFATYYC | 425 | FGGGTKVEIK |
| 3 | 415 | DIQMTQSPSSLSASVGDR VTITC | 418 | WYQQKPGKAPKLLIY | 421 | GVPSRFSGSGSGTDFTLTISSLQPE DFATYYC | 425 | FGGGTKVEIK |
| 4 | 415 | DIQMTQSPSSLSASVGDR VTITC | 418 | WYQQKPGKAPKLLIY | 421 | GVPSRFSGSGSGTDFTLTISSLQPE DFATYYC | 425 | FGGGTKVEIK |
| 5 | 415 | DIQMTQSPSSLSASVGDR VTITC | 418 | WYQQKPGKAPKLLIY | 421 | GVPSRFSGSGSGTDFTLTISSLQPE DFATYYC | 426 | FGQGTKLEIK |
| 6 | 415 | DIQMTQSPSSLSASVGDR VTITC | 418 | WYQQKPGKAPKLLIY | 421 | GVPSRFSGSGSGTDFTLTISSLQPE DFATYYC | 427 | FGQGTKVEIK |
| 7 | 415 | DIQMTQSPSSLSASVGDR VTITC | 418 | WYQQKPGKAPKLLIY | 421 | GVPSRFSGSGSGTDFTLTISSLQPE DFATYYC | 428 | FGQGTRLEIK |
| 8 | 415 | DIQMTQSPSSLSASVGDR VTITC | 418 | WYQQKPGKAPKLLIY | 421 | GVPSRFSGSGSGTDFTLTISSLQPE DFATYYC | 427 | FGQGTKVEIK |
| 9 | 415 | DIQMTQSPSSLSASVGDR VTITC | 418 | WYQQKPGKAPKLLIY | 421 | GVPSRFSGSGSGTDFTLTISSLQPE DFATYYC | 426 | FGQGTKLEIK |
| 10 | 415 | DIQMTQSPSSLSASVGDR VTITC | 418 | WYQQKPGKAPKLLIY | 421 | GVPSRFSGSGSGTDFTLTISSLQPE DFATYYC | 427 | FGQGTKVEIK |
| 11 | 415 | DIQMTQSPSSLSASVGDR VTITC | 418 | WYQQKPGKAPKLLIY | 421 | GVPSRFSGSGSGTDFTLTISSLQPE DFATYYC | 425 | FGGGTKVEIK |
| 12 | 415 | DIQMTQSPSSLSASVGDR VTITC | 418 | WYQQKPGKAPKLLIY | 421 | GVPSRFSGSGSGTDFTLTISSLQPE DFATYYC | 428 | FGQGTRLEIK |

*Fig. 7A*

| | | | | | | | | |
|---|---|---|---|---|---|---|---|---|
| 13 | 415 | DIQMTQSPSSLSASVGDR VTITC | 418 | WYQQKPGKAPKLLIY | 421 | GVPSRFSGSGSGTDFTLTISSLQPE DFATYYC | 427 | FGQGTKVEIK |
| 14 | 415 | DIQMTQSPSSLSASVGDR VTITC | 418 | WYQQKPGKAPKLLIY | 421 | GVPSRFSGSGSGTDFTLTISSLQPE DFATYYC | 425 | FGGGTKVEIK |
| 15 | 416 | EIVMTQSPATLSVSPGER ATLSC | 419 | WYQQKPGQAPRLLIY | 422 | GIPARFSGSGSGTEFTLTISSLQSED FAVYYC | 428 | FGQGTRLEIK |
| 16 | 415 | DIQMTQSPSSLSASVGDR VTITC | 418 | WYQQKPGKAPKLLIY | 421 | GVPSRFSGSGSGTDFTLTISSLQPE DFATYYC | 426 | FGQGTKLEIK |
| 17 | 415 | DIQMTQSPSSLSASVGDR VTITC | 418 | WYQQKPGKAPKLLIY | 421 | GVPSRFSGSGSGTDFTLTISSLQPE DFATYYC | 426 | FGQGTKLEIK |
| 18 | 415 | DIQMTQSPSSLSASVGDR VTITC | 418 | WYQQKPGKAPKLLIY | 421 | GVPSRFSGSGSGTDFTLTISSLQPE DFATYYC | 427 | FGQGTKVEIK |
| 19 | 417 | DIQITHSPSSLSASVGYRL TITC | 420 | WYHQKPWNAPKLMIY | 423 | GVPSRFSGSGSGTYFTLTISSLQPE DFATYYC | 427 | FGQGTKVEIK |
| 20 | 415 | DIQMTQSPSSLSASVGDR VTITC | 418 | WYQQKPGKAPKLLIY | 421 | GVPSRFSGSGSGTDFTLTISSLQPE DFATYYC | 427 | FGQGTKVEIK |
| 21 | 415 | DIQMTQSPSSLSASVGDR VTITC | 418 | WYQQKPGKAPKLLIY | 424 | GVPSRFSGSGSGTDFTLTISSLQPE DFAPYYC | 429 | FGPGTKVDIK |

*Fig. 7B*

| Binding agent | SEQ ID NO: | VH |
|---|---|---|
| 1 | 430 | QVQLVQSGAEVKKPGASVKVSCKASGYTFSSDYMHWVRQAPGQGLEWMGWMSPYNGITGYAQKFQGRVTMTRDTSTSTVYMELSSLRSED TAVYYCARDRFSGSYDYWGQGTLVTVSS |
| 2 | 431 | QVQLVQSGAEVKKPGASVKVSCKASGYTFTGYYMHWVRQAPGQGLEWMGWMSPSSGITGYAQKFQGRVTMTRDTSTSTVYMELSSLRSED TAVYYCARDRGWFDPWGQGTLVTVSS |
| 3 | 432 | QVQLVQSGAEVKKPGASVKVSCKASGYTFSSYYMHWVRQAPGQGLEWMGWMTTNSGITGYAQKFQGRVTMTRDTSTSTVYMELSSLRSED TAVYYCAREGYSSGLDYWGQGTLVTVSS |
| 4 | 433 | QVQLVQSGAEVKKPGSSVKVSCKASGYTFTGYYIHWVRQAPGQGLEWMGGIIPIFGTASYAQKFQGRVTITADESTSTAYMELSSLRSEDTAV YYCARDGRFWSGYPDYWGQGTLVTVSS |
| 5 | 434 | QVQLVQSGAEVKKPGASVKVSCKASGYTFSTHYMHWVRQAPGQGLEWMGWMNPNSGHAGSAQKFQGRVTMTRDTSTSTVYMELSSLRSE DTAVYYCARESIAVAGYDYWGQGTLVTVSS |
| 6 | 435 | QVQLVQSGAEVKKPGASVKVSCKASGYTFTSHDINWVRQAPGQGLEWMGWMNPNSGNTGYAQKFQGRVTMTRDTSTSTVYMELSSLRSED TAVYYCARDRWYMGSADYWGQGTLVTVSS |
| 7 | 436 | QVQLVQSGAEVKKPGASVKVSCKASGYTFTSYYMHWVRQAPGQGLEWMGWMNPNSGNTGYAQKFQGRVTMTRDTSTSTVYMELSSLRSE DTAVYYCARDDWGGDWFDPWGQGTLVTVSS |
| 8 | 437 | QVQLVQSGAEVKKPGASVKVSCKASGYTFSTHYMHWVRQAPGQGLEWMGWMNPNSGNTGYSQKFQGRVTMTRDTSTSTVYMELSSLRSE DTAVYYCARERLSVAGFDYWGQGTLVTVSS |
| 9 | 438 | QVQLVQSGAEVKEPGASVKVSCKASGYTFTDHYLHWVRQAPGQGLEWMGWMNPNIGNTGYAQKFQGRVTMTRDTSTSTVYMELSSLRSED TAVYYCAREPLQLGGFDYWGQGTLVTVSS |
| 10 | 439 | QVQLVQSGAEVKKPGASVKVSCKASGYTFTGYYMHWVRQAPGQGLEWMGWMNPNGGTTGYAQNFQGRVTMTRDTSTSTVYMELSSLRSE DTAVYYCAREGFGPNAFDIWGQGTTVTVSS |
| 11 | 440 | QVQLVQSGAEVKKPGASVKVSCKASGYTFTGYYMHWVRQAPGQGLEWMGWMNPNSGNTGYAQKFQGRVTMTRDTSTSTVYMELSSLRSED TAVYYCARDSWYGDWFDPWGQGTLVTVSS |

*Fig. 8A*

| | | |
|---|---|---|
| 12 | 441 | QVQLVQSGAEVKKPGASVKVSCKASGYTFTGYYMHWMRQAPGQGLEWIGWMSPYNGITGYAQKFQGRVTMTRDTSTSTVYMELSSLRSEDTAVYYCAREVIEVGMDVWGQGTTVTVSS |
| 13 | 442 | QVQLVQSGAEVKKPGASVKVSCKASGYTFTNYYMHWVRQAPGQGLEWMGWMSPSSGITGYAQKFQGRVTMTRDTSTSTVYMELSSLRSEDTAVYYCAREAWFGELSTWGQGTLVTVSS |
| 14 | 443 | QVQLVQSGAEVKKPGASVKVSCKASGYNFSAYYVHWVRQAPGQGLEWMGWMNPNRGITDSAQKFQGRVTMTRDTSTSTVYMELSSLRSEDTAVYYCAREAYVAAFDIWGQGTTVTVSS |
| 15 | 444 | QVQLVQSGAEVKKPGASVKVSCKASGYTFTRHYVHWVRQAPGQGLEWMGWMNPNSGSAGYAQKFQGRVTMTRDTSTSTVYMELSSLRSEDTAVYYCARERGYNAFDYWGQGTLVTVSS |
| 16 | 445 | QVQLVQSGAEVKKPGASVKVSCKASGYTLPNYIHWVRQAPGQGLEWMGWIHPRSGATGYAPKFQGRVTMTRDTSTSTVYMELSSLRSEDTAVYYCARDSVFGLDYWGQGTLVTVSS |
| 17 | 446 | QVQLVQSGAEVKKPGASVKVSCKASGYTFTSYYMHWVRQAPGQGLEWMGWISPRSGVTSYAQKFQGRVTMTRDTSTSTVYMELSSLRSEDTAVYYCARDLDYVRAFDIWGQGTTVTVSS |
| 18 | 447 | QVQLVQSGAEVKKPGASVKVSCKASGYSFTSYYMHWVRQAPGQGLEWMGWMDPNSGNTGYAQKFQGRVTMTRDTSTSTVYMELSSLRSEDTAVYYCARESWGGYFDLWGRGTLVTVSS |
| 19 | 448 | QVQLVQSGAEVKKPGASVKVSCKASGYTFINHYVHWVRQAPGQGLEWMGWMNPTGGITGYAQKFQGRVTMTRDTSTSTVYMELSSLRSEDTAVYYCARDRTTYAFDIWGQGTMVTVSS |
| 20 | 449 | QVQLVQSGAEVKKPGASVKVSCKASGYTFTSHYMHWVRQAPGQGLEWMGWMNPNSGHTGNAQKFQGRVTMTRDTSTSTVYMELSSLRSEDTAVYYCARGNWVDAFDIWGQGTMVTVSS |
| 21 | 450 | QVQLVQSGAEVKKPGSSVKVSCKASGYTFTRHLLHWVRQAPGQGLEWMGWVSPIHGLTGYAPRFQGRVTITADESTSTAYMELSSLRSEDTAVYYCARVHGSGSDGMDVWGQGTTVTVSS |

*Fig. 8B*

| Binding agent | SEQ ID NO: | VL |
|---|---|---|
| 1 | 451 | DIQMTQSPSSLSASVGDRVTITCRASQSISSWLAWYQQKPGKAPKLLIYAASSLQSGVPSRFSGSGSGTDFTLTISSLQPEDFATYYCQQSYSTPYTFGGGTKVEIK |
| 2 | 452 | DIQMTQSPSSLSASVGDRVTITCRASQSVGTWLAWYQQKPGKAPKLLIYAASTLENGVPSRFSGSGSGTDFTLTISSLQPEDFATYYCQQSFSTPYTFGGGTKVEIK |
| 3 | 453 | DIQMTQSPSSLSASVGDRVTITCRASQSISSWLAWYQQKPGKAPKLLIYAASSLQSGVPSRFSGSGSGTDFTLTISSLQPEDFATYYCQQSYSTPYTFGGGTKVEIK |
| 4 | 454 | DIQMTQSPSSLSASVGDRVTITCRASQGISNYLAWYQQKPGKAPKLLIYRASNLESGVPSRFSGSGSGTDFTLTISSLQPEDFATYYCQQSYSTPLTFGGGTKVEIK |
| 5 | 455 | DIQMTQSPSSLSASVGDRVTITCRASQSISSWLAWYQQKPGKAPKLLIYAASTLQRGVPSRFSGSGSGTDFTLTISSLQPEDFATYYCQQSYSTPYTFGQGTKLEIK |
| 6 | 456 | DIQMTQSPSSLSASVGDRVTITCRASQSISTWLAWYQQKPGKAPKLLIYAASTLQSGVPSRFSGSGSGTDFTLTISSLQPEDFATYYCQQSYSTPFTFGQGTKVEIK |
| 7 | 457 | DIQMTQSPSSLSASVGDRVTITCQASQDISNHLNWYQQKPGKAPKLLIYGASNLQRGVPSRFSGSGSGTDFTLTISSLQPEDFATYYCQQSYSTPITFGQGTRLEIK |
| 8 | 458 | DIQMTQSPSSLSASVGDRVTITCRASQGISSWLAWYQQKPGKAPKLLIYAASSLQSGVPSRFSGSGSGTDFTLTISSLQPEDFATYYCQQSYSTPYTFGQGTKVEIK |
| 9 | 459 | DIQMTQSPSSLSASVGDRVTITCRASESISSWLAWYQQKPGKAPKLLIYAASSLQSGVPSRFSGSGSGTDFTLTISSLQPEDFATYYCQQSYSTPLTFGQGTKLEIK |
| 10 | 460 | DIQMTQSPSSLSASVGDRVTITCRASQSISSWLAWYQQKPGKAPKLLIYAASNLQSGVPSRFSGSGSGTDFTLTISSLQPEDFATYYCQQYYSTPYTFGQGTKVEIK |
| 11 | 461 | DIQMTQSPSSLSASVGDRVTITCRASQSVGSWLAWYQQKPGKAPKLLIYGASSLQSGVPSRFSGSGSGTDFTLTISSLQPEDFATYYCQQSYSTPLTFGGGTKVEIK |
| 12 | 462 | DIQMTQSPSSLSASVGDRVTITCRASQSISSWLAWYQQKPGKAPKLLIYAASHLQSGVPSRFSGSGSGTDFTLTISSLQPEDFATYYCQQSYSTPYTFGQGTRLEIK |

*Fig. 8C*

| | | |
|---|---|---|
| 13 | 463 | DIQMTQSPSSLSASVGDRVTITCRASQNISNFLNWYQQKPGKAPKLLIYAASSLQSGVPSRFSGSGSGTDFTLTISSLQPEDFATYYCQQSYSLPYTF<br>GQGTKVEIK |
| 14 | 464 | DIQMTQSPSSLSASVGDRVTITCRASQGISSWLAWYQQKPGKAPKLLIYAASSLQSGVPSRFSGSGSGTDFTLTISSLQPEDFATYYCQQSYSTPLTF<br>GGGTKVEIK |
| 15 | 465 | EIVMTQSPATLSVSPGERATLSCRASQSLSSSYLAWYQQKPGQAPRLLIYGASTRATGIPARFSGSGSGTEFTLTISSLQSEDFAVYYCHQYFTTPLT<br>FGQGTRLEIK |
| 16 | 466 | DIQMTQSPSSLSASVGDRVTITCRASQSISSYLNWYQQKPGKAPKLLIYAASTLQSGVPSRFSGSGSGTDFTLTISSLQPEDFATYYCQQSYSMPYTF<br>GQGTKLEIK |
| 17 | 467 | DIQMTQSPSSLSASVGDRVTITCRASQSISRWLAWYQQKPGKAPKLLIYAASSLQSGVPSRFSGSGSGTDFTLTISSLQPEDFATYYCQQSYSTPYTF<br>GQGTKLEIK |
| 18 | 468 | DIQMTQSPSSLSASVGDRVTITCRASQSISSWLAWYQQKPGKAPKLLIYDSSSLQTGVPSRFSGSGSGTDFTLTISSLQPEDFATYYCQQSYSTPVTF<br>GQGTKVEIK |
| 19 | 469 | DIQITHSPSSLSASVGYRLTITCRDSHSITTWLAWYHQKPWNAPKLMIYAASNLES<br>GVPSRFSGSGSGTYFTLTISSLQPEDFATYYCQHFYNTQYTFGQGTKVEIK |
| 20 | 470 | DIQMTQSPSSLSASVGDRVTITCRASQVIRNDLAWYQQKPGKAPKLLIYAASTLQSGVPSRFSGSGSGTDFTLTISSLQPEDFATYYCQQSLQYPSHF<br>FGQGTKVEIK |
| 21 | 471 | DIQMTQSPSSLSASVGDRVTITCRASQSISRYLNWYQQKPGKAPKLLIYAASTLQSGVPSRFSGSGSGTDFTLTISSLQPEDFAPYYCQQSYSTPLTF<br>GPGTKVDIK |

*Fig. 8D*

THIENOAZEPINE IMMUNOCONJUGATES, AND USES THEREOF

CROSS REFERENCE TO RELATED APPLICATIONS

This divisional application claims the benefit of priority to U.S. application Ser. No. 17/078,467, filed 23 Oct. 2020, which claims the benefit of priority to U.S. Provisional Application No. 62/926,333, filed 25 Oct. 2019, and to U.S. Provisional Application No. 62/984,184, filed 2 Mar. 2020, each of which is incorporated by reference in its entirety.

SEQUENCE LISTING

The instant application contains a Sequence Listing which has been submitted electronically in XML format and is hereby incorporated by reference in its entirety. Said XML copy, created on 31 Jan. 2023, is named 17019.006US2_ST26XML and is 792,876 bytes in size.

FIELD OF THE INVENTION

The invention relates generally to an immunoconjugate comprising an antibody conjugated to one or more thienoazepine molecules.

BACKGROUND OF THE INVENTION

New compositions and methods for the delivery of antibodies and immune adjuvants are needed in order to reach inaccessible tumors and/or to expand treatment options for cancer patients and other subjects. The invention provides such compositions and methods.

SUMMARY OF THE INVENTION

The invention is generally directed to immunoconjugates comprising an antibody linked by conjugation to one or more thienoazepine derivatives. The invention is further directed to thienoazepine derivative intermediate compositions comprising a reactive functional group. Such intermediate compositions are suitable substrates for formation of immunoconjugates wherein an antibody may be covalently bound by a linker L to a thienoazepine (TAZ) moiety having the formula:

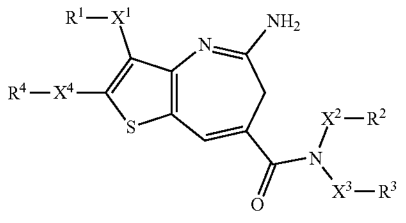

where one of $R^1$, $R^2$, $R^3$ and $R^4$ is attached to L. The $R^1$, $R^2$, $R^3$ and $R^4$ substituents are defined herein.

The invention is further directed to use of such an immunoconjugates in the treatment of an illness, in particular cancer.

An aspect of the invention is an immunoconjugate comprising an antibody covalently attached to a linker which is covalently attached to one or more thienoazepine moieties.

Another aspect of the invention is a thienoazepine-linker compound.

Another aspect of the invention is a method for treating cancer comprising administering a therapeutically effective amount of an immunoconjugate comprising an antibody linked by conjugation to one or more thienoazepine moieties.

Another aspect of the invention is a use of an immunoconjugate comprising an antibody linked by conjugation to one or more thienoazepine moieties for treating cancer.

Another aspect of the invention is a method of preparing an immunoconjugate by conjugation of one or more thienoazepine moieties with an antibody.

BRIEF DESCRIPTION OF THE DRAWINGS

FIGS. 1A-D show heavy chain and light chain CDRs of PD-L1 Type A binding agents 1-42.

FIGS. 2A-D show first (HFW1), second (HFW2), third (HFW3), and fourth (HFW4) heavy chain framework region polypeptides of PD-L1 Type A binding agents 1-42.

FIGS. 3A-D show first (LFW1), second (LFW2), third (LFW3), and fourth (LFW4) light chain framework region polypeptides of PD-L1 Type A binding agents 1-42.

FIGS. 4 A-D show heavy chain variable region (VH) of PD-L1 Type A binding agents 1-42.

FIGS. 4 E-G show light chain variable region (VL) of PD-L1 Type A binding agents 1-42.

FIGS. 5A-B show heavy chain and light chain CDRs of PD-L1 Type B binding agents 1-21.

FIGS. 6A-B show first (HFW1), second (HFW2), third (HFW3), and fourth (HFW4) heavy chain framework region polypeptides of PD-L1 Type B binding agents 1-21.

FIGS. 7A-B show first (LFW1), second (LFW2), third (LFW3), and fourth (LFW4) light chain framework region polypeptides of PD-L1 Type B binding agents 1-21.

FIGS. 8A-B show heavy chain variable region (VH) of PD-L1 Type B binding agents 1-21.

FIGS. 8C-D show light chain variable region (VL) of PD-L1 Type B binding agents 1-21.

DETAILED DESCRIPTION OF THE INVENTION

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents, which may be included within the scope of the invention as defined by the claims.

One skilled in the art will recognize many methods and materials similar or equivalent to those described herein, which could be used in the practice of the present invention. The invention is in no way limited to the methods and materials described.

DEFINITIONS

The term "immunoconjugate" refers to an antibody construct that is covalently bonded to an adjuvant moiety via a linker, the term "adjuvant" refers to a substance capable of eliciting an immune response in a subject exposed to the adjuvant. The phrase "adjuvant moiety" refers to an adjuvant that is covalently bonded to an antibody construct. e.g., through a linker, as described herein. The adjuvant moiety can elicit the immune response while bonded to the antibody construct or after cleavage (e.g., enzymatic cleavage) from the antibody construct following administration of an immunoconjugate to the subject.

"Adjuvant" refers to a substance capable of eliciting an immune response in a subject exposed to the adjuvant. The phrase "adjuvant moiety" refers to an adjuvant that is covalently bonded to an antibody construct, e.g., through a linker, as described herein. The adjuvant moiety can elicit the immune response while bonded to the antibody construct or after cleavage (e.g., enzymatic cleavage) from the antibody construct following administration of an immunoconjugate to the subject.

The terms "Toll-like receptor" and "TLR" refer to any member of a family of highly-conserved mammalian proteins which recognizes pathogen-associated molecular patterns and acts as key signaling elements in innate immunity. TLR polypeptides share a characteristic structure that includes an extracellular domain that has leucine-rich repeats, a transmembrane domain, and an intracellular domain that is involved in TLR signaling.

The terms "Toll-like receptor 7" and "TLR7" refer to nucleic acids or polypeptides sharing at least about 70%, about 80%, about 90%, about 95%, about 96%, about 97%, about 98%, about 99%, or more sequence identity to a publicly-available TLR7 sequence, e.g., GenBank accession number AAZ99026 for human TLR7 polypeptide, or GenBank accession number AAK62676 for murine TLR7 polypeptide.

The terms "Toll-like receptor 8" and "TLR8" refer to nucleic acids or polypeptides sharing at least about 70%, about 80%, about 90%, about 95%, about 96%, about 97%, about 98%, about 99%, or more sequence identity to a publicly-available TLR7 sequence, e.g., GenBank accession number AAZ95441 for human TLR8 polypeptide, or GenBank accession number AAK62677 for murine TLR8 polypeptide.

A "TLR agonist" is a substance that binds, directly or indirectly, to a TLR (e.g., TLR7 and/or TLR8) to induce TLR signaling. Any detectable difference in TLR signaling can indicate that an agonist stimulates or activates a TLR. Signaling differences can be manifested, for example, as changes in the expression of target genes, in the phosphorylation of signal transduction components, in the intracellular localization of downstream elements such as nuclear factor-κB (NF-κB), in the association of certain components (such as IL-1 receptor associated kinase (IRAK)) with other proteins or intracellular structures, or in the biochemical activity of components such as kinases (such as mitogen-activated protein kinase (MAPK)).

"Antibody" refers to a polypeptide comprising an antigen binding region (including the complementarity determining region (CDRs)) from an immunoglobulin gene or fragments thereof. The term "antibody" specifically encompasses monoclonal antibodies (including full length monoclonal antibodies), polyclonal antibodies, multispecific antibodies (e.g., bispecific antibodies), and antibody fragments that exhibit the desired biological activity. An exemplary immunoglobulin (antibody) structural unit comprises a tetramer. Each tetramer is composed of two identical pairs of polypeptide chains, each pair having one "light" (about 25 kDa) and one "heavy" chain (about 50-70 kDa) connected by disulfide bonds. Each chain is composed of structural domains, which are referred to as immunoglobulin domains. These domains are classified into different categories by size and function, e.g., variable domains or regions on the light and heavy chains ($V_L$ and $V_H$, respectively) and constant domains or regions on the light and heavy chains ($C_L$ and $C_H$, respectively). The N-terminus of each chain defines a variable region of about 100 to 110 or more amino acids, referred to as the paratope, primarily responsible for antigen recognition, i.e., the antigen binding domain. Light chains are classified as either kappa or lambda. Heavy chains are classified as gamma, mu, alpha, delta, or epsilon, which in turn define the immunoglobulin classes, IgG, IgM, IgA, IgD and IgE, respectively. IgG antibodies are large molecules of about 150 kDa composed of four peptide chains. IgG antibodies contain two identical class γ heavy chains of about 50 kDa and two identical light chains of about 25 kDa, thus a tetrameric quaternary structure. The two heavy chains are linked to each other and to a light chain each by disulfide bonds. The resulting tetramer has two identical halves, which together form the Y-like shape. Each end of the fork contains an identical antigen binding domain. There are four IgG subclasses (IgG1, IgG2, IgG3, and IgG4) in humans, named in order of their abundance in serum (i.e., IgG1 is the most abundant).

Typically, the antigen binding domain of an antibody will be most critical in specificity and affinity of binding to cancer cells.

"Antibody construct" refers to an antibody or a fusion protein comprising (i) an antigen binding domain and (ii) an Fc domain.

In some embodiments, the binding agent is an antigen-binding antibody "fragment," which is a construct that comprises at least an antigen-binding region of an antibody, alone or with other components that together constitute the antigen-binding construct. Many different types of antibody "fragments" are known in the art, including, for instance, (i) a Fab fragment, which is a monovalent fragment consisting of the $V_L$, $V_H$, $C_L$, and $C_H$, domains, (ii) a $F(ab')_2$ fragment, which is a bivalent fragment comprising two Fab fragments linked by a disulfide bridge at the hinge region, (iii) a Fv fragment consisting of the $V_L$ and $V_H$ domains of a single arm of an antibody, (iv) a Fab' fragment, which results from breaking the disulfide bridge of an $F(ab')_2$ fragment using mild reducing conditions, (v) a disulfide-stabilized Fv fragment (dsFv), and (vi) a single chain Fv (scFv), which is a monovalent molecule consisting of the two domains of the Fv fragment (i.e., $V_L$ and $V_H$) joined by a synthetic linker which enables the two domains to be synthesized as a single polypeptide chain.

The antibody or antibody fragments can be part of a larger construct, for example, a conjugate or fusion construct of the antibody fragment to additional regions. For instance, in some embodiments, the antibody fragment can be fused to an Fc region as described herein. In other embodiments, the antibody fragment (e.g., a Fab or scFv) can be part of a chimeric antigen receptor or chimeric T-cell receptor, for instance, by fusing to a transmembrane domain (optionally with an intervening linker or "stalk" (e.g., hinge region)) and optional intercellular signaling domain. For instance, the antibody fragment can be fused to the gamma and/or delta chains of a t-cell receptor, so as to provide a T-cell receptor like construct that binds PD-L1. In yet another embodiment, the antibody fragment is part of a bispecific T-cell engager (BiTEs) comprising a CD1 or CD3 binding domain and linker.

"Epitope" means any antigenic determinant or epitopic determinant of an antigen to which an antigen binding domain binds (i.e., at the paratope of the antigen binding domain). Antigenic determinants usually consist of chemically active surface groupings of molecules, such as amino acids or sugar side chains, and usually have specific three dimensional structural characteristics, as well as specific charge characteristics.

The terms "Fc receptor" or "FcR" refer to a receptor that binds to the Fc region of an antibody. There are three main classes of Fc receptors: (1) FcγR which bind to IgG, (2) FcαR which binds to IgA, and (3) FcεR which binds to IgE. The FcγR family includes several members, such as FcγI (CD64), FcγRIIA (CD32A), FcγRIIB (CD32B), FcγRIIIA (CD16A), and FcγRIIIB (CD16B). The Fcγ receptors differ in their affinity for IgG and also have different affinities for the IgG subclasses (e.g., IgG1, IgG2, IgG3, and IgG4).

Nucleic acid or amino acid sequence "identity," as referenced herein, can be determined by comparing a nucleic acid or amino acid sequence of interest to a reference nucleic acid or amino acid sequence. The percent identity is the number of nucleotides or amino acid residues that are the same (i.e., that are identical) as between the optimally aligned sequence of interest and the reference sequence divided by the length of the longest sequence (i.e., the length of either the sequence of interest or the reference sequence, whichever is longer). Alignment of sequences and calculation of percent identity can be performed using available software programs. Examples of such programs include CLUSTAL-W, T-Coffee, and ALIGN (for alignment of nucleic acid and amino acid sequences), BLAST programs (e.g., BLAST 2.1, BL2SEQ, BLASTp, BLASTn, and the like) and FASTA programs (e.g., FASTA3x, FASTM, and SSEARCH) (for sequence alignment and sequence similarity searches). Sequence alignment algorithms also are disclosed in, for example, Altschul et al., *J Molecular Biol.,* 215(3): 403-410 (1990), Beigert et al., *Proc. Natl. Acad. Sci. USA,* 106(10): 3770-3775 (2009), Durbin et al., eds., *Biological Sequence Analysis: Probalistic Models of Proteins and Nucleic Acids*, Cambridge University Press, Cambridge, UK (2009), Soding, *Bioinformatics,* 21(7): 951-960 (2005), Altschul et al., *Nucleic Acids Res.,* 25(17): 3389-3402 (1997), and Gusfield, *Algorithms on Strings, Trees and Sequences*, Cambridge University Press, Cambridge UK (1997)). Percent (%) identity of sequences can be also calculated, for example, as 100×[(identical positions)/min($TG_A$, $TG_B$)], where $TG_A$ and $TG_B$ are the sum of the number of residues and internal gap positions in peptide sequences A and B in the alignment that minimizes $TG_A$ and $TG_B$. See, e.g., Russell et al., *J. Mol Biol.,* 244: 332-350 (1994).

The binding agent comprises Ig heavy and light chain variable region polypeptides that together form the antigen binding site. Each of the heavy and light chain variable regions are polypeptides comprising three complementarity determining regions (CDR1, CDR2, and CDR3) connected by framework regions. The binding agent can be any of a variety of types of binding agents known in the art that comprise Ig heavy and light chains. For instance, the binding agent can be an antibody, an antigen-binding antibody "fragment," or a T-cell receptor.

"Biosimilar" refers to an approved antibody construct that has active properties similar to, for example, a PD-L1-targeting antibody construct previously approved such as atezolizumab (TECENTRIQ™, Genentech, Inc.), durvalumab (IMFINZI™, AstraZeneca), and avelumab (BAVENCIO™, EMD Serono, Pfizer); a HER2-targeting antibody construct previously approved such as trastuzumab (HERCEPTIN™, Genentech, Inc.), and pertuzumab (PERJETA™, Genentech. Inc.): or a CEA-targeting antibody such as labetuzumab (CEA-CIDE™, MN-14, hMN14, Immunomedics) CAS Reg. No. 219649-07-7).

"Biobetter" refers to an approved antibody construct that is an improvement of a previously approved antibody construct, such as atezolizumab, durvalumab, avelumab, trastuzumab, pertuzumab, and labetuzumab. The biobetter can have one or more modifications (e.g., an altered glycan profile, or a unique epitope) over the previously approved antibody construct.

"Amino acid" refers to any monomeric unit that can be incorporated into a peptide, polypeptide, or protein. Amino acids include naturally-occurring a-amino acids and their stereoisomers, as well as unnatural (non-naturally occurring) amino acids and their stereoisomers. "Stereoisomers" of a given amino acid refer to isomers having the same is molecular formula and intramolecular bonds but different three-dimensional arrangements of bonds and atoms (e.g., an L-amino acid and the corresponding D-amino acid). The amino acids can be glycosylated (e.g., N-linked glycans, O-linked glycans, phosphoglycans, C-linked glycans, or glypication) or deglycosylated. Amino acids may be referred to herein by either the commonly known three letter symbols or by the one-letter symbols recommended by the IUPAC-IUB Biochemical Nomenclature Commission.

Naturally-occurring amino acids are those encoded by the genetic code, as well as those amino acids that are later modified, e.g., hydroxyproline, y-carboxyglutamate, and O-phosphoserine. Naturally-occurring a-amino acids include, without limitation, alanine (Ala), cysteine (Cys), aspartic acid (Asp), glutamic acid (Glu), phenylalanine (Phe), glycine (Gly), histidine (His), isoleucine (Ile), arginine (Arg), lysine (Lys), leucine (Leu), methionine (Met), asparagine (Asn), proline (Pro), glutamine (Gin), serine (Ser), threonine (Thr), valine (Val), tryptophan (Trp), tyrosine (Tyr), and combinations thereof. Stereoisomers of naturally-occurring α-amino acids include, without limitation, D-alanine (D-Ala), D-cysteine (D-Cys), D-aspartic acid (D-Asp), D-glutamic acid (D-Glu), D-phenylalanine (D-Phe). D-histidine (D-His), D-isoleucine (D-Ile), D-arginine (D-Arg), D-lysine (D-Lys), D-leucine (D-Leu). D-methionine (D-Met), D-asparagine (D-Asn), D-proline (D-Pro), D-glutamine (D-Gln), D-serine (D-Ser), D-threonine (D-Thr), D-valine (D-Val), D-tryptophan (D-Trp), D-tyrosine (D-Tyr), and combinations thereof.

Naturally-occurring amino acids include those formed in proteins by post-translational modification, such as citrulline (Cit).

Unnatural (non-naturally occurring) amino acids include, without limitation, amino acid analogs, amino acid mimetics, synthetic amino acids. N-substituted glycines, and N-methyl amino acids in either the L- or D-configuration that function in a manner similar to the naturally-occurring amino acids. For example, "amino acid analogs" can be unnatural amino acids that have the same basic chemical structure as naturally-occurring amino acids (i.e., a carbon that is bonded to a hydrogen, a carboxyl group, an amino group) but have modified side-chain groups or modified peptide backbones, e.g., homoserine, norleucine, methionine sulfoxide, and methionine methyl sulfonium. "Amino acid mimetics" refer to chemical compounds that have a structure that is different from the general chemical structure of an amino acid, but that functions in a manner similar to a naturally-occurring amino acid.

"Linker" refers to a functional group that covalently bonds two or more moieties in a compound or material. For example, the linking moiety can serve to covalently bond an adjuvant moiety to an antibody construct in an immunoconjugate.

"Linking moiety" refers to a functional group that covalently bonds two or more moieties in a compound or material. For example, the linking moiety can serve to covalently bond an adjuvant moiety to an antibody in an immunoconjugate. Useful bonds for connecting linking moieties to proteins and other materials include, but are not limited to, amides, amines, esters, carbamates, ureas, thioethers, thiocarbamates, thiocarbonates, and thioureas.

"Divalent" refers to a chemical moiety that contains two points of attachment for linking two functional groups; polyvalent linking moieties can have additional points of attachment for linking further functional groups. Divalent radicals may be denoted with the suffix "diyl". For example, divalent linking moieties include divalent polymer moieties such as divalent poly(ethylene glycol), divalent cycloalkyl, divalent heterocycloalkyl, divalent aryl, and divalent heteroaryl group. A "divalent cycloalkyl, heterocycloalkyl, aril, or heteroaryl group" refers to a cycloalkyl, heterocycloalkyl, aril, or heteroaryl group having two points of attachment for covalently linking two moieties in a molecule or material. Cycloalkyl, heterocycloalkyl, aryl, or heteroaryl groups can be substituted or unsubstituted. Cycloalkyl, heterocycloalkyl, aryl, or heteroaryl groups can be substituted with one or more groups selected from halo, hydroxy, amino, alkylamino, amido, acyl, nitro, cyano, and alkoxy.

A wavy line ("∿") represents a point of attachment of the specified chemical moiety. If the specified chemical moiety has two wavy lines ("∿") present, it will be understood that the chemical moiety can be used bilaterally, i.e., as read from left to right or from right to left. In some embodiments, a specified moiety having two wavy lines ("∿") present is considered to be used as read from left to right.

"Alkyl" refers to a straight (linear) or branched, saturated, aliphatic radical having the number of carbon atoms indicated. Alkyl can include any number of carbons, for example from one to twelve. Examples of alkyl groups include, but are not limited to, methyl (Me, $—CH_3$), ethyl (Et, $—CH_2CH_3$), 1-propyl (n-Pr, n-propyl, $—CH_2CH_2CH_3$), 2-propyl (i-Pr, i-propyl, $—CH(CH_3)_2$), 1-butyl (n-Bu, n-butyl, $—CH_2CH_2CH_2CH_3$), 2-methyl-1-propyl (i-Bu, i-butyl, $—CH_2CH(CH_3)_2$), 2-butyl (s-Bu, s-butyl, $—CH(CH_3)CH_2CH_3$), 2-methyl-2-propyl (t-Bu, t-butyl, $—C(CH_3)_3$), 1-pentyl (n-pentyl, $—CH_2CH_2CH_2CH_2CH_3$), 2-pentyl ($—CH(CH_3)CH_2CH_2CH_3$), 3-pentyl ($—CH(CH_2CH_3)_2$), 2-methyl-2-butyl ($—C(CH_3)_2CH_2CH_3$), 3-methyl-2-butyl ($—CH(CH_3)CH(CH_3)_2$), 3-methyl-1-butyl ($—CH_2CH_2CH(CH_3)_2$), 2-methyl-1-butyl ($—CH_2CH(CH_3)CH_2CH_3$), 1-hexyl ($—CH_2CH_2CH_2CH_2CH_2CH_3$), 2-hexyl ($—CH(CH_3)CH_2CH_2CH_2CH_3$), 3-hexyl ($—CH(CH_2CH_3)(CH_2CH_2CH_3)$), 2-methyl-2-pentyl ($—C(CH_3)_2CH_2CH_2CH_3$), 3-methyl-2-pentyl ($—CH(CH_3)CH(CH_3)CH_2CH_3$), 4-methyl-2-pentyl ($—CH(CH_3)CH_2CH(CH_3)_2$), 3-methyl-3-pentyl ($—C(CH_3)(CH)_2$), 2-methyl-3-pentyl ($—CH(CH_2CH_3)CH(CH_3)_2$), 2,3-dimethyl-2-butyl ($—C(CH_3)_2CH(CH_3)_2$), 3,3-dimethyl-2-butyl ($—CH(CH_3)C(CH_3)_3$, 1-heptyl, 1-octyl, and the like. Alkyl groups can be substituted or unsubstituted, "Substituted alkyl" groups can be substituted with one or more groups selected from halo, hydroxy, amino, oxo (=O), alkylamino, amido, acyl, nitro, cyano, and alkoxy.

The term "alkyldiyl" refers to a divalent alkyl radical. Examples of alkyldiyl groups include, but are not limited to, methylene ($—CH_2—$), ethylene ($—CH_2CH_2—$), propylene ($—CH_2CH_2CH_2—$), and the like. An alkyldiyl group may also be referred to as an "alkylene" group.

"Alkenyl" refers to a straight (linear) or branched, unsaturated, aliphatic radical having the number of carbon atoms indicated and at least one carbon-carbon double bond, sp2. Alkenyl can include from two to about 12 or more carbons atoms. Alkenyl groups are radicals having "cis" and "trans" orientations, or alternatively, "E" and "Z" orientations. Examples include, but are not limited to, ethylenyl or vinyl ($—CH=CH_2$), allyl ($—CH_2CH=CH_2$), butenyl, pentenyl, and isomers thereof. Alkenyl groups can be substituted or unsubstituted. "Substituted alkenyl" groups can be substituted with one or more groups selected from halo, hydroxy, amino, oxo (=O), alkylamino, amido, acyl, nitro, cyano, and alkoxy.

The terms "alkenylene" or "alkenyldiyl" refer to a linear or branched-chain divalent hydrocarbon radical. Examples include, but are not limited to, ethylenylene or vinylene ($—CH=CH—$), allyl ($—CH_2CH=CH—$), and the like.

"Alkynyl" refers to a straight (linear) or branched, unsaturated, aliphatic radical having the number of carbon atoms indicated and at least one carbon-carbon triple bond, sp. Alkynyl can include from two to about 12 or more carbons atoms. For example, $C_2$-$C_6$ alkynyl includes, but is not limited to ethynyl ($—C≡CH$), propynyl (propargyl, $—CH_2C≡CH$), butynyl, pentynyl, hexynyl, and isomers thereof. Alkynyl groups can be substituted or unsubstituted. "Substituted alkynyl" groups can be substituted with one or more groups selected from halo, hydroxy, amino, oxo (=O), alkylamino, amido, acyl, nitro, cyano, and alkoxy.

The term "alkynylene" or "alkynyldiyl" refer to a divalent alkynl radical.

The terms "carbocycle", "carbocyclyl", "carbocyclic ring" and "cycloalkyl" refer to a saturated or partially unsaturated, monocyclic, fused bicyclic, or bridged polycyclic ring assembly containing from 3 to 12 ring atoms, or the number of atoms indicated. Saturated monocyclic carbocyclic rings include, for example, cyclopropyl, cyclobutyl, cyclopentyl, cyclohexyl, and cyclooctyl. Saturated bicyclic and polycyclic carbocyclic rings include, for example, norbomane, [2.2.2]bicyclooctane, decahydronaphthalene and adamantane. Carbocyclic groups can also be partially unsaturated, having one or more double or triple bonds in the ring. Representative carbocyclic groups that are partially unsaturated include, but are not limited to, cyclobutene, cyclopentene, cyclohexene, cyclohexadiene (1,3- and 1,4-isomers), cycloheptene, cycloheptadiene, cyclooctene, cyclooctadiene (1,3-, 1,4- and 1,5-isomers), is norbomene, and norbornadiene.

The term "cycloalkyldiyl" refers to a divalent cycloalkyl radical.

"Aryl" refers to a monovalent aromatic hydrocarbon radical of 6-20 carbon atoms ($C_6$-$C_{20}$) derived by the removal of one hydrogen atom from a single carbon atom of a parent aromatic ring system. Aryl groups can be monocyclic, fused to form bicyclic or tricyclic groups, or linked by a bond to form a biaryl group. Representative aryl groups include phenyl, naphthyl and biphenyl. Other aryl groups include benzyl, having a methylene linking group. Some aryl groups have from 6 to 12 ring members, such as phenyl, naphthyl or biphenyl. Other aryl groups have from 6 to 10 ring members, such as phenyl or naphthyl.

The terms "arylene" or "aryldiyl" mean a divalent aromatic hydrocarbon radical of 6-20 carbon atoms ($C_6$-$C_{20}$) derived by the removal of two hydrogen atom from a two carbon atoms of a parent aromatic ring system. Some aryldiyl groups are represented in the exemplary structures as "Ar". Aryldiyl includes bicyclic radicals comprising an aromatic ring fused to a saturated, partially unsaturated ring, or aromatic carbocyclic ring. Typical aryldiyl groups include, but are not limited to, radicals derived from benzene (phenyldiyl), substituted benzenes, naphthalene, anthracene, biphenylene, indenylene, indanylene, 1,2-dihydronaphthalene, 1,2,3,4-tetrahydronaphthyl, and the like. Aryldiyl groups are also referred to as "arylene", and are optionally substituted with one or more substituents described herein.

The terms "heterocycle," "heterocyclyl" and "heterocyclic ring" are used interchangeably herein and refer to a saturated or a partially unsaturated (i.e., having one or more double and/or triple bonds within the ring) carbocyclic radical of 3 to about 20 ring atoms in which at least one ring atom is a heteroatom selected from nitrogen, oxygen, phosphorus and sulfur, the remaining ring atoms being C, where one or more ring atoms is optionally substituted independently with one or more substituents described below. A heterocycle may be a monocycle having 3 to 7 ring members (2 to 6 carbon atoms and 1 to 4 heteroatoms selected from N, O, P, and S) or a bicycle having 7 to 10 ring members (4 to 9 carbon atoms and 1 to 6 heteroatoms selected from N, O, P, and S), for example: a bicyclo [4,5], [5,5], [5,6], or [6,6] system. Heterocycles are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566. "Heterocyclyl" also includes radicals where heterocycle radicals are fused with a saturated, partially unsaturated ring, or aromatic carbocyclic or heterocyclic ring. Examples of heterocyclic rings include, but are not limited to, morpholin-4-yl, piperidin-1-yl, piperazinyl, piperazin-4-yl-2-one, piperazin-4-yl-3-one, pyrrolidin-1-yl, thiomorpholin-4-yl, S-dioxothiomorpholin-4-yl, azocan-1-yl, azetidin-1-yl, octahydropyrido[1,2-a]pyrazin-2-yl, [1,4]diazepan-1-yl, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 3-azabicyco[3.1.0]hexanyl, 3-azabicyclo[4.1.0]heptanyl, azabicyclo[2.2.2]hexanyl, 3H-indolyl quinolizinyl and N-pyridyl ureas. Spiro heterocyclyl moieties are also included within the scope of this definition. Examples of spiro heterocyclyl moieties include azaspiro[2.5]octanyl and azaspiro[2.4]heptanyl. Examples of a heterocyclic group wherein 2 ring atoms are substituted with oxo (=O) moieties are pyrimidinonyl and 1,1-dioxo-thiomorpholinyl. The heterocycle groups herein are optionally substituted independently with one or more substituents described herein.

The term "heterocyclyldiyl" refers to a divalent, saturated or a partially unsaturated (i.e., having one or more double and/or triple bonds within the ring) carbocyclic radical of 3 to about 20 ring atoms in which at least one ring atom is a heteroatom selected from nitrogen, oxygen, phosphorus and sulfur, the remaining ring atoms being C, where one or more ring atoms is optionally substituted independently with one or more substituents as described. Examples of 5-membered and 6-membered heterocyclyldiyls include morpholinyldiyl, piperidinyldiyl, piperazinyldiyl, pyrrolidinyldiyl, dioxanyldiyl, thiomorpholinyldiyl, and S-dioxothiomorpholinyldiyl.

The term "heteroaryl" refers to a monovalent aromatic radical of 5-, 6-, or 7-membered rings, and includes fused ring systems (at least one of which is aromatic) of 5-20 atoms, containing one or more heteroatoms independently selected from nitrogen, oxygen, and sulfur.

Examples of heteroaryl groups are pyridinyl (including, for example, 2-hydroxypyridinyl), imidazolyl, imidazopyridinyl, pyrimidinyl (including, for example, 4-hydroxypyrimidinyl), pyrazolyl, triazolyl, pyrazinyl, tetrazolyl, furyl, thienyl, isoxazolyl, thiazolyl, oxadiazolyl, oxazolyl, isothiazolyl, pyrrolyl, quinolinyl, isoquinolinyl, tetrahydroisoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. Heteroaryl groups are optionally substituted independently with one or more substituents described herein.

The term "heteroaryldiyl" refers to a divalent aromatic radical of 5-, 6-, or 7-membered rings, and includes fused ring systems (at least one of which is aromatic) of 5-20 atoms, containing one or more heteroatoms independently selected from nitrogen, oxygen, and sulfur. Examples of 5-membered and 6-membered heteroaryldiyls include pyridyldiyl, imidazolyldiyl, pyrimidinyldiyl, pyrazolyldiyl, triazolyldiyl, pyrazinyldiyl, tetrazolyldiyl, furyldiyl, thienyldiyl, isoxazolyldiyldiyl, thiazolyldiyl, oxadiazolyldiyl, oxazolyldiyl, isothiazolyldiyl, and pyrrolyldiyl.

The heterocycle or heteroaryl groups may be carbon (carbon-linked), or nitrogen (nitrogen-linked) bonded where such is possible. By way of example and not limitation, carbon bonded heterocycles or heteroaryls are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline.

By way of example and not limitation, nitrogen bonded heterocycles or heteroaryls are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or O-carboline.

The terms "halo" and "halogen," by themselves or as part of another substituent, refer to a fluorine, chlorine, bromine, or iodine atom.

The term "carbonyl," by itself or as part of another substituent, refers to C(=O) or —C(=O)—, i.e., a carbon atom double-bonded to oxygen and bound to two other groups in the moiety having the carbonyl.

As used herein, the phrase "quaternary ammonium salt" refers to a tertiary amine that has been quaternized with an alkyl substituent (e.g., a $C_1$-$C_4$ alkyl such as methyl, ethyl, propyl, or butyl).

The terms "treat," "treatment," and "treating" refer to any indicia of success in the treatment or amelioration of an injury, pathology, condition (e.g., cancer), or symptom (e.g., cognitive impairment), including any objective or subjective parameter such as abatement; remission; diminishing of symptoms or making the symptom, injury, pathology, or condition more tolerable to the patient; reduction in the rate of symptom progression; decreasing the frequency or duration of the symptom or condition; or, in some situations, preventing the onset of the symptom. The treatment or amelioration of symptoms can be based on any objective or subjective parameter, including, for example, the result of a physical examination.

The terms "cancer," "neoplasm," and "tumor" are used herein to refer to cells which exhibit autonomous, unregulated growth, such that the cells exhibit an aberrant growth phenotype characterized by a significant loss of control over cell proliferation. Cells of interest for detection, analysis, and/or treatment in the context of the invention include cancer cells (e.g., cancer cells from an individual with cancer), malignant cancer cells, pre-metastatic cancer cells, metastatic cancer cells, and non-metastatic cancer cells. Cancers of virtually every tissue are known. The phrase "cancer burden" refers to the quantum of cancer cells or cancer volume in a subject. Reducing cancer burden accordingly refers to reducing the number of cancer cells or the cancer cell volume in a subject. The term "cancer cell" as used herein refers to any cell that is a cancer cell (e.g., from any of the cancers for which an individual can be treated, e.g., isolated from an individual having cancer) or is derived from a cancer cell, e.g., clone of a cancer cell. For example, a cancer cell can be from an established cancer cell line, can be a primary cell isolated from an individual with cancer, can be a progeny cell from a primary cell isolated from an individual with cancer, and the like. In some embodiments, the term can also refer to a portion of a cancer cell, such as a sub-cellular portion, a cell membrane portion, or a cell lysate of a cancer cell. Many types of cancers are known to those of skill in the art, including solid tumors such as carcinomas, sarcomas, glioblastomas, melanomas, lymphomas, and myelomas, and circulating cancers such as leukemias.

As used herein, the term "cancer" includes any form of cancer, including but not limited to, solid tumor cancers (e.g., skin, lung, prostate, breast, gastric, bladder, colon, ovarian, pancreas, kidney, liver, glioblastoma, medulloblastoma, leiomyosarcoma, head & neck squamous cell carcinomas, melanomas, and neuroendocrine) and liquid cancers (e.g., hematological cancers); carcinomas; soft tissue tumors; sarcomas; teratomas; melanomas; leukemias: lymphomas; and brain cancers, including minimal residual disease, and including both primary and metastatic tumors.

"PD-L1 expression" refers to a cell that has a PD-L1 receptor on the cell's surface. As used herein "PD-L1 overexpression" refers to a cell that has more PD-L1 receptors as compared to corresponding non-cancer cell.

"HER2" refers to the protein human epidermal growth factor receptor 2.

"HER2 expression" refers to a cell that has a HER2 receptor on the cell's surface. For example, a cell may have from about 20,000 to about 50,000 HER2 receptors on the cell's surface. As used herein "HER2 overexpression" refers to a cell that has more than about 50,000 HER2 receptors. For example, a cell 2, 5, 10, 100, 1,000, 10,000, 100,000, or 1,000,000 times the number of HER2 receptors as compared to corresponding non-cancer cell (e.g., about 1 or 2 million HER2 receptors). It is estimated that HER2 is overexpressed in about 25% to about 30% of breast cancers.

The "pathology" of cancer includes all phenomena that compromise the well-being of the patient. This includes, without limitation, abnormal or uncontrollable cell growth, metastasis, interference with the normal functioning of neighboring cells, release of cytokines or other secretory products at abnormal levels, suppression or aggravation of inflammatory or immunological response, neoplasia, premalignancy, malignancy, and invasion of surrounding or distant tissues or organs, such as lymph nodes.

As used herein, the phrases "cancer recurrence" and "tumor recurrence." and grammatical variants thereof, refer to further growth of neoplastic or cancerous cells after diagnosis of cancer. Particularly, recurrence may occur when further cancerous cell growth occurs in the cancerous tissue. "Tumor spread." similarly, occurs when the cells of a tumor disseminate into local or distant tissues and organs, therefore, tumor spread encompasses tumor metastasis. "Tumor invasion" occurs when the tumor growth spread out locally to compromise the function of involved tissues by compression, destruction, or prevention of normal organ function.

As used herein, the term "metastasis" refers to the growth of a cancerous tumor in an organ or body part, which is not directly connected to the organ of the original cancerous tumor. Metastasis will be understood to include micrometastasis, which is the presence of an undetectable amount of cancerous cells in an organ or body part that is not directly connected to the organ of the original cancerous tumor. Metastasis can also be defined as several steps of a process, such as the departure of cancer cells from an original tumor site, and migration and/or invasion of cancer cells to other parts of the body.

The phrases "effective amount" and "therapeutically effective amount" refer to a dose or amount of a substance such as an immunoconjugate that produces therapeutic effects for which it is administered. The exact dose will depend on the purpose of the treatment, and will be ascertainable by one skilled in the art using known techniques (see, e.g., Lieberman, *Pharmaceutical Dosage Forms* (vols. 1-3, 1992): Lloyd, *The Art, Science and Technology of Pharmaceutical Compounding* (1999); Pickar, *Dosage Calculations* (1999) *Goodman & Gilman's The Pharmacological Basis of Therapeutics,* $11^{th}$ Edition (McGraw-Hill, 2006); and *Remington: The Science and Practice of Pharmacy,* $22^{nd}$ Edition, (Pharmaceutical Press, London, 2012)). In the case of cancer, the therapeutically effective amount of the immunoconjugate may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the immunoconjugate may prevent growth and/or kill existing cancer cells, it may be cytostatic and/or cytotoxic. For cancer therapy, efficacy can, for example, be measured by assessing the time to disease progression (TTP) and/or determining the response rate (RR)

"Recipient," "individual," "subject," "host," and "patient" are used interchangeably and refer to any mammalian subject for whom diagnosis, treatment, or therapy is desired (e.g., humans). "Mammal" for purposes of treatment refers to any animal classified as a mammal, including humans, domestic and farm animals, and zoo, sports, or pet animals, such as dogs, horses, cats, cows, sheep, goats, pigs, camels, etc. In certain embodiments, the mammal is human.

The phrase "synergistic adjuvant" or "synergistic combination" in the context of this invention includes the combination of two immune modulators such as a receptor agonist, cytokine, and adjuvant polypeptide, that in combination elicit a synergistic effect on immunity relative to either administered alone. Particularly, the immunoconjugates disclosed herein comprise synergistic combinations of the claimed adjuvant and antibody construct. These synergistic combinations upon administration elicit a greater effect on immunity, e.g., relative to when the antibody construct or adjuvant is administered in the absence of the other moiety. Further, a decreased amount of the immunoconjugate may be administered (as measured by the total number of antibody constructs or the total number of adjuvants administered as part of the immunoconjugate) compared to when either the antibody construct or adjuvant is administered alone.

As used herein, the term "administering" refers to parenteral, intravenous, intraperitoneal, intramuscular, intratumoral, intralesional, intranasal, or subcutaneous administration, oral administration, administration as a suppository, topical contact, intrathecal administration, or the implantation of a slow-release device, e.g., a mini-osmotic pump, to the subject.

The terms "about" and "around," as used herein to modify a numerical value, indicate a close range surrounding the numerical value. Thus, if "X" is the value, "about X" or "around X" indicates a value of from 0.9X to 1.1X, e.g., from 0.95X to 1.05X or from 0.99X to 1.01X. A reference to "about X" or "around X" specifically indicates at least the values X, 0.95X, 0.96X, 0.97X, 0.98X, 0.99X, 1.01X, 1.02X, 1.03X, 1.04X, and 1.05X. Accordingly, "about X" and "around X" are intended to teach and provide written description support for a claim limitation of, e.g., "0.98X."

Antibodies

The immunoconjugate of the invention comprises an antibody. Included in the scope of the embodiments of the invention are functional variants of the antibody constructs or antigen binding domain described herein. The term "functional variant" as used herein refers to an antibody construct having an antigen binding domain with substantial or significant sequence identity or similarity to a parent antibody construct or antigen binding domain, which functional variant retains the biological activity of the antibody construct or antigen binding domain of which it is a variant. Functional variants encompass, for example, those variants of the antibody constructs or antigen binding domain described herein (the parent antibody construct or antigen binding domain) that retain the ability to recognize target cells expressing PD-L1, HER2 or CEA to a similar extent, the same extent, or to a higher extent, as the parent antibody construct or antigen binding domain.

In reference to the antibody construct or antigen binding domain, the functional variant can, for instance, be at least about 30%, about 50%, about 75%, about 80%, about 85%, about 90%, about 91%, about 92%, about 93%, about 94%, about 95%, about 96%, about 97%, about 98%, about 99% or more identical in amino acid sequence to the antibody construct or antigen binding domain.

A functional variant can, for example, comprise the amino acid sequence of the parent antibody construct or antigen binding domain with at least one conservative amino acid substitution. Alternatively, or additionally, the functional variants can comprise the amino acid sequence of the parent antibody construct or antigen binding domain with at least one non-conservative amino acid substitution. In this case, it is preferable for the non-conservative amino acid substitution to not interfere with or inhibit the biological activity of the functional variant. The non-conservative amino acid substitution may enhance the biological activity of the functional variant, such that the biological activity of the functional variant is increased as compared to the parent antibody construct or antigen binding domain.

The antibodies comprising the immunoconjugates of the invention include Fc engineered variants. In some embodiments, the mutations in the Fc region that result in modulated binding to one or more Fc receptors can include one or more of the following mutations: SD (S239D), SDIE (S239D/I332E), SE (S267E), SELF (S267E/L328F), SDIE (S239D/I332E), SDIEAL (S239D/1332E/A330L), GA (G236A), ALIE (A330L/1332E), GASDALIE (G236A/S239D/A330L/I332E), V9 (G237D/P238D/P271G/A330R), and V11 (G237D/P238D/H268D/P271G/A330R), and/or one or more mutations at the following amino acids: E345R, E233, G237, P238, H268, P271, L328 and A330. Additional Fc region is modifications for modulating Fc receptor binding are described in, for example, U.S. Patent Application Publication 2016/0145350 and U.S. Pat. Nos. 7,416,726 and 5,624,821, which are hereby incorporated by reference in their entireties herein.

The antibodies comprising the immunoconjugates of the invention include glycan variants, such as afucosylation. In some embodiments, the Fc region of the binding agents are modified to have an altered glycosylation pattern of the Fc region compared to the native non-modified Fc region.

Amino acid substitutions of the inventive antibody constructs or antigen binding domains are preferably conservative amino acid substitutions. Conservative amino acid substitutions are known in the art, and include amino acid substitutions in which one amino acid having certain physical and/or chemical properties is exchanged for another amino acid that has the same or similar chemical or physical properties. For instance, the conservative amino acid substitution can be an acidic/negatively charged polar amino acid substituted for another acidic/negatively charged polar amino acid (e.g., Asp or Glu), an amino acid with a nonpolar side chain substituted for another amino acid with a nonpolar side chain (e.g., Ala, Gly, Val, Ile, Leu. Met, Phe, Pro, Trp, Cys, Val, etc.), a basic/positively charged polar amino acid substituted for another basic/positively charged polar amino acid (e.g., Lys, His, Arg, etc.), an uncharged amino acid with a polar side chain substituted for another uncharged amino acid with a polar side chain (e.g., Asn, Gln, Ser, Thr, Tyr, etc.), an amino acid with a beta-branched side-chain substituted for another amino acid with a beta-branched side-chain (e.g., Ile, Thr, and Val), an amino acid with an aromatic side-chain substituted for another amino acid with an aromatic side chain (e.g., His, Phe, Trp, and Tyr), etc.

The antibody construct or antigen binding domain can consist essentially of the specified amino acid sequence or sequences described herein, such that other components, e.g., other amino acids, do not materially change the biological activity of the antibody construct or antigen binding domain functional variant.

In some embodiments, the antibodies in the immunoconjugates contain a modified Fc region, wherein the modification modulates the binding of the Fc region to one or more Fc receptors.

In some embodiments, the antibodies in the immunoconjugates (e.g., antibodies conjugated to at least two adjuvant moieties) contain one or more modifications (e.g., amino acid insertion, deletion, and/or substitution) in the Fc region that results in modulated binding (e.g., increased binding or decreased binding) to one or more Fc receptors (e.g., FcγRI (CD64), FcγRIIA (CD32A), FcγRIIB (CD32B), FcγRIIIA (CD16a), and/or FcγRIIIB (CD16b)) as compared to the native antibody lacking the mutation in the Fc region. In some embodiments, the antibodies in the immunoconjugates contain one or more modifications (e.g., amino acid insertion, deletion, and/or substitution) in the Fc region that reduce the binding of the Fc region of the antibody to FcγRIIB. In some embodiments, the antibodies in the immunoconjugates contain one or more modifications (e.g., amino acid insertion, deletion, and/or substitution) in the Fc region of the antibody that reduce the binding of the antibody to FcγRIIB while maintaining the same binding or having increased binding to Fc-γRI (CD64), FcγRIIA (CD32A), and/or FcR-γIIIA (CD16a) as compared to the native antibody lacking the mutation in the Fc region. In some embodiments, the antibodies in the immunoconjugates contain one of more modifications in the Fc region that increase the binding of the Fc region of the antibody to FcγRIIB.

In some embodiments, the modulated binding is provided by mutations in the Fc region of the antibody relative to the native Fc region of the antibody. The mutations can be in a $CH_2$ domain, a $CH_3$ domain, or a combination thereof. A "native Fc region" is synonymous with a "wild-type Fc region" and comprises an amino acid sequence that is identical to the amino acid sequence of an Fc region found in nature or identical to the amino acid sequence of the Fc region found in the native antibody (e.g., cetuximab). Native sequence human Fc regions include a native sequence human IgG1 Fc region, native sequence human IgG2 Fc region, native sequence human IgG3 Fc region, and native sequence human IgG4 Fc region, as well as naturally occurring variants thereof. Native sequence Fc includes the various allotypes of Fcs (Jefferis et al., (2009) *mAbs,* 1(4):332-338).

In some embodiments, the mutations in the Fc region that result in modulated binding to one or more Fc receptors can include one or more of the following mutations: SD (S239D), SDIE (S239D/I332E), SE (S267E), SELF (S267E/L328F), SDIE (S239D/I332E), SDIEAL (S239D/1332E/A330L), GA (G236A), ALIE (A330L/I332E), GASDALIE (G236A/S239D/A330L/I332E), V9 (G237D/P238D/P271G/A330R), and V11 (G237D/P238D/H268D/P271G/A330R), and/or one or more mutations at the following amino acids: E233, G237, P238, H268, P271, L328 and A330. Additional Fc region modifications for modulating Fc receptor binding are described in, for example, US 2016/0145350 and U.S. Pat. Nos. 7,416,726 and 5,624,821, which are hereby incorporated by reference in their entireties.

In some embodiments, the Fc region of the antibodies of the immunoconjugates are modified to have an altered glycosylation pattern of the Fc region compared to the native non-modified Fc region.

Human immunoglobulin is glycosylated at the Asn297 residue in the Cγ2 domain of each heavy chain. This N-linked oligosaccharide is composed of a core heptasaccharide, N-acetylglucosamine4Mannose3 (GlcNAc4Man3). Removal of the heptasaccharide with endoglycosidase or PNGase F is known to lead to conformational changes in the antibody Fc region, which can significantly reduce antibody-binding affinity to activating FcγR and lead to decreased effector function. The core heptasaccharide is often decorated with galactose, bisecting GlcNAc, fucose, or sialic acid, which differentially impacts Fc binding to activating and inhibitory FcγR. Additionally, it has been demonstrated that α2,6-sialyation enhances anti-inflammatory activity in vivo, while defucosylation leads to improved FcγRIIIa binding and a 10-fold increase in antibody-dependent cellular cytotoxicity and antibody-dependent phagocytosis. Specific glycosylation patterns, therefore, can be used to control inflammatory effector functions.

In some embodiments, the modification to alter the glycosylation pattern is a mutation. For example, a substitution at Asn297. In some embodiments, Asn297 is mutated to glutamine (N297Q). Methods for controlling immune response with antibodies that modulate FcγR-regulated signaling are described, for example, in U.S. Pat. No. 7,416,726 and U.S. Patent Application Publications 2007/0014795 and 2008/0286819, which are hereby incorporated by reference in their entireties.

In some embodiments, the antibodies of the immunoconjugates are modified to contain an engineered Fab region with a non-naturally occurring glycosylation pattern. For example, hybridomas can be genetically engineered to secrete afucosylated mAb, desialylated mAb or deglycosylated Fc with specific mutations that enable increased FcRγIIIa binding and effector function. In some embodiments, the antibodies of the immunoconjugates are engineered to be afucosylated.

In some embodiments, the entire Fc region of an antibody in the immunoconjugates is exchanged with a different Fc region, so that the Fab region of the antibody is conjugated to a non-native Fc region. For example, the Fab region of cetuximab, which normally comprises an IgG1 Fc region, can be conjugated to IgG2, IgG3, IgG4, or IgA, or the Fab region of nivolumab, which normally comprises an IgG4 Fc region, can be conjugated to IgG1, IgG2, IgG3, IgA1, or IgG2. In some embodiments, the Fc modified antibody with a non-native Fc domain also comprises one or more amino acid modification, such as the S228P mutation within the IgG4 Fc, that modulate the stability of the Fc domain described. In some embodiments, the Fc modified antibody with a non-native Fc domain also comprises one or more amino acid modifications described herein that modulate Fc binding to FcR.

In some embodiments, the modifications that modulate the binding of the Fc region to FcR do not alter the binding of the Fab region of the antibody to its antigen when compared to is the native non-modified antibody. In other embodiments, the modifications that modulate the binding of the Fc region to FcR also increase the binding of the Fab region of the antibody to its antigen when compared to the native non-modified antibody.

In an exemplary embodiment, the immunoconjugates of the invention comprise an antibody construct that comprises an antigen binding domain that specifically recognizes and binds PD-L1.

Programmed Death-Ligand 1 (PD-L1, cluster of differentiation 274, CD274, B7-homolog 1, or B7-H1) belongs to the B7 protein superfamily, and is a ligand of programmed cell death protein 1 (PD-1, PDCD1, cluster of differentiation 279, or CD279). PD-L1 can also interact with B7.1 (CD80) and such interaction is believed to inhibit T cell priming. The PD-L1/PD-1 axis plays a large role in suppressing the adaptive immune response. More specifically, it is believed that engagement of PD-L1 with its receptor, PD-1, delivers a signal that inhibits activation and proliferation of T-cells. Agents that bind to PD-L1 and prevent the ligand from binding to the PD-1 receptor prevent this immunosuppression, and can, therefore, enhance an immune response when desired, such as for the treatment of cancers, or infections. PD-L1/PD-1 pathway also contributes to preventing autoimmunity and therefore agonistic agents against PD-L1 or agents that deliver immune inhibitory payloads may help treatment of autoimmune disorders.

Several antibodies targeting PD-L1 have been developed for the treatment of cancer, including atezolizumab (TECENTRIQ™), durvalumab (IMFINZI™), and avelumab (BAVENCIO™). Nevertheless, there continues to be a need for new PD-L1-binding agents, including agents that bind PD-L1 with high affinity and effectively prevent PD-L1/PD-1 signaling and agents that can deliver therapeutic payloads to PD-L1 expressing cells. In addition, there is a need for new PD-L1-binding agents to treat autoimmune disorders and infections.

A method is provided of delivering a thienoazepine derivative payload to a cell expressing PD-L1 comprising administering to the cell, or mammal comprising the cell, an immunoconjugate comprising an anti-PD-L1 antibody covalently attached to a linker which is covalently attached to one or more thienoazepine moieties.

Also provided is a method for enhancing or reducing or inhibiting an immune response in a mammal, and a method for treating a disease, disorder, or condition in a mammal that is responsive to PD-L1 inhibition, which methods comprise administering a PD-L1 immunoconjugate thereof, to the mammal.

The invention provides a PD-L1 binding agent comprising an immunoglobulin heavy chain variable region polypeptide and an immunoglobulin light chain variable region is polypeptide.

The PD-L1 binding agent specifically binds PD-L1. The binding specificity of the agent allows for targeting PD-L1 expressing cells, for instance, to deliver therapeutic payloads to such cells.

In some embodiments, the PD-L1 binding agent (Type A or Type B) binds to human PD-L1, for example, a protein comprising SEQ ID NO: 307. However, binding agents that bind to any PD-L1 homolog or paralog also are encompassed. In some embodiments, the PD-L1 protein comprises at least about 70%, about 75%, about 80%, about 85%, about 90%, about 91%, about 92%, about 93%, about 94%, about 95%, about 96%, about 97%, about 98%, about 99%, or more sequence identity to SEQ ID NO: 307. In some embodiments, the binding agent binds human PD-L1 and cynomolgus PD-L1; or human, cynomolgus and mouse PD-L1.

SEQ ID NO: 307

MRIFAVFIFMTYWHLLNAFTVTVPKDLYVVEYGSNMTIECKFPVEKQLDL

AALIVYWEMEDKNITQFVHGEEDLKVQHSSYRQRARLLKDQLSLGNAALQ

ITDVKLQDAGVYRCMISYGGADYKRITVKVNAPYNKINQRILVVDPVTSE

HELTCQAEGYPKAEVIWTSSDHQVLSGKTTTTNSKREEKLFNVTSTLRIN

TTTNEIFYCTFRRLDPEENHTAELVIPELPLAHPPNERTHLVILGAILLC

LGVALTFIFRLRKGRMMDVKKCGIQDTNSKKQSDTHLEET

In some embodiments, the PD-L1 binding agent binds PD-L1 without substantially inhibiting or preventing PD-L1 from binding to its receptor, PD-1. However, in other embodiments, the PD-L1 binding agent can completely or partially block (inhibit or prevent) binding of PD-L1 to its receptor, PD-1, such that the antibody can be used to inhibit PD-L1/PD-1 signaling (e.g., for therapeutic purposes).

The antibody or antigen-binding antibody fragment can be monospecific for PD-L1, or can be bispecific or multispecific. For instance, in bivalent or multivalent antibodies or antibody fragments, the binding domains can be different targeting different epitopes of the same antigen or targeting different antigens. Methods of constructing multivalent binding constructs are known in the art. Bispecific and multispecific antibodies are known in the art. Furthermore, a diabody, triabody, or tetrabody can be provided, which is a dimer, trimer, or tetramer of polypeptide chains each comprising a $V_H$ connected to a $V_L$ by a peptide linker that is too short to allow pairing between the $V_H$ and $V_L$ on the same polypeptide chain, thereby driving the pairing between the complementary domains on different $V_H$-$V_L$ polypeptide chains to generate a multimeric molecule having two, three, or four functional antigen binding sites. Also, bis-scFv fragments, which are small scFv fragments with two different variable domains can be generated to produce bispecific bis-scFv fragments capable of binding two different epitopes. Fab dimers (Fab2) and Fab trimers (Fab3) can be produced using genetic engineering methods to create multispecific constructs based on Fab fragments.

The PD-L1-binding agent also can be an antibody conjugate. In this respect, the PD-L1-binding agent can be a conjugate of (1) an antibody, an alternative scaffold, or fragments thereof, and (2) a protein or non-protein moiety. For example, the PD-L1 binding agent can be conjugated to a peptide, a fluorescent molecule, chemotherapeutic or other cytotoxic payload, immune-activating or immune-suppressive agent.

The PD-L1-binding agent can be, or can be obtained from, a human antibody, a non-human antibody, a humanized antibody, or a chimeric antibody, or corresponding antibody fragments. A "chimeric" antibody is an antibody or fragment thereof typically comprising human constant regions and non-human variable regions. A "humanized" antibody is a monoclonal antibody typically comprising a human antibody scaffold but with non-human origin amino acids or sequences in at least one CDR (e.g., 1, 2, 3, 4, 5, or all six CDRs).

PD-L1-Binding Agents—Type A

Provided herein are PD-L1 binding agents comprising an immunoglobulin heavy chain variable region polypeptide and an immunoglobulin light chain variable region polypeptide. In some embodiments, the PD-L1 binding agents (Type A) comprise an immunoglobulin heavy chain variable region of any one of SEQ ID NOs: 223-264, or at least the CDRs thereof, and an immunoglobulin light chain variable region of any one of SEQ ID NOs: 265-306 or at least the CDRs thereof. In other embodiments, the PD-L1 binding agents (Type A) comprise an immunoglobulin heavy chain variable region polypeptide with an amino acid sequence that is at least 90% identical to any one of SEQ ID NOs: 223-264, and an immunoglobulin light chain variable region polypeptide with an amino acid sequence that is at least 90% identical to any one of SEQ ID NOs: 265-306. In yet other embodiments, the PD-L1 binding agent (Type A), the immunoglobulin heavy chain variable region polypeptide comprises a complementarity determining region 1 (HCDR1) comprising any one of SEQ ID NOs: 1-23, a complementarity determining region 2 (HCDR2) comprising any one of SEQ ID NOs: 24-57, and a complementarity determining region 3 (HCDR3) comprising any one of SEQ ID NOs: 58-95; and/or the immunoglobulin light chain variable region polypeptide comprises a complementarity determining region 1 (LCDR1) comprising any one of SEQ ID NOs: 96-128, a complementarity determining region 2 (LCDR2) comprising any one of SEQ ID NOs: 129-151, and a complementarity determining region 3 (LCDR3) comprising any one of SEQ ID NOs: 152-155. Also provided are nucleic acids encoding the PD-L1 binding agents, or the individual heavy and light chains thereof; vectors and cells comprising the nucleic acids, and compositions comprising the binding agents or nucleic acids.

Furthermore, in some embodiments, the PD-L1 binding agents (Type A) provided herein cause cellular internalization of PD-L1 or the PD-L i/PD-L1 binding agent complex upon binding to PD-L1 on the cell surface. Without wishing to be bound by any particular theory or mechanism of action, it is believed that the PD-L1 binding agents according to this embodiment cause PD-L1 internalization upon binding, and remain bound to PD-L1 during internalization resulting in internalization of the binding agent along with PD-L1. Cellular internalization of PD-L1 and bound PD-L1 binding agent can be determined by any suitable method, such as assaying for persistence on the cell surface and/or detection of internalized antibodies. In some embodiments, the PD-L1 binding agent internalizes strongly enough that at least about 25% (e.g., at least about 35%, at least about 50%, at least about 75%, or at least about 90%) of the PD-L1 binding agent that binds PD-L1 on the cell surface is internalized (e.g., using a surface persistence assay, about 75% or less, about 65% or less, about 50% or less, about 25% or less or about 10% or less of PD-L1 binding agent molecules bound to PD-L1 on the cell surface at the beginning of the assay remain bound at the end of the assay).

In an embodiment, the PD-L1 binding agent (Type A) comprises an immunoglobulin heavy chain variable region of any one of SEQ ID NOs: 223-264, a sequence that is at least about 90%, at least about 91%, at least about 92%, at least about 93%, at least about 94%, at least about 95%, at least about 96%, at least about 97%, at least about 98%, or at least about 99% identical to SEQ ID NOs: 223-264, or at least the CDRs thereof; and/or an immunoglobulin light chain variable region of any one of SEQ ID NOs: 265-306, a sequence that is at least about 90%, at least about 91%, at least about 92%, at least about 93%, at least about 94%, at least about 95%, at least about 96%, at least about 97%, at least about 98%, or at least about 99% identical to SEQ ID NOs: 265-306, or at least the CDRs thereof.

By way of further illustration, the PD-L1 binding agent (Type A) can comprise:

(1) an immunoglobulin heavy chain variable region of SEQ ID NO: 223, or at least the CDRs thereof, and/or an immunoglobulin light chain variable region of SEQ ID NO: 265, or at least the CDRs thereof;

(2) an immunoglobulin heavy chain variable region of SEQ ID NO: 224, or at least the CDRs thereof, and/or an immunoglobulin light chain variable region of SEQ ID NO: 266, or at least the CDRs thereof;

(3) an immunoglobulin heavy chain variable region of SEQ ID NO: 225, or at least the CDRs thereof, and/or an immunoglobulin light chain variable region of SEQ ID NO: 267, or at least the CDRs thereof;

(4) an immunoglobulin heavy chain variable region of SEQ ID NO: 226, or at least the CDRs thereof, and/or an immunoglobulin light chain variable region of SEQ ID NO: 268, or at least the CDRs thereof;

(5) an immunoglobulin heavy chain variable region of SEQ ID NO: 227, or at least the CDRs thereof, and/or an immunoglobulin light chain variable region of SEQ ID NO: 269, or at least the CDRs thereof;

(6) an immunoglobulin heavy chain variable region of SEQ ID NO: 228, or at least the CDRs thereof, and/or an immunoglobulin light chain variable region of SEQ ID NO: 270, or at least the CDRs thereof;

(7) an immunoglobulin heavy chain variable region of SEQ ID NO: 229, or at least the CDRs thereof, and/or an immunoglobulin light chain variable region of SEQ ID NO: 271, or at least the CDRs thereof;

(8) an immunoglobulin heavy chain variable region of SEQ ID NO: 230, or at least the CDRs thereof, and/or an immunoglobulin light chain variable region of SEQ ID NO: 272, or at least the CDRs thereof;

(9) an immunoglobulin heavy chain variable region of SEQ ID NO: 231, or at least the CDRs thereof, and/or an immunoglobulin light chain variable region of SEQ ID NO: 273, or at least the CDRs thereof;

(10) an immunoglobulin heavy chain variable region of SEQ ID NO: 232, or at least the CDRs thereof, and/or an immunoglobulin light chain variable region of SEQ ID NO: 274, or at least the CDRs thereof;

(11) an immunoglobulin heavy chain variable region of SEQ ID NO: 233, or at least the CDRs thereof, and/or an immunoglobulin light chain variable region of SEQ ID NO: 275, or at least the CDRs thereof;

(12) an immunoglobulin heavy chain variable region of SEQ ID NO: 234, or at least the CDRs thereof, and/or an immunoglobulin light chain variable region of SEQ ID NO: 276, or at least the CDRs thereof;

(13) an immunoglobulin heavy chain variable region of SEQ ID NO: 235, or at least the CDRs thereof, and/or an immunoglobulin light chain variable region of SEQ ID NO: 277, or at least the CDRs thereof;

(14) an immunoglobulin heavy chain variable region of SEQ ID NO: 236, or at least the CDRs thereof, and/or an immunoglobulin light chain variable region of SEQ ID NO: 278, or at least the CDRs thereof;

(15) an immunoglobulin heavy chain variable region of SEQ ID NO: 237, or at least the CDRs thereof, and/or an immunoglobulin light chain variable region of SEQ ID NO: 279, or at least the CDRs thereof;

(16) an immunoglobulin heavy chain variable region of SEQ ID NO: 238, or at least the CDRs thereof, and/or an immunoglobulin light chain variable region of SEQ ID NO: 280, or at least the CDRs thereof;

(17) an immunoglobulin heavy chain variable region of SEQ ID NO: 239, or at least the CDRs thereof, and/or an immunoglobulin light chain variable region of SEQ ID NO: 281, or at least the CDRs thereof;

(18) an immunoglobulin heavy chain variable region of SEQ ID NO: 240, or at least the CDRs thereof, and/or an immunoglobulin light chain variable region of SEQ ID NO: 282, or at least the CDRs thereof;

(19) an immunoglobulin heavy chain variable region of SEQ ID NO: 241, or at least the CDRs thereof, and/or an immunoglobulin light chain variable region of SEQ ID NO: 283, or at least the CDRs thereof;

(20) an immunoglobulin heavy chain variable region of SEQ ID NO: 242, or at least the CDRs thereof, and/or an immunoglobulin light chain variable region of SEQ ID NO: 284, or at least the CDRs thereof;

(21) an immunoglobulin heavy chain variable region of SEQ ID NO: 243, or at least the CDRs thereof, and/or an immunoglobulin light chain variable region of SEQ ID NO: 285, or at least the CDRs thereof,

(22) an immunoglobulin heavy chain variable region of SEQ ID NO: 244, or at least the CDRs thereof, and/or an immunoglobulin light chain variable region of SEQ ID NO: 286, or at least the CDRs thereof;

(23) an immunoglobulin heavy chain variable region of SEQ ID NO: 245, or at least the CDRs thereof, and/or an immunoglobulin light chain variable region of SEQ ID NO: 287, or at least the CDRs thereof;

(24) an immunoglobulin heavy chain variable region of SEQ ID NO: 246, or at least the CDRs thereof, and/or an immunoglobulin light chain variable region of SEQ ID NO: 288, or at least the CDRs thereof;

(25) an immunoglobulin heavy chain variable region of SEQ ID NO: 247, or at least the CDRs thereof, and/or an immunoglobulin light chain variable region of SEQ ID NO: 289, or at least the CDRs thereof;

(26) an immunoglobulin heavy chain variable region of SEQ ID NO: 248, or at least the CDRs thereof, and/or an immunoglobulin light chain variable region of SEQ ID NO: 290, or at least the CDRs thereof;

(27) an immunoglobulin heavy chain variable region of SEQ ID NO: 249, or at least the CDRs thereof, and/or an immunoglobulin light chain variable region of SEQ ID NO: 291, or at least the CDRs thereof;

(28) an immunoglobulin heavy chain variable region of SEQ ID NO: 250, or at least the CDRs thereof, and/or an immunoglobulin light chain variable region of SEQ ID NO: 292, or at least the CDRs thereof;

(29) an immunoglobulin heavy chain variable region of SEQ ID NO: 251, or at least the CDRs thereof, and/or an immunoglobulin light chain variable region of SEQ ID NO: 293, or at least the CDRs thereof;

(30) an immunoglobulin heavy chain variable region of SEQ ID NO: 252, or at least the CDRs thereof, and/or an immunoglobulin light chain variable region of SEQ ID NO: 294, or at least the CDRs thereof;

(31) an immunoglobulin heavy chain variable region of SEQ ID NO: 253, or at least the CDRs thereof, and/or an immunoglobulin light chain variable region of SEQ ID NO: 295, or at least the CDRs thereof;

(32) an immunoglobulin heavy chain variable region of SEQ ID NO: 254, or at least the CDRs thereof, and/or an immunoglobulin light chain variable region of SEQ ID NO: 296, or at least the CDRs thereof,

(33) an immunoglobulin heavy chain variable region of SEQ ID NO: 255, or at least the CDRs thereof, and/or an immunoglobulin light chain variable region of SEQ ID NO: 297, or at least the CDRs thereof;

(34) an immunoglobulin heavy chain variable region of SEQ ID NO: 256, or at least the CDRs thereof, and/or an immunoglobulin light chain variable region of SEQ ID NO: 298, or at least the CDRs thereof;

(35) an immunoglobulin heavy chain variable region of SEQ ID NO: 257, or at least the CDRs thereof, and/or an immunoglobulin light chain variable region of SEQ ID NO: 299, or at least the CDRs thereof;

(36) an immunoglobulin heavy chain variable region of SEQ ID NO: 258, or at least the CDRs thereof, and/or an immunoglobulin light chain variable region of SEQ ID NO: 300, or at least the CDRs thereof;

(37) an immunoglobulin heavy chain variable region of SEQ ID NO: 259, or at least the CDRs thereof, and/or an immunoglobulin light chain variable region of SEQ ID NO: 301, or at least the CDRs thereof;

(38) an immunoglobulin heavy chain variable region of SEQ ID NO: 260, or at least the CDRs thereof, and/or an immunoglobulin light chain variable region of SEQ ID NO: 302, or at least the CDRs thereof;

(39) an immunoglobulin heavy chain variable region of SEQ ID NO: 261, or at least the CDRs thereof, and/or an immunoglobulin light chain variable region of SEQ ID NO: 303, or at least the CDRs thereof;

(40) an immunoglobulin heavy chain variable region of SEQ ID NO: 262, or at least the CDRs thereof, and/or an immunoglobulin light chain variable region of SEQ ID NO: 304, or at least the CDRs thereof;

(41) an immunoglobulin heavy chain variable region of SEQ ID NO: 263, or at least the CDRs thereof, and/or an immunoglobulin light chain variable region of SEQ ID NO: 305, or at least the CDRs thereof;

(42) an immunoglobulin heavy chain variable region of SEQ ID NO: 164, or at least the CDRs thereof, and/or an immunoglobulin light chain variable region of SEQ ID NO: 306, or at least the CDRs thereof; and/or

(43) an immunoglobulin heavy chain variable region of FIGS. 4A-D and/or an immunoglobulin light chain variable region of FIGS. 4E-G, or at least the CDRs thereof.

The CDRs of a given heavy or light chain Ig sequence can be determined in accordance with any of the various known Ig numbering schemes (e.g., Kabat, Chothia. Martin (Enhanced Chothia), IGMT, AbM). In certain embodiments, the PD-L1 binding agent (Type A) comprises one or more of the following CDRs:

a HCDR1 comprising or consisting of any one of SEQ ID NOs: 1-23 or a sequence that is at least about 90%, at least about 91%, at least about 92%, at least about 93%, at least about 94%, at least about 95%, at least about 96%, at least about 97%, at least about 98%, or at least about 99% identical to SEQ ID NOs: 1-23;

a HCDR2 comprising or consisting of any one of SEQ ID NOs: 24-57 or a sequence that is at least about 90%, at least about 91%, at least about 92%, at least about 93%, at least about 94%, at least about 95%, at least about 96%, at least about 97%, at least about 98%, or at least about 99% identical to SEQ ID NOs: 24-57; and a HCDR3 comprising or consisting of any one of SEQ ID NOs: 58-95 or a sequence that is at least about 90%, at least about 91%, at least about 92%, at least about 93%, at least about 94%, at least about 95%, at least about 96%, at least about 97%, at least about 98%, or at least about 99% identical to SEQ ID NOs: 58-95; and/or the immunoglobulin light chain polypeptide comprises a LCDR1 comprising or consisting of any one of SEQ ID NOs: 96-128 or a sequence that is at least about 90%, at least about 91%, at least about 92%, at least about 93%, at least about 94%, at least about 95%, at least about 96%, at least about 97%, at least about 98%, or at least about 99% identical to SEQ ID NOs: 96-128;

a LCDR2 comprising or consisting of any one of SEQ ID NOs: 129-151 or a sequence that is at least about 90%, at least about 91%, at least about 92%, at least about 93%, at least about 94%, at least about 95%, at least about 96%, at least about 97%, at least about 98%, or at least about 99% identical to SEQ ID NOs: 129-151; and a LCDR3 comprising or consisting of any one of SEQ ID NOs: 152-155 or a sequence that is at least about 90%, at least about 91%, at least about 92%, at least about 93%, at least about 94%, at least about 95%, at least about 96%, at least about 97%, at least about 98%, or at least about 99% identical to SEQ ID NOs: 152-155.

In particular embodiments, the binding agent (Type A) comprises an immunoglobulin heavy chain polypeptide and an immunoglobulin light chain polypeptide, wherein:

(1) the immunoglobulin heavy chain polypeptide comprises a HCDR1 comprising or consisting of SEQ ID NO: 1, a HCDR2 comprising or consisting of SEQ ID NO: 24, and a HCDR3 comprising or consisting of SEQ ID NO: 58; and/or the immunoglobulin light chain polypeptide comprises a LCDR1 comprising or consisting of SEQ ID NO; 96, a LCDR2 comprising or consisting of SEQ ID NO: 129, and a LCDR3 comprising or consisting of SEQ ID NO: 152;

(2) the immunoglobulin heavy chain polypeptide comprises a HCDR1 comprising or consisting of SEQ ID NO: 2, a HCDR2 comprising or consisting of SEQ ID NO: 25, and a HCDR3 comprising or consisting of SEQ ID NO: 59; and/or the immunoglobulin light chain polypeptide comprises a LCDR1 comprising or consisting of SEQ ID NO: 97, a LCDR2 comprising or consisting of SEQ ID NO: 129, and a LCDR3 comprising or consisting of SEQ ID NO: 153;

(3) the immunoglobulin heavy chain polypeptide comprises a HCDR1 comprising or consisting of SEQ ID NO: 3, a HCDR2 comprising or consisting of SEQ ID NO: 26, and a HCDR3 comprising or consisting of SEQ ID NO: 60; and/or the immunoglobulin light chain polypeptide comprises a LCDR1 comprising or consisting of SEQ ID NO: 98, a LCDR2 comprising or consisting of SEQ ID NO: 129, and a LCDR3 comprising or consisting of SEQ ID NO: 154;

(4) the immunoglobulin heavy chain polypeptide comprises a HCDR1 comprising or consisting of SEQ ID NO: 4, a HCDR2 comprising or consisting of SEQ ID NO: 27, and a HCDR3 comprising or consisting of SEQ ID NO: 61; and/or the immunoglobulin light chain polypeptide comprises a LCDR1 comprising or consisting of SEQ ID NO: 99, a LCDR2 comprising or consisting of SEQ ID NO: 130, and a LCDR3 comprising or consisting of SEQ ID NO: 155;

(5) the immunoglobulin heavy chain polypeptide comprises a HCDR1 comprising or consisting of SEQ ID NO: 5, a HCDR2 comprising or consisting of SEQ ID NO: 28, and a HCDR3 comprising or consisting of SEQ ID NO: 62; and/or the immunoglobulin light chain polypeptide comprises a LCDR1 comprising or consisting of SEQ ID NO: 100, a LCDR2 comprising or consisting of SEQ ID NO: 129, and a LCDR3 comprising or consisting of SEQ ID NO: 153;

(6) the immunoglobulin heavy chain polypeptide comprises a HCDR1 comprising or consisting of SEQ ID NO: 6, a HCDR2 comprising or consisting of SEQ ID NO: 29, and a HCDR3 comprising or consisting of SEQ ID NO: 63; and/or the immunoglobulin light chain polypeptide comprises a LCDR1 comprising or consisting of SEQ ID NO: 101, a LCDR2 comprising or consisting of SEQ ID NO: 131, and a LCDR3 comprising or consisting of SEQ ID NO: 156;

(7) the immunoglobulin heavy chain polypeptide comprises a HCDR1 comprising or consisting of SEQ ID NO: 7, a HCDR2 comprising or consisting of SEQ ID NO: 30, and a HCDR3 comprising or consisting of SEQ ID NO: 64; and/or the immunoglobulin light chain polypeptide comprises a LCDR1 comprising or consisting of SEQ ID NO: 102, a LCDR2 comprising or consisting of SEQ ID NO: 132, and a LCDR3 comprising or consisting of SEQ ID NO: 157;

(8) the immunoglobulin heavy chain polypeptide comprises a HCDR1 comprising or consisting of SEQ ID NO: 2, a HCDR2 comprising or consisting of SEQ ID NO: 31, and a HCDR3 comprising or consisting of SEQ ID NO: 65; and/or the immunoglobulin light chain polypeptide comprises a LCDR1 comprising or consisting of SEQ ID NO: 103, a LCDR2 comprising or consisting of SEQ ID NO: 133, and a LCDR3 comprising or consisting of SEQ ID NO: 155;

(9) the immunoglobulin heavy chain polypeptide comprises a HCDR1 comprising or consisting of SEQ ID NO: 8, a HCDR2 comprising or consisting of SEQ ID NO: 32, and a HCDR3 comprising or consisting of SEQ ID NO: 66; and/or the immunoglobulin light chain polypeptide comprises a LCDR1 comprising or consisting of SEQ ID NO: 104, a LCDR2 comprising or consisting of SEQ ID NO: 134, and a LCDR3 comprising or consisting of SEQ ID NO: 158;

(10) the immunoglobulin heavy chain polypeptide comprises a HCDR1 comprising or consisting of SEQ ID NO: 9, a HCDR2 comprising or consisting of SEQ ID NO: 33, and a HCDR3 comprising or consisting of SEQ ID NO: 67; and/or the immunoglobulin light chain polypeptide comprises a LCDR1 comprising or consisting of SEQ ID NO: 97, a LCDR2 comprising or consisting of SEQ ID NO: 135, and a LCDR3 comprising or consisting of SEQ ID NO: 159;

(11) the immunoglobulin heavy chain polypeptide comprises a HCDR1 comprising or consisting of SEQ ID NO: 7, a HCDR2 comprising or consisting of SEQ ID NO: 34, and a HCDR3 comprising or consisting of SEQ ID NO: 64; and/or the immunoglobulin light chain polypeptide comprises a LCDR1 comprising or consisting of SEQ ID NO: 102, a LCDR2 comprising or consisting of SEQ ID NO: 132, and a LCDR3 comprising or consisting of SEQ ID NO: 160;

(12) the immunoglobulin heavy chain polypeptide comprises a HCDR1 comprising or consisting of SEQ ID NO: 10, a HCDR2 comprising or consisting of SEQ ID NO: 35, and a HCDR3 comprising or consisting of SEQ ID NO: 68; and/or the immunoglobulin light chain polypeptide comprises a LCDR1 comprising or consisting of SEQ ID NO: 105, a LCDR2 comprising or consisting of SEQ ID NO: 136, and a LCDR3 comprising or consisting of SEQ ID NO: 161;

(13) the immunoglobulin heavy chain polypeptide comprises a HCDR1 comprising or consisting of SEQ ID NO: 2, a HCDR2 comprising or consisting of SEQ ID NO: 25, and a HCDR3 comprising or consisting of SEQ ID NO: 69; and/or the immunoglobulin light chain polypeptide comprises a LCDR1 comprising or consisting of SEQ ID NO: 106, a LCDR2 comprising or consisting of SEQ ID NO: 129, and a LCDR3 comprising or consisting of SEQ ID NO: 162;

(14) the immunoglobulin heavy chain polypeptide comprises a HCDR1 comprising or consisting of SEQ ID NO: 11, a HCDR2 comprising or consisting of SEQ ID NO: 36, and a HCDR3 comprising or consisting of SEQ ID NO: 70; and/or the immunoglobulin light chain polypeptide comprises a LCDR1 comprising or consisting of SEQ ID NO: 107, a LCDR2 comprising or consisting of SEQ ID NO: 129, and a LCDR3 comprising or consisting of SEQ ID NO: 163;

(15) the immunoglobulin heavy chain polypeptide comprises a HCDR1 comprising or consisting of SEQ ID NO: 12, a HCDR2 comprising or consisting of SEQ ID NO: 37, and a HCDR3 comprising or consisting of SEQ ID NO: 71; and/or the immunoglobulin light chain polypeptide comprises a LCDR1 comprising or consisting of SEQ ID NO: 108, a LCDR2 comprising or consisting of SEQ ID NO: 137, and a LCDR3 comprising or consisting of SEQ ID NO: 164;

(16) the immunoglobulin heavy chain polypeptide comprises a HCDR1 comprising or consisting of SEQ ID NO: 1, a HCDR2 comprising or consisting of SEQ ID NO: 38, and a HCDR3 comprising or consisting of SEQ ID NO: 72; and/or the immunoglobulin light chain polypeptide comprises a LCDR1 comprising or consisting of SEQ ID NO: 109, a LCDR2 comprising or consisting of SEQ ID NO: 138, and a LCDR3 comprising or consisting of SEQ ID NO: 165;

(17) the immunoglobulin heavy chain polypeptide comprises a HCDR1 comprising or consisting of SEQ ID NO: 13, a HCDR2 comprising or consisting of SEQ ID NO: 39, and a HCDR3 comprising or consisting of SEQ ID NO: 73; and/or the immunoglobulin light chain polypeptide comprises a LCDR1 comprising or consisting of SEQ ID NO: 98, a LCDR2 comprising or consisting of SEQ ID NO: 129, and a LCDR3 comprising or consisting of SEQ ID NO: 155;

(18) the immunoglobulin heavy chain polypeptide comprises a HCDR1 comprising or consisting of SEQ ID NO: 2, a HCDR2 comprising or consisting of SEQ ID NO: 40, and a HCDR3 comprising or consisting of SEQ ID NO: 74; and/or the immunoglobulin light chain polypeptide comprises a LCDR1 comprising or consisting of SEQ ID NO: 110, a LCDR2 comprising or consisting of SEQ ID NO: 137, and a LCDR3 comprising or consisting of SEQ ID NO: 166;

(19) the immunoglobulin heavy chain polypeptide comprises a HCDR1 comprising or consisting of SEQ ID NO: 14, a HCDR2 comprising or consisting of SEQ ID NO: 41, and a HCDR3 comprising or consisting of SEQ ID NO: 75; and/or the immunoglobulin light chain polypeptide comprises a LCDR1 comprising or consisting of SEQ ID NO: 111, a LCDR2 comprising or consisting of SEQ ID NO: 129, and a LCDR3 comprising or consisting of SEQ ID NO: 165;

(20) the immunoglobulin heavy chain polypeptide comprises a HCDR1 comprising or consisting of SEQ ID NO: 15, a HCDR2 comprising or consisting of SEQ ID NO: 42, and a HCDR3 comprising or consisting of SEQ ID NO: 74; and/or the immunoglobulin light chain polypeptide comprises a LCDR1 comprising or consisting of SEQ ID NO: 97, a LCDR2 comprising or consisting of SEQ ID NO: 139, and a LCDR3 comprising or consisting of SEQ ID NO: 152;

(21) the immunoglobulin heavy chain polypeptide comprises a HCDR1 comprising or consisting of SEQ ID NO: 14, a HCDR2 comprising or consisting of SEQ ID NO: 43, and a HCDR3 comprising or consisting of SEQ ID NO: 76; and/or the immunoglobulin light chain polypeptide comprises a LCDR1 comprising or consisting of SEQ ID NO: 112, a LCDR2 comprising or consisting of SEQ ID NO: 137, and a LCDR3 comprising or consisting of SEQ ID NO: 155;

(22) the immunoglobulin heavy chain polypeptide comprises a HCDR1 comprising or consisting of SEQ ID NO: 16, a HCDR2 comprising or consisting of SEQ ID NO: 44, and a HCDR3 comprising or consisting of SEQ ID NO: 77; and/or the immunoglobulin light chain polypeptide comprises a LCDR1 comprising or consisting of SEQ ID NO: 113, a LCDR2 comprising or consisting of SEQ ID NO: 140, and a LCDR3 comprising or consisting of SEQ ID NO: 165;

(23) the immunoglobulin heavy chain polypeptide comprises a HCDR1 comprising or consisting of SEQ ID NO: 9, a HCDR2 comprising or consisting of SEQ ID NO: 45, and a HCDR3 comprising or consisting of SEQ ID NO: 78; and/or the immunoglobulin light chain polypeptide comprises a LCDR1 comprising or consisting of SEQ ID NO: 114, a LCDR2 comprising or consisting of SEQ ID NO: 141, and a LCDR3 comprising or consisting of SEQ ID NO: 165;

(24) the immunoglobulin heavy chain polypeptide comprises a HCDR1 comprising or consisting of SEQ ID NO: 17, a HCDR2 comprising or consisting of SEQ ID NO: 46, and a HCDR3 comprising or consisting of SEQ ID NO: 79; and/or the immunoglobulin light chain polypeptide comprises a LCDR1 comprising or consisting of SEQ ID NO: 98, a LCDR2 comprising or consisting of SEQ ID NO: 129, and a LCDR3 comprising or consisting of SEQ ID NO: 155;

(25) the immunoglobulin heavy chain polypeptide comprises a HCDR1 comprising or consisting of SEQ ID NO: 9, a HCDR2 comprising or consisting of SEQ ID NO: 25, and a HCDR3 comprising or consisting of SEQ ID NO: 80; and/or the immunoglobulin light chain polypeptide comprises a LCDR1 comprising or consisting of SEQ ID NO: 115, a LCDR2 comprising or consisting of SEQ ID NO: 142, and a LCDR3 comprising or consisting of SEQ ID NO: 165;

(26) the immunoglobulin heavy chain polypeptide comprises a HCDR1 comprising or consisting of SEQ ID NO: 17, a HCDR2 comprising or consisting of SEQ ID NO: 41, and a HCDR3 comprising or consisting of SEQ ID NO: 81; and/or the immunoglobulin light chain polypeptide comprises a LCDR1 comprising or consisting of SEQ ID NO: 116, a LCDR2 comprising or consisting of SEQ ID NO: 143, and a LCDR3 comprising or consisting of SEQ ID NO: 167;

(27) the immunoglobulin heavy chain polypeptide comprises a HCDR1 comprising or consisting of SEQ ID NO: 7, a HCDR2 comprising or consisting of SEQ ID NO: 47, and a HCDR3 comprising or consisting of SEQ ID NO: 82; and/or the immunoglobulin light chain polypeptide comprises a LCDR1 comprising or consisting of SEQ ID NO: 117, a LCDR2 comprising or consisting of SEQ ID NO: 144, and a LCDR3 comprising or consisting of SEQ ID NO: 155;

(28) the immunoglobulin heavy chain polypeptide comprises a HCDR1 comprising or consisting of SEQ ID NO: 2, a HCDR2 comprising or consisting of SEQ ID NO: 41, and a HCDR3 comprising or consisting of SEQ ID NO: 83; and/or the immunoglobulin light chain polypeptide comprises a LCDR1 comprising or consisting of SEQ ID NO: 118, a LCDR2 comprising or consisting of SEQ ID NO: 131, and a LCDR3 comprising or consisting of SEQ ID NO: 168;

(29) the immunoglobulin heavy chain polypeptide comprises a HCDR1 comprising or consisting of SEQ ID NO: 18, a HCDR2 comprising or consisting of SEQ ID NO: 48, and a HCDR3 comprising or consisting of SEQ ID NO: 84; and/or the immunoglobulin light chain polypeptide comprises a LCDR1 comprising or consisting of SEQ ID NO: 119, a LCDR2 comprising or consisting of SEQ ID NO: 145, and a LCDR3 comprising or consisting of SEQ ID NO: 165;

(30) the immunoglobulin heavy chain polypeptide comprises a HCDR1 comprising or consisting of SEQ ID NO: 19, a HCDR2 comprising or consisting of SEQ ID NO: 49, and a HCDR3 comprising or consisting of SEQ ID NO: 85; and/or the immunoglobulin light chain polypeptide comprises a LCDR1 comprising or consisting of SEQ ID NO: 120, a LCDR2 comprising or consisting of SEQ ID NO: 146, and a LCDR3 comprising or consisting of SEQ ID NO: 155;

(31) the immunoglobulin heavy chain polypeptide comprises a HCDR1 comprising or consisting of SEQ ID NO: 2, a HCDR2 comprising or consisting of SEQ ID NO: 50, and a HCDR3 comprising or consisting of SEQ ID NO: 86; and/or the immunoglobulin light chain polypeptide comprises a LCDR1 comprising or consisting of SEQ ID NO: 121, a LCDR2 comprising or consisting of SEQ ID NO: 147, and a LCDR3 comprising or consisting of SEQ ID NO: 169;

(32) the immunoglobulin heavy chain polypeptide comprises a HCDR1 comprising or consisting of SEQ ID NO: 2, a HCDR2 comprising or consisting of SEQ ID NO: 51, and a HCDR3 comprising or consisting of SEQ ID NO: 87; and/or the immunoglobulin light chain polypeptide comprises a LCDR1 comprising or consisting of SEQ ID NO: 122, a LCDR2 comprising or consisting of SEQ ID NO: 137, and a LCDR3 comprising or consisting of SEQ ID NO: 155;

(33) the immunoglobulin heavy chain polypeptide comprises a HCDR1 comprising or consisting of SEQ ID NO: 20, a HCDR2 comprising or consisting of SEQ ID NO: 44, and a HCDR3 comprising or consisting of SEQ ID NO: 88; and/or the immunoglobulin light chain polypeptide comprises a LCDR1 comprising or consisting of SEQ ID NO: 123, a LCDR2 comprising or consisting of SEQ ID NO: 148, and a LCDR3 comprising or consisting of SEQ ID NO: 170;

(34) the immunoglobulin heavy chain polypeptide comprises a HCDR1 comprising or consisting of SEQ ID NO: 3, a HCDR2 comprising or consisting of SEQ ID NO: 52, and a HCDR3 comprising or consisting of SEQ ID NO: 60; and/or the immunoglobulin light chain polypeptide comprises a LCDR1 comprising or consisting of SEQ ID NO: 98, a LCDR2 comprising or consisting of SEQ ID NO: 129, and a LCDR3 comprising or consisting of SEQ ID NO: 171;

(35) the immunoglobulin heavy chain polypeptide comprises a HCDR1 comprising or consisting of SEQ ID NO: 2, a HCDR2 comprising or consisting of SEQ ID NO: 53, and a HCDR3 comprising or consisting of SEQ ID NO: 89; and/or the immunoglobulin light chain polypeptide comprises a LCDR1 comprising or consisting of SEQ ID NO: 97, a LCDR2 comprising or consisting of SEQ ID NO: 147, and a LCDR3 comprising or consisting of SEQ ID NO: 172;

(36) the immunoglobulin heavy chain polypeptide comprises a HCDR1 comprising or consisting of SEQ ID NO: 21, a HCDR2 comprising or consisting of SEQ ID NO: 38, and a HCDR3 comprising or consisting of SEQ ID NO: 90; and/or the immunoglobulin light chain polypeptide comprises a LCDR1 comprising or consisting of SEQ ID NO: 109, a LCDR2 comprising or consisting of SEQ ID NO: 150, and a LCDR3 comprising or consisting of SEQ ID NO: 165;

(37) the immunoglobulin heavy chain polypeptide comprises a HCDR1 comprising or consisting of SEQ ID NO: 22, a HCDR2 comprising or consisting of SEQ ID NO: 41, and a HCDR3 comprising or consisting of SEQ ID NO: 91; and/or the immunoglobulin light chain polypeptide comprises a LCDR1 comprising or consisting of SEQ ID NO: 124, a LCDR2 comprising or consisting of SEQ ID NO: 151, and a LCDR3 comprising or consisting of SEQ ID NO: 173;

(38) the immunoglobulin heavy chain polypeptide comprises a HCDR1 comprising or consisting of SEQ ID NO: 2, a HCDR2 comprising or consisting of SEQ ID NO: 54, and a HCDR3 comprising or consisting of SEQ ID NO: 92; and/or the immunoglobulin light chain polypeptide comprises a LCDR1 comprising or consisting of SEQ ID NO: 126, a LCDR2 comprising or consisting of SEQ ID NO: 129, and a LCDR3 comprising or consisting of SEQ ID NO: 165;

(39) the immunoglobulin heavy chain polypeptide comprises a HCDR1 comprising or consisting of SEQ ID NO: 2, a HCDR2 comprising or consisting of SEQ ID NO: 55, and a HCDR3 comprising or consisting of SEQ ID NO: 93; and/or the immunoglobulin light chain polypeptide comprises a LCDR1 comprising or consisting of SEQ ID NO: 97, a LCDR2 comprising or consisting of SEQ ID NO: 149, and a LCDR3 comprising or consisting of SEQ ID NO: 174;

(40) the immunoglobulin heavy chain polypeptide comprises a HCDR1 comprising or consisting of SEQ ID NO: 23, a HCDR2 comprising or consisting of SEQ ID NO: 56, and a HCDR3 comprising or consisting of SEQ ID NO: 94; and/or the immunoglobulin light chain polypeptide comprises a LCDR1 comprising or consisting of SEQ ID NO: 125, a LCDR2 comprising or consisting of SEQ ID NO: 142, and a LCDR3 comprising or consisting of SEQ ID NO: 175;

(41) the immunoglobulin heavy chain polypeptide comprises a HCDR1 comprising or consisting of SEQ ID NO: 14, a HCDR2 comprising or consisting of SEQ ID NO: 43, and a HCDR3 comprising or consisting of SEQ ID NO: 76; and/or the immunoglobulin light chain polypeptide comprises a LCDR1 comprising or consisting of SEQ ID NO: 127, a LCDR2 comprising or consisting of SEQ ID NO: 137, and a LCDR3 comprising or consisting of SEQ ID NO: 176;

(42) the immunoglobulin heavy chain polypeptide comprises a HCDR1 comprising or consisting of SEQ ID NO: 3, a HCDR2 comprising or consisting of SEQ ID NO: 57, and a HCDR3 comprising or consisting of SEQ ID NO: 95; and/or the immunoglobulin light chain polypeptide comprises a LCDR1 comprising or consisting of SEQ ID NO: 128, a LCDR2 comprising or consisting of SEQ ID NO: 137, and a LCDR3 comprising or consisting of SEQ ID NO: 155; and/or

(43) the immunoglobulin heavy chain polypeptide and light chain polypeptide comprises any combination of the CDRs listed in FIGS. 1A-D of PD-L1 Type A binding agents 1-42

In particular embodiments, the binding agent comprises an immunoglobulin heavy chain polypeptide and an immunoglobulin light chain polypeptide, wherein the immunoglobulin heavy chain polypeptide comprises a first framework region, a second framework region, a third framework region, and/or a fourth framework region; and/or the immunoglobulin light chain polypeptide comprises a first framework region, a second framework region, a third framework region, and/or a fourth framework region; and/or the immunoglobulin heavy chain polypeptide and light chain polypeptide comprises any combination of the framework regions listed in FIGS. 2A-D and FIGS. 3A-D, respectively.

PD-L1-Binding Agents—Type B

Provided herein are PD-L1 binding agents (Type B) comprising an immunoglobulin heavy chain variable region polypeptide and an immunoglobulin light chain variable region polypeptide. In some embodiments, the PD-L1 binding agents (Type B) comprise an immunoglobulin heavy chain variable region of any one of SEQ ID NOs: 430-450, or at least the CDRs thereof, and an immunoglobulin light chain variable region of any one of SEQ ID NOs: 451-471, or at least the CDRs thereof. In other embodiments, the PD-L1 binding agents comprise an immunoglobulin heavy chain variable region polypeptide with an amino acid sequence that is at least 90% identical to any one of SEQ ID NOs: 430-450, and an immunoglobulin light chain variable region polypeptide with an amino acid sequence that is at least 90% identical to any one of SEQ ID NOs: 451-471. In yet other embodiments, the PD-L1 binding agent, the immunoglobulin heavy chain variable region polypeptide comprises a complementarity determining region 1 (HCDR1)

comprising any one of SEQ ID NOs: 308-321, a complementarity determining region 2 (HCDR2) comprising any one of SEQ ID NOs: 322-338, and a complementarity determining region 3 (HCDR3) comprising any one of SEQ ID NOs: 339-359; and/or the immunoglobulin light chain variable region polypeptide comprises a complementarity determining region 1 (LCDR1) comprising any one of SEQ ID NOs: 360-374, a complementarity determining region 2 (LCDR2) comprising any one of SEQ ID NOs: 131 and 375-386, and a complementarity determining region 3 (LCDR3) comprising any one of SEQ ID NOs: 387-398. Also provided are nucleic acids encoding the PD-L1 binding agents, or the individual heavy and light chains thereof; vectors and cells comprising the nucleic acids; and compositions comprising the binding agents or nucleic acids.

In an embodiment, the PD-L1 binding agent (Type B) comprises an immunoglobulin heavy chain variable region of any one of SEQ ID NOs: 430-450, a sequence that is at least about 90%, at least about 91%, at least about 92%, at least about 93%, at least about 94%, at least about 95%, at least about 96%, at least about 97%, at least about 98%, or at least about 99% identical to SEQ ID NOs: 430-450, or at least the CDRs thereof; and/or an immunoglobulin light chain variable region of any one of SEQ ID NOs: 451-471, a sequence that is at least about 90%, at least about 91%, at least about 92%, at least about 93%, at least about 94%, at least about 95%, at least about 96%, at least about 97%, at least about 98%, or at least about 99% identical to SEQ ID NOs: 451-471, or at least the CDRs thereof.

By way of further illustration, the PD-L1 binding agent (Type B) can comprise;

(1) an immunoglobulin heavy chain variable region of SEQ ID NO: 429, or at least the CDRs thereof, and/or an immunoglobulin light chain variable region of SEQ ID NO: 450, or at least the CDRs thereof;

(2) an immunoglobulin heavy chain variable region of SEQ ID NO: 430, or at least the CDRs thereof, and/or an immunoglobulin light chain variable region of SEQ ID NO: 451, or at least the CDRs thereof;

(3) an immunoglobulin heavy chain variable region of SEQ ID NO: 431, or at least the CDRs thereof, and/or an immunoglobulin light chain variable region of SEQ ID NO: 452, or at least the CDRs thereof;

(4) an immunoglobulin heavy chain variable region of SEQ ID NO: 432, or at least the CDRs thereof, and/or an immunoglobulin light chain variable region of SEQ ID NO: 453, or at least the CDRs thereof;

(5) an immunoglobulin heavy chain variable region of SEQ ID NO: 433, or at least the CDRs thereof, and/or an immunoglobulin light chain variable region of SEQ ID NO: 454, or at least the CDRs thereof;

(6) an immunoglobulin heavy chain variable region of SEQ ID NO: 434, or at least the CDRs thereof, and/or an immunoglobulin light chain variable region of SEQ ID NO: 455, or at least the CDRs thereof;

(7) an immunoglobulin heavy chain variable region of SEQ ID NO: 435, or at least the CDRs thereof, and/or an immunoglobulin light chain variable region of SEQ ID NO: 456, or at least the CDRs thereof;

(8) an immunoglobulin heavy chain variable region of SEQ ID NO: 436, or at least the CDRs thereof, and/or an immunoglobulin light chain variable region of SEQ ID NO: 457, or at least the CDRs thereof;

(9) an immunoglobulin heavy chain variable region of SEQ ID NO: 437, or at least the CDRs thereof, and/or an immunoglobulin light chain variable region of SEQ ID NO: 458, or at least the CDRs thereof;

(10) an immunoglobulin heavy chain variable region of SEQ ID NO: 438, or at least the CDRs thereof, and/or an immunoglobulin light chain variable region of SEQ ID NO: 459, or at least the CDRs thereof;

(11) an immunoglobulin heavy chain variable region of SEQ ID NO: 439, or at least the CDRs thereof, and/or an immunoglobulin light chain variable region of SEQ ID NO: 460, or at least the CDRs thereof;

(12) an immunoglobulin heavy chain variable region of SEQ ID NO: 440, or at least the CDRs thereof, and/or an immunoglobulin light chain variable region of SEQ ID NO: 461, or at least the CDRs thereof;

(13) an immunoglobulin heavy chain variable region of SEQ ID NO: 441, or at least the CDRs thereof, and/or an immunoglobulin light chain variable region of SEQ ID NO: 462, or at least the CDRs thereof;

(14) an immunoglobulin heavy chain variable region of SEQ ID NO: 442, or at least the CDRs thereof, and/or an immunoglobulin light chain variable region of SEQ ID NO: 463, or at least the CDRs thereof;

(15) an immunoglobulin heavy chain variable region of SEQ ID NO: 443, or at least the CDRs thereof, and/or an immunoglobulin light chain variable region of SEQ ID NO: 464, or at least the CDRs thereof;

(16) an immunoglobulin heavy chain variable region of SEQ ID NO: 444, or at least the CDRs thereof, and/or an immunoglobulin light chain variable region of SEQ ID NO: 465, or at least the CDRs thereof;

(17) an immunoglobulin heavy chain variable region of SEQ ID NO: 445, or at least the CDRs thereof, and/or an immunoglobulin light chain variable region of SEQ ID NO: 466, or at least the CDRs thereof;

(18) an immunoglobulin heavy chain variable region of SEQ ID NO: 446, or at least the CDRs thereof, and/or an immunoglobulin light chain variable region of SEQ ID NO: 467, or at least the CDRs thereof,

(19) an immunoglobulin heavy chain variable region of SEQ ID NO: 447, or at least the CDRs thereof, and/or an immunoglobulin light chain variable region of SEQ ID NO: 468, or at least the CDRs thereof;

(20) an immunoglobulin heavy chain variable region of SEQ ID NO: 448, or at least the CDRs thereof, and/or an immunoglobulin light chain variable region of SEQ ID NO: 469, or at least the CDRs thereof, and/or

(21) an immunoglobulin heavy chain variable region of SEQ ID NO: 449, or at least the CDRs thereof, and/or an immunoglobulin light chain variable region of SEQ ID NO: 470, or at least the CDRs thereof; and/or

(22) an immunoglobulin heavy chain variable region of FIGS. 8A-B and/or an immunoglobulin light chain variable region of FIGS. 8C-D, or at least the CDRs thereof.

The CDRs of a given heavy or light chain Ig sequence can be determined in accordance with any of the various known Ig numbering schemes (e.g., Kabat, Chothia, Martin (Enhanced Chothia), IGMT, AbM). In certain embodiments, the PD-L1 binding agent comprises one or more of the following CDRs:

a HCDR1 comprising or consisting of any one of SEQ ID NOs: 308-321 or a sequence that is at least about 90%, at least about 91%, at least about 92%, at least about 93%, at least about 94%, at least about 95%, at least about 96%, at least about 97%, at least about 98%, or at least about 99% identical to SEQ ID NOs: 308-321;

a HCDR2 comprising or consisting of any one of SEQ ID NOs: 322-338 or a sequence that is at least about 90%, at least about 91%, at least about 92%, at least about 93%, at least about 94%, at least about 95%, at least about 96%, at least about 97%, at least about 98%, or at least about 99% identical to SEQ ID NOs: 322-338; and a HCDR3 comprising or consisting of any one of SEQ ID NOs: 339-359 or a sequence that is at least about 90%, at least about 91%, at least about 92%, at least about 93%, at least about 94%, at least about 95%, at least about 96%, at least about 97%, at least about 98%, or at least about 99% identical to SEQ ID NOs: 339-359; and/or the immunoglobulin light chain polypeptide comprises a LCDR1 comprising or consisting of any one of SEQ ID NOs: 360-374 or a sequence that is at least about 90%, at least about 91%, at least about 92%, at least about 93%, at least about 94%, at least about 95%, at least about 96%, at least about 97%, at least about 98%, or at least about 99% identical to SEQ ID NOs: 360-374;

a LCDR2 comprising or consisting of any one of SEQ ID NOs: 375-386 or a sequence that is at least about 90%, at least about 91%, at least about 92%, at least about 93%, at least about 94%, at least about 95%, at least about 96%, at least about 97%, at least about 98%, or at least about 99% identical to SEQ ID NOs: 375-386; and a LCDR3 comprising or consisting of any one of SEQ ID NOs: 387-398 or a sequence that is at least about 90%, at least about 91%, at least about 92%, at least about 93%, at least about 94%, at least about 95%, at least about 96%, at least about 97%, at least about 98%, or at least about 99% identical to SEQ ID NOs: 387-398.

In particular embodiments, the binding agent comprises an immunoglobulin heavy chain polypeptide and an immunoglobulin light chain polypeptide, wherein;

(1) the immunoglobulin heavy chain polypeptide comprises a HCDR1 comprising or consisting of SEQ ID NO: 308, a HCDR2 comprising or consisting of SEQ ID NO: 322, and a HCDR3 comprising or consisting of SEQ ID NO: 339; and/or the immunoglobulin light chain polypeptide comprises a LCDR1 comprising or consisting of SEQ ID NO: 360, a LCDR2 comprising or consisting of SEQ ID NO: 375, and a LCDR3 comprising or consisting of SEQ ID NO: 387;

(2) the immunoglobulin heavy chain polypeptide comprises a HCDR1 comprising or consisting of SEQ ID NO: 309, a HCDR2 comprising or consisting of SEQ ID NO: 323, and a HCDR3 comprising or consisting of SEQ ID NO: 340; and/or the immunoglobulin light chain polypeptide comprises a LCDR1 comprising or consisting of SEQ ID NO: 361, a LCDR2 comprising or consisting of SEQ ID NO: 376, and a LCDR3 comprising or consisting of SEQ ID NO: 388;

(3) the immunoglobulin heavy chain polypeptide comprises a HCDR1 comprising or consisting of SEQ ID NO: 310, a HCDR2 comprising or consisting of SEQ ID NO: 324, and a HCDR3 comprising or consisting of SEQ ID NO: 341; and/or the immunoglobulin light chain polypeptide comprises a LCDR1 comprising or consisting of SEQ ID NO: 360, a LCDR2 comprising or consisting of SEQ ID NO: 375, and a LCDR3 comprising or consisting of SEQ ID NO: 387;

(4) the immunoglobulin heavy chain polypeptide comprises a HCDR1 comprising or consisting of SEQ ID NO: 311, a HCDR2 comprising or consisting of SEQ ID NO: 325, and a HCDR3 comprising or consisting of SEQ ID NO: 342; and/or the immunoglobulin light chain polypeptide comprises a LCDR1 comprising or consisting of SEQ ID NO: 362, a LCDR2 comprising or consisting of SEQ ID NO: 377, and a LCDR3 comprising or consisting of SEQ ID NO: 389;

(5) the immunoglobulin heavy chain poly peptide comprises a HCDR1 comprising or consisting of SEQ ID NO: 312, a HCDR2 comprising or consisting of SEQ ID NO: 326, and a HCDR3 comprising or consisting of SEQ ID NO: 343; and/or the immunoglobulin light chain polypeptide comprises a LCDR1 comprising or consisting of SEQ ID NO: 360, a LCDR2 comprising or consisting of SEQ ID NO: 378, and a LCDR3 comprising or consisting of SEQ ID NO: 387;

(6) the immunoglobulin heavy chain polypeptide comprises a HCDR1 comprising or consisting of SEQ ID NO: 313, a HCDR2 comprising or consisting of SEQ ID NO: 327, and a HCDR3 comprising or consisting of SEQ ID NO: 344; and/or the immunoglobulin light chain polypeptide comprises a LCDR1 comprising or consisting of SEQ ID NO: 363, a LCDR2 comprising or consisting of SEQ ID NO: 379, and a LCDR3 comprising or consisting of SEQ ID NO: 390;

(7) the immunoglobulin heavy chain polypeptide comprises a HCDR1 comprising or consisting of SEQ ID NO: 314, a HCDR2 comprising or consisting of SEQ ID NO: 327, and a HCDR3 comprising or consisting of SEQ ID NO: 345; and/or the immunoglobulin light chain polypeptide comprises a LCDR1 comprising or consisting of SEQ ID NO: 364, a LCDR2 comprising or consisting of SEQ ID NO: 380, and a LCDR3 comprising or consisting of SEQ ID NO: 391;

(8) the immunoglobulin heavy chain polypeptide comprises a HCDR1 comprising or consisting of SEQ ID NO: 312, a HCDR2 comprising or consisting of SEQ ID NO: 328, and a HCDR3 comprising or consisting of SEQ ID NO: 346; and/or the immunoglobulin light chain polypeptide comprises a LCDR1 comprising or consisting of SEQ ID NO: 365, a LCDR2 comprising or consisting of SEQ ID NO: 375, and a LCDR3 comprising or consisting of SEQ ID NO: 387;

(9) the immunoglobulin heavy chain polypeptide comprises a HCDR1 comprising or consisting of SEQ ID NO: 314, a HCDR2 comprising or consisting of SEQ ID NO: 329, and a HCDR3 comprising or consisting of SEQ ID NO: 347; and/or the immunoglobulin light chain polypeptide comprises a LCDR1 comprising or consisting of SEQ ID NO: 366, a LCDR2 comprising or consisting of SEQ ID NO: 375, and a LCDR3 comprising or consisting of SEQ ID NO: 389;

(10) the immunoglobulin heavy chain polypeptide comprises a HCDR1 comprising or consisting of SEQ ID NO: 309, a HCDR2 comprising or consisting of SEQ ID NO: 330, and a HCDR3 comprising or consisting of SEQ ID NO: 348; and/or the immunoglobulin light chain polypeptide comprises a LCDR1 comprising or consisting of SEQ ID NO: 360, a LCDR2 comprising or consisting of SEQ ID NO: 381, and a LCDR3 comprising or consisting of SEQ ID NO: 392;

(11) the immunoglobulin heavy chain polypeptide comprises a HCDR1 comprising or consisting of SEQ ID NO: 309, a HCDR2 comprising or consisting of SEQ ID NO: 327, and a HCDR3 comprising or consisting of SEQ ID NO: 349; and/or the immunoglobulin light chain polypeptide comprises a LCDR1 comprising or consisting of SEQ ID NO: 367, a LCDR2 comprising or consisting of SEQ ID NO: 382, and a LCDR3 comprising or consisting of SEQ ID NO: 389;

(12) the immunoglobulin heavy chain polypeptide comprises a HCDR1 comprising or consisting of SEQ ID NO: 309, a HCDR2 comprising or consisting of SEQ ID NO: 322, and a HCDR3 comprising or consisting of SEQ ID NO: 350; and/or the immunoglobulin light chain polypeptide comprises a LCDR1 comprising or consisting of SEQ ID NO: 360, a LCDR2 comprising or consisting of SEQ ID NO: 383, and a LCDR3 comprising or consisting of SEQ ID NO: 387;

(13) the immunoglobulin heavy chain polypeptide comprises a HCDR1 comprising or consisting of SEQ ID NO: 315, a HCDR2 comprising or consisting of SEQ ID NO: 323, and a HCDR3 comprising or consisting of SEQ ID NO: 351; and/or the immunoglobulin light chain polypeptide comprises a LCDR1 comprising or consisting of SEQ ID NO: 368, a LCDR2 comprising or consisting of SEQ ID NO: 375, and a LCDR3 comprising or consisting of SEQ ID NO: 393;

(14) the immunoglobulin heavy chain polypeptide comprises a HCDR1 comprising or consisting of SEQ ID NO:316, a HCDR2 comprising or consisting of SEQ ID NO: 331, and a HCDR3 comprising or consisting of SEQ ID NO: 352; and/or the immunoglobulin light chain polypeptide comprises a LCDR1 comprising or consisting of SEQ ID NO: 365, a LCDR2 comprising or consisting of SEQ ID NO: 375, and a LCDR3 comprising or consisting of SEQ ID NO: 389;

(15) the immunoglobulin heavy chain polypeptide comprises a HCDR1 comprising or consisting of SEQ ID NO: 317, a HCDR2 comprising or consisting of SEQ ID NO: 332, and a HCDR3 comprising or consisting of SEQ ID NO: 353; and/or the immunoglobulin light chain polypeptide comprises a LCDR1 comprising or consisting of SEQ ID NO: 369, a LCDR2 comprising or consisting of SEQ ID NO: 384, and a LCDR3 comprising or consisting of SEQ ID NO: 394;

(16) the immunoglobulin heavy chain polypeptide comprises a HCDR1 comprising or consisting of SEQ ID NO: 318, a HCDR2 comprising or consisting of SEQ ID NO: 333, and a HCDR3 comprising or consisting of SEQ ID NO: 354; and/or the immunoglobulin light chain polypeptide comprises a LCDR1 comprising or consisting of SEQ ID NO: 370, a LCDR2 comprising or consisting of SEQ ID NO: 379, and a LCDR3 comprising or consisting of SEQ ID NO: 395;

(17) the immunoglobulin heavy chain polypeptide comprises a HCDR1 comprising or consisting of SEQ ID NO:310, a HCDR2 comprising or consisting of SEQ ID NO: 334, and a HCDR3 comprising or consisting of SEQ ID NO: 355; and/or the immunoglobulin light chain polypeptide comprises a LCDR1 comprising or consisting of SEQ ID NO: 371, a LCDR2 comprising or consisting of SEQ ID NO: 375, and a LCDR3 comprising or consisting of SEQ ID NO: 387;

(18) the immunoglobulin heavy chain polypeptide comprises a HCDR1 comprising or consisting of SEQ ID NO:310, a HCDR2 comprising or consisting of SEQ ID NO: 335, and a HCDR3 comprising or consisting of SEQ ID NO: 356; and/or the immunoglobulin light chain polypeptide comprises a LCDR1 comprising or consisting of SEQ ID NO: 360, a LCDR2 comprising or consisting of SEQ ID NO: 385, and a LCDR3 comprising or consisting of SEQ ID NO: 396;

(19) the immunoglobulin heavy chain polypeptide comprises a HCDR1 comprising or consisting of SEQ ID NO: 319, a HCDR2 comprising or consisting of SEQ ID NO: 336, and a HCDR3 comprising or consisting of SEQ ID NO: 357; and/or the immunoglobulin light chain polypeptide comprises a LCDR1 comprising or consisting of SEQ ID NO: 372, a LCDR2 comprising or consisting of SEQ ID NO: 386, and a LCDR3 comprising or consisting of SEQ ID NO: 397;

(20) the immunoglobulin heavy chain polypeptide comprises a HCDR1 comprising or consisting of SEQ ID NO: 320, a HCDR2 comprising or consisting of SEQ ID NO: 337, and a HCDR3 comprising or consisting of SEQ ID NO: 358; and/or the immunoglobulin light chain polypeptide comprises a LCDR1 comprising or consisting of SEQ ID NO: 373, a LCDR2 comprising or consisting of SEQ ID NO: 379, and a LCDR3 comprising or consisting of SEQ ID NO: 398;

(21) the immunoglobulin heavy chain polypeptide comprises a HCDR1 comprising or consisting of SEQ ID NO: 321, a HCDR2 comprising or consisting of SEQ ID NO: 338, and a HCDR3 comprising or consisting of SEQ ID NO: 359; and/or the immunoglobulin light chain polypeptide comprises a LCDR1 comprising or consisting of SEQ ID NO: 374, a LCDR2 comprising or consisting of SEQ ID NO: 379, and a LCDR3 comprising or consisting of SEQ ID NO: 389; and/or

(22) the immunoglobulin heavy chain polypeptide and light chain polypeptide comprises any combination of the CDRs listed in FIGS. 5A-B (Type B).

In particular embodiments, the binding agent comprises an immunoglobulin heavy chain polypeptide and an immunoglobulin light chain polypeptide, wherein the immunoglobulin heavy chain polypeptide comprises a first framework region, a second framework region, a third framework region, and/or a fourth framework region; and/or the immunoglobulin light chain polypeptide comprises a first framework region, a second framework region, a third framework region, and/or a fourth framework region; and/or the immunoglobulin heavy chain polypeptide and light chain polypeptide comprises any combination of the framework regions listed in FIGS. 6A-B and/or FIGS. 7A-B (Type B), respectively.

In an exemplary embodiment, the immunoconjugates of the invention comprise an antibody construct that comprises an antigen binding domain that specifically recognizes and binds HER2.

In certain embodiments, immunoconjugates of the invention comprise anti-HER2 antibodies. In one embodiment of the invention, an anti-HER2 antibody of an immunoconjugate of the invention comprises a humanized anti-HER2 antibody, e.g., huMAb4D5-1, huMAb4D5-2, huMAb4D5-3, huMAb4D5-4, huMAb4D5-5, huMAb4D5-6, huMAb4D5-7 and huMAb4D5-8, as described in Table 3 of U.S. Pat. No. 5,821,337, which is specifically incorporated by reference herein. Those antibodies contain human framework regions with the complementarity-determining regions of a murine antibody (4D5) that binds to HER2. The humanized antibody huMAb4D5-8 is also referred to as trastuzumab, commercially available under the tradename HERCEPTIN™ (Genentech, Inc.).

Trastuzumab (CAS 180288-69-1, HERCEPTIN®, huMAb4D5-8, rhuMAb HER2, Genentech) is a recombinant DNA-derived, IgG1 kappa, monoclonal antibody that is a humanized version of a murine anti-HER2 antibody (4D5) that selectively binds with high affinity in a cell-based assay (Kd=5 nM) to the extracellular domain of HER2 (U.S. Pat. Nos. 5,677,171; 5,821,337; 6,054,297; 6,165,464; 6,339,142; 6,407,213; 6,639,055; 6,719,971; 6,800,738; 7,074, 404; Coussens et al (1985) *Science* 230:1132-9; Slamon et al (1989) *Science* 244:707-12: Slamon et al (2001) *New Engl. J Med.* 344:783-792).

In an embodiment of the invention, the antibody construct or antigen binding domain comprises the CDR regions of trastuzumab. In an embodiment of the invention, the anti-HER2 antibody further comprises the framework regions of the trastuzumab. In an embodiment of the invention, the anti-HER2 antibody further comprises one or both variable regions of trastuzumab.

In another embodiment of the invention, an anti-HER2 antibody of an immunoconjugate of the invention comprises a humanized anti-HER2 antibody. e.g., humanized 2C4, as described in U.S. Pat. No. 7,862,817. An exemplary humanized 2C4 antibody is pertuzumab (CAS Reg. No. 380610-27-5). PERJETA™ (Genentech, Inc.). Pertuzumab is a HER dimerization inhibitor (HDI) and functions to inhibit the ability of HER2 to form active heterodimers or homodimers with other HER receptors (such as EGFR/HER1, HER2, HER3 and HER4). See, for example, Harari and Yarden, Oncogene 19:6102-14 (2000); Yarden and Sliwkowski. *Nat Rev Mol Cell Biol* 2:127-37 (2001); Sliwkowski *Nat Struct Biol* 10:158-9 (2003); Cho et al. *Nature* 421:756-60 (2003); and Malik et al. *Pro Am Soc Cancer Res* 44:176-7 (2003). PERJETA™ is approved for the treatment of breast cancer.

In an embodiment of the invention, the antibody construct or antigen binding domain comprises the CDR regions of pertuzumab. In an embodiment of the invention, the anti-HER2 antibody further comprises the framework regions of the pertuzumab. In an embodiment of the invention, the anti-HER2 antibody further comprises one or both variable regions of pertuzumab.

In an exemplary embodiment, the immunoconjugates of the invention comprise an antibody construct that comprises an antigen binding domain that specifically recognizes and binds CEA. Carcinoembryonic antigen-related cell adhesion molecule 5 (CEACAM5) also known as CD66e (Cluster of Differentiation 66e), is a member of the carcinoembryonic antigen (CEA) gene family.

In an exemplary embodiment, the immunoconjugates of the invention comprise an antibody construct that comprises an antigen binding domain that specifically recognizes and binds Caprin-1 (Ellis J A, Luzio J P (1995)*J Biol Chem.* 270(35):20717-23; Wang B, et al (2005) *J Immunol.* 175 (7):4274-82; Solomon S, et al (2007)*Mol Cell Biol.* 27(6): 2324-42). Caprin-1 is also known as GPIAP1, GPIP137, GRIP137, M11S1, RNG105, p137GPI, and cell cycle associated protein 1.

Cytoplasmic activation/proliferation-associated protein-1 (caprin-1) is an RNA-binding protein that participates in the regulation of cell cycle control-associated genes. Caprin-1 selectively binds to c-Myc and cyclin D2 mRNAs, which accelerates cell progression through the $G_1$ phase into the S phase, enhances cell viability and promotes cell growth, indicating that it may serve an important role in tumorigenesis (Wang B, et al (2005) *J Immunol.* 175:4274-4282). Caprin-1 acts alone or in combination with other RNA-binding proteins, such as RasGAP SH3-domain-binding protein 1 and fragile X mental retardation protein. In the tumorigenesis process, caprin-1 primarily functions by activating cell proliferation and upregulating the expression of immune checkpoint proteins. Through the formation of stress granules. Caprin-1 is also involved in the process by which tumor cells adapt to adverse conditions, which contributes to radiation and chemotherapy resistance. Given its role in various clinical malignancies, caprin-1 holds the potential to be used as a biomarker and a target for the development of novel therapeutics (Yang, Z—S, et al (2019) *Oncology Letters* 18:15-21).

Antibodies that target caprin-1 for treatment and detection have been described (WO 2011/096519; WO 2013/125654: WO 2013/125636; WO 2013/125640; WO 2013/125630; WO 2013/018889; WO 2013/018891: WO 2013/018883; WO 2013/018892; WO 2014/014082; WO 2014/014086; WO 2015/020212: WO 2018/079740).

In an exemplary embodiment, the immunoconjugates of the invention comprise an antibody construct that comprises an antigen binding domain that specifically recognizes and binds CEA.

Elevated expression of carcinoembryonic antigen (CEA, CD66e, CEACAM5) has been implicated in various biological aspects of neoplasia, especially tumor cell adhesion, metastasis, the blocking of cellular immune mechanisms, and having antiapoptosis functions. CEA is also used as a blood marker for many carcinomas. Labetuzumab (CEA-CIDE™, Immunomedics, CAS Reg. No. 219(49-07-7), also known as MN-14 and hMN14, is a humanized IgG1 monoclonal antibody and has been studied for the treatment of colorectal cancer (Blumenthal, R. et al (2005) Cancer Immunology Immunotherapy 54(4):315-327). Labetuzumab conjugated to a camptothecin analog (labetuzumab govitecan, IMMU-130) targets carcinoembryonic antigen-related cell adhesion mol. 5 (CEACAM5) and is being studied in patients with relapsed or refractory metastatic colorectal cancer (Sharkey. R. et al, (2018), Molecular Cancer Therapeutics 17(1):196-203; Cardillo, T. et al (2018) Molecular Cancer Therapeutics 17(1):150-160).

In an embodiment of the invention, the CEA-targeting antibody construct or antigen binding domain comprises the Variable light chain (VL kappa) of hMN-14/labetuzumab SEQ ID NO. 472 (U.S. Pat. No. 6,676,924).

SEQ ID NO. 472

```
DIQLTQSPSSLSASVGDRVTITCKASQDVGTSVAWYQQKPGKAPKLLIYW

TSTRHTGVPSRFSGSGSGTDFTFTISSLQPEDIATYYCQQYSLYRSFGQG

TKVEIK
```

In an embodiment of the invention, the CEA-targeting antibody construct or antigen binding domain comprises the light chain CDR (complementarity determining region) or light chain framework (LFR) sequences of hMN-14/labetuzumab SEQ ID NO. 473-479 (U.S. Pat. No. 6,676,924).

| Region | Sequence Fmgment | Residues | Length | SEQ ID NO. |
|---|---|---|---|---|
| LFR1 | DIQLTQSPSSLSASVGDRVTITC | 1-23 | 23 | 473 |
| CDR-L1 | KASQDVGTSVA | 24-34 | 11 | 474 |
| LFR2 | WYQQKPGKAPKLLIY | 35-49 | 15 | 475 |
| CDR-L2 | WTSTRHT | 50-56 | 7 | 476 |

-continued

| Region | Sequence Fmgment | Residues | Length | SEQ ID NO. |
|---|---|---|---|---|
| LFR3 | GVPSRFSGSGSGTDFTFTISSLQPEDIATYYC | 57-88 | 32 | 477 |
| CDR-L3 | QQYSLYRS | 89-96 | 8 | 478 |
| LFR4 | FGQGTKVEIK | 97-106 | 10 | 479 |

In an embodiment of the invention, the CEA-targeting antibody construct or antigen binding domain comprises the Variable heavy chain (VH) of hMN-14/labetuzumab SEQ ID NO. 480 (U.S. Pat. No. 6,676,924).

SEQ ID NO. 480
EVQLVESGGGVVQPGRSLRLSCSSSGFDFTTYWMSWVRQAPGKGLEWVA

EIHPDSSTINYAPSLKDRFTISRDNSKNTLFLQMDSLRPEDTGVYFCAS

LYFGFPWFAYWGQGTPVTVSS

In an embodiment of the invention, the CEA-targeting antibody construct or antigen binding domain comprises the heavy chain CDR (complementarity determining region) or heavy chain framework (HFR) sequences of hMN-14/labetuzumab SEQ ID NO. 481-487 (U.S. Pat. No. 6,676,924).

| Region | Sequence Fragment | Residues | Length | SEQ ID NO. |
|---|---|---|---|---|
| HFR1 | EVQLVESGGGVVQPGRSLRLSCSSSGFDFT | 1-30 | 30 | 481 |
| CDR-H1 | TYWMS | 31-35 | 5 | 482 |
| HFR2 | WVRQAPGKGLEWVA | 36-49 | 14 | 483 |
| CDR-H2 | EIHPDSSTINYAPSLKD | 50-66 | 17 | 484 |
| HFR3 | RFTISRDNSKNTLFLQMDSLRPEDTGVYFCAS | 67-98 | 32 | 485 |
| CDR-H3 | LYFGFPWFAY | 99-108 | 10 | 486 |
| HFR4 | WGQGTPVTVSS | 109-119 | 11 | 487 |

In an embodiment of the invention, the CEA-targeting antibody construct or antigen binding domain comprises the Variable light chain (VL kappa) of hPR1A3 SEQ ID NO. 488 (U.S. Pat. No. 8,642,742).

SEQ ID NO. 488
DIQMTQSPSSLSASVGDRVTITCKASAAVGTYVAWYQQKPGKAPKLLIY

SASYRKRGVPSRFSGSGSGTDFTLTISSLQPEDFATYYCHQYYTYPLFT

FGQGTKLEIK

In an embodiment of the invention, the CEA-targeting antibody construct or antigen binding domain comprises the light chain CDR (complementarity determining region) or light chain framework (LFR) sequences of hPR1A3 SEQ ID NO. 489-495 (U.S. Pat. No. 8,642,742).

| Region | Sequence Fragment | Residues | Length | SEQ ID NO. |
|---|---|---|---|---|
| LFR1 | DIQMTQSPSSLSASVGDRVTITC | 1-23 | 23 | 489 |
| CDR-L1 | KASAAVGTYVA | 24-34 | 11 | 490 |
| LFR2 | WYQQKPGKAPKLLIY | 35-49 | 15 | 491 |
| CDR-L2 | SASYRKR | 50-56 | 7 | 492 |
| LFR3 | GVPSRFSGSGSGTDFTLTISSLQPEDFATYYC | 57-88 | 32 | 493 |
| CDR-L3 | HQYYTYPLFT | 89-98 | 10 | 494 |
| LFR4 | FGQGTKLEIK | 99-108 | 10 | 495 |

In an embodiment of the invention, the CEA-targeting antibody construct or antigen binding domain comprises the heavy chain CDR (complementarity determining region) or heavy chain framework (HFR) sequences of hPR1A3 SEQ ID NO. 496-502 (U.S. Pat. No. 8,642,742).

| Region | Sequence Fragment | Residues | Length | SEQ ID NO. |
|---|---|---|---|---|
| HFR1 | QVQLVQSGAEVKKPGASVKVSCKASGYTFT | 1-30 | 30 | 496 |
| CDR-H1 | EFGMN | 31-35 | 5 | 497 |
| HFR2 | WVRQAPGQGLEWMG | 36-49 | 14 | 498 |
| CDR-H2 | WINTKTGEATYVEEFKG | 50-66 | 17 | 499 |
| HFR3 | RVTFTTDTSTSTAYMELRSLRSDDTAVYYCAR | 67-98 | 32 | 500 |
| CDR-H3 | WDFAYYVEAMDY | 99-110 | 12 | 501 |
| HFR4 | WGQGTTVTVSS | 111-121 | 11 | 502 |

In an embodiment of the invention, the CEA-targeting antibody construct or antigen binding domain comprises the Variable light chain (VL kappa) of hMFE-23 SEQ ID NO. 503 (U.S. Pat. No. 723,288).

SEQ ID NO. 503

ENVLTQSPSSMSASVGDRVNIACSASSSVSYMHWFQQKPGKSPKLWIYST

SNLASGVPSRFSGSGSGTDYSLTISSMQPEDAATYYCQQRSSYPLTFGGG

TKLEIK

In an embodiment of the invention, the CEA-targeting antibody construct or antigen binding domain comprises the light chain CDR (complementarity determining region) or light chain framework (LFR) sequences of hMFE-23 SEQ ID NO. 504-510 (U.S. Pat. No. 723,288).

| Region | Sequence Fragment | Residues | Length | SEQ ID NO. |
|---|---|---|---|---|
| LFR1 | ENVLTQSPSSMSASVGDRVNIAC | 1-23 | 23 | 504 |
| CDR-L1 | SASSSVSYMH | 24-33 | 10 | 505 |
| LFR2 | WFQQKPGKSPKLWIY | 34-48 | 15 | 506 |
| CDR-L2 | STSNLAS | 49-55 | 7 | 507 |
| LFR3 | GVPSRFSGSGSGTDYSLTISSMQPEDAATYYC | 56-87 | 32 | 508 |

-continued

| Region | Sequence Fragment | Residues | Length | SEQ ID NO. |
|---|---|---|---|---|
| CDR-L3 | QQRSSYPLT | 88-96 | 9 | 509 |
| LFR4 | FGGGTKLEIK | 97-106 | 10 | 510 |

In an embodiment of the invention, the CEA-targeting antibody construct or antigen binding domain comprises the Variable heavy chain ($V_H$) of hMFE-23 SEQ ID NO. 511 (U.S. Pat. No. 723,288).

SEQ ID NO. 511
QVKLEQSGAEVVKPGASVKLSCKASGFNIKDSYMHWLRQGPGQRLEWIGW

IDPENGDTEYAPKFQGKATFTTDTSANTAYLGLSSLRPEDTAVYYCNEGT

PTGPYYFDYWGQGTLVTVSS

In an embodiment of the invention, the CEA-targeting antibody construct or antigen binding domain comprises the heavy chain CDR (complementarity determining region) or heavy chain framework (HFR) sequences of hMFE-23 SEQ ID NO. 512-518 (U.S. Pat. No. 723,288).

| Region | Sequence Fragment | Residues | Length | SEQ ID NO. |
|---|---|---|---|---|
| HFR1 | QVKLEQSGAEVVKPGASVKLSCKASGFNIK | 1-30 | 30 | 512 |
| CDR-H1 | DSYMH | 31-35 | 5 | 513 |
| HFR2 | WLRQGPGQRLEWIG | 36-49 | 14 | 514 |
| CDR-H2 | WIDPENGDTEYAPKFQG | 50-66 | 17 | 515 |
| HFR3 | KATFTTDTSANTAYLGLSSLRPEDTAVYYCNE | 67-98 | 32 | 516 |
| CDR-H3 | GTPTGPYYFDY | 99-109 | 11 | 517 |
| HFR4 | WGQGTLVTVSS | 110-120 | 11 | 518 |

In an embodiment of the invention, the CEA-targeting antibody construct or antigen binding domain comprises the Variable light chain (VL kappa) of SW3E SEQ ID NO. 519 (U.S. Pat. No. 723,288).

SEQ ID NO. 519
ENVLTQSPSSMSVSVGDRVTIACSASSSVPYMHWLQQKPGKSPKLLIYLT

SNLASGVPSRFSGSGSGTDYSLTISSVQPEDAATYYCQQRSSYPLTFGGG

TKLEIK

In an embodiment of the invention, the CEA-targeting antibody construct or antigen binding domain comprises the light chain CDR (complementarity determining region) or light chain framework (LFR) sequences of SM3E SEQ ID NO. 520-526 (U.S. Pat. No. 723,288).

| Region | Sequence Fragment | Residues | Length | SEQ ID NO. |
|---|---|---|---|---|
| LFR1 | ENVLTQSPSSMSVSVGDRVTIAC | 1-23 | 23 | 520 |
| CDR-L1 | SASSSVPYMH | 24-33 | 10 | 521 |
| LFR2 | WLQQKPGKSPKLLIY | 34-48 | 15 | 522 |
| CDR-L2 | LTSNLAS | 49-55 | 7 | 523 |
| LFR3 | GVPSRFSGSGSGTDYSLTISSVQPEDAATYYC | 56-87 | 32 | 524 |
| CDR-L3 | QQRSSYPLT | 88-96 | 9 | 525 |
| LFR4 | FGGGTKLEIK | 97-106 | 10 | 526 |

In an embodiment of the invention, the CEA-targeting antibody construct or antigen binding domain comprises the Variable heavy chain (VH) of SM3E SEQ ID NO. 527 (U.S. Pat. No. 723,288).

SEQ ID NO. 527

QVKLEQSGAEVVKPGASVKLSCKASGFNIKDSYMHWLRQGPGQRLEWIGW

IDPENGDTEYAPKFQGKATFTTDTSANTAYLGLSSLRPEDTAVYYCNEGT

PTGPYYFDYWGQGTLVTVSS

In an embodiment of the invention, the CEA-targeting antibody construct or antigen binding domain comprises the heavy chain CDR (complementarity determining region) or heavy chain framework (HFR) sequences of SM3E SEQ ID NO. 528-534 (U.S. Pat. No. 723,288).

| Region | Sequence Fmgment | Residues | Length | SEQ ID NO. |
|---|---|---|---|---|
| HFR1 | QVKLEQSGAEVVKPGASVKLSCKASGFNIK | 1-30 | 30 | 528 |
| CDR-H1 | DSYMH | 31-35 | 5 | 529 |
| HFR2 | WLRQGPGQRLEWIG | 36-49 | 14 | 530 |
| CDR-H2 | WIDPENGDTEYAPKFQG | 50-66 | 17 | 531 |
| HFR3 | KATFTTDTSANTAYLGLSSLRPEDTAVYYCNE | 67-98 | 32 | 532 |
| CDR-H3 | GTPTGPYYFDY | 99-109 | 11 | 533 |
| HFR4 | WGQGTLVTVSS | 110-120 | 11 | 534 |

In an embodiment of the invention, the CEA-targeting antibody construct or antigen binding domain comprises the light chain CDR (complementarity determining region) or light chain framework (LFR) sequences of NP-4/arcitumomab SEQ ID NO. 535-541.

| Region | Sequence Fmgment | Residues | Length | SEQ ID NO. |
|---|---|---|---|---|
| LFR1 | QTVLSQSPAILSASPGEKVTMTC | 1-23 | 23 | 535 |
| CDR-L1 | RASSSVTYIH | 24-33 | 10 | 536 |
| LFR2 | WYQQKPGSSPKSWIY | 34-48 | 15 | 537 |
| CDR-L2 | ATSNLAS | 49-55 | 7 | 538 |
| LFR3 | GVPARFSGSGSGTSYSLTISRVEAEDAATYYC | 56-87 | 32 | 539 |
| CDR-L3 | QHWSSKPPT | 88-96 | 9 | 540 |
| LFR4 | FGGGTKLEIK | 97-106 | 10 | 541 |

In an embodiment of the invention, the CEA-targeting antibody construct or antigen binding domain comprises the Variable heavy chain (VH) of NP-4/arcitumomab SEQ ID NO. 542.

SEQ ID NO. 542

EVKLVESGGGLVQPGGSLRLSCATSGFTFTDYYMNWVRQPPGKALEWLGFI

GNKANGYTTEYSASVKGRFTISRDKSQSILYLQMNTLRAEDSATYYCTRDR

GLRFYFDYWGQGTTLTVSS.

In an embodiment of the invention, the CEA-targeting antibody construct or antigen binding domain comprises the heavy chain CDR (complementarity determining region) or heavy chain framework (HFR) sequences of NP-4 SEQ ID NO. 543-549.

| Region | Sequence Fragment | Residues | Length | SEQ ID NO. |
|---|---|---|---|---|
| HFR1 | EVKLVESGGGLVQPGGSLRLSCATSGFTFT | 1-30 | 30 | 543 |
| CDR-H1 | DYYMN | 31-35 | 5 | 544 |
| HFR2 | WVRQPPGKALEWLG | 36-49 | 14 | 545 |
| CDR-H2 | FIGNKANGYTTEYSASVKG | 50-68 | 19 | 546 |
| HFR3 | RFTISRDKSQSILYLQMNTLRAEDSATYYCTR | 69-100 | 32 | 547 |
| CDR-H3 | DRGLRFYFDY | 101-110 | 10 | 548 |
| HFR4 | WGQGTTLTVSS | 111-121 | 11 | 549 |

In an embodiment of the invention, the CEA-targeting antibody construct or antigen binding domain comprises the Variable light chain (VL kappa) of M5A/hT84.66 SEQ ID NO. 550 (U.S. Pat. No. 7,776,330).

SEQ ID NO. 550

DIQLTQSPSSLSASVGDRVTITCRAGESVDIFGVGFLHWYQQKPGKAPKL

LIYRASNLESGVPSRFSGSGSRTDFTLTISSLQPEDFATYYCQQTNEDPY

TFGQGTKVEIK

In an embodiment of the invention, the CEA-targeting antibody construct or antigen binding domain comprises the light chain CDR (complementarity determining region) or light chain framework (LFR) sequences of M5A/hT84.00 SEQ ID NO. 551-557 (U.S. Pat. No. 7,776,330).

| Region | Sequence Fragment | Residues | Length | SEQ ID NO. |
|---|---|---|---|---|
| LFR1 | DIQLTQSPSSLSASVGDRVTITC | 1-23 | 23 | 551 |
| CDR-L1 | RAGESVDIFGVGFLH | 24-38 | 15 | 552 |
| LFR2 | WYQQKPGKAPKLLIY | 39-53 | 15 | 553 |
| CDR-L2 | RASNLES | 54-60 | 7 | 554 |
| LFR3 | GVPSRFSGSGSRTDFTLTISSLQPEDFATYYC | 61-92 | 32 | 555 |
| CDR-L3 | QQTNEDPYT | 93-101 | 9 | 556 |
| LFR4 | FGQGTKVEIK | 102-111 | 10 | 557 |

In an embodiment of the invention, the CEA-targeting antibody construct or antigen binding domain comprises the Variable heavy chain (VH) of M5A/hT84.66 SEQ ID NO. 558 (U.S. Pat. No. 7,776,330).

SEQ ID NO. 558
EVQLVESGGGLVQPGGSLRLSCAASGFNIKDTYMHWVRQAPGKGLEWVAR

IDPANGNSKYADSVKGRFTISADTSKNTAYLQMNSLRAEDTAVYYCAPFG

YYVSDYAMAYWGQGTLVTVSS

In an embodiment of the invention, the CEA-targeting antibody construct or antigen binding domain comprises the heavy chain CDR (complementarity determining region) or heavy chain framework (HFR) sequences of M5A/hT84.66 SEQ ID NO. 559-565 (U.S. Pat. No. 7,776,330).

| Region | Sequence Fmgment | Residues | Length | SEQ ID NO. |
|---|---|---|---|---|
| HFR1 | EVQLVESGGGLVQPGGSLRLSCAASGFNIK | 1-30 | 30 | 559 |
| CDR-H1 | DTYMH | 31-35 | 5 | 560 |
| HFR2 | WVRQAPGKGLEWVA | 36-49 | 14 | 561 |
| CDR-H2 | RIDPANGNSKYADSVKG | 50-66 | 17 | 562 |
| HFR3 | RFTISADTSKNTAYLQMNSLRAEDTAVYYCAP | 67-98 | 32 | 563 |
| CDR-H3 | FGYYVSDYAMAY | 99-110 | 12 | 564 |
| HFR4 | WGQGTLVTVSS | 111-121 | 11 | 565 |

In an embodiment of the invention, the CEA-targeting antibody construct or antigen binding domain comprises the Variable light chain (VL kappa) of hAb2-3 SEQ ID NO. 566 (U.S. Pat. No. 9,617,345).

SEQ ID NO. 566
DIQMTQSPASLSASVGDRVTITCRASENIFSYLAWYQQKPGKSPKLLVYN

TRTLAEGVPSRFSGSGSGTDFSLTISSLQPEDFATYYCQHHYGTPFTFGS

GTKLEIK

In an embodiment of the invention, the CEA-targeting antibody construct or antigen binding domain comprises the light chain CDR (complementarity determining, region) or light chain framework (LFR) sequences of hAb2-3 SEQ ID NO. 567-573 (U.S. Pat. No. 9,617,345).

| Region | Sequence Fmgment | Residues | Length | SEQ ID NO. |
|---|---|---|---|---|
| LFR1 | DIQMTQSPASLSASVGDRVTITC | 1-23 | 23 | 567 |
| CDR-L1 | RASENIFSYLA | 24-34 | 11 | 568 |
| LFR2 | WYQQKPGKSPKLLVY | 35-49 | 15 | 569 |
| CDR-L2 | NTRTLAE | 50-56 | 7 | 570 |
| LFR3 | GVPSRFSGSGSGTDFSLTISSLQPEDFATYYC | 57-88 | 32 | 571 |
| CDR-L3 | QHHYGTPFT | 89-97 | 9 | 572 |
| LFR4 | FGSGTKLEIK | 98-107 | 10 | 573 |

In an embodiment of the invention, the CEA-targeting antibody construct or antigen binding domain comprises the Variable heavy chain (VH) of SEQ ID NO. 574 (U.S. Pat. No. 9,617,345).

SEQ ID NO. 574
EVQLQESGPGLVKPGGSLSLSCAASGFVFSSYDMSWVRQTPERGLEWVAY

ISSGGGITYAPSTVKGRFTVSRDNAKNTLYLQMNSLTSEDTAVYYCAAHY

FGSSGPFAYWGQGTLVTVSS

In an embodiment of the invention, the CEA-targeting antibody construct or antigen binding domain comprises the heavy chain CDR (complementarity determining region) or heavy chain framework (HFR) sequences of hAb2-3 SEQ ID NO. 575-581.

| Region | Sequence Fragment | Residues | Length | SEQ ID NO. |
|---|---|---|---|---|
| HFR1 | EVQLQESGPGLVKPGGSLSLSCAASGFVFS | 1-30 | 30 | 575 |
| CDR-H1 | SYDMS | 31-35 | 5 | 576 |
| HFR2 | WVRQTPERGLEWVA | 36-49 | 14 | 577 |
| CDR-H2 | YISSGGGITYAPSTVKG | 50-66 | 17 | 578 |
| HFR3 | RFTVSRDNAKNTLYLQMNSLTSEDTAVYYCAA | 67-98 | 32 | 579 |
| CDR-H3 | HYFGSSGPFAY | 99-109 | 11 | 580 |
| HFR4 | WGQGTLVTVSS | 110-120 | 11 | 581 |

In an embodiment of the invention, the CEA-targeting antibody construct or antigen binding domain comprises the Variable light chain (VL kappa) of A240VL-B9VH/AMG-211 SEQ ID NO. 582 (U.S. Pat. No. 9,982,063).

SEQ ID NO. 582
QAVLTQPASLSASPGASASLTCTLRRGINVGAYSIYWYQQKPGSPPQYL

LRYKSDSDKQQGSGVSSRFSASKDASANAGILLISGLQSEDEADYYCMI

WHSGASAVFGGGTKLTVL

In an embodiment of the invention, the CEA-targeting antibody construct or antigen binding domain comprises the light chain CDR (complementarity determining region) or light chain framework (LFR) sequences of A240VL-B9VH/AMG-211 SEQ ID NO. 583-589 (U.S. Pat. No. 9,982,063).

| Region | Sequence Fmgment | Residues | Length | SEQ ID NO. |
|---|---|---|---|---|
| LFR1 | QAVLTQPASLSASPGASASLTC | 1-22 | 22 | 583 |
| CDR-L1 | TLRRGINVGAYSIY | 23-36 | 14 | 584 |
| LFR2 | WYQQKPGSPPQYLLR | 37-51 | 15 | 585 |
| CDR-L2 | YKSDSDKQQGS | 52-62 | 11 | 586 |
| LFR3 | GVSSRFSASKDASANAGILLISGLQSEDEADYYC | 63-96 | 34 | 587 |
| CDR-L3 | MIWHSGASAV | 97-106 | 10 | 588 |
| LFR4 | FGGGTKLTVL | 107-116 | 10 | 589 |

In an embodiment of the invention, the CEA-targeting antibody construct or antigen binding domain comprises the Variable heavy chain (VH) of B9VH SEQ ID NO. 590 (U.S. Pat. No. 9,982,003).

SEQ ID NO. 590
EVQLVESGGGLVQPGRSLRLSCAASGFTVSSYWMHWVRQAPGKGLEWVG

FIRNKANGGTTEYAASVKGRFTISRDDSKNTLYLQMNSLRAEDTAVYYC

ARDRGLRFYFDYWGQGTTVTVSS

In an embodiment of the invention, the CEA-targeting antibody construct or antigen binding domain comprises the heavy chain CDR (complementarity determining region) or heavy chain framework (HFR) sequences of SEQ ID NO. 591-598 (U.S. Pat. No. 9,982,063). The embodiment includes two variants of CDR-H2, SEQ ID NO.:594 and SEQ ID NO.:595.

| Region | Sequence Fragment | Residues | Length | SEQ ID NO. |
|---|---|---|---|---|
| HFR1 | EVQLVESGGGLVQPGRSLRLSCAASGFTVS | 1-30 | 30 | 591 |
| CDR-H1 | SYWMH | 31-35 | 5 | 592 |
| HFR2 | WVRQAPGKGLEWVG | 36-49 | 14 | 593 |
| CDR-H2 | FIRNKANGGTTEYAASVKG | 50-68 | 19 | 594 |
| CDR-H2 | FIRNKANSGTTEYAASVKG | 50-68 | 19 | 595 |
| HFR3 | RFTISRDDSKNTLYLQMNSLRAEDTAVYYCAR | 69-100 | 32 | 596 |
| CDR-H3 | DRGLRFYFDY | 101-110 | 10 | 597 |
| HFR4 | WGQGTTVTVSS | 111-121 | 11 | 598 |

In an embodiment of the invention, the CEA-targeting antibody construct or antigen binding domain comprises the Variable heavy chain (VH) of E12VH SEQ ID NO. 599 (U.S. Pat. No. 9,982,063).

SEQ ID NO. 599
EVQLVESGGGLVQPGRSLRLSCAASGFTVSSYWMHWVRQAPGKGLEWVG

FILNKANGGTTEYAASVKGRFTISRDDSKNTLYLQMNSLRAEDTAVYYC

ARDRGLRFYFDYWGQGTTVTVSS

In an embodiment of the invention, the CEA-targeting antibody construct or antigen binding domain comprises the heavy chain CDR (complementarity determining region) or heavy chain framework (HFR) sequences of SEQ ID NO. 600-606 (U.S. Pat. No. 9,982,063).

| Region | Sequence Fragment | Residues | Length | SEQ ID NO. |
|---|---|---|---|---|
| HFR1 | EVQLVESGGGLVQPGRSLRLSCAASGFTVS | 1-30 | 30 | 600 |
| CDR-H1 | SYWMH | 31-35 | 5 | 601 |
| HFR2 | WVRQAPGKGLEWVG | 36-49 | 14 | 602 |
| CDR-H2 | FILNKANGGTTEYAASVKG | 50-68 | 19 | 603 |
| HFR3 | RFTISRDDSKNTLYLQMNSLRAEDTAVYYCAR | 69-100 | 32 | 604 |
| CDR-H3 | DRGLRFYFDY | 101-110 | 10 | 605 |
| HFR4 | WGQGTTVTVSS | 111-121 | 11 | 606 |

In some embodiments, the antibody construct further comprises an Fc domain. In certain embodiments, the antibody construct is an antibody. In certain embodiments, the antibody construct is a fusion protein. The antigen binding domain can be a single-chain variable region fragment (scFv). A single-chain variable region fragment (scFv), which is a truncated Fab fragment including the variable (V) domain of an antibody heavy chain linked to a V domain of a light antibody chain via a synthetic peptide, can be generated using routine recombinant DNA technology techniques. Similarly, disulfide-stabilized variable region fragments (dsFv) can be prepared by recombinant DNA technology. The antibody construct or antigen binding domain may comprise one or more variable regions (e.g., two variable regions) of an antigen binding domain of an anti-PD-L1 antibody, an anti-HER2 antibody, or an anti-CEA antibody, each variable region comprising a CDR1, a CDR2, and a CDR3.

In some embodiments, the antibodies in the immunoconjugates contain a modified Fc region, wherein the modification modulates the binding of the Fc region to one or more Fc receptors.

In some embodiments, the Fc region is modified by inclusion of a transforming growth factor beta 1 (TGFβ1) receptor, or a fragment thereof, that is capable of binding TGFβ1. For example, the receptor can be TGFβ receptor II (TGFβRII). In some embodiments, the TGFβ receptor is a human TGFβ receptor. In some embodiments, the IgG has a C-terminal fusion to a TGFβRII extracellular domain (ECD) as described in U.S. Pat. No. 9,676,863, incorporated herein. An "Fc linker" may be used to attach the IgG to the TGFβRII extracellular domain. The Fc linker may is be a short, flexible peptide that allows for the proper three-dimensional folding of the molecule while maintaining the binding-specificity to the targets. In some embodiments, the N-terminus of the TGFβ receptor is fused to the Fc of the antibody construct (with or without an Fc linker). In some embodiments, the C-terminus of the antibody construct heavy chain is fused to the TGFβ receptor (with or without an Fc linker). In some embodiments, the C-terminal lysine residue of the antibody construct heavy chain is mutated to alanine.

In some embodiments, the antibodies in the immunoconjugates are glycosylated.

In some embodiments, the antibodies in the immunoconjugates is a cysteine-engineered antibody which provides for site-specific conjugation of an adjuvant, label, or drug moiety to the antibody through cysteine substitutions at sites where the engineered cysteines are available for conjugation but do not perturb immunoglobulin folding and assembly or alter antigen binding and effector functions (Junutula, et al., 2008b *Nature Biotech.,* 26(8):925-932; Doman et al. (2009) *Blood* 114(13):2721-2729; U.S. Pat. No. 7,521,541: U.S. Pat. No. 7,723,485; US 2012/0121615; WO 2009/052249). A "cysteine engineered antibody" or "cysteine engineered antibody variant" is an antibody in which one or more residues of an antibody are substituted with cysteine residues. Cysteine-engineered antibodies can be conjugated to the thienoazepine adjuvant moiety as a thienoazepine-linker compound with uniform stoichiometry (e.g., up to two thienoazepine moieties per antibody in an antibody that has a single engineered cysteine site).

In some embodiments, cysteine-engineered antibodies used to prepare the immunoconjugates of Table 3 have a cysteine residue introduced at the 149-lysine site of the light chain (LC K149C). In other embodiments, the cysteine-engineered antibodies have a cysteine residue introduced at the 118-alanine site (EU numbering) of the heavy chain (HC A118C). This site is alternatively numbered 121 by Sequential numbering or 114 by Kabat numbering. In other embodiments, the cysteine-engineered antibodies have a cysteine residue introduced in the light chain at G64C or R142C according to Kabat numbering, or in the heavy chain at D101C, V184C or T205C according to Kabat numbering.

Thienoazepine Adjuvant Compounds

The immunoconjugate of the invention comprises a thienoazepine adjuvant moiety. The adjuvant moiety described herein is a compound that elicits an immune response (i.e., an immunostimulatory agent). Generally, the adjuvant moiety described herein is a TLR agonist. TLRs are type-I transmembrane proteins that are responsible for the initiation of innate immune responses in vertebrates. TLRs recognize a variety of pathogen-associated molecular patterns from bacteria, viruses, and fungi and act as a first line of defense against invading pathogens. TLRs elicit overlapping yet distinct biological responses due to differences in cellular expression and in the signaling pathways that they initiate. Once engaged (e.g., by a natural stimulus or a synthetic TLR agonist), TLRs initiate a signal transduction cascade leading to activation of nuclear factor-κB (NF-κB) via the adapter protein myeloid differentiation primary response gene 88 (MyD88) and recruitment of the IL-1 receptor associated kinase (IRAK). Phosphorylation of IRAK then leads to recruitment of TNF-receptor associated factor 6 (TRAF6), which results in the phosphorylation of the NF-κB inhibitor I-κB. As a result, NF-κB enters the cell nucleus and initiates transcription of genes whose promoters contain NF-κB binding sites, such as cytokines. Additional modes of regulation for TLR signaling include TIR-domain containing adapter-inducing interferon-β (TRIF)-dependent induction of TNF-receptor associated factor 6 (TRAF6) and activation of MyD88 independent pathways via TRIF and TRAF3, leading to the phosphorylation of interferon response factor three (IRF3). Similarly, the MyD88 dependent pathway also activates several IRF family members, including IRF5 and IRF7 whereas the TRIF dependent pathway also activates the NF-κB pathway.

Typically, the adjuvant moiety described herein is a TLR7 and/or TLR8 agonist. TLR7 and TLR8 are both expressed in monocytes and dendritic cells. In humans, TLR7 is also expressed in plasmacytoid dendritic cells (pDCs) and B cells. TLR8 is expressed mostly in cells of myeloid origin. i.e., monocytes, granulocytes, and myeloid dendritic cells. TLR7 and TLR8 are capable of detecting the presence of "foreign" single-stranded RNA within a cell, as a means to respond to viral invasion. Treatment of TLR8-expressing cells, with TLR8 agonists can result in production of high levels of IL-12, IFN-γ, IL-1, TNF-α, IL-6, and other inflammatory cytokines. Similarly, stimulation of TLR7-expressing cells, such as pDCs, with TLR7 agonists can result in production of high levels of IFN-α and other inflammatory cytokines. TLR7/TLR8 engagement and resulting cytokine production can activate dendritic cells and other antigen-presenting cells, driving diverse innate and acquired immune response mechanisms leading to tumor destruction.

Exemplary thienoazepine compounds (TAZ) of the invention are shown in Tables 1a-c. Each compound was synthesized, purified, and characterized by mass spectrometry and shown to have the mass indicated. Additional experimental procedures are found in the Examples. Activity against HEK293 NFκB reporter cells expressing human TLR7 or human TLR8 was measured according to Example 202. The thienoazepine compounds of Tables 1a-c demonstrate the surprising and unexpected property of TLR8 agonist selectivity which may predict useful therapeutic activity to treat cancer and other disorders.

TABLE 1a

Thienoazepine compounds (TAZ)

| TAZ No. | Structure | MW | HEK293 hTLR7 EC50 (nM) | HEK293 hTLR8 EC50 (nM) |
|---|---|---|---|---|
| TAZ-1 | 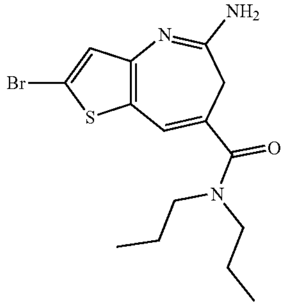 [SMILES: CCCN(CCC)C(=O)C1=Cc2sc(Br)cc2N=C(N)C1] | 370.3 | >9000 | >9000 |

TABLE 1a-continued
| Thienoazepine compounds (TAZ) | | | | |
|---|---|---|---|---|
| TAZ No. | Structure | MW | HEK293 hTLR7 EC50 (nM) | HEK293 hTLR8 EC50 (nM) |
| TAZ-2 | 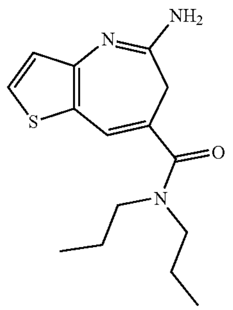 [SMILES: CCCN(CCC)C(=O)C1=Cc2sccc2N=C(N)C1] | 291.4 | >9000 | 2390 |
| TAZ-3 | 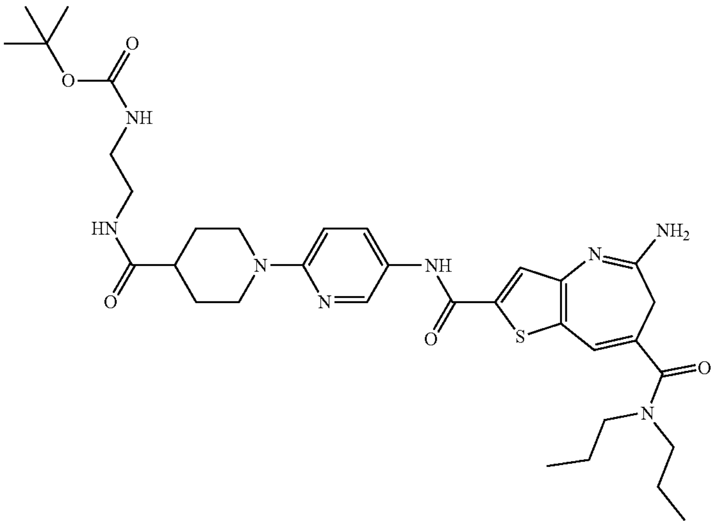 [SMILES: CCCN(CCC)C(=O)C1=Cc2sc(C(=O)Nc3ccc(N4CCC(C(=O)NCCNC(=O)OC(C)(C)C)CC4)nc3)cc2N=C(N)C1] | 680.9 | >9000 | >9000 |
| TAZ-4 | 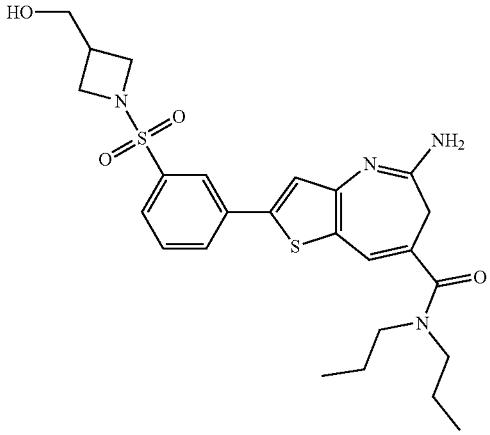 [SMILES: CCCN(CCC)C(=O)C1=Cc2sc(-c3cccc(S(=O)(=O)N4CC(CO)C4)c3)cc2N=C(N)C1] | 516.7 | >9000 | >9000 |

TABLE 1a-continued
| Thienoazepine compounds (TAZ) | | | | |
|---|---|---|---|---|
| TAZ No. | Structure | MW | HEK293 hTLR7 EC50 (nM) | HEK293 hTLR8 EC50 (nM) |
| TAZ-5 | 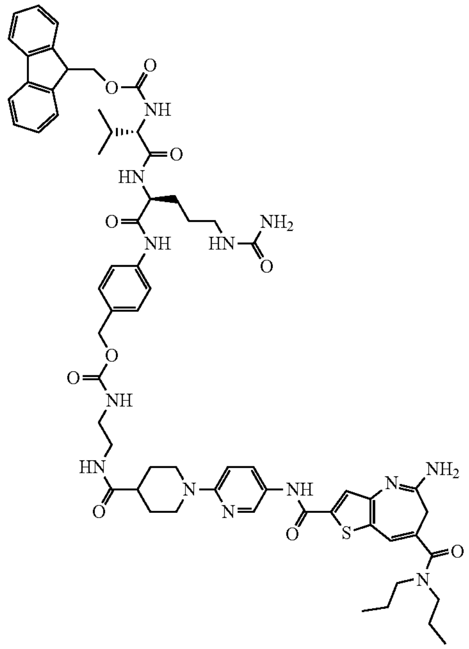 [SMILES: CCCN(CCC)C(=O)C1=Cc2sc(C(=O)Nc3ccc(N4CCC(C(=O)NCCNC(=O)OCc5ccc(NC(=O)[C@H](CCCNC(N)=O)NC(=O)[C@@H](NC(=O)OCC6c7ccccc7-c7ccccc76)C(C)C)cc5)CC4)nc3)cc2N=C(N)C1] | 1208.4 | Not Determined | Not Determined |
| TAZ-6 | 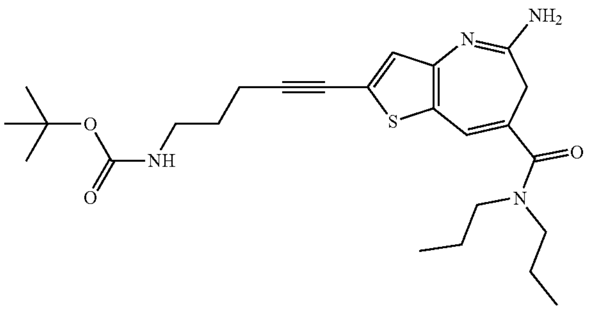 [SMILES: CCCN(CCC)C(=O)C1=Cc2sc(C#CCCCNC(=O)OC(C)(C)C)cc2N=C(N)C1] | 472.7 | >9000 | >9000 |
| TAZ-7 | 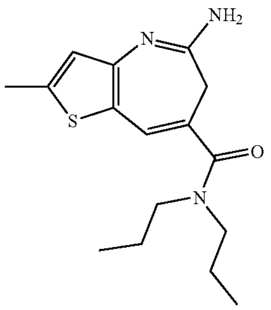 [SMILES: CCCN(CCC)C(=O)C1=Cc2sc(C)cc2N=C(N)C1] | 305.4 | >9000 | >9000 |

TABLE 1a-continued
Thienoazepine compounds (TAZ)
| TAZ No. | Structure | MW | HEK293 hTLR7 EC50 (nM) | HEK293 hTLR8 EC50 (nM) |
|---|---|---|---|---|
| TAZ-8 | 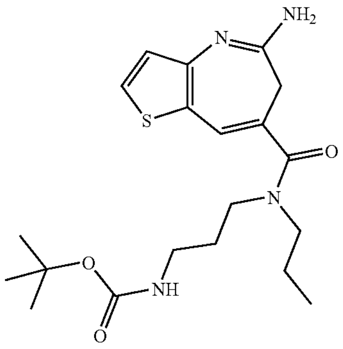 [SMILES: CCCN(CCCNC(=O)OC(C)(C)C)C(=O)C1=Cc2sccc2N=C(N)C1] | 406.5 | 589 | 1533 |
| TAZ-9 | 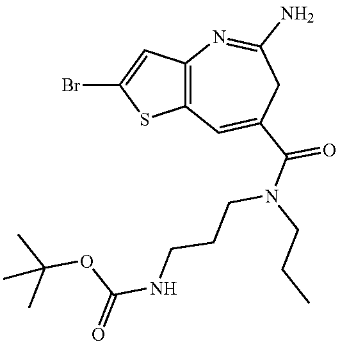 [SMILES: CCCN(CCCNC(=O)OC(C)(C)C)C(=O)C1=Cc2sc(Br)cc2N=C(N)C1] | 485.4 | >9000 | >9000 |
| TAZ-10 | 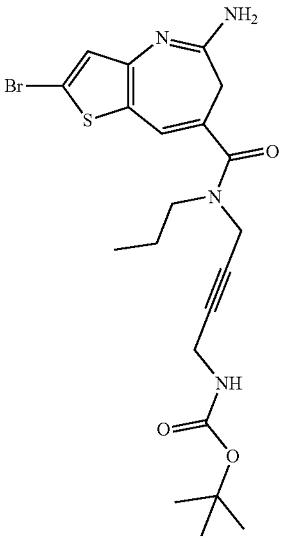 [SMILES: CCCN(CC#CCNC(=O)OC(C)(C)C)C(=O)C1=Cc2sc(Br)cc2N=C(N)C1] | 495.4 | 7767 | >9000 |

TABLE 1a-continued
| Thienoazepine compounds (TAZ) | | | | |
|---|---|---|---|---|
| TAZ No. | Structure | MW | HEK293 hTLR7 EC50 (nM) | HEK293 hTLR8 EC50 (nM) |
| TAZ-11 | 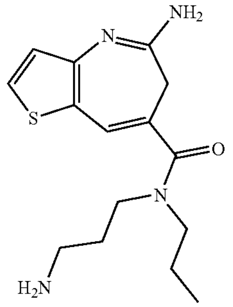 [SMILES: CCCN(CCCN)C(=O)C1=Cc2sccc2N=C(N)C1] | 306.4 | >9000 | >9000 |
| TAZ-12 | 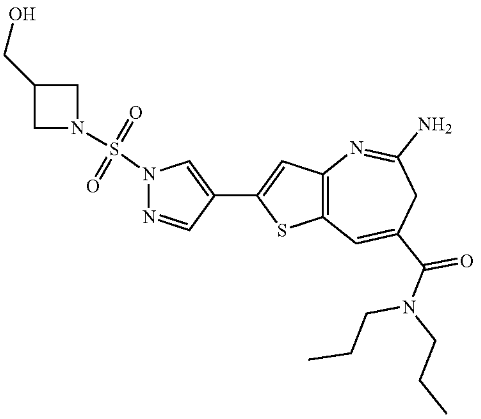 [SMILES: CCCN(CCC)C(=O)C1=Cc2sc(-c3cnn(S(=O)(=O)N4CC(CO)C4)c3)cc2N=C(N)C1] | 506.6 | >9000 | >9000 |
| TAZ-13 | 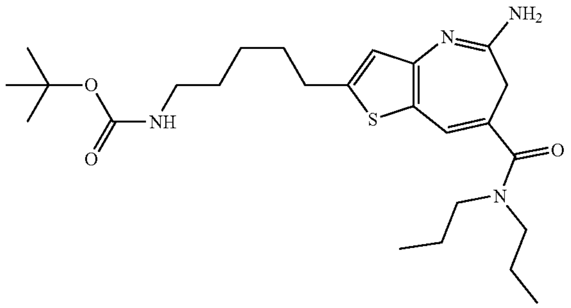 [SMILES: CCCN(CCC)C(=O)C1=Cc2sc(CCCCCNC(=O)OC(C)(C)C)cc2N=C(N)C1] | 476.7 | >9000 | >9000 |
| TAZ-14 | 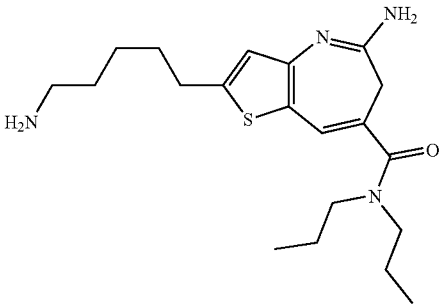 [SMILES: CCCN(CCC)C(=O)C1=Cc2sc(CCCCCN)cc2N=C(N)C1] | 376.6 | >9000 | 4940 |

TABLE 1a-continued
| Thienoazepine compounds (TAZ) | | | | |
|---|---|---|---|---|
| TAZ No. | Structure | MW | HEK293 hTLR7 EC50 (nM) | HEK293 hTLR8 EC50 (nM) |
| TAZ-15 | 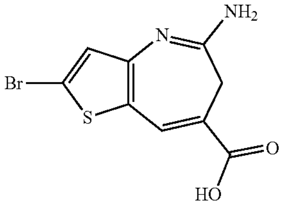 [SMILES: NC1=Nc2cc(Br)sc2C=C(C(=O)O)C1] | 287.1 | Not Determined | Not Determined |
| TAZ-16 | 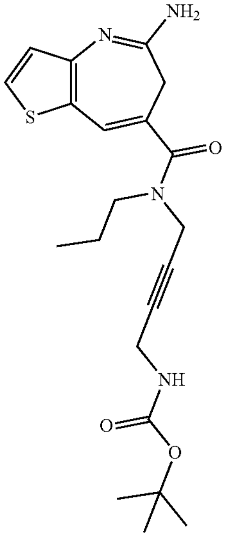 [SMILES: CCCN(CC#CCNC(=O)OC(C)(C)C)C(=O)C1=Cc2sccc2N=C(N)C1] | 416.5 | >9000 | 6111 |
| TAZ-17 | 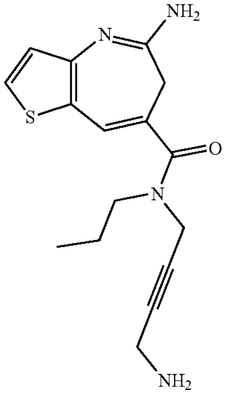 [SMILES: CCCN(CC#CCN)C(=O)C1=Cc2sccc2N=C(N)C1] | 316.4 | >9000 | 4101 |
| TAZ-18 | 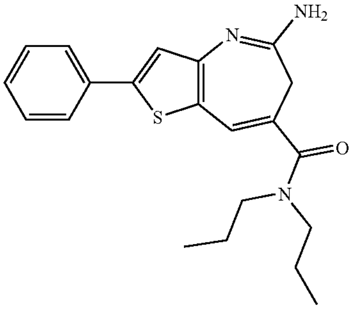 [SMILES: CCCN(CCC)C(=O)C1=Cc2sc(-c3ccccc3)cc2N=C(N)C1] | 367.5 | >9000 | >9000 |

TABLE 1a-continued
| Thienoazepine compounds (TAZ) | | | | |
|---|---|---|---|---|
| TAZ No. | Structure | MW | HEK293 hTLR7 EC50 (nM) | HEK293 hTLR8 EC50 (nM) |
| TAZ-19 | 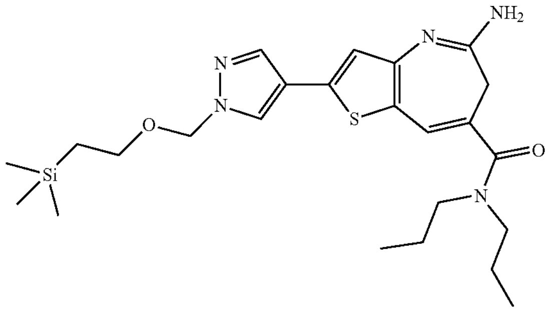 [SMILES: CCCN(CCC)C(=O)C1=Cc2sc(-c3cnn(COCC[Si](C)(C)C)c3)cc2N=C(N)C1] | 487.7 | >9000 | >9000 |
| TAZ-20 | 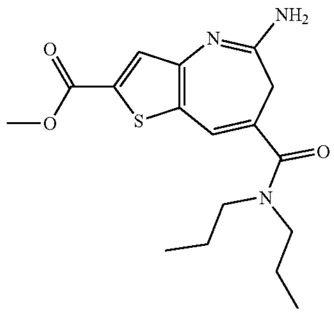 [SMILES: CCCN(CCC)C(=O)C1=Cc2sc(C(=O)OC)cc2N=C(N)C1] | 349.4 | >9000 | >9000 |
| TAZ-21 | 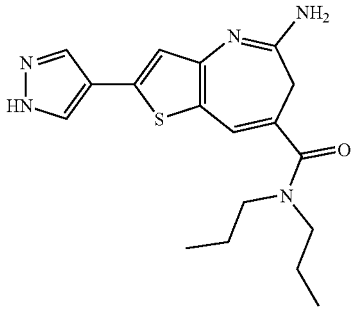 [SMILES: CCCN(CCC)C(=O)C1=Cc2sc(-c3cn[nH]c3)cc2N=C(N)C1] | 357.5 | >9000 | >9000 |
| TAZ-22 | 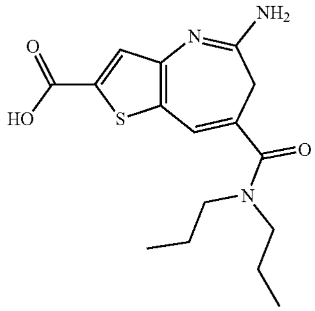 [SMILES: CCCN(CCC)C(=O)C1=Cc2sc(C(=O)O)cc2N=C(N)C1] | 335.4 | >9000 | >9000 |

TABLE 1a-continued
| Thienoazepine compounds (TAZ) | | | | |
|---|---|---|---|---|
| TAZ No. | Structure | MW | HEK293 hTLR7 EC50 (nM) | HEK293 hTLR8 EC50 (nM) |
| TAZ-23 | 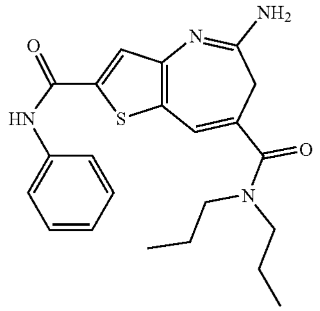 [SMILES: CCCN(CCC)C(=O)C1=Cc2sc(C(=O)Nc3ccccc3)cc2N=C(N)C1] | 410.5 | >9000 | >9000 |
| TAZ-24 | 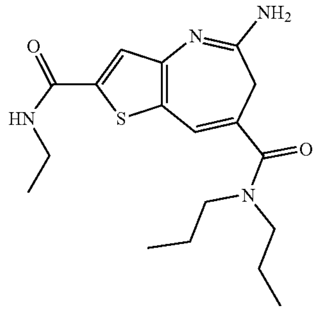 [SMILES: CCCN(CCC)C(=O)C1=Cc2sc(C(=O)NCC)cc2N=C(N)C1] | 362.5 | >9000 | >9000 |
| TAZ-25 | 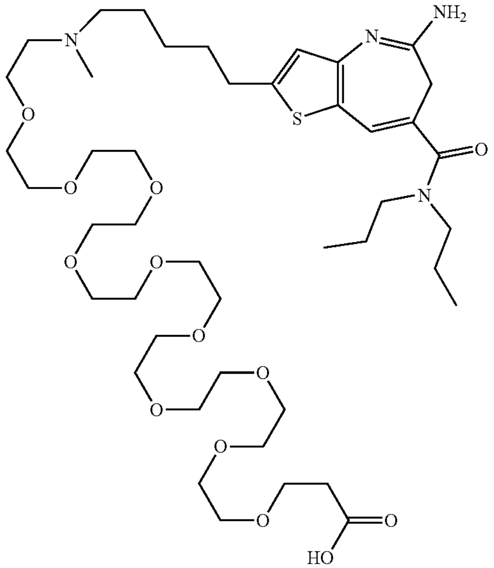 [SMILES: CCCN(CCC)C(=O)C1=Cc2sc(CCCCCN(C)CCOCCOCCOCCOCCOCCOCCOCCOCCOCCOCCC(=O)O)cc2N=C(N)C1] | 903.2 | Not Determined | Not Determined |
| TAZ-26 | 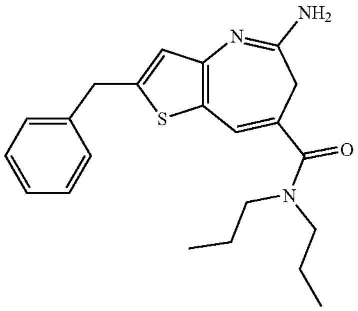 [SMILES: CCCN(CCC)C(=O)C1=Cc2sc(Cc3ccccc3)cc2N=C(N)C1] | 381.5 | >9000 | >9000 |

TABLE 1a-continued
| Thienoazepine compounds (TAZ) | | | | |
|---|---|---|---|---|
| TAZ No. | Structure | MW | HEK293 hTLR7 EC50 (nM) | HEK293 hTLR8 EC50 (nM) |
| TAZ-27 | 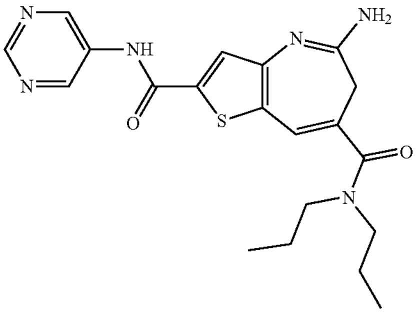 [SMILES: CCCN(CCC)C(=O)C1=Cc2sc(C(=O)Nc3cncnc3)cc2N=C(N)C1] | 412.5 | >9000 | >9000 |
| TAZ-28 | 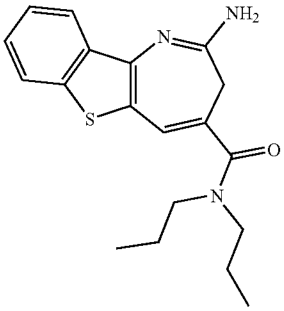 [SMILES: CCCN(CCC)C(=O)C1=Cc2sc3ccccc3c2N=C(N)C1] | 341.5 | >9000 | >9000 |
| TAZ-29 | 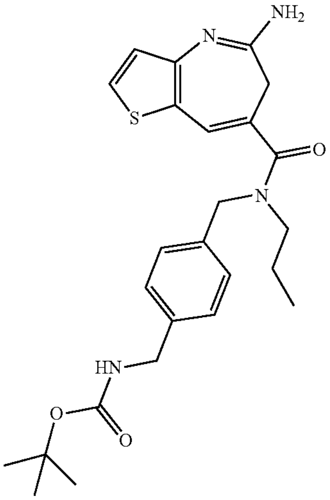 [SMILES: CCCN(Cc1ccc(CNC(=O)OC(C)(C)C)cc1)C(=O)C1=Cc2sccc2N=C(N)C1] | 468.6 | >9000 | >9000 |
| TAZ-30 | 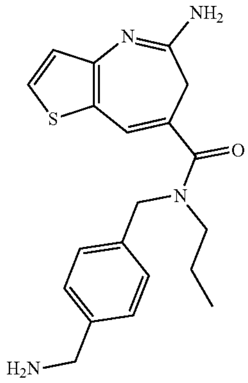 [SMILES: CCCN(Cc1ccc(CN)cc1)C(=O)C1=Cc2sccc2N=C(N)C1] | 368.5 | >9000 | 641 |

TABLE 1b
| TAZ No. | Structure | MW | HEK293 hTLR7 EC50 (nM) | HEK293 hTLR8 EC50 (nM) |
| --- | --- | --- | --- | --- |
| Thienoazepine compounds (TAZ) | | | | |
| TAZ-31 | 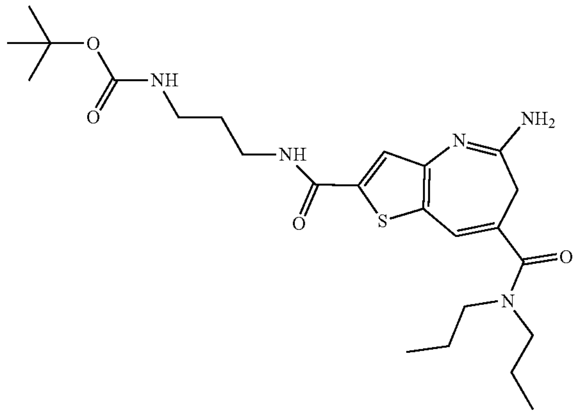 [SMILES: CCCN(CCC)C(=O)C1=Cc2sc(C(=O)NCCCNC(=O)OC(C)(C)C)cc2N=C(N)C1] | 491.65 | >9000 | >9000 |
| TAZ-32 | 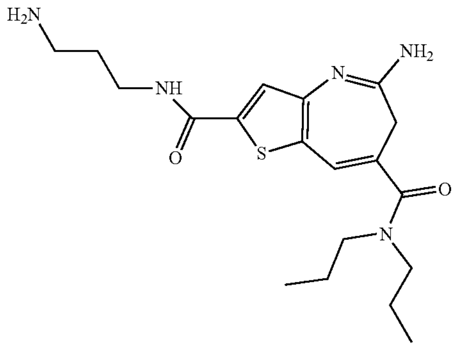 [SMILES: CCCN(CCC)C(=O)C1=Cc2sc(C(=O)NCCCN)cc2N=C(N)C1] | 391.53 | >9000 | >9000 |
| TAZ-33 | 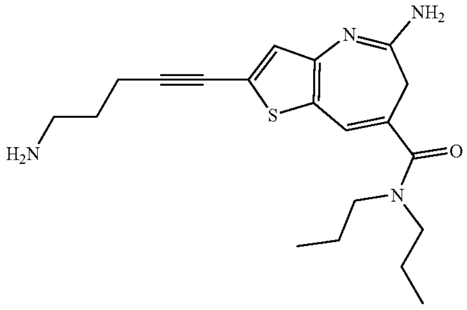 [SMILES: CCCN(CCC)C(=O)C1=Cc2sc(C#CCCCN)cc2N=C(N)C1] | 372.53 | >9000 | >9000 |

TABLE 1b-continued
| Thienoazepine compounds (TAZ) | | | | |
|---|---|---|---|---|
| TAZ No. | Structure | MW | HEK293 hTLR7 EC50 (nM) | HEK293 hTLR8 EC50 (nM) |
| TAZ-34 | 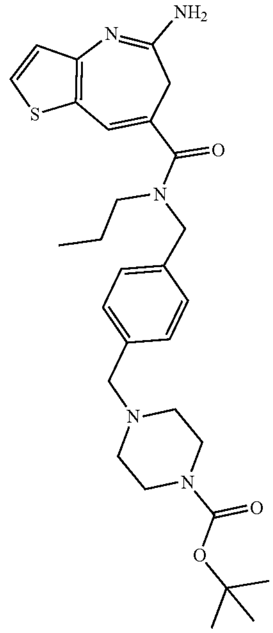 [SMILES: CCCN(Cc1ccc(CN2CCN(C(=O)OC(C)(C)C)CC2)cc1)C(=O)C1=Cc2sccc2N=C(N)C1] | 537.72 | >9000 | 339 |
| TAZ-35 | 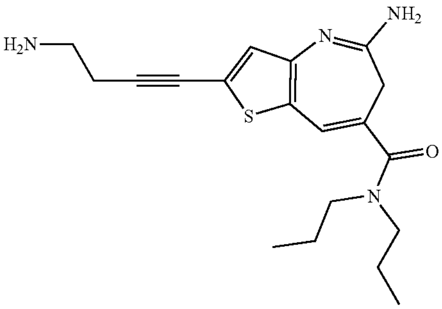 [SMILES: CCCN(CCC)C(=O)C1=Cc2sc(C#CCCN)cc2N=C(N)C1] | 358.5 | >9000 | 2870 |
| TAZ-36 | 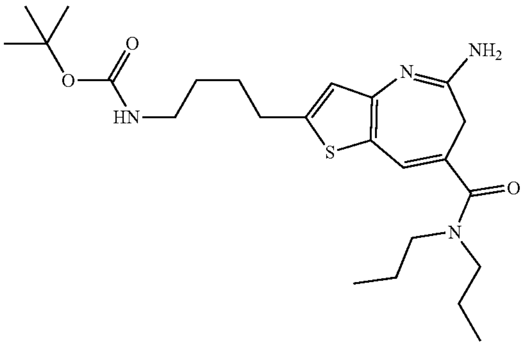 [SMILES: CCCN(CCC)C(=O)C1=Cc2sc(CCCCNC(=O)OC(C)(C)C)cc2N=C(N)C1] | 462.65 | 8524 | >9000 |

TABLE 1b-continued
| Thienoazepine compounds (TAZ) | | | | |
|---|---|---|---|---|
| TAZ No. | Structure | MW | HEK293 hTLR7 EC50 (nM) | HEK293 hTLR8 EC50 (nM) |
| TAZ-37 | 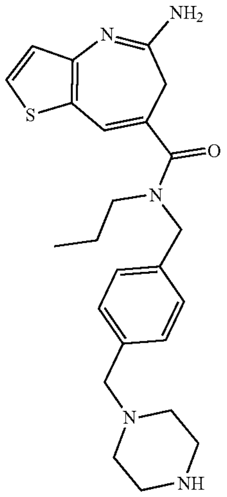 [SMILES: CCCN(Cc1ccc(CN2CCNCC2)cc1)C(=O)C1=Cc2sccc2N=C(N)C1] | 437.6 | >9000 | 2938 |
| TAZ-38 | 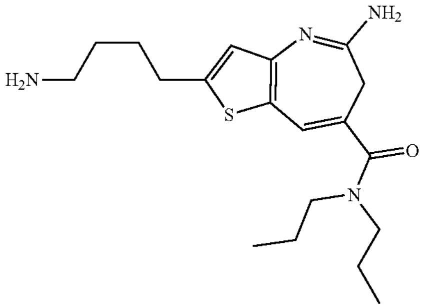 [SMILES: CCCN(CCC)C(=O)C1=Cc2sc(CCCCN)cc2N=C(N)C1] | 362.53 | 4148 | 3752 |
| TAZ-39 | 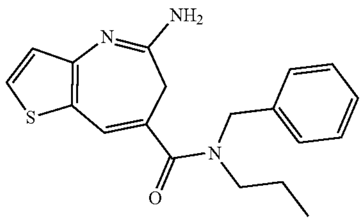 [SMILES: CCCN(Cc1ccccc1)C(=O)C1=Cc2sccc2N=C(N)C1] | 339.46 | >9000 | >9000 |

TABLE 1b-continued
| TAZ No. | Structure | MW | HEK293 hTLR7 EC50 (nM) | HEK293 hTLR8 EC50 (nM) |
|---|---|---|---|---|
| Thienoazepine compounds (TAZ) | | | | |
| TAZ-40 | 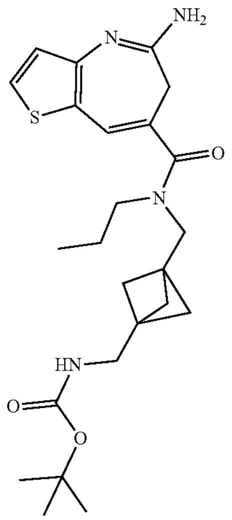 [SMILES: CCCN(CC12CC(CNC(=O)OC(C)(C)C)(C1)C2)C(=O)C1=Cc2sccc2N=C(N)C1] | 458.62 | >9000 | >9000 |
| TAZ-41 | 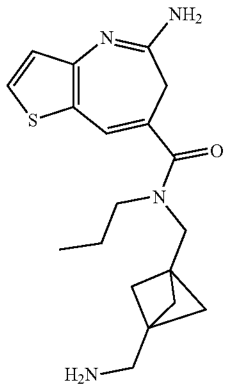 [SMILES: CCCN(CC12CC(CN)(C1)C2)C(=O)C1=Cc2sccc2N=C(N)C1] | 358.5 | >9000 | >9000 |
| TAZ-42 | 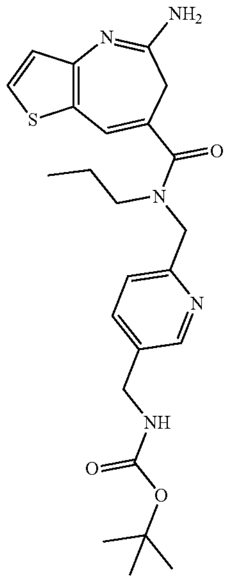 [SMILES: CCCN(Cc1ccc(CNC(=O)OC(C)(C)C)cn1)C(=O)C1=Cc2sccc2N=C(N)C1] | 469.6 | >9000 | >9000 |

TABLE 1b-continued
Thienoazepine compounds (TAZ)
| TAZ No. | Structure | MW | HEK293 hTLR7 EC50 (nM) | HEK293 hTLR8 EC50 (nM) |
|---|---|---|---|---|
| TAZ-43 | 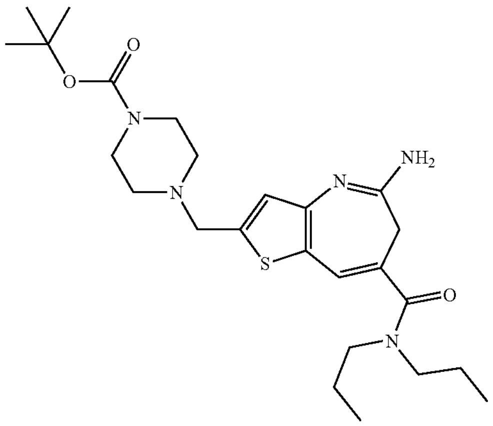 [SMILES: CCCN(CCC)C(=O)C1=Cc2sc(CN3CCN(C(=O)OC(C)(C)C)CC3)cc2N=C(N)C1] | 489.68 | >9000 | >9000 |
| TAZ-44 | 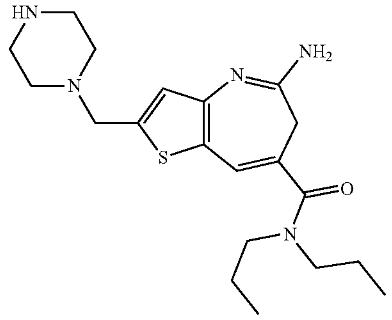 [SMILES: CCCN(CCC)C(=O)C1=Cc2sc(CN3CCNCC3)cc2N=C(N)C1] | 389.56 | 4526 | 593 |
| TAZ-45 | 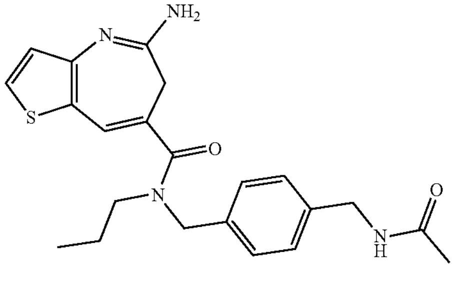 [SMILES: CCCN(Cc1ccc(CNC(C)=O)cc1)C(=O)C1=Cc2sccc2N=C(N)C1] | 410.53 | >9000 | 1779 |
| TAZ-46 | 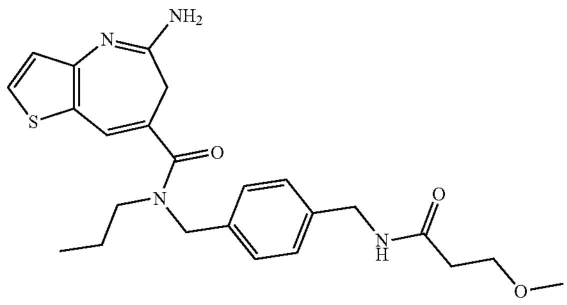 [SMILES: CCCN(Cc1ccc(CNC(=O)CCOC)cc1)C(=O)C1=Cc2sccc2N=C(N)C1] | 454.59 | >9000 | 1576 |

TABLE 1b-continued
| Thienoazepine compounds (TAZ) | | | | |
|---|---|---|---|---|
| TAZ No. | Structure | MW | HEK293 hTLR7 EC50 (nM) | HEK293 hTLR8 EC50 (nM) |
| TAZ-47 | 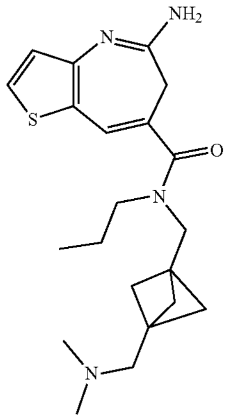 [SMILES: CCCN(CC12CC(CN(C)C)(C1)C2)C(=O)C1=Cc2sccc2N=C(N)C1] | 386.56 | >9000 | >9000 |
| TAZ-48 | 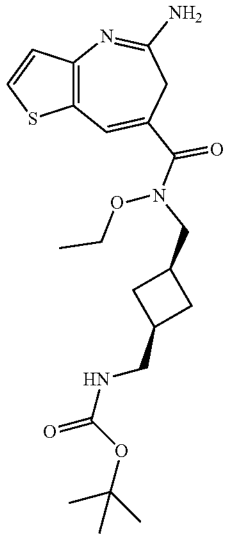 [SMILES: CCON(C[C@H]1C[C@@H](CNC(=O)OC(C)(C)C)C1)C(=O)C1=Cc2sccc2N=C(N)C1] | 446.61 | >9000 | >9000 |
| TAZ-49 | 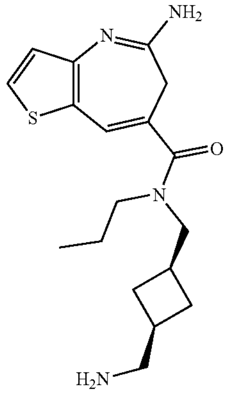 [SMILES: CCCN(C[C@H]1C[C@@H](CN)C1)C(=O)C1=Cc2sccc2N=C(N)C1] | 346.49 | >9000 | >9000 |

TABLE 1b-continued
| Thienoazepine compounds (TAZ) | | | | |
|---|---|---|---|---|
| TAZ No. | Structure | MW | HEK293 hTLR7 EC50 (nM) | HEK293 hTLR8 EC50 (nM) |
| TAZ-50 | 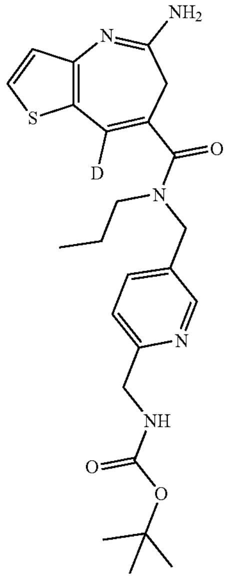 [SMILES: [2H]C1=C(C(=O)N(CCC)Cc2ccc(CNC(=O)OC(C)(C)C)nc2)CC(N)=Nc2ccsc21] | 469.6 | 7125 | 7938 |
| TAZ-51 | 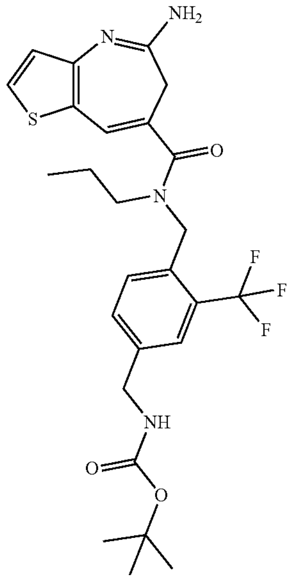 [SMILES: CCCN(Cc1ccc(CNC(=O)OC(C)(C)C)cc1C(F)(F)F)C(=O)C1=Cc2sccc2N=C(N)C1] | 536.61 | >9000 | 5635 |

TABLE 1b-continued
| Thienoazepine compounds (TAZ) | | | | |
|---|---|---|---|---|
| TAZ No. | Structure | MW | HEK293 hTLR7 EC50 (nM) | HEK293 hTLR8 EC50 (nM) |
| TAZ-52 | 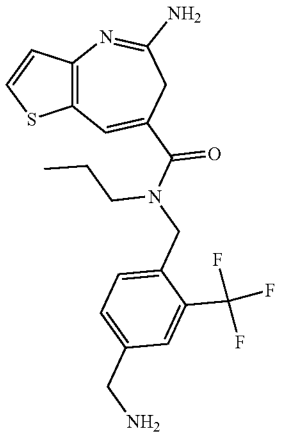 [SMILES: CCCN(Cc1ccc(CN)cc1C(F)(F)F)C(=O)C1=Cc2sccc2N=C(N)C1] | 436.5 | 2705 | 151 |
| TAZ-53 | 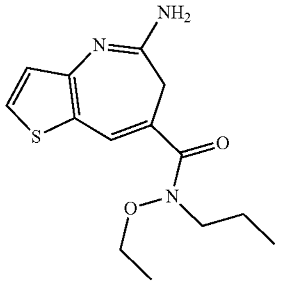 [SMILES: CCCN(OCC)C(=O)C1=Cc2sccc2N=C(N)C1] | 293.39 | 3621 | 181 |
| TAZ-54 | 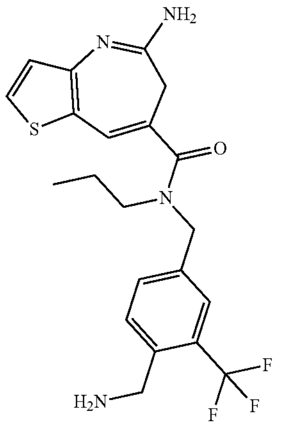 [SMILES: CCCN(Cc1ccc(CN)c(C(F)(F)F)c1)C(=O)C1=Cc2sccc2N=C(N)C1] | 436.5 | 905 | 35 |

TABLE 1b-continued
| Thienoazepine compounds (TAZ) | | | | |
|---|---|---|---|---|
| TAZ No. | Structure | MW | HEK293 hTLR7 EC50 (nM) | HEK293 hTLR8 EC50 (nM) |
| TAZ-55 | 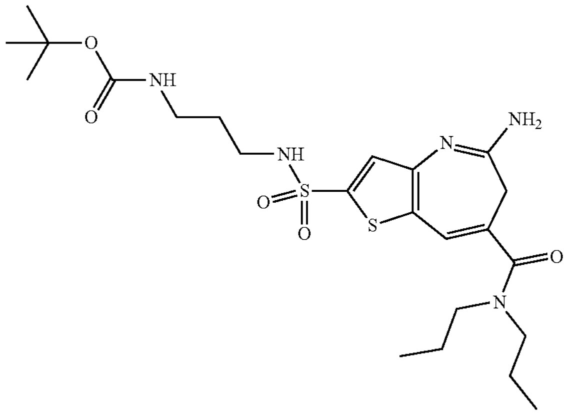 [SMILES: CCCN(CCC)C(=O)C1=Cc2sc(S(=O)(=O)NCCCNC(=O)OC(C)(C)C)cc2N=C(N)C1] | 527.7 | >9000 | >9000 |
| TAZ-56 | 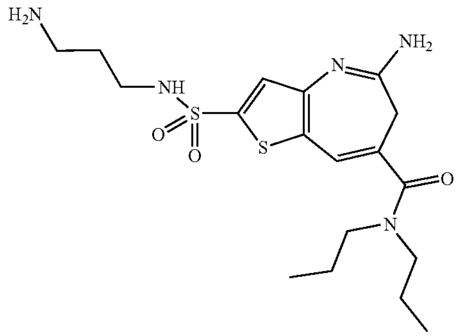 [SMILES: CCCN(CCC)C(=O)C1=Cc2sc(S(=O)(=O)NCCCN)cc2N=C(N)C1] | 427.58 | >9000 | >9000 |
| TAZ-57 | 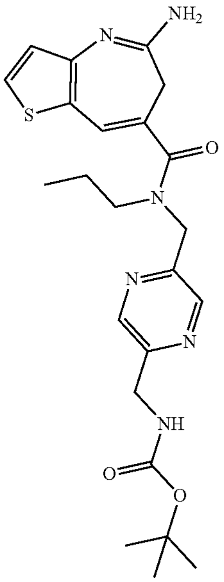 [SMILES: CCCN(Cc1cnc(CNC(=O)OC(C)(C)C)cn1)C(=O)C1=Cc2sccc2N=C(N)C1] | 470.59 | 1053 | 3850 |

TABLE 1b-continued
| TAZ No. | Structure | MW | HEK293 hTLR7 EC50 (nM) | HEK293 hTLR8 EC50 (nM) |
|---|---|---|---|---|
| Thienoazepine compounds (TAZ) | | | | |
| TAZ-58 | 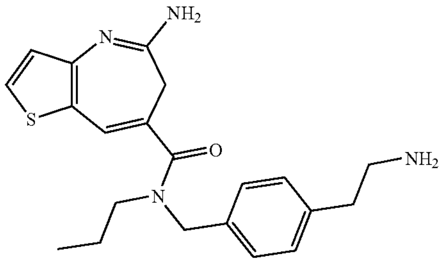 [SMILES: CCCN(Cc1ccc(CCN)cc1)C(=O)C1=Cc2sccc2N=C(N)C1] | 382.52 | >9000 | 1296 |
| TAZ-59 | 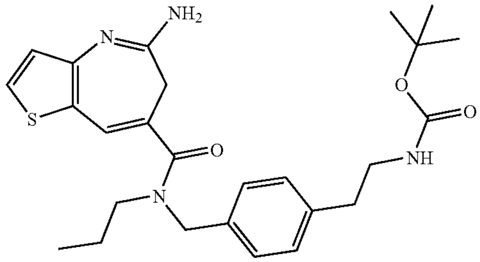 [SMILES: CCCN(Cc1ccc(CCNC(=O)OC(C)(C)C)cc1)C(=O)C1=Cc2sccc2N=C(N)C1] | 482.64 | >9000 | >9000 |
| TAZ-60 | 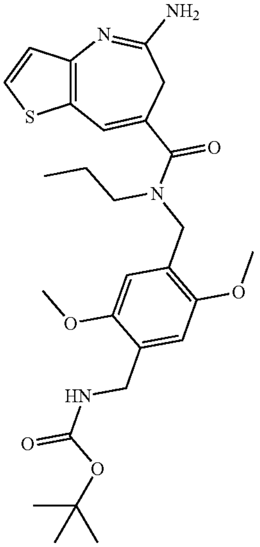 [SMILES: CCCN(Cc1cc(OC)c(CNC(=O)OC(C)(C)C)cc1OC)C(=O)C1=Cc2sccc2N=C(N)C1] | 528.67 | Not available | Not available |
| TAZ-61 | 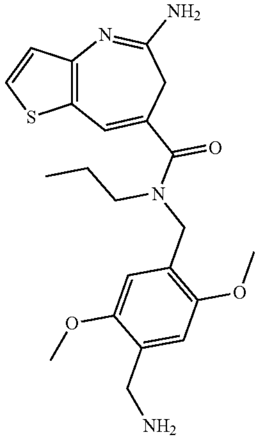 [SMILES: CCCN(Cc1cc(OC)c(CN)cc1OC)C(=O)C1=Cc2sccc2N=C(N)C1] | 428.55 | Not available | Not available |

TABLE 1b-continued
| Thienoazepine compounds (TAZ) | | | | |
|---|---|---|---|---|
| TAZ No. | Structure | MW | HEK293 hTLR7 EC50 (nM) | HEK293 hTLR8 EC50 (nM) |
| TAZ-62 | 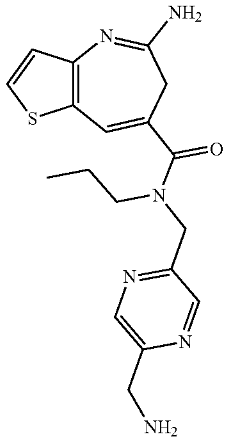 [SMILES: CCCN(Cc1cnc(CN)cn1)C(=O)C1=Cc2sccc2N=C(N)C1] | 370.47 | 8317 | 178 |
| TAZ-63 | 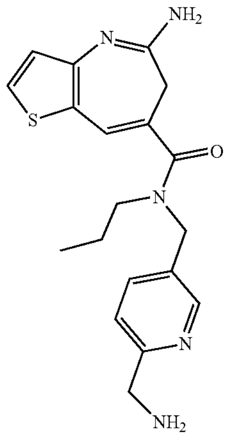 [SMILES: CCCN(Cc1ccc(CN)nc1)C(=O)C1=Cc2sccc2N=C(N)C1] | 369.48 | 4209 | 517 |
| TAZ-64 | 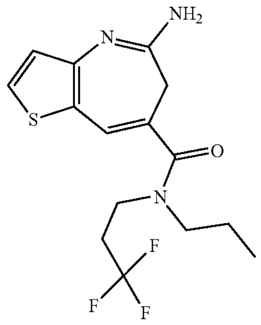 [SMILES: CCCN(CCC(F)(F)F)C(=O)C1=Cc2sccc2N=C(N)C1] | 345.38 | 5057 | 2742 |

TABLE 1b-continued
Thienoazepine compounds (TAZ)
| TAZ No. | Structure | MW | HEK293 hTLR7 EC50 (nM) | HEK293 hTLR8 EC50 (nM) |
|---|---|---|---|---|
| TAZ-65 | 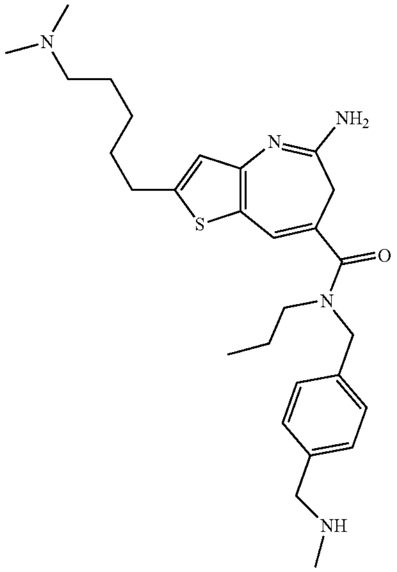 [SMILES: CCCN(Cc1ccc(CNC)cc1)C(=O)C1=Cc2sc(CCCCCN(C)C)cc2N=C(N)C1] | 495.73 | >9000 | 311 |
| TAZ-66 | 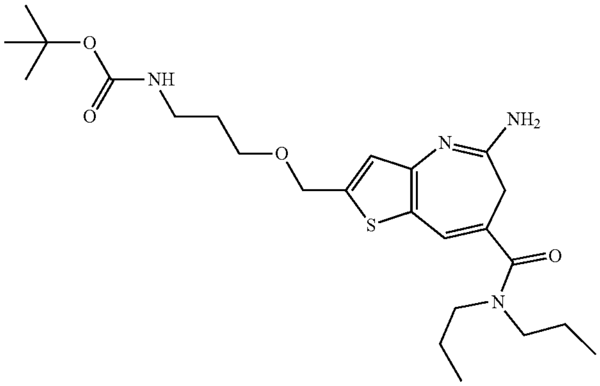 [SMILES: CCCN(CCC)C(=O)C1=Cc2sc(COCCCNC(=O)OC(C)(C)C)cc2N=C(N)C1] | 478.65 | 4423 | 4236 |
| TAZ-67 | 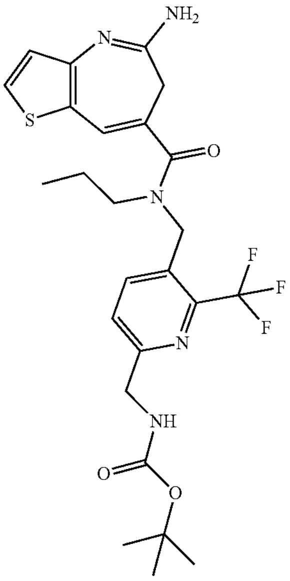 [SMILES: CCCN(Cc1ccc(CNC(=O)OC(C)(C)C)nc1C(F)(F)F)C(=O)C1=Cc2sccc2N=C(N)C1] | 537.6 | Not available | Not available |

TABLE 1b-continued
| TAZ No. | Structure | MW | HEK293 hTLR7 EC50 (nM) | HEK293 hTLR8 EC50 (nM) |
|---|---|---|---|---|
| Thienoazepine compounds (TAZ) | | | | |
| TAZ-68 | 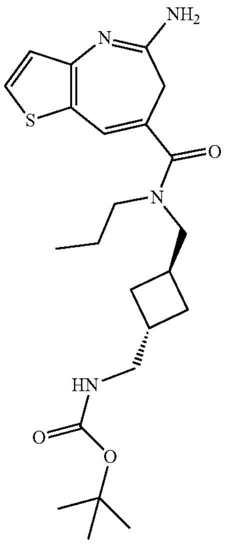 [SMILES: CCCN(C[C@H]1C[C@H](CNC(=O)OC(C)(C)C)C1)C(=O)C1=Cc2sccc2N=C(N)C1] | 446.61 | Not available | Not available |
| TAZ-69 | 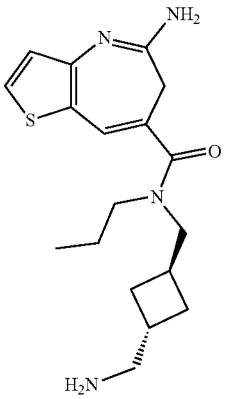 [SMILES: CCCN(C[C@H]1C[C@H](CN)C1)C(=O)C1=Cc2sccc2N=C(N)C1] | 346.49 | >9000 | 4297 |
| TAZ-70 | 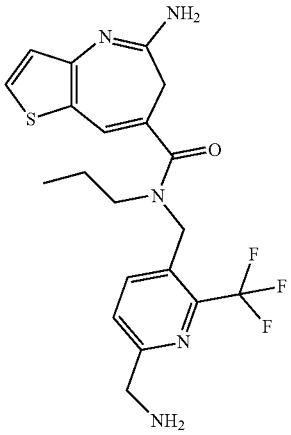 [SMILES: CCCN(Cc1ccc(CN)nc1C(F)(F)F)C(=O)C1=Cc2sccc2N=C(N)C1] | 437.48 | 6613 | 75 |

TABLE 1b-continued
| Thienoazepine compounds (TAZ) | | | | |
|---|---|---|---|---|
| TAZ No. | Structure | MW | HEK293 hTLR7 EC50 (nM) | HEK293 hTLR8 EC50 (nM) |
| TAZ-71 | 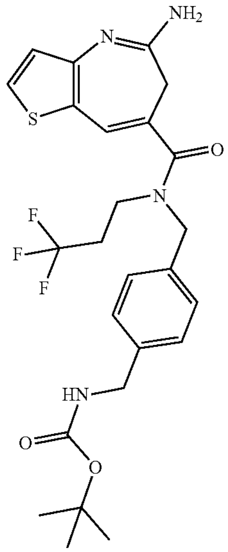 [SMILES: CC(C)(C)OC(=O)NCc1ccc(CN(CCC(F)(F)F)C(=O)C2=Cc3sccc3N=C(N)C2)cc1] | 522.58 | | |
| TAZ-72 | 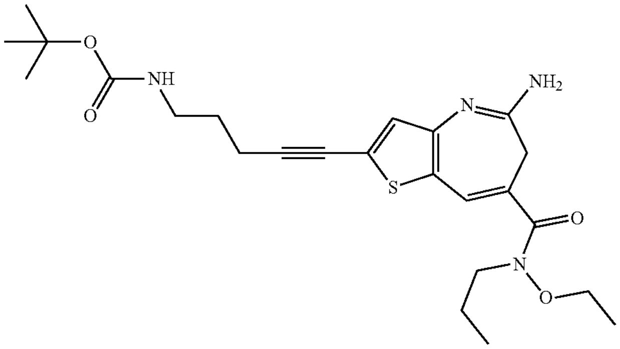 [SMILES: CCCN(OCC)C(=O)C1=Cc2sc(C#CCCCNC(=O)OC(C)(C)C)cc2N=C(N)C1] | 474.62 | 3146 | 2834 |
| TAZ-73 | 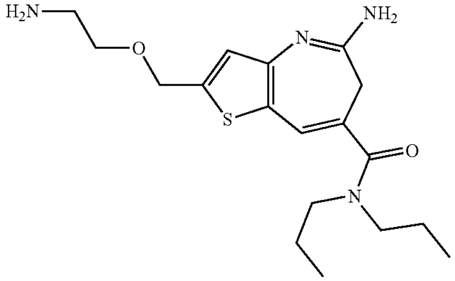 [SMILES: CCCN(CCC)C(=O)C1=Cc2sc(COCCN)cc2N=C(N)C1] | 378.53 | >9000 | 2985 |
| TAZ-74 | 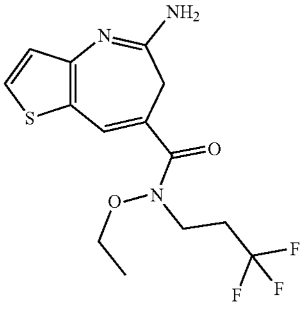 [SMILES: CCON(CCC(F)(F)F)C(=O)C1=Cc2sccc2N=C(N)C1] | 347.36 | 4108 | 301 |

TABLE 1b-continued
| Thienoazepine compounds (TAZ) | | | | |
|---|---|---|---|---|
| TAZ No. | Structure | MW | HEK293 hTLR7 EC50 (nM) | HEK293 hTLR8 EC50 (nM) |
| TAZ-75 | 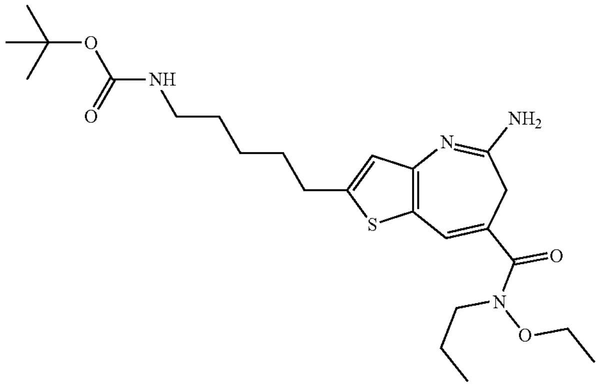 [SMILES: CCCN(OCC)C(=O)C1=Cc2sc(CCCCCNC(=O)OC(C)(C)C)cc2N=C(N)C1] | 478.65 | 5079 | 2025 |
| TAZ-76 | 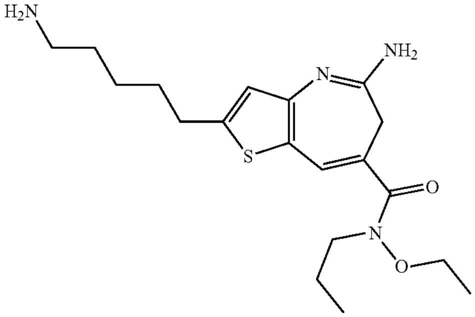 [SMILES: CCCN(OCC)C(=O)C1=Cc2sc(CCCCCN)cc2N=C(N)C1] | 378.53 | 3436 | 1418 |
| TAZ-77 | 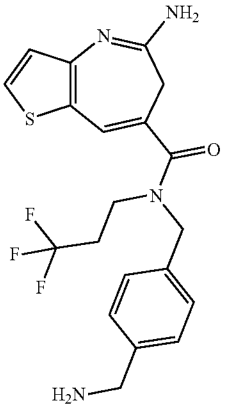 [SMILES: NCc1ccc(CN(CCC(F)(F)F)C(=O)C2=Cc3sccc3N=C(N)C2)cc1] | 422.47 | 3896 | 59 |

TABLE 1b-continued
| Thienoazepine compounds (TAZ) | | | | |
|---|---|---|---|---|
| TAZ No. | Structure | MW | HEK293 hTLR7 EC50 (nM) | HEK293 hTLR8 EC50 (nM) |
| TAZ-78 | 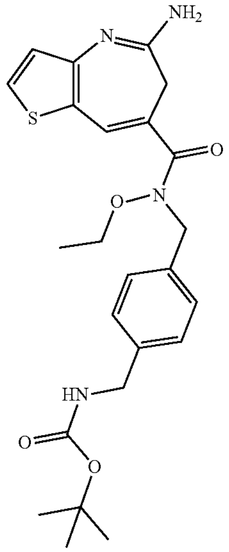 [SMILES: CCON(Cc1ccc(CNC(=O)OC(C)(C)C)cc1)C(=O)C1=Cc2sccc2N=C(N)C1] | 470.59 | Not available | Not available |
| TAZ-79 | 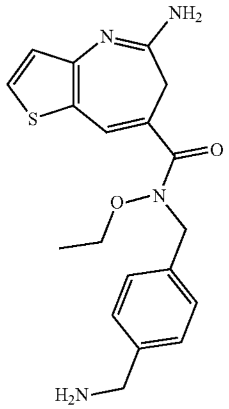 [SMILES: CCON(Cc1ccc(CN)cc1)C(=O)C1=Cc2sccc2N=C(N)C1] | 370.47 | >9000 | 4126 |
| TAZ-80 | 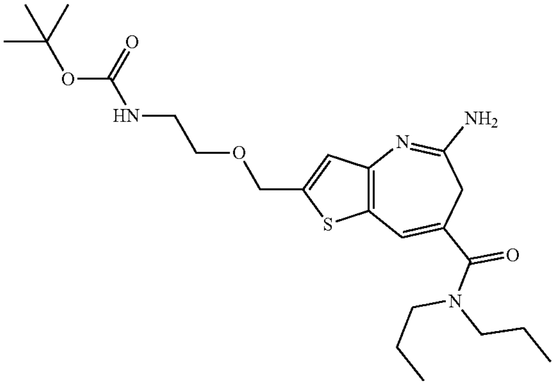 [SMILES: CCCN(CCC)C(=O)C1=Cc2sc(COCCNC(=O)OC(C)(C)C)cc2N=C(N)C1] | 464.62 | 4002 | 3793 |

TABLE 1b-continued
| Thienoazepine compounds (TAZ) | | | | |
|---|---|---|---|---|
| TAZ No. | Structure | MW | HEK293 hTLR7 EC50 (nM) | HEK293 hTLR8 EC50 (nM) |
| TAZ-81 | 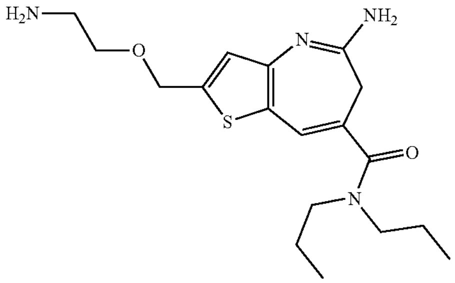 [SMILES: CCCN(CCC)C(=O)C1=Cc2sc(COCCN)cc2N=C(N)C1] | 364.51 | >9000 | 7951 |
| TAZ-82 | 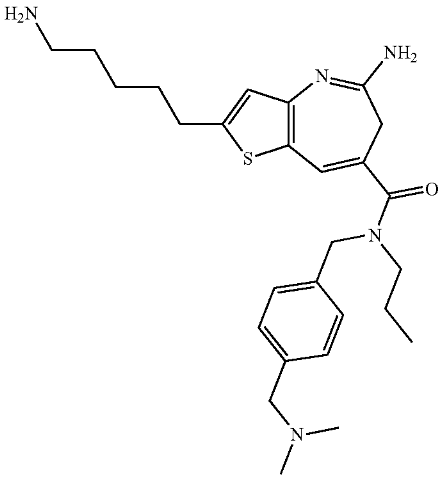 [SMILES: CCCN(Cc1ccc(CN(C)C)cc1)C(=O)C1=Cc2sc(CCCCCN)cc2N=C(N)C1] | 481.7 | 4998 | 2870 |
| TAZ-83 | 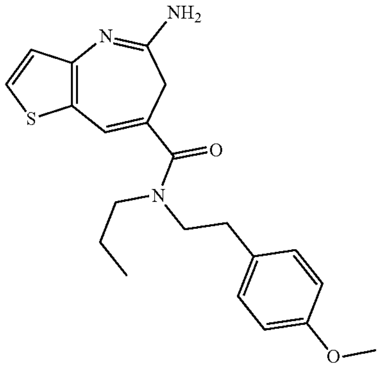 [SMILES: CCCN(CCc1ccc(OC)cc1)C(=O)C1=Cc2sccc2N=C(N)C1] | 383.51 | 3519 | 3369 |
| TAZ-84 | 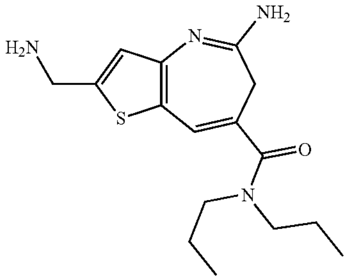 [SMILES: CCCN(CCC)C(=O)C1=Cc2sc(CN)cc2N=C(N)C1] | 320.45 | 4950 | 1373 |

TABLE 1b-continued
| Thienoazepine compounds (TAZ) | | | | |
|---|---|---|---|---|
| TAZ No. | Structure | MW | HEK293 hTLR7 EC50 (nM) | HEK293 hTLR8 EC50 (nM) |
| TAZ-85 | 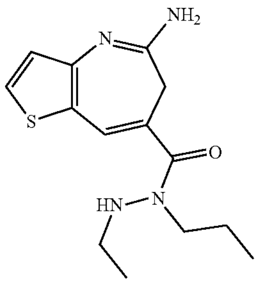 [SMILES: CCCN(NCC)C(=O)C1=Cc2sccc2N=C(N)C1] | 292.4 | >9000 | 4026 |
| TAZ-86 | 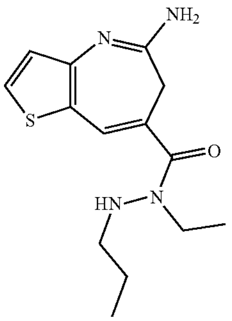 [SMILES: CCCNN(CC)C(=O)C1=Cc2sccc2N=C(N)C1] | 292.4 | >9000 | 4919 |
| TAZ-87 | 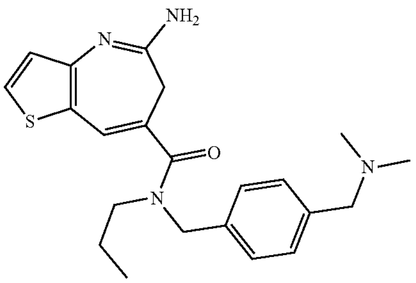 [SMILES: CCCN(Cc1ccc(CN(C)C)cc1)C(=O)C1=Cc2sccc2N=C(N)C1] | 396.55 | 1939 | 214 |
| TAZ-88 | 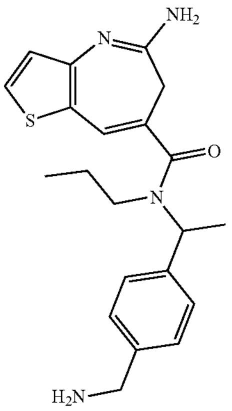 [SMILES: CCCN(C(=O)C1=Cc2sccc2N=C(N)C1)C(C)c1ccc(CN)cc1] | 382.52 | >9000 | 2270 |

TABLE 1b-continued
| Thienoazepine compounds (TAZ) | | | | |
|---|---|---|---|---|
| TAZ No. | Structure | MW | HEK293 hTLR7 EC50 (nM) | HEK293 hTLR8 EC50 (nM) |
| TAZ-89 | 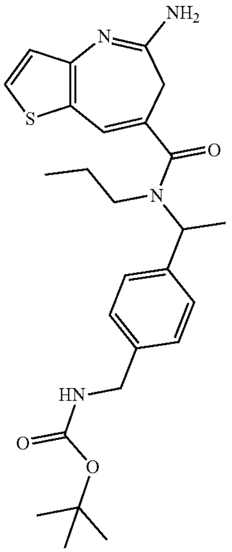 [SMILES: CCCN(C(=O)C1=Cc2sccc2N=C(N)C1)C(C)c1ccc(CNC(=O)OC(C)(C)C)cc1] | 482.64 | Not available | Not available |
| TAZ-90 | 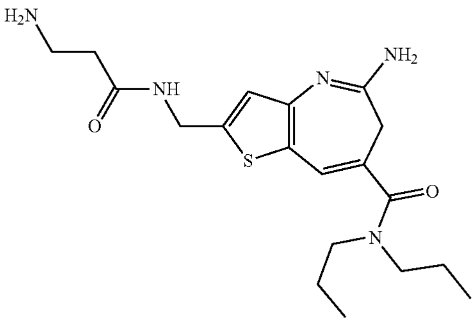 [SMILES: CCCN(CCC)C(=O)C1=Cc2sc(CNC(=O)CCN)cc2N=C(N)C1] | 391.53 | 909 | 3190 |
| TAZ-91 | 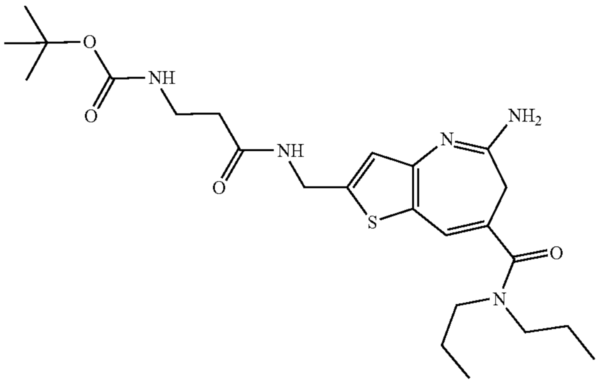 [SMILES: CCCN(CCC)C(=O)C1=Cc2sc(CNC(=O)CCNC(=O)OC(C)(C)C)cc2N=C(N)C1] | 491.65 | 4276 | 4151 |

TABLE 1b-continued
| Thienoazepine compounds (TAZ) | | | | |
|---|---|---|---|---|
| TAZ No. | Structure | MW | HEK293 hTLR7 EC50 (nM) | HEK293 hTLR8 EC50 (nM) |
| TAZ-92 | 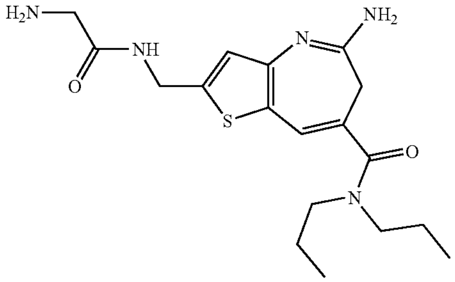 [SMILES: CCCN(CCC)C(=O)C1=Cc2sc(CNC(=O)CN)cc2N=C(N)C1] | 377.51 | >9000 | 2835 |
| TAZ-93 | 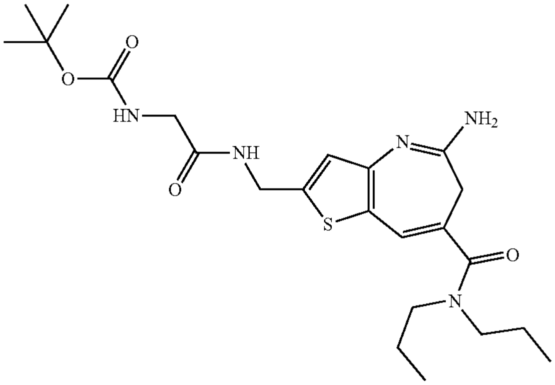 [SMILES: CCCN(CCC)C(=O)C1=Cc2sc(CNC(=O)CNC(=O)OC(C)(C)C)cc2N=C(N)C1] | 477.62 | 4494 | 3134 |
| TAZ-94 | 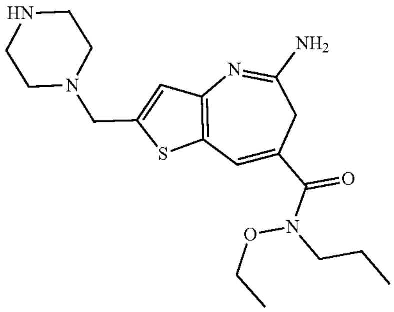 [SMILES: CCCN(OCC)C(=O)C1=Cc2sc(CN3CCNCC3)cc2N=C(N)C1] | 391.53 | 6202 | 101 |
| TAZ-95 | 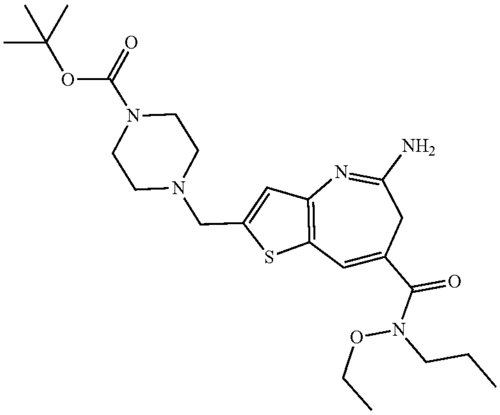 [SMILES: CCCN(OCC)C(=O)C1=Cc2sc(CN3CCN(C(=O)OC(C)(C)C)CC3)cc2N=C(N)C1] | 491.65 | Not available | Not available |

TABLE 1b-continued
| Thienoazepine compounds (TAZ) | | | | |
|---|---|---|---|---|
| TAZ No. | Structure | MW | HEK293 hTLR7 EC50 (nM) | HEK293 hTLR8 EC50 (nM) |
| TAZ-96 | 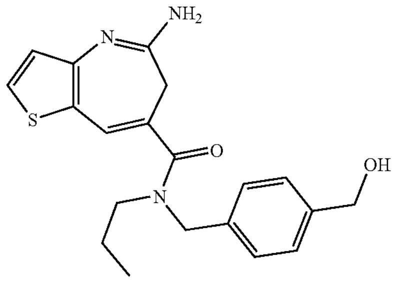 [SMILES: CCCN(Cc1ccc(CO)cc1)C(=O)C1=Cc2sccc2N=C(N)C1] | 369.48 | 2964 | 326 |
| TAZ-97 | 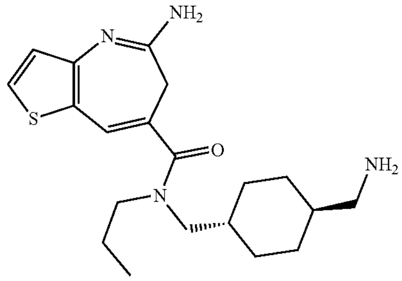 [SMILES: CCCN(C[C@H]1CC[C@H](CN)CC1)C(=O)C1=Cc2sccc2N=C(N)C1] | 374.54 | Not available | >9000 |
| TAZ-98 | 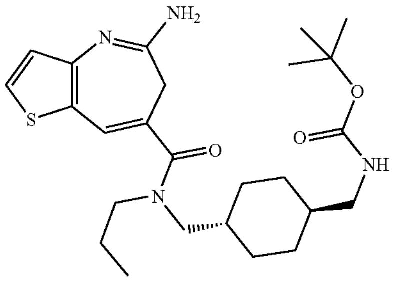 [SMILES: CCCN(C[C@H]1CC[C@H](CNC(=O)OC(C)(C)C)CC1)C(=O)C1=Cc2sccc2N=C(N)C1] | 474.66 | Not available | 631 |
| TAZ-99 | 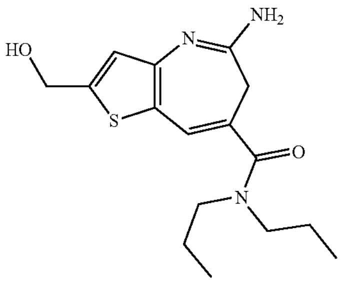 [SMILES: CCCN(CCC)C(=O)C1=Cc2sc(CO)cc2N=C(N)C1] | 321.44 | >9000 | 3622 |
| TAZ-100 | 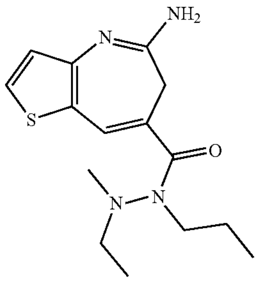 [SMILES: CCCN(C(=O)C1=Cc2sccc2N=C(N)C1)N(C)CC] | 306.43 | Not available | >9000 |

TABLE 1b-continued
| Thienoazepine compounds (TAZ) | | | | |
|---|---|---|---|---|
| TAZ No. | Structure | MW | HEK293 hTLR7 EC50 (nM) | HEK293 hTLR8 EC50 (nM) |
| TAZ-101 | 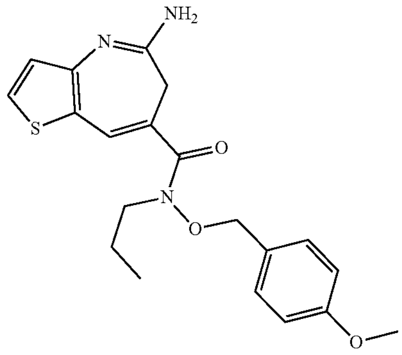 [SMILES: CCCN(OCc1ccc(OC)cc1)C(=O)C1=Cc2sccc2N=C(N)C1] | 385.48 | Not available | 203 |
| TAZ-102 | 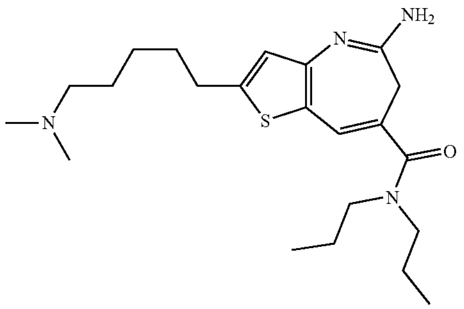 [SMILES: CCCN(CCC)C(=O)C1=Cc2sc(CCCCCN(C)C)cc2N=C(N)C1] | 404.61 | 793 | 384 |
| TAZ-103 | 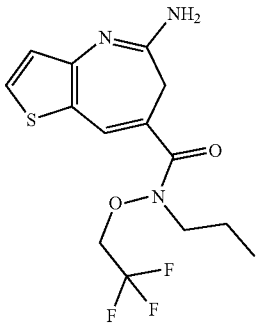 [SMILES: CCCN(OCC(F)(F)F)C(=O)C1=Cc2sccc2N=C(N)C1] | 347.36 | 3824 | 1377 |
| TAZ-104 | 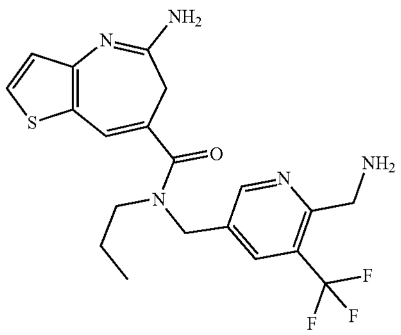 [SMILES: CCCN(Cc1cnc(CN)c(C(F)(F)F)c1)C(=O)C1=Cc2sccc2N=C(N)C1] | 437.48 | 31.73 | 1444 |

TABLE 1b-continued
| Thienoazepine compounds (TAZ) | | | | |
|---|---|---|---|---|
| TAZ No. | Structure | MW | HEK293 hTLR7 EC50 (nM) | HEK293 hTLR8 EC50 (nM) |
| TAZ-105 | 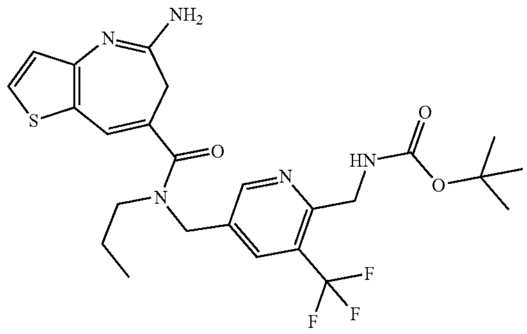 [SMILES: CCCN(Cc1cnc(CNC(=O)OC(C)(C)C)c(C(F)(F)F)c1)C(=O)C1=Cc2sccc2N=C(N)C1] | 537.6 | Not available | Not available |
| TAZ-106 | 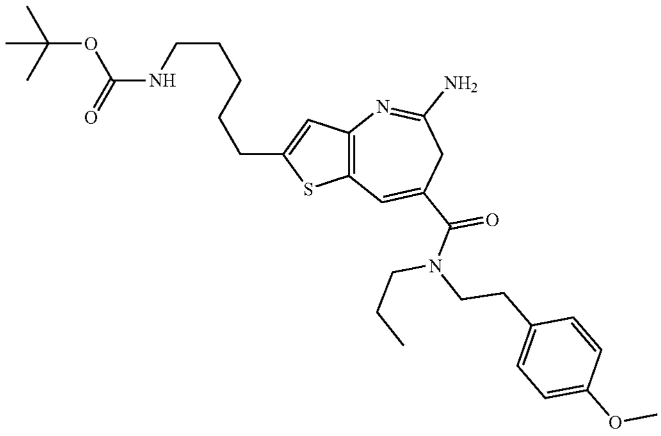 [SMILES: CCCN(CCc1ccc(OC)cc1)C(=O)C1=Cc2sc(CCCCCNC(=O)OC(C)(C)C)cc2N=C(N)C1] | 568.77 | 4732 | >9000 |
| TAZ-107 | 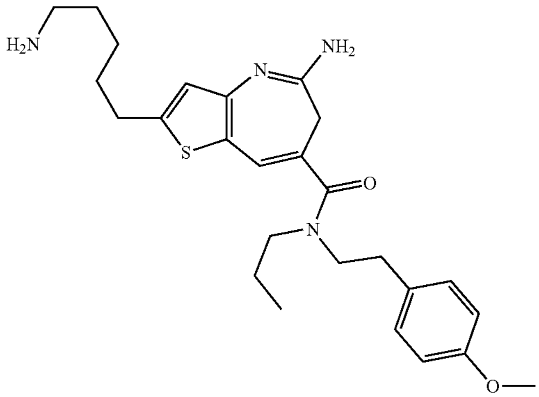 [SMILES: CCCN(CCc1ccc(OC)cc1)C(=O)C1=Cc2sc(CCCCCN)cc2N=C(N)C1] | 468.66 | 3579 | 6984 |

TABLE 1b-continued
| Thienoazepine compounds (TAZ) | | | | |
|---|---|---|---|---|
| TAZ No. | Structure | MW | HEK293 hTLR7 EC50 (nM) | HEK293 hTLR8 EC50 (nM) |
| TAZ-108 | 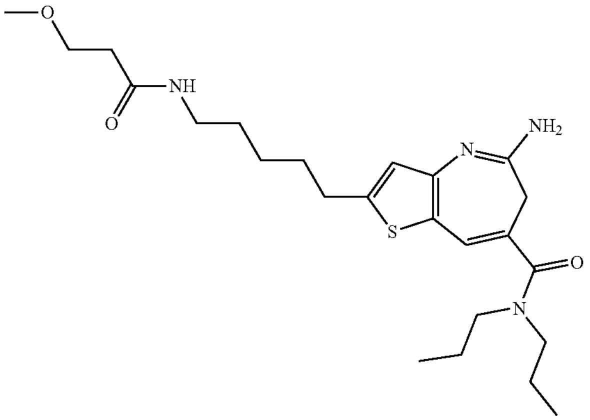 [SMILES: CCCN(CCC)C(=O)C1=Cc2sc(CCCCCNC(=O)CCOC)cc2N=C(N)C1] | 462.65 | 3852 | 3472 |
| TAZ-109 | 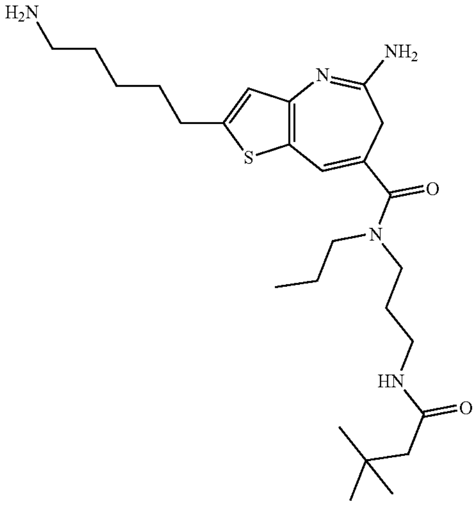 [SMILES: CCCN(CCCNC(=O)CC(C)(C)C)C(=O)C1=Cc2sc(CCCCCN)cc2N=C(N)C1] | 489.72 | | |
| TAZ-110 | 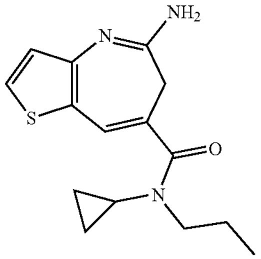 [SMILES: CCCN(C(=O)C1=Cc2sccc2N=C(N)C1)C1CC1] | 289.4 | | |
| TAZ-111 | 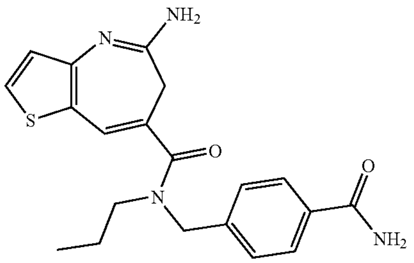 [SMILES: CCCN(Cc1ccc(C(N)=O)cc1)C(=O)C1=Cc2sccc2N=C(N)C1] | 382.48 | | |

TABLE 1b-continued
| Thienoazepine compounds (TAZ) | | | | |
|---|---|---|---|---|
| TAZ No. | Structure | MW | HEK293 hTLR7 EC50 (nM) | HEK293 hTLR8 EC50 (nM) |
| TAZ-112 | 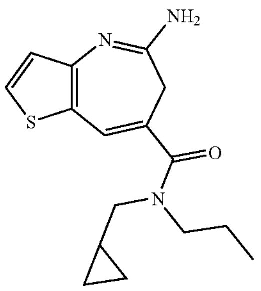 [SMILES: CCCN(CC1CC1)C(=O)C1=Cc2sccc2N=C(N)C1] | 303.42 | | |
| TAZ-113 | 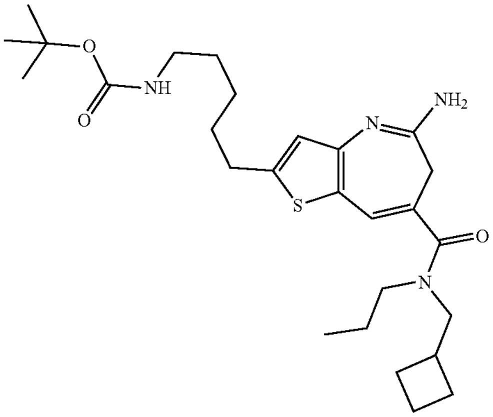 [SMILES: CCCN(CC1CCC1)C(=O)C1=Cc2sc(CCCCCNC(=O)OC(C)(C)C)cc2N=C(N)C1] | 502.71 | | |
| TAZ-114 | 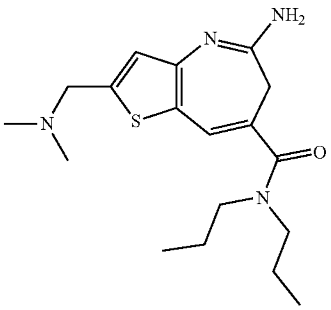 [SMILES: CCCN(CCC)C(=O)C1=Cc2sc(CN(C)C)cc2N=C(N)C1] | 348.51 | | |

TABLE 1b-continued
| Thienoazepine compounds (TAZ) | | | | |
|---|---|---|---|---|
| TAZ No. | Structure | MW | HEK293 hTLR7 EC50 (nM) | HEK293 hTLR8 EC50 (nM) |
| TAZ-115 | 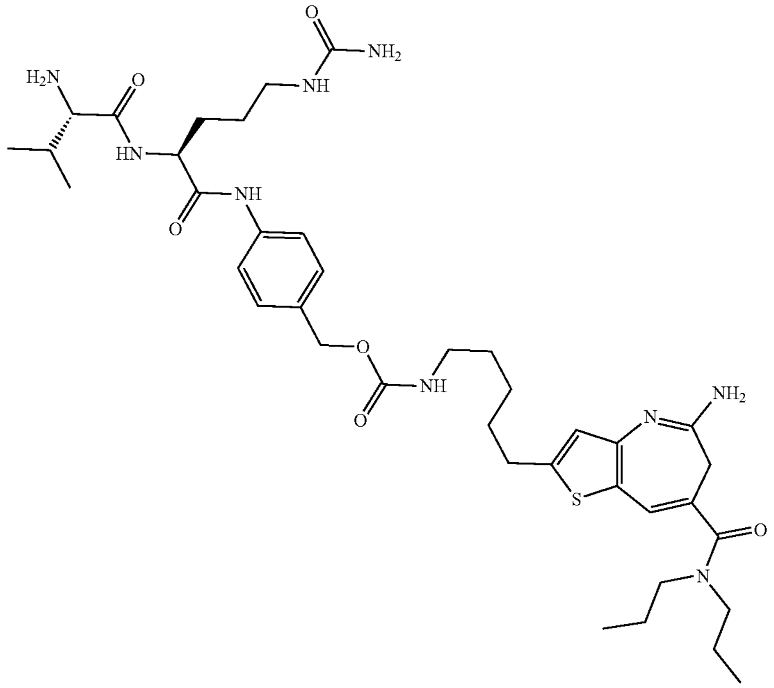 [SMILES: CCCN(CCC)C(=O)C1=Cc2sc(CCCCCNC(=O)OCc3ccc(NC(=O)[C@H](CCCNC(N)=O)NC(=O)[C@@H](N)C(C)C)cc3)cc2N=C(N)C1] | 782.01 | | |
TABLE 1c
| Thienoazepine compounds (TAZ) | | | | |
|---|---|---|---|---|
| TAZ No. | Structure | MW | HEK293 hTLR7 EC50 (nM) | HEK293 hTLR8 EC50 (nM) |
| TAZ-116 | 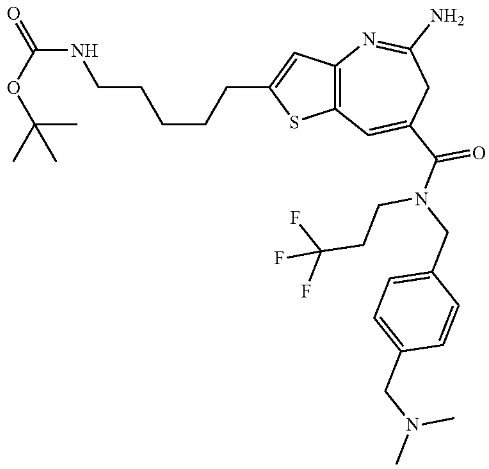 [SMILES: CN(C)Cc1ccc(CN(CCC(F)(F)F)C(=O)C2=Cc3sc(CCCCCNC(=O)OC(C)(C)C)cc3N=C(N)C2)cc1] | 635.8 | 1617 | |

TABLE 1c-continued
| Thienoazepine compounds (TAZ) | | | | |
|---|---|---|---|---|
| TAZ No. | Structure | MW | HEK293 hTLR7 EC50 (nM) | HEK293 hTLR8 EC50 (nM) |
| TAZ-117 | 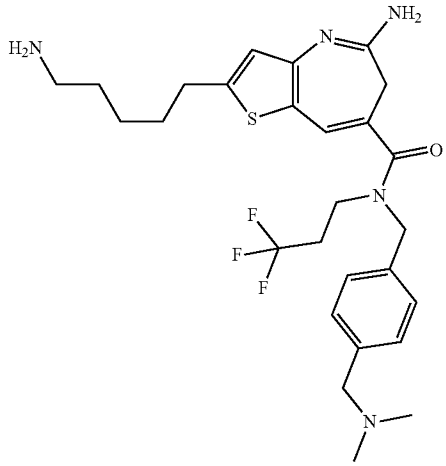 [SMILES: CN(C)Cc1ccc(CN(CCC(F)(F)F)C(=O)C2=Cc3sc(CCCCCN)cc3N=C(N)C2)cc1] | 535.7 | 9000 | 9000 |
| TAZ-118 | 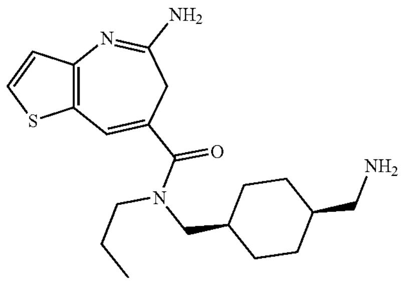 [SMILES: CCCN(C[C@H]1CC[C@@H](CN)CC1)C(=O)C1=Cc2sccc2N=C(N)C1] | 374.5 | 9000 | 4438 |
| TAZ-119 | 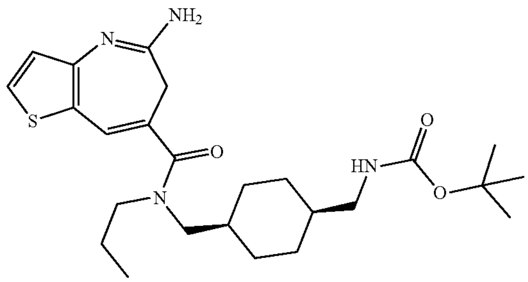 [SMILES: CCCN(C[C@H]1CC[C@@H](CNC(=O)OC(C)(C)C)CC1)C(=O)C1=Cc2sccc2N=C(N)C1] | 474.7 | 2875 | 9000 |
| TAZ-120 | 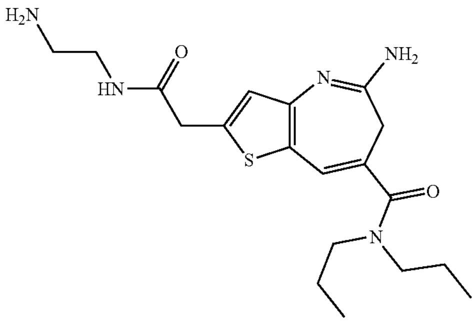 [SMILES: CCCN(CCC)C(=O)C1=Cc2sc(CC(=O)NCCN)cc2N=C(N)C1] | 391.5 | 9000 | 9000 |

TABLE 1c-continued
| Thienoazepine compounds (TAZ) | | | | |
|---|---|---|---|---|
| TAZ No. | Structure | MW | HEK293 hTLR7 EC50 (nM) | HEK293 hTLR8 EC50 (nM) |
| TAZ-121 | 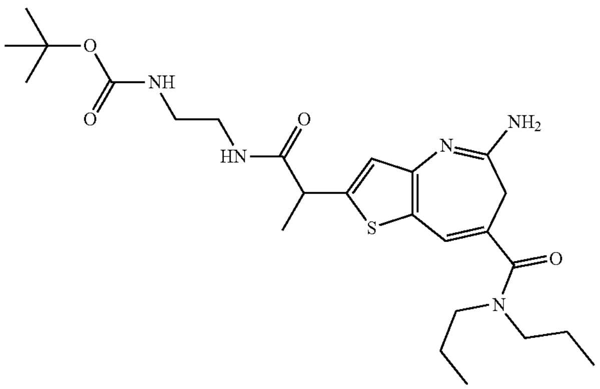 [SMILES: CCCN(CCC)C(=O)C1=Cc2sc(C(C)C(=O)NCCNC(=O)OC(C)(C)C)cc2N=C(N)C1] | 491.7 | | |
| TAZ-122 | 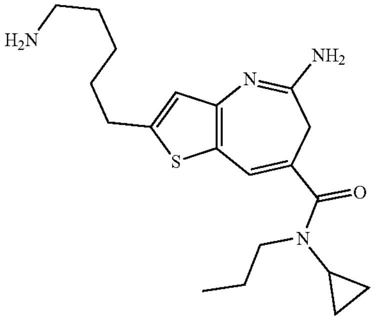 [SMILES: CCCN(C(=O)C1=Cc2sc(CCCCCN)cc2N=C(N)C1)C1CC1] | 374.5 | 3349 | 3244 |
| TAZ-123 | 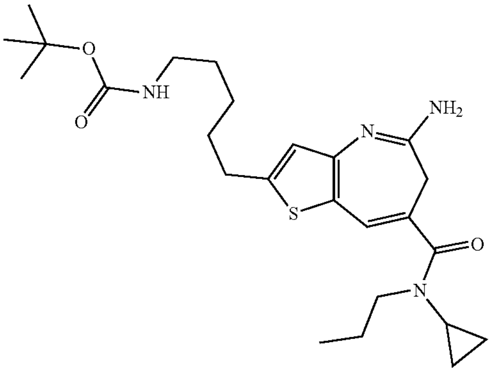 [SMILES: CCCN(C(=O)C1=Cc2sc(CCCCCNC(=O)OC(C)(C)C)cc2N=C(N)C1)C1CC1] | 474.7 | 4629 | 9000 |
| TAZ-124 | 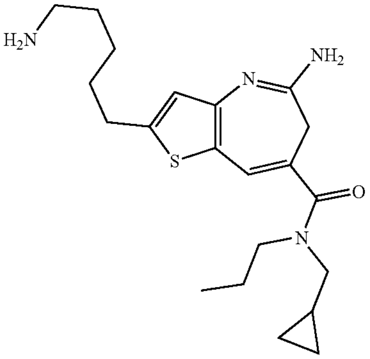 [SMILES: CCCN(CC1CC1)C(=O)C1=Cc2sc(CCCCCN)cc2N=C(N)C1] | 388.6 | 1727 | 1942 |

TABLE 1c-continued
| Thienoazepine compounds (TAZ) | | | | |
|---|---|---|---|---|
| TAZ No. | Structure | MW | HEK293 hTLR7 EC50 (nM) | HEK293 hTLR8 EC50 (nM) |
| TAZ-125 | 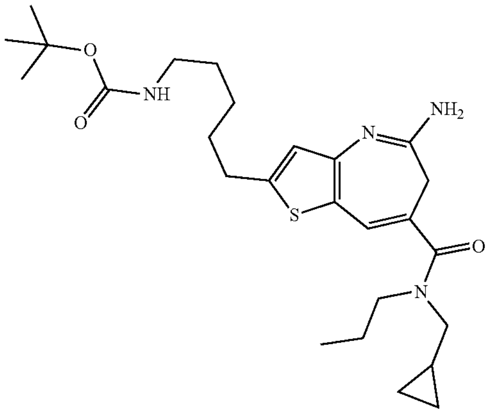 [SMILES: CCCN(CC1CC1)C(=O)C1=Cc2sc(CCCCCNC(=O)OC(C)(C)C)cc2N=C(N)C1] | 488.7 | 2705 | 9000 |
| TAZ-126 | 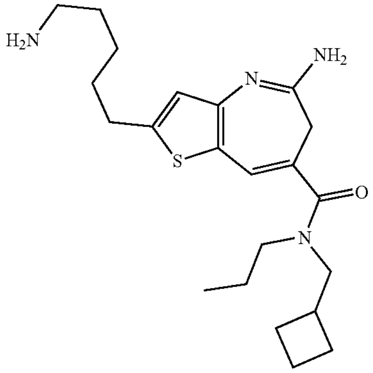 [SMILES: CCCN(CC1CCC1)C(=O)C1=Cc2sc(CCCCCN)cc2N=C(N)C1] | 402.6 | 950 | 633 |
| TAZ-127 | 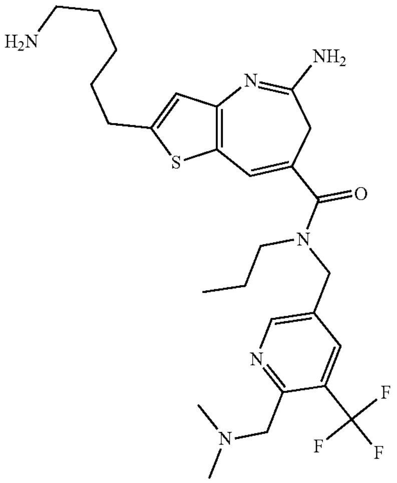 [SMILES: CCCN(Cc1cnc(CN(C)C)c(C(F)(F)F)c1)C(=O)C1=Cc2sc(CCCCCN)cc2N=C(N)C1] | 550.7 | 9000 | |

TABLE 1c-continued
| Thienoazepine compounds (TAZ) | | | | |
|---|---|---|---|---|
| TAZ No. | Structure | MW | HEK293 hTLR7 EC50 (nM) | HEK293 hTLR8 EC50 (nM) |
| TAZ-128 | 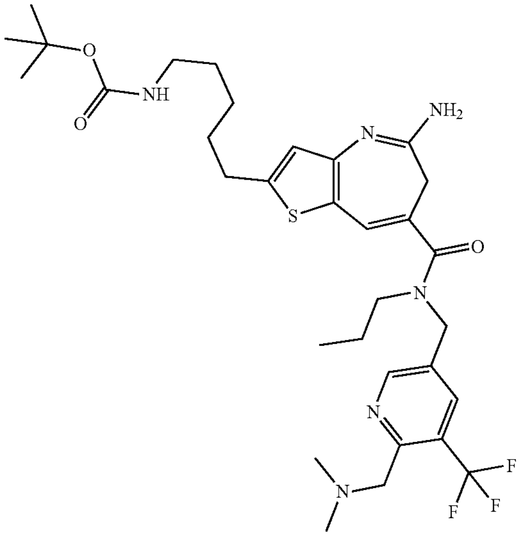 [SMILES: CCCN(Cc1cnc(CN(C)C)c(C(F)(F)F)c1)C(=O)C1=Cc2sc(CCCCCNC(=O)OC(C)(C)C)cc2N=C(N)C1] | 650.8 | 9000 | 9000 |
| TAZ-129 | 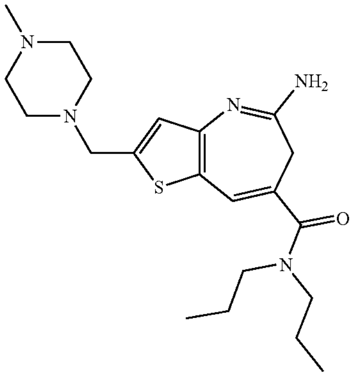 [SMILES: CCCN(CCC)C(=O)C1=Cc2sc(CN3CCN(C)CC3)cc2N=C(N)C1] | 403.6 | 5571 | 848 |
| TAZ-130 | 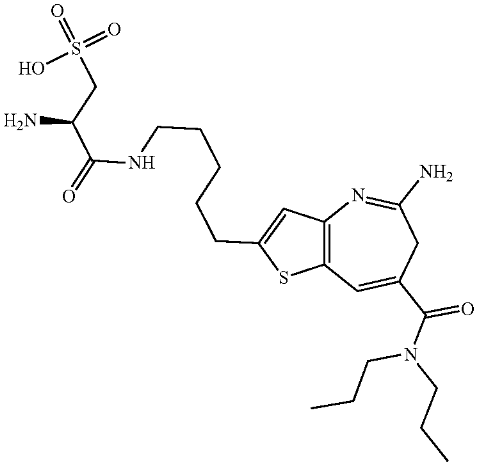 [SMILES: CCCN(CCC)C(=O)C1=Cc2sc(CCCCCNC(=O)[C@@H](N)CS(=O)(=O)O)cc2N=C(N)C1] | 527.7 | | |

TABLE 1c-continued
| Thienoazepine compounds (TAZ) | | | | |
|---|---|---|---|---|
| TAZ No. | Structure | MW | HEK293 hTLR7 EC50 (nM) | HEK293 hTLR8 EC50 (nM) |
| TAZ-131 | 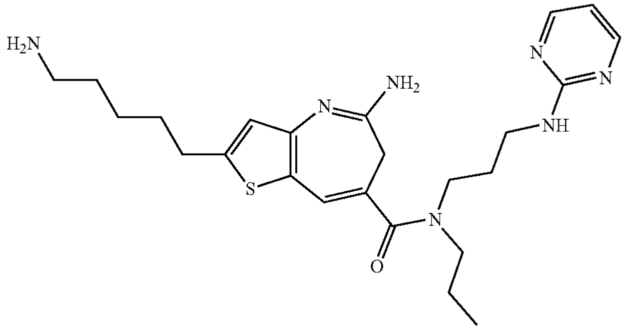 [SMILES: CCCN(CCCNc1ncccn1)C(=O)C1=Cc2sc(CCCCCN)cc2N=C(N)C1] | 469.7 | | |
| TAZ-132 | 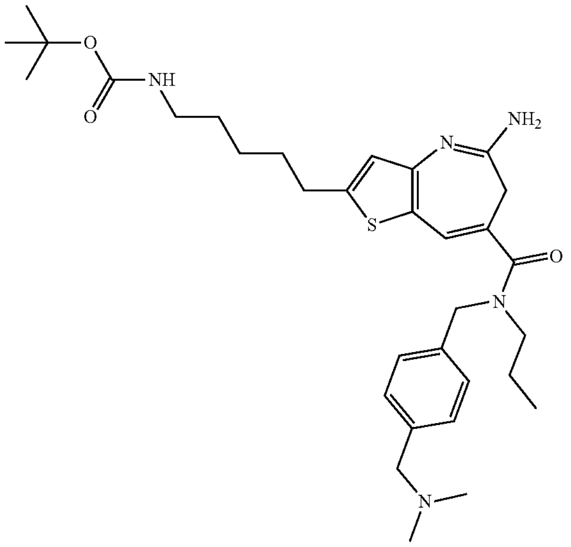 [SMILES: CCCN(Cc1ccc(CN(C)C)cc1)C(=O)C1=Cc2sc(CCCCCNC(=O)OC(C)(C)C)cc2N=C(N)C1] | 581.8 | | |
| TAZ-133 | 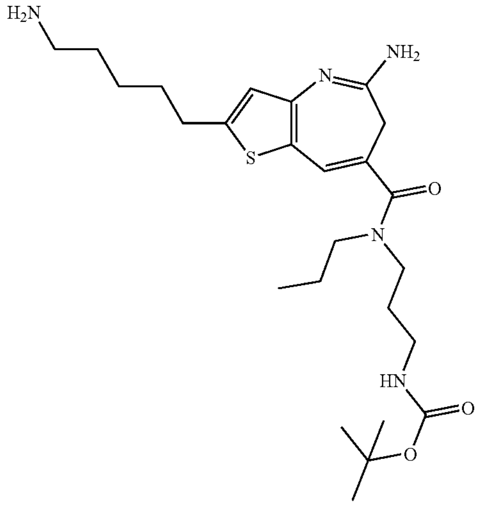 [SMILES: CCCN(CCCNC(=O)OC(C)(C)C)C(=O)C1=Cc2sc(CCCCCN)cc2N=C(N)C1] | 491.7 | 586 | 3008 |

TABLE 1c-continued
| TAZ No. | Structure | MW | HEK293 hTLR7 EC50 (nM) | HEK293 hTLR8 EC50 (nM) |
|---|---|---|---|---|
| Thienoazepine compounds (TAZ) | | | | |
| TAZ-134 | 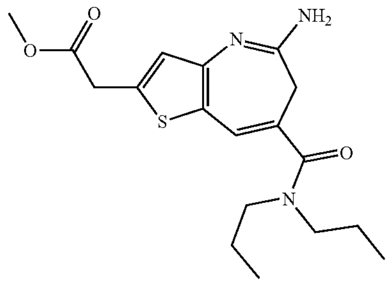 [SMILES: CCCN(CCC)C(=O)C1=Cc2sc(CC(=O)OC)cc2N=C(N)C1] | 363.5 | 4697 | 3420 |
| TAZ-135 | 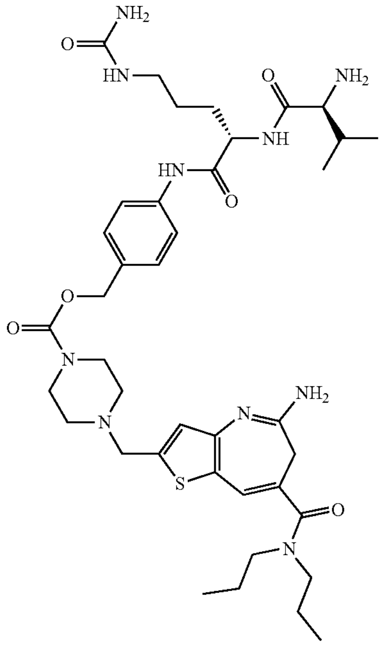 [SMILES: CCCN(CCC)C(=O)C1=Cc2sc(CN3CCN(C(=O)OCc4ccc(NC(=O)[C@H](CCCNC(N)=O)NC(=O)[C@@H](N)C(C)C)cc4)CC3)cc2N=C(N)C1] | 795.0 | | |
| TAZ-136 | 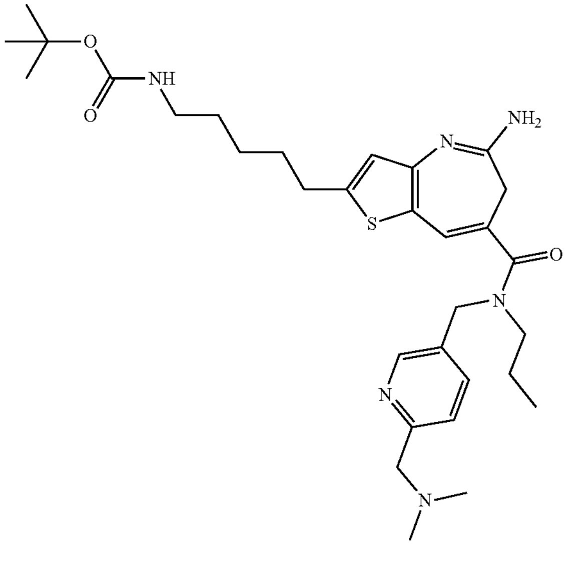 [SMILES: CCCN(Cc1ccc(CN(C)C)nc1)C(=O)C1=Cc2sc(CCCCCNC(=O)OC(C)(C)C)cc2N=C(N)C1] | 582.8 | | |

TABLE 1c-continued
| Thienoazepine compounds (TAZ) | | | | |
|---|---|---|---|---|
| TAZ No. | Structure | MW | HEK293 hTLR7 EC50 (nM) | HEK293 hTLR8 EC50 (nM) |
| TAZ-137 | 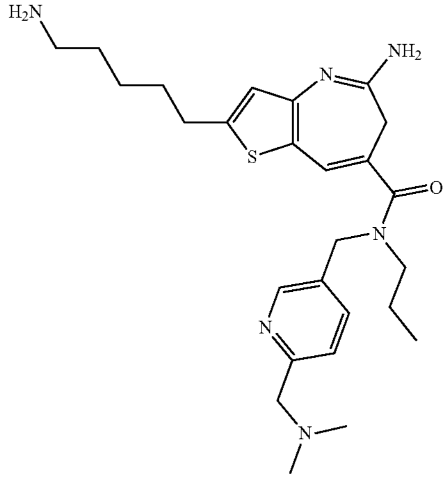 [SMILES: CCCN(Cc1ccc(CN(C)C)nc1)C(=O)C1=Cc2sc(CCCCCN)cc2N=C(N)C1] | 482.7 | | |
| TAZ-138 | 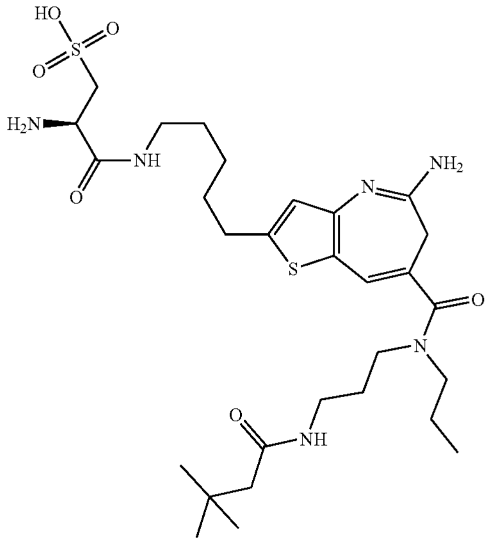 [SMILES: CCCN(CCCNC(=O)CC(C)(C)C)C(=O)C1=Cc2sc(CCCCCNC(=O)[C@@H](N)CS(=O)(=O)O)cc2N=C(N)C1] | 640.9 | | |
| TAZ-139 | 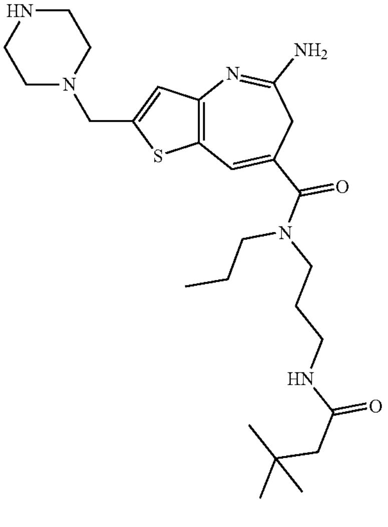 [SMILES: CCCN(CCCNC(=O)CC(C)(C)C)C(=O)C1=Cc2sc(CN3CCNCC3)cc2N=C(N)C1] | 502.7 | 4206 | 9000 |

TABLE 1c-continued
| TAZ No. | Structure | MW | HEK293 hTLR7 EC50 (nM) | HEK293 hTLR8 EC50 (nM) |
| --- | --- | --- | --- | --- |
| Thienoazepine compounds (TAZ) | | | | |
| TAZ-140 | 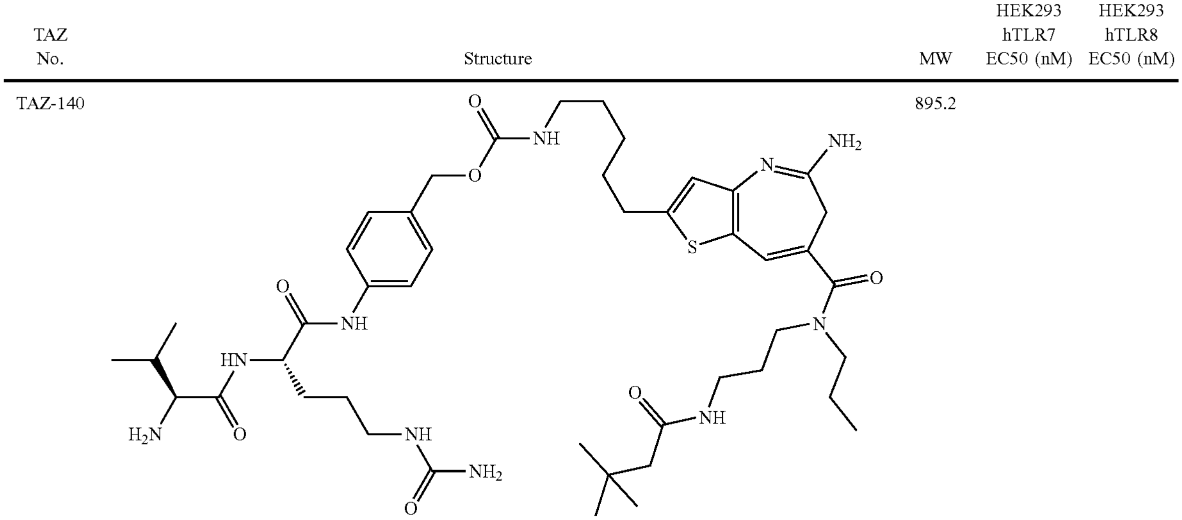 | 895.2 | | |
| TAZ-141 | 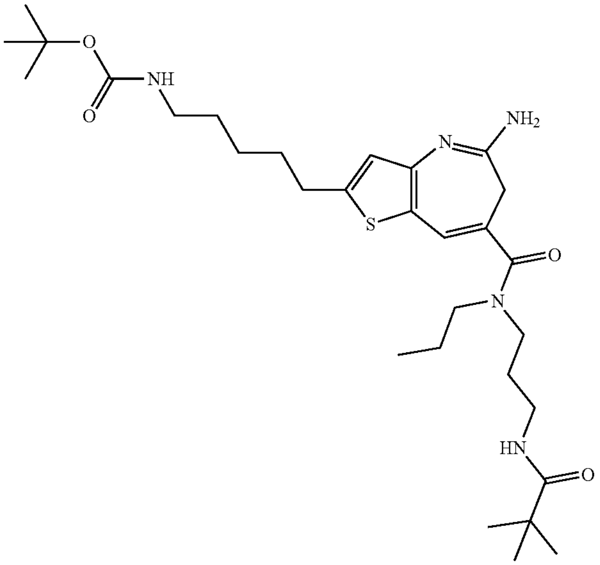 [SMILES: CCCN(CCCNC(=O)C(C)(C)C)C(=O)C1=Cc2sc(CCCCCNC(=O)OC(C)(C)C)cc2N=C(N)C1] | 575.8 | 380 | 3583 |
| TAZ-142 | 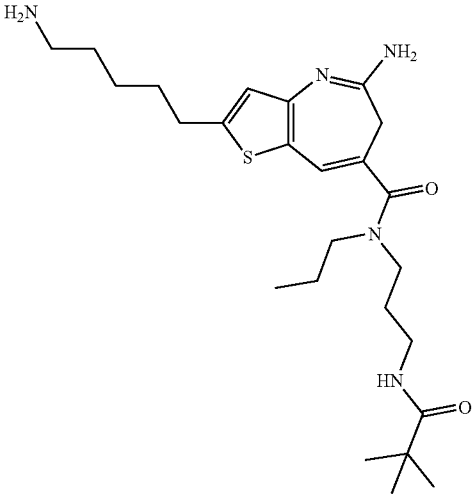 [SMILES: CCCN(CCCNC(=O)C(C)(C)C)C(=O)C1=Cc2sc(CCCCCN)cc2N=C(N)C1] | 475.7 | 827 | 9000 |

TABLE 1c-continued
| Thienoazepine compounds (TAZ) | | | | |
|---|---|---|---|---|
| TAZ No. | Structure | MW | HEK293 hTLR7 EC50 (nM) | HEK293 hTLR8 EC50 (nM) |
| TAZ-143 | 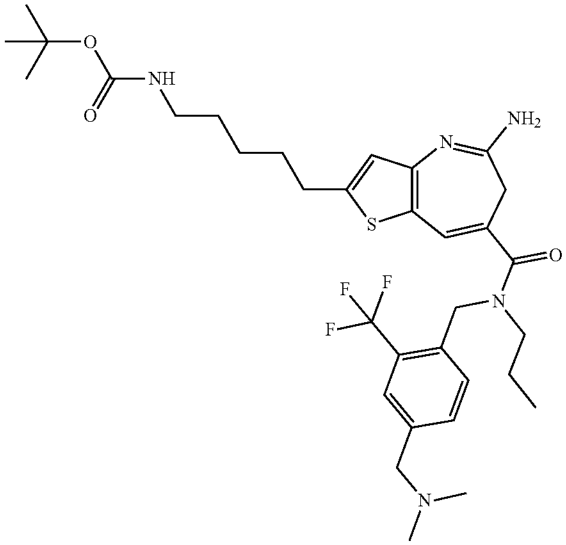 [SMILES: CCCN(Cc1ccc(CN(C)C)cc1C(F)(F)F)C(=O)C1=Cc2sc(CCCCCNC(=O)OC(C)(C)C)cc2N=C(N)C1] | 649.8 | 1884 | 9000 |
| TAZ-144 | 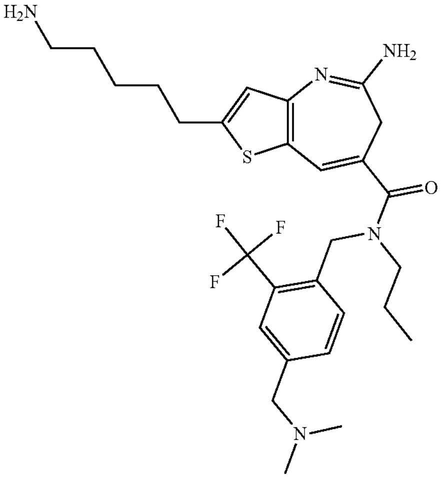 [SMILES: CCCN(Cc1ccc(CN(C)C)cc1C(F)(F)F)C(=O)C1=Cc2sc(CCCCCN)cc2N=C(N)C1] | 549.7 | 1282 | 2855 |
| TAZ-145 | 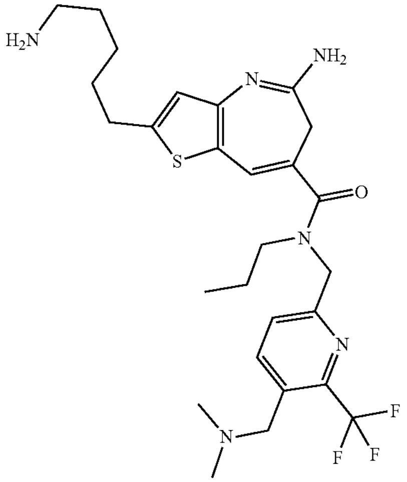 [SMILES: CCCN(Cc1ccc(CN(C)C)c(C(F)(F)F)n1)C(=O)C1=Cc2sc(CCCCCN)cc2N=C(N)C1] | 550.7 | 5940 | 4009 |

TABLE 1c-continued
Thienoazepine compounds (TAZ)
| TAZ No. | Structure | MW | HEK293 hTLR7 EC50 (nM) | HEK293 hTLR8 EC50 (nM) |
|---|---|---|---|---|
| TAZ-146 | 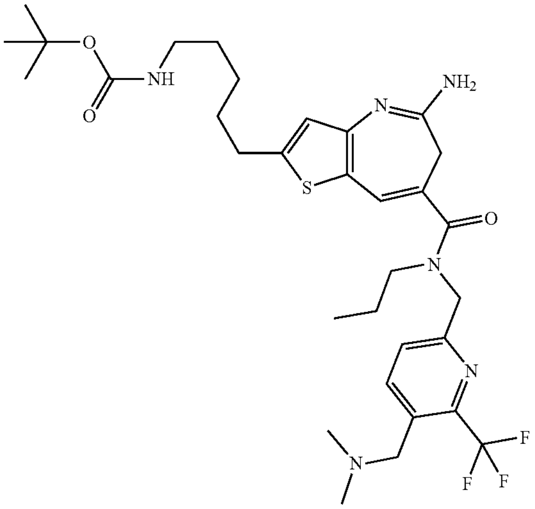 [SMILES: CCCN(Cc1ccc(CN(C)C)c(C(F)(F)F)n1)C(=O)C1=Cc2sc(CCCCCNC(=O)OC(C)(C)C)cc2N=C(N)C1] | 650.8 | 9000 | 9000 |
| TAZ-147 | 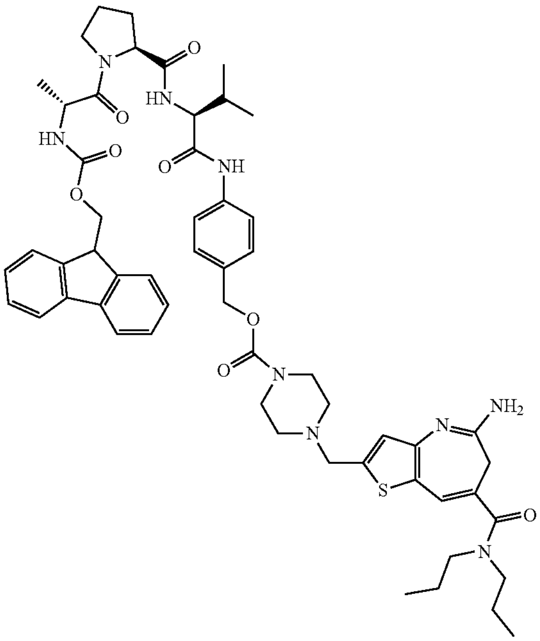 [SMILES: CCCN(CCC)C(=O)C1=Cc2sc(CN3CCN(C(=O)OCc4ccc(NC(=O)[C@@H](NC(=O)[C@@H]5CCCN5C(=O)[C@@H](C)NC(=O)OCC5c6ccccc6-c6ccccc65)C(C)C)cc4)CC3)cc2N=C(N)C1] | 1028.3 | | |

TABLE 1c-continued
| Thienoazepine compounds (TAZ) | | | | |
|---|---|---|---|---|
| TAZ No. | Structure | MW | HEK293 hTLR7 EC50 (nM) | HEK293 hTLR8 EC50 (nM) |
| TAZ-148 | 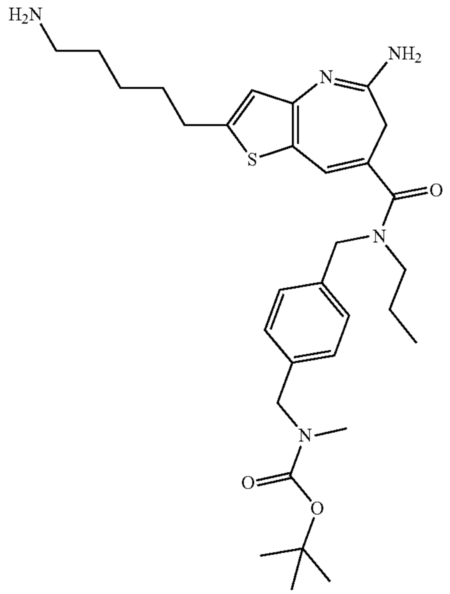 [SMILES: CCCN(Cc1ccc(CN(C)C(=O)OC(C)(C)C)cc1)C(=O)C1=Cc2sc(CCCCCN)cc2N=C(N)C1] | 567.8 | | |
| TAZ-149 | 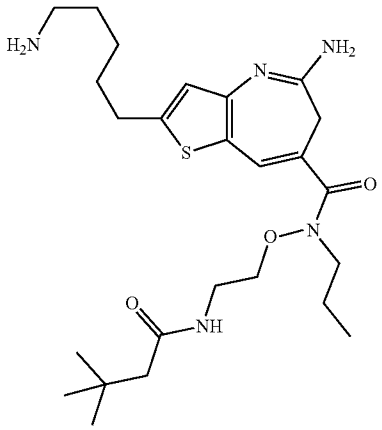 [SMILES: CCCN(OCCNC(=O)CC(C)(C)C)C(=O)C1=Cc2sc(CCCCCN)cc2N=C(N)C1] | 491.7 | 534 | 2237 |
| TAZ-150 | 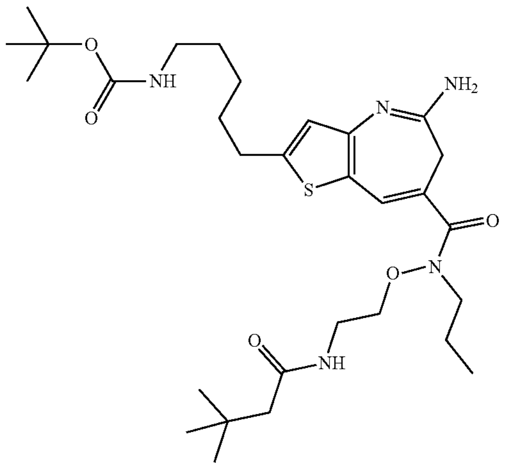 [SMILES: CCCN(OCCNC(=O)CC(C)(C)C)C(=O)C1=Cc2sc(CCCCCNC(=O)OC(C)(C)C)cc2N=C(N)C1] | 591.8 | 1990 | 1668 |

TABLE 1c-continued
| Thienoazepine compounds (TAZ) | | | | |
|---|---|---|---|---|
| TAZ No. | Structure | MW | HEK293 hTLR7 EC50 (nM) | HEK293 hTLR8 EC50 (nM) |
| TAZ-151 | 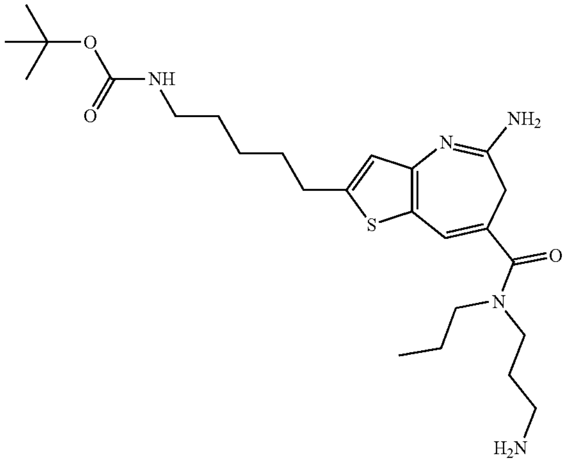 [SMILES: CCCN(CCCN)C(=O)C1=Cc2sc(CCCCCNC(=O)OC(C)(C)C)cc2N=C(N)C1] | 491.7 | | |
| TAZ-152 | 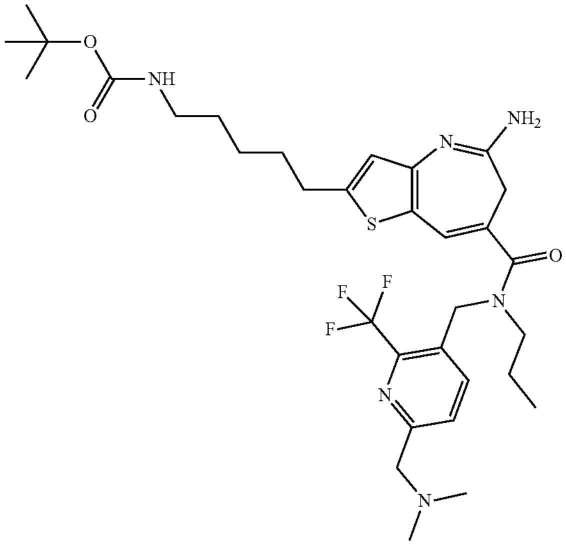 [SMILES: CCCN(Cc1ccc(CN(C)C)nc1C(F)(F)F)C(=O)C1=Cc2sc(CCCCCNC(=O)OC(C)(C)C)cc2N=C(N)C1] | 650.8 | | |
| TAZ-153 | 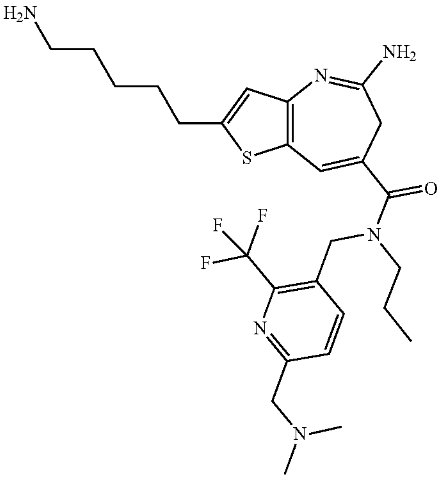 [SMILES: CCCN(Cc1ccc(CN(C)C)nc1C(F)(F)F)C(=O)C1=Cc2sc(CCCCCN)cc2N=C(N)C1] | 550.7 | | |

TABLE 1c-continued
| Thienoazepine compounds (TAZ) | | | | |
|---|---|---|---|---|
| TAZ No. | Structure | MW | HEK293 hTLR7 EC50 (nM) | HEK293 hTLR8 EC50 (nM) |
| TAZ-154 | 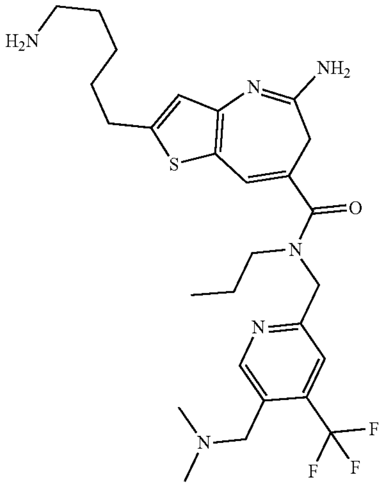 [SMILES: CCCN(Cc1cc(C(F)(F)F)c(CN(C)C)cn1)C(=O)C1=Cc2sc(CCCCCN)cc2N=C(N)C1] | 550.7 | | |
| TAZ-155 | 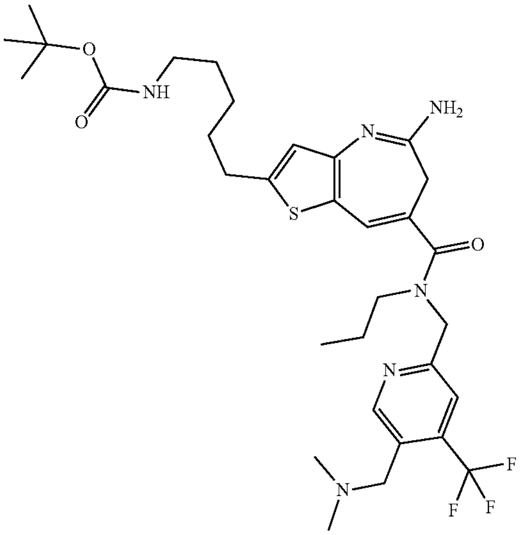 [SMILES: CCCN(Cc1cc(C(F)(F)F)c(CN(C)C)cn1)C(=O)C1=Cc2sc(CCCCCNC(=O)OC(C)(C)C)cc2N=C(N)C1] | 650.8 | | |

TABLE 1c-continued
| TAZ No. | Structure | MW | HEK293 hTLR7 EC50 (nM) | HEK293 hTLR8 EC50 (nM) |
|---|---|---|---|---|
| Thienoazepine compounds (TAZ) | | | | |
| TAZ-156 | 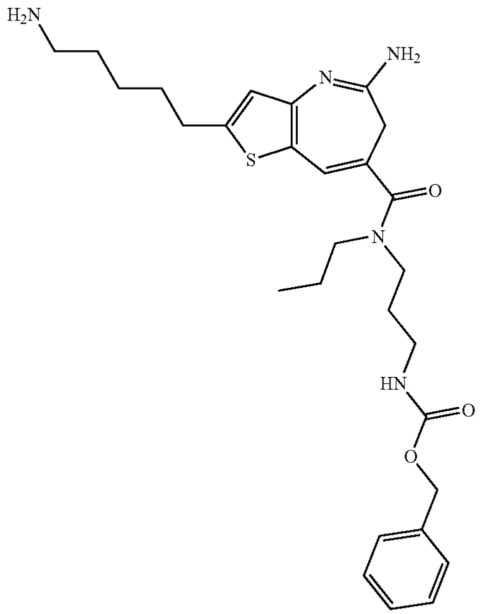 [SMILES: CCCN(CCCNC(=O)OCc1ccccc1)C(=O)C1=Cc2sc(CCCCCN)cc2N=C(N)C1] | 525.7 | | |
| TAZ-157 | 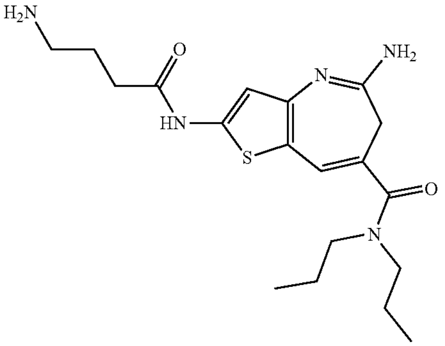 [SMILES: CCCN(CCC)C(=O)C1=Cc2sc(NC(=O)CCCN)cc2N=C(N)C1] | 391.5 | | |
| TAZ-158 | 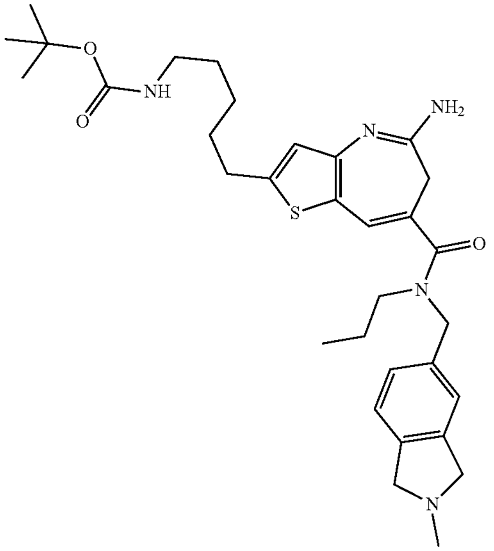 [SMILES: CCCN(Cc1ccc2c(c1)CN(C)C2)C(=O)C1=Cc2sc(CCCCCNC(=O)OC(C)(C)C)cc2N=C(N)C1] | 578.8 | | |

TABLE 1c-continued
| Thienoazepine compounds (TAZ) | | | | |
|---|---|---|---|---|
| TAZ No. | Structure | MW | HEK293 hTLR7 EC50 (nM) | HEK293 hTLR8 EC50 (nM) |
| TAZ-159 | 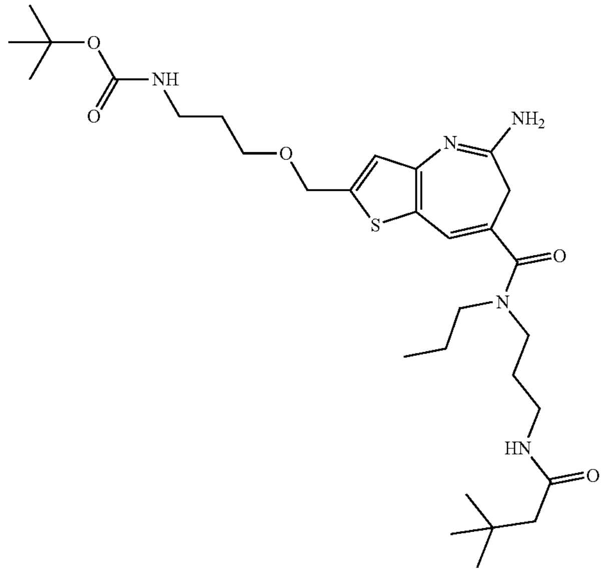 [SMILES: CCCN(CCCNC(=O)CC(C)(C)C)C(=O)C1=Cc2sc(COCCCNC(=O)OC(C)(C)C)cc2N=C(N)C1] | 591.8 | | |
| TAZ-160 | 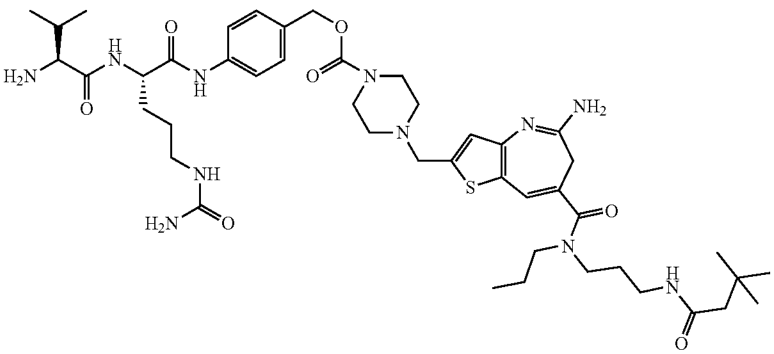 [SMILES: CCCN(CCCNC(=O)CC(C)(C)C)C(=O)C1=Cc2sc(CN3CCN(C(=O)OCc4ccc(NC(=O)[C@H](CCCNC(N)=O)NC(=O)[C@@H](N)C(C)C)cc4)CC3)cc2N=C(N)C1] | 908.2 | | |

TABLE 1c-continued
| Thienoazepine compounds (TAZ) | | | | |
|---|---|---|---|---|
| TAZ No. | Structure | MW | HEK293 hTLR7 EC50 (nM) | HEK293 hTLR8 EC50 (nM) |
| TAZ-161 | 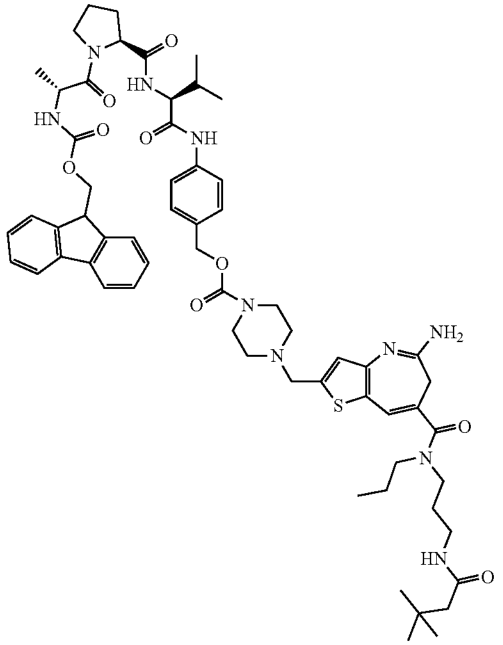 [SMILES: CCCN(CCCNC(=O)CC(C)(C)C)C(=O)C1=Cc2sc(CN3CCN(C(=O)OCc4ccc(NC(=O)[C@@H](NC(=O)[C@@H]5CCCN5C(=O)[C@@H](C)NC(=O)OCC5c6ccccc6-c6ccccc65)C(C)C)cc4)CC3)cc2N=C(N)C1] | 1141.4 | | |
| TAZ-162 | 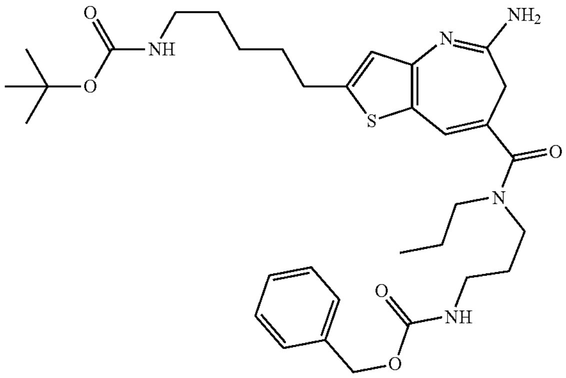 [SMILES: CCCN(CCCNC(=O)OCc1ccccc1)C(=O)C1=Cc2sc(CCCCCNC(=O)OC(C)(C)C)cc2N=C(N)C1] | 625.8 | 1238 | 1247 |
| TAZ-163 | 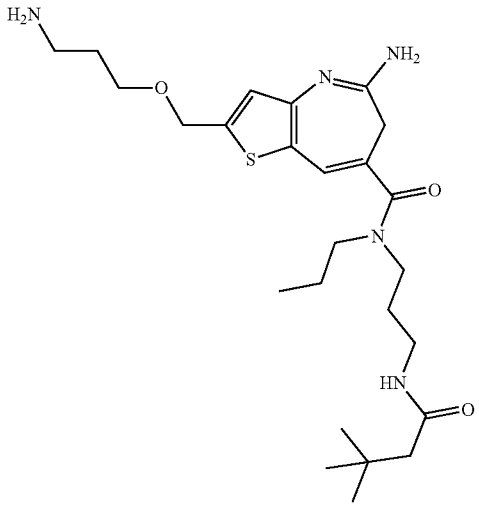 [SMILES: CCCN(CCCNC(=O)CC(C)(C)C)C(=O)C1=Cc2sc(COCCCN)cc2N=C(N)C1] | 491.7 | | |

TABLE 1c-continued
| Thienoazepine compounds (TAZ) | | | | |
|---|---|---|---|---|
| TAZ No. | Structure | MW | HEK293 hTLR7 EC50 (nM) | HEK293 hTLR8 EC50 (nM) |
| TAZ-164 | 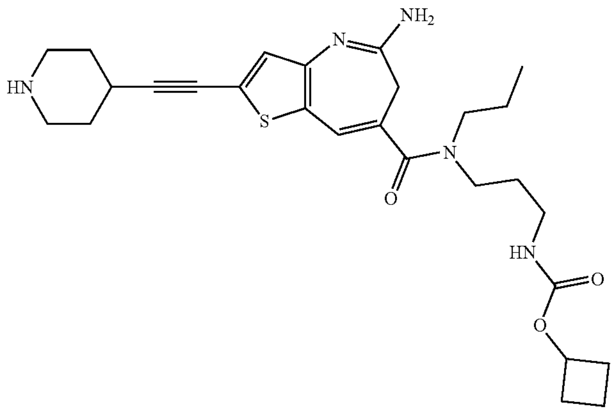 [SMILES: CCCN(CCCNC(=O)OC1CCC1)C(=O)C1=Cc2sc(C#CC3CCNCC3)cc2N=C(N)C1] | 511.7 | 476 | 3889 |
| TAZ-165 | 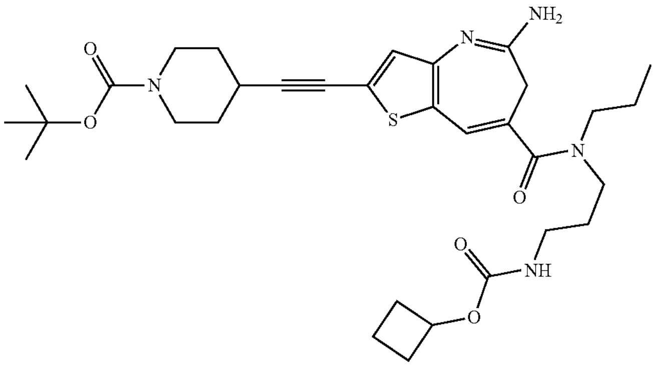 [SMILES: CCCN(CCCNC(=O)OC1CCC1)C(=O)C1=Cc2sc(C#CC3CCN(C(=O)OC(C)(C)C)CC3)cc2N=C(N)C1] | 611.8 | 9000 | |
| TAZ-166 | 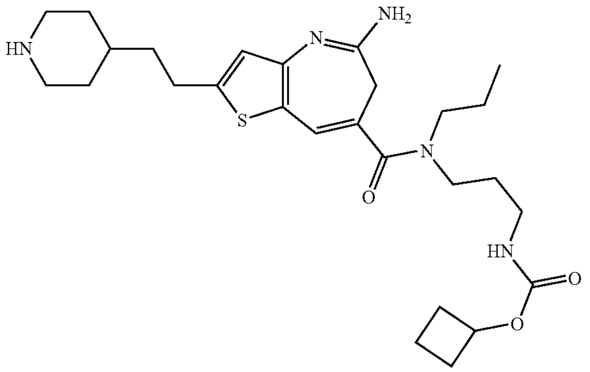 [SMILES: CCCN(CCCNC(=O)OC1CCC1)C(=O)C1=Cc2sc(CCC3CCNCC3)cc2N=C(N)C1] | 515.7 | 802 | 3697 |

TABLE 1c-continued
| Thienoazepine compounds (TAZ) | | | | |
|---|---|---|---|---|
| TAZ No. | Structure | MW | HEK293 hTLR7 EC50 (nM) | HEK293 hTLR8 EC50 (nM) |
| TAZ-167 | 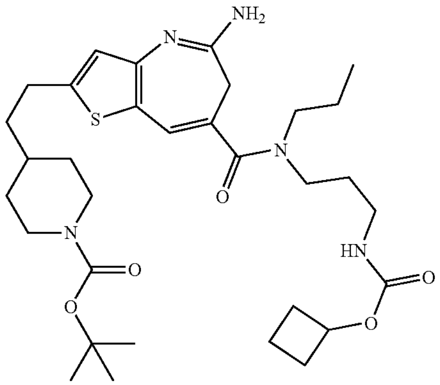 [SMILES: CCCN(CCCNC(=O)OC1CCC1)C(=O)C1=Cc2sc(CCC3CCN(C(=O)OC(C)(C)C)CC3)cc2N=C(N)C1] | 615.8 | 3129 | |
| TAZ-168 | 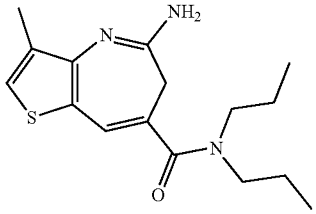 [SMILES: CCCN(CCC)C(=O)C1=Cc2scc(C)c2N=C(N)C1] | 305.4 | 9000 | 3875 |
| TAZ-169 | 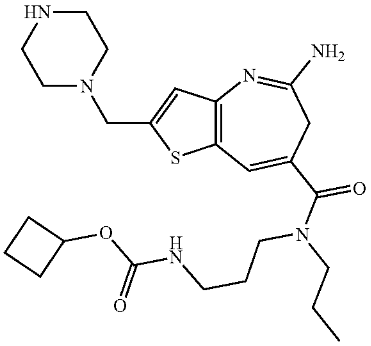 [SMILES: CCCN(CCCNC(=O)OC1CCC1)C(=O)C1=Cc2sc(CN3CCNCC3)cc2N=C(N)C1] | 502.7 | 3174 | 9000 |
| TAZ-170 | 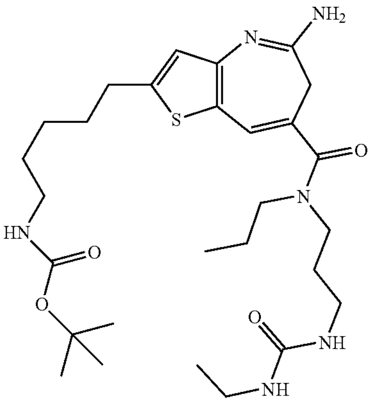 [SMILES: CCCN(CCCNC(=O)NCC)C(=O)C1=Cc2sc(CCCCCNC(=O)OC(C)(C)C)cc2N=C(N)C1] | 562.8 | 282 | 3371 |

TABLE 1c-continued
| Thienoazepine compounds (TAZ) | | | | |
|---|---|---|---|---|
| TAZ No. | Structure | MW | HEK293 hTLR7 EC50 (nM) | HEK293 hTLR8 EC50 (nM) |
| TAZ-171 | 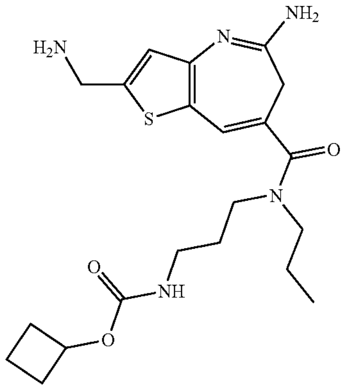 [SMILES: CCCN(CCCNC(=O)OC1CCC1)C(=O)C1=Cc2sc(CN)cc2N=C(N)C1] | 433.6 | 5288 | 3128 |
| TAZ-172 | 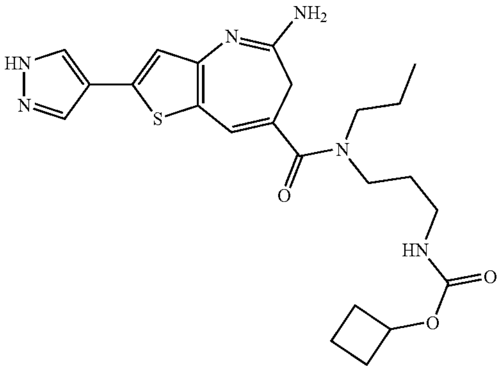 [SMILES: CCCN(CCCNC(=O)OC1CCC1)C(=O)C1=Cc2sc(-c3cn[nH]c3)cc2N=C(N)C1] | 470.6 | 153 | 3695 |
| TAZ-173 | 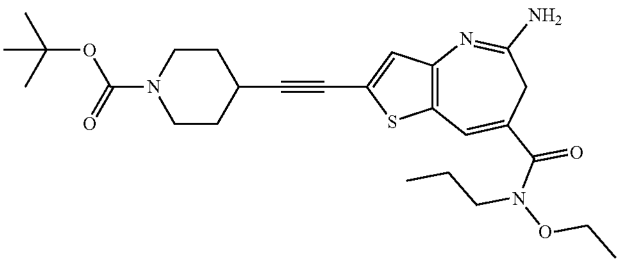 [SMILES: CCCN(OCC)C(=O)C1=Cc2sc(C#CC3CCN(C(=O)OC(C)(C)C)CC3)cc2N=C(N)C1] | 500.7 | 7689 | 9000 |
| TAZ-174 | 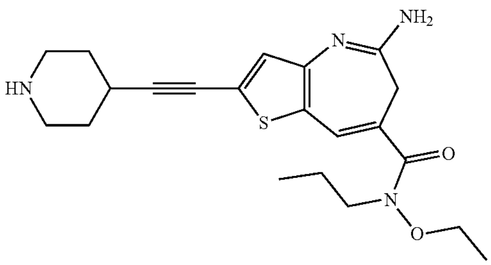 [SMILES: CCCN(OCC)C(=O)C1=Cc2sc(C#CC3CCNCC3)cc2N=C(N)C1] | 400.5 | 5809 | 1641 |

TABLE 1c-continued
Thienoazepine compounds (TAZ)
| TAZ No. | Structure | MW | HEK293 hTLR7 EC50 (nM) | HEK293 hTLR8 EC50 (nM) |
|---|---|---|---|---|
| TAZ-175 | 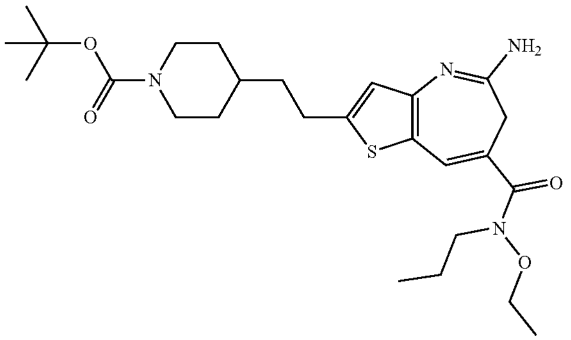 [SMILES: CCCN(OCC)C(=O)C1=Cc2sc(CCC3CCN(C(=O)OC(C)(C)C)CC3)cc2N=C(N)C1] | 504.7 | 4178 | 474 |
| TAZ-176 | 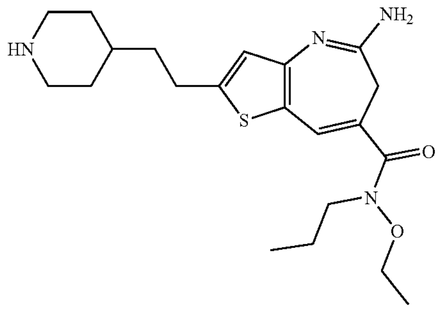 [SMILES: CCCN(OCC)C(=O)C1=Cc2sc(CCC3CCNCC3)cc2N=C(N)C1] | 404.6 | 915 | 249 |
| TAZ-177 | 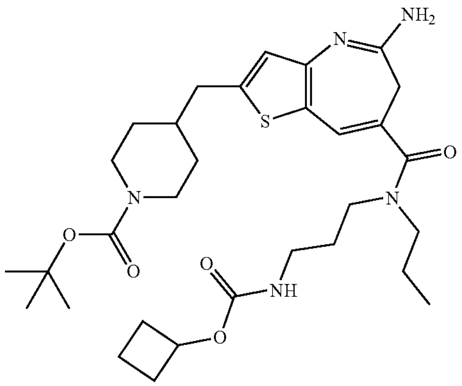 [SMILES: CCCN(CCCNC(=O)OC1CCC1)C(=O)C1=Cc2sc(CC3CCN(C(=O)OC(C)(C)C)CC3)cc2N=C(N)C1] | 601.8 | 882 | 3402 |
| TAZ-178 | 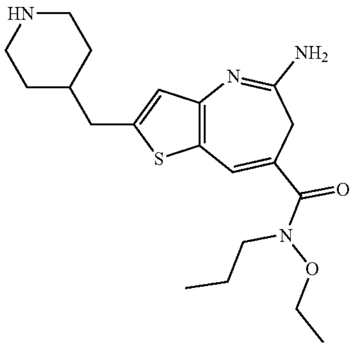 [SMILES: CCCN(OCC)C(=O)C1=Cc2sc(CC3CCNCC3)cc2N=C(N)C1] | 390.5 | 714 | 124 |

TABLE 1c-continued
| Thienoazepine compounds (TAZ) | | | | |
|---|---|---|---|---|
| TAZ No. | Structure | MW | HEK293 hTLR7 EC50 (nM) | HEK293 hTLR8 EC50 (nM) |
| TAZ-179 | 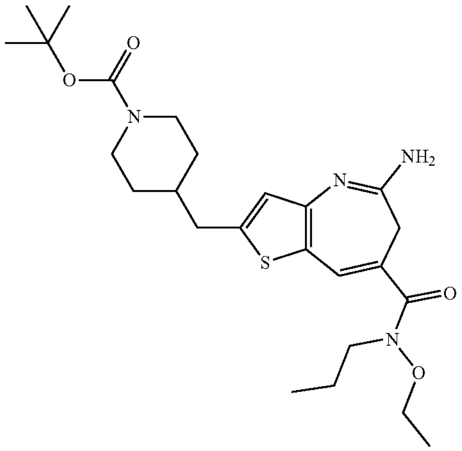 [SMILES: CCCN(OCC)C(=O)C1=Cc2sc(CC3CCN(C(=O)OC(C)(C)C)CC3)cc2N=C(N)C1] | 490.7 | 9000 | 2543 |
| TAZ-180 | 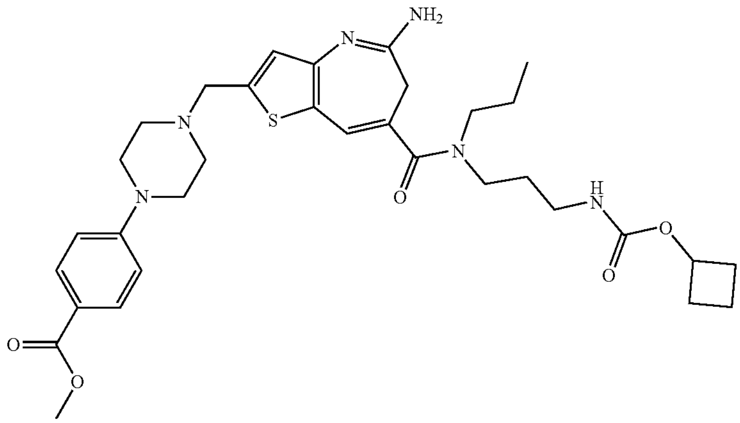 [SMILES: CCCN(CCCNC(=O)OC1CCC1)C(=O)C1=Cc2sc(CN3CCN(c4ccc(C(=O)OC)cc4)CC3)cc2N=C(N)C1] | 636.8 | 3648 | 9000 |
| TAZ-181 | 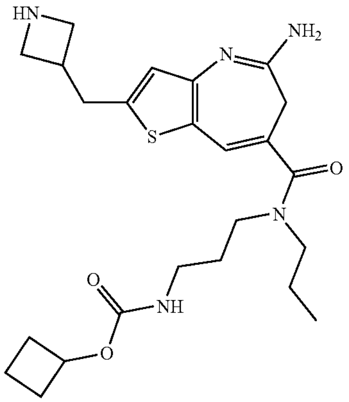 [SMILES: CCCN(CCCNC(=O)OC1CCC1)C(=O)C1=Cc2sc(CC3CNC3)cc2N=C(N)C1] | 473.6 | 2032 | 9000 |

TABLE 1c-continued
| Thienoazepine compounds (TAZ) | | | | |
|---|---|---|---|---|
| TAZ No. | Structure | MW | HEK293 hTLR7 EC50 (nM) | HEK293 hTLR8 EC50 (nM) |
| TAZ-182 | 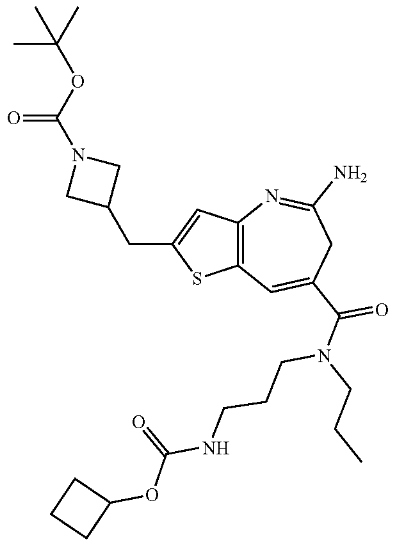 [SMILES: CCCN(CCCNC(=O)OC1CCC1)C(=O)C1=Cc2sc(CC3CN(C(=O)OC(C)(C)C)C3)cc2N=C(N)C1] | 573.8 | 101 | 840 |
| TAZ-183 | 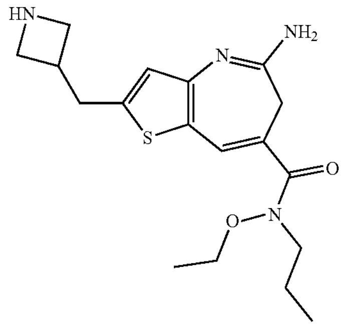 [SMILES: CCCN(OCC)C(=O)C1=Cc2sc(CC3CNC3)cc2N=C(N)C1] | 362.5 | 3560 | 485 |
| TAZ-184 | 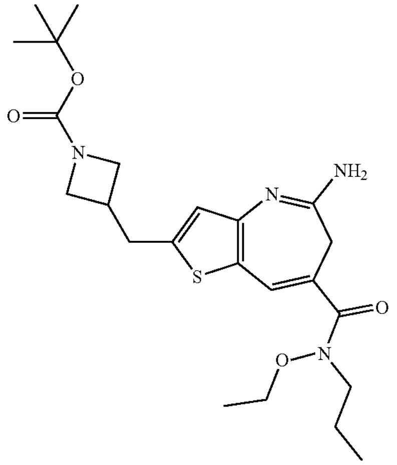 [SMILES: CCCN(OCC)C(=O)C1=Cc2sc(CC3CN(C(=O)OC(C)(C)C)C3)cc2N=C(N)C1] | 462.6 | 922 | 930 |

TABLE 1c-continued
| Thienoazepine compounds (TAZ) | | | | |
|---|---|---|---|---|
| TAZ No. | Structure | MW | HEK293 hTLR7 EC50 (nM) | HEK293 hTLR8 EC50 (nM) |
| TAZ-185 | 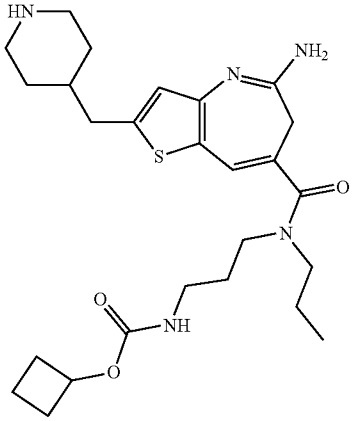 [SMILES: CCCN(CCCNC(=O)OC1CCC1)C(=O)C1=Cc2sc(CC3CCNCC3)cc2N=C(N)C1] | 501.7 | 3704 | 9000 |
| TAZ-186 | 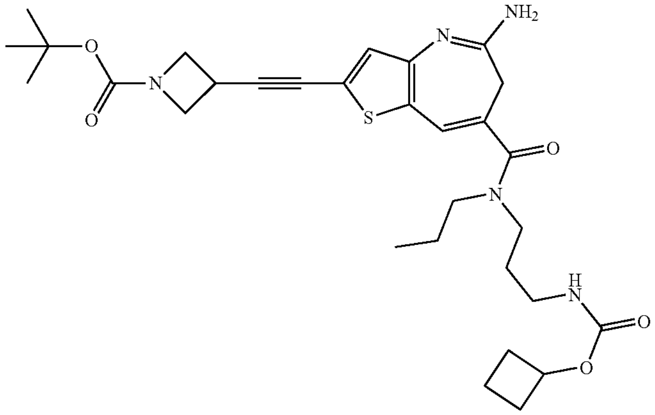 [SMILES: CCCN(CCCNC(=O)OC1CCC1)C(=O)C1=Cc2sc(C#CC3CN(C(=O)OC(C)(C)C)C3)cc2N=C(N)C1] | 583.7 | | |
| TAZ-187 | 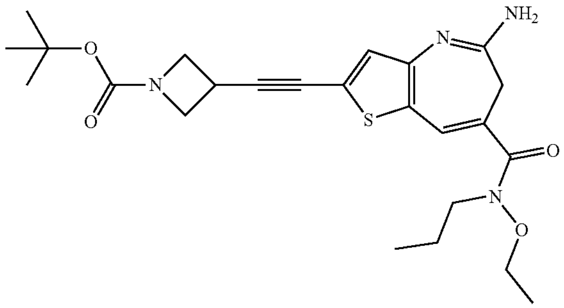 [SMILES: CCCN(OCC)C(=O)C1=Cc2sc(C#CC3CN(C(=O)OC(C)(C)C)C3)cc2N=C(N)C1] | 472.6 | 9000 | 964 |
| TAZ-188 | 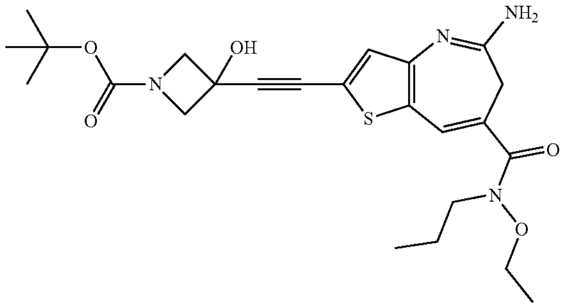 [SMILES: CCCN(OCC)C(=O)C1=Cc2sc(C#CC3(O)CN(C(=O)OC(C)(C)C)C3)cc2N=C(N)C1] | 488.6 | 9000 | 7798 |

TABLE 1c-continued
| Thienoazepine compounds (TAZ) | | | | |
|---|---|---|---|---|
| TAZ No. | Structure | MW | HEK293 hTLR7 EC50 (nM) | HEK293 hTLR8 EC50 (nM) |
| TAZ-189 | 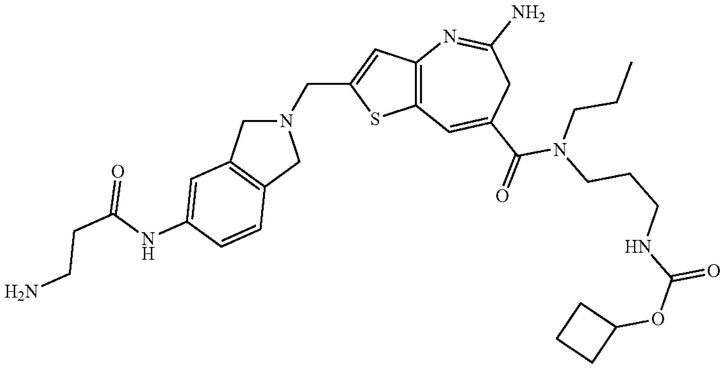 [SMILES: CCCN(CCCNC(=O)OC1CCC1)C(=O)C1=Cc2sc(CN3Cc4ccc(NC(=O)CCN)cc4C3)cc2N=C(N)C1] | 621.8 | 5721 | 3391 |
| TAZ-190 | 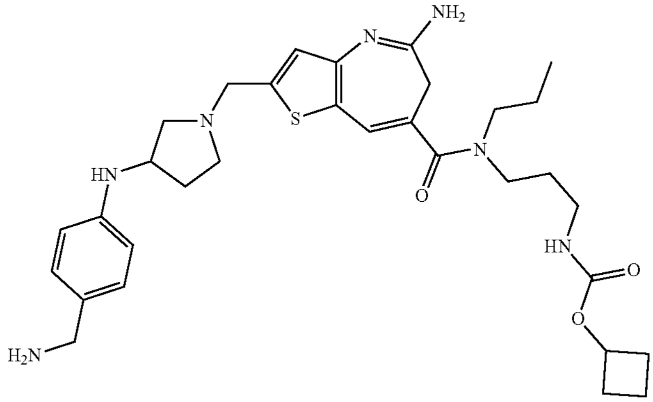 [SMILES: CCCN(CCCNC(=O)OC1CCC1)C(=O)C1=Cc2sc(CN3CCC(Nc4ccc(CN)cc4)C3)cc2N=C(N)C1] | 607.8 | 2988 | 4803 |
| TAZ-191 | 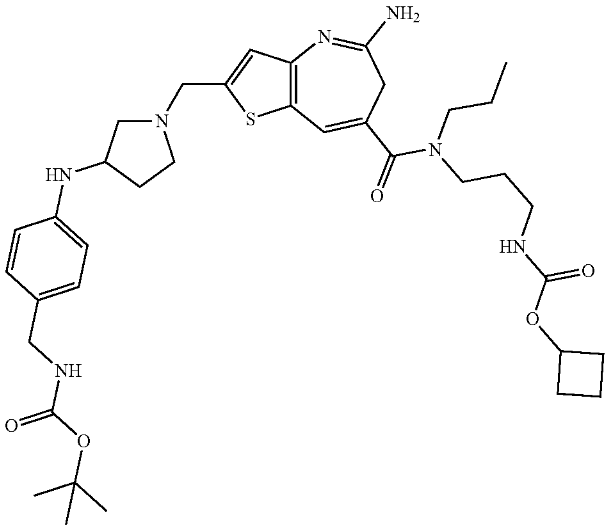 [SMILES: CCCN(CCCNC(=O)OC1CCC1)C(=O)C1=Cc2sc(CN3CCC(Nc4ccc(CNC(=O)OC(C)(C)C)cc4)C3)cc2N=C(N)C1] | 707.9 | | |

TABLE 1c-continued
| Thienoazepine compounds (TAZ) | | | | |
|---|---|---|---|---|
| TAZ No. | Structure | MW | HEK293 hTLR7 EC50 (nM) | HEK293 hTLR8 EC50 (nM) |
| TAZ-192 | 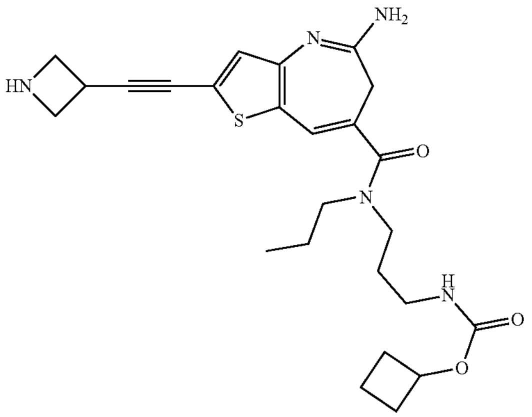 [SMILES: CCCN(CCCNC(=O)OC1CCC1)C(=O)C1=Cc2sc(C#CC3CNC3)cc2N=C(N)C1] | 483.6 | 824 | 3484 |
| TAZ-193 | 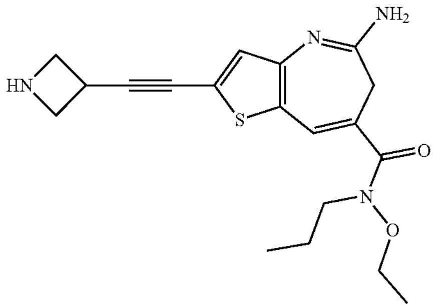 [SMILES: CCCN(OCC)C(=O)C1=Cc2sc(C#CC3CNC3)cc2N=C(N)C1] | 372.5 | 3362 | 1517 |
| TAZ-194 | 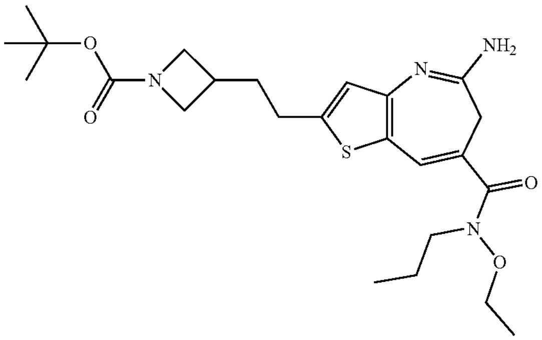 [SMILES: CCCN(OCC)C(=O)C1=Cc2sc(CCC3CN(C(=O)OC(C)(C)C)C3)cc2N=C(N)C1] | 476.6 | 467 | 631 |
| TAZ-195 | 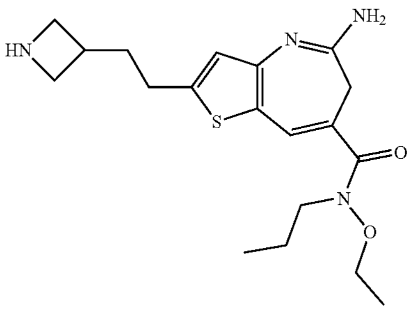 [SMILES: CCCN(OCC)C(=O)C1=Cc2sc(CCC3CNC3)cc2N=C(N)C1] | 376.5 | 6603 | 953 |

TABLE 1c-continued
Thienoazepine compounds (TAZ)
| TAZ No. | Structure | MW | HEK293 hTLR7 EC50 (nM) | HEK293 hTLR8 EC50 (nM) |
|---|---|---|---|---|
| TAZ-196 | 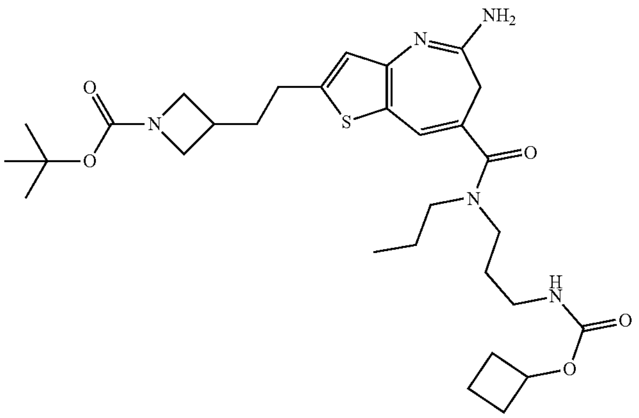 [SMILES: CCCN(CCCNC(=O)OC1CCC1)C(=O)C1=Cc2sc(CCC3CN(C(=O)OC(C)(C)C)C3)cc2N=C(N)C1] | 587.8 | | |
| TAZ-197 | 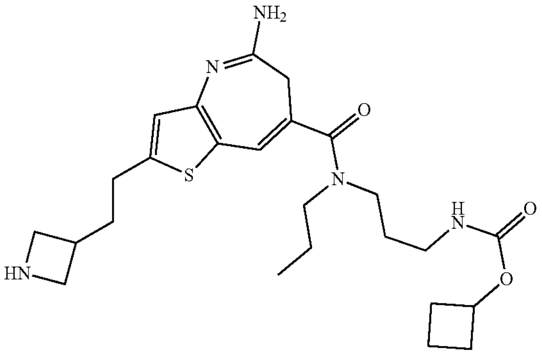 [SMILES: CCCN(CCCNC(=O)OC1CCC1)C(=O)C1=Cc2sc(CCC3CNC3)cc2N=C(N)C1] | 487.7 | 1808 | 9000 |
| TAZ-198 | 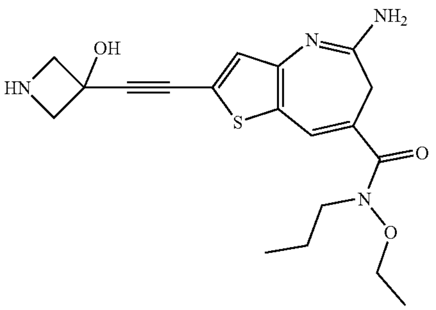 [SMILES: CCCN(OCC)C(=O)C1=Cc2sc(C#CC3(O)CNC3)cc2N=C(N)C1] | 388.5 | 9000 | 4275 |
| TAZ-199 | 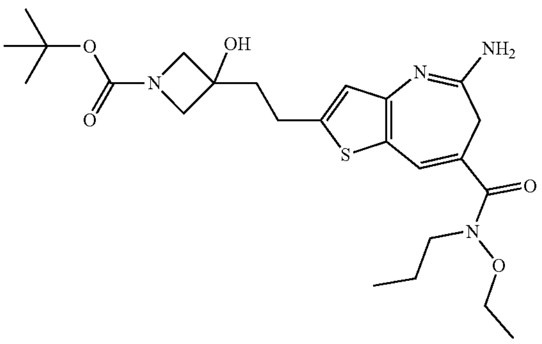 [SMILES: CCCN(OCC)C(=O)C1=Cc2sc(CCC3(O)CN(C(=O)OC(C)(C)C)C3)cc2N=C(N)C1] | 492.6 | 31 | 1614 |

TABLE 1c-continued
| Thienoazepine compounds (TAZ) | | | | |
|---|---|---|---|---|
| TAZ No. | Structure | MW | HEK293 hTLR7 EC50 (nM) | HEK293 hTLR8 EC50 (nM) |
| TAZ-200 | 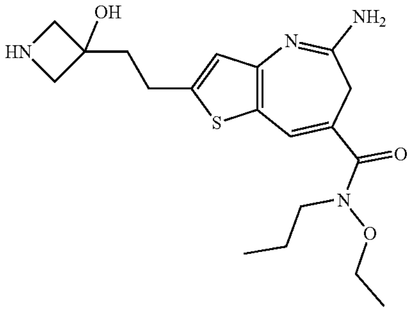 [SMILES: CCCN(OCC)C(=O)C1=Cc2sc(CCC3(O)CNC3)cc2N=C(N)C1] | 392.5 | 2916 | 4071 |
| TAZ-201 | 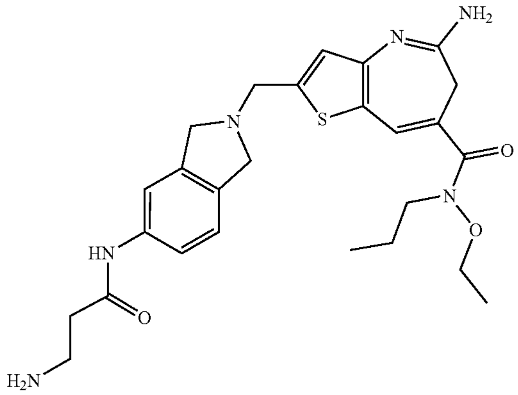 [SMILES: CCCN(OCC)C(=O)C1=Cc2sc(CN3Cc4ccc(NC(=O)CCN)cc4C3)cc2N=C(N)C1] | 510.7 | 9000 | 2957 |
| TAZ-202 | 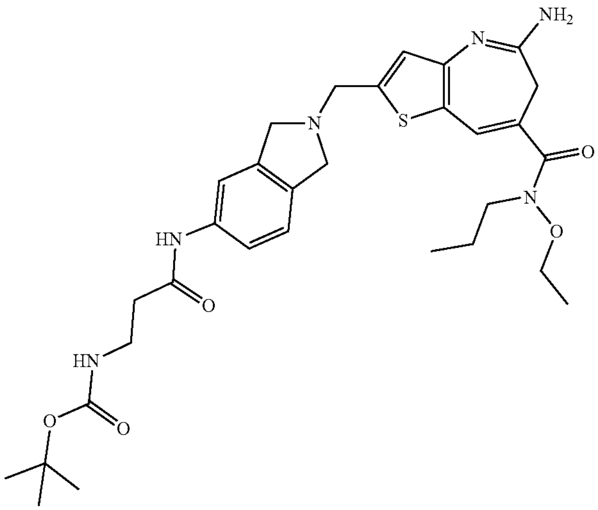 [SMILES: CCCN(OCC)C(=O)C1=Cc2sc(CN3Cc4ccc(NC(=O)CCNC(=O)OC(C)(C)C)cc4C3)cc2N=C(N)C1] | 610.8 | 3680 | 1373 |

TABLE 1c-continued
Thienoazepine compounds (TAZ)
| TAZ No. | Structure | MW | HEK293 hTLR7 EC50 (nM) | HEK293 hTLR8 EC50 (nM) |
|---|---|---|---|---|
| TAZ-203 | 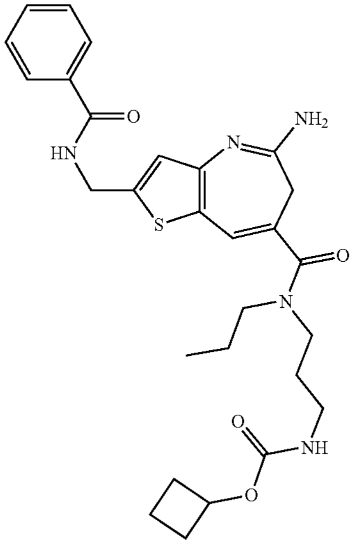 [SMILES: CCCN(CCCNC(=O)OC1CCC1)C(=O)C1=Cc2sc(CNC(=O)c3ccccc3)cc2N=C(N)C1] | 537.7 | 3261 | 3251 |
| TAZ-204 | 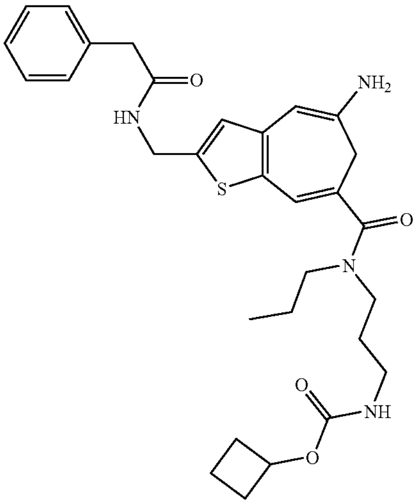 [SMILES: CCCN(CCCNC(=O)OC1CCC1)C(=O)C1=Cc2sc(CNC(=O)Cc3ccccc3)cc2C=C(N)C1] | 551.7 | 2665 | 2550 |
| TAZ-205 | 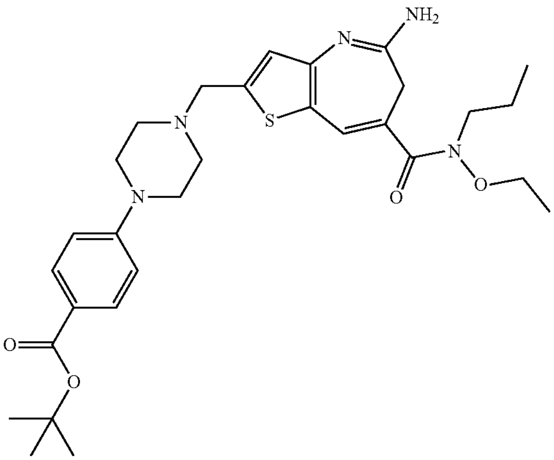 [SMILES: CCCN(OCC)C(=O)C1=Cc2sc(CN3CCN(c4ccc(C(=O)OC(C)(C)C)cc4)CC3)cc2N=C(N)C1] | 567.8 | 9000 | 9000 |

TABLE 1c-continued
Thienoazepine compounds (TAZ)
| TAZ No. | Structure | MW | HEK293 hTLR7 EC50 (nM) | HEK293 hTLR8 EC50 (nM) |
|---|---|---|---|---|
| TAZ-206 | 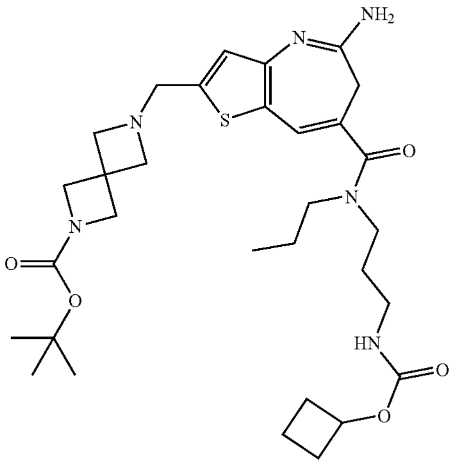 [SMILES: CCCN(CCCNC(=O)OC1CCC1)C(=O)C1=Cc2sc(CN3CC4(C3)CN(C(=O)OC(C)(C)C)C4)cc2N=C(N)C1] | 614.8 | | |
| TAZ-207 | 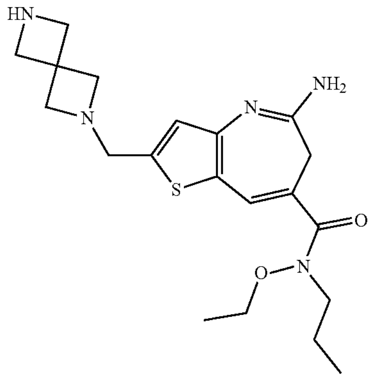 [SMILES: CCCN(OCC)C(=O)C1=Cc2sc(CN3CC4(CNC4)C3)cc2N=C(N)C1] | 403.5 | 9000 | 9000 |
| TAZ-208 | 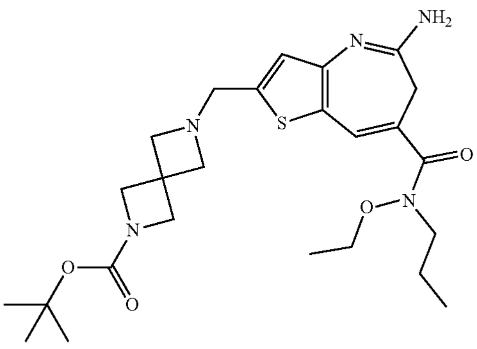 [SMILES: CCCN(OCC)C(=O)C1=Cc2sc(CN3CC4(C3)CN(C(=O)OC(C)(C)C)C4)cc2N=C(N)C1] | 503.7 | 3614 | 8507 |

TABLE 1c-continued
Thienoazepine compounds (TAZ)
| TAZ No. | Structure | MW | HEK293 hTLR7 EC50 (nM) | HEK293 hTLR8 EC50 (nM) |
|---|---|---|---|---|
| TAZ-209 | 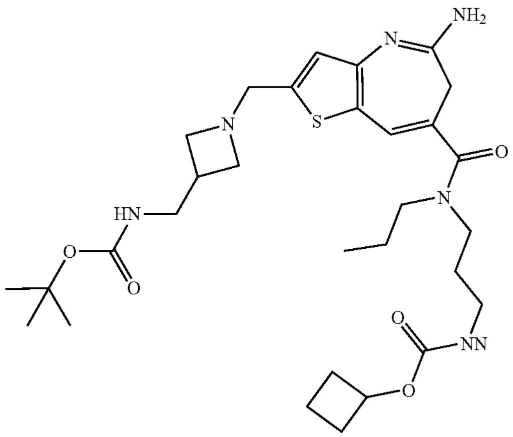 | 602.8 | | |
| TAZ-210 | 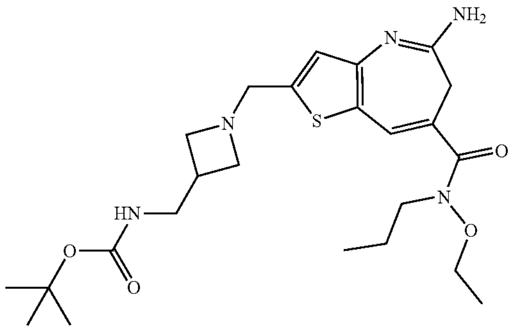 [SMILES: CCCN(OCC)C(=O)C1=Cc2sc(CN3CC(CNC(=O)OC(C)(C)C)C3)cc2N=C(N)C1] | 491.7 | 1546 | 2939 |
| TAZ-211 | 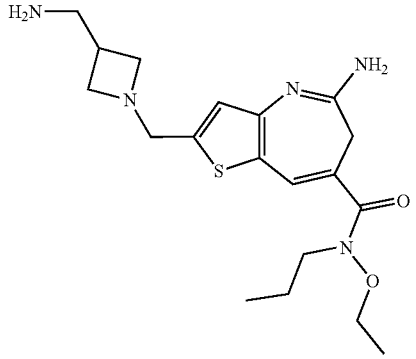 [SMILES: CCCN(OCC)C(=O)C1=Cc2sc(CN3CC(CN)C3)cc2N=C(N)C1] | 391.5 | 9000 | 4316 |
| TAZ-212 | 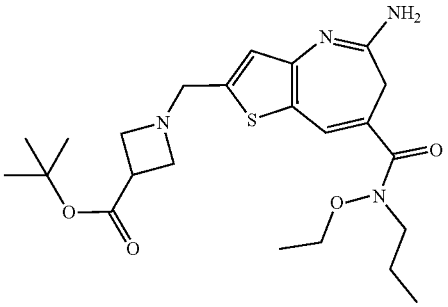 [SMILES: CCCN(OCC)C(=O)C1=Cc2sc(CN3CC(C(=O)OC(C)(C)C)C3)cc2N=C(N)C1] | 462.6 | 1265 | 2542 |

TABLE 1c-continued
Thienoazepine compounds (TAZ)
| TAZ No. | Structure | MW | HEK293 hTLR7 EC50 (nM) | HEK293 hTLR8 EC50 (nM) |
|---|---|---|---|---|
| TAZ-213 | 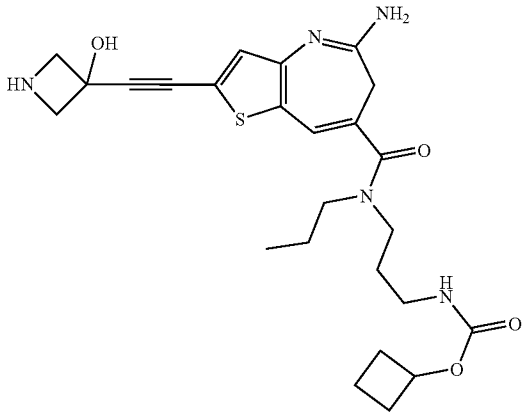 [SMILES: CCCN(CCCNC(=O)OC1CCC1)C(=O)C1=Cc2sc(C#CC3(O)CNC3)cc2N=C(N)C1] | 499.6 | | |
| TAZ-214 | 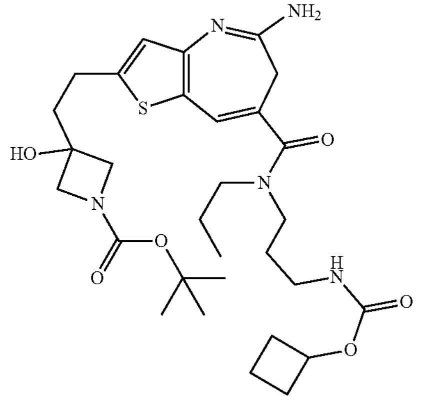 [SMILES: CCCN(CCCNC(=O)OC1CCC1)C(=O)C1=Cc2sc(CCC3(O)CN(C(=O)OC(C)(C)C)C3)cc2N=C(N)C1] | 603.8 | | |
| TAZ-215 | 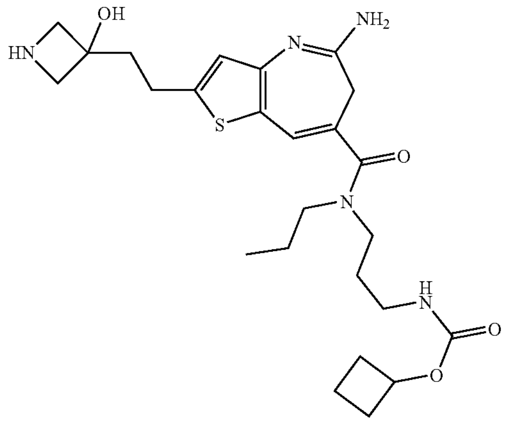 [SMILES: CCCN(CCCNC(=O)OC1CCC1)C(=O)C1=Cc2sc(CCC3(O)CNC3)cc2N=C(N)C1] | 503.7 | | |

TABLE 1c-continued
| Thienoazepine compounds (TAZ) | | | | |
|---|---|---|---|---|
| TAZ No. | Structure | MW | HEK293 hTLR7 EC50 (nM) | HEK293 hTLR8 EC50 (nM) |
| TAZ-216 | 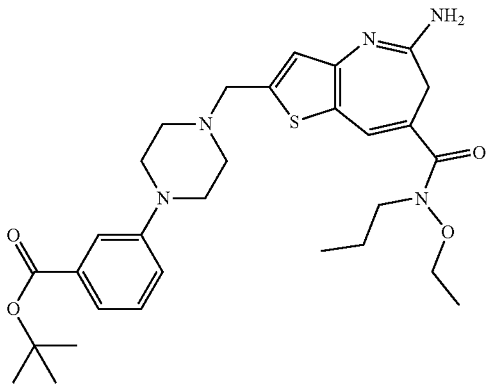 [SMILES: CCCN(OCC)C(=O)C1=Cc2sc(CN3CCN(c4cccc(C(=O)OC(C)(C)C)c4)CC3)cc2N=C(N)C1] | 567.8 | 9000 | |
| TAZ-217 | 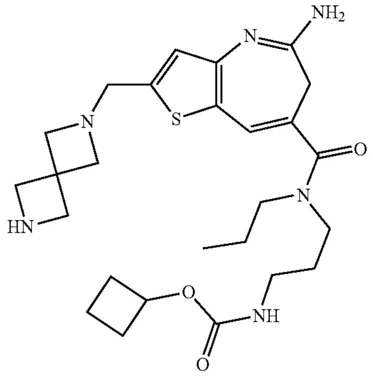 [SMILES: CCCN(CCCNC(=O)OC1CCC1)C(=O)C1=Cc2sc(CN3CC4(CNC4)C3)cc2N=C(N)C1] | 514.7 | | |
| TAZ-218 | 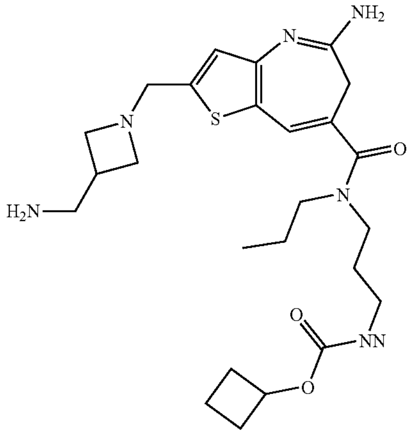 | 502.7 | | |

TABLE 1c-continued
| Thienoazepine compounds (TAZ) | | | | |
|---|---|---|---|---|
| TAZ No. | Structure | MW | HEK293 hTLR7 EC50 (nM) | HEK293 hTLR8 EC50 (nM) |
| TAZ-219 | 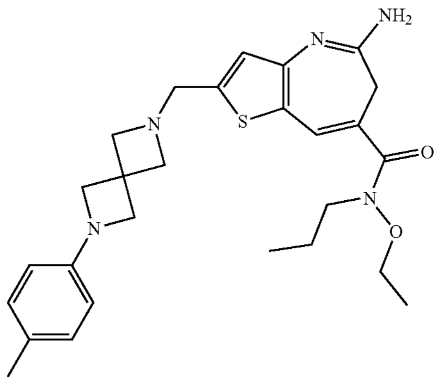 [SMILES: CCCN(OCC)C(=O)C1=Cc2sc(CN3CC4(C3)CN(c3ccc(C)cc3)C4)cc2N=C(N)C1] | 493.7 | 3197 | 847 |
| TAZ-220 | 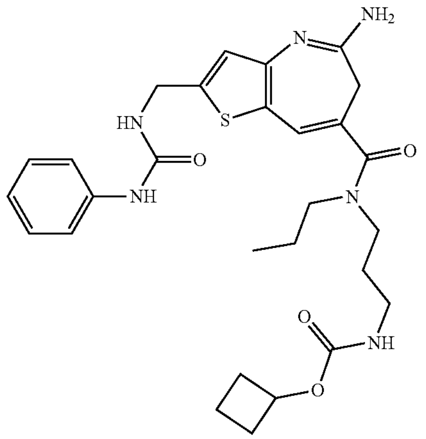 [SMILES: CCCN(CCCNC(=O)OC1CCC1)C(=O)C1=Cc2sc(CNC(=O)Nc3ccccc3)cc2N=C(N)C1] | 552.7 | | |
| TAZ-221 | 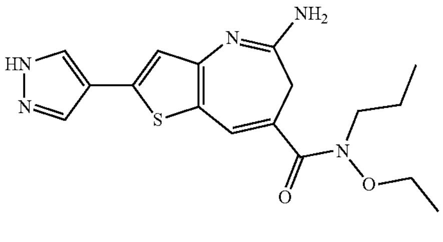 | 359.5 | 6118 | 6698 |
| TAZ-222 | 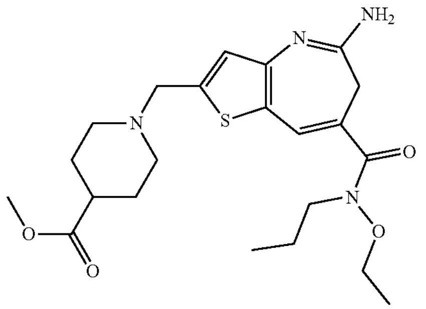 [SMILES: CCCN(OCC)C(=O)C1=Cc2sc(CN3CCC(C(=O)OC)CC3)cc2N=C(N)C1] | 448.6 | 4892 | 2826 |

TABLE 1c-continued
| Thienoazepine compounds (TAZ) | | | | |
|---|---|---|---|---|
| TAZ No. | Structure | MW | HEK293 hTLR7 EC50 (nM) | HEK293 hTLR8 EC50 (nM) |
| TAZ-223 | 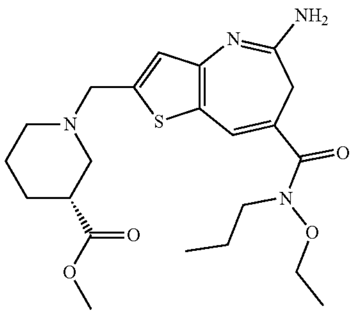 [SMILES: CCCN(OCC)C(=O)C1=Cc2sc(CN3CCC[C@@H](C(=O)OC)C3)cc2N=C(N)C1] | 448.6 | 3803 | 3138 |
| TAZ-224 | 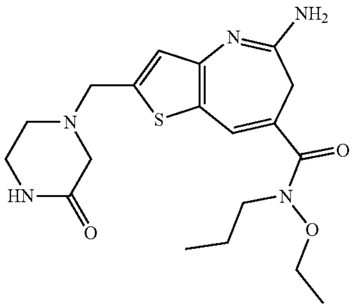 [SMILES: CCCN(OCC)C(=O)C1=Cc2sc(CN3CCNC(=O)C3)cc2N=C(N)C1] | 405.5 | 3410 | 2723 |
| TAZ-225 | 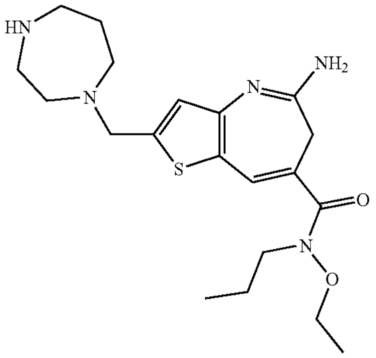 [SMILES: CCCN(OCC)C(=O)C1=Cc2sc(CN3CCCNCC3)cc2N=C(N)C1] | 405.6 | 2560 | 1212 |
| TAZ-226 | 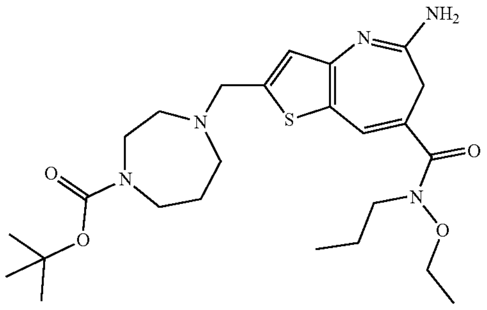 [SMILES: CCCN(OCC)C(=O)C1=Cc2sc(CN3CCCN(C(=O)OC(C)(C)C)CC3)cc2N=C(N)C1] | 505.7 | 436 | 4434 |

TABLE 1c-continued
| Thienoazepine compounds (TAZ) | | | | |
|---|---|---|---|---|
| TAZ No. | Structure | MW | HEK293 hTLR7 EC50 (nM) | HEK293 hTLR8 EC50 (nM) |
| TAZ-227 | 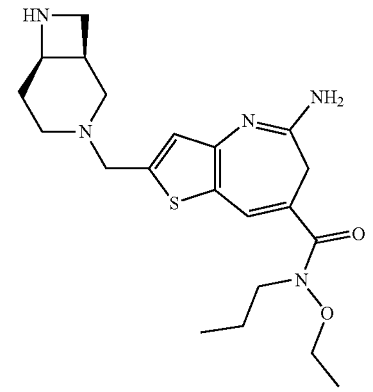 [SMILES: CCCN(OCC)C(=O)C1=Cc2sc(CN3CC[C@H]4NC[C@H]4C3)cc2N=C(N)C1] | 417.6 | 4393 | 2289 |
| TAZ-228 | 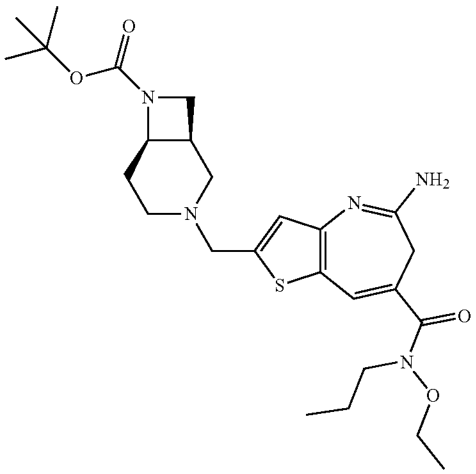 [SMILES: CCCN(OCC)C(=O)C1=Cc2sc(CN3CC[C@@H]4[C@H](C3)CN4C(=O)OC(C)(C)C)cc2N=C(N)C1] | 517.7 | 3759 | 3237 |
| TAZ-229 | 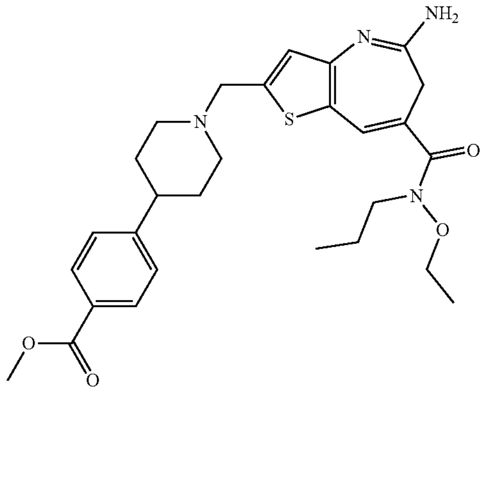 [SMILES: CCCN(OCC)C(=O)C1=Cc2sc(CN3CCC(c4ccc(C(=O)OC)cc4)CC3)cc2N=C(N)C1] | 524.7 | 9000 | 9000 |

TABLE 1c-continued
| TAZ No. | Structure | MW | HEK293 hTLR7 EC50 (nM) | HEK293 hTLR8 EC50 (nM) |
|---|---|---|---|---|
| Thienoazepine compounds (TAZ) | | | | |
| TAZ-230 | 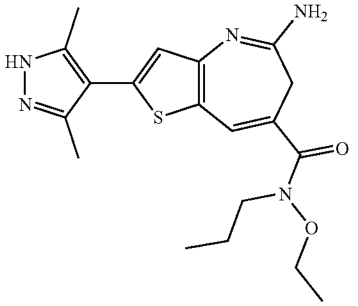 [SMILES: CCCN(OCC)C(=O)C1=Cc2sc(-c3c(C)n[nH]c3C)cc2N=C(N)C1] | 387.5 | | |
| TAZ-231 | 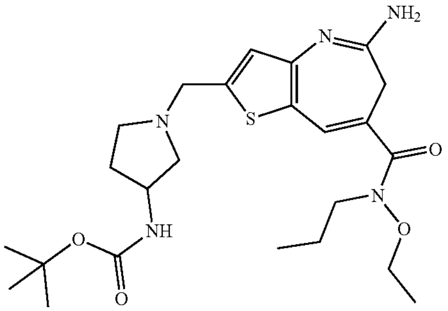 [SMILES: CCCN(OCC)C(=O)C1=Cc2sc(CN3CCC(NC(=O)OC(C)(C)C)C3)cc2N=C(N)C1] | 491.7 | | |
| TAZ-232 | 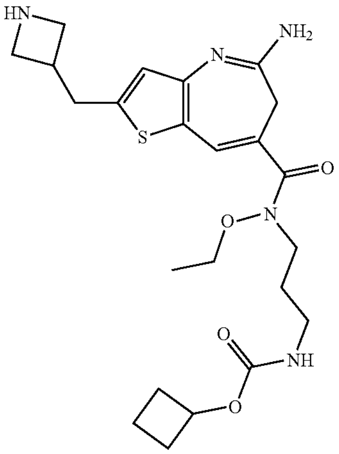 [SMILES: CCON(CCCNC(=O)OC1CCC1)C(=O)C1=Cc2sc(CC3CNC3)cc2N=C(N)C1] | 475.6 | | |
| TAZ-233 | 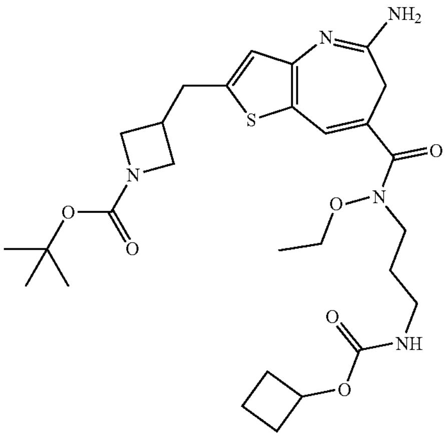 | 575.7 | | |

TABLE 1c-continued
Thienoazepine compounds (TAZ)
| TAZ No. | Structure | MW | HEK293 hTLR7 EC50 (nM) | HEK293 hTLR8 EC50 (nM) |
|---|---|---|---|---|
| TAZ-234 | 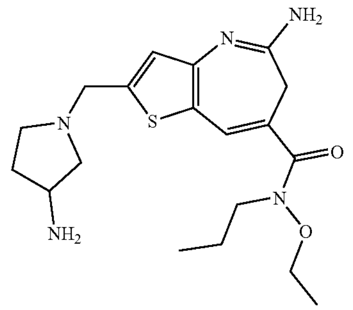 | 391.5 | 3326 | 361 |
| TAZ-235 | 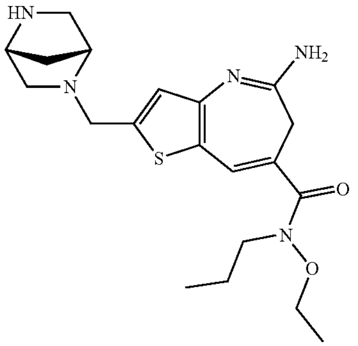 | 403.5 | 4570 | 3052 |
| TAZ-236 | 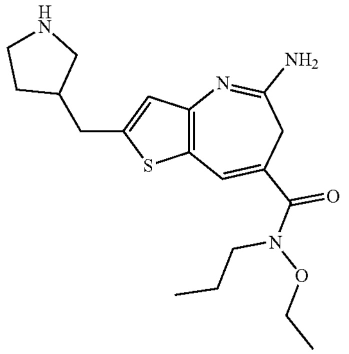 [SMILES: CCCN(OCC)C(=O)C1=Cc2sc(CC3CCNC3)cc2N=C(N)C1] | 376.5 | 2216 | 423 |
| TAZ-237 | 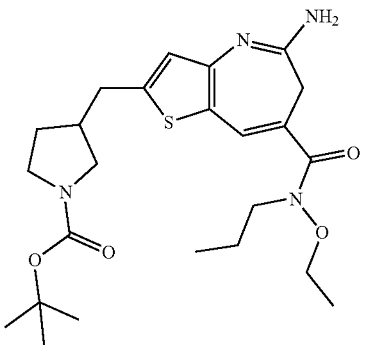 | 476.6 | | |

TABLE 1c-continued
| Thienoazepine compounds (TAZ) | | | | |
|---|---|---|---|---|
| TAZ No. | Structure | MW | HEK293 hTLR7 EC50 (nM) | HEK293 hTLR8 EC50 (nM) |
| TAZ-238 | 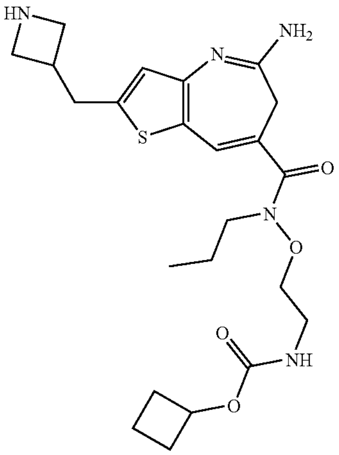 [SMILES: CCCN(OCCNC(=O)OC1CCC1)C(=O)C1=Cc2sc(CC3CNC3)cc2N=C(N)C1] | 475.6 | 112 | 286 |
| TAZ-239 | 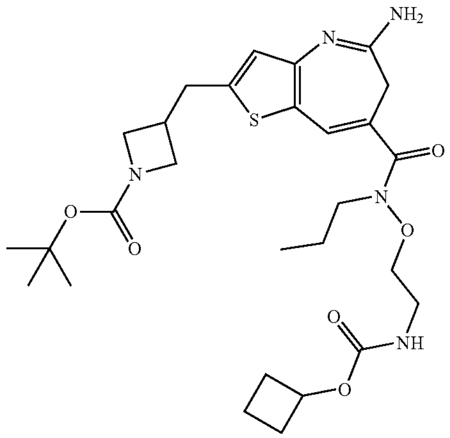 [SMILES: CCCN(OCCNC(=O)OC1CCC1)C(=O)C1=Cc2sc(CC3CN(C(=O)OC(C)(C)C)C3)cc2N=C(N)C1] | 575.7 | | |
| TAZ-240 | 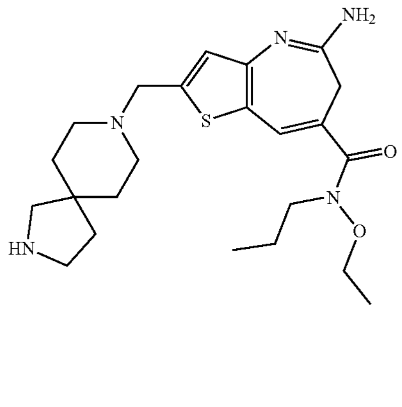 | 445.6 | 4245 | 5461 |

TABLE 1c-continued
| Thienoazepine compounds (TAZ) | | | | |
|---|---|---|---|---|
| TAZ No. | Structure | MW | HEK293 hTLR7 EC50 (nM) | HEK293 hTLR8 EC50 (nM) |
| TAZ-241 | 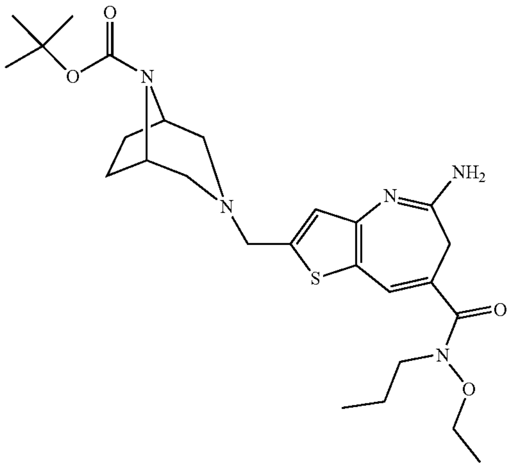 | 517.7 | 2815 | 3061 |
| TAZ-242 | 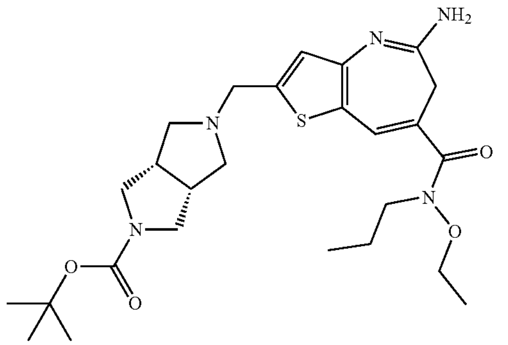 | 517.7 | 9000 | 3777 |
| TAZ-243 | 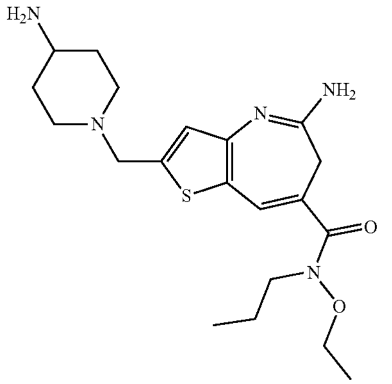 | 405.6 | 9000 | 164 |
| TAZ-244 | 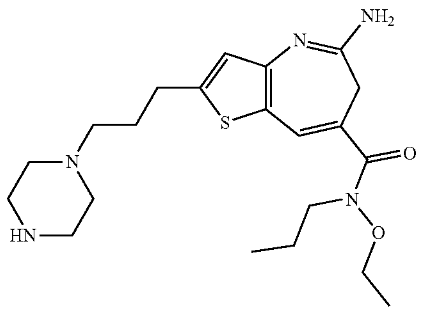 | 419.6 | 2460 | 146 |

TABLE 1c-continued
Thienoazepine compounds (TAZ)
| TAZ No. | Structure | MW | HEK293 hTLR7 EC50 (nM) | HEK293 hTLR8 EC50 (nM) |
|---|---|---|---|---|
| TAZ-245 | 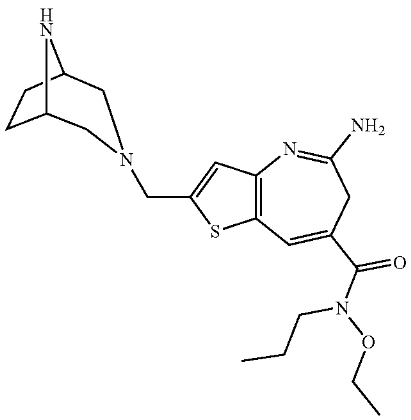 | 417.6 | 5023 | 145 |
| TAZ-246 | 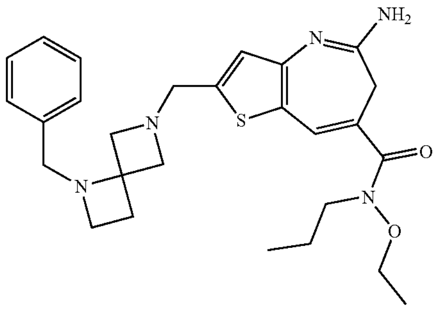 [SMILES: CCCN(OCC)C(=O)C1=Cc2sc(CN3CC4(CCN4Cc4ccccc4)C3)cc2N=C(N)C1] | 493.7 | 9000 | 1107 |
| TAZ-247 | 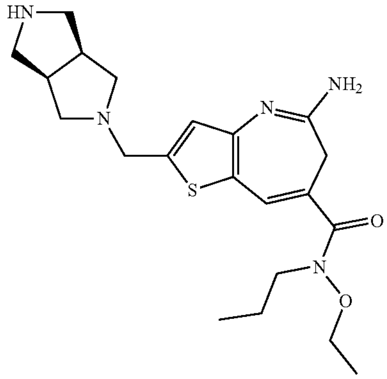 | 417.6 | 9000 | 418 |
| TAZ-248 | 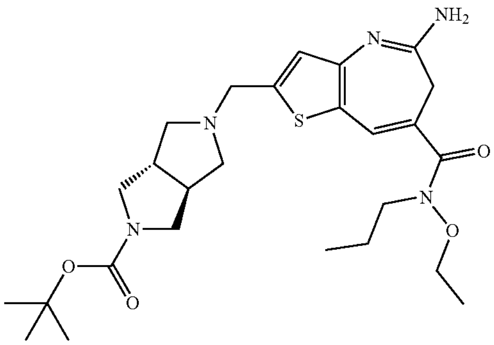 | 517.7 | 9000 | 1114 |

TABLE 1c-continued
| Thienoazepine compounds (TAZ) | | | | |
|---|---|---|---|---|
| TAZ No. | Structure | MW | HEK293 hTLR7 EC50 (nM) | HEK293 hTLR8 EC50 (nM) |
| TAZ-249 | 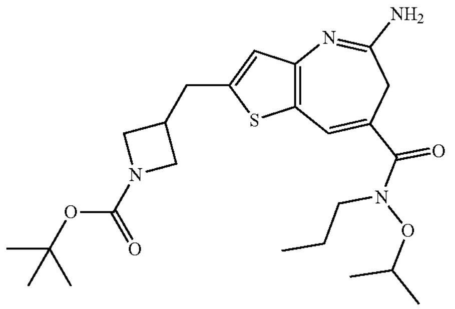 [SMILES: CCCN(OC(C)C)C(=O)C1=Cc2sc(CC3CN(C(=O)OC(C)(C)C)C3)cc2N=C(N)C1] | 476.6 | 362 | 640 |
| TAZ-250 | 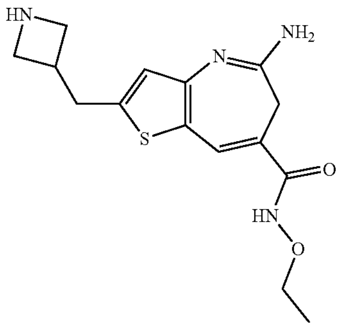 [SMILES: CCONC(=O)C1=Cc2sc(CC3CNC3)cc2N=C(N)C1] | 320.4 | 9000 | 9000 |
| TAZ-251 | 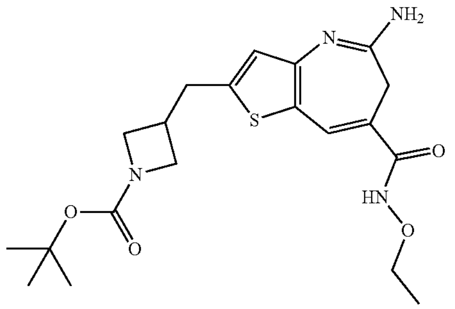 [SMILES: CCONC(=O)C1=Cc2sc(CC3CN(C(=O)OC(C)(C)C)C3)cc2N=C(N)C1] | 420.5 | | |
| TAZ-252 | 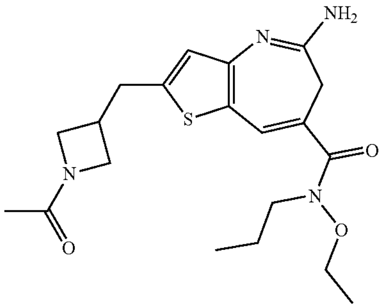 [SMILES: CCCN(OCC)C(=O)C1=Cc2sc(CC3CN(C(C)=O)C3)cc2N=C(N)C1] | 404.5 | 4453 | 868 |

TABLE 1c-continued
| Thienoazepine compounds (TAZ) | | | | |
|---|---|---|---|---|
| TAZ No. | Structure | MW | HEK293 hTLR7 EC50 (nM) | HEK293 hTLR8 EC50 (nM) |
| TAZ-253 | 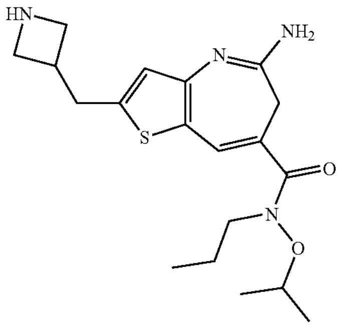 [SMILES: CCCN(OC(C)C)C(=O)C1=Cc2sc(CC3CNC3)cc2N=C(N)C1] | 376.5 | 7166 | 192 |
| TAZ-254 | 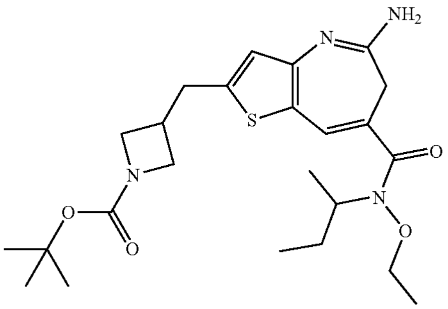 [SMILES: CCON(C(=O)C1=Cc2sc(CC3CN(C(=O)OC(C)(C)C)C3)cc2N=C(N)C1)C(C)CC] | 476.6 | 8133 | 8267 |
| TAZ-255 | 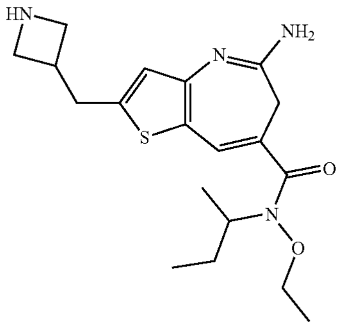 [SMILES: CCON(C(=O)C1=Cc2sc(CC3CNC3)cc2N=C(N)C1)C(C)CC] | 376.5 | | |
| TAZ-256 | 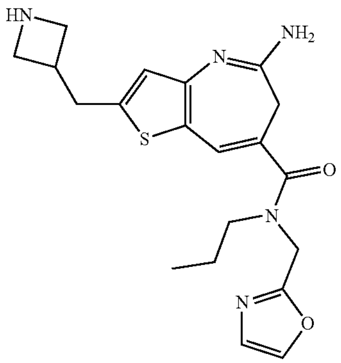 [SMILES: CCCN(Cc1ncco1)C(=O)C1=Cc2sc(CC3CNC3)cc2N=C(N)C1] | 399.5 | 9000 | 3409 |

TABLE 1c-continued
| Thienoazepine compounds (TAZ) | | | | |
|---|---|---|---|---|
| TAZ No. | Structure | MW | HEK293 hTLR7 EC50 (nM) | HEK293 hTLR8 EC50 (nM) |
| TAZ-257 | 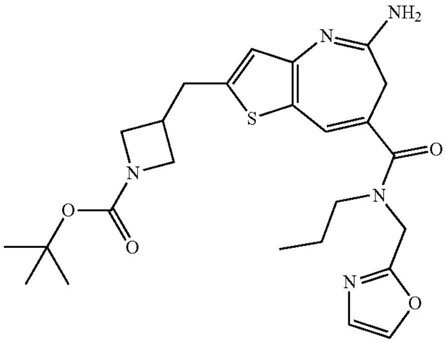 [SMILES: CCCN(Cc1ncco1)C(=O)C1=Cc2sc(CC3CN(C(=O)OC(C)(C)C)C3)cc2N=C(N)C1] | 499.6 | | |
| TAZ-258 | 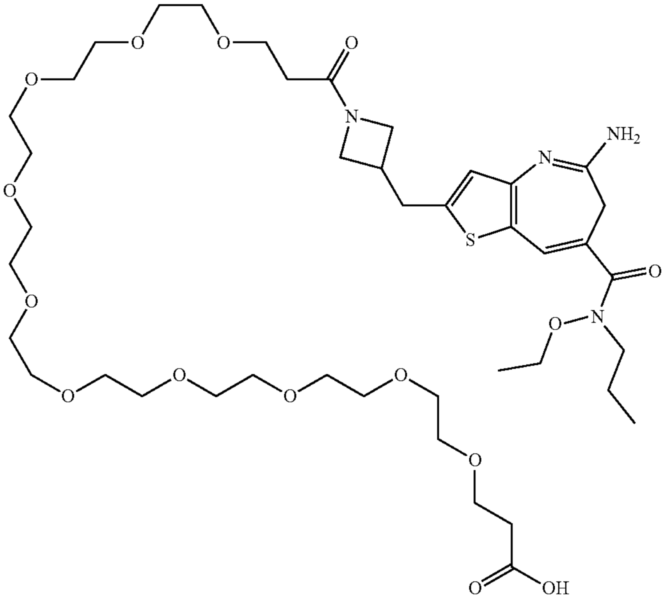 [SMILES: CCCN(OCC)C(=O)C1=Cc2sc(CC3CN(C(=O)CCOCCOCCOCCOCCOCCOCCOCCOCCOCCOCCC(=O)O)C3)cc2N=C(N)C1] | 903.1 | | |
| TAZ-259 | 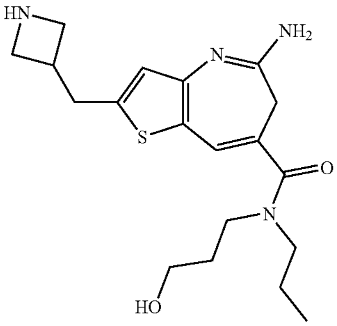 [SMILES: CCCN(CCCO)C(=O)C1=Cc2sc(CC3CNC3)cc2N=C(N)C1] | 376.5 | | |

TABLE 1c-continued
| Thienoazepine compounds (TAZ) | | | | |
|---|---|---|---|---|
| TAZ No. | Structure | MW | HEK293 hTLR7 EC50 (nM) | HEK293 hTLR8 EC50 (nM) |
| TAZ-260 | 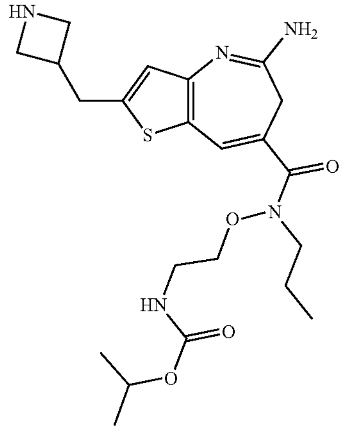 [SMILES: CCCN(OCCNC(=O)OC(C)C)C(=O)C1=Cc2sc(CC3CNC3)cc2N=C(N)C1] | 463.6 | | |
| TAZ-261 | 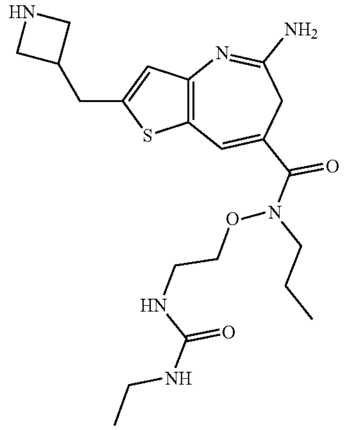 [SMILES: CCCN(OCCNC(=O)NCC)C(=O)C1=Cc2sc(CC3CNC3)cc2N=C(N)C1] | 448.6 | | |
| TAZ-262 | 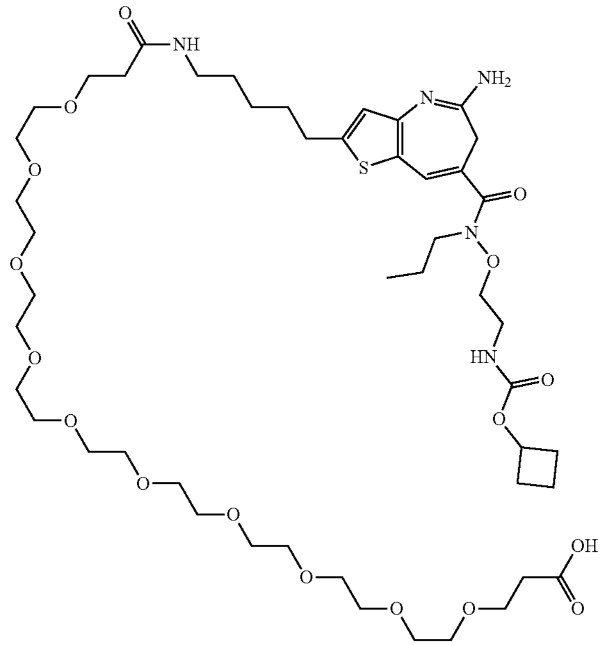 [SMILES: CCCN(OCCNC(=O)OC1CCC1)C(=O)C1=Cc2sc(CCCCCNC(=O)CCOCCOCCOCCOCCOCCOCCOCCOCCOCCOCCC(=O)O)cc2N=C(N)C1] | 1032.2 | | |

TABLE 1c-continued

| Thienoazepine compounds (TAZ) | | | | |
|---|---|---|---|---|
| TAZ No. | Structure | MW | HEK293 hTLR7 EC50 (nM) | HEK293 hTLR8 EC50 (nM) |
| TAZ-263 | 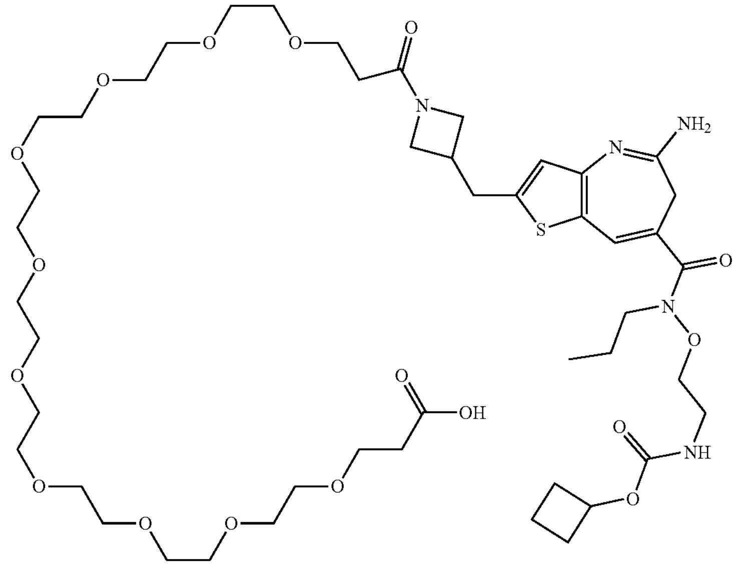 [SMILES: CCCN(OCCNC(=O)OC1CCC1)C(=O)C1=Cc2sc(CC3CN(C(=O)CCOCCOCCOCCOCCOCCOCCOCCOCCOCCOCCC(=O)O)C3)cc2N=C(N)C1] | 1016.2 | | |

Thienoazepine-Linker Compounds

The immunoconjugates of the invention are prepared by conjugation of an antibody with a thienoazepine-linker compound. The thienoazepine-linker compounds comprise a thienoazepine (TAZ) moiety covalently attached to a linker unit. The linker units comprise functional groups and subunits which affect stability, permeability, solubility, and other pharmacokinetic, safety, and efficacy properties of the immunoconjugates. The linker unit includes a reactive functional group which reacts, i.e. conjugates, with a reactive functional group of the antibody. For example, a nucleophilic group such as a lysine side chain amino of the antibody reacts with an electrophilic reactive functional group of the TAZ-linker compound to form the immunoconjugate. Also, for example, a cysteine thiol of the antibody reacts with a maleimide or bromoacetamide group of the TAZ-linker compound to form the immunoconjugate.

Electrophilic reactive functional groups suitable for the TAZ-linker compounds include, but are not limited to, N-hydroxysuccinimidyl (NHS) esters and N-hydroxysulfosuccinimidyl (sulfo-NHS) esters (amine reactive); carbodiimides (amine and carboxyl reactive); hydroxymethyl phosphines (amine reactive); maleimides (thiol reactive); halogenated acetamides such as N-iodoacetamides (thiol reactive): aryl azides (primary amine reactive); fluorinated aryl azides (reactive via carbon-hydrogen (C—H) insertion): pentafluorophenyl (PFP) esters (amine reactive); tetrafluorophenyl (TFP) esters (amine reactive): imidoesters (amine reactive): isocyanates (hydroxyl reactive): vinyl sulfones (thiol, amine, and hydroxyl reactive); pyridyl disulfides (thiol reactive); and benzophenone derivatives (reactive via C—H bond insertion). Further reagents include, but are not limited, to those described in Hermanson, *Bioconjugate Techniques* 2$^{nd}$ Edition, Academic Press, 2008.

The invention provides solutions to the limitations and challenges to the design, preparation and use of immunoconjugates. Some linkers may be labile in the blood stream, thereby releasing unacceptable amounts of the adjuvant/drug prior to internalization in a target cell (Khot, A. et al (2015) *Bioanalysis* 7(13):1633-1648). Other linkers may provide stability in the bloodstream, but intracellular release effectiveness may be negatively impacted. Linkers that provide for desired intracellular release typically have poor stability in the bloodstream. Alternatively stated, bloodstream stability and intracellular release are typically inversely related. In addition, in standard conjugation processes, the amount of adjuvant/drug moiety loaded on the antibody, i.e. drug loading, the amount of aggregate that is formed in the conjugation reaction, and the yield of final purified conjugate that can be obtained are interrelated. For example, aggregate formation is generally positively correlated to the number of equivalents of adjuvant/drug moiety and derivatives thereof conjugated to the antibody. Under high drug loading, formed aggregates must be removed for therapeutic applications. As a result, drug loading-mediated aggregate formation decreases immunoconjugate yield and can render process scale-up difficult.

Exemplary embodiments include a 5-aminothienoazepine-linker compound of Formula II:

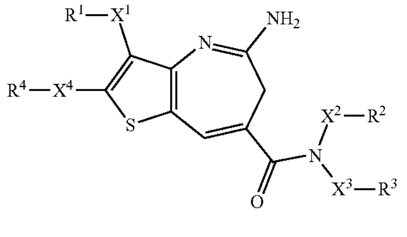

II where one of $R^1$, $R^2$, $R^3$, and $R^4$ is attached to L;

$R^1$, $R^2$, $R^3$, and $R^4$ are independently selected from the group consisting of H, $C_1$-$C_{12}$ alkyl, $C_2$-$C_6$ alkenyl, $C_2$-$C_6$ alkynyl, $C_3$-$C_{12}$ carbocyclyl, $C_6$-$C_{20}$ aryl, $C_2$-$C_9$ heterocyclyl, and $C_1$-$C_{20}$ heteroaryl, where alkyl, alkenyl, alkynyl, carbocyclyl, aryl, heterocyclyl, and heteroaryl are independently and optionally substituted with one or more groups selected from:

—($C_1$-$C_{12}$ alkyldiyl)-N($R^5$)—*;
—($C_1$-$C_{12}$ alkyldiyl)-N($R^5$)$_2$;
—($C_1$-$C_{12}$ alkyldiyl)-O$R^5$;
—($C_3$-$C_{12}$ carbocyclyl);
—($C_3$-$C_2$ carbocyclyl)-*;
—($C_3$-$C_{12}$ carbocyclyl)-($C_1$-$C_{12}$ alkyldiyl)-N$R^5$—*;
—($C_3$-$C_{12}$ carbocyclyl)-($C_1$-$C_{12}$ alkyldiyl)-N($R^5$)$_2$;
—($C_3$-$C_{12}$ carbocyclyl)-N$R^5$—C(═N$R^5$)N$R^5$—*;
—($C_6$-$C_{20}$ aryl);
—($C_6$-$C_{20}$ aryl)-*;
—($C_6$-$C_{20}$ aryldiyl)-N($R^5$)—*;
—($C_6$-$C_{20}$ aryldiyl)-($C_1$-$C_{12}$ alkyldiyl)-N($R^5$)—*;
—($C_6$-$C_{20}$ aryldiyl)-($C_1$-$C_{12}$ alkyldiyl)-($C_2$-$C_{20}$ heterocyclyldiyl)-*;
—($C_6$-$C_{20}$ aryldiyl)-($C_1$-$C_{12}$ alkyldiyl)-N($R^5$)$_2$;
—($C_6$-$C_{20}$ aryldiyl)-($C_1$-$C_{12}$ alkyldiyl)-N$R^5$—C(═N$R^{5a}$)N($R^5$)—*;
—($C_2$-$C_{20}$ heterocyclyl);
—($C_2$-$C_{20}$ heterocyclyl)-*;
—($C_2$-$C_9$ heterocyclyl)-($C_1$-$C_{12}$ alkyldiyl)-N$R^5$—*;
—($C_2$-$C_9$ heterocyclyl)-($C_1$-$C_{12}$ alkyldiyl)-N($R^5$)$_2$;
—($C_2$-$C_9$ heterocyclyl)-C(═O)—($C_1$-$C_{12}$ alkyldiyl)-N($R^5$)—*;
—($C_2$-$C_9$ heterocyclyl)-N$R^5$—C(═N$R^{5a}$)N$R^5$—*;
—($C_2$-$C_9$ heterocyclyl)-N$R^5$—($C_6$-$C_{20}$ aryldiyl)-($C_1$-$C_{12}$ alkyldiyl)-N($R^5$)—*;
—($C_2$-$C_9$ heterocyclyl)-($C_6$-$C_{20}$ aryldiyl)-*;
—($C_1$-$C_{20}$ heteroaryl);
—($C_1$-$C_{20}$ heteroaryl)-*;
—($C_1$-$C_{20}$ heteroaryl)-($C_1$-$C_{12}$ alkyldiyl)-N($R^5$)—*;
—($C_1$-$C_{20}$ heteroaryl)-($C_1$-$C_{12}$ alkyldiyl)-N($R^5$)$_2$;
—($C_1$-$C_{20}$ heteroaryl)-N$R^5$—C(═N$R^{5a}$)N($R^5$)—*;
—($C_1$-$C_{20}$ heteroaryl)-N($R^5$)C(═O)—($C_1$-$C_{12}$ alkyldiyl)-N($R^5$)—*;
—C(═O)—*;
—C(═O)—$C_1$-$C_{12}$ alkyldiyl)-N($R^5$)—*;
—C(═O)—$C_2$-$C_{20}$ heterocyclyldiyl)-*;
—C(═O)N($R^5$)$_2$;
—C(═O)N($R^5$)—*;
—C(═O)N($R^5$)—($C_1$-$C_{12}$ alkyldiyl)-N($R^5$)C(═O)$R^5$;
—C(═O)N($R^5$)—($C_1$-$C_{12}$ alkyldiyl)-N($R^5$)C(═O)N($R^5$)$_2$;
—C(═O)N$R^5$—($C_1$-$C_{12}$ alkyldiyl)-N($R^5$)CO$_2$$R^5$;
—C(═O)N$R^5$—($C_1$-$C_{12}$ alkyldiyl)-N($R^5$)C(═N$R^{5a}$)N($R^5$)$_2$;
—C(═O)N$R^5$—($C_1$-$C_{12}$ alkyldiyl)-N$R^5$C(═N$R^{5a}$)$R^5$;
—C(═O)N$R^5$—($C_1$-$C_8$ alkyldiyl)-N$R^5$($C_2$-$C_5$ heteroaryl);
—C(═O)N$R^5$—($C_1$-$C_{20}$ heteroaryldiyl)-N($R^5$)—*;
—C(═O)N$R^5$—($C_1$-$C_{20}$ heteroaryldiyl)-*;
—C(═O)N$R^5$—($C_1$-$C_{20}$ heteroaryldiyl)($C_1$-$C_{12}$ alkyldiyl)-N($R^5$)$_2$;
—C(═O)N$R^5$—($C_1$-$C_{20}$ heteroaryldiyl)-($C_2$-$C_{20}$ heterocyclyldiyl)-C(═O)N$R^5$—($C_1$-$C_{12}$ alkyldiyl)-N$R^5$—*;
—N($R^5$)$_2$;
N($R^5$)—*;
—N($R^5$)C(═O)$R^5$;
—N($R^5$)C(═O)—*;
—N($R^5$)C(═O)N($R^5$)$_2$;
N($R^5$)C(═O)N($R^5$)—*;
—N($R^5$)CO$_2$$R^5$;
—N$R^5$C(═N$R^{5a}$)N($R^5$)$_2$;
—N$R^5$C(═N$R^{5a}$)N($R^5$)—*;
—N$R^5$C(═N$R^{5a}$)$R^5$;
—N($R^5$)C(═O)—($C_1$-$C_{12}$ alkyldiyl)-N($R^5$)—*;
—N($R^5$)—($C_2$-$C_5$ heteroaryl);
—N($R^5$)—S(═O)$_2$—($C_1$-$C_{12}$ alkyl);
—O—($C_1$-$C_{12}$ alkyl);
—O—($C_1$-$C_{12}$ alkyldiyl)-N($R^5$)$_2$;
—O—($C_1$-$C_{12}$ alkyldiyl)-N($R^5$)—*;
—S(═O)$_2$—($C_2$-$C_{20}$ heterocyclyldiyl)-*;
—S(═O)$_2$—($C_2$-$C_{20}$ heterocyclyldiyl)-($C_1$-$C_{12}$ alkyldiyl)-N($R^5$)$_2$;
—S(═O)$_2$—($C_2$-$C_{20}$ heterocyclyldiyl)-($C_1$-$C_{12}$ alkyldiyl)-N$R^5$—*; and
—S(═O)$_2$—($C_2$-$C_{20}$ heterocyclyldiyl)-($C_1$-$C_{12}$ alkyldiyl)-OH;

or $R^2$ and $R^3$ together form a 5- or 6-membered heterocyclyl ring;

$X^1$, $X^2$, $X^3$, and $X^4$ are independently selected from the group consisting of a bond, C(═O), C(═O)N($R^5$), O, N($R^5$), S, S(O)$_2$, and S(O)$_2$N($R^5$);

$R^5$ is selected from the group consisting of H, $C_6$-$C_{20}$ aryl, $C_1$-$C_{12}$ carbocyclyl, $C_6$-$C_{20}$ aryldiyl, $C_1$-$C_{12}$ alkyl, and $C_1$-$C_{12}$ alkyldiyl, or two $R^5$ groups together form a 5- or 6-membered heterocyclyl ring;

$R^{5a}$ is selected from the group consisting of $C_6$-$C_{20}$ aryl and $C_1$-$C_{20}$ heteroaryl;

where the asterisk * indicates the attachment site of L, and where one of $R^1$, $R^2$, $R^3$ and $R^4$ is attached to L;

L is the linker selected from the group consisting of:

Q-C(═O)—(PEG)-;
Q-C(═O)—(PEG)-C(═O)—;
Q-C(═O)—(PEG)-O—;
Q-C(═O)—(PEG)-C(═O)—(PEP)-;
Q-C(═O)—(PEG)-C(═O)N($R^5$)—($C_1$-$C_{12}$ alkyldiyl)-;
Q-C(═O)—(PEG)-C(═O)N($R^5$)—($C_1$-$C_{12}$ alkyldiyl)-N($R^5$)C(═O)—($C_2$-$C_5$ monoheterocyclyldiyl)-;
Q-C(═O)—(PEG)-C(═O)N($R^5$)—($C_1$-$C_{12}$ alkyldiyl)-(Mcgluc)-;
Q-C(═O)—(PEG)-C(═O)-(Mcgluc)-;
Q-C(═O)—(PEG)-C(═O)—(PEP)—N($R^5$)—$C_1$-$C_{12}$ alkyldiyl)-;
Q-C(═O)—(PEG)-C(═O)—(PEP)—N($R^5$)—($C_1$-$C_{12}$ alkyldiyl)-N($R^5$)C(═O)—($C_2$-$C_5$ monoheterocyclyldiyl)-;
Q-C(═O)—(PEG)-N($R^5$)—;
Q-C(═O)—(PEG)-N($R^5$)C(═O)—;
Q-C(═O)—(PEG)-N($R^5$)—(PEG)-C(═O)—(PEP)-;
Q-C(═O)—(PEG)-N$^+$($R^5$)$_2$—(PEG)-C(═O)—(PEP)-;
Q-C(═O)—(PEG)-C(═O)—N($R^5$)CH($AA_1$)C(═O)—(PEG)-C(═O)—(PEP)-;
Q-C(═O)—(PEG)-C(═O)—N($R^5$)CH($AA_1$)C(═O)—N($R^5$)—($C_1$-$C_{12}$ alkyldiyl)-;
Q-C(═O)—(PEG)-SS—($C_1$-$C_{12}$ alkyldiyl)-OC(═O)—;
Q-C(═O)—(PEG)-SS—($C_1$-$C_{12}$ alkyldiyl)-C(═O)—;
Q-C(═O)—($C_1$-$C_{12}$ alkyldiyl)-C(═O)—(PEP)-;
Q-C(═O)—($C_1$-$C_{12}$ alkyldiyl)-C(═O)—(PEP)—N($R^5$)—($C_1$-$C_{12}$ alkyldiyl)-;
Q-C(═OHC$_1$-$C_{12}$ alkyldiyl)-C(═O)—(PEP)—N($R^5$)—($C_1$-$C_{12}$ alkyldiyl)-N($R^5$)—C(═O);
Q-C(═O)—($C_1$-$C_{12}$ alkyldiyl)-C(═O)—(PEP)—N($R^5$)—($C_1$-$C_{12}$ alkyldiyl)-N($R^5$)C(═O)—($C_2$-$C_5$ monoheterocyclyldiyl)-;
Q-C(═O)—$CH_2CH_2OCH_2CH_2$—($C_1$-$C_{20}$ heteroaryldiyl)-$CH_2O$—(PEG)-C(═O)-(Mcgluc)-;

Q-C(=O)—$CH_2CH_2OCH_2CH_2$—($C_1$-$C_{20}$ heteroaryldiyl)-$CH_2O$—(PEG)-C(=O)-(Mcgluc)-N($R^5$)—($C_1$-$C_{12}$ alkyldiyl)-N($R^5$)C(=O)—($C_2$-$C_5$ monoheterocyclyldiyl)-; and Q-$(CH_2)_m$—C(=O)—(PEP)—N($R^5$)—($C_1$-$C_{12}$ alkyldiyl)-N($R^5$)C(=O)—($C_2$-$C_5$ monoheterocyclyldiyl)-;

where PEG has the formula —$(CH_2CH_2O)_n$—$(CH_2)_m$—; m is an integer from 1 to 5, and n is an integer from 2 to 50;

PEP has the formula:

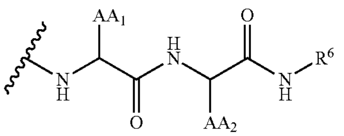

where $AA_1$ and $AA_2$ are independently selected from an amino acid side chain, or $AA_1$ or $AA_2$ and an adjacent nitrogen atom form a 5-membered ring proline amino acid, and the wavy line indicates a point of attachment and;

$R^6$ is selected from the group consisting of $C_6$-$C_{20}$ aryldiyl and $C_1$-$C_{20}$ heteroaryldiyl, substituted with —$CH_2O$—C(=O)— and optionally with:

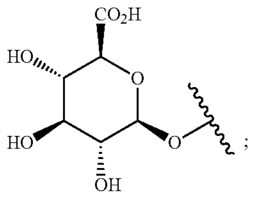 [SMILES: *O[C@@H]1O[C@H](C(=O)O)[C@@H](O)[C@H](O)[C@H]1O ; ";"]

and

Mcgluc is selected from the groups:

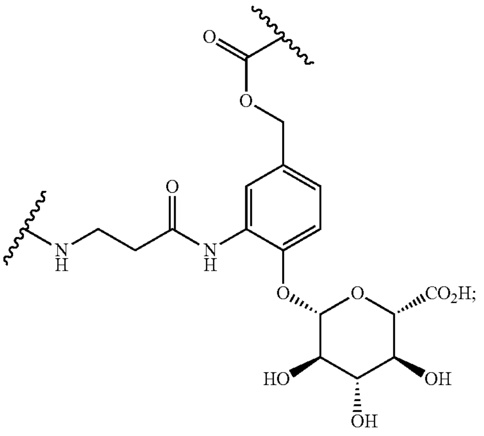

-continued

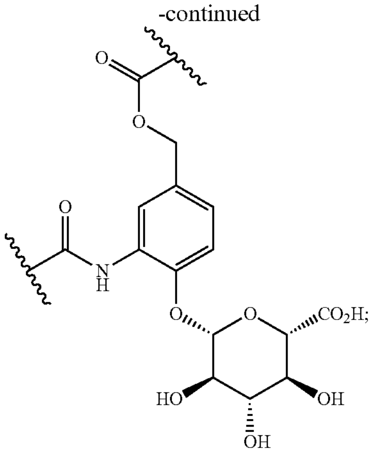

and

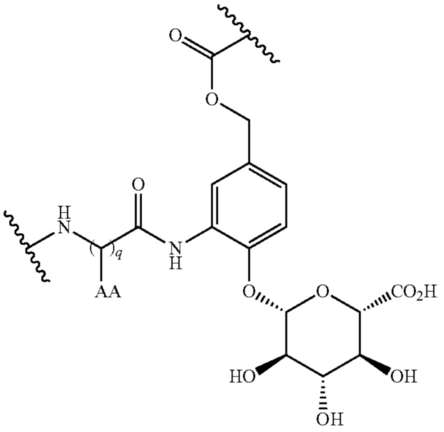

where q is 1 to 8, and AA is an amino acid side chain; and

Q is selected from the group consisting of N-hydroxysuccinimidyl, N-hydroxysulfosuccinimidyl, maleimide, and phenoxy substituted with one or more groups independently selected from F, Cl, $NO_2$, and $SO_3^-$;

where alkyl, alkyldiyl, alkenyl, alkenyldiyl, alkynyl, alkynyldiyl, aryl, aryldiyl carbocyclyl, carbocyclyldiyl, heterocyclyl, heterocyclyldiyl, heteroaryl, and heteroaryldiyl are independently and optionally substituted with one or more groups independently selected from F, Cl, Br, I, —CN, —$CH_3$, —$CH_2CH_3$, —CH=$CH_2$, —C≡CH, —C≡$CCH_3$, —$CH_2CH_2CH_3$, —$CH(CH_3)_2$, —$CH_2CH(CH_3)_2$, —$CH_2OH$, —$CH_2OCH_3$, —$CH_2CH_2OH$, —$C(CH_3)_2OH$, —$CH(OH)CH(CH_3)_2$, —$C(CH_3)_2CH_2OH$, —$CH_2CH_2SO_2CH_3$, —$CH_2OP(O)(OH)_2$, —$CH_2F$, —$CHF_2$, —$CF_3$, —$CH_2CF_3$, —$CH_2CHF_2$, —$CH(CH_3)CN$, —$C(CH_3)_2CN$, —$CH_2CN$, —$CH_2NH_2$, —$CH_2NHSO_2CH_3$, —$CH_2NHCH_3$, —$CH_2N(CH_3)_2$, —$CO_2H$, —$COCH_3$, —$CO_2CH_3$, —$CO_2C(CH_3)_3$, —$COCH(OH)CH_3$, —$CONH_2$, —$CONHCH_3$, —$CON(CH_3)_2$, —$C(CH_3)_2CONH_2$, —$NH_2$, —$NHCH_3$, —$N(CH_3)_2$, —$NHCOCH_3$, —$N(CH_3)COCH_3$, —$NHS(O)_2CH_3$, —$N(CH_3)C(CH_3)_2CONH_2$, —$N(CH_3)CH_2CH_2S(O)_2CH_3$, —NHC(=NH)H, —NHC(=NH)$CH_3$, —NHC(=NH)$NH_2$, —NHC(=O)$NH_2$, —$NO_2$, =O, —OH, —$OCH_3$, —$OCH_2CH_3$, —$OCH_2CH_2OCH_3$, —$OCH_2CH_2OH$, —$OCH_2CH_2N(CH_3)_2$, —$O(CH_2CH_2O)_n$—$CH_2)_mCO_2H$, —$O(CH_2CH_2O)_nH$, —$OCH_2F$, —$OCHF_2$, —$OCF_3$, —$OP(O)(OH)_2$, —$S(O)_2N(CH_3)_2$, —$SCH_3$, —$S(O)_2CH_3$, and —$S(O)_3H$.

An exemplary embodiment of the thienoazepine-linker compound of Formula II includes wherein PEP has the formula:

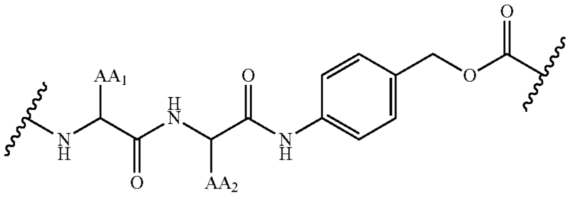

wherein $AA_1$ and $AA_2$ are independently selected from a side chain of a naturally-occurring amino acid.

An exemplary embodiment of the thienoazepine-linker compound of Formula II includes wherein $AA_1$ or $AA_2$ with an adjacent nitrogen atom form a 5-membered ring to form a proline amino acid.

An exemplary embodiment of the thienoazepine-linker compound of Formula II includes wherein PEP has the formula:

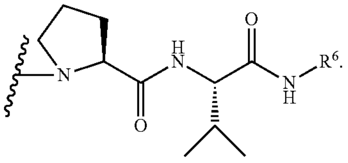

An exemplary embodiment of the thienoazepine-linker compound of Formula II includes wherein Mcgluc has the formula:

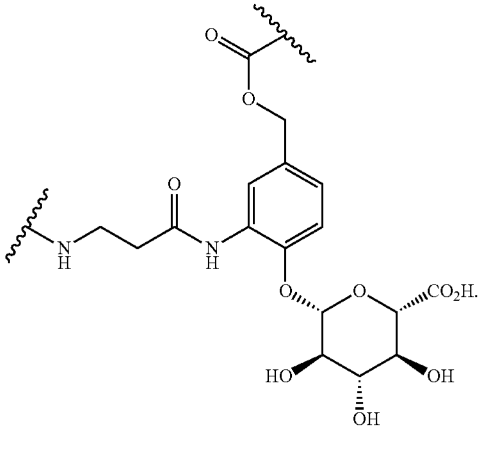 [SMILES: *NCCC(=O)Nc1cc(COC(*)=O)ccc1O[C@@H]1O[C@H](C(=O)O)[C@@H](O)[C@H](O)[C@H]1O]

An exemplary embodiment of the thienoazepine-linker compound of Formula II includes wherein $AA_1$ and $AA_2$ are independently selected from H, $—CH_3$, $—CH(CH_3)_2$, $—CH_2(C_6H_5)$, $—CH_2CH_2CH_2CH_2NH_2$, $—CH_2CH_2CH_2NHC(NH)NH_2$, $—CHCH(CH_3)CH_3$, $—CH_2SO_3H$, and $—CH_2CH_2CH_2NHC(O)NH_2$.

An exemplary embodiment of the thienoazepine-linker compound of Formula II includes wherein $AA_1$ is $—CH(CH_3)_2$, and $AA_2$ is $—CH_2CH_2CH_2NHC(O)NH_2$.

An exemplary embodiment of the thienoazepine-linker compound of Formula II includes wherein $AA_1$ and $AA_2$ are independently selected from GlcNAc aspartic acid, $—CH_2SO_3H$, and $—CH_2OPO_3H$.

An exemplary embodiment of the thienoazepine-linker compound of Formula II includes wherein $NR^5(C_2-C_5$ heteroaryl) of $R^1$ or $R^3$ is selected from:

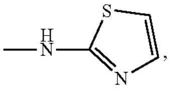, 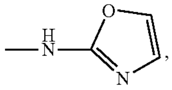, 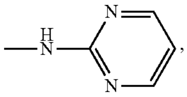, and

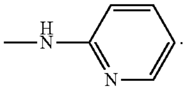.

An exemplary embodiment of the thienoazepine-linker compound of Formula II includes wherein $X^1$ is a bond, and $R^1$ is H.

An exemplary embodiment of the thienoazepine-linker compound of Formula II includes wherein $X^2$ is a bond, and $R^2$ is $C_1-C_8$ alkyl.

An exemplary embodiment of the thienoazepine-linker compound of Formula II includes wherein $X^2$ and $X^3$ are each a bond, and $R^2$ and $R^3$ are independently selected from $C_1-C_8$ alkyl, $—O—(C_1-C_{12}$ alkyl), $—(C_1-C_{12}$ alkyldiyl)-$OR^5$, $—(C_1-C_8$ alkyldiyl)-$N(R^5)CO_2R^5$, and $—O—(C_1-C_{12}$ alkyl)-$N(R^5)CO_2R^5$.

An exemplary embodiment of the thienoazepine-linker compound of Formula II includes wherein $R^2$ and $R^3$ are each independently selected from $—CH_2CH_2CH_3$, $—OCH_2CH_3$, $—CH_2CH_2CF_3$, and $—CH_2CH_2CH_2OH$.

An exemplary embodiment of the thienoazepine-linker compound of Formula II includes wherein $R^2$ is $C_1-C_8$ alkyl and $R^3$ is $—(C_1-C_8$ alkyldiyl)-$N(R^5)CO_2R^4$.

An exemplary embodiment of the thienoazepine-linker compound of Formula II includes wherein $R^2$ is $—CH_2CH_2CH_3$ and $R^3$ is $—CH_2CH_2CH_2NHCO_2$(t-Bu).

An exemplary embodiment of the thienoazepine-linker compound of Formula II includes wherein $R^2$ and $R^3$ are each $—CH_2CH_2CH_3$.

An exemplary embodiment of the thienoazepine-linker compound of Formula II includes wherein $X^3—R^3$ is selected from the group consisting of:

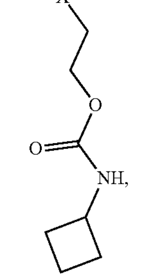

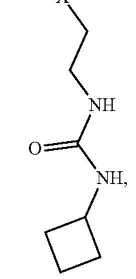

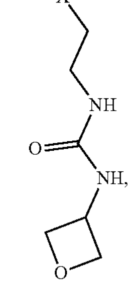

-continued

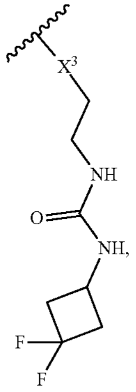

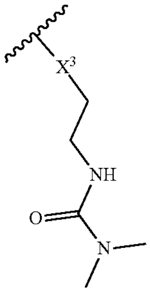,

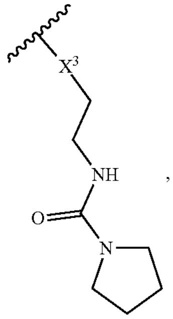,

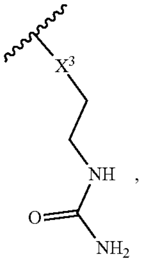,

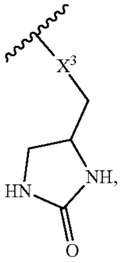

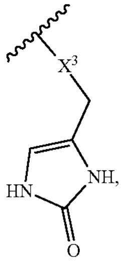

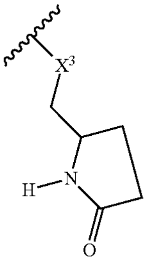,

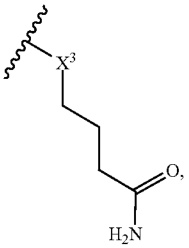

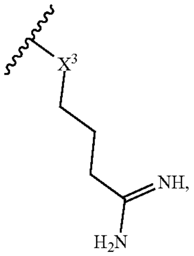

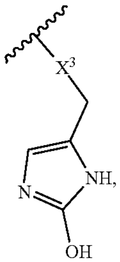

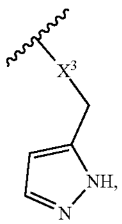

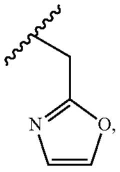

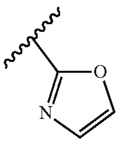,

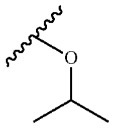,

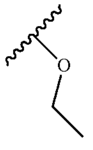, and

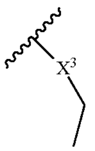

An exemplary embodiment of the thienoazepine-linker compound of Formula II includes wherein one of $R^2$ and $R^3$ is selected from;

—($C_1$-$C_{12}$ alkyldiyl)-N($R^5$)—*;

—($C_1$-$C_{12}$ alkyldiyl)-O—($C_1$-$C_{12}$ alkyldiyl)-N($R^5$)—*;

—($C_1$-$C_{12}$ alkyldiyl)-N($R^5$)C(=N$R^5$)—N($R^5$)—*;

—($C_1$-$C_{12}$ alkyldiyl)-($C_6$-$C_{20}$ aryldiyl)-($C_1$-$C_{12}$ alkyldiyl)-N($R^5$)—*;

—($C_1$-$C_{12}$ alkyldiyl)-($C_6$-$C_{20}$ aryldiyl)-($C_1$-$C_{12}$ alkyldiyl)-N($R^5$)—C(=N$R^5$)N($R^5$)—*;

—($C_2$-$C_6$ alkynyldiyl)-N($R^5$)—*; and

—($C_2$-$C_6$ alkynyldiyl)-N($R^5$)C(=N$R^5$)N($R^5$)—*;

$X^2$ and $X^3$ are a bond, and where the asterisk * indicates the attachment site of L.

An exemplary embodiment of the thienoazepine-linker compound of Formula II includes wherein L is selected from the group consisting of:

Q-C(=O)—(PEG)-;

Q-C(=O)—(PEG)-C(=O)—;

Q-C(=O)—(PEG)-O—;

Q-C(=O)—(PEG)-N($R^5$)—; and

Q-C(=O)—(PEG)-N($R^5$)C(=O)—.

An exemplary embodiment of the thienoazepine-linker compound of Formula II is selected from Formulae IIa-IIc:

IIa

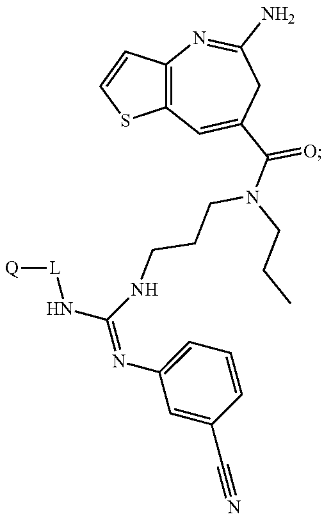

IIb

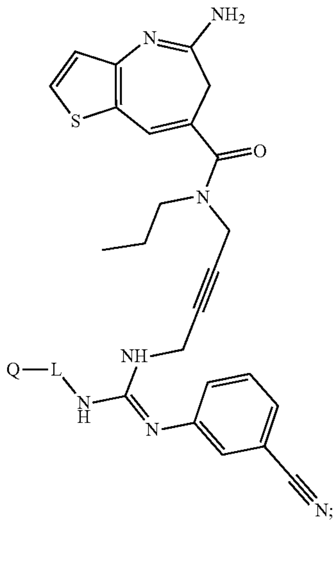

and

-continued

IIc

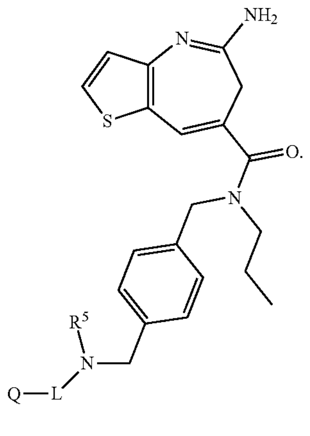

An exemplary embodiment of the thienoazepine-linker compound of Formula II is selected from Formulae IId-IIh:

IId

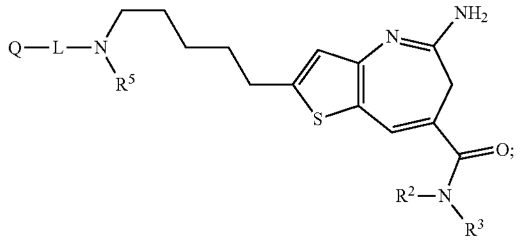

IIe

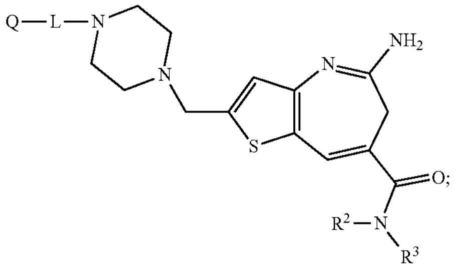

IIf

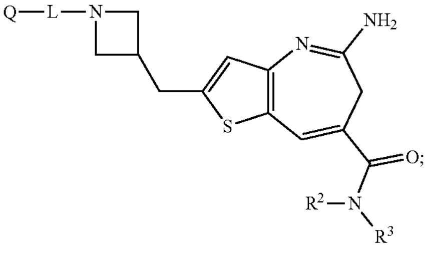

IIg

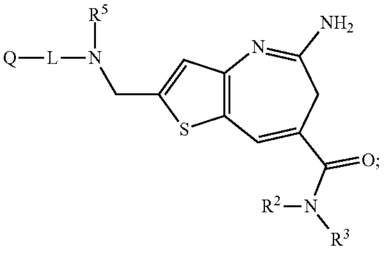

and

-continued

IIh

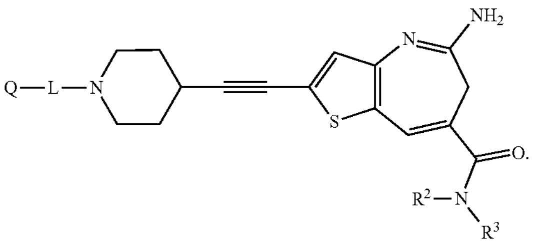

An exemplary embodiment of the thienoazepine-linker compound of Formula II includes wherein Q is selected from:

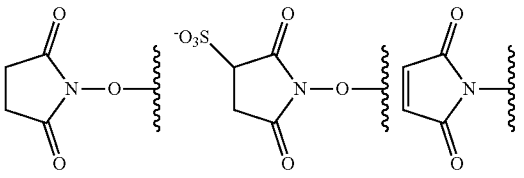

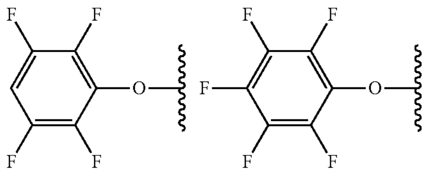

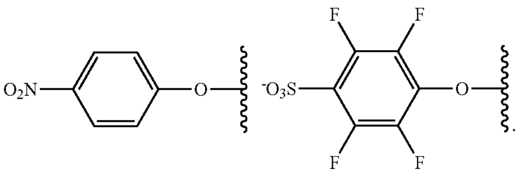

An exemplary embodiment of the thienoazepine-linker compound of Formula II includes wherein Q is phenoxy substituted with one or more F.

An exemplary embodiment of the thienoazepine-linker compound of Formula II includes wherein Q is 2,3,5,6-tetrafluorophenoxy.

An exemplary embodiment of the thienoazepine-linker (TAZ-L) compound is selected from Tables 2a-c. Each compound was synthesized, purified, and characterized by mass spectrometry and shown to have the mass indicated. Additional experimental procedures are found in the Examples. The thienoazepine-linker compounds of Tables 2a-c demonstrate the surprising and unexpected property of TLR8 agonist selectivity which may predict useful therapeutic activity to treat cancer and other disorders. The thienoazepine-linker compounds of Tables 2a-c are used in conjugation with antibodies by the methods of Example 201 to form the Immunoconjugates of Tables 3a-c.

TABLE 2a
| Thienoazepine-linker (TAZ-L) Formula II compounds | | |
|---|---|---|
| TAZ-L No. | Structure | MW |
| TAZ-L-1 | 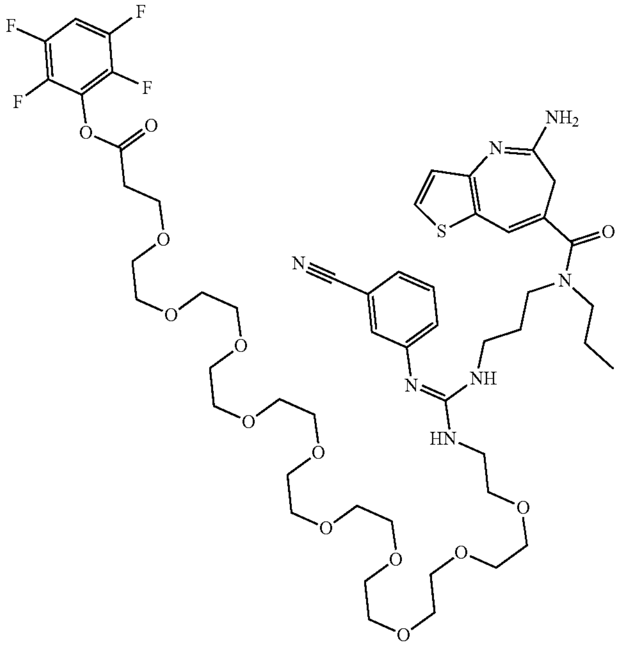 [SMILES: CCCN(CCCN/C(=N\c1cccc(C#N)c1)NCCOCCOCCOCCOCCOCCOCCOCCOCCOCCOCCC(=O)Oc1c(F)c(F)cc(F)c1F)C(=O)C1=Cc2sccc2N=C(N)C1] | 1110.2 |
| TAZ-L-2 | 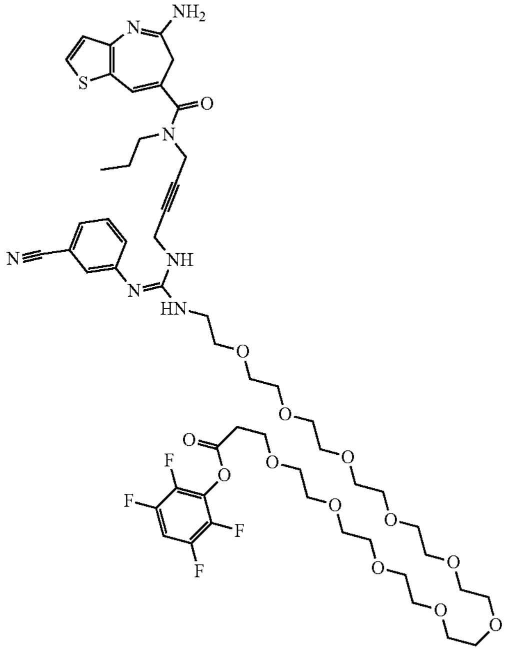 [SMILES: CCCN(CC#CCN/C(=N\c1cccc(C#N)c1)NCCOCCOCCOCCOCCOCCOCCOCCOCCOCCOCCC(=O)Oc1c(F)c(F)cc(F)c1F)C(=O)C1=Cc2sccc2N=C(N)C1] | 1120.2 |

TABLE 2a-continued
| Thienoazepine-linker (TAZ-L) Formula II compounds | | |
|---|---|---|
| TAZ-L No. | Structure | MW |
| TAZ-L-3 | 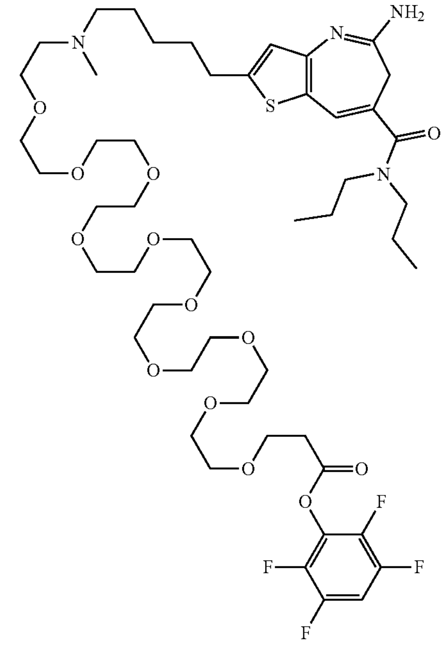 [SMILES: CCCN(CCC)C(=O)C1=Cc2sc(CCCCCN(C)CCOCCOCCOCCOCCOCCOCCOCCOCCOCCOCCC(=O)Oc3c(F)c(F)cc(F)c3F)cc2N=C(N)C1] | 1051.2 |
| TAZ-L-4 | 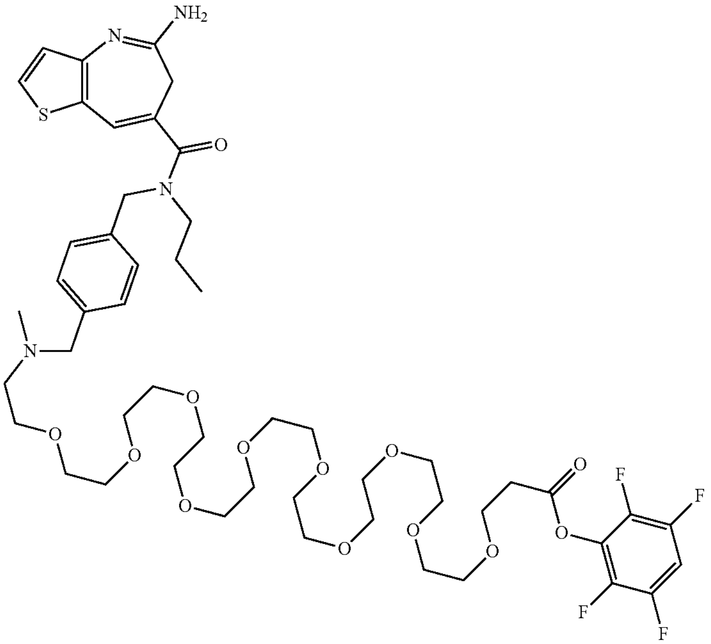 [SMILES: CCCN(Cc1ccc(CN(C)CCOCCOCCOCCOCCOCCOCCOCCOCCOCCOCCC(=O)Oc2c(F)c(F)cc(F)c2F)cc1)C(=O)C1=Cc2sccc2N=C(N)C1] | 1043.2 |

TABLE 2b
| Thienoazepine-linker (TAZ-L) Formula II compounds | | |
|---|---|---|
| TAZ-L No. | Structure | MW |
| TAZ-L-5 | 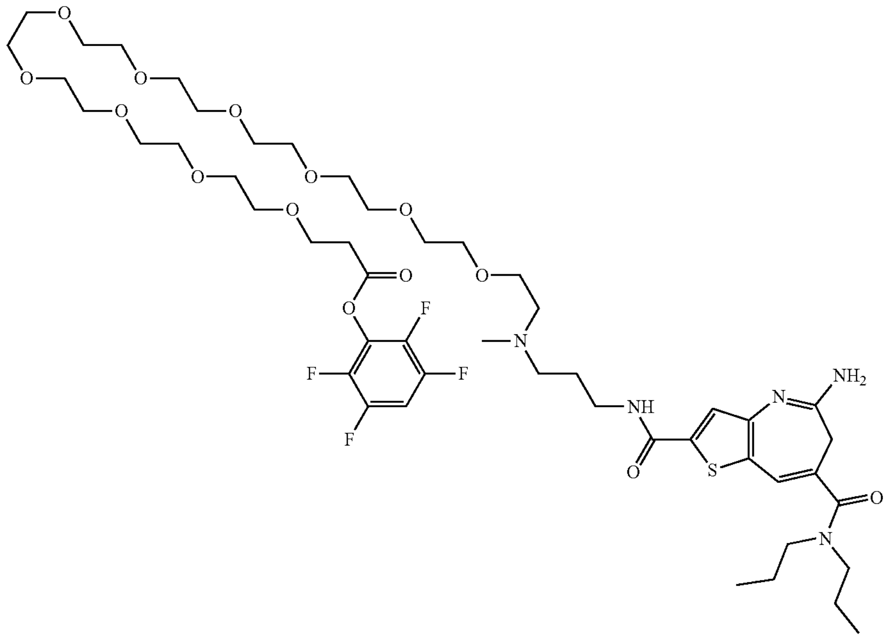 [SMILES: CCCN(CCC)C(=O)C1=Cc2sc(C(=O)NCCCN(C)CCOCCOCCOCCOCCOCCOCCOCCOCCOCCOCCC(=O)Oc3c(F)c(F)cc(F)c3F)cc2N=C(N)C1] | 1066.2 |
| TAZ-L-6 | 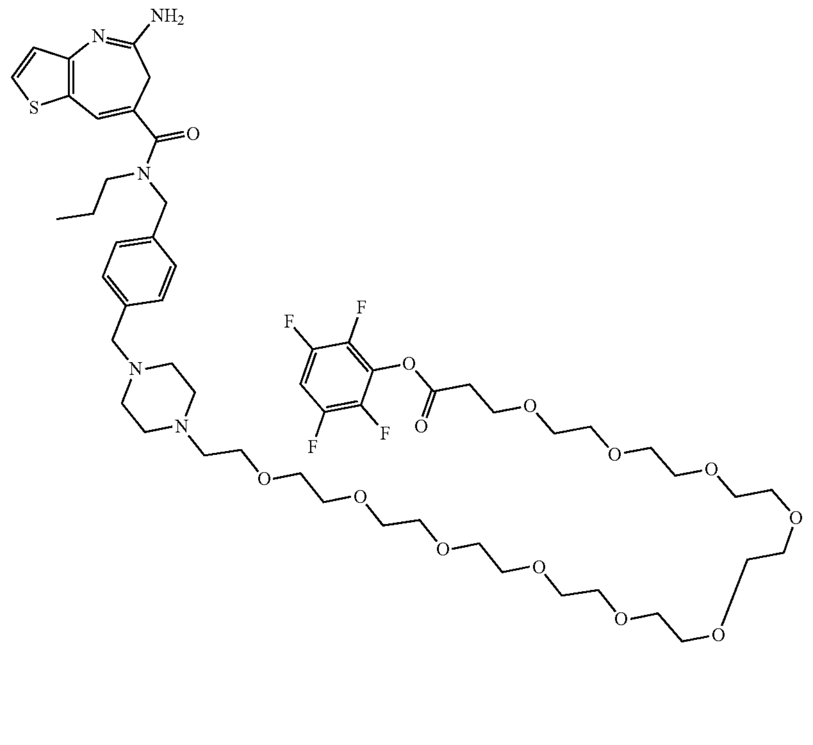 [SMILES: CCCN(Cc1ccc(CN2CCN(CCOCCOCCOCCOCCOCCOCCOCCOCCOCCOCCC(=O)Oc3c(F)c(F)cc(F)c3F)CC2)cc1)C(=O)C1=Cc2sccc2N=C(N)C1] | 1098.3 |

TABLE 2b-continued
| TAZ-L No. | Structure | MW |
|---|---|---|
| Thienoazepine-linker (TAZ-L) Formula II compounds | | |
| TAZ-L-7 | 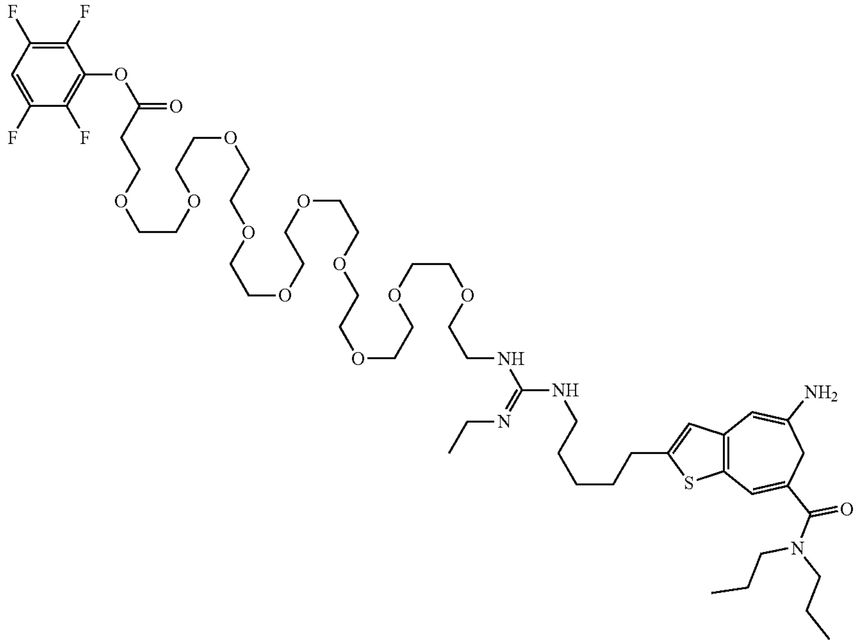 [SMILES: CCCN(CCC)C(=O)C1=Cc2sc(CCCCCN/C(=N/CC)NCCOCCOCCOCCOCCOCCOCCOCCOCCOCCOCCC(=O)Oc3c(F)c(F)cc(F)c3F)cc2C=C(N)C1] | 1107.3 |
| TAZ-L-8 | 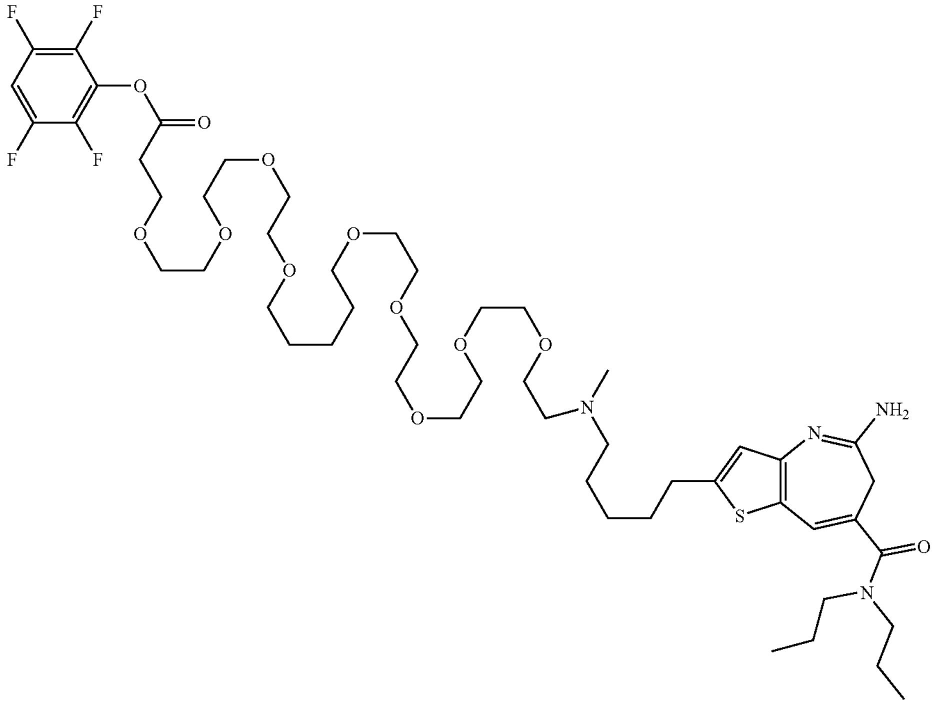 [SMILES: CCCN(CCC)C(=O)C1=Cc2sc(CCCCCN(C)CCOCCOCCOCCOCCOCCCCCOCCOCCOCCOCCC(=O)Oc3c(F)c(F)cc(F)c3F)cc2N=C(N)C1] | 1037.2 |

TABLE 2b-continued
| Thienoazepine-linker (TAZ-L) Formula II compounds | | |
|---|---|---|
| TAZ-L No. | Structure | MW |
| TAZ-L-9 | 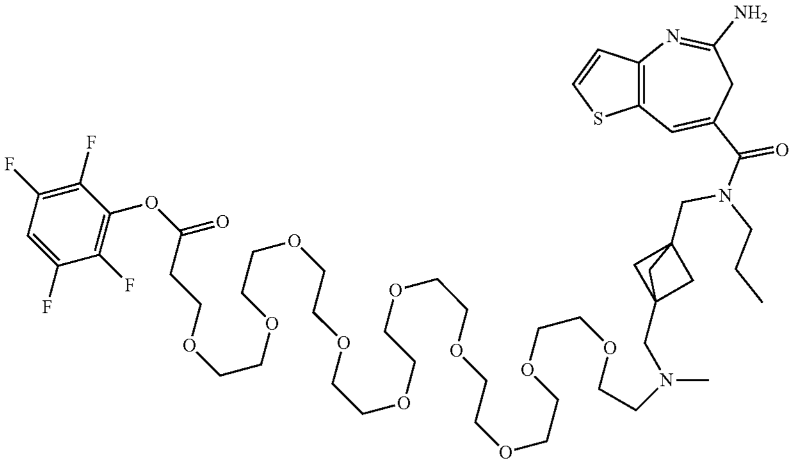 [SMILES: CCCN(CC12CC(CN(C)CCOCCOCCOCCOCCOCCOCCOCCOCCOCCOCCC(=O)Oc3c(F)c(F)cc(F)c3F)(C1)C2)C(=O)C1=Cc2sccc2N=C(N)C1] | 1033.2 |
| TAZ-L-10 | 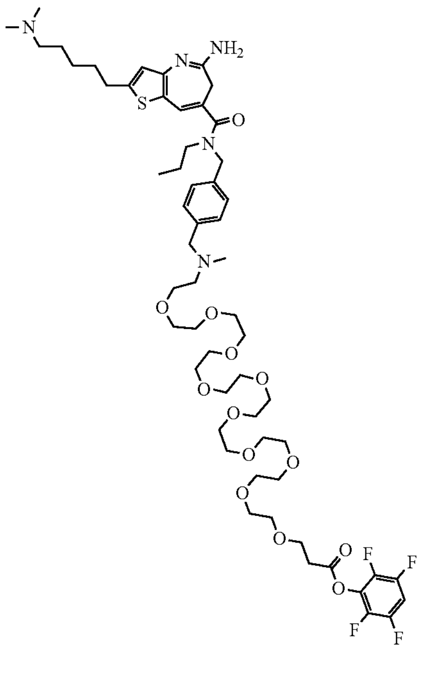 [SMILES: CCCN(Cc1ccc(CN(C)CCOCCOCCOCCOCCOCCOCCOCCOCCOCCOCCC(=O)Oc2c(F)c(F)cc(F)c2F)cc1)C(=O)C1=Cc2sc(CCCCCN(C)C)cc2N=C(N)C1] | 1156.4 |

TABLE 2b-continued
| Thienoazepine-linker (TAZ-L) Formula II compounds | | |
|---|---|---|
| TAZ-L No. | Structure | MW |
| TAZ-L-11 | 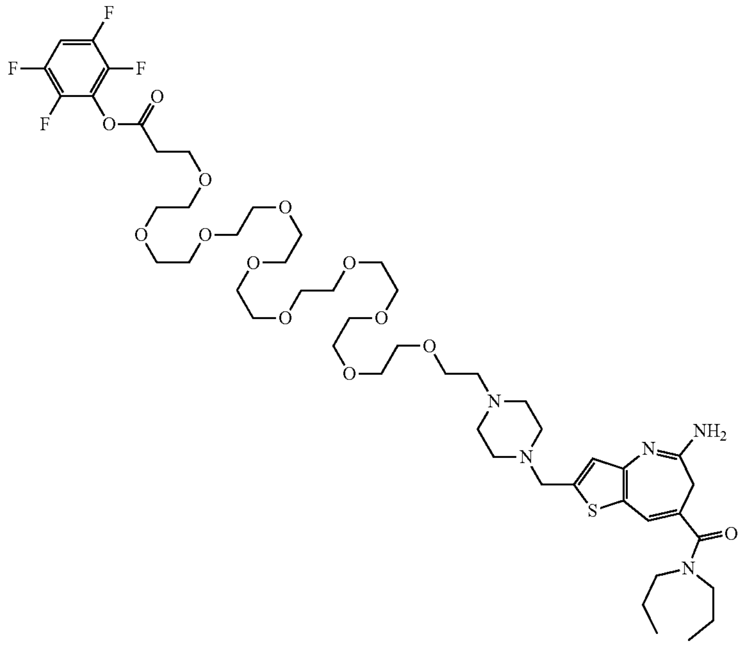 [SMILES: CCCN(CCC)C(=O)C1=Cc2sc(CN3CCN(CCOCCOCCOCCOCCOCCOCCOCCOCCOCCOCCC(=O)Oc4c(F)c(F)cc(F)c4F)CC3)cc2N=C(N)C1] | 1050.2 |
| TAZ-L-12 | 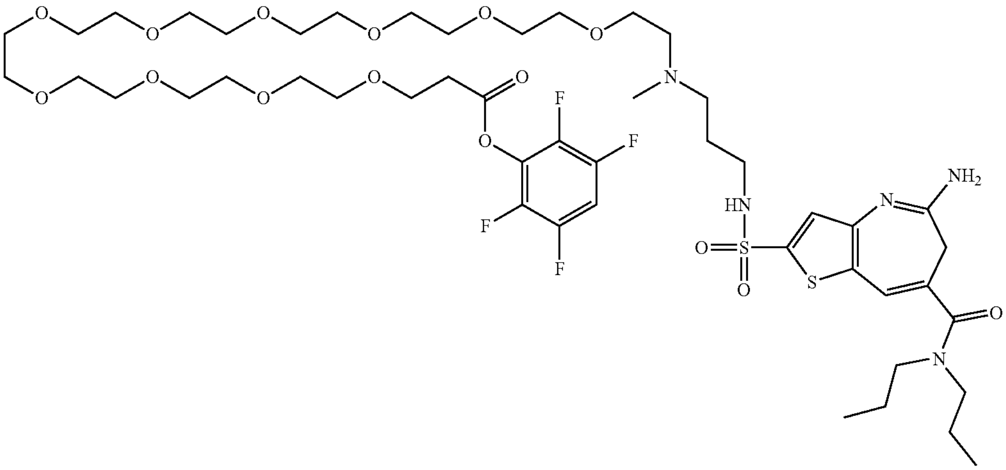 [SMILES: CCCN(CCC)C(=O)C1=Cc2sc(S(=O)(=O)NCCCN(C)CCOCCOCCOCCOCCOCCOCCOCCOCCOCCOCCC(=O)Oc3c(F)c(F)cc(F)c3F)cc2N=C(N)C1] | 1102.3 |

TABLE 2b-continued
| Thienoazepine-linker (TAZ-L) Formula II compounds | | |
|---|---|---|
| TAZ-L No. | Structure | MW |
| TAZ-L-13 | 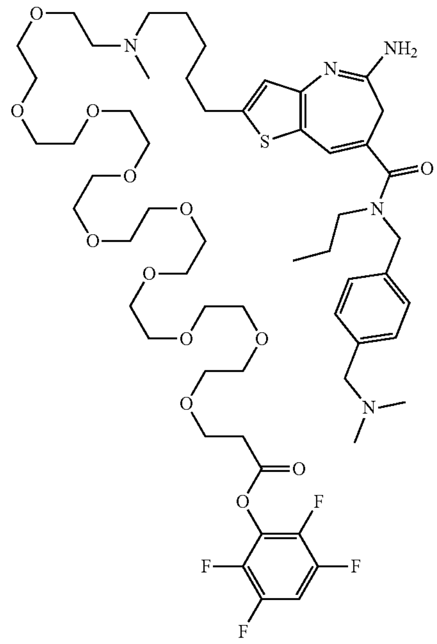 [SMILES: CCCN(Cc1ccc(CN(C)C)cc1)C(=O)C1=Cc2sc(CCCCCN(C)CCOCCOCCOCCOCCOCCOCCOCCOCCOCCOCCC(=O)Oc3c(F)c(F)cc(F)c3F)cc2N=C(N)C1] | 1156.4 |
| TAZ-L-14 | 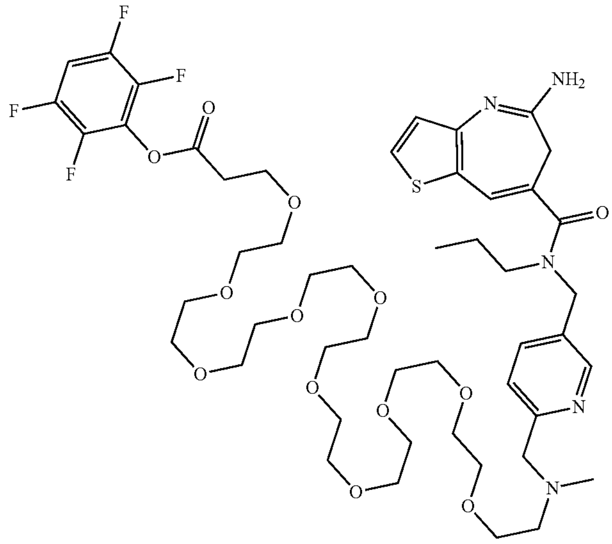 [SMILES: CCCN(Cc1ccc(CN(C)CCOCCOCCOCCOCCOCCOCCOCCOCCOCCOCCC(=O)Oc2c(F)c(F)cc(F)c2F)nc1)C(=O)C1=Cc2sccc2N=C(N)C1] | 1044.2 |

TABLE 2b-continued
| Thienoazepine-linker (TAZ-L) Formula II compounds | | |
|---|---|---|
| TAZ-L No. | Structure | MW |
| TAZ-L-15 | 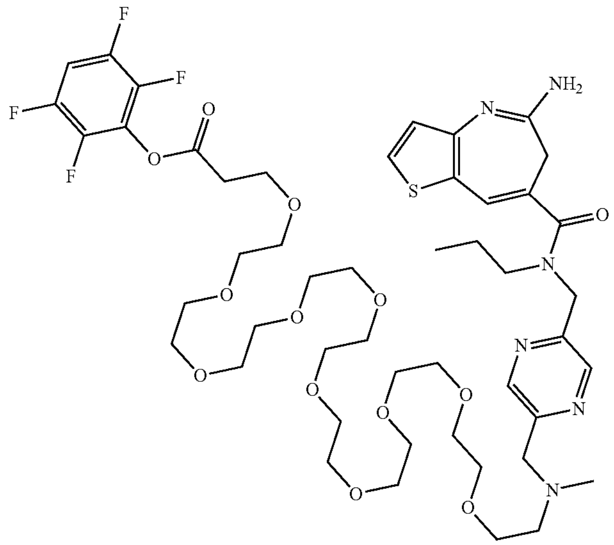 [SMILES: CCCN(Cc1cnc(CN(C)CCOCCOCCOCCOCCOCCOCCOCCOCCOCCOCCC(=O)Oc2c(F)c(F)cc(F)c2F)cn1)C(=O)C1=Cc2sccc2N=C(N)C1] | 1045.1 |
| TAZ-L-16 | 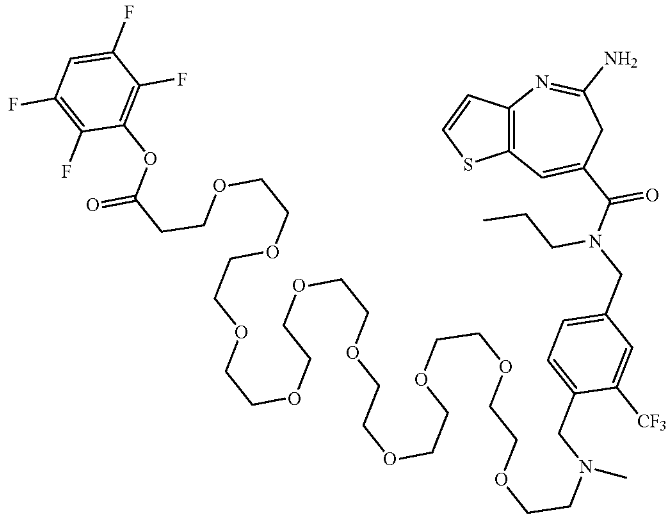 [SMILES: CCCN(Cc1ccc(CN(C)CCOCCOCCOCCOCCOCCOCCOCCOCCOCCOCCC(=O)Oc2c(F)c(F)cc(F)c2F)c(C(F)(F)F)c1)C(=O)C1=Cc2sccc2N=C(N)C1] | 1111.2 |

TABLE 2b-continued
| Thienoazepine-linker (TAZ-L) Formula II compounds | | |
|---|---|---|
| TAZ-L No. | Structure | MW |
| TAZ-L-17 | 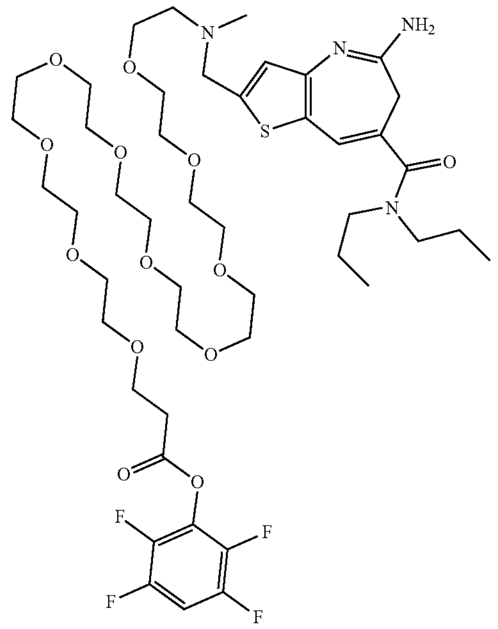 [SMILES: CCCN(CCC)C(=O)C1=Cc2sc(CN(C)CCOCCOCCOCCOCCOCCOCCOCCOCCOCCOCCC(=O)Oc3c(F)c(F)cc(F)c3F)cc2N=C(N)C1] | 995.13 |
| TAZ-L-18 | 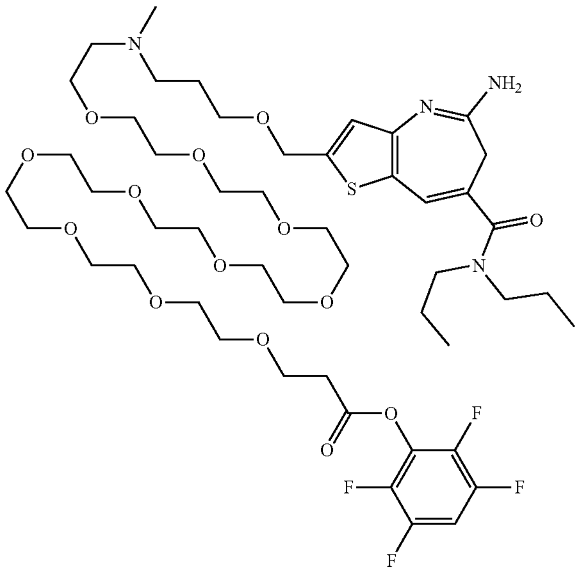 [SMILES: CCCN(CCC)C(=O)C1=Cc2sc(COCCCN(C)CCOCCOCCOCCOCCOCCOCCOCCOCCOCCOCCC(=O)Oc3c(F)c(F)cc(F)c3F)cc2N=C(N)C1] | 1053.2 |

TABLE 2b-continued
| Thienoazepine-linker (TAZ-L) Formula II compounds | | |
|---|---|---|
| TAZ-L No. | Structure | MW |
| TAZ-L-19 | 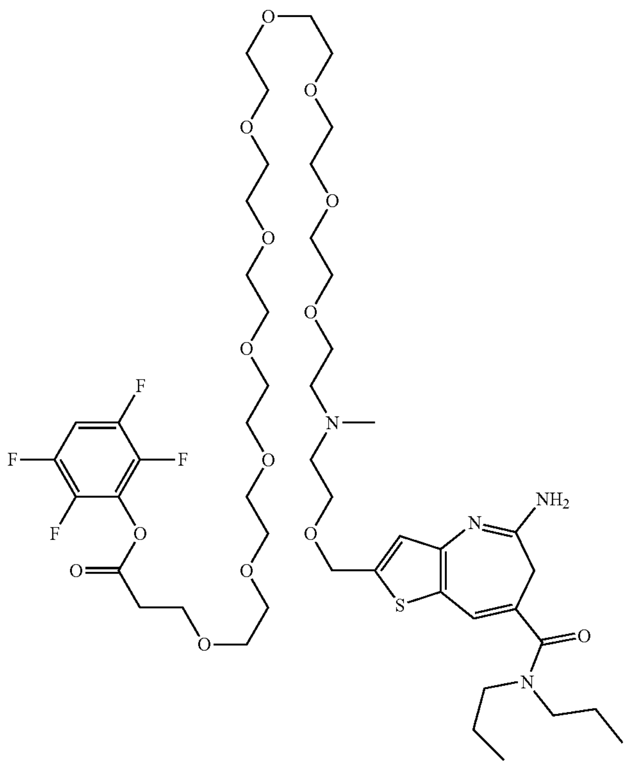 [SMILES: CCCN(CCC)C(=O)C1=Cc2sc(COCCN(C)CCOCCOCCOCCOCCOCCOCCOCCOCCOCCOCCC(=O)Oc3c(F)c(F)cc(F)c3F)cc2N=C(N)C1] | 1039.2 |
| TAZ-L-20 | 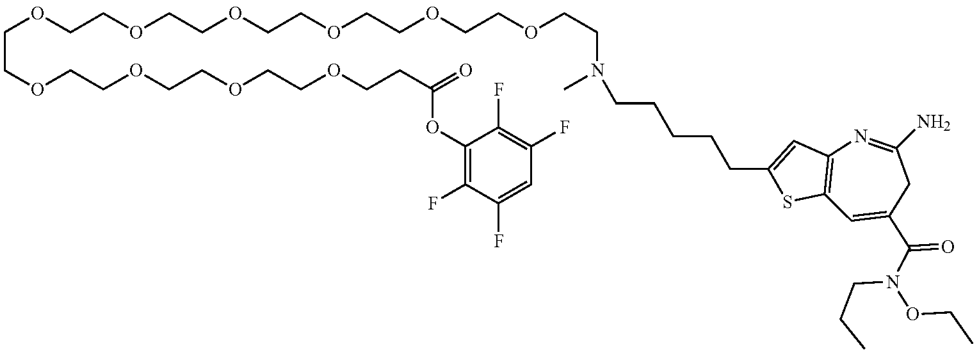 [SMILES: CCCN(OCC)C(=O)C1=Cc2sc(CCCCCN(C)CCOCCOCCOCCOCCOCCOCCOCCOCCOCCOCCC(=O)Oc3c(F)c(F)cc(F)c3F)cc2N=C(N)C1] | 1053.2 |

TABLE 2b-continued
| Thienoazepine-linker (TAZ-L) Formula II compounds | | |
|---|---|---|
| TAZ-L No. | Structure | MW |
| TAZ-L-21 | 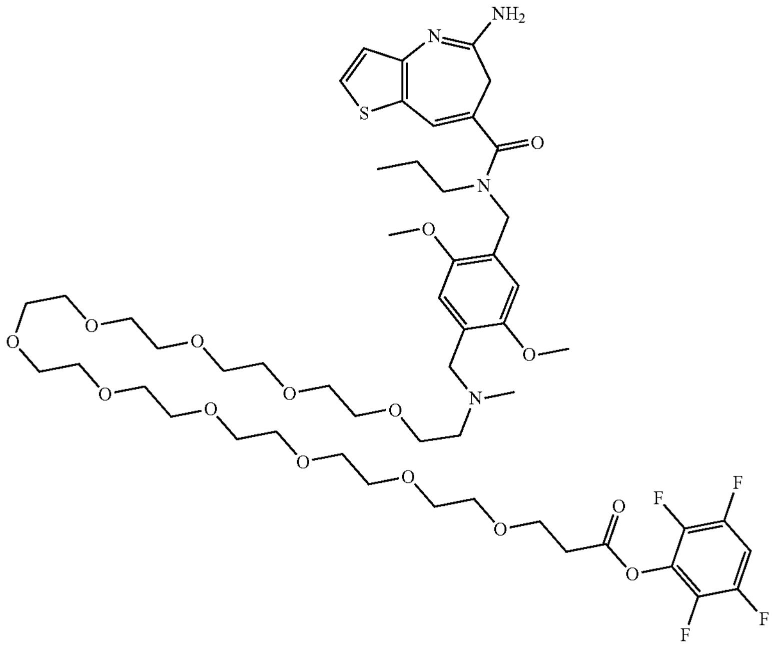 [SMILES: CCCN(Cc1cc(OC)c(CN(C)CCOCCOCCOCCOCCOCCOCCOCCOCCOCCOCCC(=O)Oc2c(F)c(F)cc(F)c2F)cc1OC)C(=O)C1=Cc2sccc2N=C(N)C1] | 1103.2 |
| TAZ-L-22 | 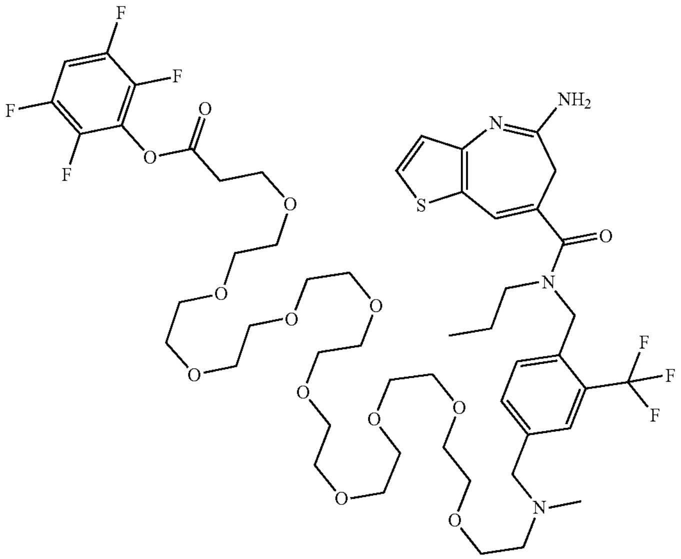 [SMILES: CCCN(Cc1ccc(CN(C)CCOCCOCCOCCOCCOCCOCCOCCOCCOCCOCCC(=O)Oc2c(F)c(F)cc(F)c2F)cc1C(F)(F)F)C(=O)C1=Cc2sccc2N=C(N)C1] | 1111.2 |

TABLE 2b-continued
Thienoazepine-linker (TAZ-L) Formula II compounds
| TAZ-L No. | Structure | MW |
| --- | --- | --- |
| TAZ-L-23 | 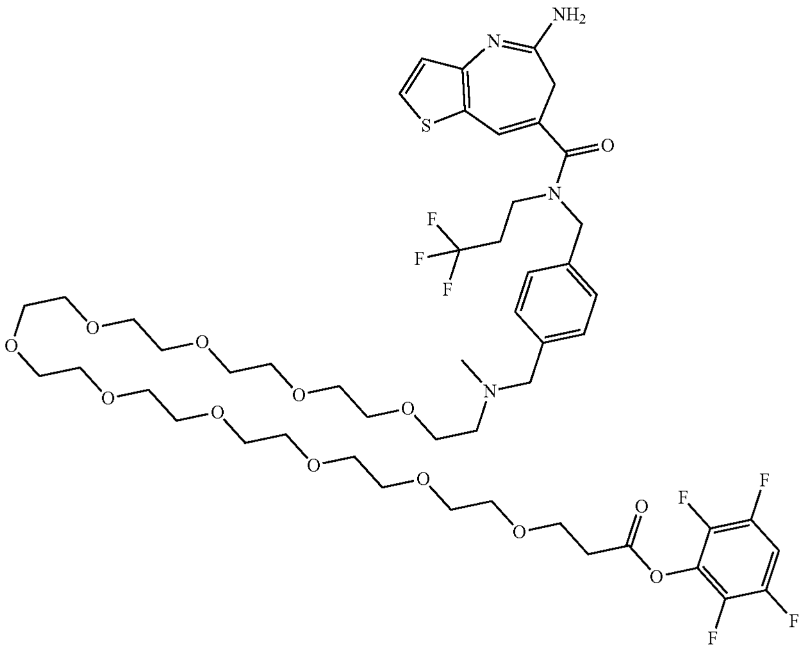 [SMILES: CN(CCOCCOCCOCCOCCOCCOCCOCCOCCOCCOCCC(=O)Oc1c(F)c(F)cc(F)c1F)Cc1ccc(CN(CCC(F)(F)F)C(=O)C2=Cc3sccc3N=C(N)C2)cc1] | 1097.1 |
| TAZ-L-24 | 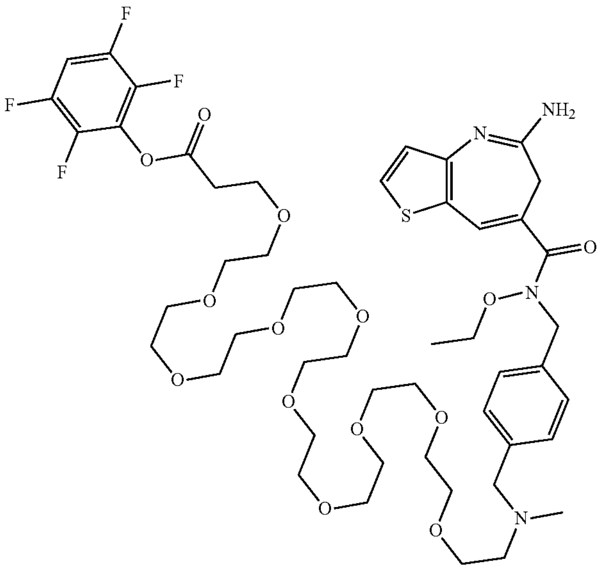 [SMILES: CCON(Cc1ccc(CN(C)CCOCCOCCOCCOCCOCCOCCOCCOCCOCCOCCC(=O)Oc2c(F)c(F)cc(F)c2F)cc1)C(=O)C1=Cc2sccc2N=C(N)C1] | 1045.1 |

TABLE 2b-continued
| Thienoazepine-linker (TAZ-L) Formula II compounds | | |
|---|---|---|
| TAZ-L No. | Structure | MW |
| TAZ-L-25 | 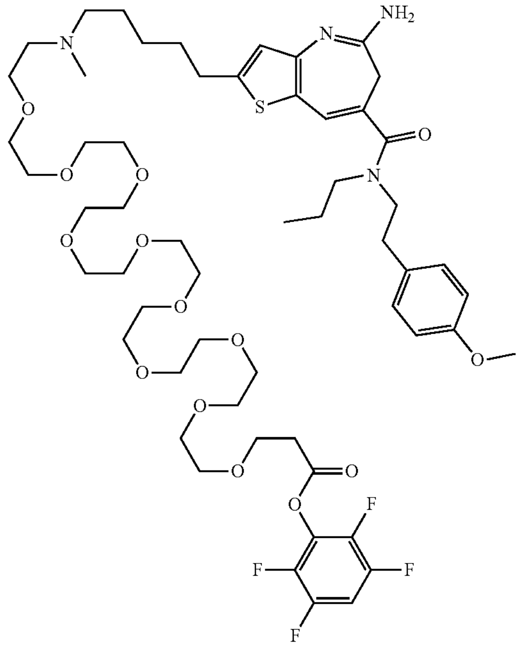 [SMILES: CCCN(CCc1ccc(OC)cc1)C(=O)C1=Cc2sc(CCCCCN(C)CCOCCOCCOCCOCCOCCOCCOCCOCCOCCOCCC(=O)Oc3c(F)c(F)cc(F)c3F)cc2N=C(N)C1] | 1143.3 |
| TAZ-L-26 | 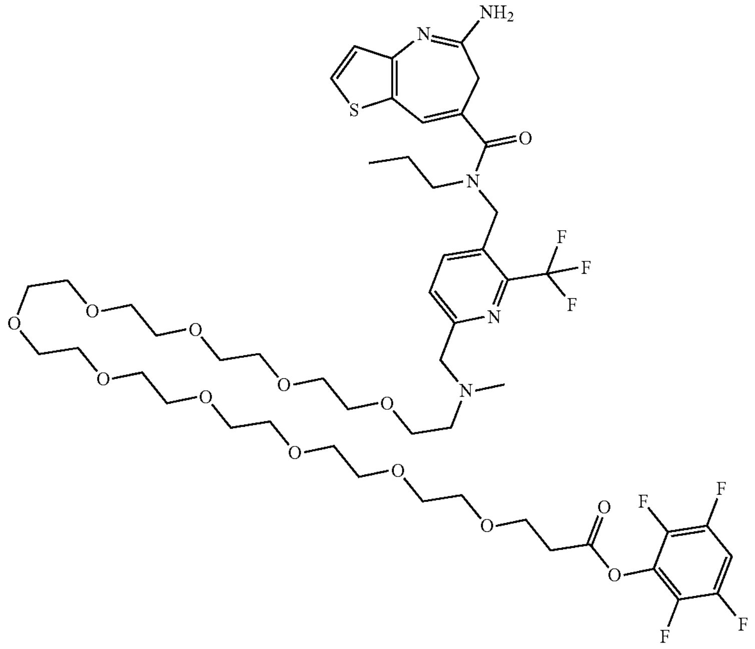 [SMILES: CCCN(Cc1ccc(CN(C)CCOCCOCCOCCOCCOCCOCCOCCOCCOCCOCCC(=O)Oc2c(F)c(F)cc(F)c2F)nc1C(F)(F)F)C(=O)C1=Cc2sccc2N=C(N)C1] | 1112.2 |

TABLE 2b-continued
| Thienoazepine-linker (TAZ-L) Formula II compounds | | |
|---|---|---|
| TAZ-L No. | Structure | MW |
| TAZ-L-27 | 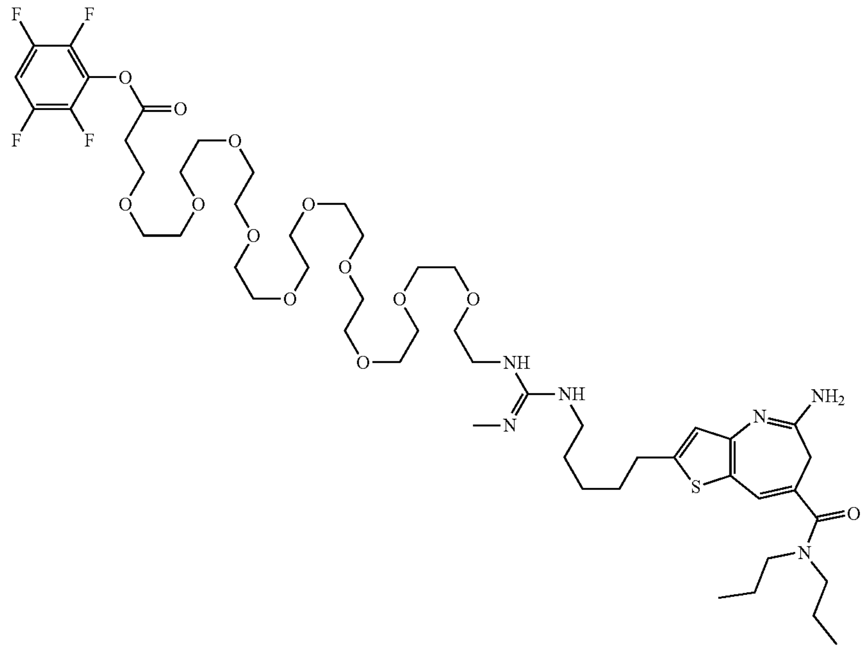 [SMILES: CCCN(CCC)C(=O)C1=Cc2sc(CCCCCN/C(=N/C)NCCOCCOCCOCCOCCOCCOCCOCCOCCOCCOCCC(=O)Oc3c(F)c(F)cc(F)c3F)cc2N=C(N)C1] | 1093.3 |
| TAZ-L-28 | 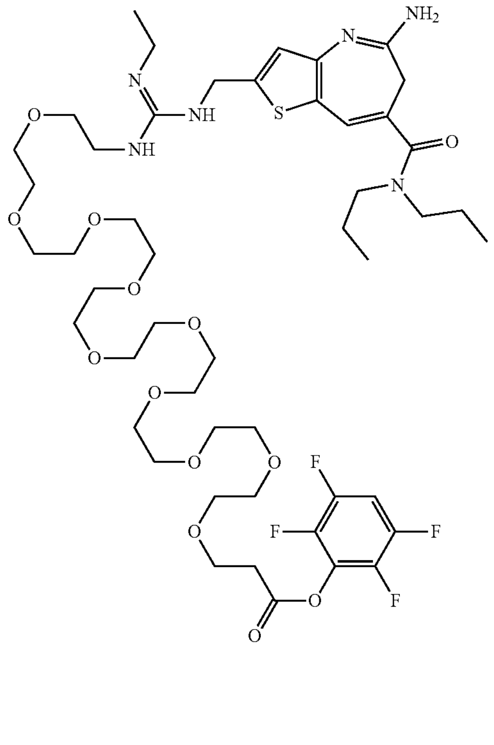 [SMILES: CCCN(CCC)C(=O)C1=Cc2sc(CN/C(=N\CC)NCCOCCOCCOCCOCCOCCOCCOCCOCCOCCOCCC(=O)Oc3c(F)c(F)cc(F)c3F)cc2N=C(N)C1] | 1051.2 |

TABLE 2b-continued
| Thienoazepine-linker (TAZ-L) Formula II compounds | | |
|---|---|---|
| TAZ-L No. | Structure | MW |
| TAZ-L-29 | 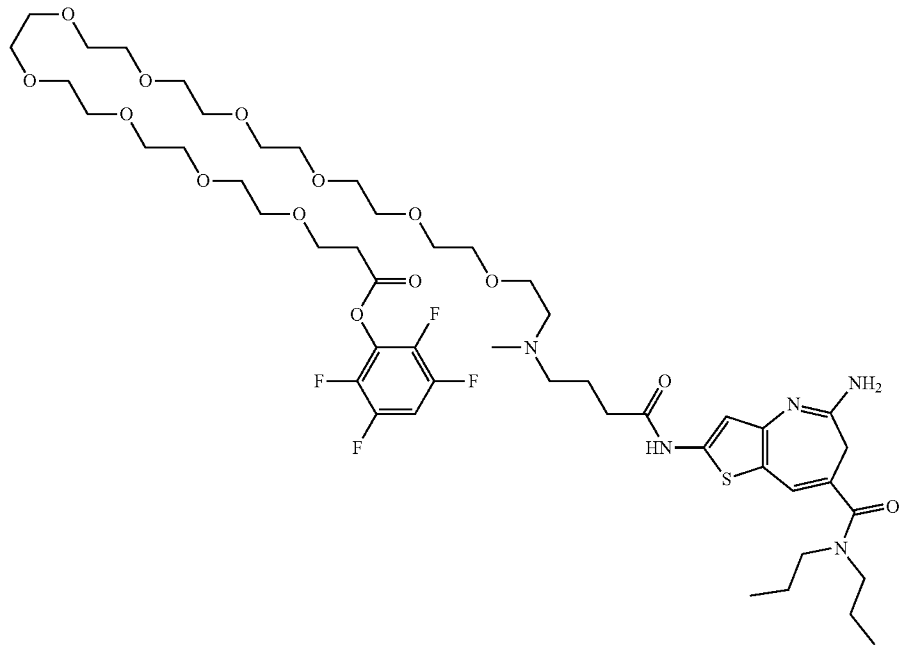 [SMILES: CCCN(CCC)C(=O)C1=Cc2sc(NC(=O)CCCN(C)CCOCCOCCOCCOCCOCCOCCOCCOCCOCCOCCC(=O)Oc3c(F)c(F)cc(F)c3F)cc2N=C(N)C1] | 1066.2 |
| TAZ-L-30 | 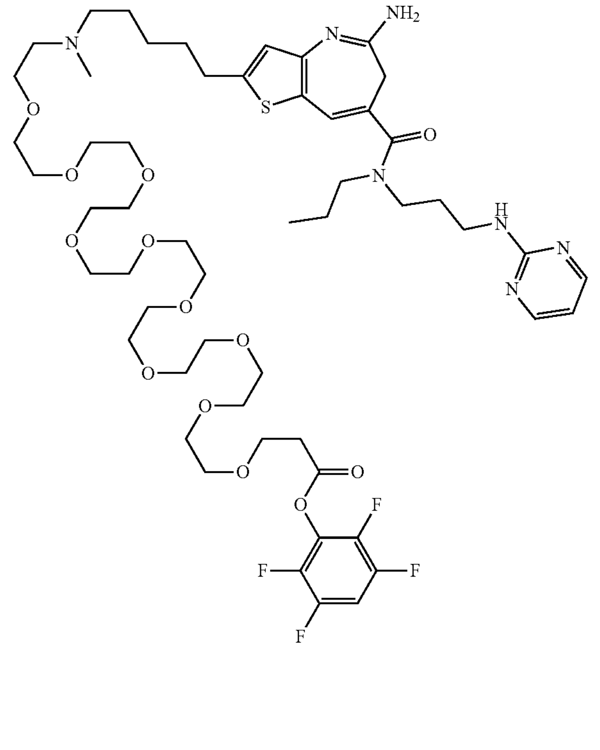 [SMILES: CCCN(CCCNc1ncccn1)C(=O)C1=Cc2sc(CCCCCN(C)CCOCCOCCOCCOCCOCCOCCOCCOCCOCCOCCC(=O)Oc3c(F)c(F)cc(F)c3F)cc2N=C(N)C1] | 1144.3 |

TABLE 2b-continued
| Thienoazepine-linker (TAZ-L) Formula II compounds | | |
|---|---|---|
| TAZ-L No. | Structure | MW |
| TAZ-L-31 | 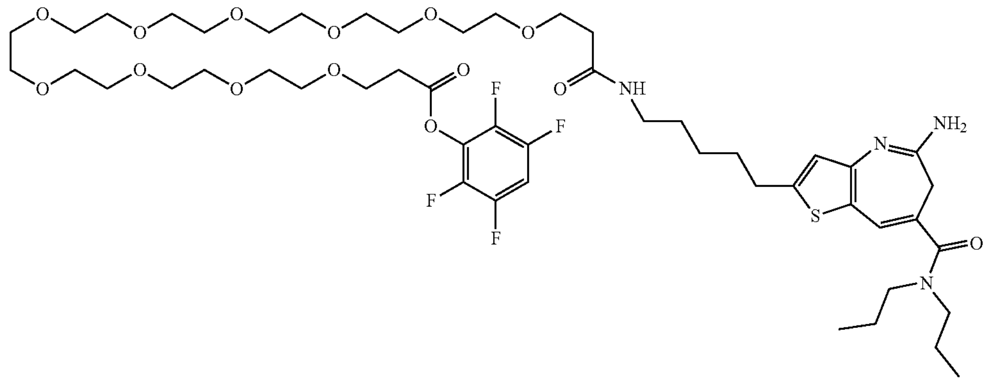 [SMILES: CCCN(CCC)C(=O)C1=Cc2sc(CCCCCNC(=O)CCOCCOCCOCCOCCOCCOCCOCCOCCOCCOCCC(=O)Oc3c(F)c(F)cc(F)c3F)cc2N=C(N)C1] | 1065.2 |
| TAZ-L-32 | 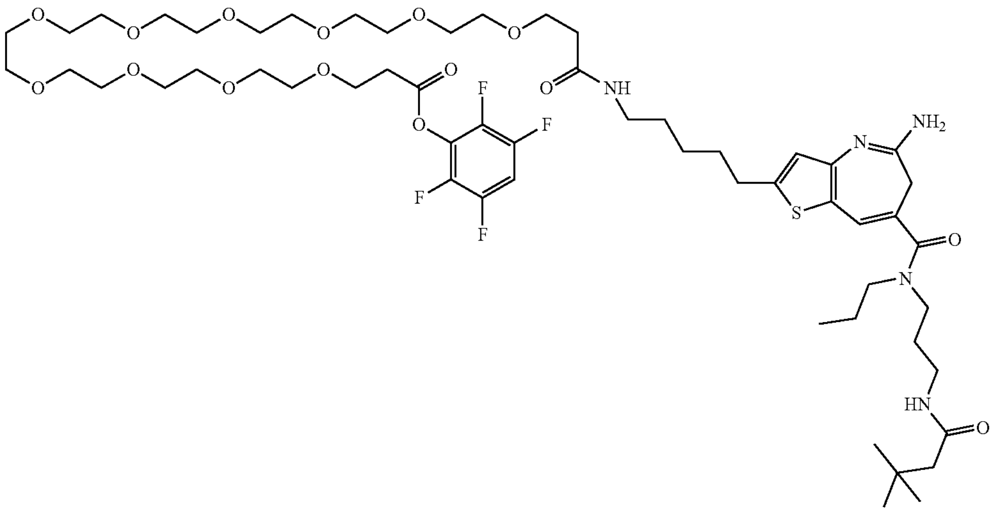 [SMILES: CCCN(CCCNC(=O)CC(C)(C)C)C(=O)C1=Cc2sc(CCCCCNC(=O)CCOCCOCCOCCOCCOCCOCCOCCOCCOCCOCCC(=O)Oc3c(F)c(F)cc(F)c3F)cc2N=C(N)C1] | 1178.4 |
| TAZ-L-33 | 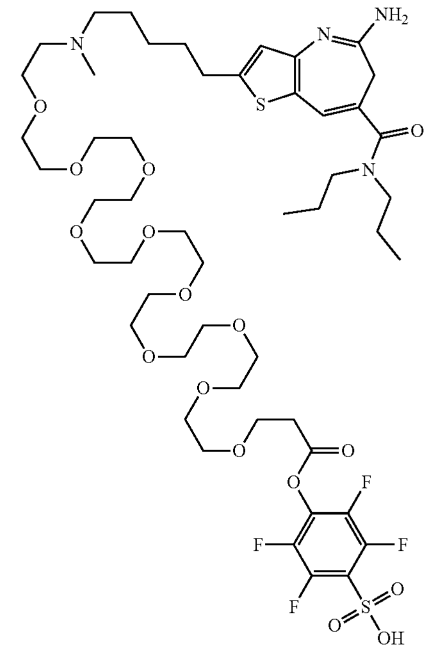 [SMILES: CCCN(CCC)C(=O)C1=Cc2sc(CCCCCN(C)CCOCCOCCOCCOCCOCCOCCOCCOCCOCCOCCC(=O)Oc3c(F)c(F)c(S(=O)(=O)O)c(F)c3F)cc2N=C(N)C1] | 1131.3 |

TABLE 2b-continued
| Thienoazepine-linker (TAZ-L) Formula II compounds | | |
|---|---|---|
| TAZ-L No. | Structure | MW |
| TAZ-L-34 | 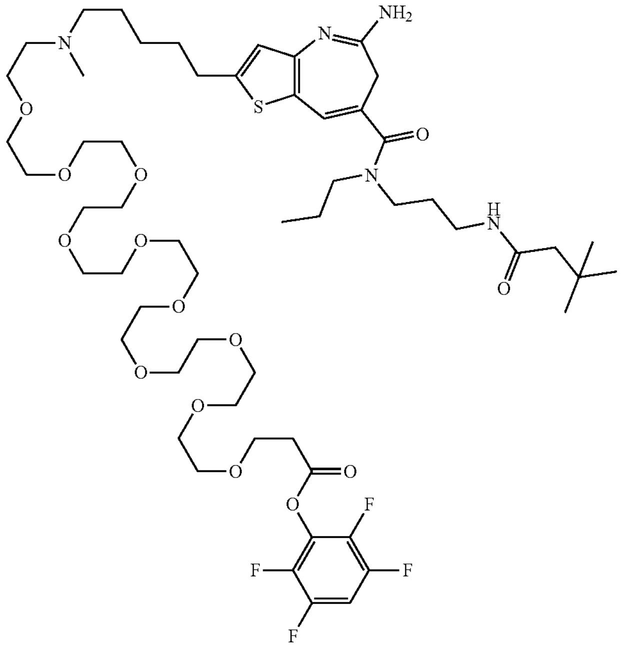 [SMILES: CCCN(CCCNC(=O)CC(C)(C)C)C(=O)C1=Cc2sc(CCCCCN(C)CCOCCOCCOCCOCCOCCOCCOCCOCCOCCOCCC(=O)Oc3c(F)c(F)cc(F)c3F)cc2N=C(N)C1] | 1164.4 |
| TAZ-L-35 | 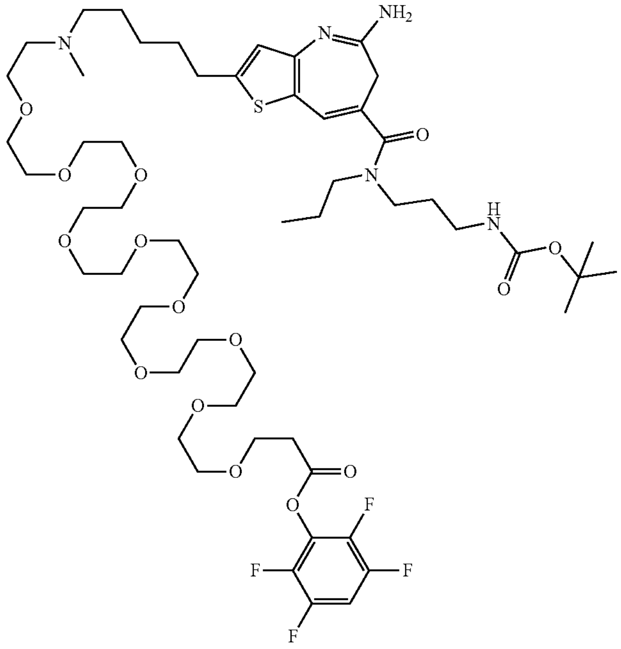 [SMILES: CCCN(CCCNC(=O)OC(C)(C)C)C(=O)C1=Cc2sc(CCCCCN(C)CCOCCOCCOCCOCCOCCOCCOCCOCCOCCOCCC(=O)Oc3c(F)c(F)cc(F)c3F)cc2N=C(N)C1] | 1166.4 |

TABLE 2b-continued
| Thienoazepine-linker (TAZ-L) Formula II compounds | | |
|---|---|---|
| TAZ-L No. | Structure | MW |
| TAZ-L-36 | 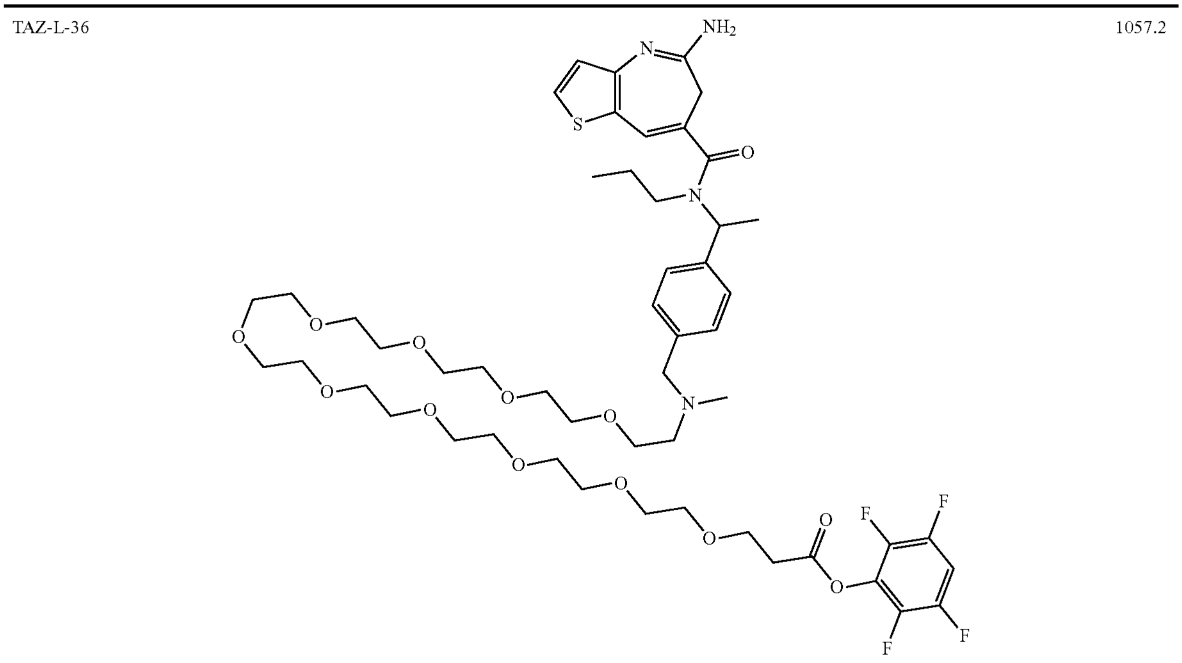 | 1057.2 |
| TAZ-L-37 | 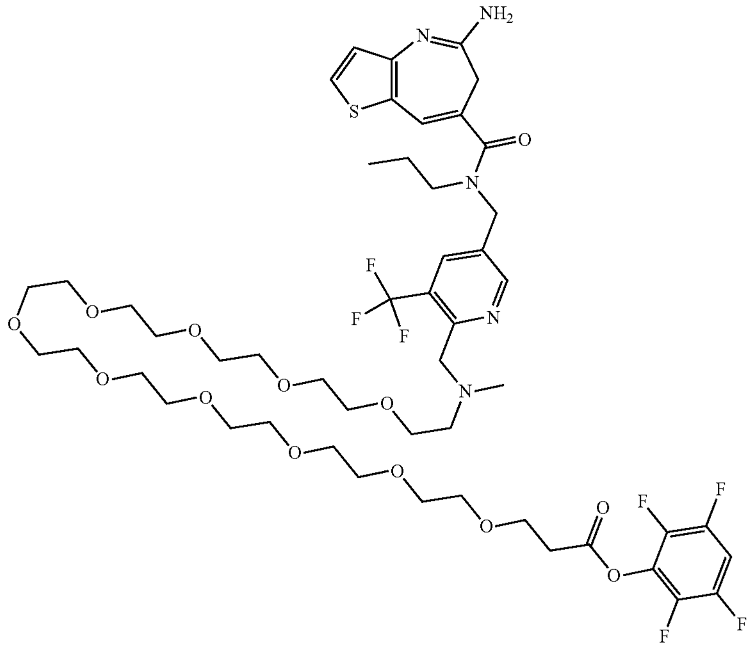 [SMILES: CCCN(Cc1cnc(CN(C)CCOCCOCCOCCOCCOCCOCCOCCOCCOCCOCCC(=O)Oc2c(F)c(F)cc(F)c2F)c(C(F)(F)F)c1)C(=O)C1=Cc2sccc2N=C(N)C1] | 1112.2 |

TABLE 2C
| Thienoazepine-linker (TAZ-L) Formula II compounds | | |
|---|---|---|
| TAZ-L No. | Structure | MW |
| TAZ-L-38 | 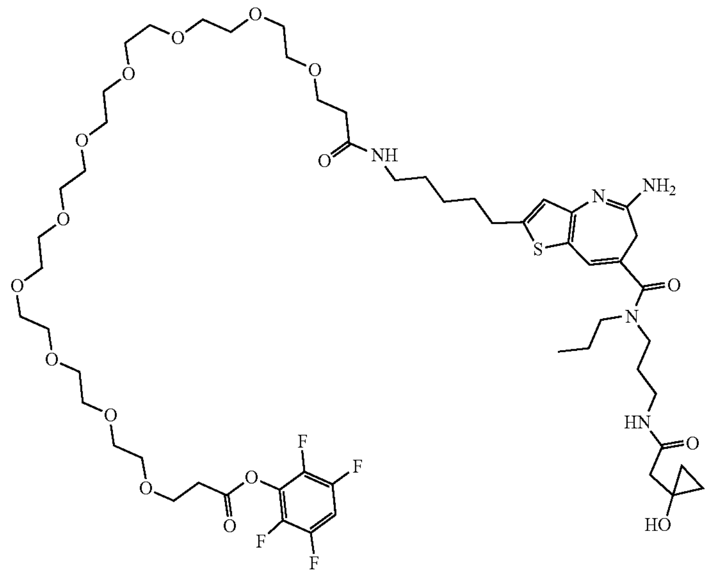 [SMILES: CCCN(CCCNC(=O)CC1(O)CC1)C(=O)C1=Cc2sc(CCCCCNC(=O)CCOCCOCCOCCOCCOCCOCCOCCOCCOCCOCCC(=O)Oc3c(F)c(F)cc(F)c3F)cc2N=C(N)C1] | 1178.3 |
| TAZ-L-39 | 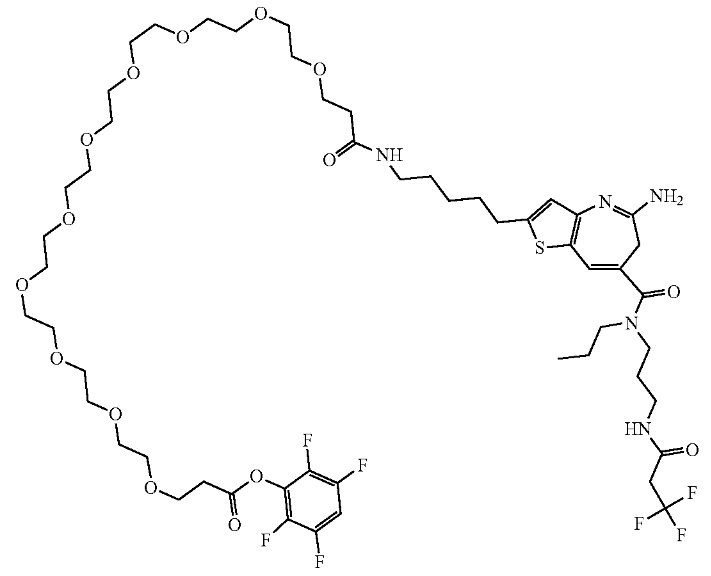 [SMILES: CCCN(CCCNC(=O)CC(F)(F)F)C(=O)C1=Cc2sc(CCCCCNC(=O)CCOCCOCCOCCOCCOCCOCCOCCOCCOCCOCCC(=O)Oc3c(F)c(F)cc(F)c3F)cc2N=C(N)C1] | 1190.3 |

TABLE 2C-continued
| Thienoazepine-linker (TAZ-L) Formula II compounds | | |
|---|---|---|
| TAZ-L No. | Structure | MW |
| TAZ-L-40 | 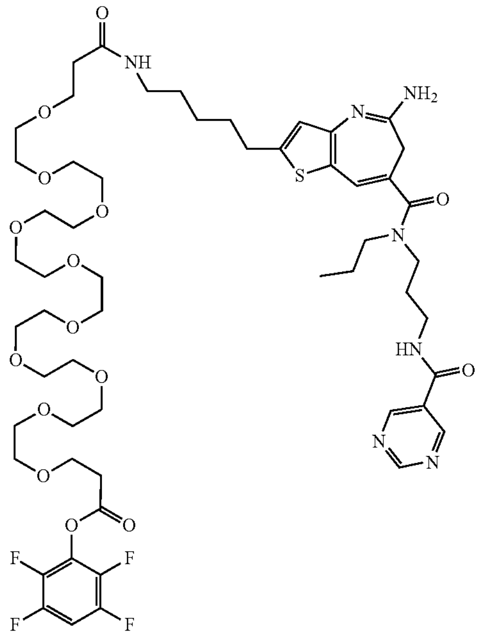 [SMILES: CCCN(CCCNC(=O)c1cncnc1)C(=O)C1=Cc2sc(CCCCCNC(=O)CCOCCOCCOCCOCCOCCOCCOCCOCCOCCOCCC(=O)Oc3c(F)c(F)cc(F)c3F)cc2N=C(N)C1] | 1186.3 |
| TAZ-L-41 | 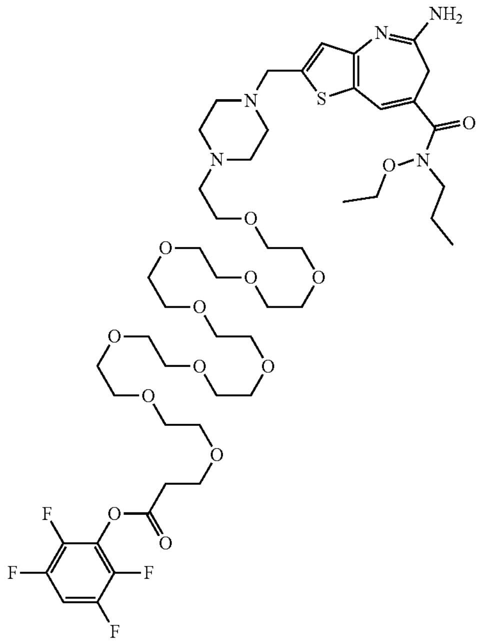 [SMILES: CCCN(OCC)C(=O)C1=Cc2sc(CN3CCN(CCOCCOCCOCCOCCOCCOCCOCCOCCOCCOCCC(=O)Oc4c(F)c(F)cc(F)c4F)CC3)cc2N=C(N)C1] | 1052.2 |

TABLE 2C-continued
| Thienoazepine-linker (TAZ-L) Formula II compounds | | |
|---|---|---|
| TAZ-L No. | Structure | MW |
| TAZ-L-42 | 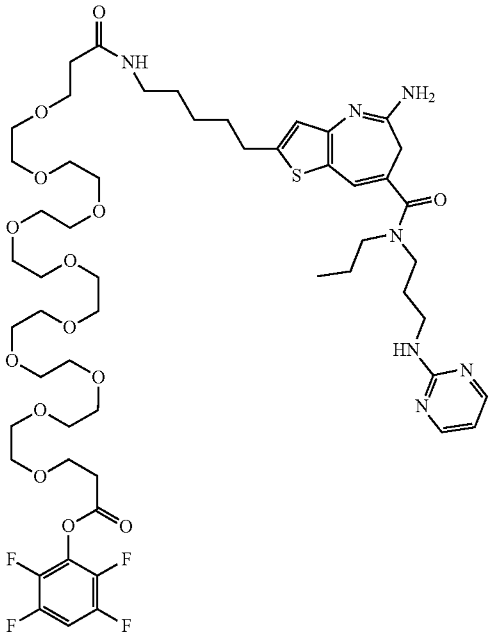 [SMILES: CCCN(CCCNc1ncccn1)C(=O)C1=Cc2sc(CCCCCNC(=O)CCOCCOCCOCCOCCOCCOCCOCCOCCOCCOCCC(=O)Oc3c(F)c(F)cc(F)c3F)cc2N=C(N)C1] | 1158.3 |
| TAZ-L-43 | 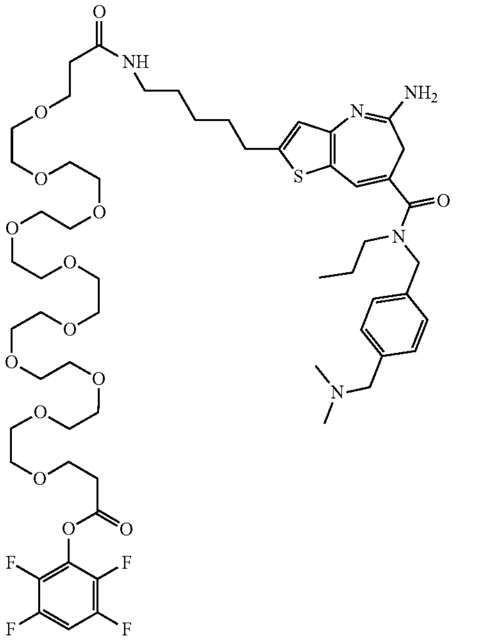 [SMILES: CCCN(Cc1ccc(CN(C)C)cc1)C(=O)C1=Cc2sc(CCCCCNC(=O)CCOCCOCCOCCOCCOCCOCCOCCOCCOCCOCCC(=O)Oc3c(F)c(F)cc(F)c3F)cc2N=C(N)C1] | 1170.4 |

TABLE 2C-continued
| Thienoazepine-linker (TAZ-L) Formula II compounds | | |
|---|---|---|
| TAZ-L No. | Structure | MW |
| TAZ-L-44 | 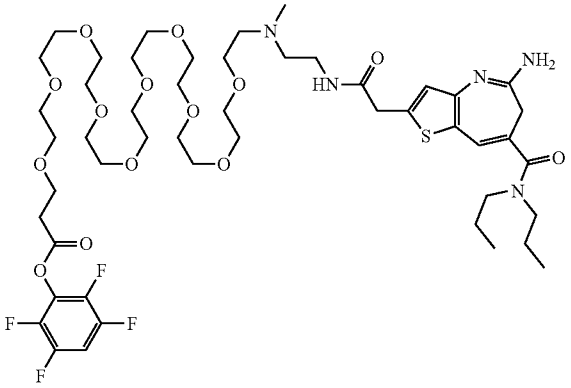 [SMILES: CCCN(CCC)C(=O)C1=Cc2sc(CC(=O)NCCN(C)CCOCCOCCOCCOCCOCCOCCOCCOCCOCCOCCC(=O)Oc3c(F)c(F)cc(F)c3F)cc2N=C(N)C1] | 1066.2 |
| TAZ-L-45 | 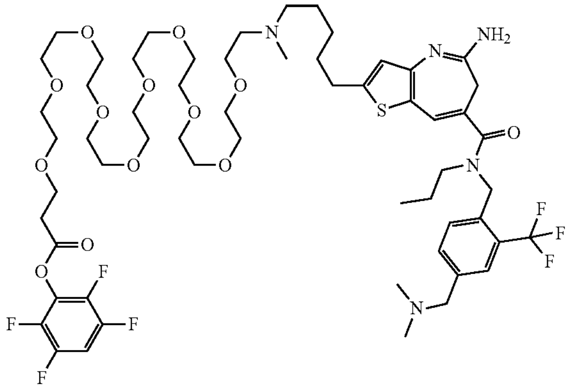 [SMILES: CCCN(Cc1ccc(CN(C)C)cc1C(F)(F)F)C(=O)C1=Cc2sc(CCCCCN(C)CCOCCOCCOCCOCCOCCOCCOCCOCCOCCOCCC(=O)Oc3c(F)c(F)cc(F)c3F)cc2N=C(N)C1] | 1224.4 |
| TAZ-L-46 | 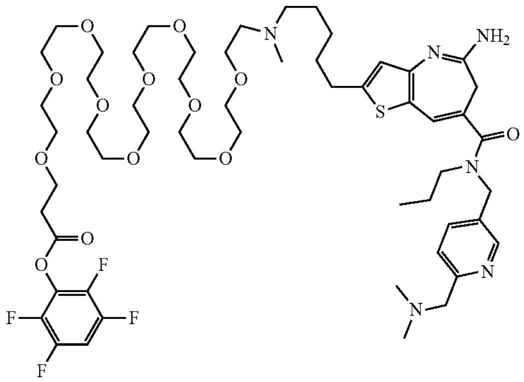 [SMILES: CCCN(Cc1ccc(CN(C)C)nc1)C(=O)C1=Cc2sc(CCCCCN(C)CCOCCOCCOCCOCCOCCOCCOCCOCCOCCOCCC(=O)Oc3c(F)c(F)cc(F)c3F)cc2N=C(N)C1] | 1157.4 |

TABLE 2C-continued
| Thienoazepine-linker (TAZ-L) Formula II compounds | | |
|---|---|---|
| TAZ-L No. | Structure | MW |
| TAZ-L-47 | 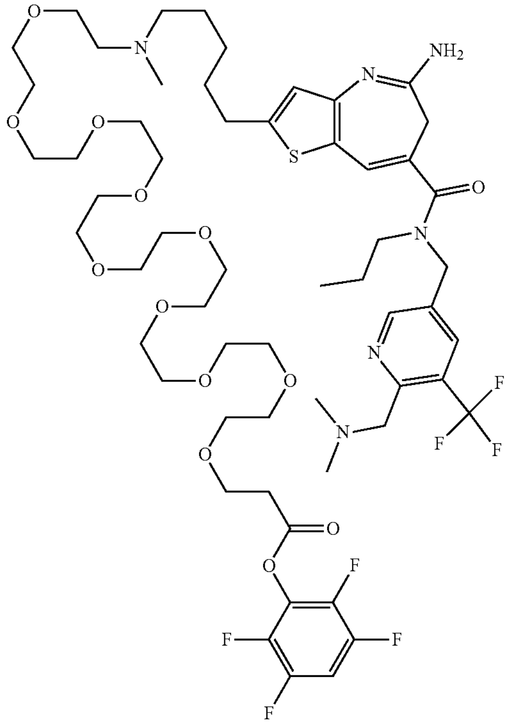 [SMILES: CCCN(Cc1cnc(CN(C)C)c(C(F)(F)F)c1)C(=O)C1=Cc2sc(CCCCCN(C)CCOCCOCCOCCOCCOCCOCCOCCOCCOCCOCCC(=O)Oc3c(F)c(F)cc(F)c3F)cc2N=C(N)C1] | 1225.4 |
| TAZ-L-48 | 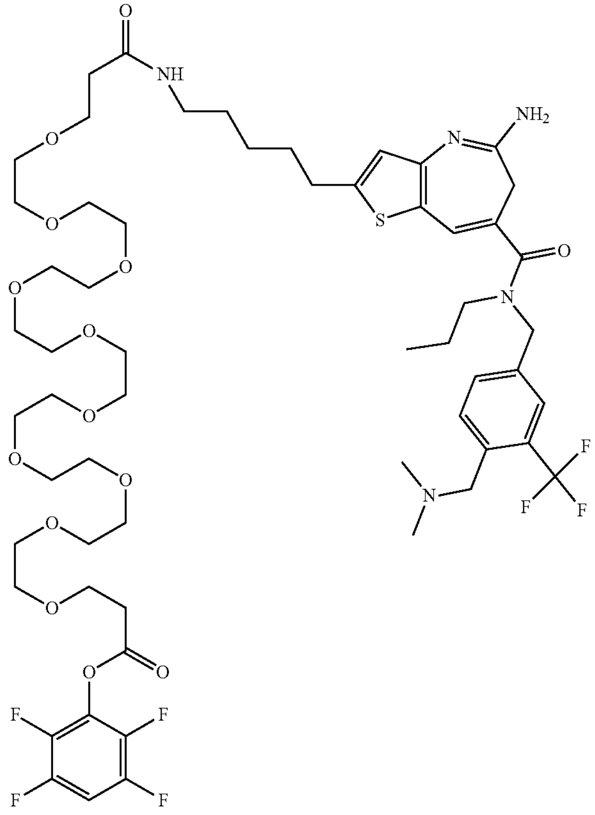 [SMILES: CCCN(Cc1ccc(CN(C)C)c(C(F)(F)F)c1)C(=O)C1=Cc2sc(CCCCCNC(=O)CCOCCOCCOCCOCCOCCOCCOCCOCCOCCOCCC(=O)Oc3c(F)c(F)cc(F)c3F)cc2N=C(N)C1] | 1238.4 |

TABLE 2C-continued
| Thienoazepine-linker (TAZ-L) Formula II compounds | | |
|---|---|---|
| TAZ-L No. | Structure | MW |
| TAZ-L-49 | 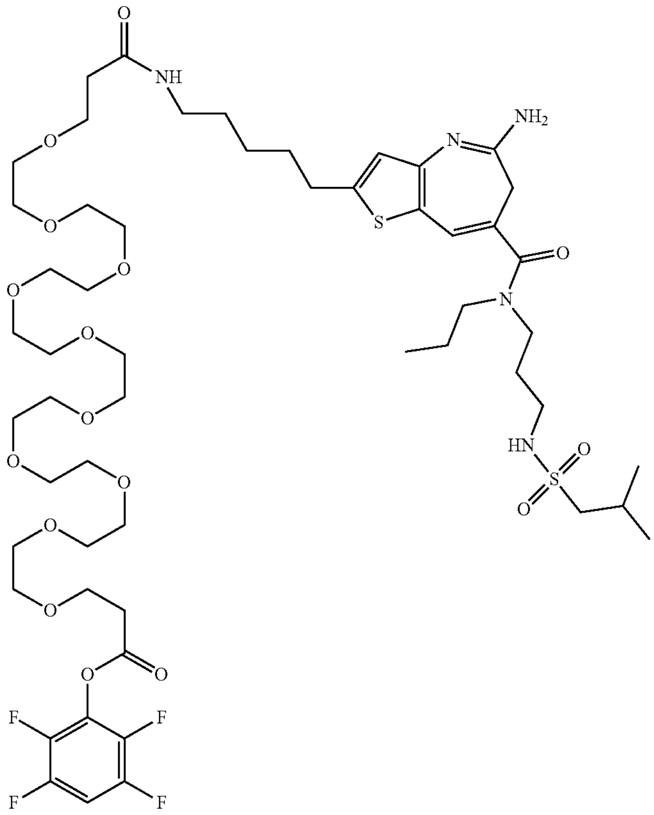 [SMILES: CCCN(CCCNS(=O)(=O)CC(C)C)C(=O)C1=Cc2sc(CCCCCNC(=O)CCOCCOCCOCCOCCOCCOCCOCCOCCOCCOCCC(=O)Oc3c(F)c(F)cc(F)c3F)cc2N=C(N)C1] | 1200.4 |

TABLE 2C-continued
| Thienoazepine-linker (TAZ-L) Formula II compounds | | |
|---|---|---|
| TAZ-L No. | Structure | MW |
| TAZ-L-50 | 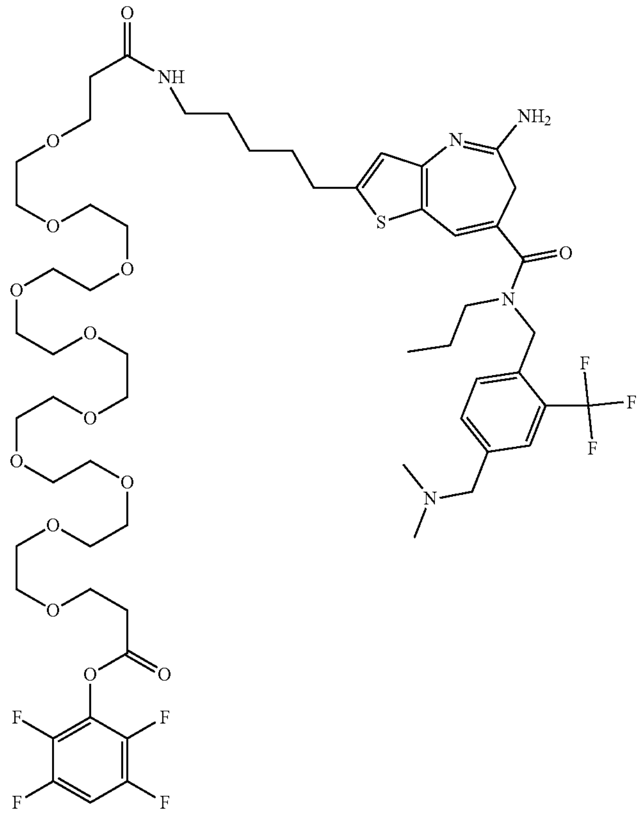 [SMILES: CCCN(Cc1ccc(CN(C)C)cc1C(F)(F)F)C(=O)C1=Cc2sc(CCCCCNC(=O)CCOCCOCCOCCOCCOCCOCCOCCOCCOCCOCCC(=O)Oc3c(F)c(F)cc(F)c3F)cc2N=C(N)C1] | 1238.4 |

TABLE 2C-continued
| Thienoazepine-linker (TAZ-L) Formula II compounds | | |
|---|---|---|
| TAZ-L No. | Structure | MW |
| TAZ-L-51 | 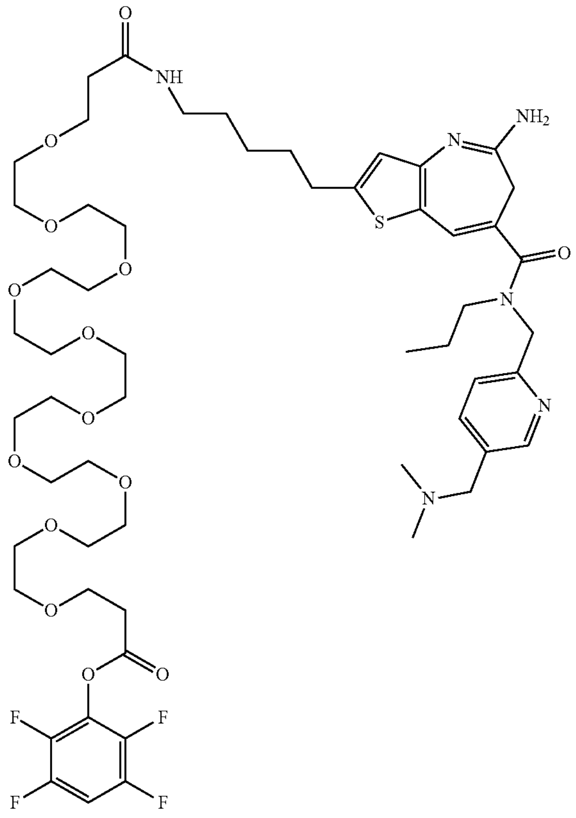 [SMILES: CCCN(Cc1ccc(CN(C)C)cn1)C(=O)C1=Cc2sc(CCCCCNC(=O)CCOCCOCCOCCOCCOCCOCCOCCOCCOCCOCCC(=O)Oc3c(F)c(F)cc(F)c3F)cc2N=C(N)C1] | 1171.3 |

TABLE 2C-continued
| Thienoazepine-linker (TAZ-L) Formula II compounds | | |
|---|---|---|
| TAZ-L No. | Structure | MW |
| TAZ-L-52 | 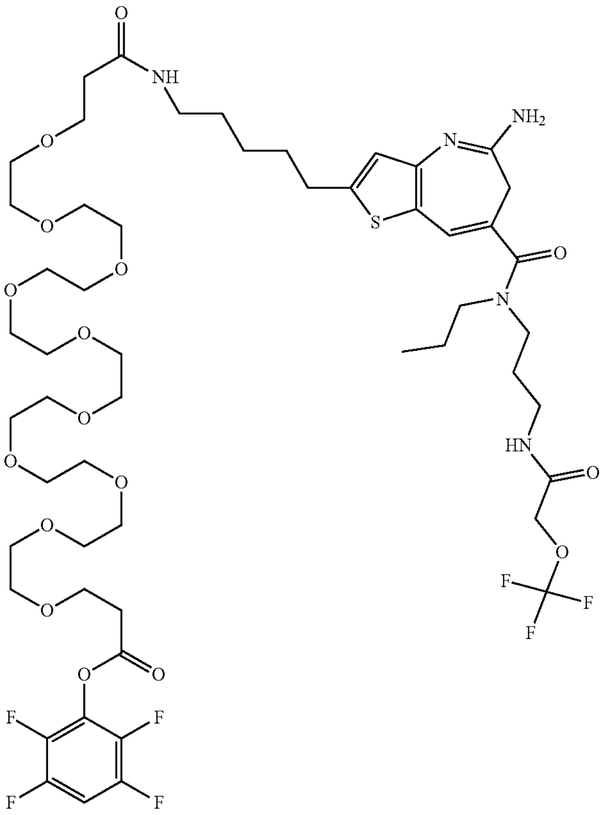 [SMILES: CCCN(CCCNC(=O)COC(F)(F)F)C(=O)C1=Cc2sc(CCCCCNC(=O)CCOCCOCCOCCOCCOCCOCCOCCOCCOCCOCCC(=O)Oc3c(F)c(F)cc(F)c3F)cc2N=C(N)C1] | 1206.3 |

TABLE 2C-continued
| Thienoazepine-linker (TAZ-L) Formula II compounds | | |
|---|---|---|
| TAZ-L No. | Structure | MW |
| TAZ-L-53 | 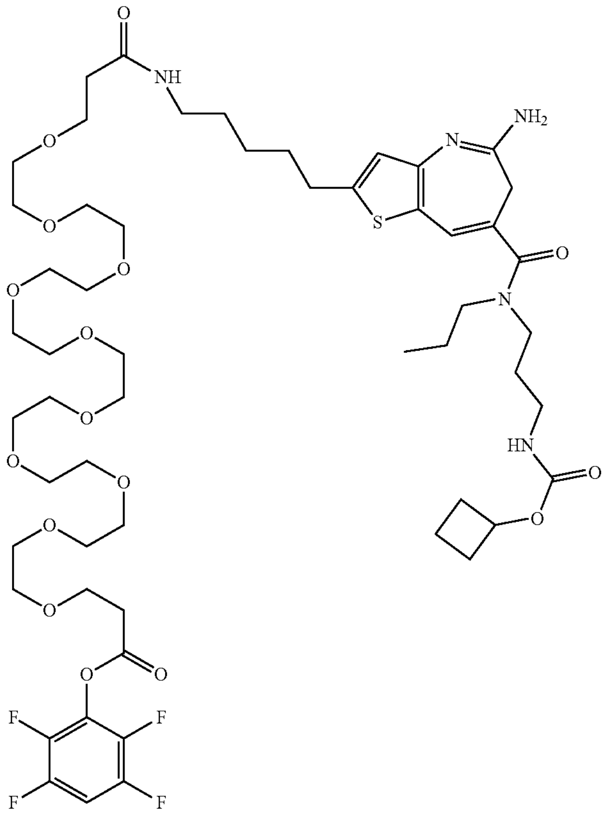 [SMILES: CCCN(CCCNC(=O)OC1CCC1)C(=O)C1=Cc2sc(CCCCCNC(=O)CCOCCOCCOCCOCCOCCOCCOCCOCCOCCOCCC(=O)Oc3c(F)c(F)cc(F)c3F)cc2N=C(N)C1] | 1178.3 |

TABLE 2C-continued
| Thienoazepine-linker (TAZ-L) Formula II compounds | | |
|---|---|---|
| TAZ-L No. | Structure | MW |
| TAZ-L-54 | 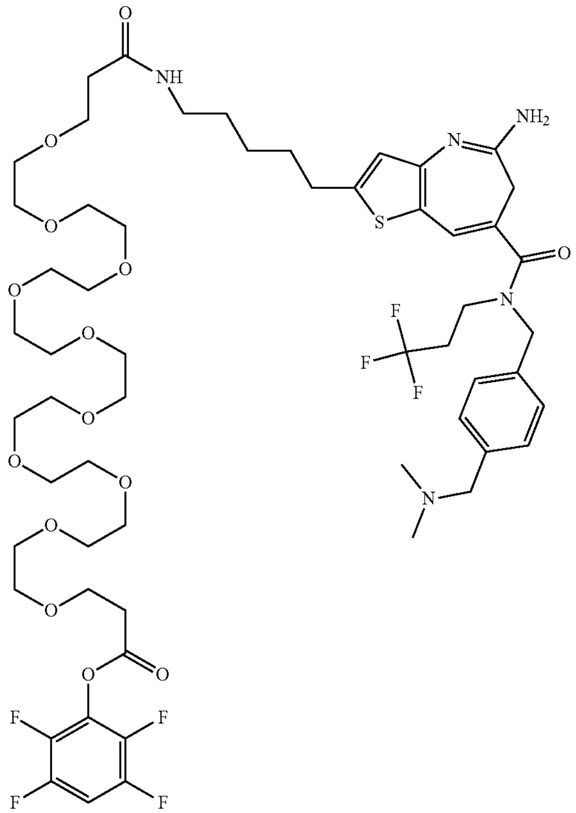 [SMILES: CN(C)Cc1ccc(CN(CCC(F)(F)F)C(=O)C2=Cc3sc(CCCCCNC(=O)CCOCCOCCOCCOCCOCCOCCOCCOCCOCCOCCC(=O)Oc4c(F)c(F)cc(F)c4F)cc3N=C(N)C2)cc1] | 1224.3 |
| TAZ-L-55 | 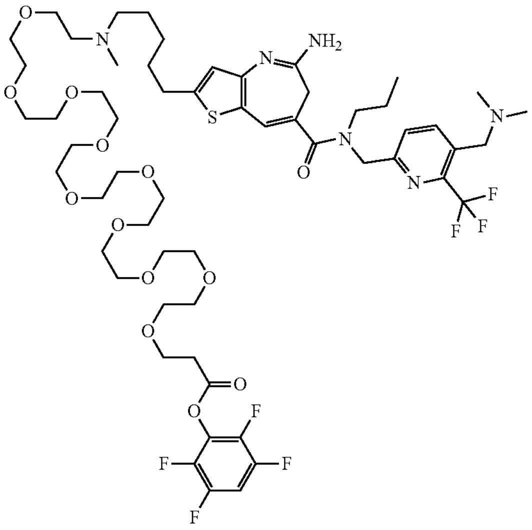 [SMILES: CCCN(Cc1ccc(CN(C)C)c(C(F)(F)F)n1)C(=O)C1=Cc2sc(CCCCCN(C)CCOCCOCCOCCOCCOCCOCCOCCOCCOCCOCCC(=O)Oc3c(F)c(F)cc(F)c3F)cc2N=C(N)C1] | 1225.4 |

TABLE 2C-continued
| Thienoazepine-linker (TAZ-L) Formula II compounds | | |
|---|---|---|
| TAZ-L No. | Structure | MW |
| TAZ-L-56 | 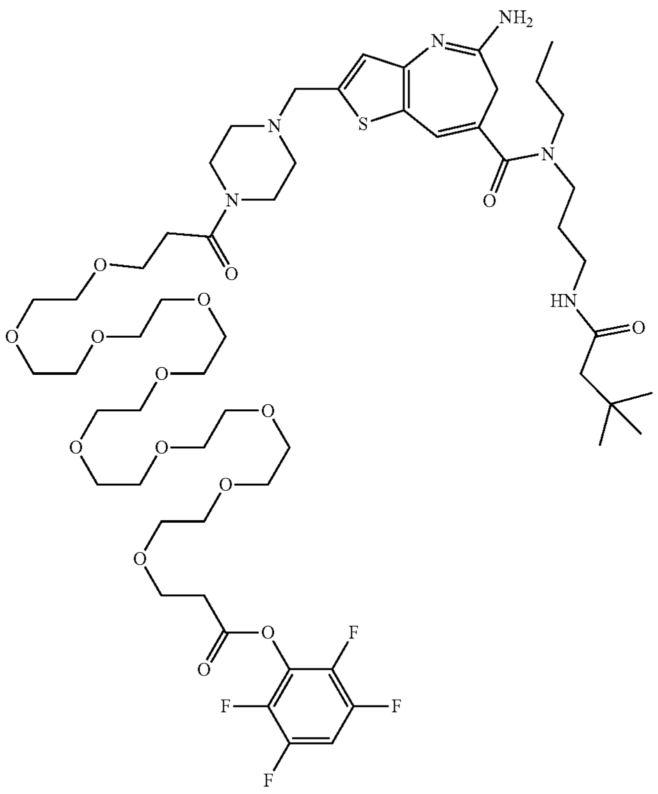 [SMILES: CCCN(CCCNC(=O)CC(C)(C)C)C(=O)C1=Cc2sc(CN3CCN(C(=O)CCOCCOCCOCCOCCOCCOCCOCCOCCOCCOCCC(=O)Oc4c(F)c(F)cc(F)c4F)CC3)cc2N=C(N)C1] | 1191.4 |
| TAZ-L-57 | 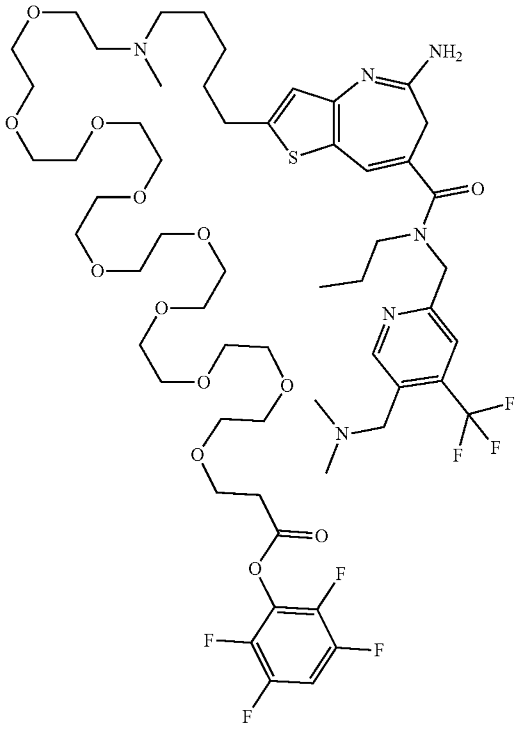 [SMILES: CCCN(Cc1cc(C(F)(F)F)c(CN(C)C)cn1)C(=O)C1=Cc2sc(CCCCCN(C)CCOCCOCCOCCOCCOCCOCCOCCOCCOCCOCCC(=O)Oc3c(F)c(F)cc(F)c3F)cc2N=C(N)C1] | 1225.4 |

TABLE 2C-continued
| Thienoazepine-linker (TAZ-L) Formula II compounds | | |
|---|---|---|
| TAZ-L No. | Structure | MW |
| TAZ-L-58 | 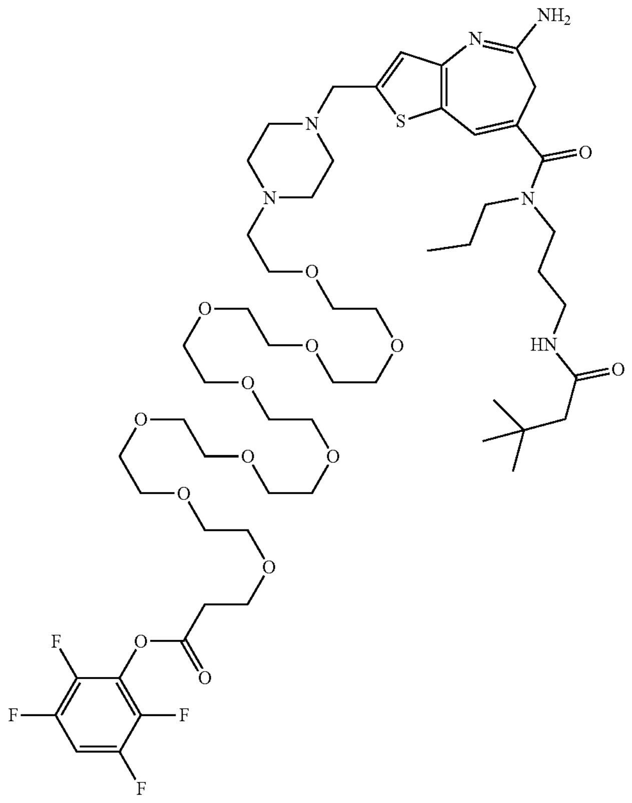 [SMILES: CCCN(CCCNC(=O)CC(C)(C)C)C(=O)C1=Cc2sc(CN3CCN(CCOCCOCCOCCOCCOCCOCCOCCOCCOCCOCCC(=O)Oc4c(F)c(F)cc(F)c4F)CC3)cc2N=C(N)C1] | 1163.4 |
| TAZ-L-59 | 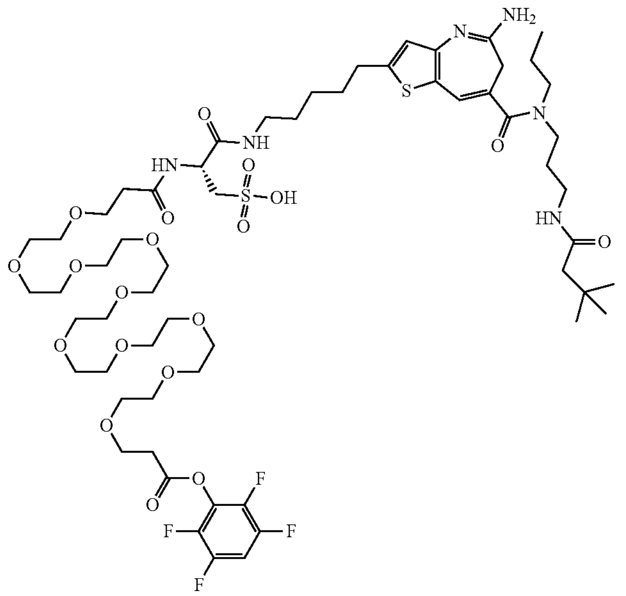 [SMILES: CCCN(CCCNC(=O)CC(C)(C)C)C(=O)C1=Cc2sc(CCCCCNC(=O)[C@H](CS(=O)(=O)O)NC(=O)CCOCCOCCOCCOCCOCCOCCOCCOCCOCCOCCC(=O)Oc3c(F)c(F)cc(F)c3F)cc2N=C(N)C1] | 1329.5 |

TABLE 2C-continued
| Thienoazepine-linker (TAZ-L) Formula II compounds | | |
|---|---|---|
| TAZ-L No. | Structure | MW |
| TAZ-L-60 | 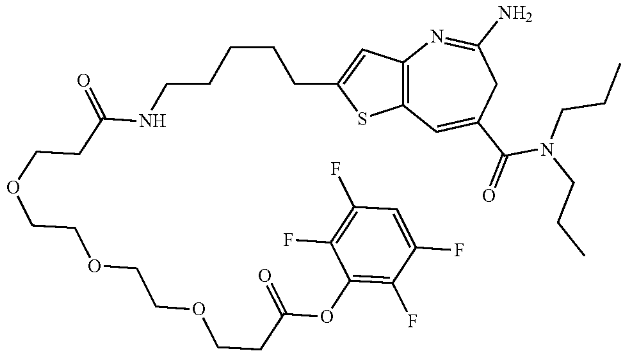 [SMILES: CCCN(CCC)C(=O)C1=Cc2sc(CCCCCNC(=O)CCOCCOCCOCCC(=O)Oc3c(F)c(F)cc(F)c3F)cc2N=C(N)C1] | 756.9 |
| TAZ-L-61 | 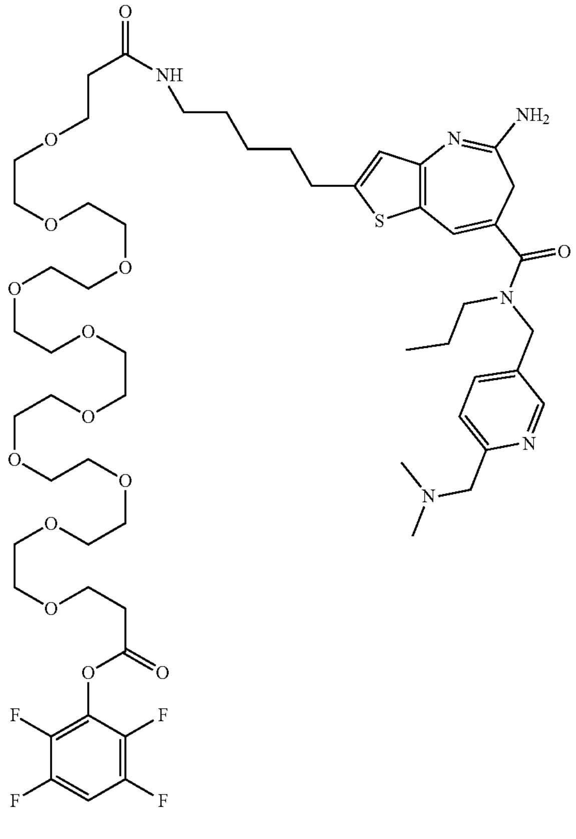 [SMILES: CCCN(Cc1ccc(CN(C)C)nc1)C(=O)C1=Cc2sc(CCCCCNC(=O)CCOCCOCCOCCOCCOCCOCCOCCOCCOCCOCCC(=O)Oc3c(F)c(F)cc(F)c3F)cc2N=C(N)C1] | 1171.3 |

TABLE 2C-continued
| Thienoazepine-linker (TAZ-L) Formula II compounds | | |
|---|---|---|
| TAZ-L No. | Structure | MW |
| TAZ-L-62 | 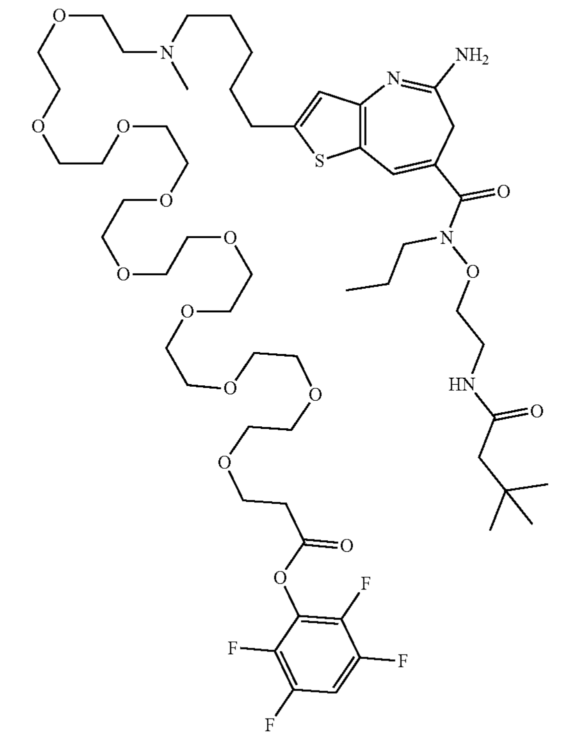 [SMILES: CCCN(OCCNC(=O)CC(C)(C)C)C(=O)C1=Cc2sc(CCCCCN(C)CCOCCOCCOCCOCCOCCOCCOCCOCCOCCOCCC(=O)Oc3c(F)c(F)cc(F)c3F)cc2N=C(N)C1] | 66.4 |
| TAZ-L-63 | 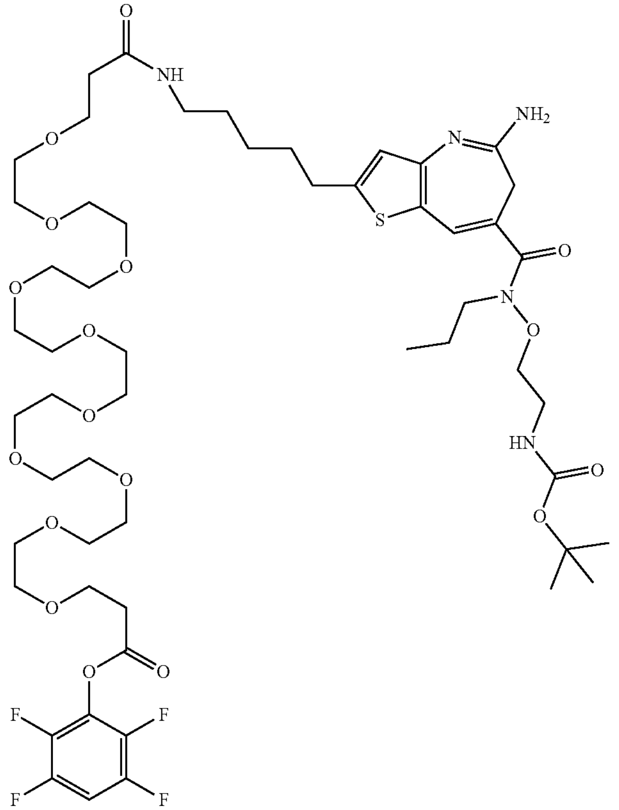 [SMILES: CCCN(OCCNC(=O)OC(C)(C)C)C(=O)C1=Cc2sc(CCCCCNC(=O)CCOCCOCCOCCOCCOCCOCCOCCOCCOCCOCCC(=O)Oc3c(F)c(F)cc(F)c3F)cc2N=C(N)C1] | 1180.4 |

TABLE 2C-continued
| Thienoazepine-linker (TAZ-L) Formula II compounds | | |
|---|---|---|
| TAZ-L No. | Structure | MW |
| TAZ-L-64 | 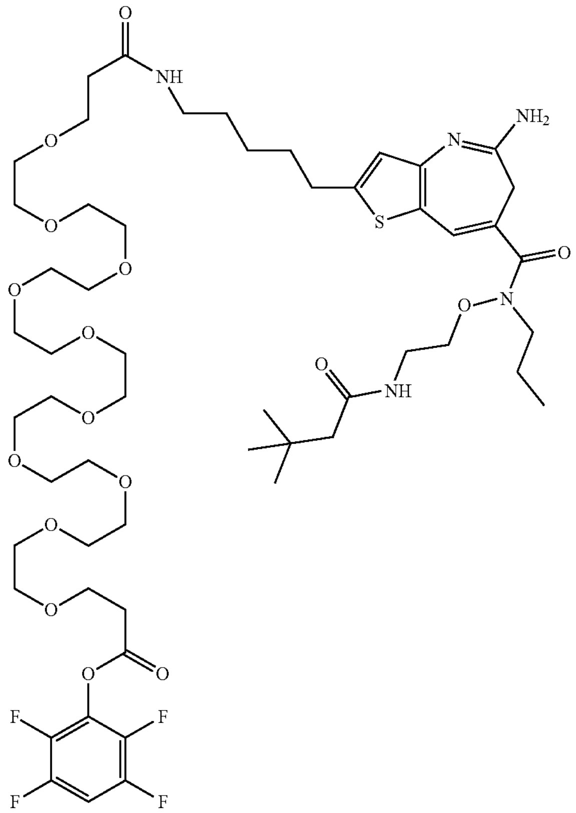 [SMILES: CCCN(OCCNC(=O)CC(C)(C)C)C(=O)C1=Cc2sc(CCCCCNC(=O)CCOCCOCCOCCOCCOCCOCCOCCOCCOCCOCCC(=O)Oc3c(F)c(F)cc(F)c3F)cc2N=C(N)C1] | 1180.4 |
| TAZ-L-65 | 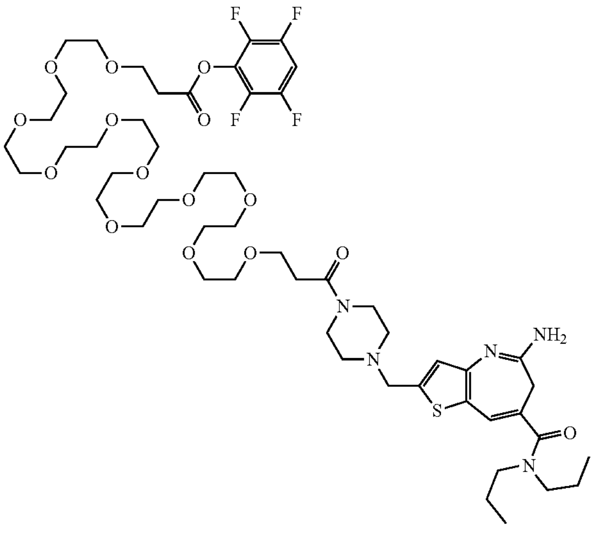 [SMILES: CCCN(OCC)C(=O)C1=Cc2sc(CN3CCN(C(=O)CCOCCOCCOCCOCCOCCOCCOCCOCCOCCOCCOCCC(=O)Oc4c(F)c(F)cc(F)c4F)CC3)cc2N=C(N)C1] | 1122.3 |

TABLE 2C-continued
| Thienoazepine-linker (TAZ-L) Formula II compounds | | |
|---|---|---|
| TAZ-L No. | Structure | MW |
| TAZ-L-66 | 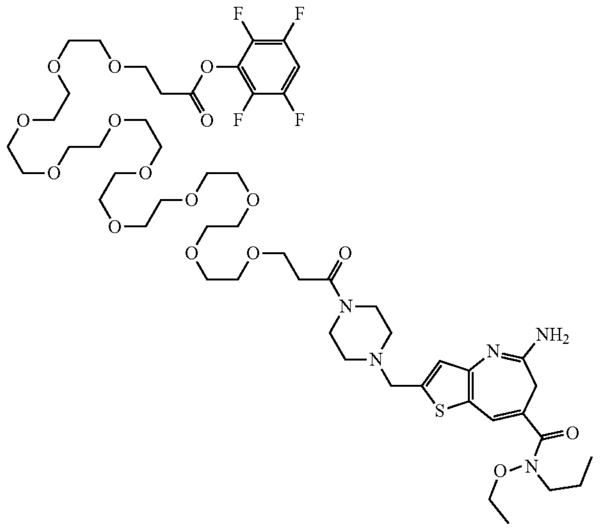 | 1124.2 |
| TAZ-L-67 | 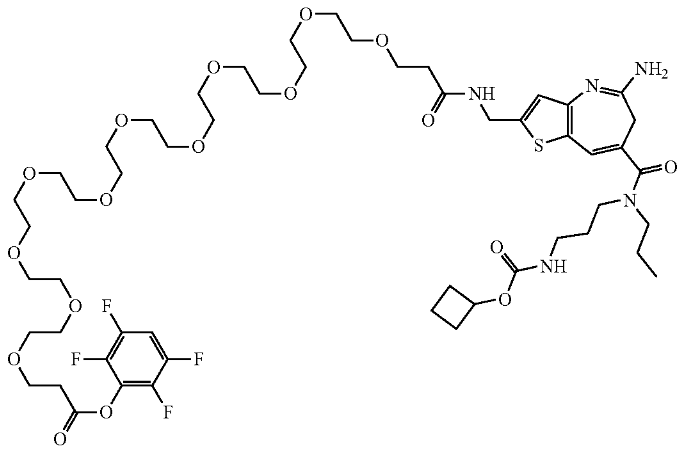 [SMILES: CCCN(CCCNC(=O)OC1CCC1)C(=O)C1=Cc2sc(CNC(=O)CCOCCOCCOCCOCCOCCOCCOCCOCCOCCOCCOCCC(=O)Oc3c(F)c(F)cc(F)c3F)cc2N=C(N)C1] | 1166.3 |
| TAZ-L-68 | 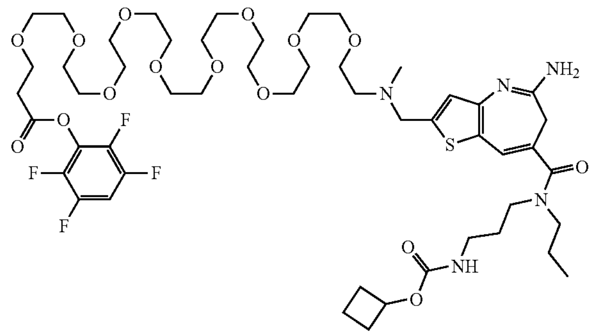 [SMILES: CCCN(CCCNC(=O)OC1CCC1)C(=O)C1=Cc2sc(CN(C)CCOCCOCCOCCOCCOCCOCCOCCOCCOCCOCCC(=O)Oc3c(F)c(F)cc(F)c3F)cc2N=C(N)C1] | 1108.2 |

TABLE 2C-continued
| Thienoazepine-linker (TAZ-L) Formula II compounds | | |
|---|---|---|
| TAZ-L No. | Structure | MW |
| TAZ-L-69 | 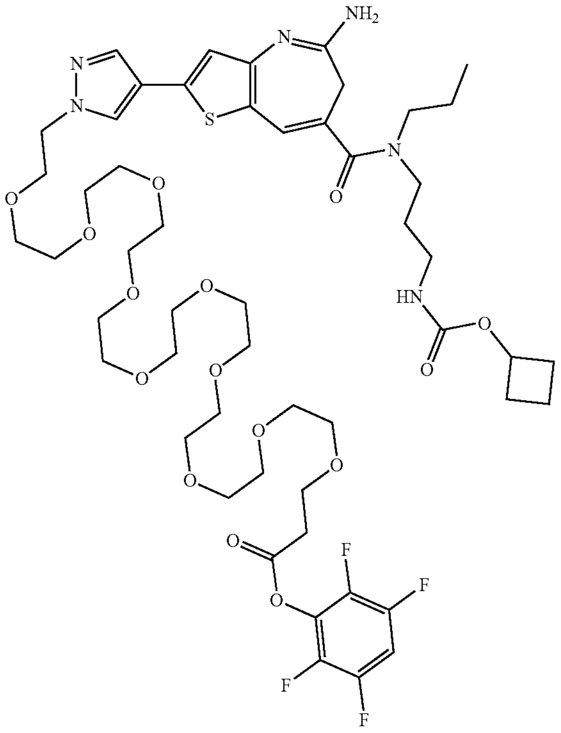 [SMILES: CCCN(CCCNC(=O)OC1CCC1)C(=O)C1=Cc2sc(-c3cnn(CCOCCOCCOCCOCCOCCOCCOCCOCCOCCOCCC(=O)Oc4c(F)c(F)cc(F)c4F)c3)cc2N=C(N)C1] | 1131.2 |
| TAZ-L-70 | 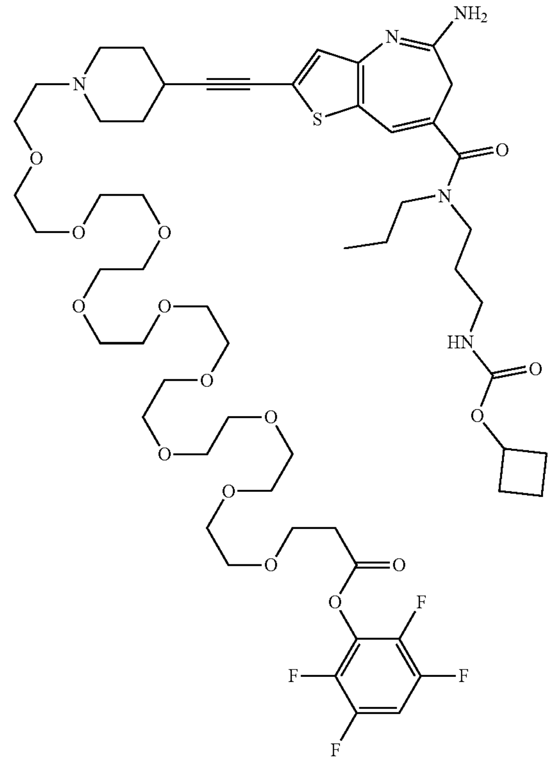 [SMILES: CCCN(CCCNC(=O)OC1CCC1)C(=O)C1=Cc2sc(C#CC3CCN(CCOCCOCCOCCOCCOCCOCCOCCOCCOCCOCCC(=O)Oc4c(F)c(F)cc(F)c4F)CC3)cc2N=C(N)C1] | 1172.3 |

TABLE 2C-continued
| Thienoazepine-linker (TAZ-L) Formula II compounds | | |
|---|---|---|
| TAZ-L No. | Structure | MW |
| TAZ-L-71 | 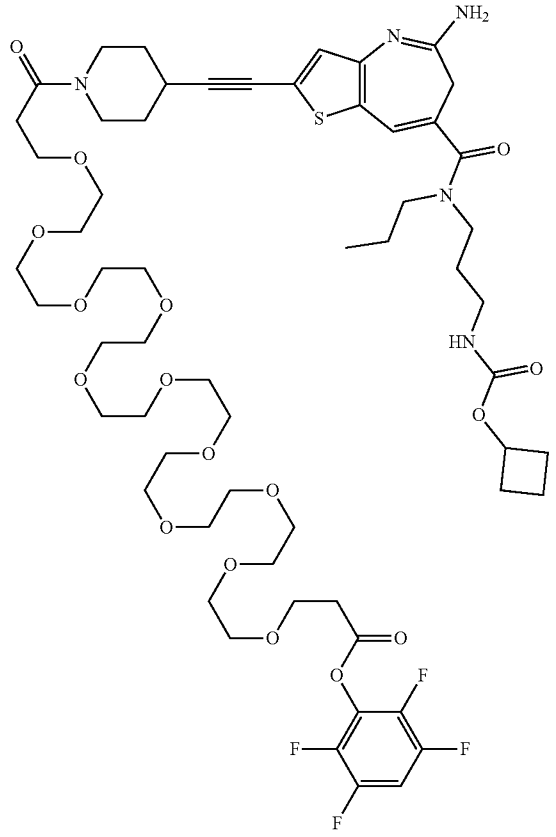 [SMILES: CCCN(CCCNC(=O)OC1CCC1)C(=O)C1=Cc2sc(C#CC3CCN(C(=O)CCOCCOCCOCCOCCOCCOCCOCCOCCOCCOCCOCCC(=O)Oc4c(F)c(F)cc(F)c4F)CC3)cc2N=C(N)C1] | 1244.4 |

TABLE 2C-continued
| Thienoazepine-linker (TAZ-L) Formula II compounds | | |
|---|---|---|
| TAZ-L No. | Structure | MW |
| TAZ-L-72 | 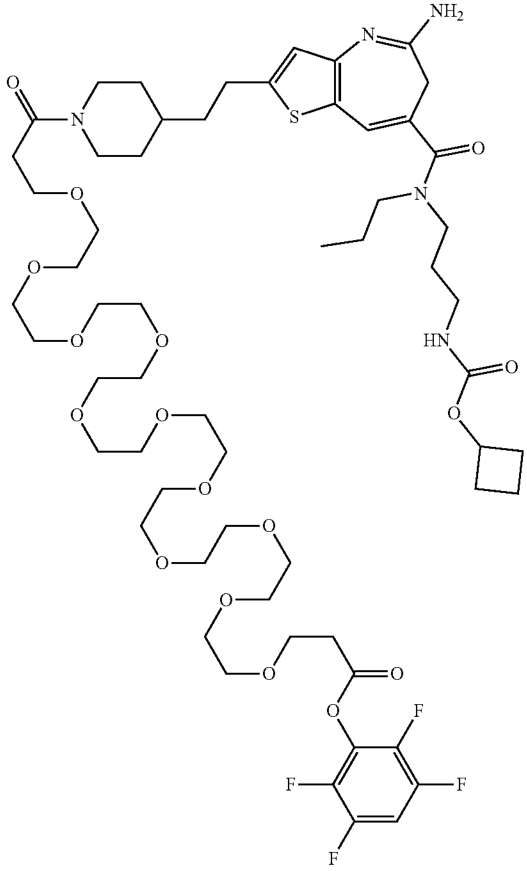 [SMILES: CCCN(CCCNC(=O)OC1CCC1)C(=O)C1=Cc2sc(CCC3CCN(C(=O)CCOCCOCCOCCOCCOCCOCCOCCOCCOCCOCCOCCC(=O)Oc4c(F)c(F)cc(F)c4F)CC3)cc2N=C(N)C1] | 1248.4 |
| TAZ-L-73 | 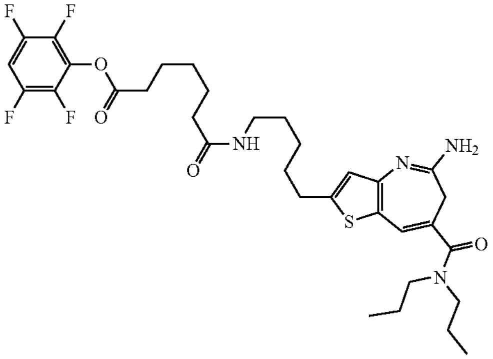 [SMILES: CCCN(CCC)C(=O)C1=Cc2sc(CCCCCNC(=O)CCCCCC(=O)Oc3c(F)c(F)cc(F)c3F)cc2N=C(N)C1] | 666.8 |

TABLE 2C-continued
| Thienoazepine-linker (TAZ-L) Formula II compounds | | |
|---|---|---|
| TAZ-L No. | Structure | MW |
| TAZ-L-74 | 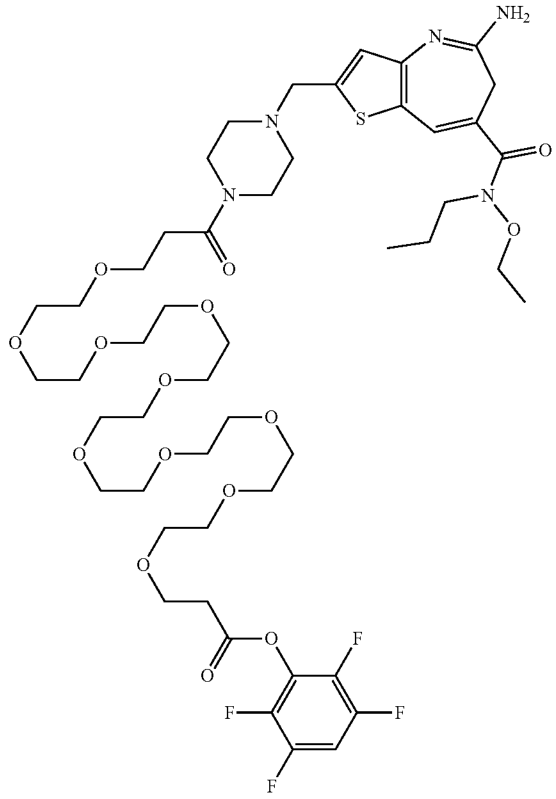 [SMILES: CCCN(CCC)C(=O)C1=Cc2sc(CN3CCN(C(=O)CCOCCOCCOCCOCCOCCOCCOCCOCCOCCOCCC(=O)Oc4c(F)c(F)cc(F)c4F)CC3)cc2N=C(N)C1] | 1080.2 |
| TAZ-L-75 | 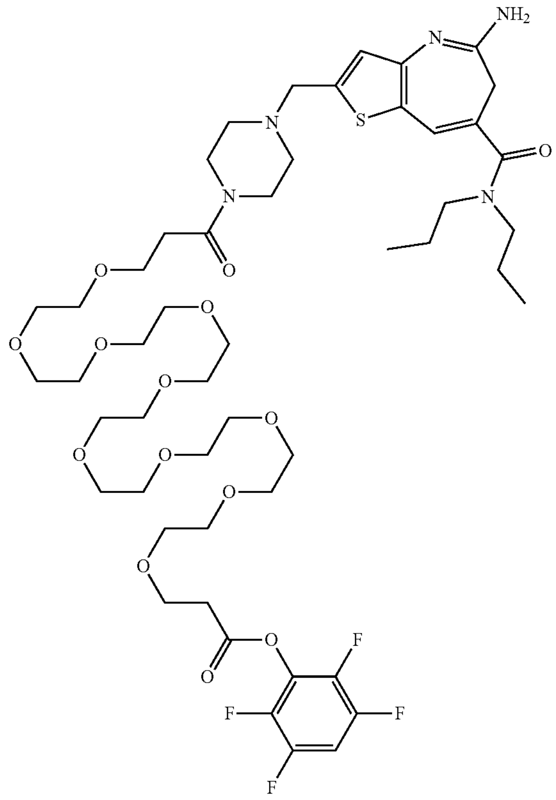 | 1078.2 |

TABLE 2C-continued
| Thienoazepine-linker (TAZ-L) Formula II compounds | | |
|---|---|---|
| TAZ-L No. | Structure | MW |
| TAZ-L-76 | 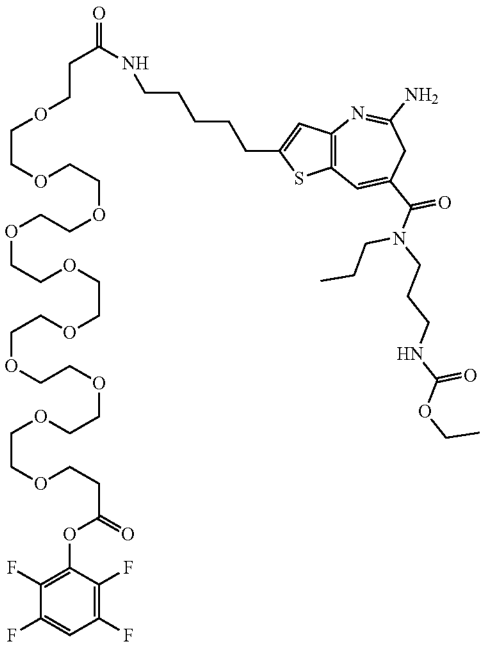 [SMILES: CCCN(CCCNC(=O)OCC)C(=O)C1=Cc2sc(CCCCCNC(=O)CCOCCOCCOCCOCCOCCOCCOCCOCCOCCOCCC(=O)Oc3c(F)c(F)cc(F)c3F)cc2N=C(N)C1] | 1152.3 |
| TAZ-L-77 | 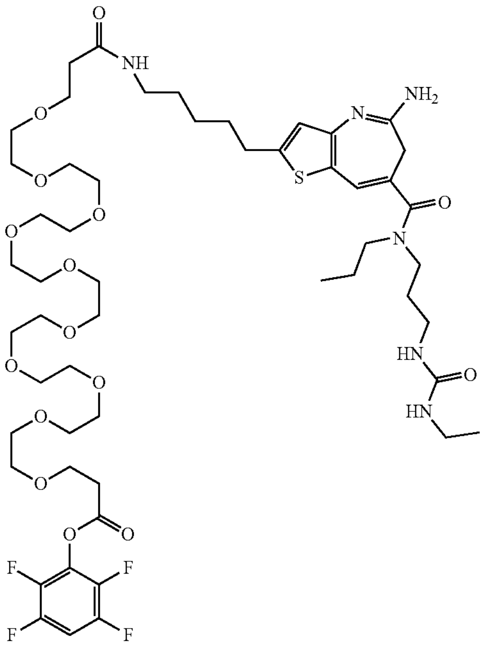 [SMILES: CCCN(CCCNC(=O)NCC)C(=O)C1=Cc2sc(CCCCCNC(=O)CCOCCOCCOCCOCCOCCOCCOCCOCCOCCOCCC(=O)Oc3c(F)c(F)cc(F)c3F)cc2N=C(N)C1] | 1151.3 |

TABLE 2C-continued
| Thienoazepine-linker (TAZ-L) Formula II compounds | | |
|---|---|---|
| TAZ-L No. | Structure | MW |
| TAZ-L-78 | 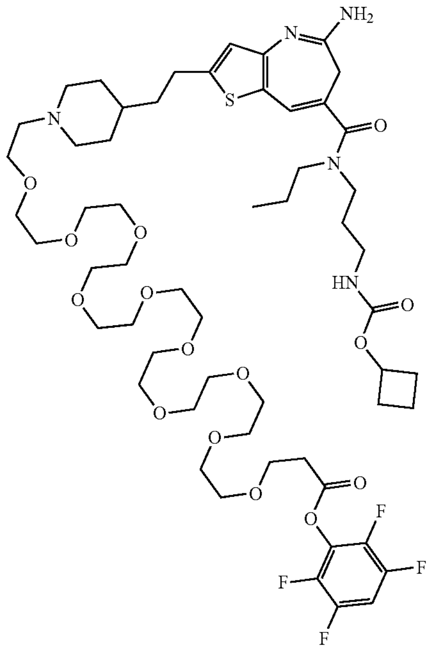 [SMILES: CCCN(CCCNC(=O)OC1CCC1)C(=O)C1=Cc2sc(CCC3CCN(CCOCCOCCOCCOCCOCCOCCOCCOCCOCCOCCC(=O)Oc4c(F)c(F)cc(F)c4F)CC3)cc2N=C(N)C1] | 1176.4 |
| TAZ-L-79 | 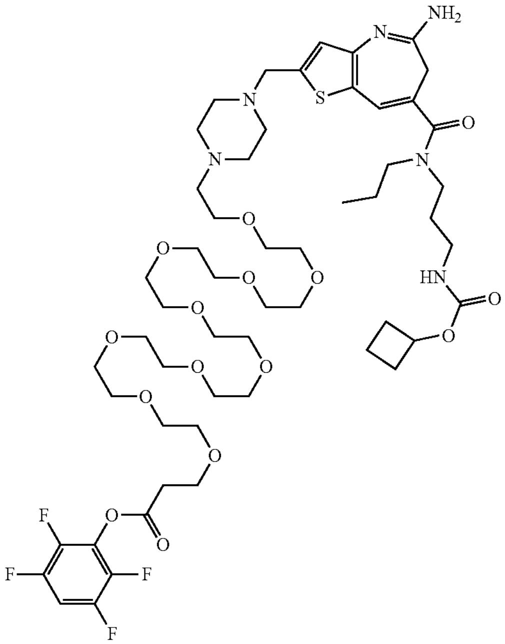 [SMILES: CCCN(CCCNC(=O)OC1CCC1)C(=O)C1=Cc2sc(CN3CCN(CCOCCOCCOCCOCCOCCOCCOCCOCCOCCOCCC(=O)Oc4c(F)c(F)cc(F)c4F)CC3)cc2N=C(N)C1] | 1163.3 |

TABLE 2C-continued
| Thienoazepine-linker (TAZ-L) Formula II compounds | | |
|---|---|---|
| TAZ-L No. | Structure | MW |
| TAZ-L-80 | 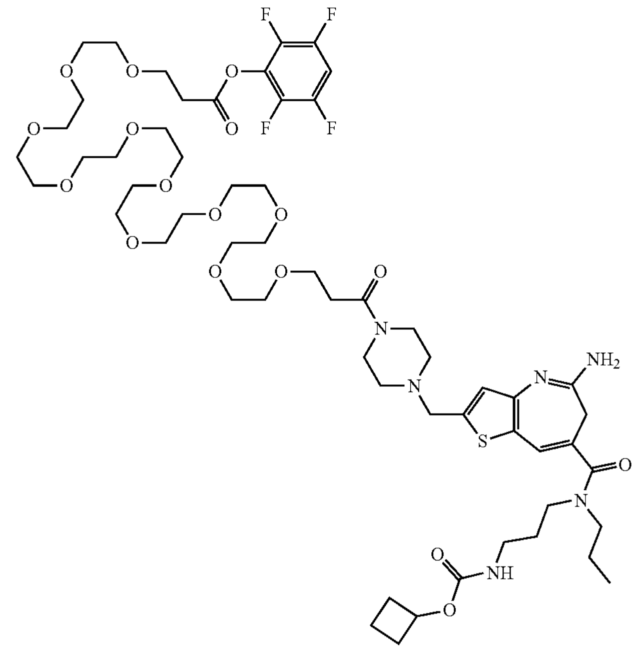 [SMILES: CCCN(CCCNC(=O)OC1CCC1)C(=O)C1=Cc2sc(CN3CCN(C(=O)CCOCCOCCOCCOCCOCCOCCOCCOCCOCCOCCOCCC(=O)Oc4c(F)c(F)cc(F)c4F)CC3)cc2N=C(N)C1] | 1235.4 |
| TAZ-L-81 | 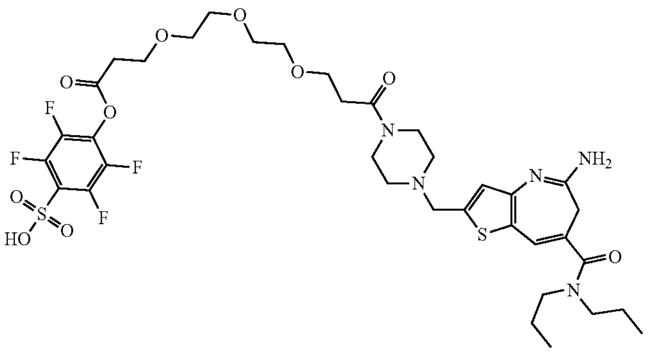 [SMILES: CCCN(CCC)C(=O)C1=Cc2sc(CN3CCN(C(=O)CCOCCOCCOCCC(=O)Oc4c(F)c(F)c(S(=O)(=O)O)c(F)c4F)CC3)cc2N=C(N)C1] | 849.9 |
| TAZ-L-82 | 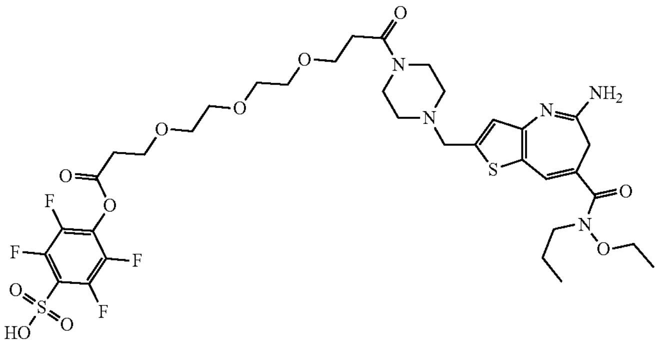 [SMILES: CCCN(OCC)C(=O)C1=Cc2sc(CN3CCN(C(=O)CCOCCOCCOCCC(=O)Oc4c(F)c(F)c(S(=O)(=O)O)c(F)c4F)CC3)cc2N=C(N)C1] | 851.9 |

TABLE 2C-continued
| Thienoazepine-linker (TAZ-L) Formula II compounds | | |
|---|---|---|
| TAZ-L No. | Structure | MW |
| TAZ-L-83 | 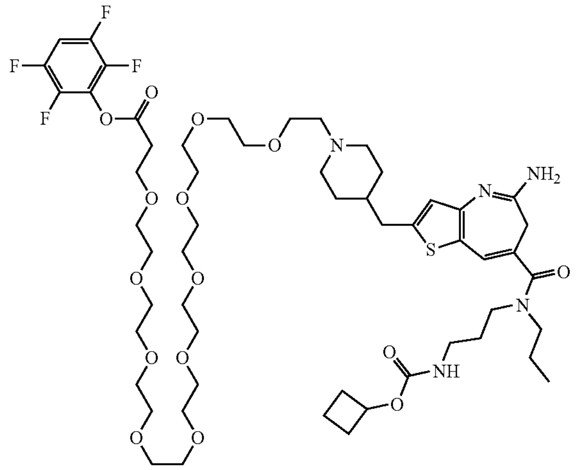 | 1162.3 |
| TAZ-L-84 | 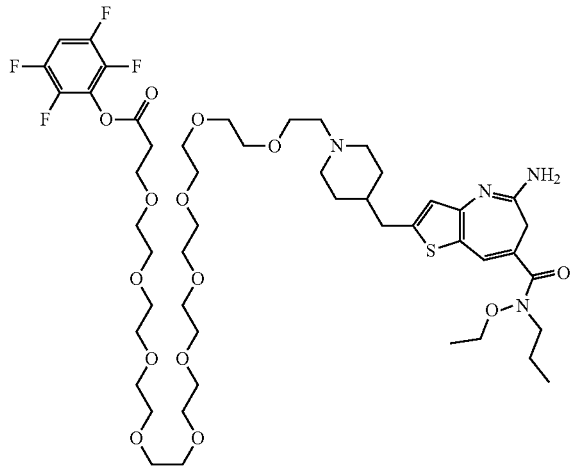 | 1051.2 |
| TAZ-L-85 | 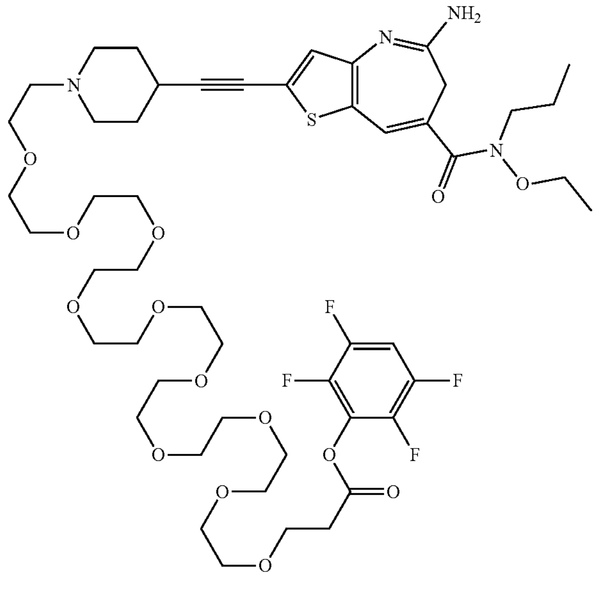 [SMILES: CCCN(OCC)C(=O)C1=Cc2sc(C#CC3CCN(CCOCCOCCOCCOCCOCCOCCOCCOCCOCCOCCC(=O)Oc4c(F)c(F)cc(F)c4F)CC3)cc2N=C(N)C1] | 1061.2 |

TABLE 2C-continued
| Thienoazepine-linker (TAZ-L) Formula II compounds | | |
|---|---|---|
| TAZ-L No. | Structure | MW |
| TAZ-L-86 | 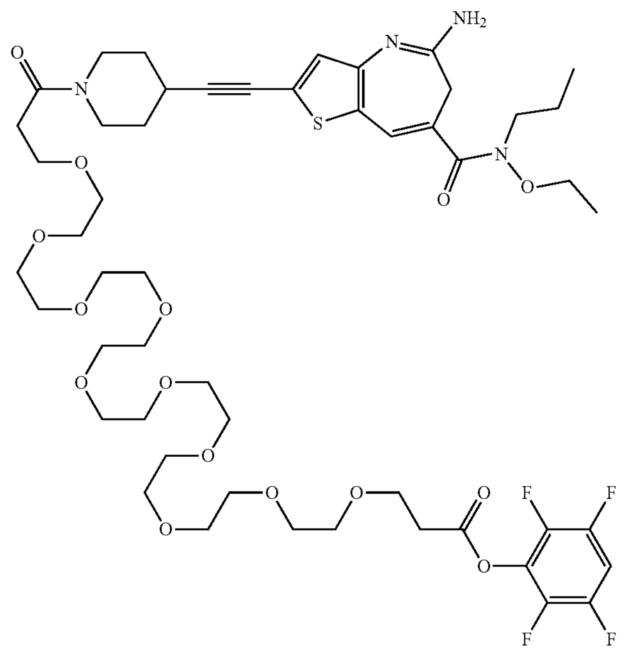 [SMILES: CCCN(OCC)C(=O)C1=Cc2sc(C#CC3CCN(C(=O)CCOCCOCCOCCOCCOCCOCCOCCOCCOCCOCCC(=O)Oc4c(F)c(F)cc(F)c4F)CC3)cc2N=C(N)C1] | 1089.2 |
| TAZ-L-87 | 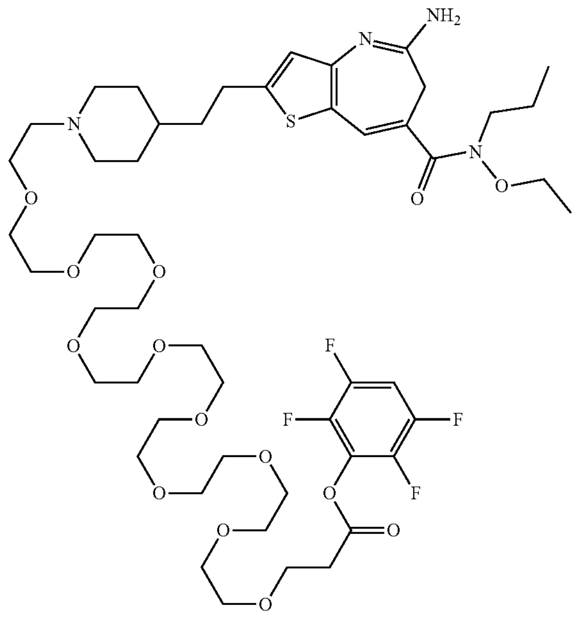 [SMILES: CCCN(OCC)C(=O)C1=Cc2sc(CCC3CCN(CCOCCOCCOCCOCCOCCOCCOCCOCCOCCOCCC(=O)Oc4c(F)c(F)cc(F)c4F)CC3)cc2N=C(N)C1] | 1065.2 |

TABLE 2C-continued
| Thienoazepine-linker (TAZ-L) Formula II compounds | | |
|---|---|---|
| TAZ-L No. | Structure | MW |
| TAZ-L-88 | 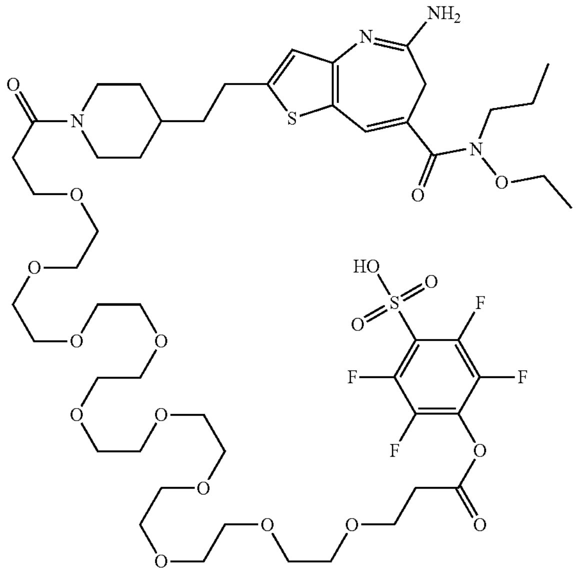 [SMILES: CCCN(OCC)C(=O)C1=Cc2sc(CCC3CCN(C(=O)CCOCCOCCOCCOCCOCCOCCOCCOCCOCCOCCC(=O)Oc4c(F)c(F)c(S(=O)(=O)O)c(F)c4F)CC3)cc2N=C(N)C1] | 1173.3 |
| TAZ-L-89 | 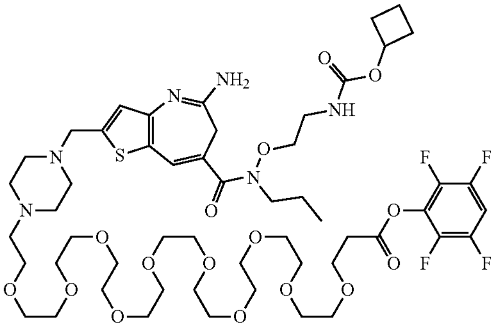 [SMILES: CCCN(OCCNC(=O)OC1CCC1)C(=O)C1=Cc2sc(CN3CCN(CCOCCOCCOCCOCCOCCOCCOCCOCCOCCOCCC(=O)Oc4c(F)c(F)cc(F)c4F)CC3)cc2N=C(N)C1] | 1165.3 |
| TAZ-L-90 | 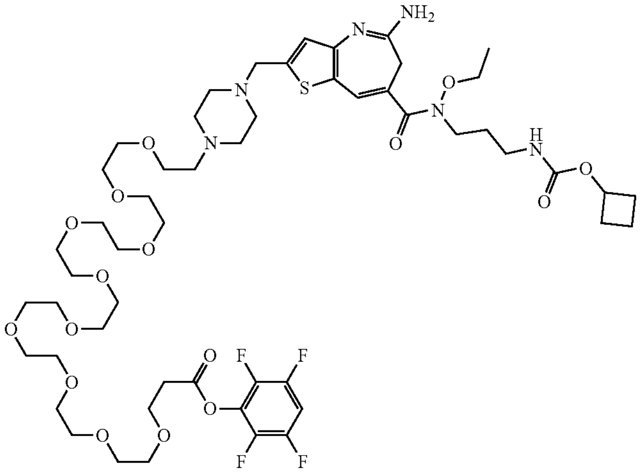 [SMILES: CCON(CCCNC(=O)OC1CCC1)C(=O)C1=Cc2sc(CN3CCN(CCOCCOCCOCCOCCOCCOCCOCCOCCOCCOCCC(=O)Oc4c(F)c(F)cc(F)c4F)CC3)cc2N=C(N)C1] | 1165.3 |

TABLE 2C-continued
| Thienoazepine-linker (TAZ-L) Formula II compounds | | |
|---|---|---|
| TAZ-L No. | Structure | MW |
| TAZ-L-91 | 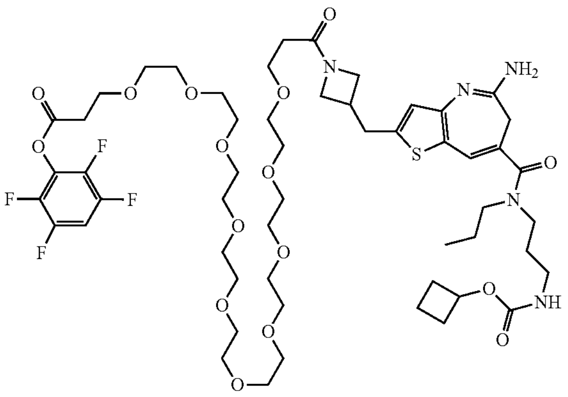 [SMILES: CCCN(CCCNC(=O)OC1CCC1)C(=O)C1=Cc2sc(CC3CN(C(=O)CCOCCOCCOCCOCCOCCOCCOCCOCCOCCOCCC(=O)Oc4c(F)c(F)cc(F)c4F)C3)cc2N=C(N)C1] | 1162.3 |
| TAZ-L-92 | 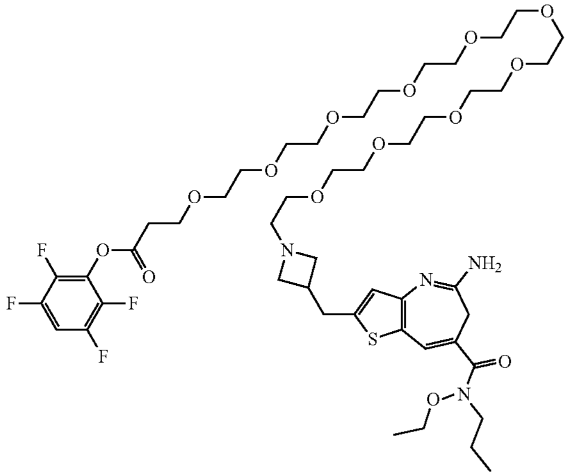 [SMILES: CCCN(OCC)C(=O)C1=Cc2sc(CC3CN(CCOCCOCCOCCOCCOCCOCCOCCOCCOCCOCCC(=O)Oc4c(F)c(F)cc(F)c4F)C3)cc2N=C(N)C1] | 1023.1 |
| TAZ-L-93 | 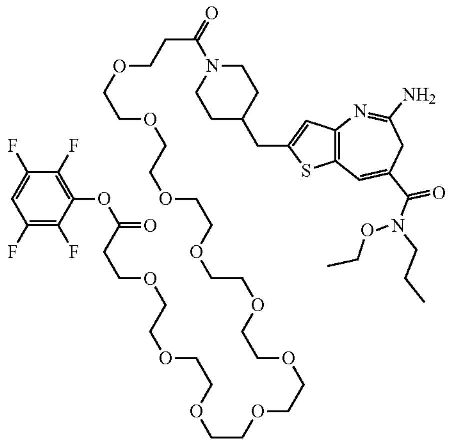 [SMILES: CCCN(OCC)C(=O)C1=Cc2sc(CC3CCN(C(=O)CCOCCOCCOCCOCCOCCOCCOCCOCCOCCOCCC(=O)Oc4c(F)c(F)cc(F)c4F)CC3)cc2N=C(N)C1] | 1079.2 |

TABLE 2C-continued
| Thienoazepine-linker (TAZ-L) Formula II compounds | | |
|---|---|---|
| TAZ-L No. | Structure | MW |
| TAZ-L-94 | 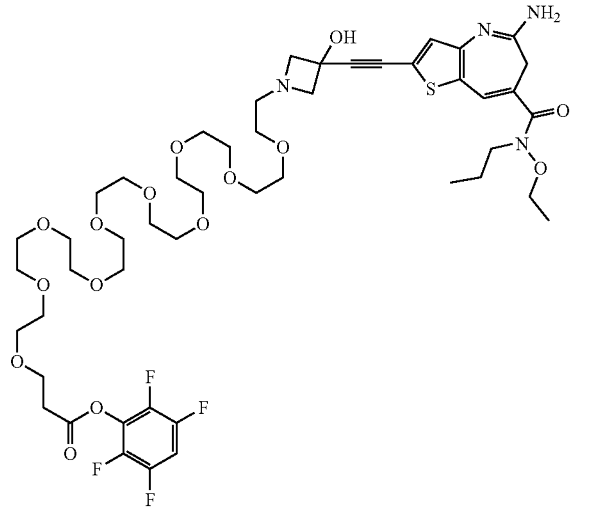 [SMILES: CCCN(OCC)C(=O)C1=Cc2sc(C#CC3(O)CN(CCOCCOCCOCCOCCOCCOCCOCCOCCOCCOCCC(=O)Oc4c(F)c(F)cc(F)c4F)C3)cc2N=C(N)C1] | 1049.1 |
| TAZ-L-95 | 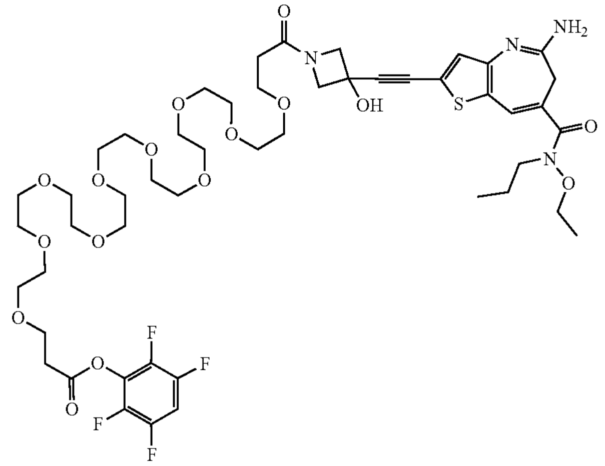 [SMILES: CCCN(OCC)C(=O)C1=Cc2sc(C#CC3(O)CN(C(=O)CCOCCOCCOCCOCCOCCOCCOCCOCCOCCOCCC(=O)Oc4c(F)c(F)cc(F)c4F)C3)cc2N=C(N)C1] | 1077.1 |
| TAZ-L-96 | 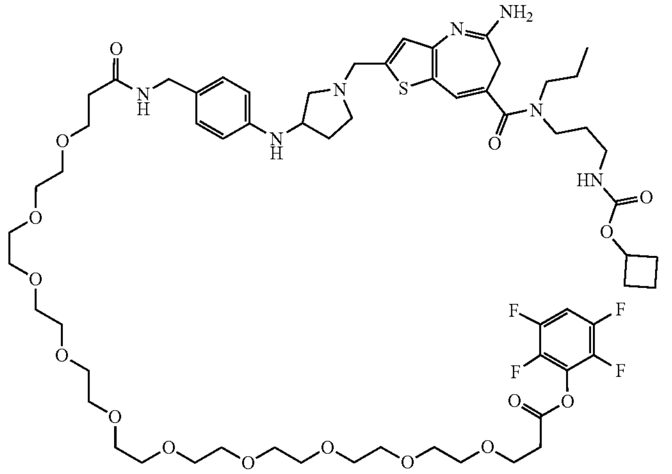 [SMILES: CCCN(CCCNC(=O)OC1CCC1)C(=O)C1=Cc2sc(CN3CCC(Nc4ccc(CNC(=O)CCOCCOCCOCCOCCOCCOCCOCCOCCOCCOCCC(=O)Oc5c(F)c(F)cc(F)c5F)cc4)C3)cc2N=C(N)C1] | 1296.5 |

TABLE 2C-continued
| Thienoazepine-linker (TAZ-L) Formula II compounds | | |
|---|---|---|
| TAZ-L No. | Structure | MW |
| TAZ-L-97 | 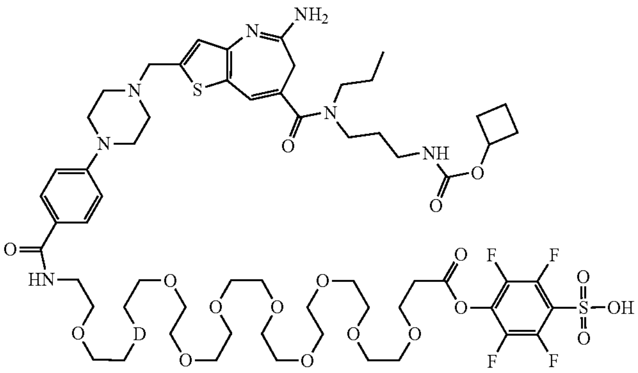 | 1362.5 |
| TAZ-L-98 | 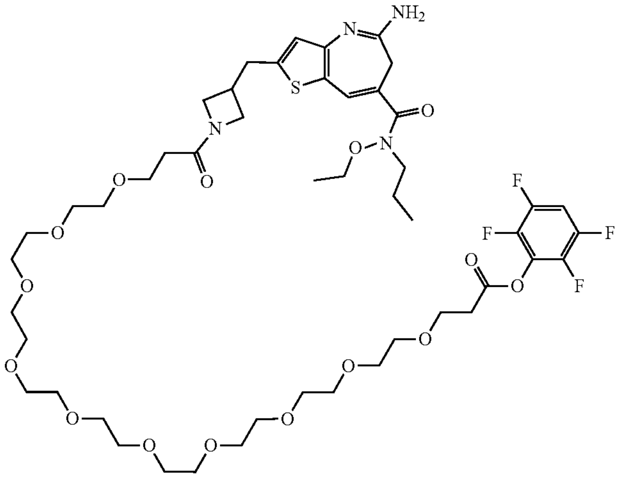 [SMILES: CCCN(OCC)C(=O)C1=Cc2sc(CC3CN(C(=O)CCOCCOCCOCCOCCOCCOCCOCCOCCOCCOCCC(=O)Oc4c(F)c(F)cc(F)c4F)C3)cc2N=C(N)C1] | 1051.2 |
| TAZ-L-99 | 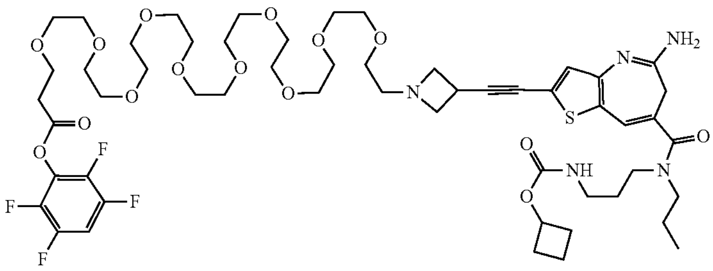 | 1144.3 |

TABLE 2C-continued
| Thienoazepine-linker (TAZ-L) Formula II compounds | | |
|---|---|---|
| TAZ-L No. | Structure | MW |
| TAZ-L-100 | 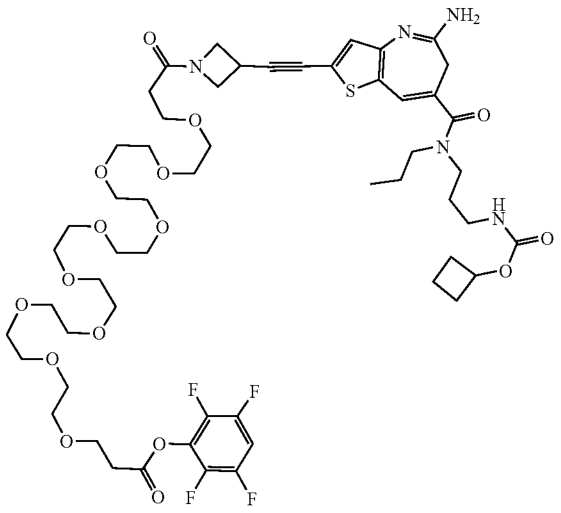 [SMILES: CCCN(CCCNC(=O)OC1CCC1)C(=O)C1=Cc2sc(C#CC3CN(C(=O)CCOCCOCCOCCOCCOCCOCCOCCOCCOCCOCCC(=O)Oc4c(F)c(F)cc(F)c4F)C3)cc2N=C(N)C1] | 1172.3 |
| TAZ-L-101 | 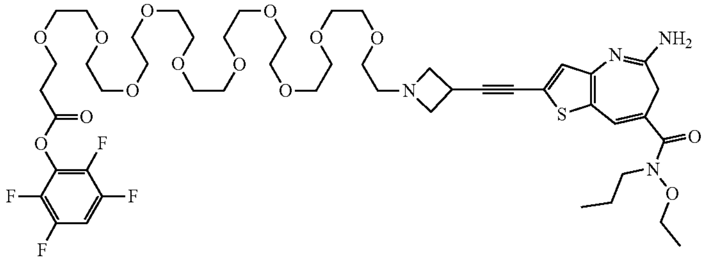 [SMILES: CCCN(OCC)C(=O)C1=Cc2sc(C#CC3CN(CCOCCOCCOCCOCCOCCOCCOCCOCCOCCOCCC(=O)Oc4c(F)c(F)cc(F)c4F)C3)cc2N=C(N)C1] | 1033.1 |
| TAZ-L-102 | 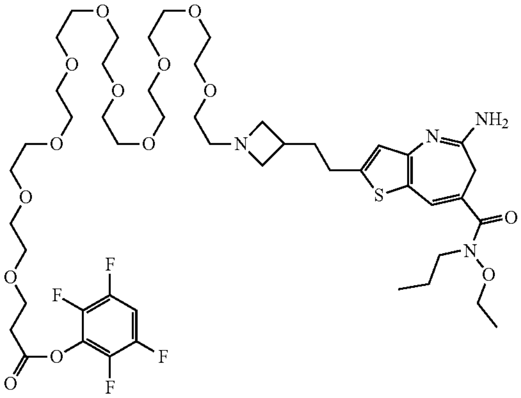 [SMILES: CCCN(OCC)C(=O)C1=Cc2sc(CCC3CN(CCOCCOCCOCCOCCOCCOCCOCCOCCOCCOCCC(=O)Oc4c(F)c(F)cc(F)c4F)C3)cc2N=C(N)C1] | 1037.2 |
| TAZ-L-103 | 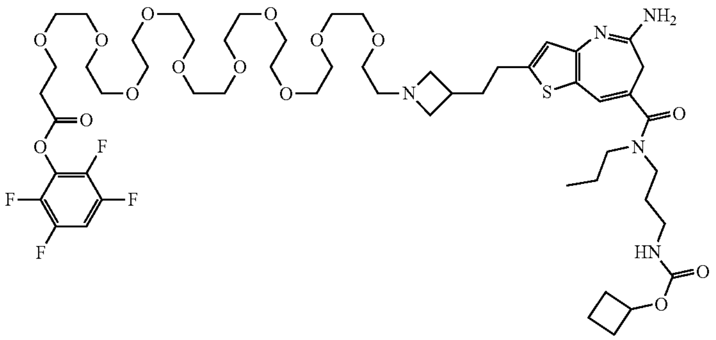 [SMILES: CCCN(CCCNC(=O)OC1CCC1)C(=O)C1=Cc2sc(CCC3CN(CCOCCOCCOCCOCCOCCOCCOCCOCCOCCOCCC(=O)Oc4c(F)c(F)cc(F)c4F)C3)cc2N=C(N)C1] | 1148.3 |

TABLE 2C-continued
| Thienoazepine-linker (TAZ-L) Formula II compounds | | |
|---|---|---|
| TAZ-L No. | Structure | MW |
| TAZ-L-104 | 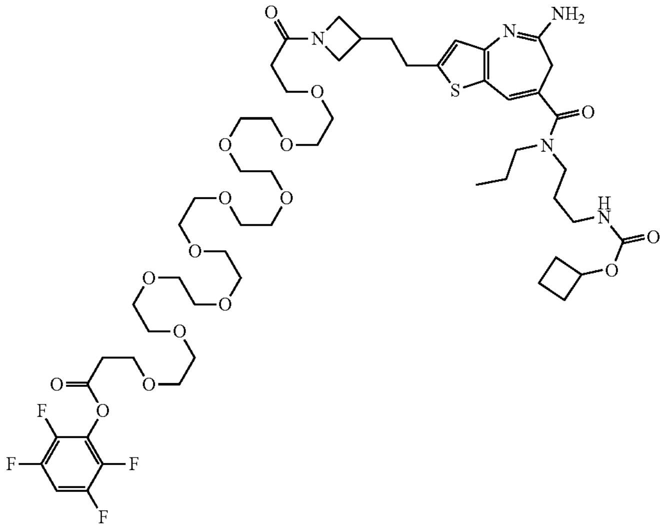 [SMILES: CCCN(CCCNC(=O)OC1CCC1)C(=O)C1=Cc2sc(CCC3CN(C(=O)CCOCCOCCOCCOCCOCCOCCOCCOCCOCCOCCC(=O)Oc4c(F)c(F)cc(F)c4F)C3)cc2N=C(N)C1] | 1176.3 |
| TAZ-L-105 | 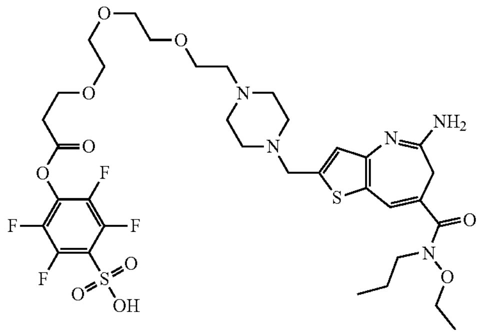 [SMILES: CCCN(OCC)C(=O)C1=Cc2sc(CN3CCN(CCOCCOCCOCCC(=O)Oc4c(F)c(F)c(S(=O)(=O)O)c(F)c4F)CC3)cc2N=C(N)C1] | 823.9 |
| TAZ-L-106 | 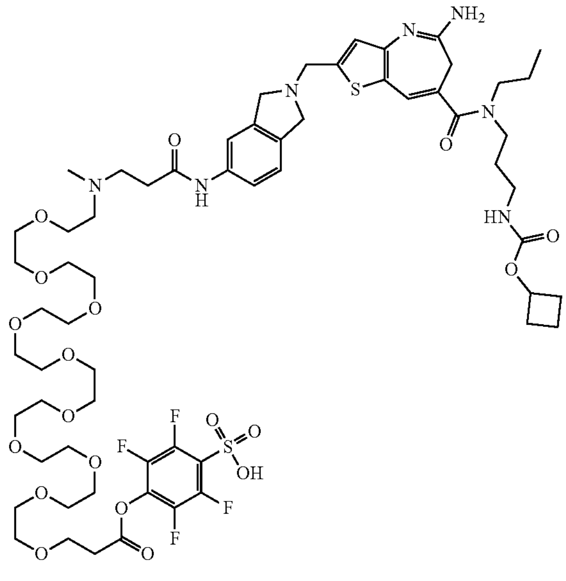 [SMILES: CCCN(CCCNC(=O)OC1CCC1)C(=O)C1=Cc2sc(CN3Cc4ccc(NC(=O)CCN(C)CCOCCOCCOCCOCCOCCOCCOCCOCCOCCOCCC(=O)Oc5c(F)c(F)c(S(=O)(=O)O)c(F)c5F)cc4C3)cc2N=C(N)C1] | 1376.5 |

TABLE 2C-continued
| TAZ-L No. | Structure | MW |
| --- | --- | --- |
| Thienoazepine-linker (TAZ-L) Formula II compounds | | |
| TAZ-L-107 | 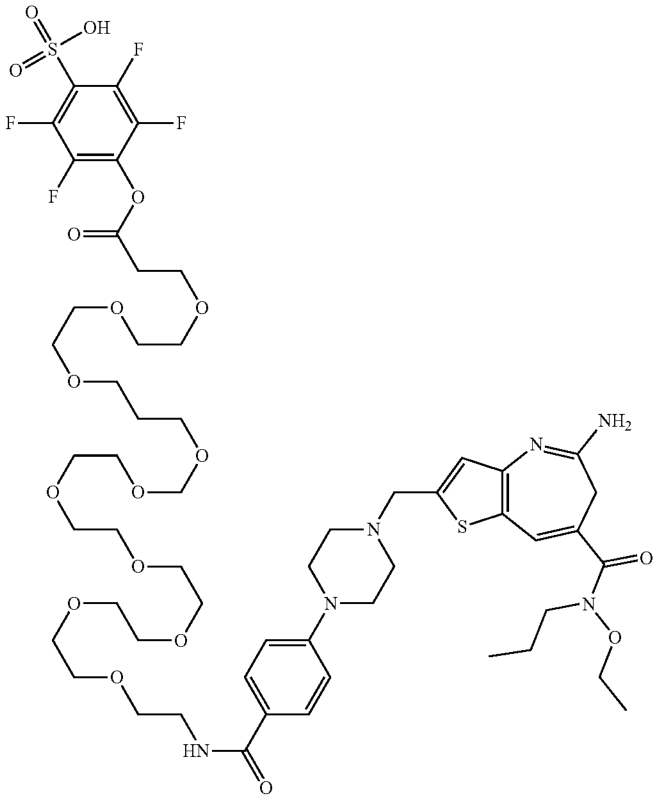 [SMILES: CCCN(OCC)C(=O)C1=Cc2sc(CN3CCN(c4ccc(C(=O)NCCOCCOCCOCCOCCOCCOCOCCCOCCOCCOCCC(=O)Oc5c(F)c(F)c(S(=O)(=O)O)c(F)c5F)cc4)CC3)cc2N=C(N)C1] | 1251.4 |
| TAZ-L-108 | 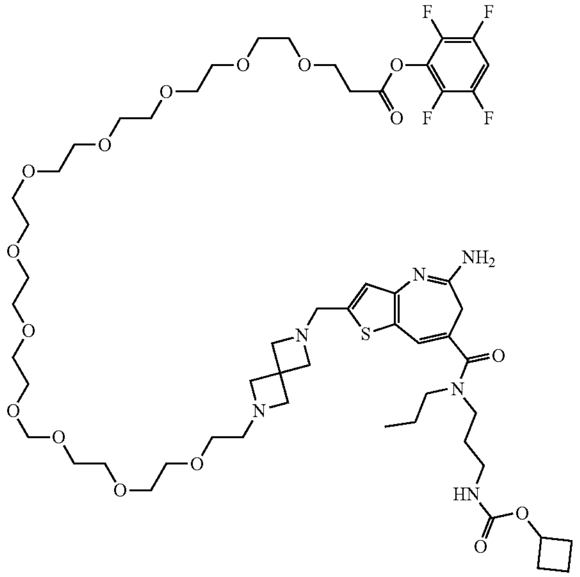 [SMILES: CCCN(CCCNC(=O)OC1CCC1)C(=O)C1=Cc2sc(CN3CC4(CN(CCOCCOCCOCOCCOCCOCCOCCOCCOCCOCCOCCC(=O)Oc5c(F)c(F)cc(F)c5F)C4)C3)cc2N=C(N)C1] | 1175.3 |

TABLE 2C-continued
| Thienoazepine-linker (TAZ-L) Formula II compounds | | |
|---|---|---|
| TAZ-L No. | Structure | MW |
| TAZ-L-109 | 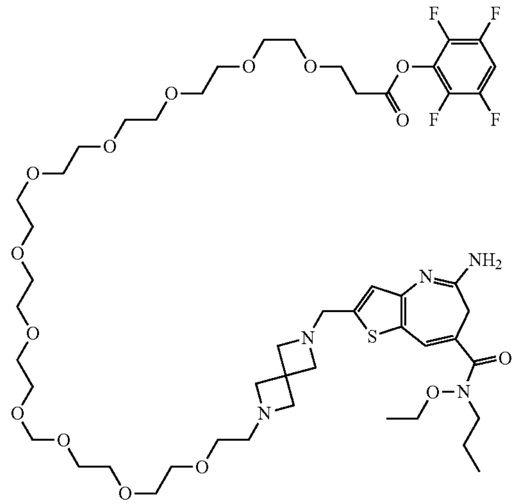 [SMILES: CCCN(OCC)C(=O)C1=Cc2sc(CN3CC4(CN(CCOCCOCCOCOCCOCCOCCOCCOCCOCCOCCOCCC(=O)Oc5c(F)c(F)cc(F)c5F)C4)C3)cc2N=C(N)C1] | 1064.2 |
| TAZ-L-110 | 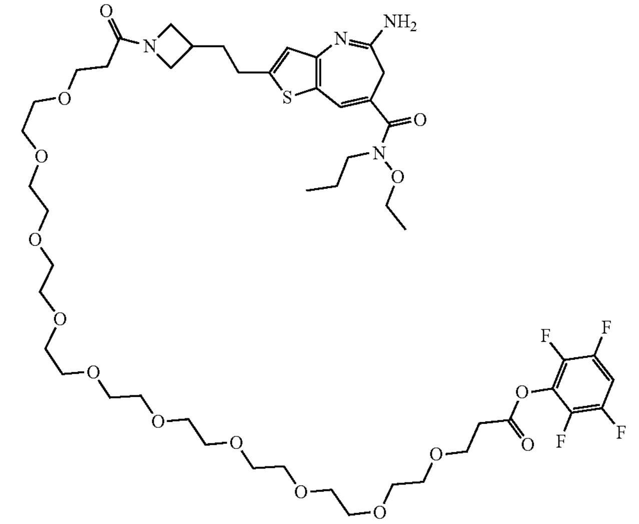 [SMILES: CCCN(OCC)C(=O)C1=Cc2sc(CCC3CN(C(=O)CCOCCOCCOCCOCCOCCOCCOCCOCCOCCOCCC(=O)Oc4c(F)c(F)cc(F)c4F)C3)cc2N=C(N)C1] | 1065.2 |
| TAZ-L-111 | 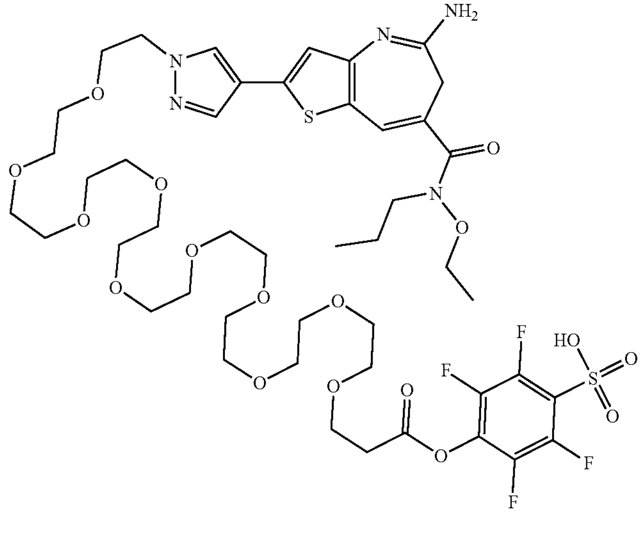 [SMILES: CCCN(OCC)C(=O)C1=Cc2sc(-c3cnn(CCOCCOCCOCCOCCOCCOCCOCCOCCOCCOCCC(=O)Oc4c(F)c(F)c(S(=O)(=O)O)c(F)c4F)c3)cc2N=C(N)C1] | 1100.2 |

TABLE 2C-continued
| Thienoazepine-linker (TAZ-L) Formula II compounds | | |
|---|---|---|
| TAZ-L No. | Structure | MW |
| TAZ-L-112 | 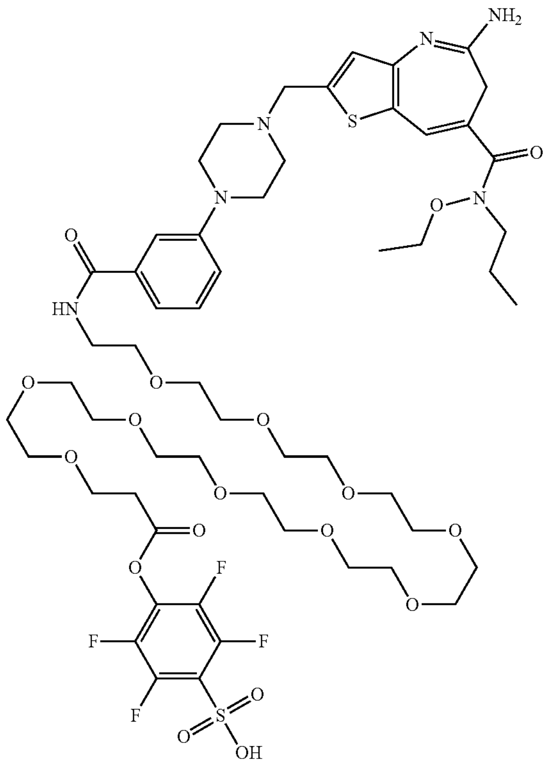 [SMILES: CCCN(OCC)C(=O)C1=Cc2sc(CN3CCN(c4cccc(C(=O)NCCOCCOCCOCCOCCOCCOCCOCCOCCOCCOCCC(=O)Oc5c(F)c(F)c(S(=O)(=O)O)c(F)c5F)c4)CC3)cc2N=C(N)C1] | 1251.4 |
| TAZ-L-113 | 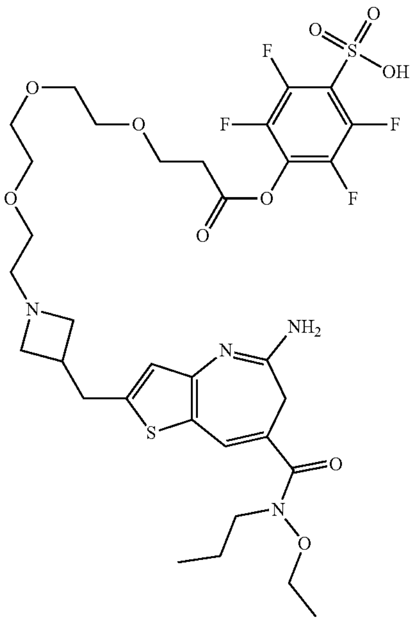 [SMILES: CCCN(OCC)C(=O)C1=Cc2sc(CC3CN(CCOCCOCCOCCC(=O)Oc4c(F)c(F)c(S(=O)(=O)O)c(F)c4F)C3)cc2N=C(N)C1] | 794.8 |

TABLE 2C-continued
| Thienoazepine-linker (TAZ-L) Formula II compounds | | |
|---|---|---|
| TAZ-L No. | Structure | MW |
| TAZ-L-114 | 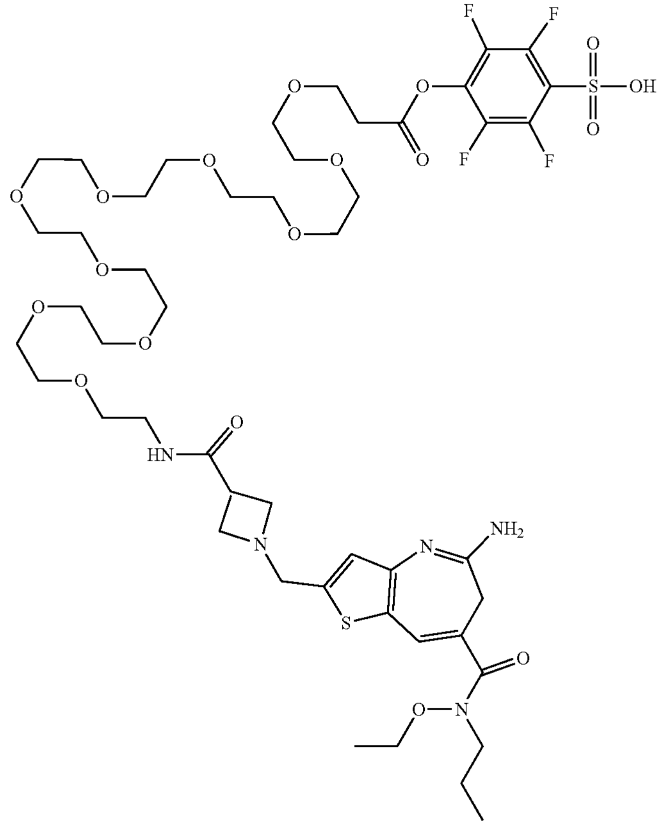 [SMILES: CCCN(OCC)C(=O)C1=Cc2sc(CN(CC)CCC(=O)NCCOCCOCCOCCOCCOCCOCCOCCOCCOCCOCCC(=O)Oc3c(F)c(F)c(S(=O)(=O)O)c(F)c3F)cc2N=C(N)C1] | 1146.2 |
| TAZ-L-115 | 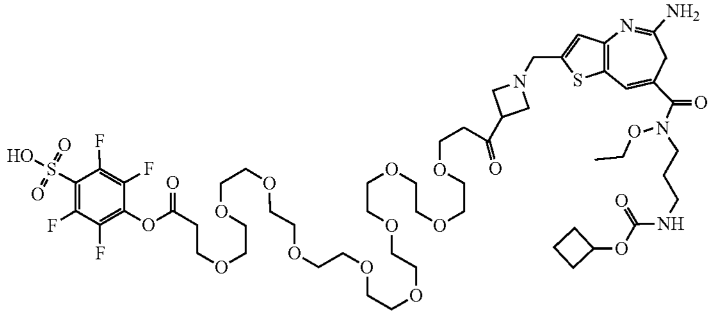 [SMILES: CCON(CCCNC(=O)OC1CCC1)C(=O)C1=Cc2sc(CN3CC(C(=O)CCOCCOCCOCCOCCOCCOCCOCCOCCOCCOCCC(=O)Oc4c(F)c(F)c(S(=O)(=O)O)c(F)c4F)C3)cc2N=C(N)C1C] | 1244.3 |

TABLE 2C-continued
| Thienoazepine-linker (TAZ-L) Formula II compounds | | |
|---|---|---|
| TAZ-L No. | Structure | MW |
| TAZ-L-116 | 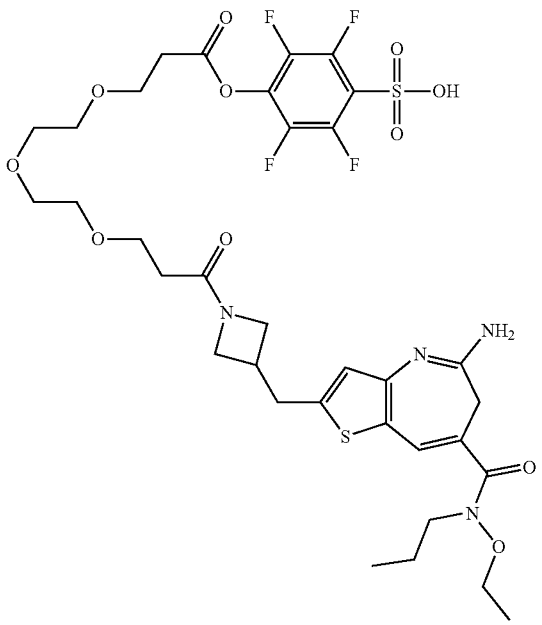 [SMILES: CCCN(OCC)C(=O)C1=Cc2sc(CC3CN(C(=O)CCOCCOCCOCCC(=O)Oc4c(F)c(F)c(S(=O)(=O)O)c(F)c4F)C3)cc2N=C(N)C1] | 822.8 |
| TAZ-L-117 | 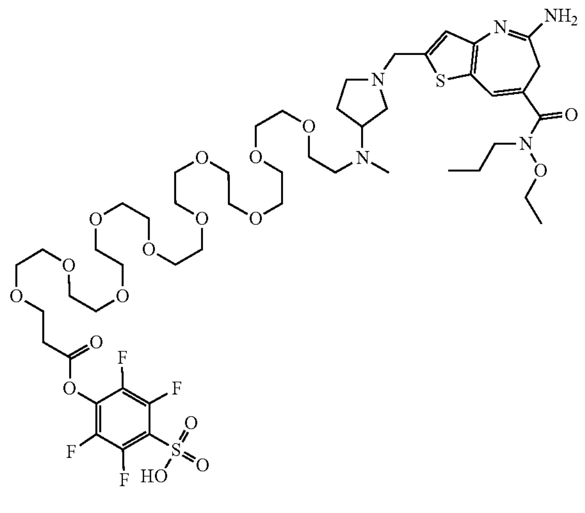 [SMILES: CCCN(OCC)C(=O)C1=Cc2sc(CN3CCC(N(C)CCOCCOCCOCCOCCOCCOCCOCCOCCOCCOCCC(=O)Oc4c(F)c(F)c(S(=O)(=O)O)c(F)c4F)C3)cc2N=C(N)C1] | 1146.3 |
| TAZ-L-118 | 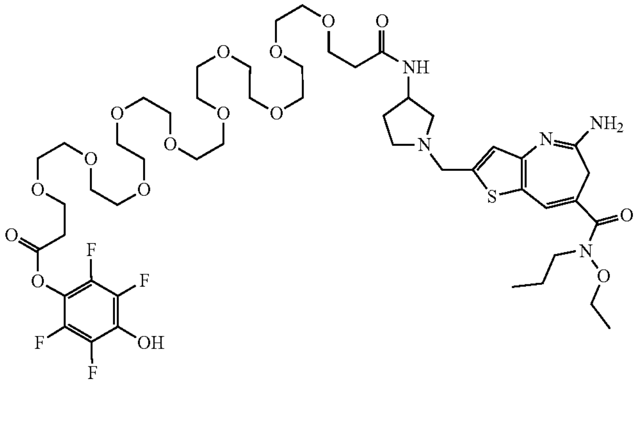 [SMILES: CCCN(OCC)C(=O)C1=Cc2sc(CN3CCC(NC(=O)CCOCCOCCOCCOCCOCCOCCOCCOCCOCCOCCC(=O)Oc4c(F)c(F)c(O)c(F)c4F)C3)cc2N=C(N)C1] | 1160.3 |

TABLE 2C-continued
| Thienoazepine-linker (TAZ-L) Formula II compounds | | |
|---|---|---|
| TAZ-L No. | Structure | MW |
| TAZ-L-119 | 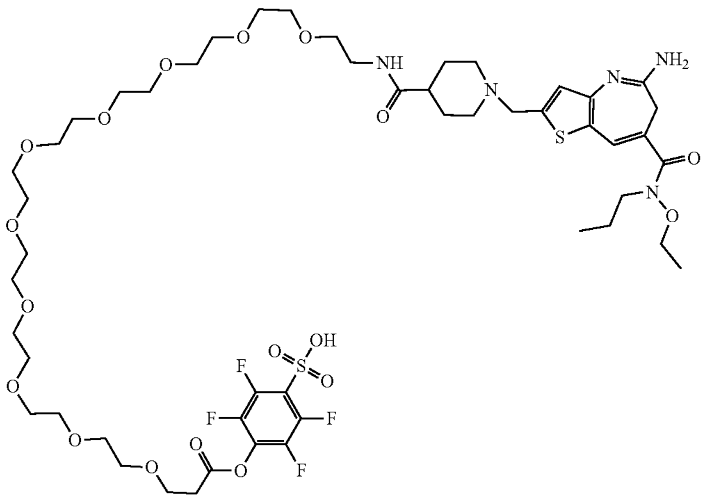 [SMILES: CCCN(OCC)C(=O)C1=Cc2sc(CN3CCC(C(=O)NCCOCCOCCOCCOCCOCCOCCOCCOCCOCCOCCC(=O)Oc4c(F)c(F)c(S(=O)(=O)O)c(F)c4F)CC3)cc2N=C(N)C1] | 1174.3 |
| TAZ-L-120 | 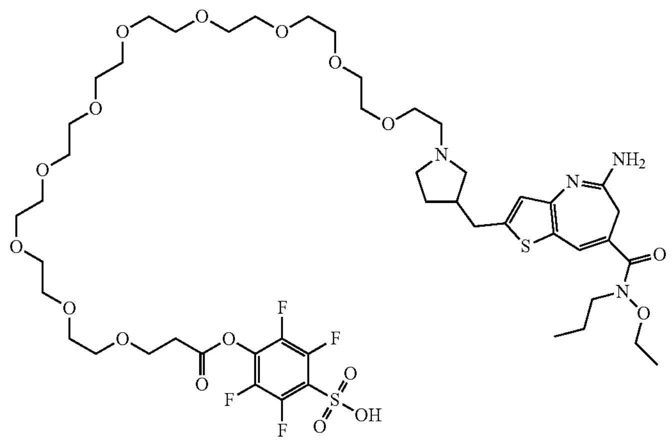 [SMILES: CCCN(OCC)C(=O)C1=Cc2sc(CC3CCN(CCOCCOCCOCCOCCOCCOCCOCCOCCOCCOCCC(=O)Oc4c(F)c(F)c(S(=O)(=O)O)c(F)c4F)C3)cc2N=C(N)C1] | 1117.2 |

TABLE 2C-continued
| Thienoazepine-linker (TAZ-L) Formula II compounds | | |
|---|---|---|
| TAZ-L No. | Structure | MW |
| TAZ-L-121 | 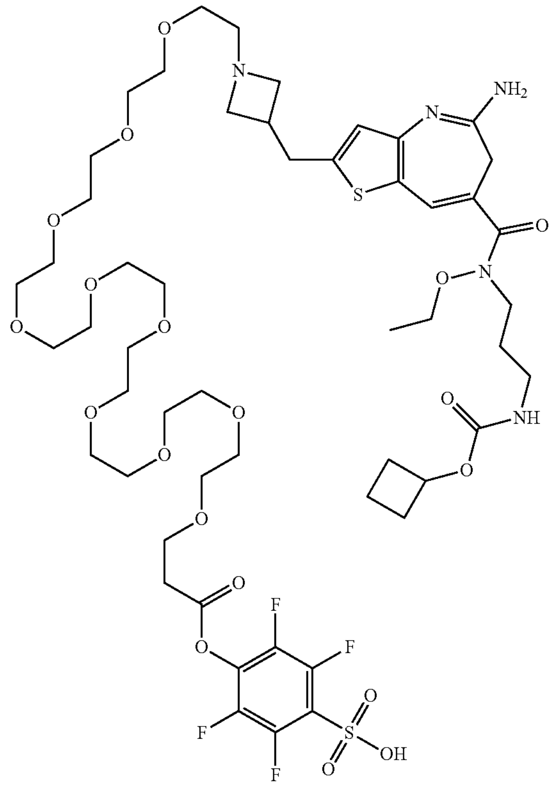 [SMILES: CCON(CCCNC(=O)OC1CCC1)C(=O)C1=Cc2sc(CC3CN(CCOCCOCCOCCOCCOCCOCCOCCOCCOCCOCCC(=O)Oc4c(F)c(F)c(S(=O)(=O)O)c(F)c4F)C3)cc2N=C(N)C1] | 1216.3 |
| TAZ-L-122 | 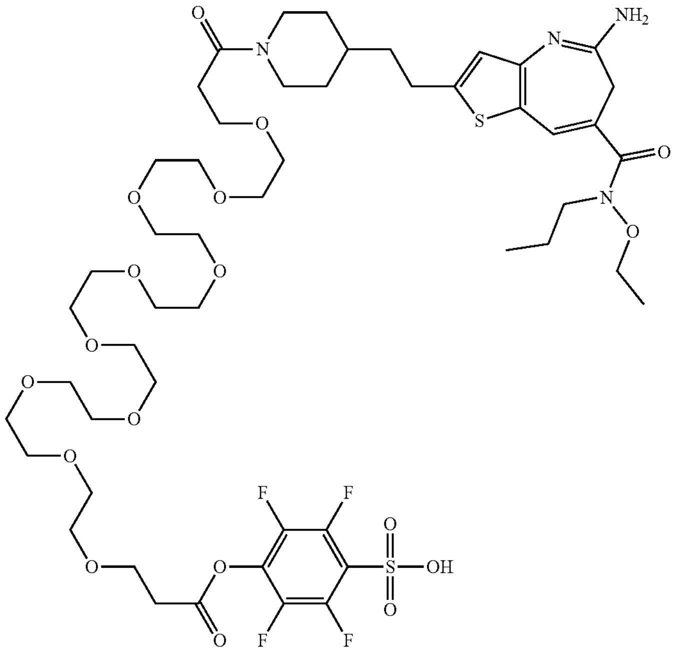 [SMILES: CCCN(OCC)C(=O)C1=Cc2sc(CCC3CCN(C(=O)CCOCCOCCOCCOCCOCCOCCOCCOCCOCCOCCC(=O)Oc4c(F)c(F)c(S(=O)(=O)O)c(F)c4F)CC3)cc2N=C(N)C1] | 1173.3 |

TABLE 2C-continued
| Thienoazepine-linker (TAZ-L) Formula II compounds | | |
|---|---|---|
| TAZ-L No. | Structure | MW |
| TAZ-L-123 | 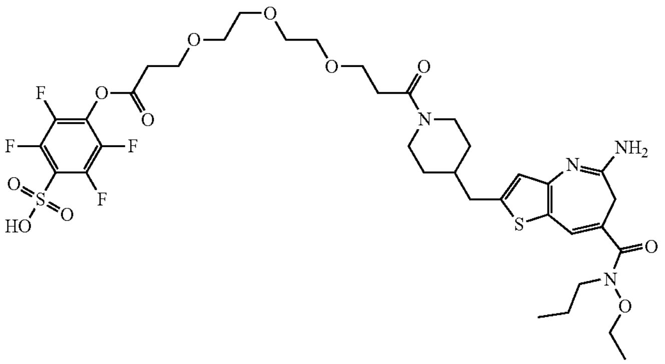 [SMILES: CCCN(OCC)C(=O)C1=Cc2sc(CC3CCN(C(=O)CCOCCOCCOCCC(=O)Oc4c(F)c(F)c(S(=O)(=O)O)c(F)c4F)CC3)cc2N=C(N)C1] | 850.9 |
| TAZ-L-124 | 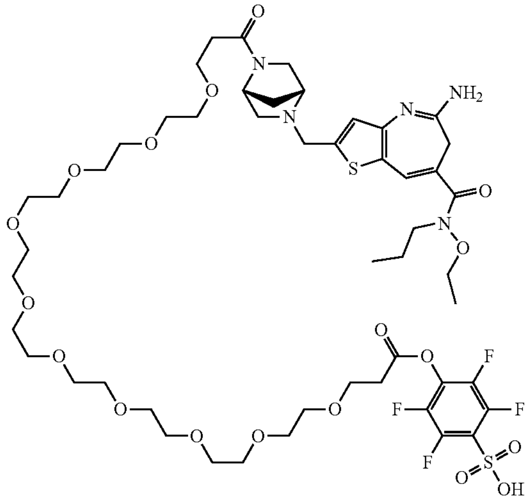 [SMILES: CCCN(OCC)C(=O)C1=Cc2sc(CN3C[C@H]4C[C@@H]3CN4C(=O)CCOCCOCCOCCOCCOCCOCCOCCOCCOCCOCCC(=O)Oc3c(F)c(F)c(S(=O)(=O)O)c(F)c3F)cc2N=C(N)C1] | 1172.3 |
| TAZ-L-125 | 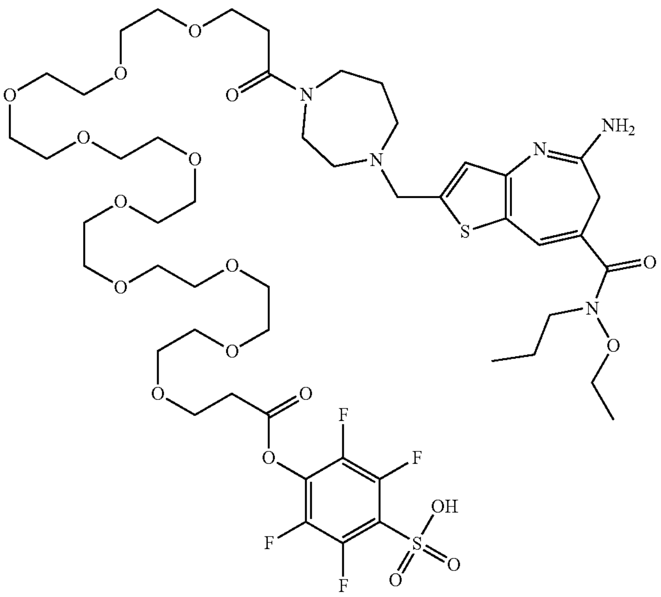 [SMILES: CCCN(OCC)C(=O)C1=Cc2sc(CN3CCCN(C(=O)CCOCCOCCOCCOCCOCCOCCOCCOCCOCCOCCC(=O)Oc4c(F)c(F)c(S(=O)(=O)O)c(F)c4F)CC3)cc2N=C(N)C1] | 1174.3 |

TABLE 2C-continued
| Thienoazepine-linker (TAZ-L) Formula II compounds | | |
|---|---|---|
| TAZ-L No. | Structure | MW |
| TAZ-L-126 | 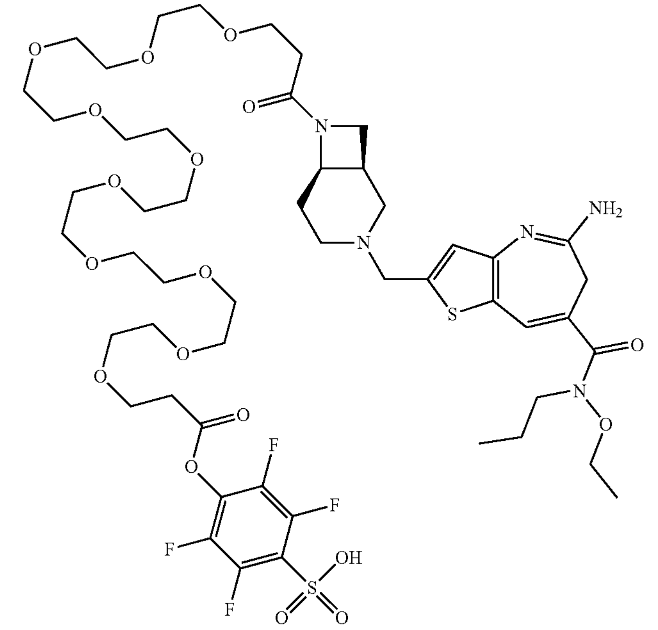 [SMILES: CCCN(OCC)C(=O)C1=Cc2sc(CN3CC[C@@H]4[C@H](C3)CN4C(=O)CCOCCOCCOCCOCCOCCOCCOCCOCCOCCOCCC(=O)Oc3c(F)c(F)c(S(=O)(=O)O)c(F)c3F)cc2N=C(N)C1] | 1186.3 |
| TAZ-L-127 | 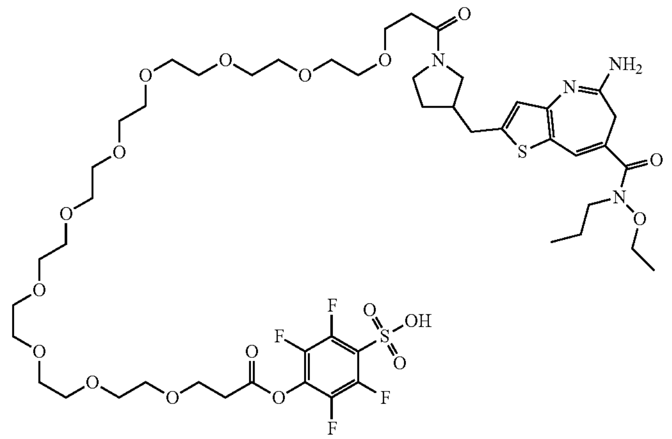 [SMILES: CCCN(OCC)C(=O)C1=Cc2sc(CC3CCN(C(=O)CCOCCOCCOCCOCCOCCOCCOCCOCCOCCOCCC(=O)Oc4c(F)c(F)c(S(=O)(=O)O)c(F)c4F)C3)cc2N=C(N)C1] | 1145.2 |
| TAZ-L-128 | 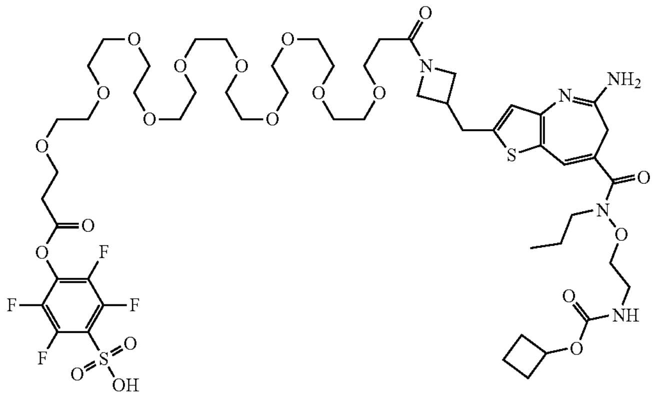 [SMILES: CCCN(OCCNC(=O)OC1CCC1)C(=O)C1=Cc2sc(CC3CN(C(=O)CCOCCOCCOCCOCCOCCOCCOCCOCCOCCOCCC(=O)Oc4c(F)c(F)c(S(=O)(=O)O)c(F)c4F)C3)cc2N=C(N)C1] | 1244.3 |

TABLE 2C-continued
| Thienoazepine-linker (TAZ-L) Formula II compounds | | |
|---|---|---|
| TAZ-L No. | Structure | MW |
| TAZ-L-129 | 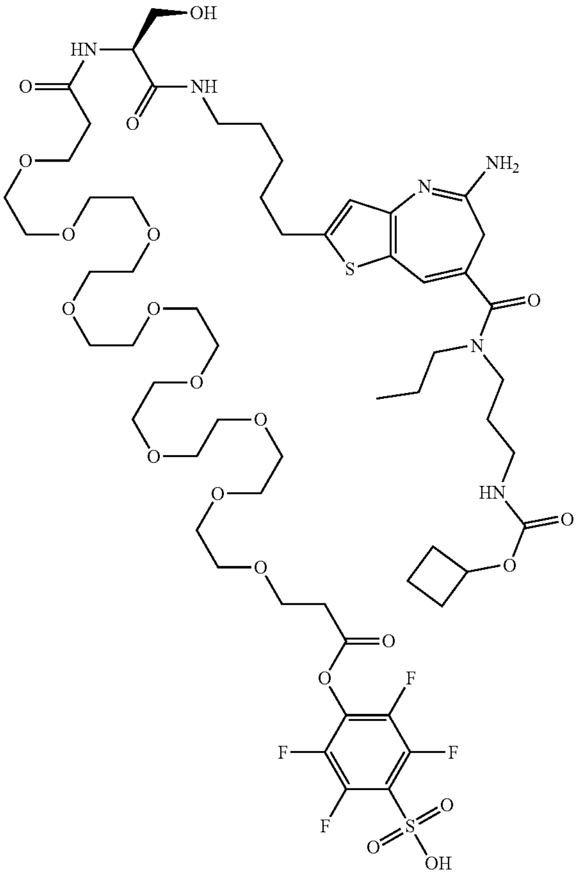 | 1409.5 |
| TAZ-L-130 | 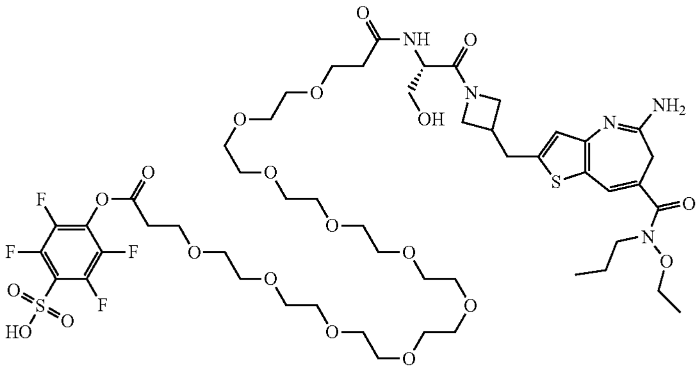 [SMILES: CCCN(OCC)C(=O)C1=Cc2sc(CC3CN(C(=O)[C@H](CO)NC(=O)CCOCCOCCOCCOCCOCCOCCOCCOCCOCCOCCC(=O)Oc4c(F)c(F)c(S(=O)(=O)O)c(F)c4F)C3)cc2N=C(N)C1] | 1282.4 |

TABLE 2C-continued
| Thienoazepine-linker (TAZ-L) Formula II compounds | | |
|---|---|---|
| TAZ-L No. | Structure | MW |
| TAZ-L-131 | 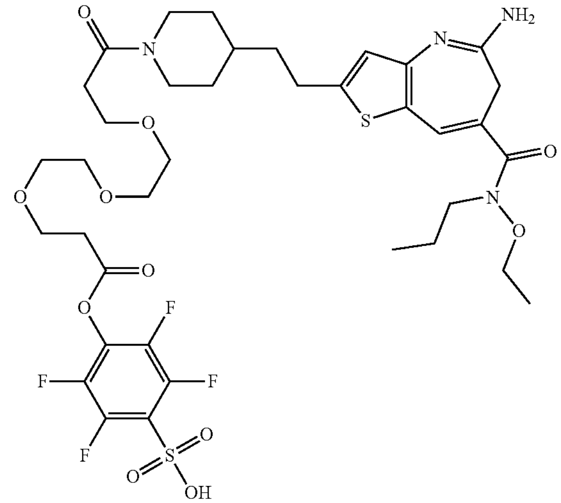 [SMILES: CCCN(OCC)C(=O)C1=Cc2sc(CCC3CCN(C(=O)CCOCCOCCOCCC(=O)Oc4c(F)c(F)c(S(=O)(=O)O)c(F)c4F)CC3)cc2N=C(N)C1] | 864.9 |
| TAZ-L-132 | 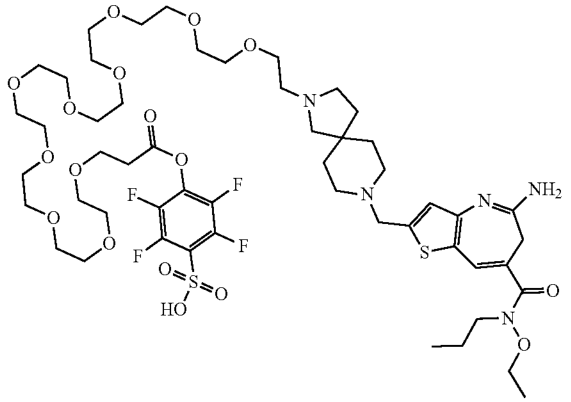 [SMILES: CCCN(OCC)C(=O)C1=Cc2sc(CN3CCC4(CC3)CCN(CCOCCOCCOCCOCCOCCOCCOCCOCCOCCOCCC(=O)Oc3c(F)c(F)c(S(=O)(=O)O)c(F)c3F)C4)cc2N=C(N)C1] | 1186.3 |
| TAZ-L-133 | 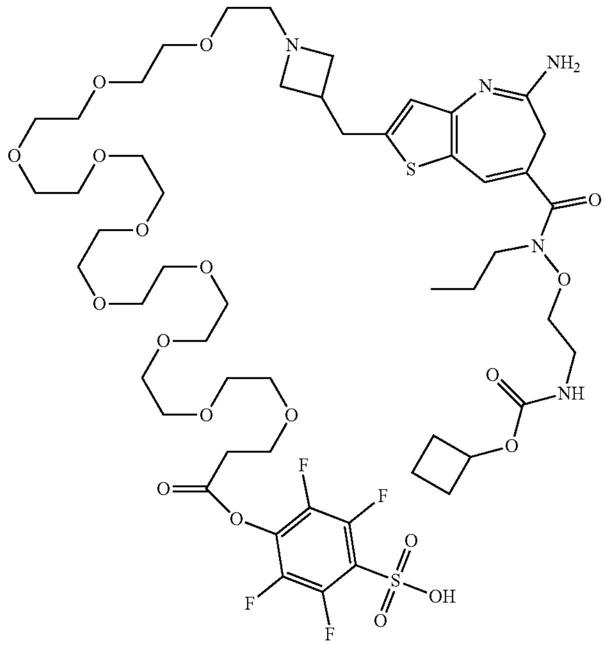 [SMILES: CCCN(OCCNC(=O)OC1CCC1)C(=O)C1=Cc2sc(CC3CN(CCOCCOCCOCCOCCOCCOCCOCCOCCOCCOCCC(=O)Oc4c(F)c(F)c(S(=O)(=O)O)c(F)c4F)C3)cc2N=C(N)C1] | 1216.3 |

TABLE 2C-continued
| Thienoazepine-linker (TAZ-L) Formula II compounds | | |
|---|---|---|
| TAZ-L No. | Structure | MW |
| TAZ-L-134 | 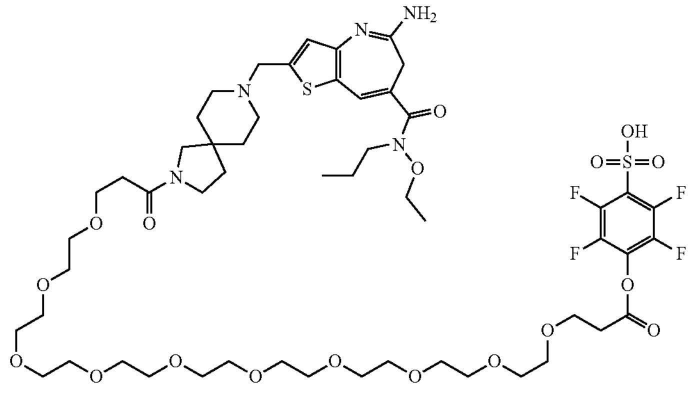 [SMILES: CCCN(OCC)C(=O)C1=Cc2sc(CN3CCC4(CC3)CCN(C(=O)CCOCCOCCOCCOCCOCCOCCOCCOCCOCCOCCC(=O)Oc3c(F)c(F)c(S(=O)(=O)O)c(F)c3F)C4)cc2N=C(N)C1] | 1214.3 |
| TAZ-L-135 | 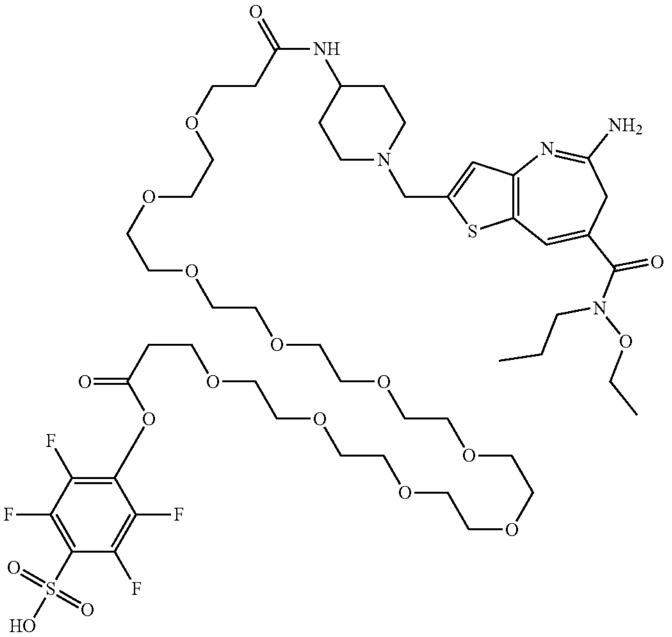 [SMILES: CCCN(OCC)C(=O)C1=Cc2sc(CN3CCC(NC(=O)CCOCCOCCOCCOCCOCCOCCOCCOCCOCCOCCC(=O)Oc4c(F)c(F)c(S(=O)(=O)O)c(F)c4F)CC3)cc2N=C(N)C1] | 1174.3 |
| TAZ-L-136 | 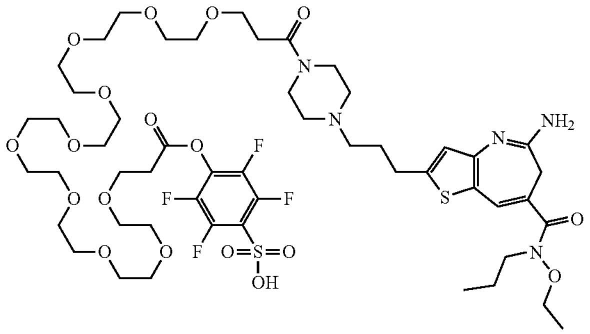 [SMILES: CCCN(OCC)C(=O)C1=Cc2sc(CCCN3CCN(C(=O)CCOCCOCCOCCOCCOCCOCCOCCOCCOCCOCCC(=O)Oc4c(F)c(F)c(S(=O)(=O)O)c(F)c4F)CC3)cc2N=C(N)C1] | 1188.3 |

TABLE 2C-continued
| Thienoazepine-linker (TAZ-L) Formula II compounds | | |
|---|---|---|
| TAZ-L No. | Structure | MW |
| TAZ-L-137 | 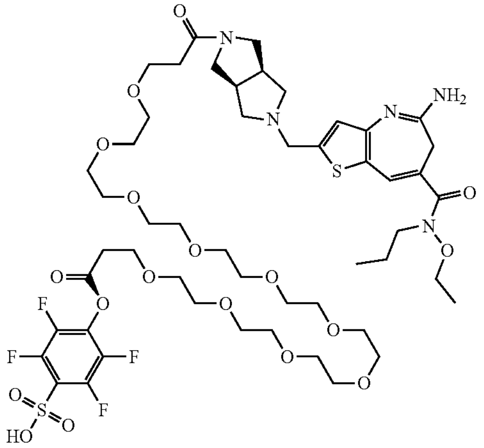 | 1186.3 |
| TAZ-L-138 | 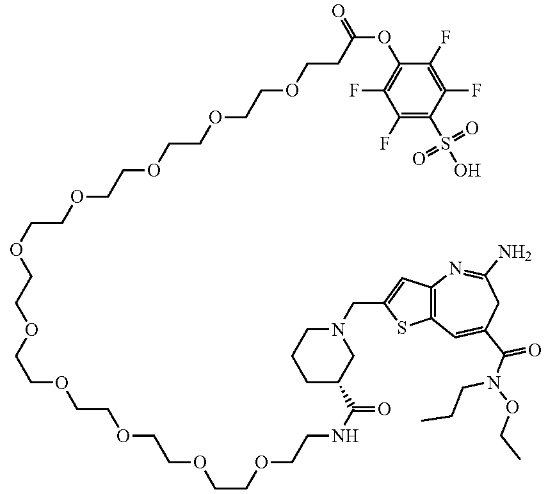 [SMILES: CCCN(OCC)C(=O)C1=Cc2sc(CN3CCC[C@@H](C(=O)NCCOCCOCCOCCOCCOCCOCCOCCOCCOCCOCCC(=O)Oc4c(F)c(F)c(S(=O)(=O)O)c(F)c4F)C3)cc2N=C(N)C1] | 1174.3 |
| TAZ-L-139 | 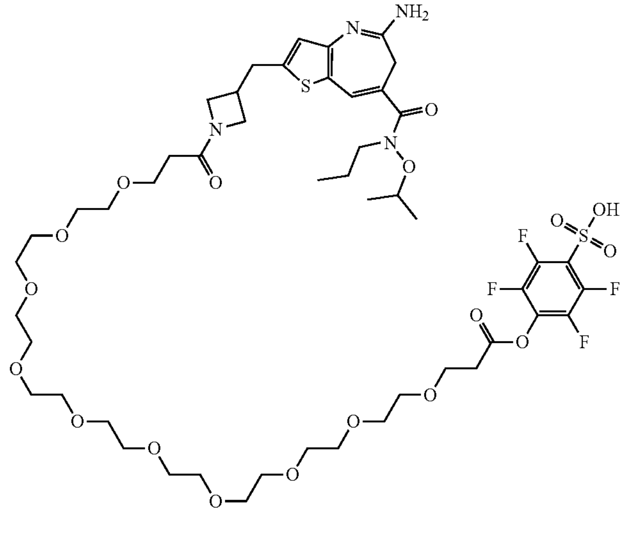 [SMILES: CCCN(OC(C)C)C(=O)C1=Cc2sc(CC3CN(C(=O)CCOCCOCCOCCOCCOCCOCCOCCOCCOCCOCCC(=O)Oc4c(F)c(F)c(S(=O)(=O)O)c(F)c4F)C3)cc2N=C(N)C1] | 1145.2 |

TABLE 2C-continued
| Thienoazepine-linker (TAZ-L) Formula II compounds | | |
| --- | --- | --- |
| TAZ-L No. | Structure | MW |
| TAZ-L-140 | 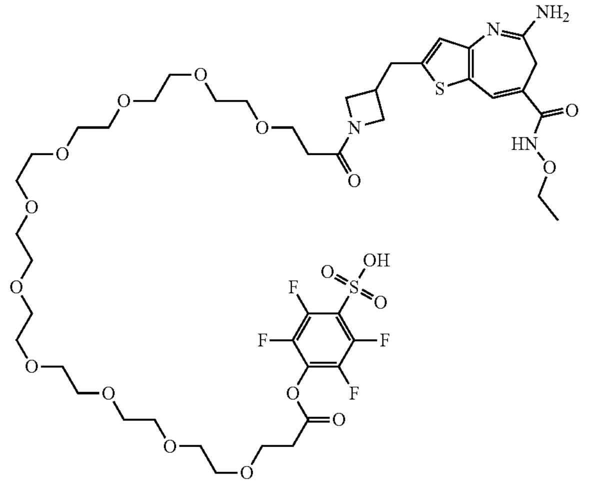 [SMILES: CCONC(=O)C1=Cc2sc(CC3CN(C(=O)CCOCCOCCOCCOCCOCCOCCOCCOCCOCCOCCC(=O)Oc4c(F)c(F)c(S(=O)(=O)O)c(F)c4F)C3)cc2N=C(N)C1] | 1089.1 |
| TAZ-L-141 | 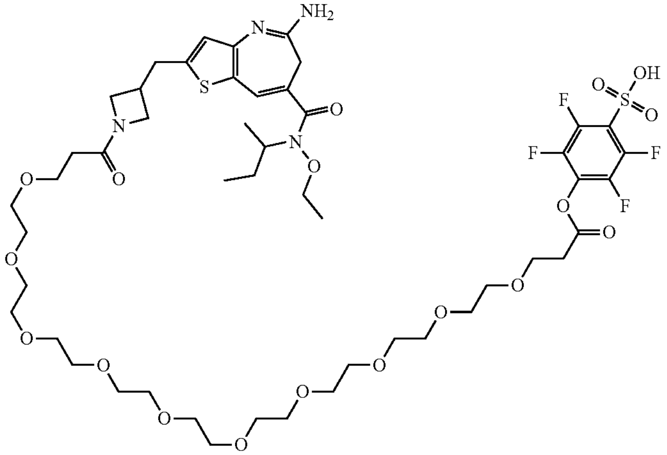 [SMILES: CCON(C(=O)C1=Cc2sc(CC3CN(C(=O)CCOCCOCCOCCOCCOCCOCCOCCOCCOCCOCCC(=O)Oc4c(F)c(F)c(S(=O)(=O)O)c(F)c4F)C3)cc2N=C(N)C1)C(C)CC] | 1145.2 |
| TAZ-L-142 | 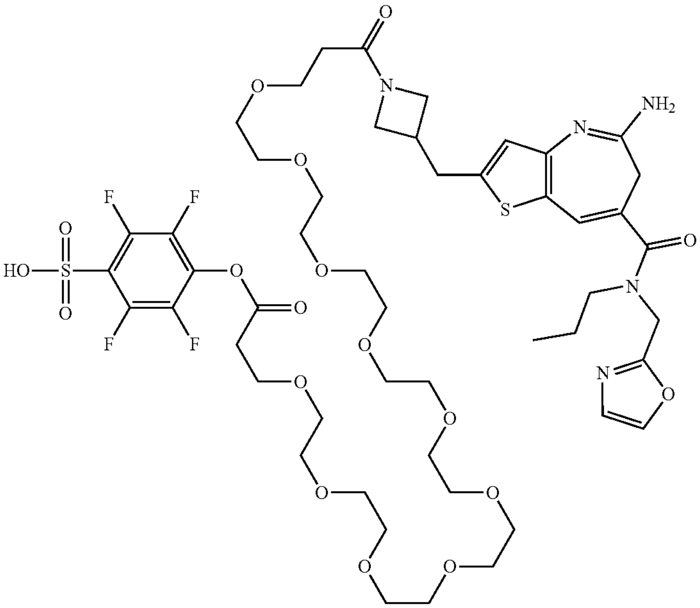 [SMILES: CCCN(Cc1ncco1)C(=O)C1=Cc2sc(CC3CN(C(=O)CCOCCOCCOCCOCCOCCOCCOCCOCCOCCOCCC(=O)Oc4c(F)c(F)c(S(=O)(=O)O)c(F)c4F)C3)cc2N=C(N)C1] | 1168.2 |

TABLE 2C-continued
| Thienoazepine-linker (TAZ-L) Formula II compounds | | |
|---|---|---|
| TAZ-L No. | Structure | MW |
| TAZ-L-143 | 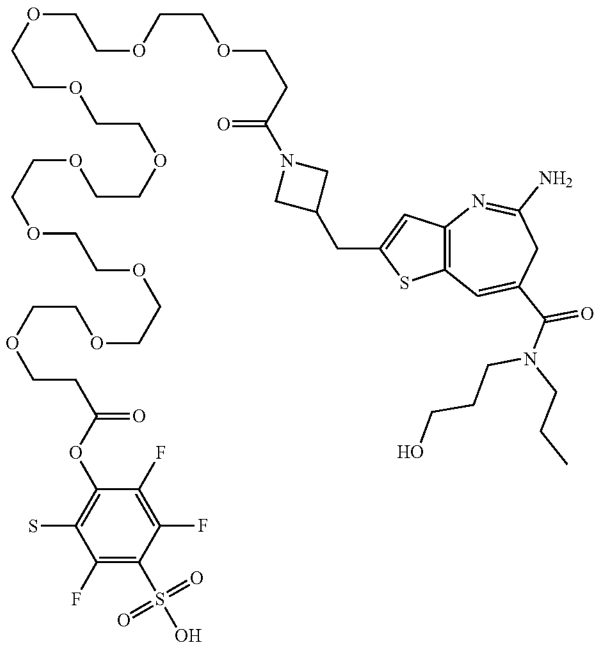 [SMILES: CCCN(CCCO)C(=O)C1=Cc2sc(CC3CN(C(=O)CCOCCOCCOCCOCCOCCOCCOCCOCCOCCOCCC(=O)Oc4c(F)c(F)c(S(=O)(=O)O)c(F)c4S)C3)cc2N=C(N)C1] | 1145.2 |
| TAZ-L-144 | 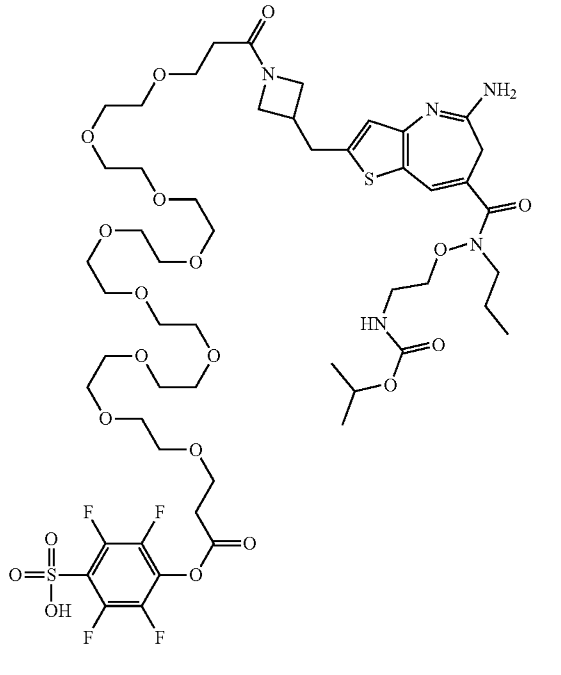 [SMILES: CCCN(OCCNC(=O)OC(C)C)C(=O)C1=Cc2sc(CC3CN(C(=O)CCOCCOCCOCCOCCOCCOCCOCCOCCOCCOCCC(=O)Oc4c(F)c(F)c(S(=O)(=O)O)c(F)c4F)C3)cc2N=C(N)C1] | 1232.3 |

TABLE 2C-continued
| Thienoazepine-linker (TAZ-L) Formula II compounds | | |
|---|---|---|
| TAZ-L No. | Structure | MW |
| TAZ-L-145 | 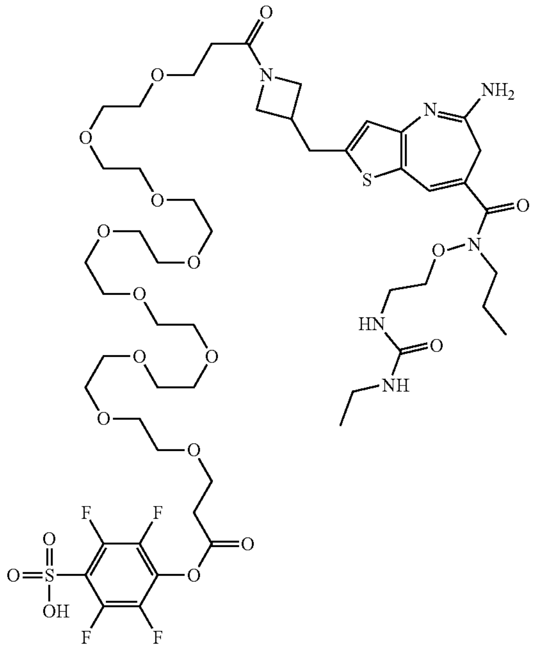 [SMILES: CCCN(OCCNC(=O)NCC)C(=O)C1=Cc2sc(CC3CN(C(=O)CCOCCOCCOCCOCCOCCOCCOCCOCCOCCOCCC(=O)Oc4c(F)c(F)c(S(=O)(=O)O)c(F)c4F)C3)cc2N=C(N)C1] | 1217.3 |
| TAZ-L-146 | 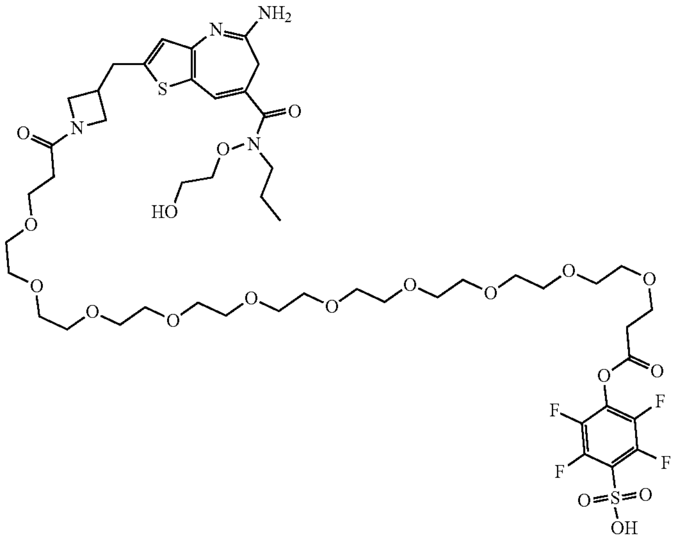 [SMILES: CCCN(OCCO)C(=O)C1=Cc2sc(CC3CN(C(=O)CCOCCOCCOCCOCCOCCOCCOCCOCCOCCOCCC(=O)Oc4c(F)c(F)c(S(=O)(=O)O)c(F)c4F)C3)cc2N=C(N)C1] | 1147.2 |

TABLE 2C-continued
| Thienoazepine-linker (TAZ-L) Formula II compounds | | |
|---|---|---|
| TAZ-L No. | Structure | MW |
| TAZ-L-147 | 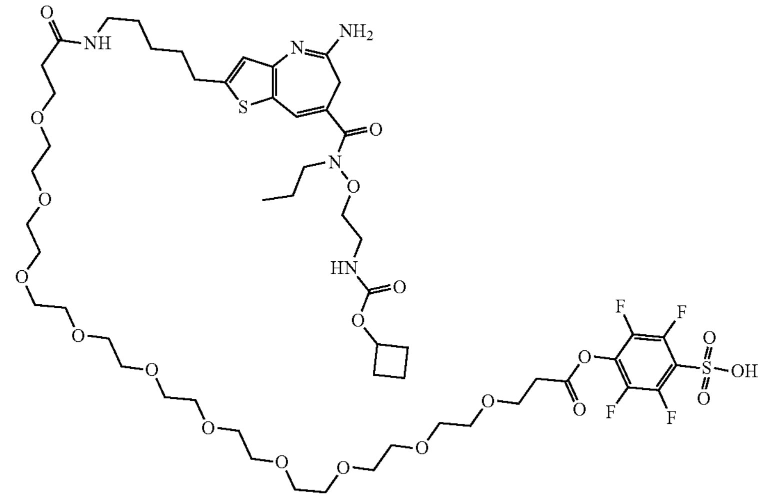 [SMILES: CCCN(OCCNC(=O)OC1CCC1)C(=O)C1=Cc2sc(CCCCCNC(=O)CCOCCOCCOCCOCCOCCOCCOCCOCCOCCOCCC(=O)Oc3c(F)c(F)c(S(=O)(=O)O)c(F)c3F)cc2N=C(N)C1] | 1260.4 |
| TAZ-L-148 | 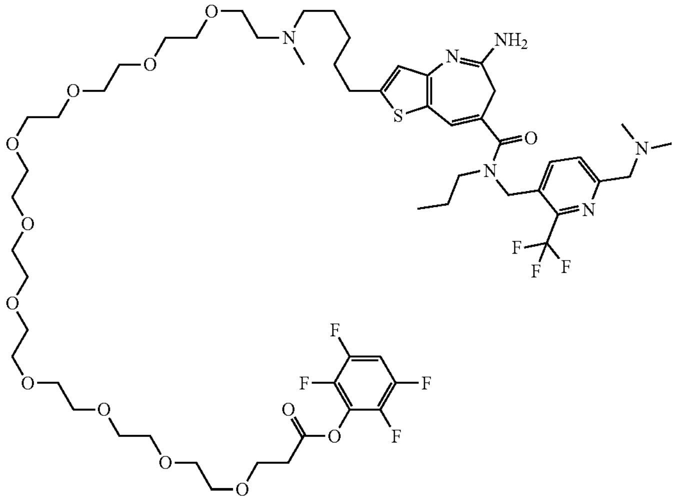 [SMILES: CCCN(Cc1ccc(CN(C)C)nc1C(F)(F)F)C(=O)C1=Cc2sc(CCCCCN(C)CCOCCOCCOCCOCCOCCOCCOCCOCCOCCOCCC(=O)Oc3c(F)c(F)cc(F)c3F)cc2N=C(N)C1] | 1225.4 |

TABLE 2C-continued
| Thienoazepine-linker (TAZ-L) Formula II compounds | | |
|---|---|---|
| TAZ-L No. | Structure | MW |
| TAZ-L-149 | 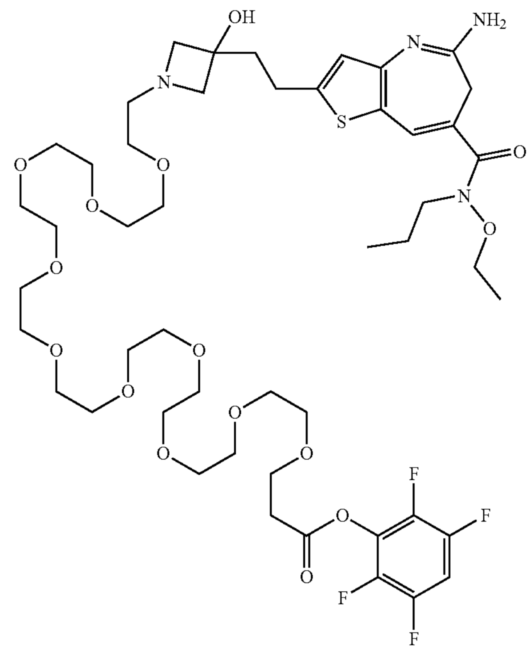 [SMILES: CCCN(OCC)C(=O)C1=Cc2sc(CCC3(O)CN(CCOCCOCCOCCOCCOCCOCCOCCOCCOCCOCCC(=O)Oc4c(F)c(F)cc(F)c4F)C3)cc2N=C(N)C1] | 1053.2 |
| TAZ-L-150 | 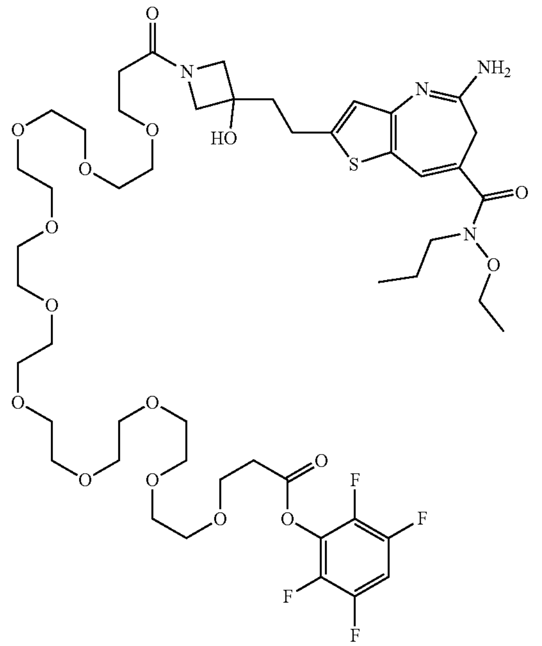 [SMILES: CCCN(OCC)C(=O)C1=Cc2sc(CCC3(O)CN(C(=O)CCOCCOCCOCCOCCOCCOCCOCCOCCOCCOCCC(=O)Oc4c(F)c(F)cc(F)c4F)C3)cc2N=C(N)C1] | 1081.2 |

Immunoconjugates

Exemplary embodiments of immunoconjugates comprise an antibody covalently attached to one or more 5-aminothienoazepine (TAZ) moieties by a linker, and having Formula I:

$$Ab—[L—TAZ]_p \quad \text{I}$$

or a pharmaceutically, acceptable salt thereof,
wherein:
Ab is the antibody;
p is an integer from 1 to 8;
TAZ is the 5-aminothienoazepine moiety having the formula:

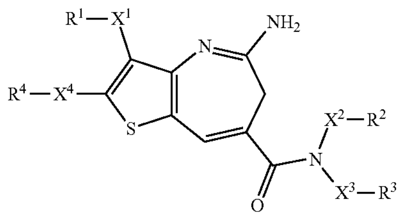

$R^1$, $R^2$, $R^3$, and $R^4$ are independently selected from the group consisting of H, $C_1$-$C_{12}$ alkyl, $C_2$-$C_6$ alkenyl, $C_2$-$C_6$ alkynyl, $C_3$-$C_{12}$ carbocyclyl, $C_6$-$C_{20}$ aryl, $C_2$-$C_9$ heterocyclyl, and $C_1$-$C_{20}$ heteroaryl, where alkyl, alkenyl, alkynyl, carbocyclyl, aryl, heterocyclyl, and heteroaryl are independently and optionally substituted with one or more groups selected from;
—($C_1$-$C_{12}$ alkyldiyl)-N($R^5$)—*;
—($C_1$-$C_1$ alkyldiyl)-N($R^5$)$_2$;
—($C_1$-$C_{12}$ alkyldiyl)-O$R^5$;
—($C_3$-$C_{12}$ carbocyclyl);
—($C_3$-$C_{12}$ carbocyclyl)-*;
—($C_3$-$C_{12}$ carbocyclyl)-($C_1$-$C_{12}$ alkyldiyl)-N$R^5$—*;
—($C_3$-$C_{12}$ carbocyclyl)-($C_1$-$C_{12}$ alkyldiyl)-N($R^5$)$_2$;
—($C_3$-$C_{12}$ carbocyclyl)-N$R^5$—C(═N$R^5$)N$R^5$—*;
—($C_6$-$C_{20}$ aryl);
—($C_6$-$C_{20}$ aryl)-*;
—($C_6$-$C_{20}$ aryldiyl)-N($R^5$)—*;
—($C_6$-$C_{20}$ aryldiyl)-($C_1$-$C_{12}$ alkyldiyl)-N($R^5$)—*;
($C_1$-$C_{20}$ aryldiyl)-($C_1$-$C_{12}$ alkyldiyl)-($C_2$-$C_{20}$ heterocyclyldiyl)-*;
—($C_6$-$C_{20}$ aryldiyl)-($C_1$-$C_{12}$ alkyldiyl)-N($R^5$)$_2$
—($C_6$-$C_{20}$ aryldiyl)-($C_1$-$C_{12}$ alkyldiyl)-N$R^5$—C(═N$R^{5a}$)N($R^5$)—*;
—($C_2$-$C_{20}$ heterocyclyl);
—($C_2$-$C_{20}$ heterocyclyl)-*;
—($C_2$-$C_9$ heterocyclyl)-($C_1$-$C_{12}$ alkyldiyl)-N$R^5$—*;
—($C_2$-$C_9$ heterocyclyl)-($C_1$-$C_{12}$ alkyldiyl)-N($R^5$)$_2$;
—($C_2$-$C_9$ heterocyclyl)-C(═O)—($C_1$-$C_{12}$ alkyldiyl)-N($R^5$)—*;
—($C_2$-$C_9$ heterocyclyl)-N$R^5$—C(═N$R^{5a}$)N$R^5$—*;
—($C_2$-$C_9$ heterocyclyl)-N$R^5$—($C_6$-$C_{20}$ aryldiyl)-($C_1$-$C_{12}$ alkyldiyl)-N($R^5$)—*;
—($C_2$-$C_9$ heterocyclyl)-($C_6$-$C_{20}$ aryldiyl)-*;
—($C_1$-$C_{20}$ heteroaryl);
—($C_1$-$C_{20}$ heteroaryl)-*;
—($C_1$-$C_2$n heteroaryl)-($C_1$-$C_{12}$ alkyldiyl)-N($R^5$)—*;
—($C_1$-$C_{12}$ heteroaryl)-($C_1$-$C_{12}$ alkyldiyl)-N($R^5$)$_2$;
—($C_1$-$C_{20}$ heteroaryl)-N$R^5$—C(═N$R^{5a}$)N($R^5$)—*;
—($C_1$-$C_{20}$ heteroaryl)-N($R^5$)C(═OHC$_1$-$C_{12}$ alkyldiyl)-N($R^5$)—*;
—C(═O)—*;
—C(═O))—($C_1$-$C_{12}$ alkyldiyl)-N($R^5$)—*;
—C(═O)—($C_2$-$C_{20}$ heterocyclyldiyl)-*;
—C(═O)N($R^5$)$_2$;
—C(═O)N($R^5$)—*;
—C(═O)N($R^5$)—($C_1$-$C_{12}$ alkyldiyl)-N($R^5$)C(═O)$R^5$;
—C(═O)N($R^5$)—($C_1$-$C_{12}$ alkyldiyl)-N($R^5$)C(═O)N($R^5$)$_2$;
—C(═O)N$R^5$—($C_1$-$C_{12}$ alkyldiyl)-N($R^5$)CO$_2$$R^5$;
—C(═O)N$R^5$—($C_1$-$C_{12}$ alkyldiyl)-N($R^5$)C(═N$R^{5a}$)N($R^5$)$_2$;
—C(═O)N$R^5$—($C_1$-$C_{12}$ alkyldiyl)-N$R^5$C(═N$R^5$a)$R^5$;
—C(═O)N$R^5$—($C_1$-$C_8$ alkyldiyl)-N$R^5$($C_2$-$C_5$ heteroaryl);
—C(═O)N$R^5$—($C_1$-$C_{20}$ heteroaryldiyl)-N($R^5$)—*;
—C(═O)N$R^5$—($C_1$-$C_{20}$ heteroaryldiyl)-*;
—C(═O)N$R^5$—($C_1$-$C_{20}$ heteroaryldiyl)-($C_1$-$C_{12}$ alkyldiyl)-N($R^5$)$_2$;
—C(═O)N$R^5$—($C_1$-$C_{20}$ heteroaryldiyl)-($C_2$-$C_{20}$ heterocyclyldiyl)-C(═O)N$R^5$—($C_1$-$C_{12}$ alkyldiyl)-N$R^5$—*;
—N($R^5$)$_2$;
—N($R^5$)—*;
—N($R^5$)C(═O)R;
N($R^5$)C(═O)—*;
N($R^5$)C(═O)N($R^5$)$_2$;
N($R^5$)C(═O)N($R^5$)—*;
—N($R^5$)CO$_2$$R^5$;
—N$R^5$C(═N$R^{5a}$)N($R^5$)$_2$;
—N$R^5$C(═N$R^{5a}$)N($R^5$)—*;
N$R^5$C(═N$R^{5a}$)$R_5$;
—N($R^5$)C(═O)—($C_1$-$C_{12}$ alkyldiyl)-N($R^5$)—*;
—N($R^5$)—($C_2$-$C_5$ heteroaryl);
—N($R^5$)—S(═O)$_2$—($C_1$-$C_2$ alkyl);
—O—($C_1$-$C_{12}$ alkyl);
—O—($C_1$-$C_{12}$ alkyldiyl)-N($R^5$)$_2$;
—O—($C_1$-$C_{12}$ alkyldiyl)-N($R^5$)—*;
—S(═O)$_2$—($C_2$-$C_{20}$ heterocyclyldiyl)-*;
—S(═O)$_2$—($C_2$-$C_{20}$ heterocyclyldiyl)-($C_1$-$C_{12}$ alkyldiyl)-N($R^5$)$_2$;
—S(═O)$_2$—($C_2$-$C_{20}$ heterocyclyldiyl)-($C_1$-$C_{12}$ alkyldiyl)-N$R^5$—*; and
—S(═O)$_2$—($C_2$-$C_{20}$ heterocyclyldiyl)-($C_1$-$C_{12}$ alkyldiyl)-OH;

or $R^2$ and $R^3$ together form a 5- or 6-membered heterocyclyl ring;

$X^1$, $X^2$, $X^3$, and $X^4$ are independently selected from the group consisting of a bond, C(═O), C(═O)N($R^5$), O, N($R^5$), S, S(O)$_2$, and S(O)$_2$N($R^5$);

$R^5$ is selected from the group consisting of H, $C_6$-$C_{20}$ aryl, $C_3$-$C_{12}$ carbocyclyl, $C_6$-$C_{20}$ aryldiyl, $C_1$-$C_{12}$ alkyl, and $C_1$-$C_{12}$ alkyldiyl, or two $R^5$ groups together form a 5- or 6-membered heterocyclyl ring;

$R^{5a}$ is selected from the group consisting of $C_6$-$C_{20}$ aryl and $C_1$-$C_{20}$ heteroaryl;

where the asterisk * indicates the attachment site of L, and where one of $R^1$, $R^2$, $R^3$ and $R^4$ is attached to L;

L is the linker selected from the group consisting of;
—C(═O)—(PEG)-;
—C(═O)—(PEG)-C(═O)—;
—C(═O)—(PEG)-O—;
—C(═O)—(PEG)-C(═O)—(PEP)-;
—C(═O)—(PEG)-C(═O)N($R^5$)—($C_1$-$C_{12}$ alkyldiyl)-;
—C(═O)—(PEG)-C(═O)N($R^5$)—($C_1$-$C_{12}$ alkyldiyl)-N($R^3$)C(═O)$C_2$-$C_5$ monoheterocyclyldiyl)-;

—C(=O)—(PEG)-C(=O)N($R^5$)—($C_1$-$C_{12}$ alkyldiyl)-(MCgluc)-;

—C(=O)—(PEG)-C(=O)-(MCgluc)-;

—C(=O)—(PEG)-C(=O)—(PEP)—N($R^5$—($C_1$-$C_{12}$ alkyldiyl)-;

—C(=O)—(PEG)-C(=O)—(PEP)—N($R^5$)—($C_1$-$C_{12}$ alkyldiyl)-N($R^5$)C(=O)—($C_2$-$C_5$ monoheterocyclyldiyl)-;

—C(=O)—(PEG)-N($R^5$)—;

—C(=O—(PEG)-N($R^5$)C(=O)—;

—C(=O)—(PEG)-N($R^5$)—(PEG)-C(=O)—(PEP)-;

—C(=O)—(PEG)-N($R^5$)$_2$—(PEG)-C(=O)—(PEP)-;

—C(=O)—(PEG)-C(=O)—N($R^5$)CH($AA_1$)C(=O)—(PEG)-C(=O)—(PEP)-;

—C(=O)—(PEG)-C(=O)—N($R^5$)CH($AA_1$)C(=O)—N($R^5$)—($C_1$-$C_{12}$ alkyldiyl)-;

—C(=O)—(PEG)-SS—($C_1$-$C_{12}$ alkyldiyl)-OC(=O)—;

—C(=O)—(PEG)-SS—($C_1$-$C_{12}$ alkyldiyl)-C(=O)—;

—C(=O)—($C_1$-$C_{12}$ alkyldiyl)-C(=O)—(PEP)-;

—C(=O)—($C_1$-$C_{12}$ alkyldiyl)-C(=O)—(PEP)—N($R^5$)—($C_1$-$C_{12}$ alkyldiyl)-;

—C(=OHC$_1$-$C_{12}$ alkyldiyl)-C(=O)—(PEP)—N($R^5$)—($C_1$-$C_{12}$ alkyldiyl)-N($R^5$)—C(=O); —C(=O)—($C_1$-$C_{12}$ alkyldiyl)-C(=O)—(PEP)—N($R^5$)—($C_1$-$C_{12}$ alkyldiyl)-N($R^5$)C(=O)—($C_2$-$C_5$ monoheterocyclyldiyl)-;

—C(=O)—$CH_2CH_2OCH_2CH_2$—($C_1$-$C_{20}$ heteroaryldiyl)-$CH_2O$—(PEG)-C(=O)-(MCgluc)-;

—C(=O)—$CH_2CH_2OCH_2CH_2$—($C_1$-$C_{20}$ heteroaryldiyl)-$CH_2O$—(PEG)-C(=O)-(MCgluc)-N($R^5$)—($C_1$-$C_{12}$ alkyldiyl)-N($R^5$)C(=OHC$_2$-$C_5$ monoheterocyclyldiyl)-, and -(succinimidyl)-$(CH_2)_m$—C(=O)—(PEP)—N($R^5$)—($C_1$-$C_{12}$ alkyldiyl)-N($R^5$)C(=O)—($C_2$-$C_5$ monoheterocyclyldiyl)-;

PEG has the formula: —$(CH_2CH_2O)_m$—$(CH_2)_m$—; m is an integer from 1 to 5, and n is an integer from 2 to 50;

PEP has the formula:

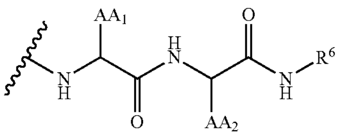

where $AA_1$ and $AA_2$ are independently selected from an amino acid side chain, or $AA_1$ or $AA_2$ and an adjacent nitrogen atom form a 5-membered ring proline amino acid, and the wavy line indicates a point of attachment;

$R^6$ is selected from the group consisting of $C_6$-$C_{20}$ aryldiyl and $C_1$-$C_{20}$ heteroaryldiyl, substituted with —$CH_2O$—C(=O)— and optionally with:

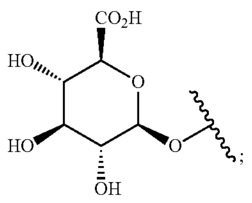 [SMILES: *O[C@@H]1O[C@H](C(=O)O)[C@@H](O)[C@H](O)[C@H]1O]

MCgluc is selected from the groups:

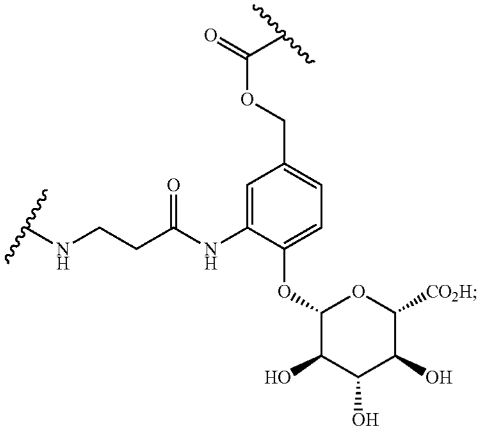

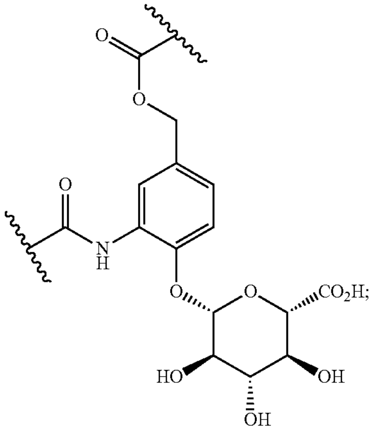

and

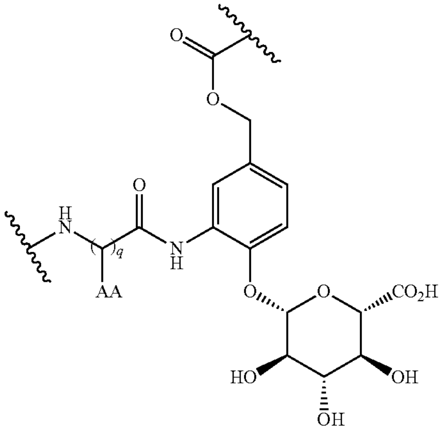

where q is 1 to 8, and AA is an amino acid side chain; and alkyl, alkyldiyl, alkenyl, alkenyldiyl, alknyl, alkynyldiyl, aryl, aryldiyl, carbocyclyl, carbocyclyldiyl, heterocyclyl, heterocyclyldiyl, heteroaryl, and heteroaryldiyl are independently and optionally substituted with one or more groups independently selected from F, Cl, Br, I, —CN, —$CH_3$, —$CH_2CH_3$, —CH=$CH_2$, —C≡CH, —C≡$CCH_3$, —$CH_2CH_2CH_3$, —$CH(CH_3)_2$, —$CH_2CH(CH_3)_2$, —$CH_2OH$, —$CH_2OCH_3$, —$CH_2CH_2OH$, —$C(CH_3)_2OH$, —CH(OH)$CH(CH_3)_2$, —$C(CH_3)_2CH_2OH$, —$CH_2CH_2SO_2CH_3$, —$CH_2OP(O)(OH)_2$, —$CH_2F$, —$CHF_2$, —$CF_3$, —$CH_2CF_3$, —$CH_2CHF_2$, —CH(CH)CN, —$C(CH_3)_2CN$, —$CH_2CN$, —$CH_2NH_2$, —$CH_2NHSO_2CH_2$, $—CH_2NHCH_3$, $—CH_2N(CH_3)_2$, $—CO_2H$, $—COCH_3$, $—CO_2CH_3$, $—CO_2C(CH_3)_3$, $—COCH(OH)CH_3$, $—CONH_2$, $—CONHCH_3$, $—CON(CH_3)_2$, $—C(CH_3)_2CONH_2$, $—NH_2$, $—NHCH_3$, $—N(CH_3)_2$, $—NHCOCH_3$, $—N(CH_3)COCH_3$, $—NHS(O)_2CH_3$, $—N(CH_3)C(CH_3)_2CONH_2$, $—N(CH_3)CH_2CH_2S(O)_2CH_3$, $—NHC(=NH)H$, $—NHC(=NH)CH_3$, $—NHC(=NH)NH_2$, $—NHC(=O)NH_2$, $—NO_2$, $=O$, $—OH$, $—OCH_3$, $—OCH_2CH_3$, $—OCH_2CH_2OCH_3$, $—OCH_2CH_2OH$, $—OCH_2CH_2N(CH_2)_2$, $—O(CH_2CH_2O)_n—(CH_2)_mCO_2H$, $—O(CH_2CH_2O)_nH$, $—OCH_2F$, $—OCHF_2$, $—OCF_3$, $—OP(O)(OH)_2$, $—S(O)_2N(CH_3)_2$, $—SCH_3$, $—S(O)_2CH_3$, and $—S(O)_3H$.

An exemplary embodiment of the immunoconjugate of Formula I includes wherein the antibody is an antibody construct that has an antigen binding domain that binds PD-L1.

An exemplary embodiment of the immunoconjugate of Formula I includes wherein the antibody is selected from the group consisting of atezolizumab, durvalumab, and avelumab, or a biosimilar or a biobetter thereof.

An exemplary embodiment of the immunoconjugate of Formula I includes wherein the antibody is an antibody construct that has an antigen binding domain that binds HER2.

An exemplary embodiment of the immunoconjugate of Formula I includes wherein the antibody is selected from the group consisting of trastuzumab and pertuzumab, or a biosimilar or a biobetter thereof.

An exemplary embodiment of the immunoconjugate of Formula I includes wherein the antibody is an antibody construct that has an antigen binding domain that binds CEA.

An exemplary embodiment of the immunoconjugate of Formula I includes wherein the antibody is labetuzumab, or a biosimilar or a biobetter thereof.

An exemplary embodiment of the immunoconjugate of Formula I includes wherein the antibody is an antibody construct that has an antigen binding domain that binds Caprin-1.

An exemplary embodiment of the immunoconjugate of Formula I includes wherein PEP has the formula:

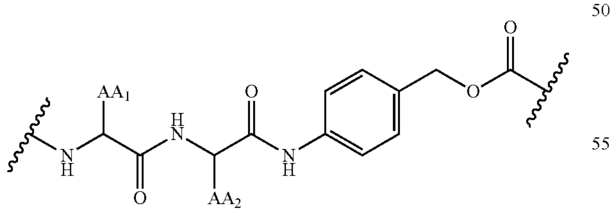

wherein $AA_1$ and $AA_2$ are independently selected from a side chain of a naturally-occurring amino acid.

An exemplary embodiment of the immunoconjugate of Formula I includes wherein $AA_1$ or $AA_2$ with an adjacent nitrogen atom form a 5-membered ring proline amino acid.

An exemplary embodiment of the immunoconjugate of Formula I includes wherein PEP has the formula:

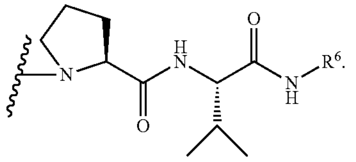

An exemplary embodiment of the immunoconjugate of Formula I includes wherein MCgluc has the formula:

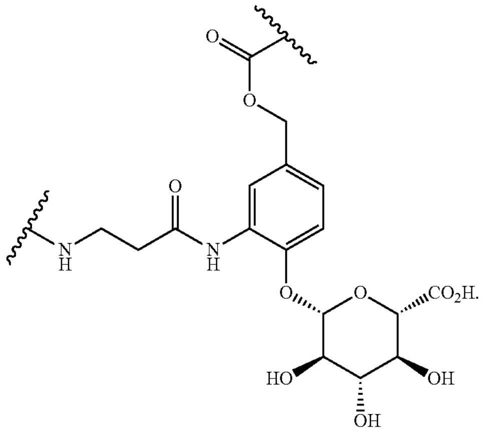 [SMILES: *NCCC(=O)Nc1cc(COC(*)=O)ccc1O[C@@H]1O[C@H](C(=O)O)[C@@H](O)[C@H](O)[C@H]1O]

An exemplary embodiment of the immunoconjugate of Formula I includes wherein $AA_1$ and $AA_2$ are independently selected from H, $—CH_3$, $—CH(CH_3)_2$, $—CH_2(C_6H_5)$, $—CH_2CH_2CH_2CH_2NH_2$, $—CH_2CH_2CH_2NHC(NH)NH_2$, $—CHCH(CH_3)CH_3$, $—CH_2SO_3H$, and $—CH_2CH_2CH_2NHC(O)NH_2$.

An exemplary embodiment of the immunoconjugate of Formula I includes wherein $AA_1$ is $—CH(CH_3)_2$, and $AA_2$ is $—CH_2CH_2CH_2NHC(O)NH_2$.

An exemplary embodiment of the immunoconjugate of Formula I includes wherein AA, and $AA_2$ are independently selected from GlcNAc aspartic acid, $—CH_2SO_3H$, and $—CH_2OPO_3H$.

An exemplary embodiment of the immunoconjugate of Formula I includes wherein one of $R^1$ and $R^4$ is selected from the formulas:

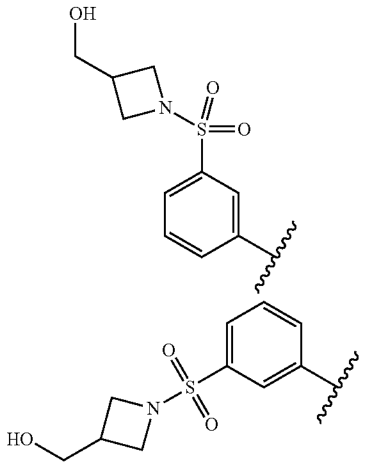

-continued

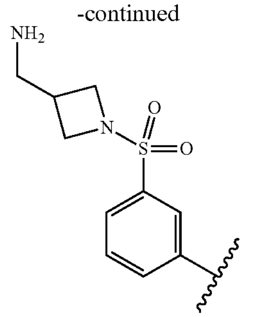

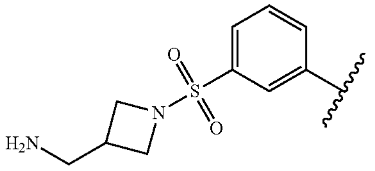

An exemplary embodiment of the immunoconjugate of Formula I includes wherein one of $R^1$ and $R^4$ is —C(=O)NR$^5$—($C_1$-$C_{20}$ heteroaryldiyl)-($C_2$-$C_{20}$ heterocyclyldiyl)-C(=O)NR$^5$—($C_1$-$C_{12}$ alkyldiyl)-NR$^L$.

An exemplary embodiment of the immunoconjugate of Formula I includes wherein $C_1$-$C_{20}$ heteroaryldiyl is pyridindiyl and $C_2$-$C_{20}$ heterocyclyldiyl is piperidyl.

An exemplary embodiment of the immunoconjugate of Formula I includes wherein one of $R^1$, $R^2$, $R^3$, and $R^4$ is —($C_1$-$C_8$ alkyldiyl)-NR$^5$($C_2$-$C_5$ heteroaryl);

An exemplary embodiment of the immunoconjugate of Formula I includes wherein NR$^5$($C_2$-$C_5$ heteroaryl) of $R^1$, $R^2$, $R^3$, and $R^4$ is selected from:

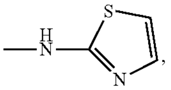

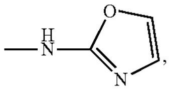

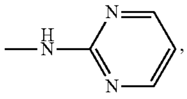

and

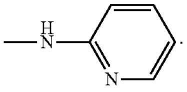

An exemplary embodiment of the immunoconjugate of Formula I includes wherein $X^1$ is a bond, and $R^1$ is H.

An exemplary embodiment of the immunoconjugate of Formula I includes wherein $X^2$ is a bond, and $R^2$ is $C_1$-$C_8$ alkyl.

An exemplary embodiment of the immunoconjugate of Formula I includes wherein $X^2$ and $X^3$ are each a bond, and $R^2$ and $R^3$ are independently selected from $C_1$-$C_8$ alkyl, —O—($C_1$-$C_{12}$ alkyl), —($C_1$-$C_{12}$ alkyldiyl)-OR$^5$, —($C_1$-$C_8$ alkyldiyl)-N(R$^5$)CO$_2$R$^5$, and —O—($C_1$-$C_{12}$ alkyl)-N(R$^5$)CO$_2$R$^5$.

An exemplary embodiment of the immunoconjugate of Formula I includes wherein $R^2$ and $R^1$ are each independently selected from —$CH_2CH_2CH_3$, —$OCH_2CH_3$, —$CH_2CH_2CF_3$, and —$CH_2CH_2CH_2OH$.

An exemplary embodiment of the immunoconjugate of Formula I includes wherein $R^2$ is $C_1$-$C_8$ alkyl and $R^3$ is —($C_1$-$C_8$ alkyldiyl)-N(R$^5$)CO$_2$R$^4$.

An exemplary embodiment of the immunoconjugate of Formula I includes wherein $R^2$ is —$CH_2CH_2CH_3$ and $R^1$ is —$CH_2CH_2CH_2NHCO_2$(t-Bu).

An exemplary embodiment of the immunoconjugate of Formula I includes wherein $R^2$ and $R^3$ are each —$CH_2CH_2CH_3$.

An exemplary embodiment of the immunoconjugate of Formula I includes wherein $X^3$—$R^3$ is selected from the group consisting of:

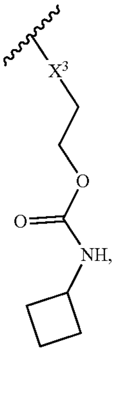

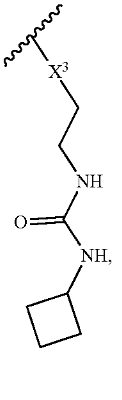

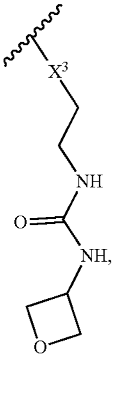

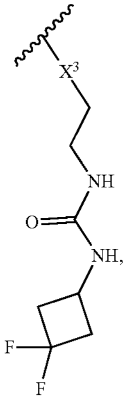

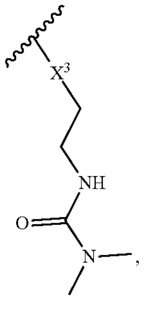

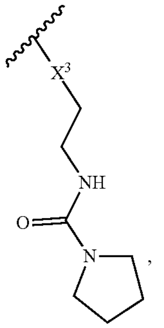

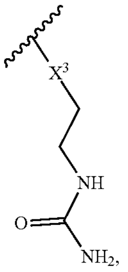

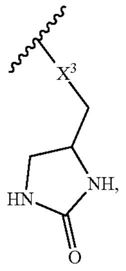

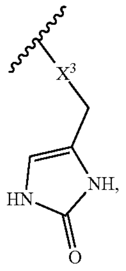

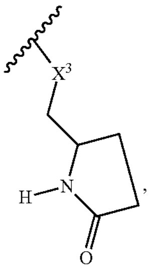

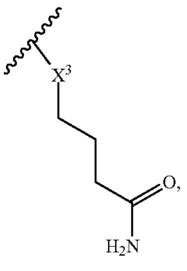

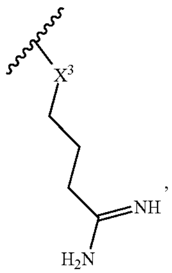

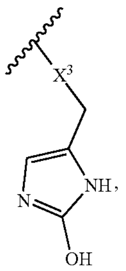

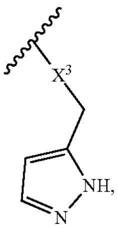

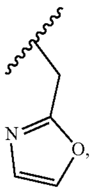

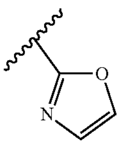

,

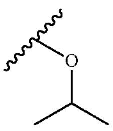

,

-continued

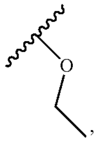

, and

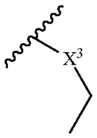

An exemplary embodiment of the immunoconjugate of Formula I includes wherein one of $R^2$ and $R^1$ is selected from;

($C_1$-$C_{12}$ alkyldiyl)-N($R^5$)—*;

($C_1$-$C_{12}$ alkyldiyl)-N($R^5$)C(=N$R^5$)—N($R^5$)—*;

($C_1$-$C_{12}$ alkyldiyl)-($C_6$-$C_{20}$ aryldiyl)-($C_1$-$C_{12}$ alkyldiyl)-N($R^5$)—*;

($C_1$-$C_{12}$ alkyldiyl)-($C_6$-$C_{20}$ aryldiyl)-($C_1$-$C_{12}$ alkyldiyl)-N($R^5$)—C(=N$R^5$)N($R^5$)—*;

($C_2$-$C_6$ alkynyldiyl)-N($R^5$)—*; and ($C_2$-$C_6$ alkynyldiyl)-N($R^5$)C(=N$R^5$)N($R^5$)—*;

$X^2$ and $X^3$ are a bond, and where the asterisk * indicates the attachment site of L.

An exemplary embodiment of the immunoconjugate of Formula I includes wherein L is selected from the group consisting of:

—C(=O)—(PEG)-;

—C(=O)—PEG)-C(=O)—;

—C(=O)—(PEG)-O—;

—C(=O)—(PEG)-N($R^5$)—; and

—C(=O)—(PEG)-N($R^5$)C(=O)—.

An exemplary embodiment of the immunoconjugate of Formula I is selected from Formulae Ia-Ic:

Ia

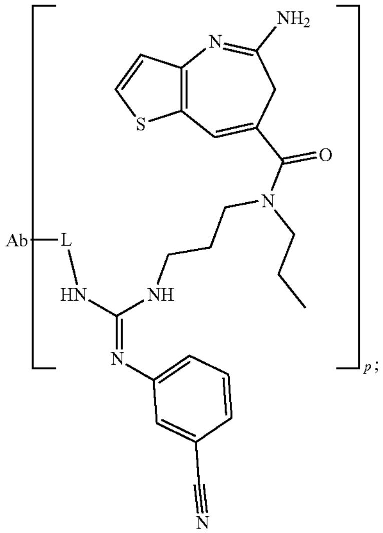

-continued

Ib

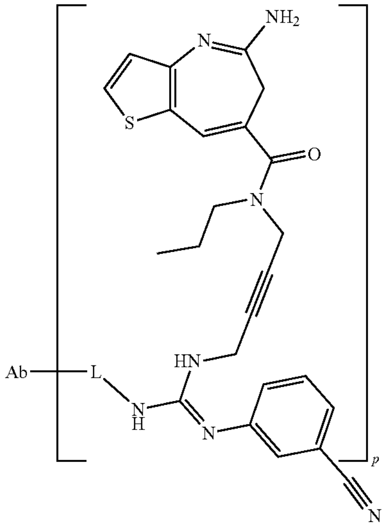

; and

Ic

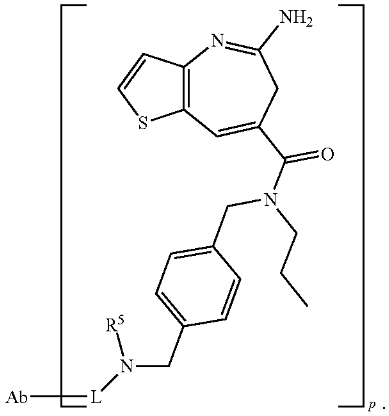

An exemplary embodiment of the immunoconjugate of Formula I is selected from Formulae Id-Ih:

Id

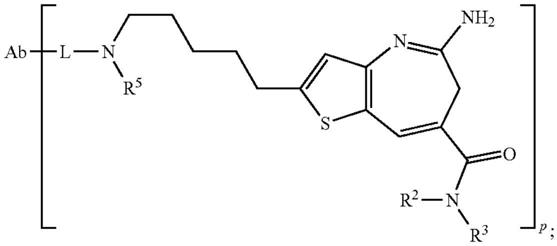

Ie

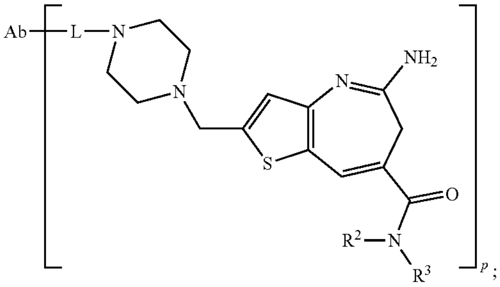

-continued

If

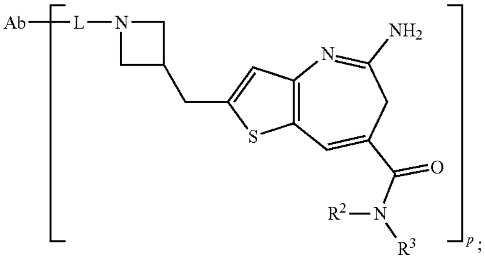

Ig

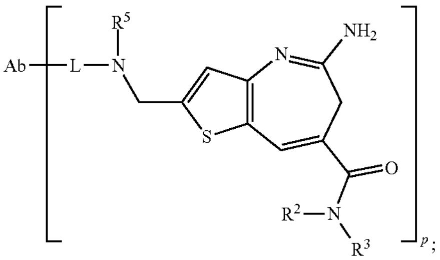

and

Ih

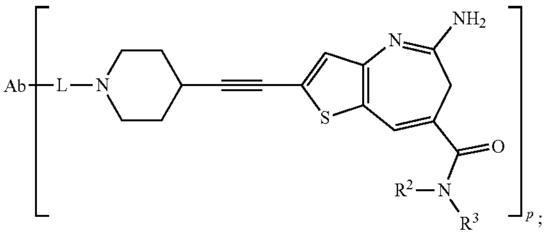

The invention includes all reasonable combinations, and permutations of the features, of the Formula I embodiments.

In certain embodiments, the immunoconjugate compounds of the invention include those with immunostimulatory activity. The antibody-drug conjugates of the invention selectively deliver an effective dose of a thienoazepine drug to tumor tissue, whereby greater selectivity (i.e., a lower efficacious dose) may be achieved while increasing the therapeutic index ("therapeutic window") relative to unconjugated thienoazepine.

Drug loading is represented by p, the number of TAZ moieties per antibody in an immunoconjugate of Formula I. Drug (TAZ) loading may range from 1 to about 8 drug moieties (D) per antibody. Immunoconjugates of Formula I include mixtures or collections of antibodies conjugated with a range of drug moieties, from 1 to about 8. In some embodiments, the number of drug moieties that can be conjugated to an antibody is limited by the number of reactive or available amino acid side chain residues such as lysine and cysteine. In some embodiments, free cysteine residues are introduced into the antibody amino acid sequence by the methods described herein. In such aspects, p may be 1, 2, 3, 4, 5, 6, 7, or 8, and ranges thereof, such as from 1 to 8 or from 2 to 5. In any such aspect, p and n are equal (i.e., p=n=1, 2, 3, 4, 5, 6, 7, or 8, or some range there between). Exemplary immunoconjugates of Formula I include, but are not limited to, antibodies that have 1, 2, 3, or 4 engineered cysteine amino acids (Lyon, R. et al. (2012) *Methods in Enzym.* 502:123-138). In some embodiments, one or more free cysteine residues are already present in an antibody forming intrachain disulfide bonds, without the use of engineering, in which case the existing free cysteine residues may be used to conjugate the antibody to a drug. In some embodiments, an antibody is exposed to reducing conditions prior to conjugation of the antibody in order to generate one or more free cysteine residues.

For some immunoconjugates, p may be limited by the number of attachment sites on the antibody. For example, where the attachment is a cysteine thiol, as in certain exemplary embodiments described herein, an antibody may have only one or a limited number of cysteine thiol groups, or may have only one or a limited number of sufficiently reactive thiol groups, to which the drug may be attached. In other embodiments, one or more lysine amino groups in the antibody may be available and reactive for conjugation with an TAZ-linker compound of Formula II. In certain embodiments, higher drug loading, e.g. p>5, may cause aggregation, insolubility, toxicity, or loss of cellular permeability, of certain antibody-drug conjugates. In certain embodiments, the average drug loading for an immunoconjugate ranges from 1 to about 8; from about 2 to about 6; or from about 3 to about 5. In certain embodiments, an antibody is subjected to denaturing conditions to reveal reactive nucleophilic groups such as lysine or cysteine.

The loading (drug/antibody ratio) of an immunoconjugate may be controlled in different ways, and for example, by: (i) limiting the molar excess of the TAZ-linker intermediate compound relative to antibody. (ii) limiting the conjugation reaction time or temperature, and (iii) partial or limiting reductive denaturing conditions for optimized antibody reactivity.

It is to be understood that where more than one nucleophilic group of the antibody reacts with a drug, then the resulting product is a mixture of immunoconjugate compounds with a distribution of one or more drug moieties attached to an antibody. The average number of drugs per antibody may be calculated from the mixture by a dual ELISA antibody assay, which is specific for antibody and specific for the drug. Individual immunoconjugate molecules may be identified in the mixture by mass spectroscopy and separated by HPLC, e.g. hydrophobic interaction chromatography (see, e.g., McDonagh et al. (2006) *Prot. Engr. Design & Selection* 19(7):299-307; Hamblett et al. (2004) *Clin. Cancer Res.* 10:7063-7070; Hamblett, K. J., et al. "Effect of drug loading on the pharmacology, pharmacokinetics, and toxicity of an anti-CD30 antibody-drug conjugate." Abstract No. 624, American Association for Cancer Research, 2004 Annual Meeting. Mar. 27-31, 2004, Proceedings of the AACR, Volume 45, March 2004; Alley. S. C., et al. "Controlling the location of drug attachment in antibody-drug conjugates, Abstract No. 627, American Association for Cancer Research 2e4 Annual Meeting, Mar. 27-31, 2004, Proceedings of the AACR. Volume 45, March 2004). In certain embodiments, a homogeneous immunoconjugate with a single loading value may be isolated from the conjugation mixture by electrophoresis or chromatography.

An exemplary embodiment of the immunoconjugate of Formula I is selected from the Tables 3a-c Immunoconjugates. Assessment of Immunoconjugate Activity In Vitro was conducted according to the methods of Example 203.

TABLE 3a

Immunoconjugates (IC)

| Immunoconjugate No. | TAZ-linker Table 2a/b | Ab Antigen | DAR | Myeloid TNFα Secretion EC50 [nM] |
|---|---|---|---|---|
| IC-1 | TAZ-L-1 | trastuzumab HER2 | 2.24 | >1000 |

TABLE 3a-continued

| Immunoconjugates (IC) | | | | |
|---|---|---|---|---|
| Immunoconjugate No. | TAZ-linker Table 2a/b | Ab Antigen | DAR | Myeloid TNFα Secretion EC50 [nM] |
| IC-2 | TAZ-L-3 | trastuzumab HER2 | 2.40<br>4.10 | 365<br>78 |
| IC~3 | TAZ-L-4 | trastuzumab HER2 | 2.57 | 612 |

TABLE 3b

| Immunoconjugates (IC) | | | | |
|---|---|---|---|---|
| Immunoconjugate No. | TAZ-linker Table 2a/b | Ab Antigen | DAR | Myeloid TNFα Secretion EC50 [nM] |
| IC-4 | TAZ-L-3 | avelumab PD-L1 | 2.46 | 58 |
| IC-5 | TAZ-L-4 | avelumab PD-L1 | 2.32 | >1000 |
| IC-6 | TAZ-L-5 | trastuzumab HER2 | 2.58 | Not Available |
| IC-7 | TAZ-L-6 | trastuzumab HER2 | 2.56 | Not Available |
| IC-8 | TAZ-L-3 | PDL1.24-GIf PD-L1 | 2.25 | Not Available |
| IC-9 | TAZ-L-3 | PDL1.85-Glf PD-L1 | 2.2 | Not Available |
| IC-10 | TAZ-L-7 | trastuzumab HER2 | 2.82 | 115 |
| IC-11 | TAZ-L-8 | trastuzumab HER2 | 2.54 | 455 |
| IC-12 | TAZ-L-3 | CEA.5-GlfhL2 CEACAM5 | 2.80 | Not Available |
| IC-13 | TAZ-L-9 | trastuzumab HER2 | 2.77 | >1000 |
| IC-14 | TAZ-L-10 | trastuzumab HER2 | 2.69 | 15 |
| IC-15 | TAZ-L-11 | trastuzumab HER2 | 2.74 | >1000 |
| IC-16 | TAZ-L-12 | trastuzumab HER2 | 2.79 | >1000 |
| IC-17 | TAZ-L-13 | trastuzumab HER2 | 2.52 | 23 |
| IC-18 | TAZ-L-15 | trastuzumab HER2 | 2.44 | >1000 |
| IC-19 | TAZ-L-14 | trastuzumab HER2 | 2.6 | >1000 |
| IC-20 | TAZ-L-19 | trastuzumab HER2 | 3.03 | >1000 |
| IC-21 | TAZ-L-16 | trastuzumab HER2 | 2.63 | 435 |
| IC-22 | TAZ-L-17 | trastuzumab HER2 | 2.72 | >1000 |
| IC-23 | TAZ-L-20 | trastuzumab HER2 | 2.67 | 504 |
| IC-24 | TAZ-L-25 | trastuzumab HER2 | 2.55 | 113 |
| IC-25 | TAZ-L-18 | trastuzumab HER2 | 2.52 | >1000 |
| IC-26 | TAZ-L-22 | trastuzumab HER2 | 2.47 | 469 |
| IC-27 | TAZ-L-23 | trastuzumab HER2 | 2.99 | >1000 |
| IC-28 | TAZ-L-30 | trastuzumab HER2 | 2.47 | 468 |
| IC-29 | TAZ-L-31 | trastuzumab HER2 | 1.94 | 907 |
| IC-30 | TAZ-L-32 | trastuzumab HER2 | 2.59 | 134 |

TABLE 3b-continued

| Immunoconjugates (IC) | | | | |
|---|---|---|---|---|
| Immunoconjugate No. | TAZ-linker Table 2a/b | Ab Antigen | DAR | Myeloid TNFα Secretion EC50 [nM] |
| IC-31 | TAZ-L-34 | trastuzumab HER2 | 3.13 | 388 |
| IC-32 | TAZ-L-28 | trastuzumab HER2 | 2.66 | Not available |

TABLE 3c

| Immunoconjugates (IC) | | | |
|---|---|---|---|
| Immunoconjugate No. | TAZ-L Table 2c | Ab Antigen | DAR |
| IC-33 | TAZ-L-32 | rituximab CD20 | 2.28 |
| IC-34 | TAZ-L-29 | trastuzumab HER2 | 2.77 |
| IC-35 | TAZ-L-35 | trastuzumab HER2 | 2.56 |
| IC-36 | TAZ-L-27 | trastuzumab HER2 | 2.50 |
| IC-37 | TAZ-L-37 | trastuzumab HER2 | 2.55 |
| IC-38 | TAZ-L-32 | Tras-G1f-N297A | 3.06 |
| IC-39 | TAZ-L-32 | CEA.9-G1fhL2 | 2.40 |
| IC-40 | TAZ-L-34 | CEA.9-G1fhL2 | 2.52 |
| IC-41 | TAZ-L-38 | trastuzumab HER2 | 2.14 |
| IC-42 | TAZ-L-39 | trastuzumab HER2 | 2.18 |
| IC-43 | TAZ-L-43 | trastuzumab HER2 | 2.28 |
| IC-44 | TAZ-L-49 | trastuzumab HER2 | 2.68 |
| IC-45 | TAZ-L-40 | trastuzumab HER2 | 2.25 |
| IC-46 | TAZ-L-47 | trastuzumab HER2 | 2.37 |
| IC-47 | TAZ-L-48 | trastuzumab HER2 | 2.15 |
| IC-48 | TAZ-L-52 | trastuzumab HER2 | 2.38 |
| IC-49 | TAZ-L-32 | PDL1.24-G1f | 2.73 |
| IC-50 | TAZ-L-42 | trastuzumab HER2 | 2.00 |
| IC-51 | TAZ-L-45 | trastuzumab HER2 | 2.17 |
| IC-52 | TAZ-L-46 | trastuzumab HER2 | 2.53 |
| IC-53 | TAZ-L-41 | trastuzumab HER2 | 2.14 |
| IC-54 | TAZ-L-44 | trastuzumab HER2 | 2.04 |
| IC-55 | TAZ-L-50 | trastuzumab HER2 | 2.10 |
| IC-56 | TAZ-L-51 | trastuzumab HER2 | 2.35 |
| IC-57 | TAZ-L-53 | trastuzumab HER2 | 2.14 |
| IC-58 | TAZ-L-56 | trastuzumab HER2 | 2.55 |
| IC-59 | TAZ-L-59 | trastuzumab HER2 | 2.39 |
| IC-60 | TAZ-L-58 | trastuzumab HER2 | 2.74 |
| IC-61 | TAZ-L-62 | trastuzumab HER2 | 2.55 |
| IC-62 | TAZ-L-63 | trastuzumab HER2 | 2.72 |

TABLE 3c-continued

| Immunoconjugates (IC) | | | |
|---|---|---|---|
| Immunoconjugate No. | TAZ-L Table 2c | Ab Antigen | DAR |
| IC-63 | TAZ-L-64 | trastuzumab HER2 | 2.5" |
| IC-64 | TAZ-L-60 | trastuzumab HER2 | 2.66 |
| IC-65 | TAZ-L-61 | trastuzumab HER2 | 2.64 |
| IC-66 | TAZ-L-74 | trastuzumab HER2 | 2.08 |
| IC-67 | TAZ-L-75 | trastuzumab HER2 | 2.03 |
| IC-68 | TAZ-L-32 | CEA.5-G1f-G236AhL2 | 2.38 |
| IC-69 | TAZ-L-59 | CEA.9-G1fhL2 | 2.71 |
| IC-70 | TAZ-L-70 | trastuzumab HER2 | 2.67 |
| IC-71 | TAZ-L-71 | trastuzumab HER2 | 3.12 |
| IC-72 | TAZ-L-76 | trastuzumab HER2 | 1.94 |
| IC-73 | TAZ-L-77 | trastuzumab HER2 | 2.35 |
| IC-74 | TAZ-L-53 | CEA.9-G1fhL2 | 2.48 |
| IC-75 | TAZ-L-78 | trastuzumab HER2 | 2.65 |
| IC-76 | TAZ-L-79 | trastuzumab HER2 | 2.91 |
| IC-77 | TAZ-L-32 | PDL1.85-G1f | 2.9 |
| IC-78 | TAZ-L-72 | trastuzumab HER2 | 2.50 |
| IC-79 | TAZ-L-73 | trastuzumab HER2 | 2.64 |
| IC-80 | TAZ-L-80 | trastuzumab HER2 | 2.17 |
| IC-81 | TAZ-L-81 | trastuzumab HER2 | 2.49 |
| IC-82 | TAZ-L-53 | PDL1.85-G1f | 2.54 |
| IC-83 | TAZ-L-67 | trastuzumab HER2 | 2.03 |
| IC-84 | TAZ-L-68 | trastuzumab HER2 | 2.33 |
| IC-85 | TAZ-L-82 | trastuzumab HER2 | 2.97 |
| IC-86 | TAZ-L-83 | trastuzumab HER2 | 1.98 |
| IC-87 | TAZ-L-84 | trastuzumab HER2 | 2.27 |
| IC-88 | TAZ-L-148 | trastuzumab HER2 | 2.12 |
| IC-89 | TAZ-L-57 | trastuzumab HER2 | 1.93 |
| IC-90 | TAZ-L-85 | trastuzumab HER2 | 2.49 |
| IC-91 | TAZ-L-86 | trastuzumab HER2 | 2.55 |
| IC-92 | TAZ-L-87 | trastuzumab HER2 | 2.53 |
| IC-93 | TAZ-L-88 | trastuzumab HER2 | 1.71 |
| IC-94 | TAZ-L-149 | trastuzumab HER2 | 2.8 |
| IC-95 | TAZ-L-150 | trastuzumab HER2 | 2.5 |
| IC-96 | TAZ-L-53 | PDL1.24-Glf | 2.54 |
| IC-97 | TAZ-L-92 | trastuzumab HER2 | 2.72 |
| IC-98 | TAZ-L-93 | trastuzumab HER2 | 2.50 |
| IC-99 | TAZ-L-94 | trastuzumab HER2 | 2.79 |
| IC-100 | TAZ-L-95 | trastuzumab HER2 | 2.56 |
| IC-101 | TAZ-L-32 | mPD-L1 | 2.21 |
| IC-102 | TAZ-L-53 | mPD-L1 | 2.28 |
| IC-103 | TAZ-L-32 | rat IgG2b isotype control | 2.53 |

TABLE 3c-continued

| Immunoconjugates (IC) | | | |
|---|---|---|---|
| Immunoconjugate No. | TAZ-L Table 2c | Ab Antigen | DAR |
| IC-104 | TAZ-L-53 | rat IgG2b isotype control | 2.54 |
| IC-105 | TAZ-L-91 | trastuzumab HER2 | 2.3 |
| IC-106 | TAZ-L-90 | trastuzumab HER2 | 2.6 |
| IC-107 | TAZ-L-89 | trastuzumab HER2 | 2.8 |
| IC-108 | TAZ-L-69 | trastuzumab HER2 | 3.1 |
| IC-109 | TAZ-L-98 | trastuzumab HER2 | 2.58 |
| IC-110 | TAZ-L-101 | trastuzumab HER2 | 1.95 |
| IC-111 | TAZ-L-102 | trastuzumab HER2 | 2.28 |
| IC-112 | TAZ-L-105 | trastuzumab HER2 | 2.33 |
| IC-113 | TAZ-L-97 | trastuzumab HER2 | 2.48 |
| IC-114 | TAZ-L-103 | trastuzumab HER2 | 2.41 |
| IC-115 | TAZ-L-104 | trastuzumab HER2 | 2.97 |
| IC-116 | TAZ-L-32 | rituximab CD20 | |
| IC-117 | TAZ-L-53 | rituximab CD20 | 2.5 |
| IC-118 | TAZ-L-113 | trastuzumab HER2 | 2.3 |
| IC-119 | TAZ-L-114 | trastuzumab HER2 | 2.4 |
| IC-120 | TAZ-L-109 | trastuzumab HER2 | 2.4 |
| IC-121 | TAZ-L-115 | trastuzumab HER2 | 2.62 |
| IC-122 | TAZ-L-117 | trastuzumab HER2 | 2.76 |
| IC-123 | TAZ-L-118 | trastuzumab HER2 | 3.05 |
| IC-124 | TAZ-L-119 | trastuzumab HER2 | 2.86 |
| IC-125 | TAZ-L-110 | trastuzumab HER2 | 2.2 |
| IC-126 | TAZ-L-116 | trastuzumab HER2 | 2.0 |
| IC-127 | TAZ-L-123 | trastuzumab HER2 | 2.4 |
| IC-128 | TAZ-L-120 | trastuzumab HER2 | 3.25 |
| IC-129 | TAZ-L-127 | trastuzumab HER2 | 2.32 |
| IC-130 | TAZ-L-128 | trastuzumab HER2 | 2.56 |
| IC-131 | TAZ-L-131 | trastuzumab HER2 | 2.61 |
| IC-132 | TAZ-L-1347 | trastuzumab HER2 | 3.1 |
| IC-133 | TAZ-L-98 | rituximab CD20 | 2.32 |
| IC-134 | TAZ-L-98 | CEA.9-G1ML2 | 2.46 |
| IC-135 | TAZ-L-124 | trastuzumab HER2 | 2.3 |
| IC-136 | TAZ-L-125 | trastuzumab HER2 | 2.6 |
| IC-137 | TAZ-L-130 | trastuzumab HER2 | 2.4 |
| IC-138 | TAZ-L-88 | trastuzumab HER2 | 1.9 |
| IC-139 | TAZ-L-132 | trastuzumab HER2 | 3.1 |

TABLE 3c-continued

| Immunoconjugates (IC) | | | |
|---|---|---|---|
| Immunoconjugate No. | TAZ-L Table 2c | Ab Antigen | DAR |
| IC-140 | TAZ-L-128 | CEA.9-G1fhL2 | 2.61 |
| IC-141 | TAZ-L-128 | rituximab CD20 | 2.08 |
| IC-142 | TAZ-L-128 | Tras-G1f-N297a | 2.13 |
| IC-143 | TAZ-L-134 | trastuzumab HER2 | 2.2 |
| IC-144 | TAZ-L-135 | trastuzumab HER2 | 2.2 |
| IC-145 | TAZ-L-136 | trastuzumab HER2 | 2.5 |
| IC-146 | TAZ-L-139 | trastuzumab HER2 | 2.32 |
| IC-147 | TAZ-L-142 | trastuzumab HER2 | 2.33 |
| IC-148 | TAZ-L-129 | trastuzumab HER2 | 1.9 |
| IC-149 | TAZ-L-141 | trastuzumab HER2 | 2.8 |
| IC-150 | TAZ-L-144 | trastuzumab HER2 | 2.66 |
| IC-151 | TAZ-L-145 | trastuzumab HER2 | 2.55 |
| IC-152 | TAZ-L-144 | rituximab CD20 | 2.59 |
| IC-153 | TAZ-L-145 | rituximab CD20 | 2.46 |
| IC-154 | TAZ-L-144 | CEA.9-G1ML2 | 2.55 |
| IC-155 | TAZ-L-145 | CEA.9-GlfhL2 | 2.49 |
| IC-156 | TAZ-L-147 | trastuzumab HER2 | 2.06 |
| IC-157 | TAZ-L-146 | trastuzumab HER2 | 2.44 |

Compositions of Immunoconjugates

The invention provides a composition, e.g., a pharmaceutically or pharmacologically acceptable composition or formulation, comprising a plurality of immunoconjugates as described herein and optionally a carrier therefor, e.g., a pharmaceutically or pharmacologically acceptable carrier. The immunoconjugates can be the same or different in the composition, i.e., the composition can comprise immunoconjugates that have the same number of adjuvants linked to the same positions on the antibody construct and/or immunoconjugates that have the same number of TAZ adjuvants linked to different positions on the antibody construct, that have different numbers of adjuvants linked to the same positions on the antibody construct, or that have different numbers of adjuvants linked to different positions on the antibody construct.

In an exemplary embodiment, a composition comprising the immunoconjugate compounds comprises a mixture of the immunoconjugate compounds, wherein the average drug (TAZ) loading per antibody in the mixture of immunoconjugate compounds is about 2 to about 5.

A composition of immunoconjugates of the invention can have an average adjuvant to antibody construct ratio (DAR) of about 0.4 to about 10. A skilled artisan will recognize that the number of thienoazepine adjuvants conjugated to the antibody construct may vary from immunoconjugate to immunoconjugate in a composition comprising multiple immunoconjugates of the invention and thus the adjuvant to antibody construct (e.g., antibody) ratio can be measured as an average which may be referred to as the drug to antibody ratio (DAR). The adjuvant to antibody construct (e.g., antibody) ratio can be assessed by any suitable means, many of which are known in the art.

The average number of adjuvant moieties per antibody (DAR) in preparations of immunoconjugates from conjugation reactions may be characterized by conventional means such as mass spectrometry, ELISA assay, and HPLC. The quantitative distribution of immunoconjugates in a composition in terms of p may also be determined. In some instances, separation, purification, and characterization of homogeneous immunoconjugates where p is a certain value from immunoconjugates with other drug loadings may be achieved by means such as reverse phase HPLC or electrophoresis.

In some embodiments, the composition further comprises one or more pharmaceutically or pharmacologically acceptable excipients. For example, the immunoconjugates of the invention can be formulated for parenteral administration, such as IV administration or administration into a body cavity or lumen of an organ. Alternatively, the immunoconjugates can be injected intra-tumorally. Compositions for injection will commonly comprise a solution of the immunoconjugate dissolved in a pharmaceutically acceptable carrier. Among the acceptable vehicles and solvents that can be employed are water and an isotonic solution of one or more salts such as sodium chloride, e.g., Ringer's solution. In addition, sterile fixed oils can conventionally be employed as a solvent or suspending medium. For this purpose, any bland fixed oil can be employed, including synthetic mono-glycerides or diglycerides. In addition, fatty acids such as oleic acid can likewise be used in the preparation of injectables. These compositions desirably are sterile and generally free of undesirable matter. These compositions can be sterilized by conventional, well known sterilization techniques. The compositions can contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like.

The composition can contain any suitable concentration of the immunoconjugate. The concentration of the immunoconjugate in the composition can vary widely, and will be selected primarily based on fluid volumes, viscosities, body weight, and the like, in accordance with the particular mode of administration selected and the patient's needs. In certain embodiments, the concentration of an immunoconjugate in a solution formulation for injection will range from about 0.1% (w/w) to about 10% (w/w).

Method of Treating Cancer with Immunoconjugates

The invention provides a method for treating cancer. The method includes administering a therapeutically effective amount of an immunoconjugate as described herein (e.g., as a composition as described herein) to a subject in need thereof, e.g., a subject that has cancer and is in need of treatment for the cancer. The method includes administering a therapeutically effective amount of an immunoconjugate (IC) selected from Tables 3a and 3b.

It is contemplated that the immunoconjugate of the present invention may be used to treat various hyperproliferative diseases or disorders, e.g. characterized by the overexpression of a tumor antigen. Exemplary hyperproliferative disorders include benign or malignant solid tumors and hematological disorders such as leukemia and lymphoid malignancies.

In another aspect, an immunoconjugate for use as a medicament is provided. In certain embodiments, the invention provides an immunoconjugate for use in a method of treating an individual comprising administering to the individual an effective amount of the immunoconjugate. In one such embodiment, the method further comprises administering to the individual an effective amount of at least one additional therapeutic agent, e.g., as described herein.

In a further aspect, the invention provides for the use of an immunoconjugate in the manufacture or preparation of a medicament. In one embodiment, the medicament is for treatment of cancer, the method comprising administering to an individual having cancer an effective amount of the medicament. In one such embodiment, the method further comprises administering to the individual an effective amount of at least one additional therapeutic agent, e.g., as described herein.

Carcinomas are malignancies that originate in the epithelial tissues. Epithelial cells cover the external surface of the body, line the internal cavities, and form the lining of glandular tissues. Examples of carcinomas include, but are not limited to, adenocarcinoma (cancer that begins in glandular (secretory) cells such as cancers of the breast, pancreas, lung, prostate, stomach, gastroesophageal junction, and colon) adrenocortical carcinoma; hepatocellular carcinoma; renal cell carcinoma; ovarian carcinoma: carcinoma in situ; ductal carcinoma; carcinoma of the breast: basal cell carcinoma: squamous cell carcinoma; transitional cell carcinoma: colon carcinoma; nasopharyngeal carcinoma; multilocular cystic renal cell carcinoma: oat cell carcinoma; large cell lung carcinoma: small cell lung carcinoma; non-small cell lung carcinoma; and the like. Carcinomas may be found in prostrate, pancreas, colon, brain (usually as secondary metastases), lung, breast, and skin. In some embodiments, methods for treating non-small cell lung carcinoma include administering an immunoconjugate containing an antibody construct that is capable of binding PD-L1 (e.g., atezolizumab, durvalumab, avelumab, biosimilars thereof, or biobetters thereof). In some embodiments, methods for treating breast cancer include administering an immunoconjugate containing an antibody construct that is capable of binding PD-L1 (e.g., atezolizumab, durvalumab, avelumab, biosimilars thereof, or biobetters thereof). In some embodiments, methods for treating triple-negative breast cancer include administering an immunoconjugate containing an antibody construct that is capable of binding PD-L1 (e.g., atezolizumab, durvalumab, avelumab, biosimilars thereof, or biobetters thereof).

Soft tissue tumors are a highly diverse group of rare tumors that are derived from connective tissue. Examples of soft tissue tumors include, but are not limited to, alveolar soft part sarcoma; angiomatoid fibrous histiocytoma; chondromyoxid fibroma; skeletal chondrosarcoma; extraskeletal myxoid chondrosarcoma: clear cell sarcoma; desmoplastic small round-cell tumor; dermatofibrosarcoma protuberans: endometrial stromal tumor: Ewing's sarcoma; fibromatosis (Desmoid); fibrosarcoma, infantile; gastrointestinal stromal tumor: bone giant cell tumor; tenosynovial giant cell tumor: inflammatory myofibroblastic tumor; uterine leiomyoma; leiomyosarcoma; lipoblastoma: typical lipoma spindle cell or pleomorphic lipoma; atypical lipoma: chondroid lipoma; well-differentiated liposarcoma; myxoid/round cell liposarcoma; pleomorphic liposarcoma; myxoid malignant fibrous histiocytoma; high-grade malignant fibrous histiocytoma: myxofibrosarcoma; malignant peripheral nerve sheath tumor; mesothelioma: neuroblastoma; osteochondroma; osteosarcoma; primitive neuroectodermal tumor: alveolar rhabdomyosarcoma; embryonal rhabdomyosarcoma: benign or malignant schwannoma; synovial sarcoma: Evan's tumor; nodular fasciitis; desmoid-type fibromatosis; solitary fibrous tumor; dermatofibrosarcoma protuberans (DFSP); angiosarcoma; epithelioid hemangioendothelioma; tenosynovial giant cell tumor (TGCT); pigmented villonodular svnovitis (PVNS); fibrous dysplasia; myxofibrosarcoma; fibrosarcoma: synovial sarcoma; malignant peripheral nerve sheath tumor; neurofibroma: pleomorphic adenoma of soft tissue; and neoplasias derived from fibroblasts, myofibroblasts, histiocytes, vascular cells/endothelial cells, and nerve sheath cells.

A sarcoma is a rare type of cancer that arises in cells of mesenchymal origin, e.g., in bone or in the soft tissues of the body, including cartilage, fat, muscle, blood vessels, fibrous tissue, or other connective or supportive tissue. Different types of sarcoma are based on where the cancer forms. For example, osteosarcoma forms in bone, liposarcoma forms in fat, and rhabdomyosarcoma forms in muscle. Examples of sarcomas include, but are not limited to, askin's tumor; sarcoma botryoides; chondrosarcoma; ewing's sarcoma; malignant hemangioendothelioma; malignant schwannoma; osteosarcoma; and soft tissue sarcomas (e.g., alveolar soft part sarcoma; angiosarcoma; cystosarcoma phyllodesdermatofibrosarcoma protuberans (DFSP); desmoid tumor; desmoplastic small round cell tumor; epithelioid sarcoma; extraskeletal chondrosarcoma; extraskeletal osteosarcoma; fibrosarcoma; gastrointestinal stromal tumor (GIST); hemangiopericytoma; hemangiosarcoma (more commonly referred to as "angiosarcoma"); kaposi's sarcoma; leiomyosarcoma; liposarcoma; lymphangiosarcoma; malignant peripheral nerve sheath tumor (MPNST); neurofibrosarcoma; synovial sarcoma; and undifferentiated pleomorphic sarcoma).

A teratoma is a type of germ cell tumor that may contain several different types of tissue (e.g., can include tissues derived from any and/or all of the three germ layers: endoderm, mesoderm, and ectoderm), including, for example, hair, muscle, and bone. Teratomas occur most often in the ovaries in women, the testicles in men, and the tailbone in children.

Melanoma is a form of cancer that begins in melanocytes (cells that make the pigment melanin). Melanoma may begin in a mole (skin melanoma), but can also begin in other pigmented tissues, such as in the eye or in the intestines.

Merkel cell carcinoma is a rare type of skin cancer that usually appears as a flesh-colored or bluish-red nodule on the face, head or neck Merkel cell carcinoma is also called neuroendocrine carcinoma of the skin. In some embodiments, methods for treating Merkel cell carcinoma include administering an immunoconjugate containing an antibody construct that is capable of binding PD-L1 (e.g., atezolizumab, durvalumab, avelumab, biosimilars thereof, or biobetters thereof). In some embodiments, the Merkel cell carcinoma has metastasized when administration occurs.

Leukemias are cancers that start in blood-forming tissue, such as the bone marrow, and cause large numbers of abnormal blood cells to be produced and enter the bloodstream. For example, leukemias can originate in bone marrow-derived cells that normally mature in the bloodstream. Leukemias are named for how quickly the disease develops and progresses (e.g., acute versus chronic) and for the type of white blood cell that is affected (e.g., myeloid versus lymphoid). Myeloid leukemias are also called myelogenous or myeloblastic leukemias. Lymphoid leukemias are also called lymphoblastic or lymphocytic leukemia. Lymphoid leukemia cells may collect in the lymph nodes, which can become swollen. Examples of leukemias include, but are not limited to, Acute myeloid leukemia (AML), Acute lymphoblastic leukemia (ALL), Chronic myeloid leukemia (CML), and Chronic lymphocytic leukemia (CLL).

Lymphomas are cancers that begin in cells of the immune system. For example, lymphomas can originate in bone marrow-derived cells that normally mature in the lymphatic system. There are two basic categories of lymphomas. One category of lymphoma is Hodgkin lymphoma (HL), which is marked by the presence of a type of cell called the Reed-Sternberg cell. There are currently 6 recognized types of HL. Examples of Hodgkin lymphomas include nodular sclerosis classical Hodgkin lymphoma (CHL), mixed cellularity CHL, lymphocyte-depletion CHL, lymphocyte-rich CHL, and nodular lymphocyte predominant HL.

The other category of lymphoma is non-Hodgkin lymphomas (NHL), which includes a large, diverse group of cancers of immune system cells. Non-Hodgkin lymphomas can be further divided into cancers that have an indolent (slow-growing) course and those that have an aggressive (fast-growing) course. There are currently 61 recognized types of NHL. Examples of non-Hodgkin lymphomas include, but are not limited to, AIDS-related Lymphomas, anaplastic large-cell lymphoma, angioimmunoblastic lymphoma, blastic NK-cell lymphoma. Burkitt's lymphoma, Burkitt-like lymphoma (small non-cleaved cell lymphoma), chronic lymphocytic leukemia/small lymphocytic lymphoma, cutaneous T-Cell lymphoma, diffuse large B-Cell lymphoma, enteropathy-type T-Cell lymphoma, follicular lymphoma, hepatosplenic gamma-delta T-Cell lymphomas. T-Cell leukemias, lymphoblastic lymphoma, mantle cell lymphoma, marginal zone lymphoma, nasal T-Cell lymphoma, pediatric lymphoma, peripheral T-Cell lymphomas, primary central nervous system lymphoma, transformed lymphomas, treatment-related T-Cell lymphomas, and Waldenstrom's macroglobulinemia.

Brain cancers include any cancer of the brain tissues. Examples of brain cancers include, but are not limited to, gliomas (e.g., glioblastomas, astrocytomas, oligodendrogliomas, ependymomas, and the like), meningiomas, pituitary adenomas, and vestibular schwannomas, primitive neuroectodermal tumors (medulloblastomas).

Immunoconjugates of the invention can be used either alone or in combination with other agents in a therapy. For instance, an immunoconjugate may be co-administered with at least one additional therapeutic agent, such as a chemotherapeutic agent. Such combination therapies encompass combined administration (where two or more therapeutic agents are included in the same or separate formulations), and separate administration, in which case, administration of the immunoconjugate can occur prior to, simultaneously, and/or following, administration of the additional therapeutic agent and/or adjuvant. Immunoconjugates can also be used in combination with radiation therapy.

The immunoconjugates of the invention (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various timepoints, bolus administration, and pulse infusion are contemplated herein.

Atezolizumab, durvalumab, avelumab, biosimilars thereof, and biobetters thereof are known to be useful in the treatment of cancer, particularly breast cancer, especially triple negative (test negative for estrogen receptors, progesterone receptors, and excess HER2 protein) breast cancer, bladder cancer, and Merkel cell carcinoma. The immunoconjugate described herein can be used to treat the same types of cancers as atezolizumab, durvalumab, avelumab, biosimilars thereof, and biobetters thereof, particularly breast cancer, especially triple negative (test negative for estrogen receptors, progesterone receptors, and excess HER2 protein) breast cancer, bladder cancer, and Merkel cell carcinoma.

The immunoconjugate is administered to a subject in need thereof in any therapeutically effective amount using any suitable dosing regimen, such as the dosing regimens utilized for atezolizumab, durvalumab, avelumab, biosimilars thereof, and biobetters thereof. For example, the methods can include administering the immunoconjugate to provide a dose of from about 100 ng/kg to about 50 mg/kg to the subject. The immunoconjugate dose can range from about 5 mg/kg to about 50 mg/kg, from about 10 μg/kg to about 5 mg/kg, or from about 100 μg/kg to about 1 mg/kg. The immunoconjugate dose can be about 100, 200, 300, 400, or 500 μg/kg. The immunoconjugate dose can be about 1, 2, 3, 4, 5, 6, 7, 8, 9, or 10 mg/kg. The immunoconjugate dose can also be outside of these ranges, depending on the particular conjugate as well as the type and severity of the cancer being treated. Frequency of administration can range from a single dose to multiple doses per week, or more frequently. In some embodiments, the immunoconjugate is administered from about once per month to about five times per week. In some embodiments, the immunoconjugate is administered once per week.

In another aspect, the invention provides a method for preventing cancer. The method comprises administering a therapeutically effective amount of an immunoconjugate (e.g., as a composition as described above) to a subject. In certain embodiments, the subject is susceptible to a certain cancer to be prevented. For example, the methods can include administering the immunoconjugate to provide a dose of from about 100 ng/kg to about 50 mg/kg to the subject. The immunoconjugate dose can range from about 5 mg/kg to about 50 mg/kg, from about 10 μg/kg to about 5 mg/kg, or from about 100 μg/kg to about 1 mg/kg. The immunoconjugate dose can be about 100, 200, 300, 400, or 500 μg/kg. The immunoconjugate dose can be about 1, 2, 3, 4, 5, 6, 7, 8, 9, or 10 mg/kg. The immunoconjugate dose can also be outside of these ranges, depending on the particular conjugate as well as the type and severity of the cancer being treated. Frequency of administration can range from a single dose to multiple doses per week, or more frequently. In some embodiments, the immunoconjugate is administered from about once per month to about five times per week. In some embodiments, the immunoconjugate is administered once per week.

Some embodiments of the invention provide methods for treating cancer as described above, wherein the cancer is breast cancer. Breast cancer can originate from different areas in the breast, and a number of different types of breast cancer have been characterized. For example, the immunoconjugates of the invention can be used for treating ductal carcinoma in situ: invasive ductal carcinoma (e.g., tubular carcinoma; medullary carcinoma; mucinous carcinoma; papillary carcinoma; or cribriform carcinoma of the breast); lobular carcinoma in situ, invasive lobular carcinoma; inflammatory breast cancer; and other forms of breast cancer such as triple negative (test negative for estrogen receptors, progesterone receptors, and excess HER2 protein) breast cancer. In some embodiments, methods for treating breast cancer include administering an immunoconjugate containing an antibody construct that is capable of binding HER2 (e.g. trastuzumab, pertuzumab, biosimilars, or biobetters thereof) and PD-L1 (e.g., atezolizumab, durvalumab, avelumab, biosimilars, or biobetters thereof). In some embodiments, methods for treating colon cancer lung cancer, renal cancer, pancreatic cancer, gastric cancer, and esophageal cancer include administering an immunoconjugate containing an antibody is construct that is capable of binding CEA, or tumors over-expressing CEA (e.g. labetuzumab, biosimilars, or biobetters thereof).

In some embodiments, the cancer is susceptible to a pro-inflammatory response induced by TLR7 and/or TLR8.

EXAMPLES

Preparation of Thienoazepine Compounds (TAZ) and Intermediates

Example 1 Synthesis of 5-amino-2-bromo-N,N-dipropyl-6H-thieno[3,2-b]azepine-7-carboxamide, TAZ-1

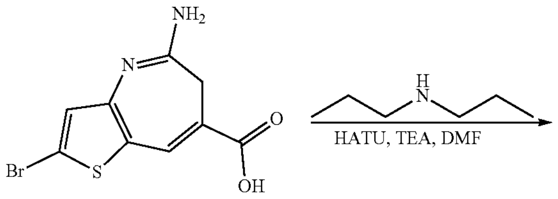

TAZ-15

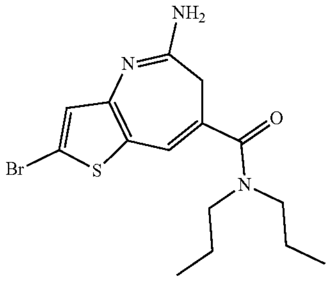

TAZ-1

To a solution of 5-amino-2-bromo-6H-thieno[3,2-b]azepine-7-carboxylic acid, TAZ-15 (70 mg, 244 µmol (micromoles), 1 eq) in DMF (1 mL) was added 1-[Bis(dimethylamino)methylene]-1H-1,2,3-triazolo[4,5-b]pyridinium 3-oxide hexafluorophosphate, Hexafluorophosphate Azabenzotriazole Tetramethyl Uronium, HATU (110 mg, 293 µmol, 1.2 eq), N-propylpropan-1-amine (74.0 mg, 731 µmol, 100 µL (microliters), 3 eq) and triethylamine, $Et_3N$ (49.0 mg, 488 µmol, 67.8 µL, 2 eq). The mixture was stirred at 25° C. for 1 h. The mixture was filtered and purified by prep-HPLC (column. Nano-micro Kromasil C18 100*30 mm 8 um; mobile phase: [water(0.1% TFA)-ACN]; B %: 20%-50%, 10 min) to give TAZ-1 (27 mg, 72.91 µmol, 29.9% yield) as white solid. $^1$H NMR ($CDCl_3$, 400 MHz)

δ11.66 (s, 1H), 7.75 (s, 1H), 7.22 (s, 1H), 6.79 (s, 1H), 3.40 (s, 4H), 3.28 (s, 2H), 1.68-1.57 (m, 4H), 0.91 (t, J=7.2 Hz, 6H). LC/MS [M+H] 370.0 (calculated); LC/MS [M+H] 370.0 (observed).

Example 2 Synthesis of 5-amino-N,N-dipropyl-6H-thieno[3,2-b]azepine-7-carboxamide, TAZ-2

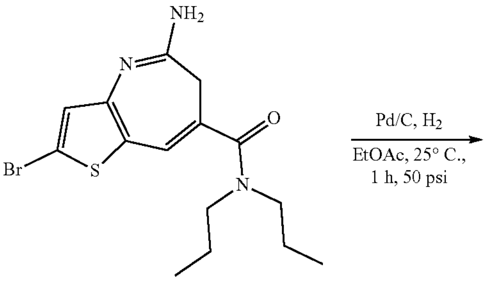

TAZ-1

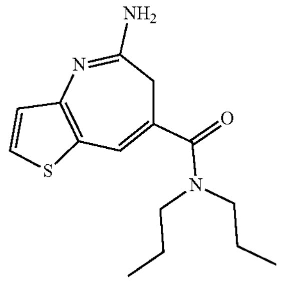

TAZ-2

To a solution of 5-amino-2-bromo-N,N-dipropyl-6H-thieno[3,2-b]azepine-7-carboxamide, TAZ-1 (70 mg, 189 µmol, 1 eq) in ethylacetate, EtOAc (5 mL) was added palladium on carbon, Pd/C (10 mg, 189 µmol, 20% purity, 1 eq) The suspension was degassed under vacuum and purged with $H_2$ several time and then stirred under $H_2$ (50 psi) at 25° C. for 1 h. The mixture was filtered and concentrated. The residue was purified by prep-HPLC (column: Nano-micro Kromasil C18 100*30 mm 8 um; mobile phase: [water(0.1% TFA)-ACN]; B %: 15%-40%, 10 min) to give TAZ-2 (12 mg, 41.18 µmol, 21.78% yield) as white solid. $^1$H NMR (MeOD-$d_4$, 400 MHz) δ 7.71 (d, J=5.6 Hz, 1H), 7.15-7.09 (m, 2H), 3.44-3.40 (m, 4H), 3.36 (s, 2H), 1.72-1.61 (m, 4H), 0.98-0.84 (m, 6H). LC/MS [M+H] 292.1 (calculated); LC/MS [M+H] 292.1 (observed)

Example 3 Synthesis of tert-butyl (2-(1-(5-(5-amino-7-(dipropylcarbamoyl)-6H-thieno[3,2-b]azepine-2-carboxamido)pyridin-2-yl)piperidine-4-carboxamido)ethyl)carbamate, TAZ-3

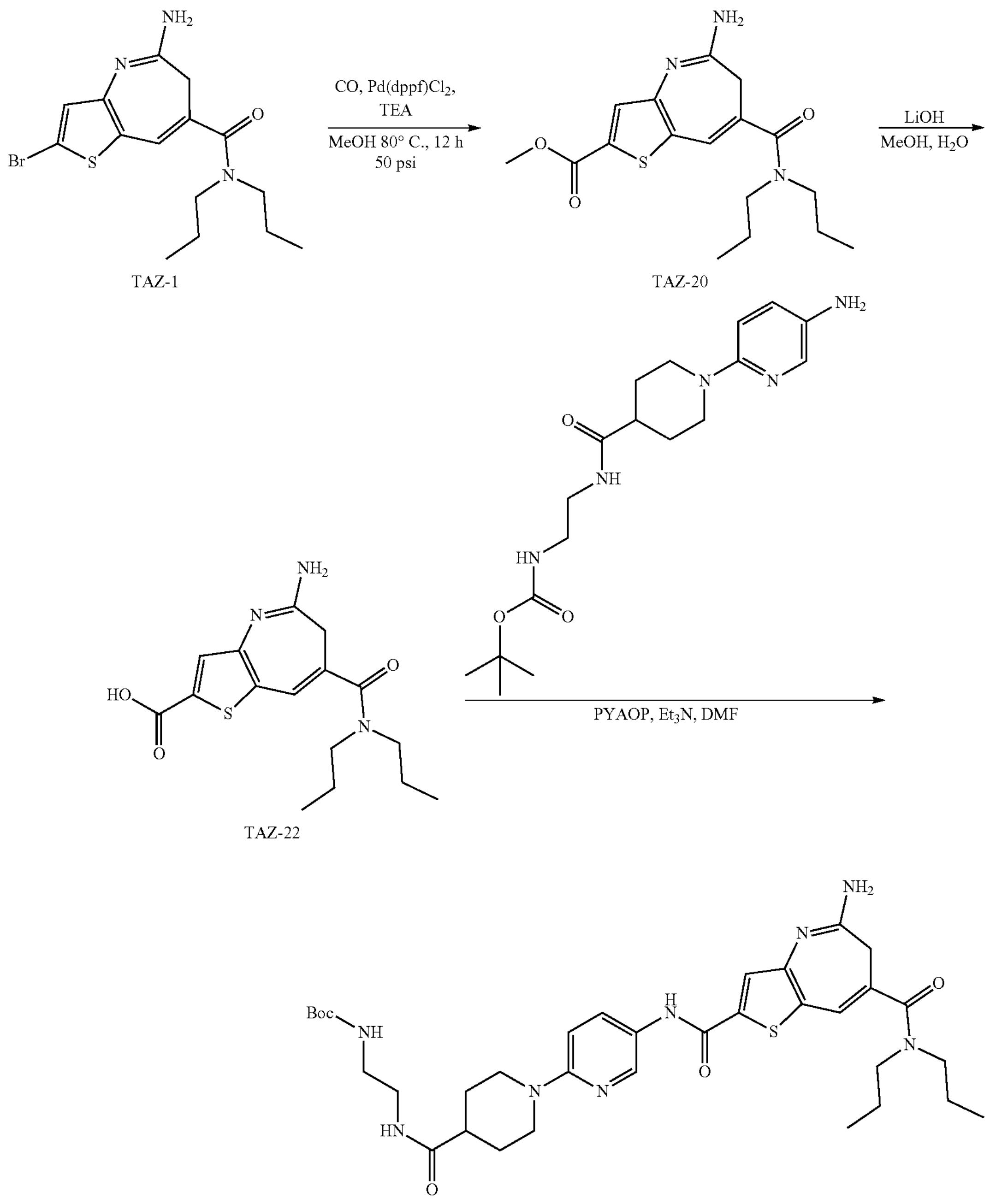

TAZ-1

TAZ-20

TAZ-22

TAZ-3

Preparation of methyl 5-amino-7-(dipropylcarbamoyl)-OH-thieno[3,2-b]azepine-2-carboxylate, TAZ-20

To a solution of 5-amino-2-bromo-N,N-dipropyl-6H-thieno[3,2-b]azepine-7-carboxamide, TAZ-1 (0.5 g, 1.30 mmol, 1 eq) in MeOH (5 mL) was added $Et_3N$ (409 mg, 4.05 mmol, 564 μL, 3 eq) and [1,1'-bis(diphenylphosphino)ferrocene]palladium(II) dichloride, $Pd(dppf)Cl_2$ (99.0 mg, 135 μmol, 0.1 eq) under $N_2$. The suspension was degassed under vacuum and purged with carbon monoxide. CO several times. The mixture was stirred under CO (50 psi) at 80° C. for 12 h. The mixture was filtered and concentrated to give TAZ-20 (0.5 g, crude) as red solid. $^1H$ NMR (MeOD-$d_4$, 400 MHz) δ 7.51 (s, 1H), 6.91 (s, 1H), 3.87 (s, 3H), 3.43-3.35 (m, 4H), 3.35 (s, 2H), 1.73-1.60 (m, 4H), 0.97-0.83 (m, 6H).

Preparation of 5-amino-7-(dipropylcarbamoyl)-6H-thieno[3,2-b]azepine-2-carboxylic acid, TAZ-22

To a solution of methyl 5-amino-7-(dipropylcarbamoyl)-6H-thieno[3,2-b]azepine-2-carboxylate, TAZ-20 (450 mg, 1.29 mmol, 1 eq) in MeOH (10 mL) and $H_2O$ (10 mL) was added $LiOH{\cdot}H_2O$ (270 mg, 6.44 mmol, 5 eq), and then stirred at 25° C. for 2 h. The reaction mixture was concentrated under reduced pressure to remove MeOH. The residue was diluted with $H_2O$ 30 mL and extracted with EtOAc (10 mL×2). The aqueous phase pH was adjusted to about 4 with aq (aqueous) HCl (1M) and extracted with EtOAc (10 mL×3). The organic layer was washed with brine (10 mL), dried over $Na_2SO_4$, filtered and concentrated to give TAZ-22 (0.2 g, 596.27 μmol, 46.30% yield) as light yellow solid. $^1H$ NMR (DMSO-$d_6$, 400 MHz) δ 7.49 (s, 1H), 6.99 (s, 1H), 3.32-3.28 (m, 4H), 3.16 (s, 2H), 1.61-1.46 (m, 4H), 0.82 (br s, 6H).

Preparation of tert-butyl (2-(1-(5-(5-amino-7-(dipropylcarbamoyl)-6H-thieno[3,2-b]azepine-2-carboxamido)pyridin-2-yl)piperidine-4-carboxamido)ethyl) carbamate, TAZ-3

To a solution of 5-amino-7-(dipropylcarbamoyl)-6H-thieno[3,2-b]azepine-2-carboxylic acid (150 mg, 447 μmol, 1 eq) in DMF (2 mL) was added 7-Aza-benzotriazol-1-yloxy-tripyrrolidino-phosphonium hexafluorophosphate, PYAOP (256 mg, 491.9 μmol, 1.1 eq), $Et_3N$ (45.0 mg, 447.2 μmol, 62.25 μL, 1 eq) and tert-butyl N-[2-[[1-(5-amino-2-pyridyl)piperidine-4-carbonyl]amino]ethyl]carbamate (195, mg, 536.6 μmol, 1.2 eq) and it was stirred at 25° C. for 12 h. The mixture was filtered and purified by prep-HPLC (column: Welch Xtimate C18 150*25 mm*5 um; mobile phase: [water(10 mM $NH_4HCO_3$)-ACN]; B %: 30%-60%, 10.5 min) to give TAZ-3 (62 mg, 91.06 μmol, 20.36% yield) as grayness solid. $^1H$ NMR (MeOD-$d_4$, 400 MHz) δ 8.35 (d, J=2.0 Hz, 1H), 7.89-7.82 (m, 1H), 7.60 (s, 1H), 7.51 (s, 1H), 6.93 (s, 1H), 6.91-6.84 (m, 1H), 4.28 (d, J=12.8 Hz, 2H), 3.44-3.35 (m, 4H), 3.27-3.21 (m, 2H), 3.18-3.12 (m, 2H), 2.97 (s, 2H), 2.88 (t, J=11.6 Hz, 2H), 2.48-2.32 (m, 1H), 1.90-1.80 (m, 2H), 1.79-1.56 (m, 6H), 1.43 (s, 9H), 0.90 (s, 6H). LC/MS [M+H] 681.3 (calculated); LC/MS [M+H] 681.4 (observed).

Example 4 Synthesis of 5-amino-2-[3-[3-(hydroxymethyl)azetidin-1-yl]sulfonylphenyl]-N,N-dipropyl-6H-thieno[3,2-b]azepine-7-carboxamide, TAZ-4

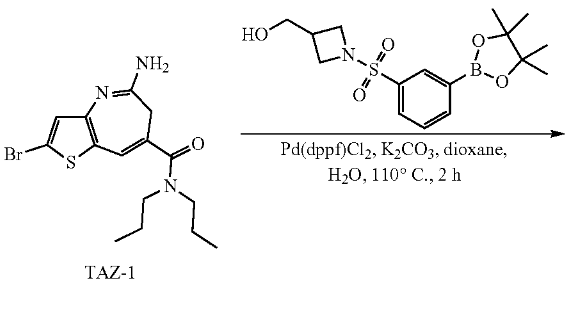

TAZ-1

-continued

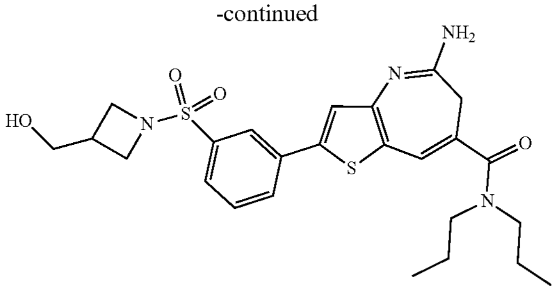

TAZ-4

To a solution of 5-amino-2-bromo-N,N-dipropyl-6H-thieno[3,2-b]azepine-7-carboxamide, TAZ-1 (71.0 mg, 192 μmol, 1.1 eq) in dioxane (1 mL) and $H_2O$ (0.5 mL) was added [1-[3-(4,4,5,5-tetramethyl-1,3,2-dioxaborolan-2-yl) phenyl]sulfonylazetidin-3-yl]methanol (62.0 mg, 174 μmol, 1 eq), $K_2CO_3$ (48.0 mg, 348 μmol, 2 eq) and [1,1'-bis (diphenylphosphino)ferrocene]palladium(II) dichloride, $Pd(dppf)Cl_2$ (6.0 mg, 8.7 μmol, 0.05 eq) at 25° C. under $N_2$ and then stirred at 110° C. for 2 h. The mixture was filtered and concentrated. The residue was purified by prep-HPLC (column: Welch Xtimate C18 150*25 mm*5 um; mobile phase: [water(10 mM $NH_4HCO_3$)-ACN]; B %: 30%-60%, 10.5 min) to give TAZ-4 (22 mg, 42.58 μmol, 24.45% yield) as light yellow solid. $^1H$ NMR (MeOD-$d_4$, 400 MHz) δ 8.04-7.97 (m, 2H), 7.79-7.75 (m, 1H), 7.73-7.67 (m, 1H), 7.31 (s, 1H), 6.92 (s, 1H), 3.85 (t, J=8.2 Hz, 2H), 3.62-3.56 (m, 2H), 3.45-3.37 (m, 6H), 2.99 (s, 2H), 2.63-2.52 (m, 1H), 1.71-1.59 (m, 4H), 0.99-0.83 (m, 6H). LC/MS [M+H] 517.2 (calculated); LC/MS [M+H] 517.2 (observed)

Example 5 Synthesis of [4-[[(2S)-2-[[(2S)-2-(9H-fluoren-9-ylmethoxycarbonylamino)-3-methyl-butanoyl]]amino]-5-ureido-pentanoyl]amino]phenyl] methylN-[2-[[1-[5-[[5-amino-7-(dipropylcarbamoyl)-6H-thieno [3,2-b]azepine-2-carbonyl]amino]-2-pyridyl]piperidine-4-carbonyl] amino]ethyl]carbamate, TAZ-5

TAZ-3
TFA
DCM, 30° C., 2 h

-continued

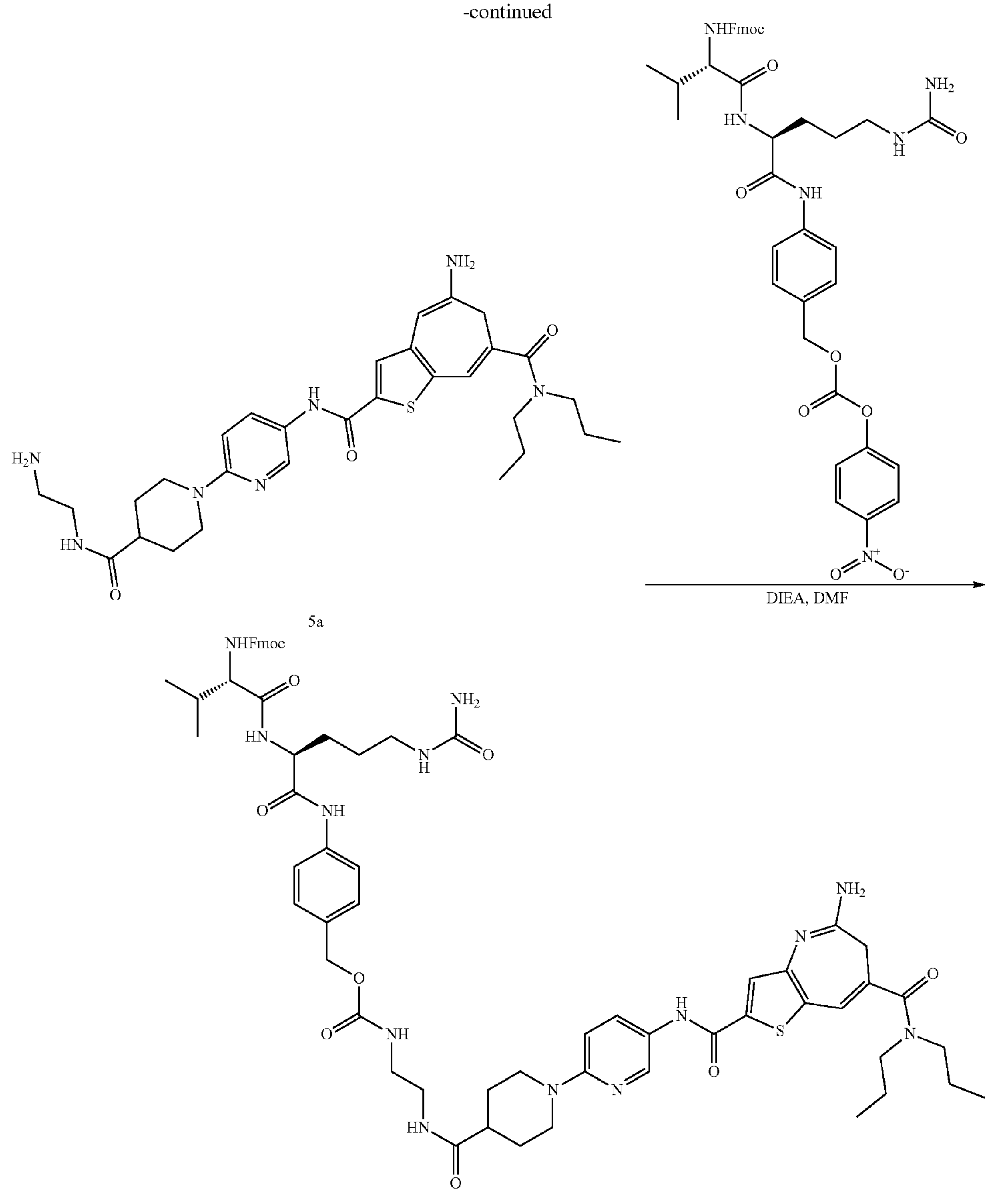

5a

TAZ-5

Preparation of 5-amino-N2-16-14-(2-aminoethylcarbamoyl)-1-piperidyl-3-pyridyl]-N7,N7-dipropyl-6H-thieno[3,2-b]azepine-2,7-dicarboxamide, 5a To a solution of tert-butyl N-[2-[[1-[5-[[5-amino-7-(dipropylcarbamoyl)-6H-thieno[3,2-b]azepine-2-carbonyl]amino]-2-pyridyl]piperidine-4-carbonylamino]ethylcarbamate, TAZ-3 (50 mg, 73.4 μmol, 1 eq) in DCM (1 mL) was added TFA (84.0 mg, 734 μmol, 54.0 μL, 10 eq). The mixture was stirred at 30° C. for 2 hi. The mixture was filtered and concentrated and then lyophilization to give 5a (59 mg, 72.95 μmol, 99.34% yield, 2TFA) as grayness solid.

$^{1}H$ NMR (MeOD-$d_4$, 400 MHz) δ 8.62 (d, J=2.4 Hz, 1H), 8.17 (dd, J=9.6, 2.8 Hz, 1H), 7.89 (s, 1H), 7.43 (d, J=9.6 Hz, 1H), 7.16 (s, 1H), 4.21 (d, J=13.6 Hz, 2H), 3.52-3.39 (m, 8H), 3.36-3.31 (m, 2H), 3.07 (t, J=6.0 Hz, 2H), 2.68-2.61 (m, 1H), 2.07-2.00 (m, 2H), 1.90-1.78 (m, 2H), 1.67 (dq, J=14.8, 7.2 Hz, 4H), 0.93 (s, 6H).

Preparation of TAZ-5

To a solution of 5a (50 mg, 61.8 μmol, 1 eq, 2TFA) in DMF (I mL) was added DIEA (32.0 mg, 247.2 μmol, 43.0 μL, 4 eq) and [4-[[(2S)-2-[[(2S)-2-(9H-fluoren-9-ylmethoxycarbonylamino)-3-methyl-butanoyl]amino]-5-ureido-pentanoyl]amino]phenyl]methyl (4-nitrophenyl) carbonate (52.0 mg, 68.0 μmol, 1.1 eq) and then stirred at 25° C. for 1 h. The mixture was filtered and purified by prep-HPLC (column: Nano-micro Kromasil C18 100*30 mm 8 um; mobile phase: [water(0.1% TFA)-ACN]; B %: 25%-45%, 10 min) to give TAZ-5 (36 mg, 27.2 μmol, 44.03% yield, TFA) as light yellow solid. $^1$H NMR (MeOD-$d_4$, 400 MHz) δ 8.58 (s, 1H), 8.07 (br d, J=10.4 Hz, 1H), 7.93 (br s, 1H), 7.86-7.72 (m, 3H), 7.63 (br t, J=7.2 Hz, 2H), 7.57 (br d, J=8.2 Hz, 2H), 7.41-7.34 (m, 2H), 7.33-7.25 (m, 4H), 7.13 (s, 1H), 5.03 (br s, 2H), 4.41-4.29 (m, 3H), 4.23-4.15 (m, 1H), 4.13-4.03 (m, 2H), 3.98-3.91 (m, 1H), 3.51-3.34 (m, 5H), 3.25-3.07 (m, 9H), 2.52-2.31 (m, 1H), 2.08 (br d, J=7.6 Hz, 1H), 1.99-1.36 (m, 12H), 1.04-0.82 (m, 12H). LC/MS [M+H] 1208.6 (calculated); LC/MS [M+H] 1208.5 (observed).

Example 6 Synthesis of tert-butyl N-[5-[5-amino-7-(dipropylcarbamoyl)-6H-thieno[3,2-b]azepin-2-yl] pent-4-ynyl] carbamate, TAZ-6

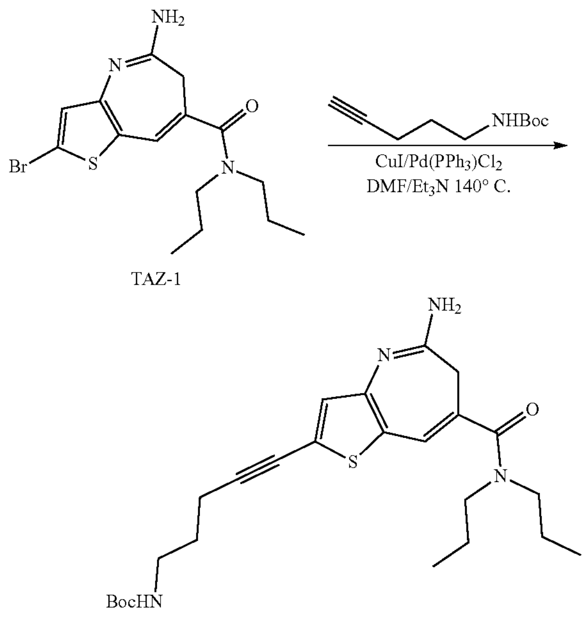

TAZ-1

TAZ-6

A mixture of 5-amino-2-bromo-N,N-dipropyl-6H-thieno [3,2-b]azepine-7-carboxamide, TAZ-1 (20 mg, 54.0 μmol, 1 eq), tert-butyl N-pent-4-ynylcarbamate (29.69 mg, 162 μmol, 3 eq), $Pd(PPh_3)_2Cl_2$ (1.90 mg, 2.70 μmol, 0.05 eq), CuI (2.06 mg, 10.8 μmol, 0.2 eq) and $PPh_3$ (2.83 mg, 10.8 μmol, 0.2 eq) in TEA (0.2 mL) and DMF (0.6 mL) was degassed and purged with $N_2$ for 3 times, and then stirred at 140° C. for 3 h under $N_2$. The reaction mixture was quenched by addition of $H_2O$ (5 mL) at 0° C. and then extracted with EtOAc (5 mL×3). The combined organic layers were washed with brine(5 mL×3), dried over $Na_2SO_4$, filtered and concentrated under reduced pressure. The residue was purified by prep-TLC ($SiO_2$, EtOAc:MeOH=10:1) to give TAZ-6 (8 mg, 16.9 μmol, 31.34% yield) as yellow solid. $^1$H NMR (MeOD-$d_4$, 400 MHz) δ 6.87 (s, 1H), 6.79 (s, 1H), 3.42-3.34 (m, 4H), 3.31 (s, 2H), 3.17 (t, J=6.8 Hz, 2H), 2.48 (t, J=7.2 Hz, 2H), 1.75 (q, J=7.2 Hz, 2H), 1.69-1.56 (m, 4H), 1.44 (s, 9H), 0.92-0.87 (m, 6H). LC/MS [M+H] 473.2 (calculated); LC/MS [M+H] 473.2 (observed)

Example 7 Synthesis of 5-amino-2-methyl-N,N-dipropyl-6H-thieno[3,2-b]azepine-7-carboxamide, TAZ-7

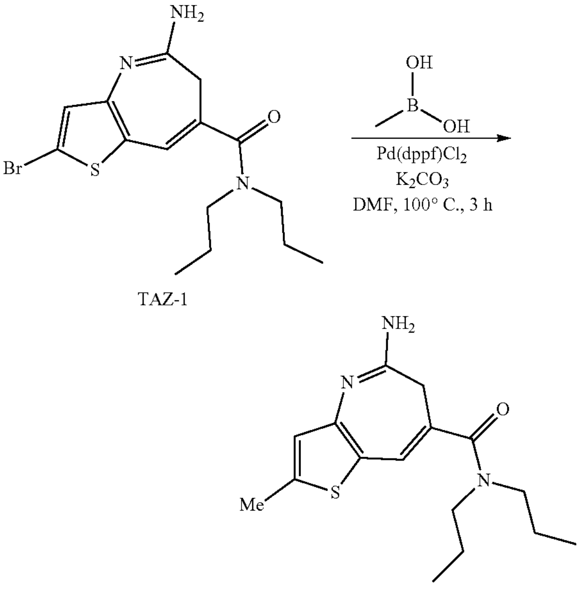

TAZ-1

TAZ-7

To a solution of 5-amino-2-bromo-N,N-dipropyl-6H-thieno[3,2-b]azepine-7-carboxamide, TAZ-1 (30 mg, 81.0 μmol, 1 eq) in DMF (1 mL) was added methylboronic acid (73.0 mg, 1.22 mmol, 15 eq), $K_2CO_3$ (22.0 mg, 162.03 μmol, 2 eq) and [1,1'-bis(diphenylphosphino)ferrocene]palladium (II) dichloride, $Pd(dppf)Cl_2$ (2.96 mg, 4.05 μmol, 0.05 eq) under $N_2$ and then stirred at 100° C. for 3 h. The mixture was filtered and concentrated. The residue was purified by prep-HPLC (column: Nano-micro Kromasil C18 100*30 mm 8 um; mobile phase: [water(0.1% TFA)-ACN]; B %: 10%-40%, 10 min) to give TAZ-7 (8 mg, 26.19 μmol, 32.33% yield) as white solid. $^1$H NMR (MeOD-d4, 400 MHz) δ 7.00 (s, 1H) 6.83 (s, 1H) 3.43 (br t, J=7.2 Hz, 4H) 3.34 (s, 2H) 2.53 (s, 3H) 1.69-1.60 (m, 4H) 0.98-0.85 (m, 6H). LC/MS [M+H] 306.2 (calculated); LC/MS [M+H] 306.2 (observed).

Example 8 Synthesis of tert-butyl N-[3-[(5-amino-6H-thieno[3,2-b]azepine-7-carbonyl)-propyl-amino] propyl]carbamate, TAZ-8

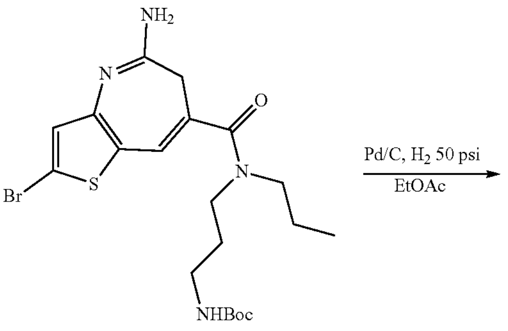

TAZ-9

-continued

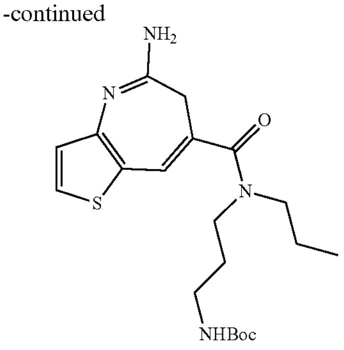

TAZ-8

To a solution of tert-butyl N-[3-1(5-amino-2-bromo-6H-thieno[3,2-b]azepine-7-carbonyl)-propyl-amino]propyl]carbamate, TAZ-9 (0.72 g, 1.48 mmol, 1 eq) in EtOAc (10 mL) was added palladium on carbon, Pd/C (10%, 0.2 g) under $N_2$. The suspension was degassed under vacuum and purged with $H_2$ several times, and then stirred under hydrogen gas, $H_2$ (50 psi) at 25° C. for 12 h. The reaction mixture was filtered and concentrated under reduced pressure. The residue was purified by column chromatography ($SiO_2$, EtOAc: EtOH=1:0 to 3:1) to give TAZ-8 (0.4 g, 984 μmol, 66.34% yield) as a light yellow solid. $^1$H NMR (MeOD, 400 MHz) δ 7.67 (d, J=5.6 Hz, 1H), 7.13-7.05 (m, 2H), 3.50 (t, J=7.6 Hz, 2H), 3.44 (t, J=7.6 Hz, 2H), 3.30-3.24 (m, 2H), 3.07 (s, 2H), 1.84-1.78 (m, 2H), 1.72-1.61 (m, 2H), 1.41 (s, 9H), 0.93-0.88 (m, 3H). LC/MS [M+H] 407.2 (calculated); LC/MS [M+H] 407.2 (observed).

Example 9 Synthesis of tert-butyl N-[3-[(5-amino-2-bromo-6H-thieno[3,2-b]azepine-7-carbonyl)-propyl-amino]propyl]carbamate, TAZ-9

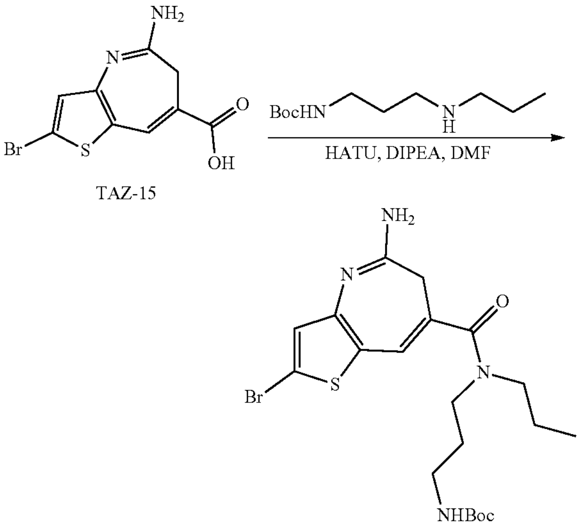

TAZ-15

TAZ-9

To a mixture of 5-amino-2-bromo-6H-thieno[3,2-b]azepine-7-carboxylic acid, TAZ-15 (0.5 g, 1.74 mmol, 1 eq) in DMF (5 mL) was added 1-[Bis(dimethylamino)methylene]-1H-1,2,3-triazolo[4,5-b]pyridinium 3-oxide hexafluorophosphate. Hexafluorophosphate Azabenzotriazole Tetramethyl Uronium, HATU (795 mg, 2.09 mmol, 1.2 eq) and DIPEA (675 mg, 5.22 mmol, 910 μL, 3 eq) at 25° C. After 15 min, tert-butyl N-[3-(propylamino)propyl]carbamate (489.70 mg, 2.26 mmol, 1.3 eq) was added at 25° C., and then stirred for 1 h. The reaction mixture was quenched by addition of $H_2O$ (30 mL) at 0° C., and then extracted with EtOAc(15 mL×3). The combined organic layers were washed with brine (10 mL×3), dried over $Na_2SO_4$, filtered and concentrated under reduced pressure. The residue was purified by column chromatography ($SiO_2$, Petroleum ether/Ethyl acetate=1/0 to 0/1) and ($SiO_2$, EtOAc:MeOH=1:0 to 5:1) to give TAZ-9 (0.73 g, 1.50 mmol, 86.36% yield) as a light yellow solid. $^1$H NMR (MeOD, 400 MHz) 56.95 (s, 1H), 6.86 (s, 1H), 3.50-3.43 (m, 2H), 3.42-3.35 (m, 2H), 3.07-3.01 (m, 4H), 1.84-1.74 (m, 2H), 1.69-1.57 (m, 2H), 1.41 (s, 9H), 0.91-0.86 (m, 3H). LC/MS [M+H] 485.1 (calculated): LC/MS [M+H] 485.1 (observed).

Example 10 Synthesis of tert-butyl N-[4-[(5-amino-2-bromo-6H-thieno[3,2-b]azepine-7-carbonyl)-propyl-amino]but-2-ynyl]carbamate, TAZ-10

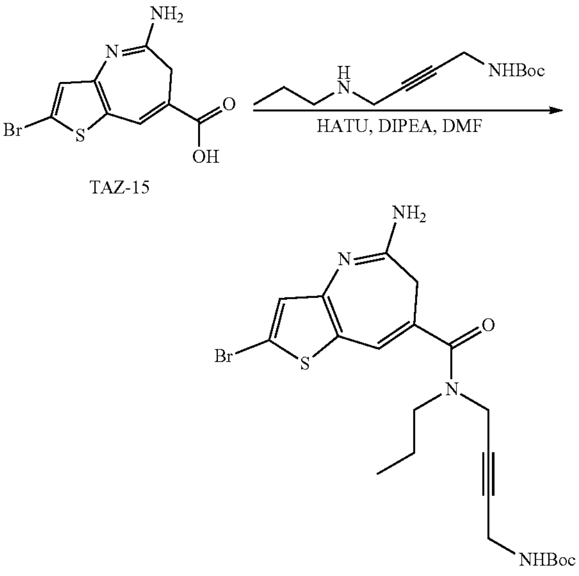

TAZ-15

TAZ-10

To a solution of 5-amino-2-bromo-6H-thieno[3,2-b]azepine-7-carboxylic acid, TAZ-15 (0.2 g, 697 μmol, 1 eq) in DMF (4 mL) was added HATU (318 mg, 836 μmol, 1.2 eq) and DIPEA (270 mg, 2.09 mmol, 3 eq) at 25° C. After 15 min, tert-butyl N-[4-(propylamino)but-2-ynyl]carbamate (205 mg, 906 μmol, 1.3 eq) was added at 25° C. and then stirred at 25° C. for 1 h. The reaction mixture was quenched by addition of $H_2O$ (20 mL) at 0° C., and then extracted with EtOAc (10 mL×3). The combined organic layers were washed with brine (5 mL×3), dried over $Na_2SO_4$, filtered and concentrated under reduced pressure. The residue was purified by column chromatography ($SiO_2$. Petroleum ether/Ethyl acetate=1/0 to 0/1) to give TAZ-10 (150 mg, 302.77 μmol, 43.47% yield) as a yellow solid. $^1$H NMR (MeOD, 400 MHz) δ 7.20-7.18 (m, 2H), 4.29 (s, 2H), 3.84 (s, 2H), 3.58-3.50 (m, 2H), 3.40 (s, 2H), 1.76-1.66 (m, 2H), 1.43 (s, 9H), 0.94 (t, J=7.2 Hz, 3H). LC/MS [M+H] 495.1 (calculated); LC/MS [M+H] 495.1 (observed).

Example 11 Synthesis of 5-amino-N-(3-aminopropyl)-N-propyl-6H-thieno[3,2-b]azepine-7-carboxamide, TAZ-11

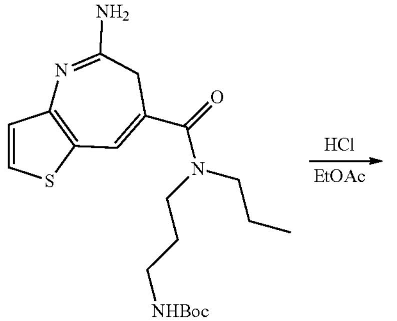

TAZ-8

-continued

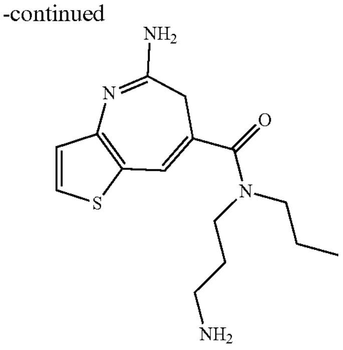

TAZ-11

To a solution of tert-butyl N-[3-[(5-amino-6H-thieno[3,2-b]azepine-7-carbonyl)-propyl-amino]propyl]carbamate, TAZ-8 (1.4 g, 3.44 mmol, 1 eq) in EtOAc (10 mL) and MeOH (1 mL) was added HCl/EtOAc (4 M, 20 mL, 23.23 eq) at 25° C. and then stirred for 0.5 h. The reaction mixture was concentrated under reduced pressure to give TAZ-11 (1.28 g, crude, HCl) as a light yellow solid. $^1$H NMR (MeOD-$d_4$, 400 MHz) δ 7.74 (d, J=5.6 Hz, 1H), 7.20 (s, 1H), 7.15 (d, J=5.6 Hz, 1H), 3.59 (t, J=6.8 Hz, 2H), 3.49 (t, J=7.2 Hz, 2H), 3.41 (s, 2H), 3.00 (t, J=7.2 Hz, 2H), 2.08-1.97 (m, 2H), 1.75-1.62 (m, 2H), 0.91 (t, J=7.2 Hz, 3H). LC/MS [M+H] 307.2 (calculated); LC/MS [M+H] 307.1 (observed).

Example 12 Synthesis of 5-amino-2-[1-[3-(hydroxymethyl)azetidin-1-yl]sulfonylpyrazol-4-yl]-N,N-dipropyl-6H-thieno[3,2-b]azepine-7-carboxamide, TAZ-12

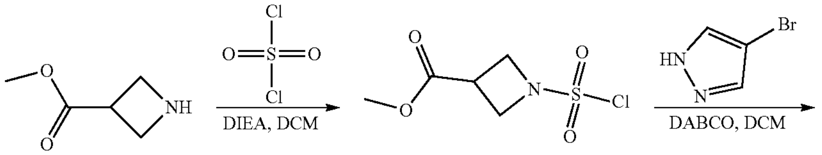

12a

12b

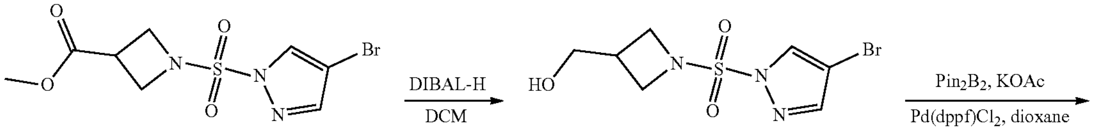

12c

12d

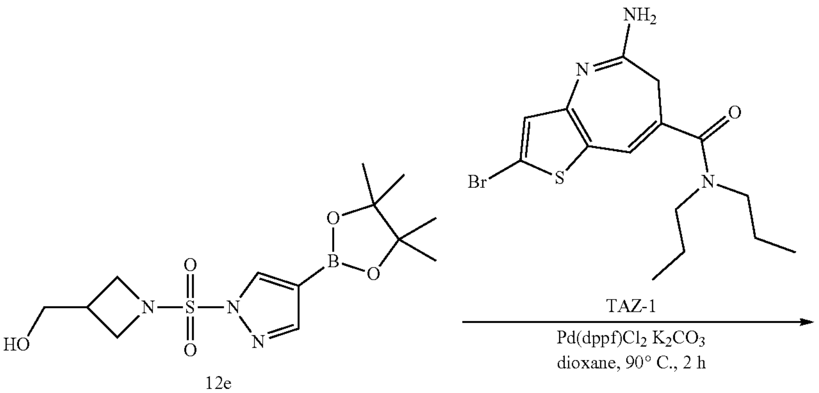

12e

-continued

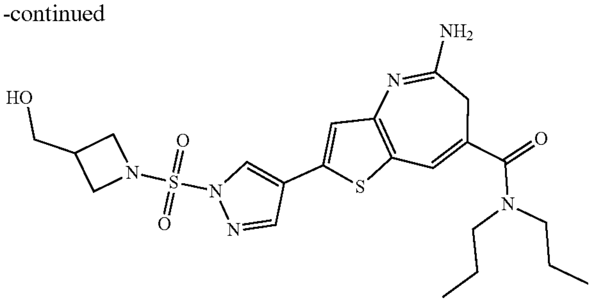

TAZ-12

Preparation of methyl 1-chlorosulfonylazetidine-3-carboxylate, 12b

To a mixture of sulfuryl chloride (3.34 g, 24.7 mmol, 2.47 mL, 1.5 eq) in DCM (50 mL) was added a solution of methyl azetidine-3-carboxylate, 12a (2.5 g, 16.49 mmol, 1 eq. HCl) and DIEA (8.53 g, 65.97 mmol, 11.49 mL, 4 eq) in DCM (30 mL) at −78° C. and then stirred for 2 h at this temperature. The mixture was diluted with water and extracted with EtOAc (60 mL×3). The organic layer was washed with the brine, dried over $Na_2SO_4$, filtered and concentrated. The residue was purified by silica gel chromatography (Petroleum ether/Ethyl acetate=1/0, 0/1) to afford 12b (2.75 g, 12.87 mmol, 78.05% yield) as colorless oil. $^1H$ NMR ($CDCl_3$, 400 MHz) 54.36-4.25 (m, 4H), 3.80 (s, 3H), 3.57-3.47 (m, 1H).

Preparation of methyl 1-(4-bromopyrazole-1-yl) sulfonylazetidine-3-carboxylate, 12c To a mixture of 4-bromo-1H-pyrazole (1.58 g, 10.77 mmol, 1.0 eq) in DCM (40 mL) was added DABCO (1.57 g, 14.0 mmol, 1.54 mL, 1.3 eq) and 12b (2.3 g, 10.8 mmol, 1.0 eq) in one portion at 25° C. and it was stirred for 2 h. The mixture was diluted with water and extracted with EtOAc (50 mL×3). The organic layer was washed with brine, dried over $Na_2SO_4$, filtered and concentrated. The residue was purified by silica gel chromatography (Petroleum ether/Ethyl acetate=1/0, 3/1) to afford 12c (3 g, 9.25 mmol, 85.97% yield) as yellow oil. $^1H$ NMR ($CDCl_3$, 400 MHz) δ 8.03 (s, 1H), 7.77 (s, 1H), 4.32-4.27 (m, 4H), 3.73 (s, 3H), 3.41-3.34 (m, 1H).

Preparation of 11-(4-bromopyrazol-1-yl)sulfonylazetidin-3-yl]methanol, 12d

To a solution of 12c (3.3 g, 10.2 mmol, 1 eq) in DCM (50 mL) was added DIBAL-H (1 M, 40.7 mL, 4 eq) slowly at 0° C. under $N_2$, and then stirred at this temperature for 2 h. The mixture was quenched with water (1.5 mL) and dried over $Na_2SO_4$, filtered and concentrated to obtain 12d (1.19 g, crude) as yellow oil. $^1H$ NMR ($CDCl_3$, 400 MHz) δ 8.04 (s, 1H), 7.77 (s, 1H), 4.18-4.14 (t, J=8.4 Hz, 2H), 3.96 (dd, J=5.6, 8.4 Hz, 2H), 3.66 (d, J=5.6 Hz, 2H).

Preparation of [1-[4-(4,4,5,5-tetramethyl-1,3,2-dioxaborolan-2-yl)pyrazol-1-yl]sulfonylazetidin-3-yl] methanol, 12e To a mixture of 12d (0.1 g, 338 μmol, 1.0 eq) in dioxane (2 mL) was added $Pin_2B_2$ (129 mg, 507 μmol, 1.5 eq), potassium acetate, KOAc (66.3 mg, 675 μmol, 2.0 eq) and Pd(dppf)$C_2$ (12.4 mg, 16.9 μmol, 0.05 eq) in one portion at 25° C. under $N_2$ and it was stirred at 100° C. for 2 h. Then the mixture was diluted with water and extracted with EtOAc (10 mL×3). The organic layer was washed with brine, dried over $Na_2SO_4$, filtered and concentrated to give 12e (0.1 g, crude) as black oil.

Preparation of TAZ-12

To a mixture of 5-amino-2-bromo-N,N-dipropyl-6H-thieno[3,2-b]azepine-7-carboxamide, TAZ-1 (54 mg, 146 μmol, 1.0 eq) and 12e (50 mg, 146 μmol, 1.0 eq) in dioxane (2 mL) and $H_2O$ (0.2 mL) was added $K_2CO_3$ (60.4 mg, 437 μmol, 3.0 eq) and Pd(dppf)$Cl_2$ (5.3 mg, 7.28 μmol, 0.05 eq) in one portion at 25° C. under $N_2$. The mixture was stirred at 90° C. for 2 h. Then the reaction was diluted with water and extracted with EtOAc (10 mL×3). The organic layer was washed with brine, dried over $Na_2SO_4$, filtered and concentrated. The residue was further purification by prep-HPLC (column: Phenomenex Gemini-NX C18 75*30 mm*3 um; mobile phase: [water(10 mM $NH_4HCO_3$)-ACN]; B %: 30%-50%, 10.5 min) to give 5-amino-2-[1-[3-(hydroxymethyl) azetidin-1-yl]sulfonylpyrazol-4-yl]-N,N-dipropyl-6H-thieno[3,2-b]azepine-7-carboxamide (9 mg, 17.8 μmol, 12.19% yield) as white solid. $^1H$ NMR (MeOD, 400 MHz) δ 8.56 (s, 1H), 8.28 (s, 1H), 7.42 (s, 1H), 7.38-7.35 (m, 2H), 6.85 (s, 1H), 4.13 (t, J=8.8 Hz, 2H), 3.89 (dd, J=6.0, 8.4 Hz, 2H), 3.49 (d, J=6.0 Hz, 2H), 3.43-3.37 (m, 4H), 2.97 (s, 2H), 2.72-2.67 (m, 1H), 1.69-1.61 (m, 4H), 0.93-0.87 (m, 6H). LC/MS [M+H] 507.2 (calculated); LC/MS [M+H] 507.2 (observed).

Example 13 Synthesis of tert-butyl N-[5-[5-amino-7-(dipropylcarbamoyl)-6H-thieno[3,2-b]azepin-2-yl] pentyl]carbamate, TAZ-13

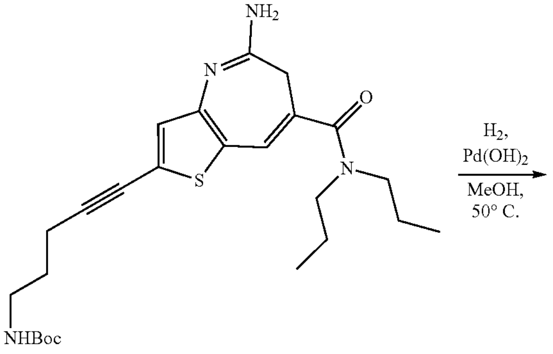

TAZ-6

-continued

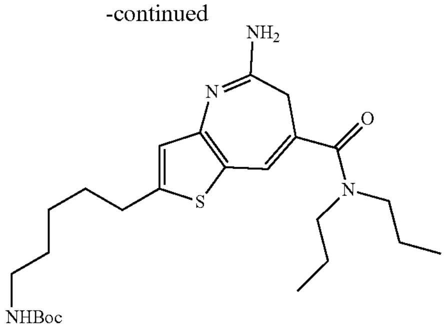

TAZ-13

To a solution of tert-butyl N-[5-[5-amino-7-(dipropylcarbamoyl)-6H-thieno[3,2-b]azepin-2-yl]pent-4-ynyl]carbamate, TAZ-6 (0.8 g, 1.69 mmol, 1.0 eq) in MeOH (30 mL) was added $Pd(OH)_2/C$ (10%, 0.3 g) under $N_2$. The suspension was degassed under vacuum and purged with $H_2$ several times. The mixture was stirred under $H_2$ (50 psi) at 25° C. for 12 hours. The reaction mixture was filtered and concentrated. The residue was purified by flash silica gel chromatography (ISCO®; 20 g SepaFlash® Silica Flash Colum, Eluent of 0-100% Ethyl acetate/Petroleum ether gradient (a 60 mL/min) to give TAZ-13 (0.6 g, 1.26 mmol, 74.37% yield) as yellow oil. $^1$H NMR (MeOD, 400 MHz) δ 6.80 (s, 1H), 6.62 (s, 1H), 3.43-3.35 (m, 4H), 3.03 (t, J=7.2 Hz, 2H), 2.91 (s, 2H), 2.78 (t, J=7.2 Hz, 2H), 1.69-1.60 (m, 6H), 1.50-1.40 (m, 13H), 0.92-0.87 (m, 6H). LC/MS [M+H] 1477.3 (calculated); LC/MS [M+H] 1477.3 (observed)

Example 14 Synthesis of 5-amino-2-(5-aminopentyl)-N,N-dipropyl-6H-thieno [3,2-b]azepine-7-carboxamide, TAZ-14

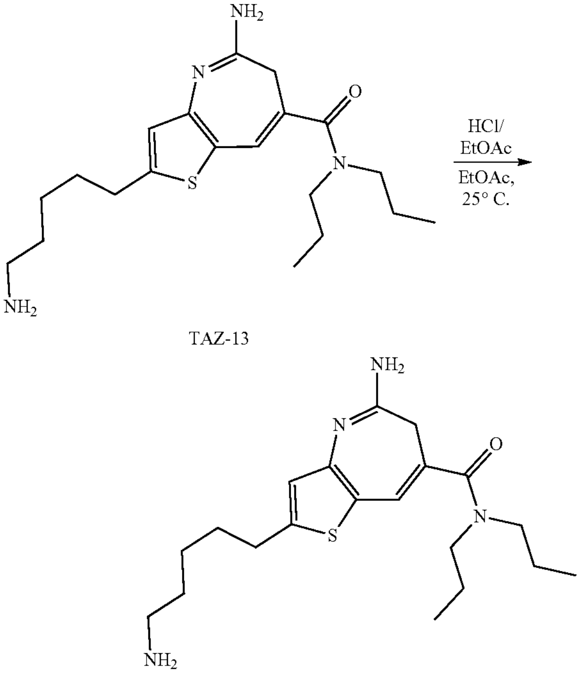

TAZ-13

TAZ-14

To a solution of tert-butyl N-[5-[5-amino-7-(dipropylcarbamoyl)-6H-thieno[3,2-b]azepin-2-yl]pentyl]carbamate, TAZ-13 (0.31 g, 650 μmol, 1.0 eq) in EtOAc (10 mL) was added HCl/EtOAc (4 M, 4.88 mL, 30.0 eq) at 25° C. and then stirred for 1 hour at this temperature. The mixture was concentrated under reduced pressure to give TAZ-14 (0.26 g, 630 μmol, 96.80% yield, HCl) as yellow solid. $^1$HNMR (MeOD, 400 MHz) δ 7.02 (s, 1H), 6.92 (s, 1H), 3.45-3.43 (m, 4H), 3.35 (s, 2H), 2.98-2.86 (m, 4H), 1.82-1.62 (m, 8H), 1.55-1.45 (m, 2H), 0.92-0.87 (m, 6H). LC/MS [M+H] 377.2 (calculated), LC/MS [M+H] 377.2 (observed).

Example 15 Synthesis of 5-amino-2-bromo-6H-thieno[3,2-b]azepine-7-carboxylic acid, TAZ-15

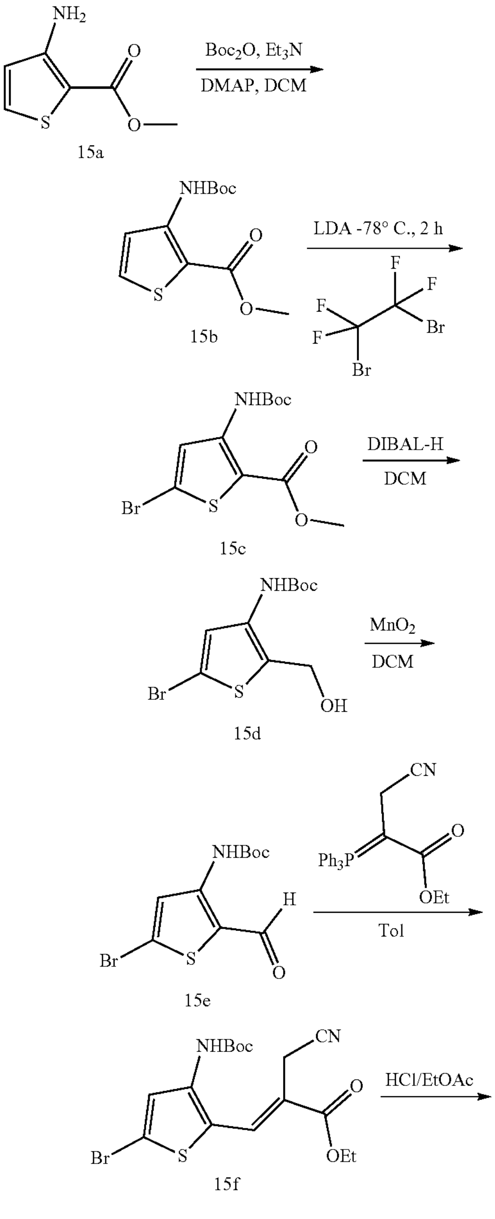

15a

15b

15c

15d

15e

15f

-continued

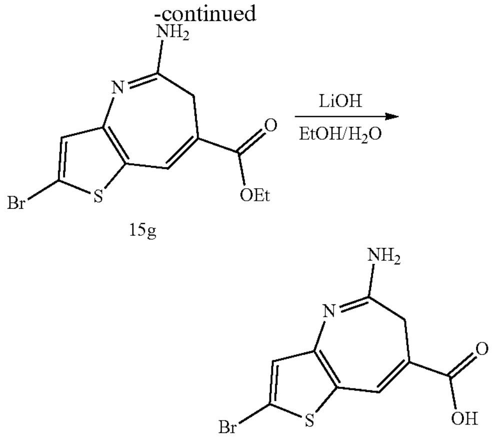

15g

TAZ-15

Preparation of methyl 3-(tert-butoxycarbonylamino) thiophene-2-carboxylate, 15b

To a solution of methyl 3-aminothiophene-2-carboxylate, 15a (19 g, 121 mmol, 1 eq) and $Et_3N$ (14.7 g, 145 mmol, 20.2 mL, 1.2 eq) in DCM (100 mL) was added $Boc_2O$ (29.0 g, 133 mmol, 30.5 mL, 1.1 eq) in DCM (50 mL) dropwise at 25° C., then DMAP (738 mg, 6.0 mmol, 0.05 eq) was added to the mixture. The resulting mixture was stirred at 25° C. for 3 h. The mixture was diluted with water (100 mL) and extracted with DCM (50 mL×3). The organic layer was washed with brine (30 mL), dried over $Na_2SO_4$, filtered and concentrated. The residue was purified by flash silica gel chromatography (ISCO®; 20 g SepaFlash® Silica Flash Colum, Eluent of 0-20% Ethyl acetate/Petroleum ether gradient J 45 mL/min) to give 15b (12 g, 46.64 mmol, 38.58% yield) as white solid. $^1H$ NMR ($CDCl_3$, 400 MHz) δ9.36 (s, 1H), 7.89 (d, J=5.6 Hz 1H), 7.42 (d, J=5.6 Hz, 1H), 3.88 (s, 3H), 1.53 (s, 9H).

Preparation of methyl 5-bromo-3-(tert-butoxycarbonylamino)thiophene-2-carboxylate, 15c To a solution of 15b (8.9 g, 34.6 mmol, 1 eq) in THF (50 mL) was added LDA (2 M, 60.0 mL, 3.5 eq) at −78° C. the mixture was stirred for 1 h at −78° C., then 1,2-dibromo-1,1,2,2-tetrafluoro-ethane (53.92 g, 207.54 mmol, 6 eq) was added and then stirred for 1 h at this temperature. The mixture was poured into cold ammonium chloride solution (100 mL) while stirring vigorously, and extracted with EtOAc (50 mL×3). The organic layer was washed with brine (50 mL), dried over $Na_2SO_4$, filtered and concentrated. The residue was purified by flash silica gel chromatography (ISCO®; 10 g SepaFlash® Silica Flash Colum, Eluent of 0-20% Ethyl acetate/Petroleum ether gradient @ 45 mL/min) to give 15c (4 g, 11.90 mmol, 34.40% yield) as off-white solid. $^1H$ NMR ($CDCl_3$, 400 MHz) δ 9.33 (s, 1H), 7.97 (s, 1H), 3.86 (s, 3H), 1.54 (s, 9H)

Preparation of tert-butyl N-[5-bromo-2-(hydroxymethyl)-3-thienyl]carbamate, 15d

To a solution of 15c (4 g, 11.9 mmol, 1 eq) in DCM (60 mL) was added DIBAL-H (1 M, 59.0 mL, 5 eq) at 0° C. under $N_2$ and then stirred at 25° C. for 2 h. The reaction mixture was quenched by addition of $H_2O$ 1 mL at 0° C., and then added 15% NaOH (0.5 mL) and $H_2O$ (1 mL) at 0° C. The mixture was stirred for 30 min at 25° C., filtered and the cake was washed with EtOAc (50 mL), the filtrate was concentrated to give 15d (3 g, 9.7 mmol, 81.82% yield) as yellow solid. $^1H$ NMR ($CDCl_3$, 400 MHz) δ 7.21 (s, 1H), 6.68 (s, 1H), 4.60 (s, 2H), 1.51 (s, 9H).

Preparation of tert-butyl N-(5-bromo-2-formyl-3-thienyl)carbamate, 15e

To a solution of 15d (3 g, 9.73 mmol, 1 eq) in DCM (30 mL) was added $MnO_2$ (8.5 g, 97.34 mmol, 10 eq) at 25° C. The mixture was stirred at 50° C. for 12 h. The mixture was filtered and concentrated to give 15e (1.5 g, 4.90 mmol, 50.33% yield) as yellow solid. $^1H$ NMR ($CDCl_3$, 40) MHz) δ 9.82 (s, 1H), 9.51 (s, 1H), 8.03 (s, 1H), 1.53 (s, 9H).

Preparation of ethyl (E)-3-[5-bromo-3-(tert-butoxycarbonylamino)-2-thienyl]-2-(cyanomethyl)prop-2-enoate, 15f To a solution of 15e (1.5 g, 4.90 mmol, 1 eq) in toluene (15 mL) was added ethyl 3-cyano-2-(triphenyl-phosphanylidene)propanoate (2.5 g, 6.4 mmol, 1.3 eq) at 25° C., and then stirred at 75° C. for 2 h. The mixture was concentrated and the residue was purified by flash silica gel chromatography (ISCO®, 2 g SepaFlash® Silica Flash Colum, Eluent of 0-80% Ethyl acetate/Petroleum ether gradient @45 mL/min) to give 15f (1.65 g, 3.97 mmol, 81.10% yield) as yellow solid. $^1H$ NMR ($CDCl_3$, 400 MHz) δ 7.81 (s, 1H), 7.73 (s, 1H), 6.72 (s, 1H), 4.35 (q, J=7.2 Hz, 2H), 3.68 (s, 2H), 1.54 (s, 9H), 1.39 (t, J=7.2 Hz, 3H).

Preparation of ethyl 5-amino-2-bromo-6H-thieno[3,2-b]azepine-7-carboxylate, 15g

To a solution of 15f (1.3 g, 3.13 mmol, 1 eq) in EtOAc (10 mL) was added HCl/EtOAc (4 M, 13.00 mL, 16.6 eq) at 25° C. The mixture was stirred at 25° C. for 2 h and then concentrated to give 15g (I g, crude) was obtained as yellow solid. $^1H$ NMR (DMSO-d&. 400 MHz) δ 10.13 (s, 1H), 9.29 (s, 1H), 7.91 (s, 1H), 7.37 (s, 1H), 4.24 (q, J=7.2 Hz, 2H), 3.52 (s, 2H), 1.28 (t, J=7.2 Hz, 3H).

Preparation of 5-amino-2-bromo-6H-thieno[3,2-b]azepine-7-carboxylic acid, TAZ-15

To a solution of 15g (1 g, 3.17 mmol, 1 eq) in EtOH (10 mL) and $H_2O$ (1 mL) was added $LiOH{\cdot}H_2O$ (665 mg, 15.8 mmol, 5 eq) and then stirred at 25° C. for 12 h. The reaction mixture was concentrated under reduced pressure to remove EtOH. The residue was diluted with $H_2O$ (30 mL), and then the pH of mixture was adjusted to 4 by aq HCl (1 M), and extracted with EtOAc (20 mL×3). The organic layer was washed with brine (10 mL), dried over $Na_2SO_4$, filtered and concentrated to give TAZ-15 (0.85 g, 2.96 mmol, 93.30% yield) as yellow solid. $^1H$ NMR (DMSO-$d_6$, 400 MHz) δ 7.65 (s, 1H), 7.34 (br s, 2H), 6.97 (s, 1H), 2.97 (s, 2H).

Example 16 Synthesis of tert-butyl N-[4-[(5-amino-6H-thieno[3,2-b]azepine-7-carbonyl)-propyl-amino]but-2-ynyl]carbamate, TAZ-16

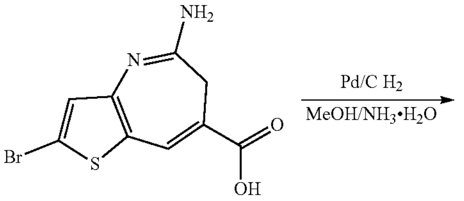

TAZ-15

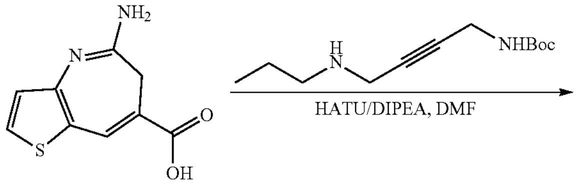

16a

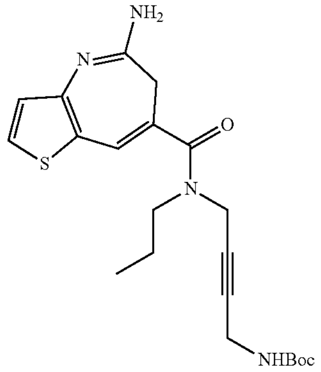

TAZ-16

Preparation of 5-amino-6H-thieno[3,2-b]azepine-7-carboxylic acid, 16a

To a solution of 5-amino-2-bromo-6H-thieno[3,2-b]azepine-7-carboxylic acid, TAZ-15 (1 g, 3.48 mmol, 1 eq) in MeOH (20 mL) was added Pd/C (10%, 0.2 g) and aqueous ammonium hydroxide, $NH_3{\cdot}H_2O$ (4.88 g, 34.8 mmol, 5.37 mL, 25% purity, 10 eq) under $N_2$. The suspension was degassed under vacuum and purged with $H_2$ several times, and then stirred under $H_2$ (50 psi) at 25° C. for 12 h. The reaction mixture was filtered through Celite® (Johns Manville) and the pH of filtrate was adjusted to ~6 with 2 N HCl at 0° C., and then concentrated under reduced pressure to remove MeOH. The solid was filtered and dried under reduced pressure to give 16a (0.54 g, 2.59 mmol, 74.46% yield) as a light yellow solid. $^1$H NMR (DMSO-d6, 400 MHz) δ 7.71 (s, 1H), 7.61 (d, J=5.2 Hz, 1H), 6.98 (br s, 2H), 6.83 (d, J=5.2 Hz, 1H), 2.91 (s, 2H).

Preparation of TAZ-16

To a solution of 16a (0.33 g, 1.58 mmol, 1 eq) in DMF (4 mL) was added HATU (662.82 mg, 1.74 mmol, 1.1 eq) and DIPEA (1.02 g, 7.92 mmol, 1.38 mL, 5 eq) at 0° C. After 10 min, tert-butyl N-[4-(propylamino)but-2-ynyl]carbamate (394.51 mg, 1.74 mmol, 1.1 eq) was added at 0° C., and then the resulting mixture was stirred at 25° C. for 30 min. The reaction mixture was quenched by addition of $H_2O$ (30 mL) at 0° C., and then extracted with EtOAc(15 mL×3). The combined organic layers were washed with brine (5 mL×3), dried over $Na_2SO_4$, filtered and concentrated under reduced pressure. The residue was purified by prep-HPLC (TFA condition; column: Phenomenex Luna C18 100*30 mm*5 um; mobile phase: [water(0.1% TFA)-ACN]; B %; 15%-45%, 10 min) to give TAZ-16 (0.185 g, 444.14 μmol, 28.03% yield) as a light yellow solid. $^1$H NMR (MeOD, 400 MHz) δ7.74 (d, J=5.6 Hz, 1H), 7.29 (s, 1H), 7.13 (d, J=5.6 Hz, 1H), 4.30 (s, 2H), 3.84 (s, 2H), 3.54-3.52 (m, 2H), 3.38 (s, 2H), 1.76-1.67 (m, 2H), 1.43 (s, 9H), 0.94 (t, J=7.6 Hz, 3H). LCMS [M+H] 417.2 (calculated); LC/MS [M+H] 417.2 (observed).

Example 17 Synthesis of 5-amino-N-(4-aminobut-2-ynyl)-N-propyl-6H-thieno[3,2-b]azepine-7-carboxamide, TAZ-17

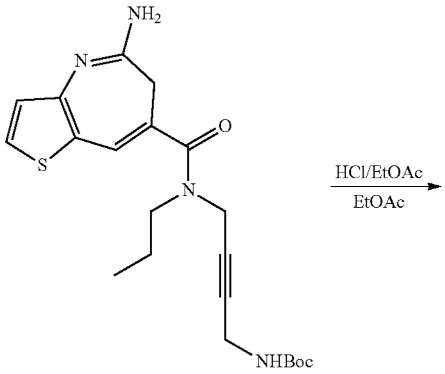

TAZ-16

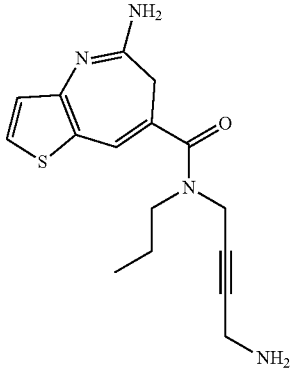

TAZ-17

To a solution of tert-butyl N-[4-[(5-amino-6H-thieno[3,2-b]azepine-7-carbonyl)-propyl-amino]but-2-ynyl]carbamate, TAZ-16 (0.45 g, 1.08 mmol, 1 eq) in EtOAc (2 mL) was added HCl/EtOAc (4 M, 15.00 mL, 55 eq) at 25° C. and then stirred for 0.5 h at this temperature. The reaction mixture was concentrated under reduced pressure to give TAZ-17 (496 mg, crude, HCl) as a light yellow solid. $^1$H NMR (MeOD, 400 MHz) δ7.76 (d, J=5.6 Hz, 1H), 7.23 (s, 1H), 7.15 (d, J=5.6 Hz, 1H), 4.40 (s, 2H), 3.87 (s, 2H), 3.57 (t, J=7.2 Hz, 2H), 3.40 (s, 2H), 1.81-1.65 (m, 2H), 0.95 (t, J=7.6 Hz, 3H). LC/MS [M+H] 317.1 (calculated); LC/MS [M+H] 317.1 (observed).

Example 18 Synthesis of 5-amino-2-phenyl-N,N-dipropyl-6H-thieno[3,2-b]azepine-7-carboxamide, TAZ-18

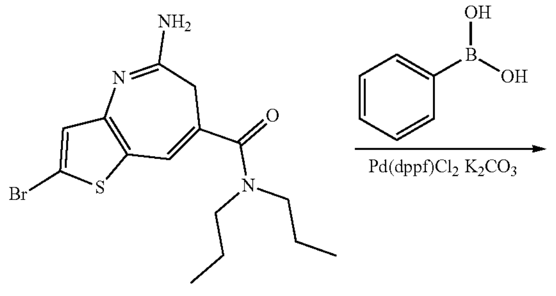

TAZ-1

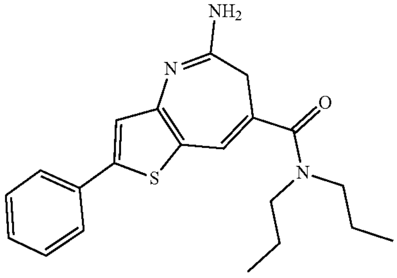

TAZ-18

To a mixture of phenylboronic acid (34.5 mg, 283 μmol, 1.5 eq), $K_2CO_3$ (52.0 mg, 378 μmol, 2.0 eq) and 5-amino-2-bromo-N,N-dipropyl-6H-thieno[3,2-b]azepine-7-carboxamide, TAZ-1 (70.0 mg, 190 μmol, 1.0 eq) in dioxane (2 mL) and $H_2O$ (0.2 mL) was added Pd(dppf)$Cl_2$ (7.0 mg, 9.45 μmol, 0.05 eq) at 25° C. under N2 and then stirred at 100° C. for 1 hours. The mixture was filtered and purified by prep-HPLC (column: Nano-micro Kromasil C18 100*30 mm 8 um; mobile phase: [water(0.1% TFA)-ACN]; B %: 25/6-50%, 10 min) to afford TAZ-18 (54 mg, 147 μmol, 77.7% yield) as white solid. $^1$H NMR (MeOD, 400 MHz) δ 7.69 (d, J=7.2 Hz, 2H), 7.49-7.37 (m, 4H), 7.11 (s, 1H), 3.54-3.38 (m, 6H), 1.68 (sxt, J=7.4 Hz, 4H), 0.99-0.92 (m, 6H). LC/MS [M+H] 368.2 (calculated); LC/MS [M+H] 368.1 (observed).

Example 19 Synthesis of 5-amino-N,N-dipropyl-2-(1-((2-(trimethylsilyl)ethoxy)methyl)-1H-pyrazol-4-yl)-6H-thieno[3,2-b]azepine-7-carboxamide, TAZ-19

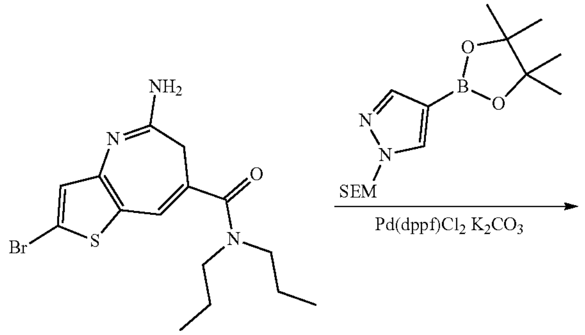

TAZ-1

-continued

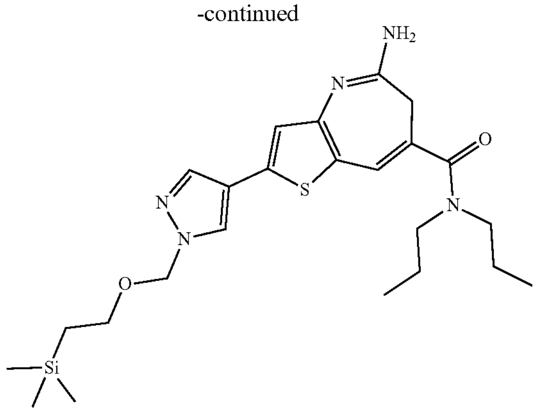

TAZ-19

To a mixture of 5-amino-2-bromo-N,N-dipropyl-6H-thieno[3,2-b]azepine-7-carboxamide, TAZ-1 (100 mg, 270 μmol, 1.0 eq), $K_2CO_3$ (75.0 mg, 540 μmol, 2.0 eq) and trimethyl-[2-[[4-(4,4,5,5-tetramethyl-1,3,2-dioxaborolan-2-yl)pyrazol-1-yl]methoxy]ethyl]silane (96 mg, 297 μmol, 1.1 eq) in dioxane (3 mL) and $H_2O$ (0.2 mL) was added Pd(dppf)$Cl_2$ (9.88 mg, 13.50 μmol, 0.05 eq) at 25° C. under $N_2$ and then stirred at 95° C. for 1 hours. The mixture was filtered and concentrated in vacuum. The residue was purified by prep-HPLC (column: Phenomenex Gemini-NX C18 75*30 mm*3 um; mobile phase: [water(10 mM $NH_4HCO_3$)-ACN]; B %: 40%-60%, 10.5 min) to afford TAZ-19 (80 mg, 164 μmol, 60.7% yield) as light yellow solid. $^1$H NMR (MeOD, 400 MHz) δ 8.09 (s, 1H), 7.80 (s, 1H), 6.97 (s, 1H), 6.85 (s, 1H), 5.45 (s, 2H), 3.61 (t, J=8.0 Hz, 2H), 3.46-3.36 (m, 4H), 2.96 (s, 2H), 1.72-1.57 (m, 4H), 0.90 (t, J=8.0 Hz, 8H), 0.00 (s, 9H). LC/MS [M+H] 488.2 (calculated); LC/MS [M+H] 488.2 (observed).

Example 20 Synthesis of methyl 5-amino-7-(dipropylcarbamoyl)-6H-thieno[3,2-b]azepine-2-carboxylate, TAZ-20

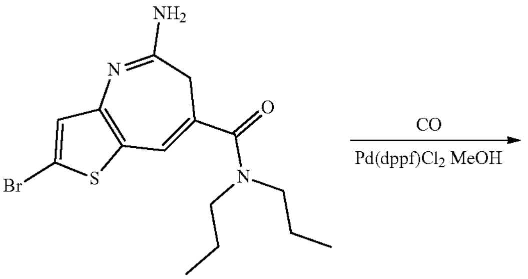

TAZ-1

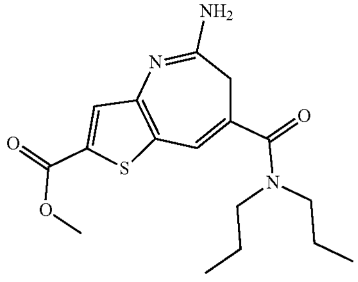

TAZ-20

To a solution of 5-amino-2-bromo-N,N-dipropyl-6H-thieno[3,2-b]azepine-7-carboxamide, TAZ-1 (1.2 g, 3.24 mmol, 1.0 eq) and $Et_3N$ (984 mg, 9.72 mmol, 1.35 mL, 3 eq) in MeOH (20 mL) was added Pd(dppf)$Cl_2$ (118.56 mg, 162.03 μmol, 0.05 eq) under N2. The suspension was degassed under vacuum and purged with CO several times. The mixture was stirred under CO (50 psi) at 80° C. for 12 hours. The mixture was filtered and concentrated in vacuum to afford TAZ-20 (1.1 g, 3.15 mmol, 97.14% yield) as white solid. IH NMR (MeOD, 400 MHz) δ 7.72 (s, 1H), 7.14 (s, 1H), 3.92 (s, 3H), 3.58-3.37 (m, 6H), 1.69-1.62 (m, 4H), 0.99-0.90 (m, 6H). LC/MS [M+H] 350.2 (calculated); LC/MS [M+H] 350.2 (observed).

Example 21 Synthesis of 5-amino-N,N-dipropyl-2-(1H-pyrazol-4-yl)-6H-thieno[3,2-b]azepine-7-carboxamide, TAZ-21

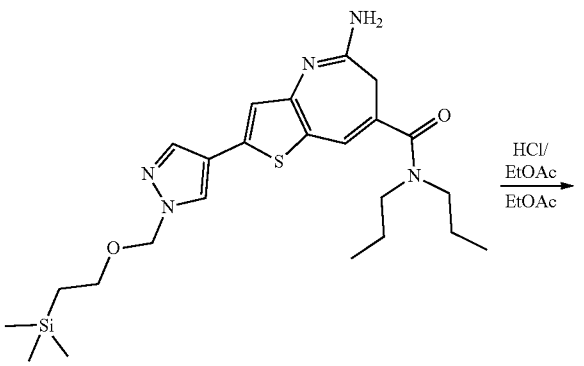

TAZ-19

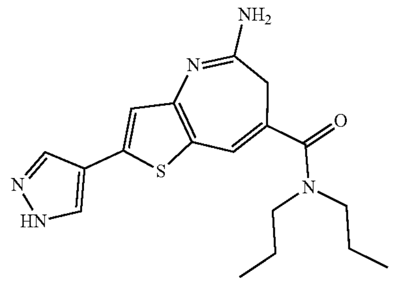

TAZ-21

To a mixture of 5-amino-N,N-dipropyl-2-1 1-(2-trimethylsilylethoxymethyl) pyrazol-4-yl]-6H-thieno[3,2-b] azepine-7-carboxamide, TAZ-19 (66.0 mg, 135 μmol, 1.0 eq) in MeOH (4 mL) was added HCl/MeOH (4 M, 338 μL, 10.0 eq) at 25° C. and then stirred for 12 hours at this temperature. The mixture was concentrated in vacuum, and the residue was purified by prep-HPLC (column: Phenomenex Gemini-NX C18 75*30 mm*3 um; mobile phase: [water(10 mM $NH_4HCO_3$)-ACN]; B %: 20%-50%, 10.5 min) to afford TAZ-21 (22 mg, 61.5 μmol, 45.5% yield) as white solid. $^1$H NMR (MeOD, 400 MHz) δ 7.87 (s, 2H), 6.95 (s, 1H), 6.85 (s, 1H), 3.44-3.35 (m, 4H), 2.96 (s, 2H), 1.66-1.60 (m, 4H), 0.99-0.89 (m, 6H). LC/MS [M+H] 358.2 (calculated), LC/MS [M+H] 358.2 (observed).

Example 22 Synthesis of 5-amino-7-(dipropylcarbamoyl)-6H-thieno[3,2-b]azepine-2-carboxylic acid, TAZ-22

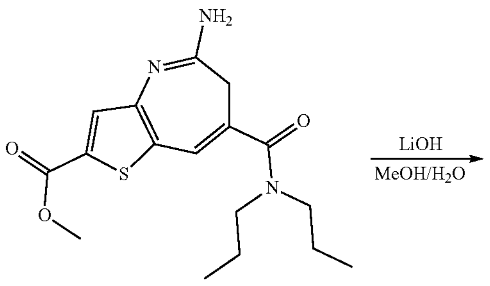

TAZ-20

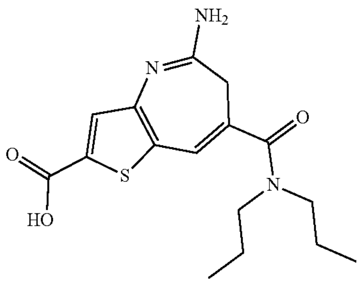

TAZ-22

To a mixture of methyl 5-amino-7-(dipropylcarbamoyl)-6H-thieno[3,2-b]azepine-2-carboxylate, TAZ-20 (1.1 g, 3.15 mmol, 1.0 eq) in MeOH (20 mL) was added LiOH—$H_2O$ (396 mg, 9.44 mmol, 3.0 eq) in $H_2O$ (5 mL) at 25° C. and then stirred for 2 hours at this temperature. The mixture was quenched with aq HCl (4 M) until pH to 5, off-white solid precipitated from the mixture and then filtered to give TAZ-22 (0.85 g, 2.53 mmol, 80.5% yield) as off white solid. $^1$H NMR (MeOD, 400 MHz) δ 7.41 (s, 1H), 6.92 (s, 1H), 3.37-3.25 (m, 4H), 3.05 (s, 2H), 1.61-1.45 (m, 4H), 0.86-0.75 (m, 6H). LC/MS [M+H] 336.1 (calculated); LC/MS [M+H] 336.1 (observed).

Example 23 Synthesis of 5-amino-N2-phenyl-N7, N7-dipropyl-6H-thieno [3,2-b]azepine-2,7-dicarboxamide, TAZ-23

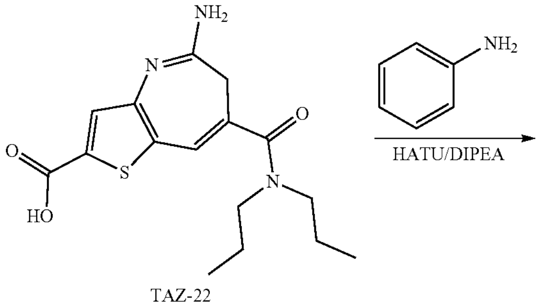

TAZ-22

-continued

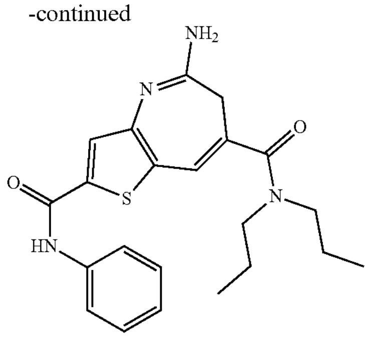

TAZ-23

To a mixture of 5-amino-7-(dipropylcarbamoyl)-6H-thieno[3,2-b]azepine-2-carboxylic acid, TAZ-22 (50 mg, 150 μmol, 1.0 eq) HATU (62 mg, 164 μmol, 1.1 eq) and DIEA (58 mg, 447 μmol, 3.0 eq) in DMF (1 mL) was added aniline (28 mg, 298 μmol, 2.0 eq) at 25° C. and then stirred at 25° C. for 30 min. The mixture was filtered and purified by prep-HPLC (column: Nano-micro Kromasil C18 100*30 mm 8 um; mobile phase: [water(0.1% TFA)-ACN]; B %: 10%-40%, 10 min) to give TAZ-23 (34 mg, 82.8 μmol, 55.6% yield) as white solid. $^1$H NMR (MeOD, 400 MHz) δ 7.87 (s, 1H), 7.67 (d, J=8.0 Hz, 2H), 7.38 (t, J=8.0 Hz, 2H), 7.18 (d, J=8.0 Hz, 1H), 7.15 (s, 1H), 3.49-3.42 (m, 6H), 1.70-1.65 (m, 4H), 0.98-0.90 (m, 6H). LC/MS [M+H] 411.2 (calculated); LC/MS [M+H] 411.1 (observed).

Example 24 Synthesis of 5-amino-N2-ethyl-N7,N7-dipropyl-6H-thieno[3,2-b]azepine-2,7-dicarboxamide, TAZ-24

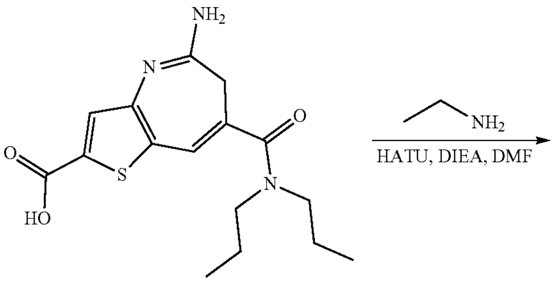

TAZ-1

-continued

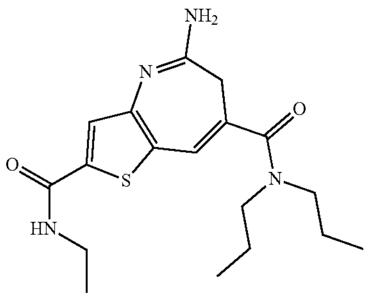

TAZ-24

To a mixture of 5-amino-7-(dipropylcarbamoyl)-6H-thieno[3,2-b]azepine-2-carboxylic acid, TAZ-1 (50 mg, 149 μmol, 1.0 eq), HATU (62.4 mg, 164 μmol, 1.1 eq) and DIEA (58 mg, 447 μmol, 3.0 eq) in DMF (1 mL) was added ethanamine (20 mg, 298 μmol, 2.0 eq) at 25° C. and then stirred for 0.5 hours at this temperature. The mixture was filtered and purified by prep-HPLC (column: Nano-micro Kromasil C18 100*30 mm 8 um; mobile phase: [water(0.1% TFA)-ACN]; B %: 5%-35%, 10 min). Afforded TAZ-24 (28 mg, 77.2 μmol, 51.8% yield) as white solid. $^1$H NMR (MeOD, 400 MHz) δ 7.62 (s, 1H), 7.13 (s, 2H), 3.54-3.35 (m, 8H), 1.73-1.61 (m, 4H), 1.23 (t, J=7.2 Hz, 3H), 0.97-0.90 (m, 6H). LC/MS [M+H] 363.2 (calculated), LC/MS [M+H] 363.2 (observed).

Example 25 Synthesis of 3-[2-[2-[2-[2-[2-[2-[2-[2-[2-[2-[5-[5-amino-7-(dipropylcarbamoyl)-6H-thieno[3,2-b]azepin-2-yl]pentyl-methylamino]ethoxy]ethoxy]ethoxy]ethoxy]ethoxy]ethoxy]ethoxy]ethoxy]ethoxy]ethoxy]propanoic acid, TAZ-25

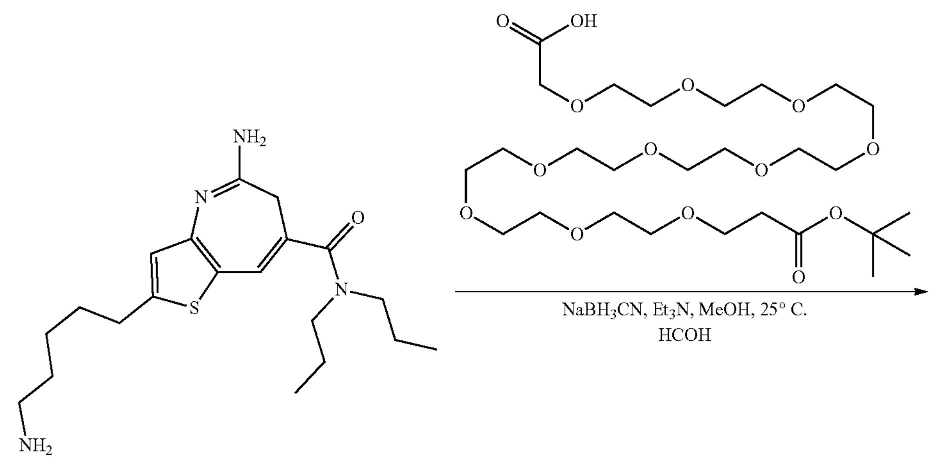

TAZ-14

-continued

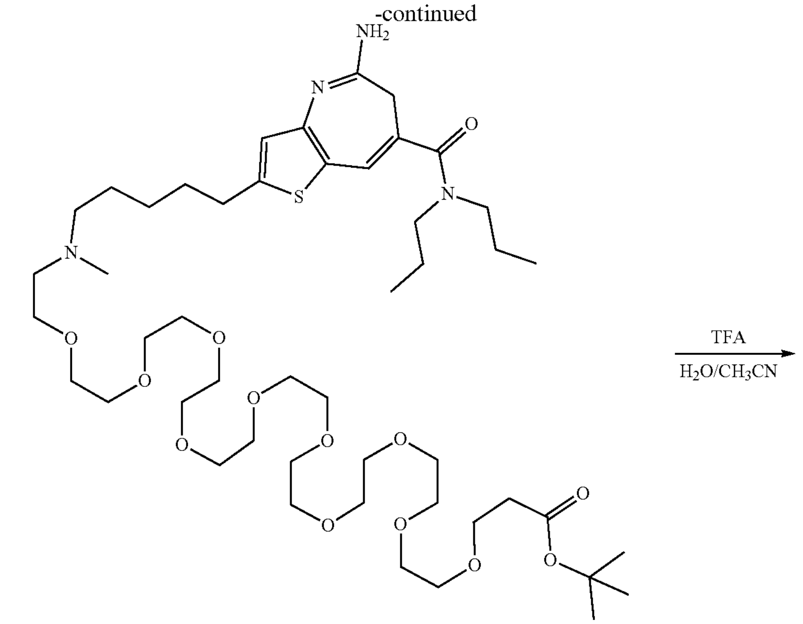

25a

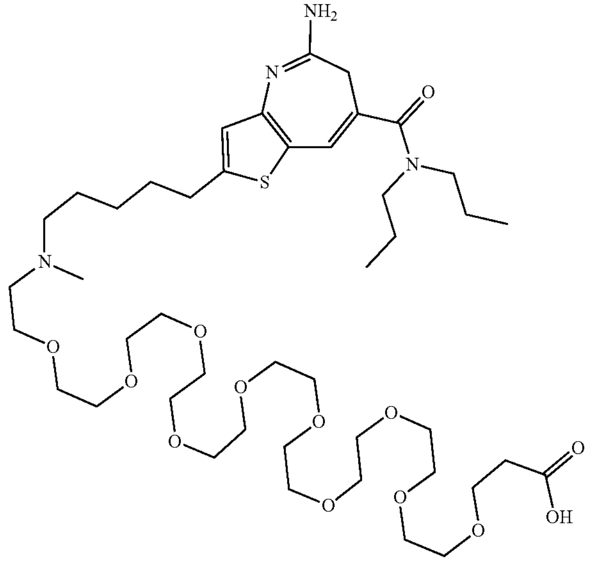

TAZ-25

Preparation of tert-butyl 3-[2-[2-[2-[2-[2-[2-[2-[2-[2-[2-[5-[5-amino-7-(dipropylcarbamoyl)-6H-thieno[3,2-b]azepin-2-yl]pentyl-methylamino]ethoxy]ethoxy]ethoxy]ethoxy]ethoxy]ethoxy]ethoxy]ethoxy]ethoxy]ethoxy]propanoate, 25a To a solution of 5-amino-2-(5-aminopentyl)-N,N-dipropyl-6H-thieno[3,2-b]azepine-7-carboxamide, TAZ-14 (0.2 g, 484 μmol, 1.0 eq, HCl) in MeOH (80 mL) was added $Et_3N$ (73.5 mg, 726 μmol, 101 μL, 1.5 eq) and tert-butyl 3-[2-[2-[2-[2-[2-[2-[2-[2-[2-(2-oxoethoxy) ethoxy]ethoxy]ethoxy]ethoxy]ethoxy]ethoxy]ethoxy]ethoxy]ethoxy]propanoate (368.1 mg, 629 μmol, 1.3 eq) at 25° C. The mixture was stirred at 25° C. for 10 min, then $NaBH_3CN$ (60.8 mg, 968 μmol, 2.0 eq) was added and it was stirred at the same temperature for 16 hours. Formaldehyde (117.9 mg, 1.45 mmol, 108 μL, 3.0 eq) was added followed by $NaBH_3CN$ (60.9 mg, 968 μmol, 2.0 eq) and then stirred at 25° C. for 2 hours. The mixture was concentrated and the residue was purified by prep-HPLC (column: Xtimate C18 100*30 mm*3 um; mobile phase: [water (0.1% TFA)-ACN]: B %: 15%-50/, 10 min) to give 25a (0.4 g, 416.98 μmol, 86.11% yield) as colorless oil.

Preparation of TAZ-25

To a solution of 25a (0.39 g, 406 μmol, 1.0 eq) in $H_2O$ (20 mL) was added TFA (927 mg, 8.13 mmol, 602 μL, 20 eq) at 25° C. The mixture was stirred at 85° C. for 1 hour and then concentrated under reduced pressure at 50° C. The residue purified by prep-HPLC (column: Nano-micro Kromasil C18 100*30 mm 8 um; mobile phase: [water (0.1% TFA)-ACN]; B %: 1°%-30%, 15 min) to afford TAZ-25 (0.18 g, 199.30 μmol, 49.02% yield) as light yellow oil. $^1H$ NMR (MeOD, 400 MHz) δ 7.02 (s, 1H), 6.90 (s, 1H), 3.84-3.82 (m, 2H), 3.75-3.59 (m, 41H), 3.45-3.42 (m, 4H), 3.35 (s, 2H), 2.96-2.87 (m, 5H), 2.54 (t, J=6.4 Hz, 2H), 1.84-1.76 (m, 4H), 1.71-1.60 (m, 4H), 1.54-1.44 (m, 2H), 0.94-0.89 (m, 6H). LC/MS [M+H] 903.5 (calculated); LC/MS [M+H] 903.5 (observed).

Example 26 Synthesis of 5-amino-2-benzyl-N,N-dipropyl-6H-thieno[3,2-b]azepine-7-carboxamide, TAZ-26

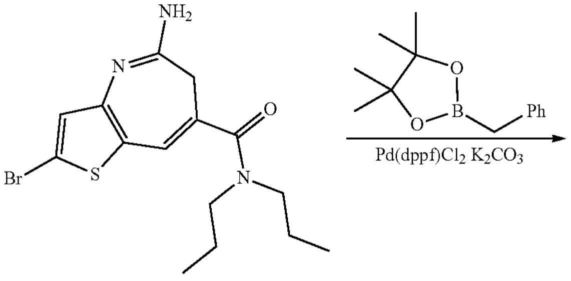

TAZ-1

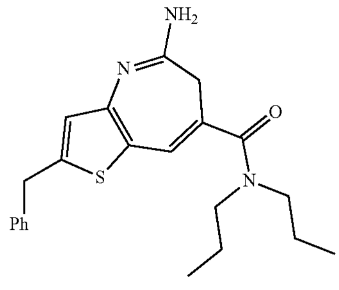

TAZ-26

To a mixture of 5-amino-2-bromo-N,N-dipropyl-6H-thieno[3,2-b]azepine-7-carboxamide, TAZ-1 (0.11 g, 297 μmol, 1.0 eq), $K_KCO_3$ (82 mg, 594 μmol, 2 eq) and 2-benzyl-4,4,5,5-tetramethyl-1,3,2-dioxaborolane (324 mg, 1.49 mmol, 5.0 eq) in DMF (3 mL) and $H_2O$ (0.2 mL) was added Pd(dppf)$Cl_2$ (11 mg, 14.8 μmol, 0.05 eq) at 25° C. under $N_2$. The mixture was stirred at 120° C. for 2 hours and then filtered and concentrated. The residue was purified by prep-HPLC (column: Xtimate C18 100*30 mm*3 um; mobile phase: [water(0.1% TFA)-ACN]; B %: 25%-45%, 10 min) to give TAZ-26 (16 mg, 41.9 μmol, 14.1% yield) as light yellow solid. $^1$H NMR (MeOD, 400 MHz) δ 7.40-7.21 (m, 5H), 6.98 (s, 1H), 6.88 (s, 1H), 4.17 (s, 2H), 3.41 (t, J=7.6 Hz, 4H), 3.34 (s, 2H), 1.66-1.62 (m, 4H), 0.96-0.86 (m, 6H). LC/MS [M+H] 382.2 (calculated); LC/MS [M+H] 382.1 (observed).

Example 27 Synthesis of 5-amino-N7,N7-dipropyl-N2-pyrimidin-5-yl-6H-thieno[3,2-b]azepine-2,7-dicarboxamide, TAZ-27

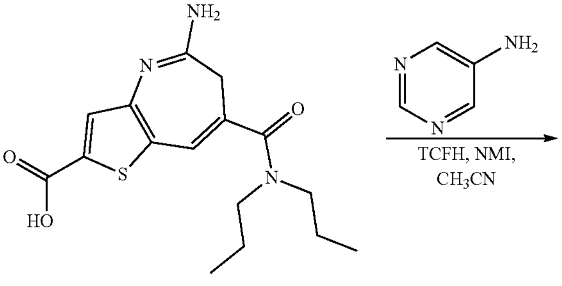

TAZ-22

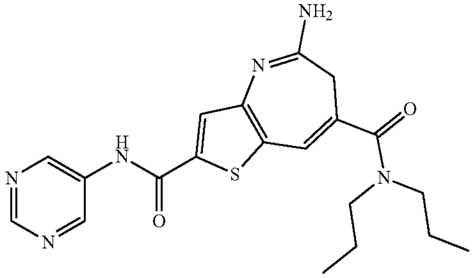

TAZ-27

To a mixture of 5-amino-7-(dipropylcarbamoyl)-6H-thieno[3,2-b]azepine-2-carboxylic acid, TAZ-22 (50 mg, 149 μmol, 1 eq), pyrimidin-5-amine (18.4 mg, 194 μmol, 1.3 eq) and 1-methylimidazole (42.8 mg, 522 μmol, 3.5 eq) in $CH_3CN$ (2 mL) was added chloro-N,N,N',N'-tetramethyl-formamidinium hexafluorophosphate, TCFH (50.19 mg, 179 μmol, 1.2 eq) at 25° C., and then stirred for 16 h at this temperature. The reaction mixture was quenched by addition of $H_2O$ (10 mL) at 0° C., and then extracted with EtOAc (10 mL×3). The combined organic layers were washed with brine (5 mL), dried over $Na_2SO_4$, filtered and concentrated under reduced pressure. The residue was purified by prep-HPLC (TFA condition; column: Phenomenex Luna C18 100*30 mm*5 um; mobile phase: [water(0.1% TFA)-ACN]; B %: 10%-40%, 10 min) to give TAZ-27 (13 mg, 31.5 μmol, 21.14% yield) as off-white solid. $^1$H NMR (MeOD, 400 MHz) δ9.17 (s, 2H), 8.94 (s, 1H), 7.90 (s, 1H), 7.18 (s, 1H), 3.54-3.40 (m, 6H), 1.76-1.59 (m, 4H), 0.99-0.90 (m, 6H). LC/MS [M+H] 413.2 (calculated); LC/MS [M+H] 413.1 (observed).

Example 28 Synthesis of 2-amino-N,N-dipropyl-3H-benzo[4,5]thieno[3,2-b]azepine-4-carboxamide, TAZ-28

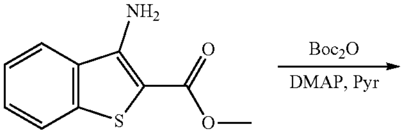

28a

-continued

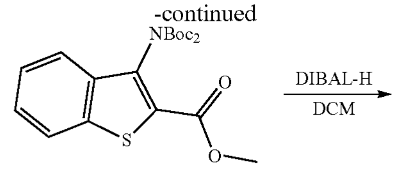

28b

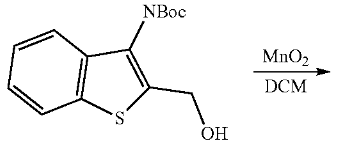

28c

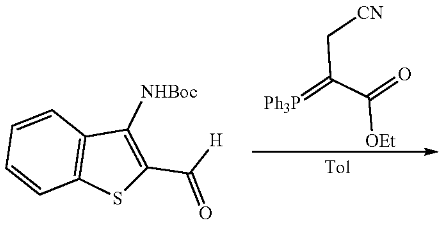

28d

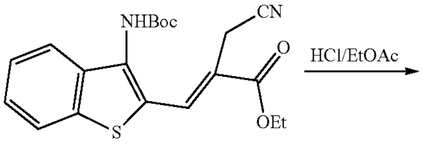

28e

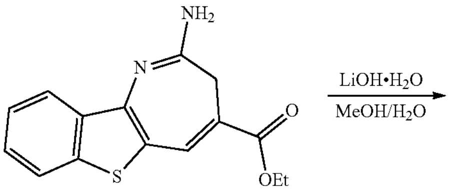

28f

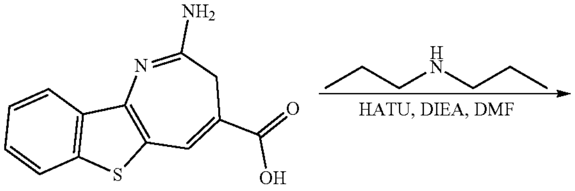

28g

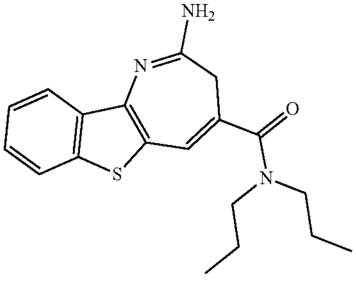

TAZ-28

Preparation of methyl 3-[bis(tert-butoxycarbonyl) amino]benzothiophene-2-carboxylate, 28b To a mixture of methyl 3-aminobenzothiophene-2-carboxylate, 28a (3 g, 14.5 mmol, 1.0 eq) in pyridine, Pyr (30 mL) was added DMAP (177 mg, 1.45 mmol, 0.1 eq). Then a solution of $Boc_2O$ (6.32 g, 29.0 mmol, 6.65 mL, 2.0 eq) in pyridine (10 mL) was added to the mixture slowly at 0° C. and then stirred at 25° C. for 16 h. The mixture was concentrated in vacuum. The residue was dissolved in EtOAc(20 ml) and washed successively with aqueous sat. $NaHCO_3$ and brine. The mixture was dried over $Na_2SO_4$, filtered and concentrated. The residue was purified by silica gel chromatography (Petroleum ether/Ethyl acetate=1/0, 5/1) to afford methyl 3-[bis(tert-butoxycarbonyl)amino]benzothiophene-2-carboxylate (5.6 g, 13.7 mmol, 94.94% yield) as yellow solid. $^1$H NMR ($CDCl_3$, 400 MHz) δ7.83 (d, J=7.6 Hz, 1H), 7.68 (d, J=7.6 Hz, 1H), 7.52-7.42 (m, 2H), 3.94 (s, 3H), 1.35 (s, 18H).

Preparation of tert-butyl N-[2-(hydroxymethyl)benzothiophen-3-yl]carbamate, 28c

To a mixture of 28b (3.8 g, 9.33 mmol, 1.0 eq) in DCM (40 mL) was added DIBAL-H (1 M, 37.3 mL, 4.0 eq) slowly at 0° C. under N2 and then stirred at the same temperature for 2 h. The reaction was quenched with water (2 mL) and dried over $Na_2SO_4$, filtered and concentrated. The residue was purified by silica gel chromatography (Petroleum ether/Ethyl acetate=1/0, 3/1) to afford 28c (2.3 g, 8.23 mmol, 88.29% yield) as yellow solid. $^1$H NMR ($CDCl_3$, 400 MHz) δ 7.83-7.78 (m, 1H), 7.63 (dd, J=2.0, 6.8 Hz, 1H), 7.43-7.35 (m, 2H), 4.75 (d, J=6.4 Hz, 2H), 1.55 (s, 9H).

Preparation of tert-butyl N-[2-formylbenzothiophen-3-yl)carbamate, 28d

To a solution of 28c (1.8 g, 6.44 mmol, 1.0 eq) in DCM (30 mL) was added $MnO_2$ (4.48 g, 51.6 mmol, 8.0 eq) in one portion at 25° C. and then stirred for 12 h. The reaction was filtered and concentrated. The residue was purified by column chromatography ($SiO_2$, Petroleum ether/Ethyl acetate=1/0 to 5/1) to afford 28d (1.2 g, 4.33 mmol, 67.15% yield) as yellow solid. $^1$H NMR ($CDCl_3$. 400 MHz) δ 10.07 (s, 1H), 8.22 (s, 1H), 8.10 (d, J=8.0 Hz, 1H), 7.83 (d, J=8.0 Hz, 1H), 7.55-7.50 (m, 1H), 7.47-7.43 (m, 1H), 1.57 (s, 9H).

Preparation of ethyl (E)-3-[3-(tert-butoxycarbonylamino)benzothiophen-2-yl]-2-(cyanomethyl) prop-2-enoate, 28e To a solution of 28d (0.6 g, 2.16 mmol, 1.0 eq) and ethyl 3-cyano-2-(triphenyl-phosphanylidene)propanoate (1.09 g, 2.81 mmol, 1.3 eq) in toluene (15 mL) at 25° C. and it was stirred at 80° C. for 12 h. Then the mixture was concentrated. The residue was diluted with water and extracted with EtOAc(30 mLx3). The organic layer was washed with brine, dried over $Na_2SO_4$, filtered and concentrated. The residue was purified by silica gel chromatography (Petroleum ether/Ethyl acetate=1/0, 5/1) to afford 28e (0.6 g, 1.55 mmol, 71.88% yield) as yellow solid. $^1$H NMR (DMSO, 400 MHz) δ 8.08 (d, J=7.2 Hz, 1H), 8.00 (s, 1H), 7.78 (d, J=7.2 Hz, 1H), 7.56-7.47 (m, 2H), 4.28 (q, J=7.2 Hz, 2H), 3.90 (s, 2H), 1.47 (s, 9H), 1.29 (t, J=7.2 Hz, 3H).

Preparation of ethyl 2-amino-3H-benzothiopheno[3,2-b]azepine-4-carboxylate, 28f

To a solution of 28e (0.2 g, 518 μmol, 1.0 eq) in EtOAc (2 mL) was added HCl/EtOAc (10 mL) in one portion at 25°

C. and it was stirred at 50° C. for 12 h. The mixture was concentrated to give 28f (0.25 g, crude) as green solid.

Preparation of 2-amino-3H-benzothiopheno[3,2-b]azepine-4-carboxylic acid, 28g To a mixture of 28f (0.25 g, 774 μmol, 1.0 eq) in MeOH (6 mL) was added a solution of $LiOH{\cdot}H_2O$ (162 mg, 3.87 mmol, 5.0 eq) in $H_2O$ (1 mL) at 25° C. The mixture was stirred at 50° C. for 12 h. The mixture was quenched with aq. HCl (1M) until pH to 5, and then concentrated to remove MeOH. The desired solid precipitated from the mixture and then filtered to obtain 28g (0.15 g, crude) as yellow solid

Preparation of 2-amino-N,N-dipropyl-3H-benzo[4,5]thieno[3,2-b]azepine-4-carboxamide, TAZ-28

To a mixture of 28 gm (0.05 g, 194 μmol, 1.0 eq) in DMF (2 mL) was added HATU (88.3 mg, 232 μmol, 1.2 eq) and DIEA (125 mg, 968 μmol, 169 μL, 5.0 eq) and it was stirred at 25° C. for 2 min. N-propylpropan-1-anine (25.5 mg, 252 μmol, 34.7 μL, 1.3 eq) was added to the mixture and then stirred for 1 h. The reaction mixture was filtered and purified by prep-HPLC (column: Nano-micro Kromasil C18 100*30 mm Sum; mobile phase: [water (0.1% TFA)-ACN]; B %: 15%-45%, 10 min) to give TAZ-28 (19 mg, 55.64 μmol, 28.74% yield) as white solid. $^1H$ NMR (MeOD, 400 MHz) δ 8.00-7.92 (m, 2H), 7.58-7.53 (m, 2H), 7.18 (s, 1H), 3.48 (s, 6H), 1.74-1.65 (m, 4H), 0.94 (s, 6H). LC/MS [M+H] 342.2 (calculated); LC/MS [M+H] 342.2 (observed).

Example 29 Synthesis of tert-butyl (4-((5-amino-N-propyl-6H-thieno[3,2-b]azepine-7-carboxamido)methyl)benzyl)carbamate, TAZ-29

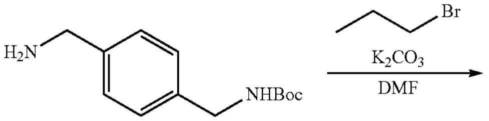

29a

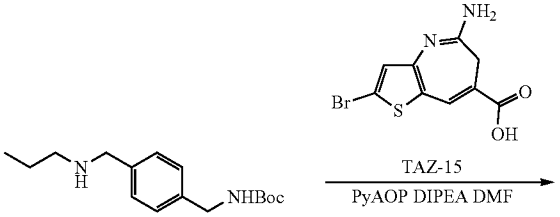

29b

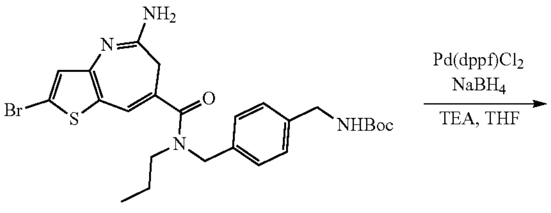

29c

-continued

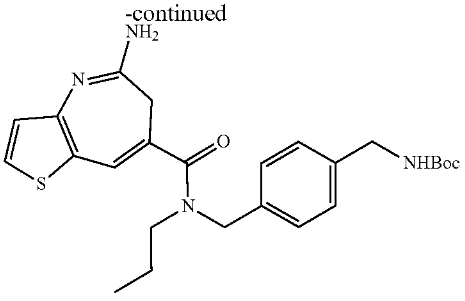

TAZ-29

Preparation of tert-butyl (4-((propylamino)methyl)benzyl)carbamate, 29b tert-Butyl (4-(aminomethyl)benzyl)carbamate, 29a (0.98 g, 4.15 mmol, 1 eq.) was dissolved in 10 ml DMF. Potassium carbonate (2.9 g, 20.7 mmol, 5 eq.) was added, followed by propyl bromide (0.38 ml, 4.15 mmol, 1 eq.). The reaction mixture was stirred for 2 hours, then filtered, concentrated, and purified by reverse-phase chromatography to give 29b (0.36 g, 1.29 mmol, 31%). LC/MS [M+H] 279.21 (calculated); LC/MS [M+H] 279.24 (observed).

Preparation of tert-butyl (4-((5-amino-2-bromo-N-propyl-6H-thieno[3,2-b]azepine-7-carboxamido)methyl)benzyl)carbamate, 29c 5-amino-2-bromo-6H-thieno[3,2-b]azepine-7-carboxylic acid, TAZ-15 (0.330 g, 1.15 mmol, 1 eq.) and 29b (0.32 g, 1.15 mmol, 1 eq.) were suspended in 5 ml DMF. DIPEA (1.2 ml, 6.9 mmol, 6 eq.) was added, followed by 7-aza-benzotriazol-1-yloxy-tripyrrolidino-phosphonium hexafluorophosphate, PyAOP (0.90 g, 1.72 mmol, 1.5 eq.). The reaction was monitored by LCMS. Upon consumption of starting material, the reaction mixture was added to 100 ml water, filtered, and the precipitate purified by flash chromatography (MeOH/DCM with 1% TEA) to give 29c (0.35 g, 0.64 mmol, 56%). LC/MS [M+H] 547.14/549.14 (calculated); LC/MS [M+H] 547.40/549.35 (observed).

Preparation of TAZ-29

Intermediate 29c (0.35 g, 0.64 mmol, 1 eq.) was dissolved in 5 ml THF. Triethylamine (0.89 ml, 6.4 mmol, 10 eq.) and [1,1'-bis(diphenylphosphino)ferocene]palladium(II) dichloride, $Pd(dppf)Cl_2$ (0.023 g, 0.032 mmol, 0.05 eq.) were added, followed by sodium borohydride (0.12 g, 3.2 mmol, 5 eq.). After 2 hours, another portion of sodium borohydride was added (0.073 g, 1.9 mmol, 3 eq.) and the reaction stirred for 30 minutes. The reaction mixture was concentrated and purified by HPLC to give TAZ-29 (0.129 g, 0.28 mmol, 43%). LC/MS [M+H) 469.23 (calculated), LU/MS [M+H] 469.42 (observed).

Example 30 Synthesis of 5-amino-N-(4-(aminomethyl)benzyl)-N-propyl-6H-thieno[3,2-b]azepine-7-carboxamide, TAZ-30

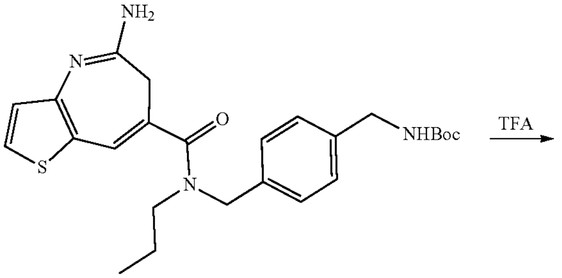

TAZ-29

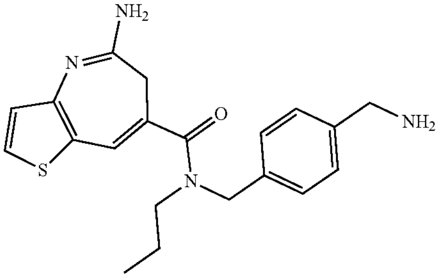

TAZ-30 tert-Butyl (4-((5-amino-N-propyl-6H-thieno[3,2-b]azepine-7-carboxamido)methyl)benzylcarbamate, TAZ-29 (0.129 g, 0.28 mmol, 1 eq.) was dissolved in 100 μl TFA. After 15 minutes, the product was concentrated and purified by HPLC to give TAZ-30 (0.063 g, 0.17 mmol, 61%). LC/MS [M+H] 547.14/549.14 (calculated); LC/MS [M+H] 547.40/%549.35 (observed).

Example 52 Synthesis of 5-amino-N-[[4-(aminomethyl)-2-(trifluoromethyl)phenyl]methyl]-N-propyl-6H-thieno[3,2-b]azepine-7-carboxamide, TAZ-52

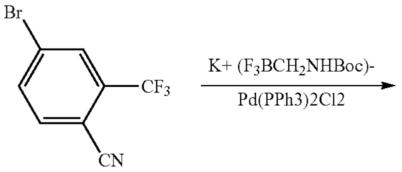

52a

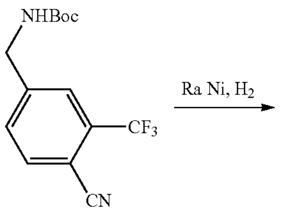

52b

-continued

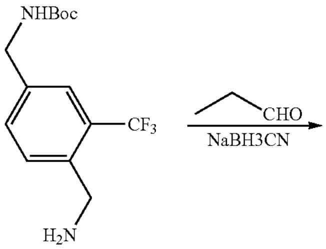

52c

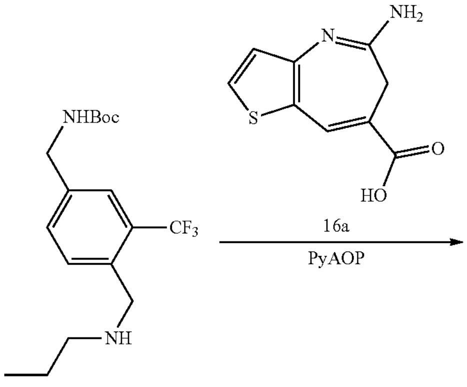

52d

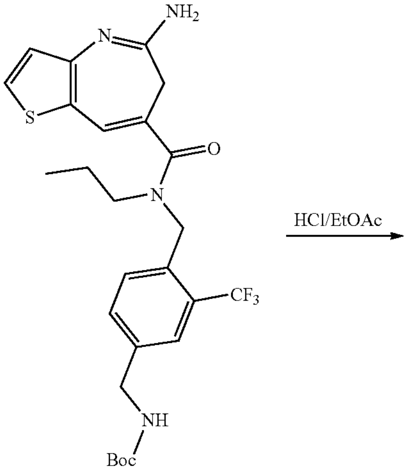

52e

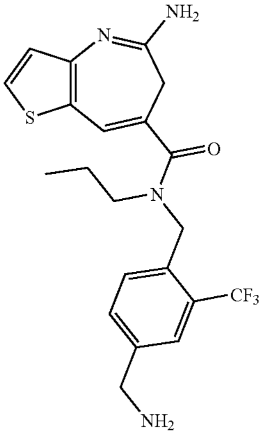

TAZ-52

Preparation of tert-butyl N-[[4-cyano-3-(trifluoromethyl)phenyl]methyl]carbamate, 52b To a mixture of 4-bromo-2-(trifluoromethyl)benzonitrile, 52a (0.5 g, 2.00 mmol, 1.0 eq), potassium;(tert-butoxycarbonylamino)methyl-trifluoro-boranuide, also known as potassium (((tert-butoxycarbonyl)amino)methyl)trifluoroborate, CAS Reg. No. 1314538-55-0 (711 mg, 3.00 mmol, 1.5 eq) and $Na_2CO_3$ (678 mg, 6.40 mmol, 3.2 eq) in EtOH (20 mL) and $H_2O$ (4 mL) was added $Pd(PPh_3)_2Cl_2$ (154 mg, 219 umol, 0.11 eq) under $N_2$. The suspension was degassed under vacuum and purged with $N_2$ several times and then stirred at 80° C. for 12 hours. The reaction was concentrated in vacuum to give a residue. The residue was poured into ice water (5 mL) and stirred for 5 min. The aqueous phase was extracted with ethyl acetate (5 mL×3). The combined organic phase was washed with brine (20 mL×2), dried with anhydrous $Na_2SO_4$, filtered and concentrated in vacuum. The residue was purified by silica gel chromatography (Petroleum ether/Ethyl acetate=10/1, 1/1) to afford 52b (0.5 g, 1.67 mmol, 83.2% yield) as yellow oil. $^1H$ NMR (MeOD, 400 MHz) δ 7.95 (d, J=6.8 Hz, 1H), 7.81 (s, 1H), 7.71 (d, J=6.8 Hz, 1H), 4.36 (s, 2H), 1.45 (s, 9H).

Preparation of tert-butyl N-[[4-(aminomethyl)-3-(trifluoromethyl)phenyl]methyl]carbamate, 52c To a solution of 52b (0.5 g, 1.67 mmol, 1.0 eq) in MeOH (10 mL) was added $NH_3 \cdot H_2O$ (17 mg, 166 umol, 33% purity, 0.1 eq) and Raney-Ni (1.43 g, 1.67 mmol, 10% purity, 1.0 eq) at 25° C. under $N_2$. The suspension was degassed under vacuum and purged with $H_2$ several times, is and then stirred under H2 (50 psi) at 25° C. for 10 hours. Then it was filtered and the filtrate was concentrated in vacuum. The residue was purified by silica gel chromatography (Petroleum ether/Ethyl acetate=10/1, 1/1) to afford 52c (200 mg, 657.23 umol, 39.47% yield) as yellow oil. $^1H$ NMR (MeOD, 400 MHz) S 6.99-6.92 (m, 2H), 6.89-6.86 (m, 1H), 3.62 (s, 2H), 2.66 (s, 2H), 0.80 (s, 9H)

Preparation of tert-butyl N-[[4-(propylaminomethyl)-3-(trifluoromethyl) phenyl]methyl]carbamate, 52d To a mixture of 52c (190 mg, 624 umol, 1 eq) in MeOH (2 mL) and THF (2 mL) was added propanal (47 mg, 812 umol, 1.3 eq), after 30 min, $NaBH_3CN$ (117 mg, 1.87 mmol, 3.0 eq) and AcOH (3 mg, 62 umol, 3 μL, 0.1 eq) was added at 25° C. and then stirred for 2 hours. The mixture was concentrated in vacuum. The residue was purified by prep-HPLC (column: Phenomenex Gemini-NX C18 75*30 mm*3 um; mobile phase: [water (10 mM $NH_4HCO_3$)-ACN]; B %: 30%-60%, 12 min) to afford 52d (100 mg, 277 umol, 44.39% yield, 96% purity) as white solid. $^1H$ NMR (MeOD, 400 MHz) δ 7.65-7.57 (m, 2H), 7.53-7.50 (m, 1H), 4.27 (s, 2H), 3.91 (s, 2H), 2.58 (t, J=7.6 Hz, 2H), 1.63-1.59 (m, 2H), 1.45 (s, 9H), 0.93 (t, J=7.2 Hz, 3H)

Preparation of tert-butyl N-[[4-[[(5-amino-6H-thieno[3,2-b]azepine-7-carbonyl)-propyl-amino]methyl]-3-(trifluoromethyl)phenyl]methyl]carbamate, 52e To a solution of 5-amino-6H-thieno[3,2-b]azepine-7-carboxylic acid, 16a (24.0 mg, 115 umol, 1.0 eq) in DMF (1 mL) was added DIEA (74 mg, 577 umol, 100 μL, 5 eq) and PyAOP (66 mg, 127 umol, 1.1 eq) in one portion at 25° C., and it was stirred for 30 min, then 52d (60 mg, 173.22 umol, 1.5 eq) was added and then stirred for another 2 hours. After that, the reaction was concentrated and purified by prep-HPLC(column: Phenomenex Synergi C18 150*25*10 um; mobile phase: [water (0.1% TFA)-ACN]; B %: 25%-50%, 10 min) to afford 52e (15 mg, 27.95 umol, 24.21% yield) as white solid. $^1H$ NMR (MeOD, 400 MHz) δ7.75-7.68 (m, 1H), 7.65 (s, 1H), 7.57 (d, J=7.6 Hz, 1H), 7.44 (d, J=7.6 Hz, 1H), 7.30-7.10 (m, 2H), 4.92 (s, 2H), 4.29 (s, 2H), 3.48 (t, J=7.2 Hz, 2H), 3.32 (s, 2H), 1.66-1.64 (m, 2H), 1.45 (s, 9H), 0.94-0.86 (m, 3H). LC/MS [M+H] 537.2 (calculated); LC/MS [M+H] 537.1 (observed).

Preparation of TAZ-52

To a solution of 52e (10 mg, 18.6 umol, 1.0 eq) in EtOAc (2 mL) was added HCl/EtOAc (4 M, 140 μL, 30 eq) in one portion at 25° C. The mixture was stirred at 25° C. for 3 hours. Followed, the mixture was concentrated to afford TAZ-52 (8 mg, 18.3 umol, 98.35% yield) as yellow solid. $^1H$ NMR (MeOD, 400 MHz) δ 7.80 (s, 1H), 7.70-7.63 (m, 2H), 7.51 (d, J=7.6 Hz, 1H), 7.20-7.17 (m, 1H), 7.03 (d, J=4.0 Hz, 1H), 4.85 (s, 2H), 4.13 (s, 2H), 3.45-3.37 (m, 2H), 3.31 (s, 2H), 1.62-1.50 (m, 2H), 0.87-0.68 (m, 3H). LC/MS [M+H] 437.2 (calculated); LC/MS [M+H] 437.1 (observed).

Example 54 Synthesis of 5-amino-N-[[4-(aminomethyl)-2-(trifluoromethyl)phenyl]methyl]-N-propyl-6H-thieno[3,2-b]azepine-7-carboxamide, TAZ-54

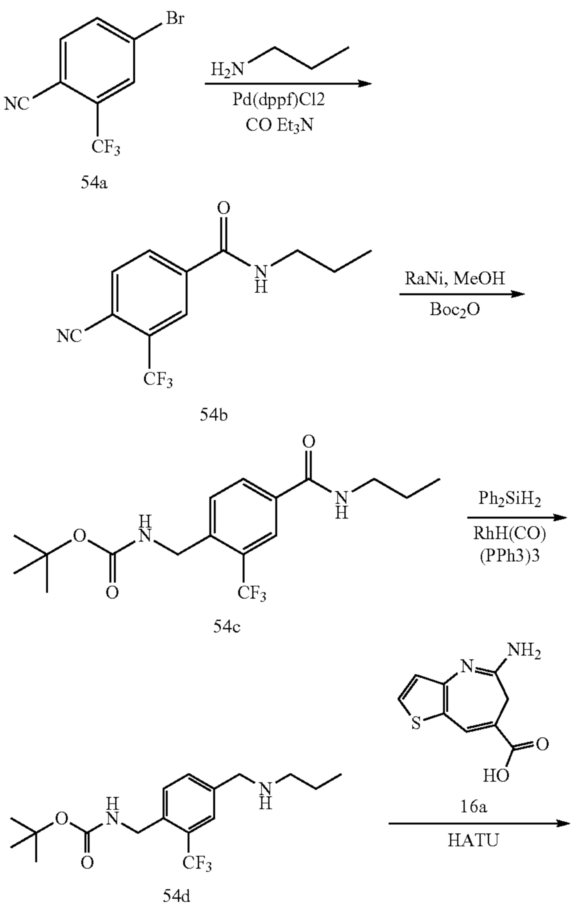

54a

54b

54c

16a

54d

-continued

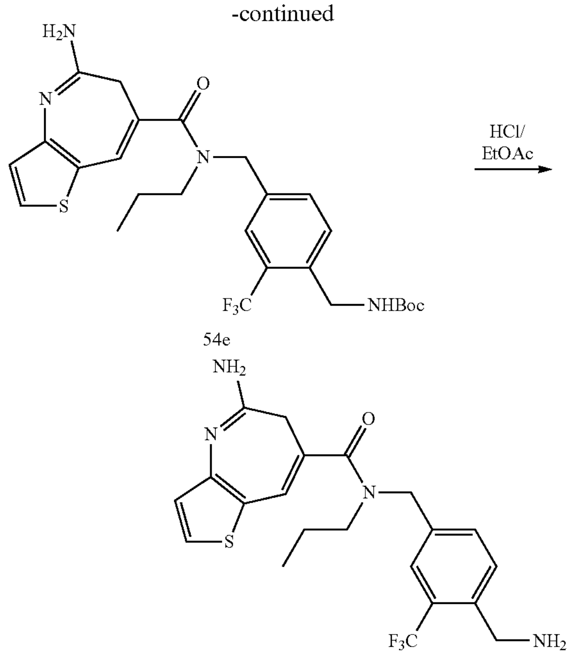

54e

TAZ-54

Hz, 1H), 6.26 (s, 1H), 5.02 (s, 1H), 4.53 (d, J=6.0 Hz, 2H), 3.44 (q, J=6.8 Hz, 2H), 1.70-1.62 (m, 2H), 1.46 (s, 9H), 1.00 (t, J=7.6 Hz, 3H).

Preparation of tert-butyl N-[[4-(propylaminomethyl)-3-(trifluoro methyl)phenyl]methyl]carbamate, 54d To a mixture of 54c (1.03 g, 2.86 mmol, 1.0 eq) and $RhH(CO)(PPh_3)_3$ (263 mg, 286 umol, 0.1 eq) in THF (30 mL) was added diphenylsilane (3.16 g, 17.1 mmol, 3.16 mL, 6.0 eq) in one portion at 20° C. under $N_2$, and then stirred at 20° C. for 8 hours. The reaction mixture was concentrated in vacuum, the residue was purified by silica gel chromatography (column height: 250 mm, diameter: 100 mm, 100-200 mesh silica gel, Petroleum ether/Ethyl acetate=10/1, 0/1 to Ethyl acetate/Methanol=5/1) to afford 54d (0.4 g, 1.15 mmol, 40.40% yield) as yellow oil. $^1$H NMR (400 MHz, MeOD) δ7.89 (s, 1H), 7.77 (d, J=8.0 Hz, 1H), 7.66 (d, J=8.0 Hz, 1H), 4.48 (s, 2H), 4.29 (s, 2H), 3.08-3.01 (m, 2H), 1.82-1.71 (m, 2H), 1.48 (s, 9H), 1.05 (t, J=7.6 Hz, 3H)

Preparation of tert-butyl N-[[4-[[(5-amino-6H-thieno[3,2-b]azepine-7-carbonyl)-propyl-amino]methyl]-3-(trifluoromethyl)phenyl]methyl]carbamate, 54e To a solution of 5-amino-6H-thieno[3,2-b]azepine-7-carboxylic acid, 16a (12.0 mg, 57.7 umol, 1.0 eq) in DMF (1 mL) was added HATU (19.7 mg, 52.0 umol, 0.9 eq) and $Et_3N$ (17.53 mg, 173 umol, 24.1 uL, 3.0 eq) at 20° C. under $N_2$, the mixture was stirred at 20° C. for 10 min, then 54d (20 mg, 57.7 umol, 1.0 eq) was added and then stirred at 20° C. for 2 hours. The reaction mixture was filtered, the filtrate was purified by prep-HPLC (column: Phenomenex Synergi C18 150*25*10 um; mobile phase: [water (0.1% TFA)-ACN]; B %: 30%-55%, 10 min) to afford 54e (5.00 mg, 7.47 umol, 12.9% yield, 97.1% purity, TFA) as white solid. $^1$H NMR (400 MHz, MeOD) δ7.74 (d, J=5.6 Hz, 1H), 7.60-7.52 (m, 3H), 7.22 (s, 1H), 7.12 (br d, J=5.6 Hz, 1H), 4.82 (br s, 2H), 4.45 (s, 2H), 3.51 (br t, J=7.2 Hz, 2H), 3.42-3.35 (m, 2H), 1.75-1.64 (m, 2H), 1.49 (s, 9H), 0.96-0.90 (m, 3H). LC/MS [M+H] 537.2 (calculated); LC/MS [M+H] 537.1 (observed).

Preparation of TAZ-54

To a solution of 54e (50.0 mg, 93.2 umol, 1.0 eq) in EtOAc (1 mL) was added HCl/EtOAc (4 M, 2.33 mL, 100 eq) at 20° C. and then stirred at 20° C. for 2 hours. The reaction is mixture was concentrated in vacuum and freeze-drying to afford TAZ-54 (30.0 mg, 62.8 umol, 67.4% yield, 99.0% purity, HCl) as yellow solid. $^1$H NMR (400 MHz, MeOD) δ7.67 (br s, 1H), 7.65-7.61 (m, 3H), 7.10 (s, 1H), 7.04 (d, J=5.2 Hz, 1H), 4.75 (s, 2H), 4.22 (s, 2H), 3.45-3.38 (m, 2H), 3.29 (br s, 2H), 1.63-1.52 (m, 2H), 0.79 (br t, J=7.2 Hz, 3H). LC/MS [M+H] 437.2 (calculated); LC/MS [M+H] 437.1 (observed).

Preparation of 4-cyano-N-propyl-2-(trifluoro methyl)benzamide, 54b

To a solution of 4-bromo-3-(trifluoromethyl)benzonitrile, 54a (4.00 g, 16.0 mmol, 1.0 eq) in DMF (20 mL) was added propan-1-amine (2.84 g, 48.0 mmol, 3.95 mL, 3.0 eq), $Et_3N$ (4.86 g, 48.0 mmol, 6.68 mL, 3.0 eq) and $Pd(dppf)Cl_2$ (585 mg, 800 umol, 0.05 eq) under $N_2$. The suspension was degassed under vacuum and purged with CO several times, and the mixture was stirred under CO (50 psi) at 80° C. for 15 hours. Water (50 mL) was added to the mixture and the aqueous phase was extracted with ethyl acetate (30 mL*3), the combined organic phase was washed with brine (50 mL), dried with anhydrous $Na_2SO_4$, filtered and concentrated in vacuum. The residue was purified by silica gel chromatography (column height: 250 mm, diameter: 100 mm, 100-200 mesh silica gel, Petroleum ether/Ethyl acetate=10/1, 1/1) to afford 54b (4.00 g, 15.6 mmol, 97.5% yield) as white solid. $^1$H NMR (400 MHz, $CDCl_3$) δ 8.13 (s, 1H), 8.01 (d, J=8.0 Hz, 1H), 7.85 (d, J=8.0 Hz, 1H), 6.49 (br s, 1H), 3.37 (q, J=7.2 Hz, 2H), 1.66-1.54 (m, 2H), 0.92 (t, J=7.2 Hz, 3H)

Preparation of tert-butyl N-[[4-(propyl carbamoyl)-3-(trifluoromethyl)phenyl]methyl]carbamate, 54c To a solution of 54b (2.30 g, 8.98 mmol, 1.0 eq) in MeOH (30 mL) was added Raney Ni (0.5 g, 1.0 eq) and $Boc_2O$ (9.80 g, 44.8 mmol, 10.3 mL, 5.0 eq) at 25° C. under $N_2$. The is suspension was degassed under vacuum and purged with H2 several times. The mixture was stirred under H2 (50 psi) at 25° C. for 5 hours. The reaction mixture was filtered and the filtrate was concentrated in vacuum. The residue was purified by silica gel chromatography (column height: 250 mm, diameter: 100 mm, 100-200 mesh silica gel, Petroleum ether/Ethyl acetate=10/1, 1/1) to afford 54c (2.50 g, 6.94 mmol, 77.2% yield) as white solid. $^1$H NMR (400 MHz, $CDCl_3$) δ 8.04 (s, 1H), 7.89 (d, J=8.0 Hz, 1H), 7.63 (d, J=8.0

Example 65 Synthesis of 5-amino-2-[5-(dimethylamino)pentyl]-N-[[4-(methylaminomethyl)phenyl]methyl]-N-propyl-6H-thieno[3,2-b]azepine-7-carboxamide, TAZ-65

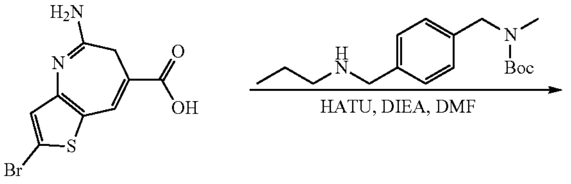

65a

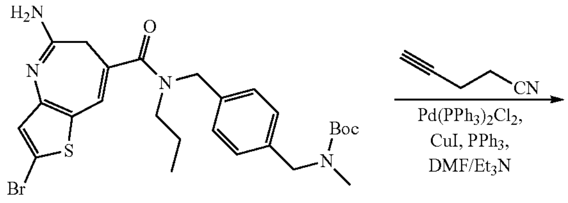

65b

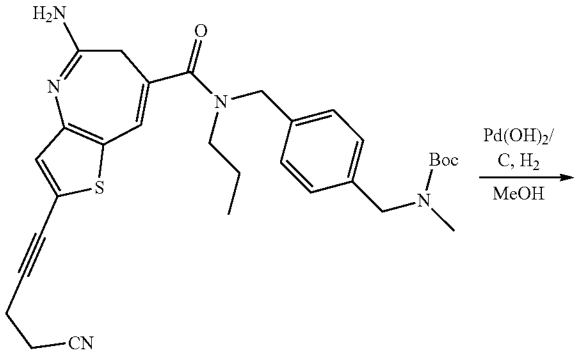

65c

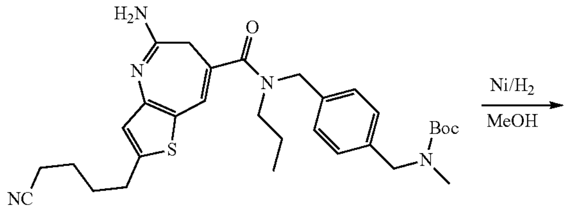

65d

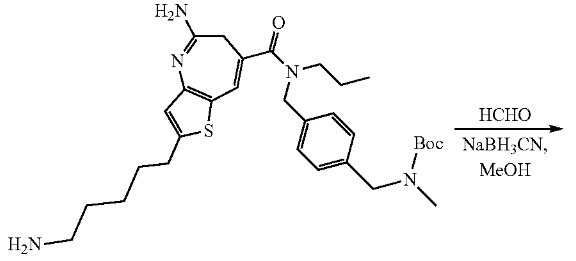

65e

-continued

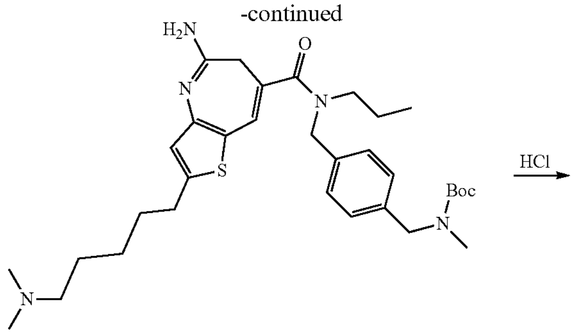

65f

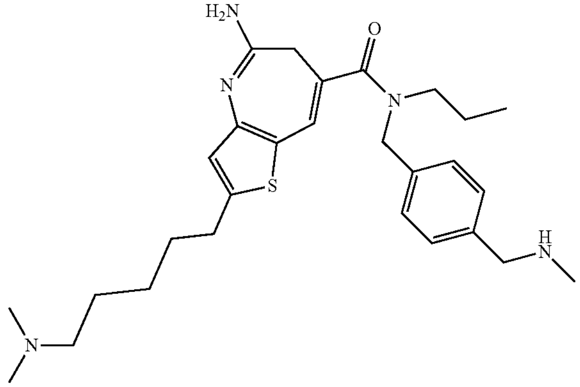

TAZ-65

Preparation of tert-butyl N-[[4-[[(5-amino-2-bromo-6H-thieno[3,2-b]azepine-7-carbonyl)-propyl-amino]methyl]phenyl]methyl]-N-methyl-carbamate, 65b To a solution of 5-amino-2-bromo-6H-thieno[3,2-b]azepine-7-carboxylic acid, 65a (1.0 g, 3.48 mmol, 1.0 eq) in DMF (20 mL) was added HATU (1.46 g, 3.83 mmol, 1.1 eq), DIEA (1.35 g, 10.45 mmol, 1.82 mL, 3.0 eq) and tert-butyl N-methyl-N-[[4-(propylaminomethyl) phenyl]methyl]carbamate (1.07 g, 3.66 mmol, 1.05 eq), and then stirred for 1 hr at 25° C. The reaction mixture was quenched by addition $H_2O$ (100 mL) and then extracted with EtOAc (100 mL×3). The combined organic layers were washed with brine (20 mL×2), dried over $Na_2SO_4$, filtered and concentrated. Finally, the residue was purified by column chromatography ($SiO_2$, Petroleum ether/Ethyl acetate=200/1 to 0/1) to give 65b (1.80 g, 3.21 mmol, 92.04% yield) as yellow oil. $^1H$ NMR ($CDCl_3$, 400 MHz) δ 7.25-7.15 (m, 4H), 6.92 (s, 1H), 6.77 (s, 1H), 4.72 (s, 2H), 4.42 (s, 2H), 3.40 (t, J=7.2 Hz, 2H), 2.86 (s, 2H), 2.81 (s, 3H), 1.69-1.58 (m, 2H), 1.49 (s, 9H), 0.89 (t, J=7.2 Hz, 3H).

Preparation of tert-butyl N-[[4-[[[5-amino-2-(4-cyanobut-1-ynyl)-6H-thieno[3,2-b]azepine-7-carbonyl]-propyl-amino]methyl]phenyl]methyl]-N-methyl-carbamate, 65c To a mixture of 65b (2.25 g, 4.01 mmol, 1.0 eq) and pent-4-ynenitrile (951 mg, 12.0 mmol, 3.0 eq) in TEA (13.2 mL) and DMF (44 mL) was added $Pd(PPh_3)_2C_{12}$ (140.6 mg, 200.34 umol, 0.050 eq), CuI (152.6 mg, 801.38 umol, 0.20 eq) and $PPh_3$ (210 mg, 801 umol, 0.20 eq) at 15° C. and then stirred for 3 hrs at 140° C. under $N_2$ atmosphere. The reaction mixture was quenched by addition $H_2O$ (220 mL)

at 25° C., and then extracted with DCM/isopropanol=3/1 (200 mL×3). The combined organic layers were washed with $H_2O$ (40 mL×4), dried over $Na_2SO_4$, filtered and concentrated. The residue was purified by column chromatography ($SiO_2$, Petroleum ether/Ethyl acetate=200/1 to 0/1 to Ethyl acetate/MeOH=50/1 to 5/1) to give 65c (1.62 g, 2.89 mmol, 72.23% yield) as yellow oil. $^1$H NMR ($CDCl_3$, 400 MHz) S 7.21-7.20 (m, 4H), 7.00 (s, 1H), 6.81 (s, 1H), 4.73 (s, 2H), 4.42 (s, 2H), 3.40 (t, J=6.4 Hz, 2H), 2.83-2.81 (m, 7H), 2.68-2.65 (m, 2H), 1.64-1.62 (m, 2H), 1.49 (s, 9H), 0.89 (t, J=7.2 Hz, 3H)

Preparation of tert-butyl N-[[4-[[[5-amino-2-(4-cyanobutyl)-6H-thieno[3,2-b]azepine-7-carbonyl]-propyl-amino]methyl]phenyl]methyl]-N-methyl-carbamate, 65d To a solution of 65c (1.47 g, 2.63 mmol, 1.0 eq) in MeOH (30 mL) was added $Pd(OH)_2/C$ (369 mg, 262 umol, 10% purity, 0.10 eq) under $N_2$ atmosphere. The suspension was degassed and purged with $H_2$ for 3 times. The mixture was stirred under $H_2$ (50 Psi) at 25° C. for 12 hrs. The reaction mixture was filtered and the filtrate was concentrated to give 65d (1.15 g, 2.04 mmol, 77.67% yield) as yellow oil. $^1$H NMR ($CDCl_3$, 400 MHz) δ7.21-7.19 (m, 4H), 6.86 (s, 1H), 6.67 (s, 1H), 4.74 (s, 2H), 4.42 (s, 2H), 3.40 (t, J=6.4 Hz, 2H), 2.86-2.82 (m, 5H), 2.37 (t, J=6.8 Hz, 2H), 1.88-1.83 (m, 2H), 1.78-1.74 (m, 2H), 1.64-1.61 (m, 2H), 1.49 (m, 9H), 0.89 (t, J=7.6 Hz, 3H).

Preparation of tert-butyl N-[[4-[[[5-amino-2-(5-aminopentyl)-6H-thieno[3,2-b]azepine-7-carbonyl]-propyl-amino]methyl]phenyl]methyl]-N-methyl-carbamate, 65e To a solution of 65d (1.15 g, 2.04 mmol, 1.0 eq) in MeOH (23 mL) was added $NH_3 \cdot H_2O$ (2.86 g, 20.4 mmol, 3.14 mL, 25% purity, 10 eq) and Ni (100 mg) under $N_2$. The suspension was degassed under vacuum and purged with $H_2$ several times. The mixture was stirred under $H_2$ (50 psi) at 25° C. for 3 hrs. The reaction mixture was filtered and the filtrate was concentrated to give 65e (1.03 g, 1.81 mmol, 88.93% yield) as yellow oil.

Preparation of tert-butyl N-[[4-[[[5-amino-2-[5-(dimethylamino)pentyl]-6H-thieno[3,2-b]azepine-7-carbonyl]-propyl-amino]methyl]phenyl]methyl]-N-methyl-carbamate, 65f To a solution of 65e (300 mg, 528 umol, 1.0 eq) in MeOH (8 mL) was added AcOH (3.1 mg, 52.8 umol, 0.10 eq), HCHO (171.5 mg, 2.11 mmol, 157.3 uL, 37% purity, 4.0 eq) and $NaBH_3CN$ (99.6 mg, 1.59 mmol, 3.0 eq), and then stirred for 1 hr at 25° C. The mixture was quenched by addition $H_2O$ (10 mL) and concentrated to remove MeOH. The aqueous phase was extracted with DCM/isopropanol=3/1 (10 mL×3). The combined organic layers were dried over $Na_2SO_4$, filtered and concentrated to give 65f (314 mg, crude) as yellow oil.

Preparation of TAZ-65

To a solution of 65f (50 mg, 83.9 umol, 1.0 eq) in $H_2O$ (0.5 mL) was added HCl (12 M, 140 μL, 20.0 eq) and then stirred for 1 hr at 80° C. The mixture was concentrated in vacuum. The residue was purified by Prep-HPLC (column: Phenomenex Synergi C18 150*25*10 um; mobile phase: [water(0.1% TFA)-ACN]; B %: 5%-35%, 10 min) to give TAZ-65 (10 mg, 13.74 umol, 16.37% yield, 99.44% purity, 2TFA) as colorless oil. $^1$H NMR (MeOD, 400 MHz,) S 7.50-7.40 (m, 4H), 7.09 (s, 1H), 6.89 (s, 1H), 4.78 (s, 2H), 4.19 (s, 2H), 3.45-3.35 (m, 4H), 3.32 (s, 2H), 3.14-3.10 (m, 2H), 2.88 (s, 6H), 2.72 (s, 3H), 1.80-1.74 (m, 4H), 1.66-1.64 (m, 2H), 1.49-1.47 (m, 2H), 0.89-0.86 (m, 3H). LC/MS [M+H] 496.3 (calculated); LC/MS [M+H] 496.3 (observed).

Example 109 Synthesis of 5-amino-2-(5-aminopentyl)-N-(3-(3,3-dimethylbutanamido)propyl)-N-propyl-6H-thieno[3,2-b]azepine-7-carboxamide, TAZ-109

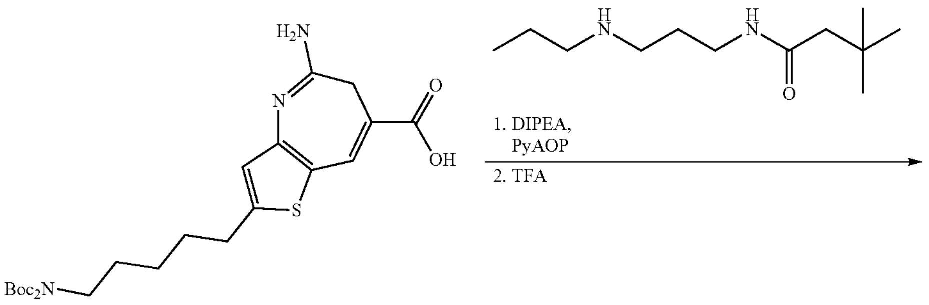

109a

-continued

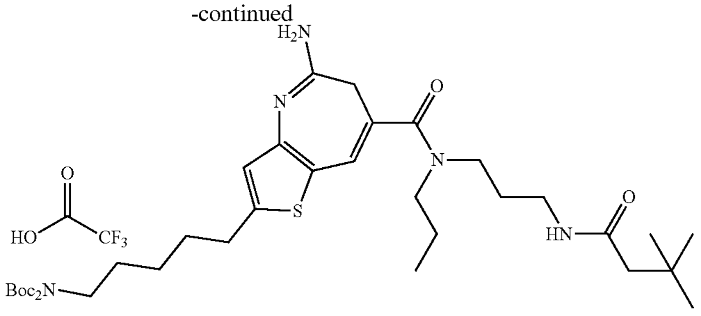

TAZ-109

5-amino-2-(5-(bis(tert-butoxycarbonyl)amino)pentyl)-6H-thieno[3,2-b]azepine-7-carboxylic acid, 109a (115 mg, 0.23 mmol, 1 eq.) and 3,3-dimethyl-N-(3-(propylamino)propyl)butanamide (50 mg, 0.23, 1 eq.) were taken up in 8:3 ACN:DCM (2.75 ml). DIPEA (0.121 ml, 0.7 mmol, 3 eq.) was added, followed by 7-Aza-benzotriazol-1-yloxy-tripyrrolidino-phosphonium hexafluorophosphate, PyAOP (0.122 m, 0.23 mmol, 1 eq.). The solution was stirred at ambient temperature. Upon completion by LCMS, the reaction mixture was concentrated and purified by HPLC to afford [amide], which was subsequently dissolved in minimal TFA and allowed to stand for 15 minutes. The solution was concentrated and triturated with diethyl ether to afford TAZ-109 as the trifluoroacetate salt (61.4 mg, 0.102 mmol, 44%). LC/MS [M+H] 490.32 (calculated); LC/MS [M+H] 490.39 (observed).

Example 133 Synthesis of tert-butyl (3-(5-amino-2-(5-aminopentyl)-N-propyl-6H-thieno[3,2-b]azepine-7-carboxamido)propyl)carbamate, TAZ-133

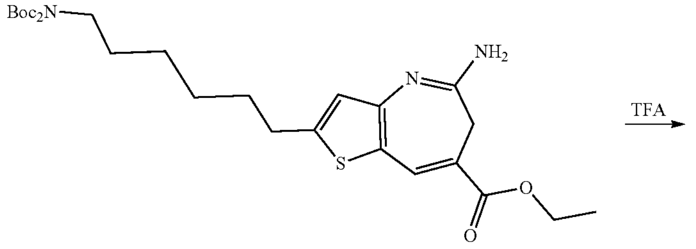

133a

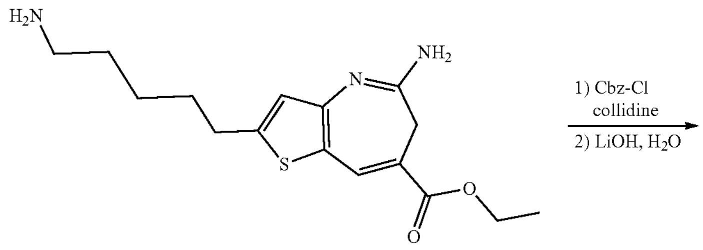

133b

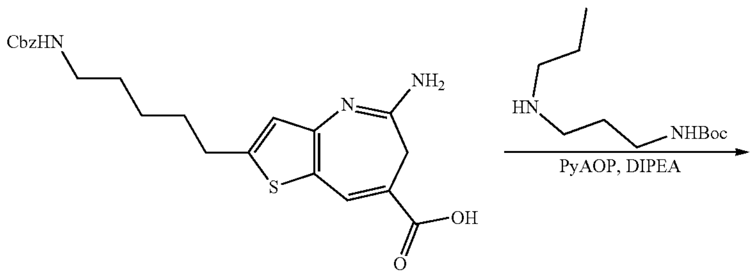

133c

-continued

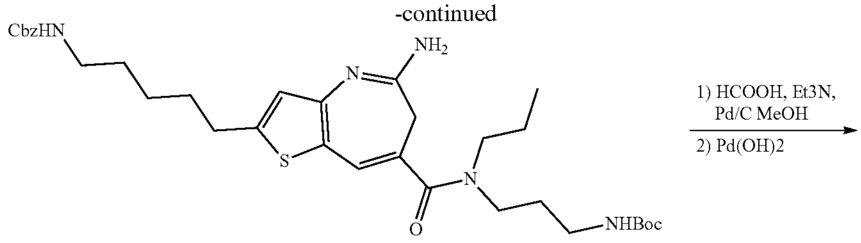

133d

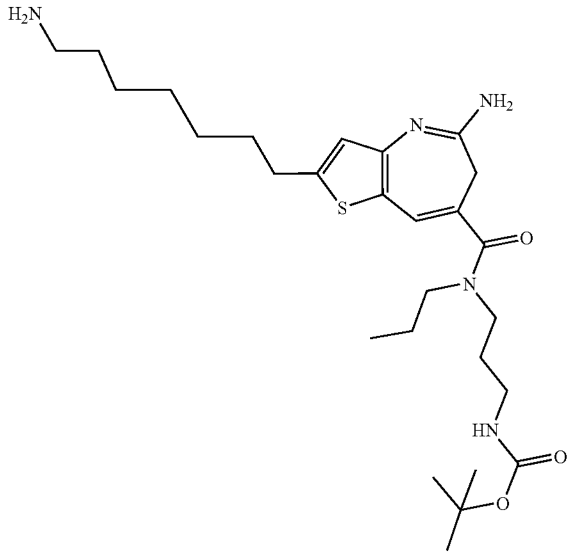

TAZ-133

Preparation of 5-(5-amino-7-(ethoxycarbonyl)-6H-thieno[3,2-b]azepin-2-yl)pentan-1-aminium trifluoroacetate, 133b Ethyl 5-amino-2-(5-(bis(tert-butoxycarbonyl)amino)pentyl)-6H-thieno[3,2-b]azepine-7-carboxylate, 133a (0.188 g, 0.36 mmol, 1 equiv.) was dissolved in minimal TFA. Upon complete deprotection, the solution was concentrated and the product precipitated from diethyl ether to give 133b (0.082 g, 0.188 mmol, 52%) as a yellow powder. LC/MS [M+H] 322.16 (calculated); LC/MS [M+H] 322.25 (observed).

Preparation of 5-amino-2-(5-(((benzyloxy)carbonyl)amino)pentyl)-6H-thieno[3,2-b]azepine-7-carboxylic acid, 133c Intermediate 133b (0.296 g, 0.68 mmol, 1 equiv.) was suspended in 2 ml DMF. Collidine (0.27 ml, 2 mmol, 3 equiv.) was added, followed by benzyl chloroformate, Cbz-Cl, CAS Reg. No. 501-53-1 (0.1 ml, 0.68 mmol, 1 equiv.). The reaction was monitored by LCMS. Upon consumption of the amine starting material, the reaction was concentrated and redissolved in 7 ml 3:1:3 THF:MeOH:water. Lithium hydroxide (0.16 g, 6.8 mmol, 10 equiv.) was added and the reaction stirred at room temperature. Upon completion, the reaction mixture was concentrated and purified by reverse-phase HPLC to give 133c (0.246 g, 0.58 mmol, 85%). LC/MS [M+H] 428.16 (calculated); LC/MS [M+H] 428.32 (observed).

Preparation of benzyl (5-(5-amino-7-((3-((tert-butoxycarbonyl)amino)propyl)(propyl)carbamoyl)-6H-thieno[3,2-b]azepin-2-yl)pentyl)carbamate, 133d Intermediate 133c (0.29 g, 0.68 mol, 1 equiv.) and tert-butyl (3-(propylamino)propyl)carbamate (0.225 g, 1.0 mmol, 1.53 equiv.) were dissolved in 1 ml DMF. Diisopropylethylamine, DIPEA (0.59 ml, 1.0 mmol, 1.53 equiv.) was added, followed by PyAOP (0.541 g, 1.0 mmol, 1.53 equiv.). The reaction was stirred at room temperature, then concentrated and purified by reverse-phase flash chromatography to give 133d (0.201 g, 0.32 mmol, 47%). LC/MS [M+H] 626.34 (calculated); LC/MS [M+H] 626.51 (observed).

Preparation of TAZ-133

Intermediate 133d (0.2 g, 0.32 mmol, 1 equiv.) was dissolved in 2 ml MeOH. Triethylamine (0.1 ml) and formic acid (0.049 ml, 1.29 mmol, 4 equiv.) were added, followed by 10% w/w Pd/C (0.04 g). The stirred reaction was heated to 60° C. After one hour, 20% w/w Pd(OH)z (0.02 g) was added. Upon completion, the reaction was filtered, concentrated, and purified by HPLC to give TAZ-133 0.139 g, 0.28 mmol, 88%). LC/MS [M+H] 492.30 (calculated), LC/MS [M+H] 492.45 (observed).

Example 176 Synthesis of 5-amino-N-ethoxy-2-[2-(4-piperidyl)ethyl]-N-propyl-6H-thieno[3,2-b]azepine-7-carboxamide, TAZ-176

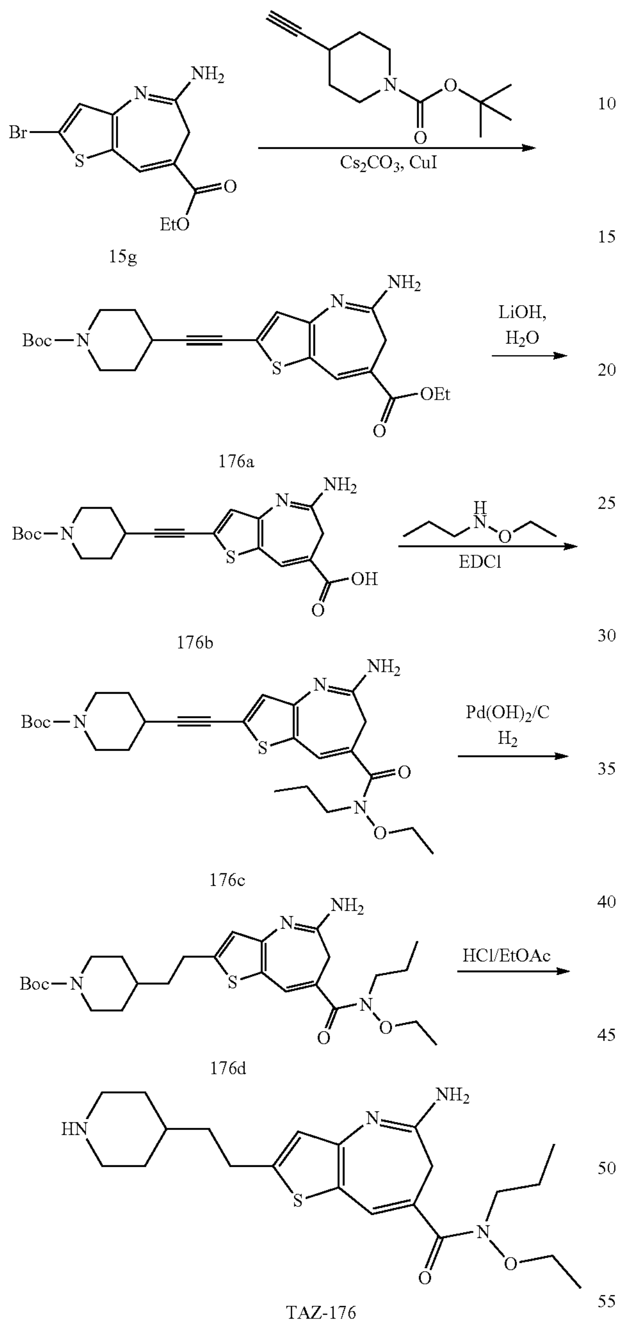

15g

176a

176b

176c

176d

TAZ-176

Preparation of ethyl 5-amino-2-[2-(1-tert-butoxycarbonyl-4-piperidyl)ethynyl]-6H-thieno[3,2-b]azepine-7-carboxylate, 176a To a mixture of ethyl 5-amino-2-bromo-6H-thieno[3,2-b]azepine-7-carboxylate, 15g (2 g, 6.35 mmol, 1.0 eq) in $CH_3CN$ (60 mL) was added tert-butyl 4-ethynylpiperidine-1-carboxylate (1.73 g, 8.25 mmol, 1.3 eq), $Cs_2CO_3$ (6.20 g, 19.0 mmol, 3.0 eq), CuI (242 mg, 1.27 mmol, 0.2 eq) and $Pd(PPh_3)_2Cl_2$ (445 mg, 635 umol, 0.1 eq) in one portion at 25° C. under $N_2$ and it was stirred at 100° C. for 2 h. The mixture was concentrated to give a residue. The residue was purified by silica gel chromatography (column height: 250 mm, diameter: 100 mm, 100-200 mesh silica gel, Petroleum ether/Ethyl acetate=1/0,10/1) to afford 176a (3.5 g, crude) as yellow solid.

Preparation of 5-amino-2-[2-(1-tert-butoxycarbonyl-4-piperidyl) ethynyl]-6H-thieno[3,2-b]azepine-7-carboxylic acid, 176b To a mixture of 176a (3.5 g, 7.89 mmol, 1.0 eq) in EtOH (50 mL) and $H_2O$ (8 mL) was added $LiOH{\cdot}H_2O$ (1.32 g, 31.6 mmol, 4.0 eq) in one portion at 25° C. and it was stirred at 30° C. for 2 h. The mixture was concentrated and the residue was diluted with water (30 mL). Then the mixture was filtered. The filter cake was triturated with $CH_3CN$ at 25° C. for 0.5 h, then filtered to afford 176b (2.3 g, 5.54 mmol, 70.2% yield) as yellow solid.

Preparation of tert-butyl 4-[2-[5-amino-7-[ethoxy (propyl)carbamoyl]-6H-thieno[3,2-b]azepin-2-yl] ethynyl]piperidine-1-carboxylate, 176c To a mixture of 176b (1 g, 2.41 mmol, 1.0 eq) in DCM (10 mL) and DMA (10 mL) was added N-ethoxypropan-1-amine (353 mg, 2.53 mmol, 1.05 eq, HCl) and EDCI (1.85 g, 9.63 mmol, 4.0 eq) in one portion at 25° C. and it was stirred at 25° C. for 1 h. The mixture was concentrated to remove DCM, the residue was diluted with water (50 mL) and the pH of the mixture was adjusted to about 8 with sat, $NaHCO_3$, and then extracted with EtOAc (30 mL×3). The organic layer was washed with brine, dried over $Na_2SO_4$, filtered and concentrated. The residue was purified by silica gel chromatography (column height: 250 mm, diameter: 100 mm, 100-200 mesh silica gel, Ethyl acetate/MeOH=1/0, 10/1) to afford 176c (0.63 g, 1.26 mmol, 52.3% yield) as light yellow solid. $^1H$ NMR (MeOD, 400 MHz) δ 7.27 (s, 1H), 6.88 (s, 1H), 3.89 (q, J=7.2 Hz, 2H), 3.74-3.70 (m, 2H), 3.69 (t, J=6.8 Hz, 2H), 3.25-3.19 (m, 3H), 2.99 (s, 2H), 1.89-1.85 (m, 2H), 1.79-1.67 (m, 2H), 1.65-1.59 (m, 2H), 1.47 (s, 9H), 1.15 (t, J=7.2 Hz, 3H), 0.95 (t, J=7.6 Hz, 3H). LC/MS [M+H] 501.2 (calculated); LC/MS [M+H] 501.1 (observed).

Preparation of tert-butyl 4-[2-[5-amino-7-[ethoxy (propyl) carbamoyl]-6H-thieno[3,2-b]azepin-2-yl] ethyl]piperidine-1-carboxylate, 176d To a solution of 176c (0.45 g, 899 umol, 1.0 eq) in MeOH (15 mL) was added $Pd(OH)_2/C$ (0.2 g, 10% purity) under $N_2$. The suspension was degassed under vacuum and purged with $H_2$ several times. The mixture was stirred under $H_2$ (50 psi) at 25° C. for 12 hours. The mixture was filtered and concentrated. The residue was purified by silica gel chromatography (column height; 250 mm, diameter: 100 mm, 100-200 mesh silica gel, Petroleum ether/Ethyl acetate=1/0, 0/1) to afford 176d (0.3 g, 594 umol, 66.13% yield) as light yellow solid. $^1H$ NMR (MeOD, 400 MHz) δ 7.32 (s, 1H), 6.65 (s, 1H), 4.06 (d, J=13.2 Hz, 2H), 3.89 (q, J=7.2 Hz, 2H), 3.69 (t, J=7.2 Hz, 2H), 2.98 (s, 2H), 2.85 (t, J=7.6 Hz, 2H), 2.73 (s, 2H), 1.77-1.73 (m, 4H), 1.69-1.60 (m, 2H), 1.58-1.50 (m, 1H), 1.45 (s, 9H), 1.16 (t, J=7.2 Hz, 3H), 1.13-1.05 (m, 2H), 0.95 (t, J=7.6 Hz, 3H). LC/MS [M+H] 501.2 (calculated); LC/MS [M+H] 505.3 (observed).

Preparation of TAZ-176

To a mixture of 176d (0.3 g, 594 umol, 1.0 eq) in EtOAc (5 mL) was added HCl/EtOAc (4 M, 10 mL) in one portion at 25° C. and it was stirred at 25° C. for 0.5 h. The mixture was concentrated to give TAZ-176 (0.3 g, crude, HCl) as a yellow solid. $^1$H NMR (MeOD, 400 MHz) δ7.45 (s, 1H), 6.93 (s, 1H), 3.93 (q, J=7.2 Hz, 2H), 3.72 (t, J=7.2 Hz, 2H), 3.45-3.37 (m, 4H), 3.05-2.91 (m, 4H), 2.02 (d, J=13.6 Hz, 2H), 1.80-1.65 (m, 5H), 1.52-1.35 (m, 2H), 1.18 (t, J=7.2 Hz, 3H), 0.97 (t, J=7.6 Hz, 3H). LC/MS [M+H] 405.2 (calculated); LC/MS [M+H] 405.1 (observed).

Example 183 Synthesis of 5-amino-2-(azetidin-3-ylmethyl)-N-ethoxy-N-propyl-6H-thieno[3,2-b]azepine-7-carboxamide, TAZ-183

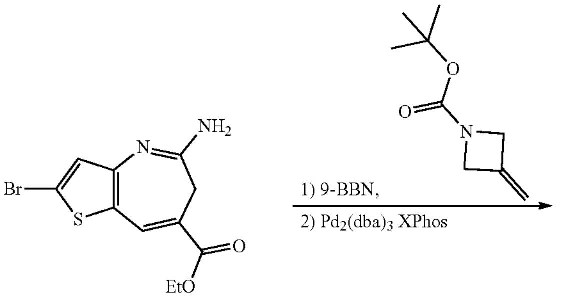

15g

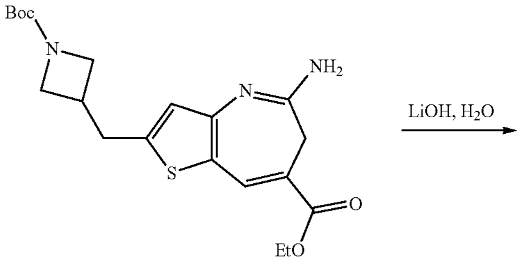

183a

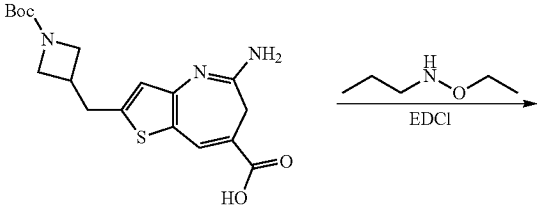

183b

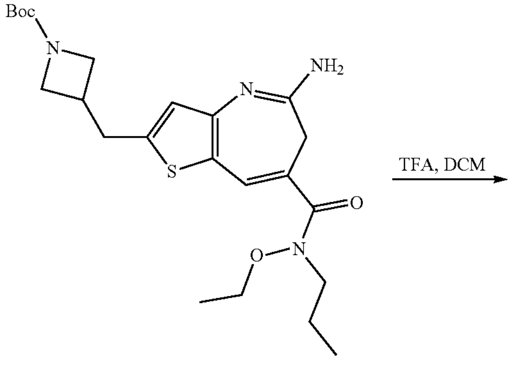

183c

-continued

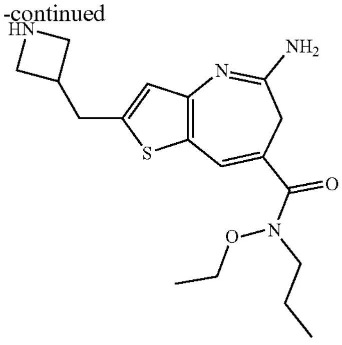

TAZ-183

Preparation of ethyl 5-amino-2-[(1-tert-butoxycarbonyl azetidin-3-yl)methyl]-6H-thieno[3,2-b]azepine-7-carboxylate, 183a tert-Butyl 3-methyleneazetidine-1-carboxylate (2.25 g, 13.3 mmol, 2 eq) was treated with a 9-BBN (0.5 M, 53.3 mL, 4 eq) in THF (50 mL) and the mixture was heated at 70° C. for 4 hrs. The resulting mixture was transferred into a stirred mixture of ethyl 5-amino-2-bromo-6H-thieno[3,2-b]azepine-7-carboxylate, 15g (2.1 g, 6.66 mmol, 1 eq), $Pd_2(dba)_3$ (610 mg, 666 umol, 0.1 eq), XPhos (953 mg, 2.00 mmol, 0.3 eq) and $Na_2CO_3$ (2.12 g, 20.0 mmol, 3 eq) in dioxane (50 mL) and $H_2O$ (5 mL). The resulting mixture was stirred at 100° C. for 12 hr under $N_2$, and then filtered, the filtrate was concentrated to remove THF and dioxane, EtOAc (100 mL) and water (100 mL) was poured into the mixture. The organic layer was washed with brine, dried over anhydrous $Na_2SO_4$, concentrated to give a residue. The residue was purified by column chromatography ($SiO_2$, Petroleum ether/Ethyl acetate=1:0 to 0:1, then EtOAc: MeOH=10:1) to give 183a (2 g, 2.47 mmol, 37.0% yield) as yellow solid.

Preparation of 5-amino-2-[(1-tert-butoxycarbonylazetidin-3-yl)methyl]-6H-thieno[3,2-b]azepine-7-carboxylic acid, 183b To a mixture of 183a (2 g, 4.93 mmol, 1 eq) in THF (10 mL) and $H_2O$ (10 mL) was added LiOH·$H_2O$ (621 mg, 14.8 mmol, 3 eq), and then stirred at 15° C. for 3 hr. The mixture was concentrated to remove THF, then the pH of the aqueous phase was adjusted to ~7 with HCl(4M). The desired solid precipitated from the mixture, and filtered to give 183b (1.5 g, 3.97 mmol, 80.6% yield) as yellow solid. $^1$H NMR (400 MHz, DMSO-$d_6$) δ7.65 (s, 1H), 6.94 (s, 2H), 6.66 (s, 1H), 4.05-3.93 (m, 2H), 3.70-3.55 (m, 2H), 3.07 (d, J=7.6 Hz, 2H), 2.88 (s, 2H), 2.80-2.65 (m, 1H), 1.43 (s, 9H).

Preparation of tert-butyl 3-[[5-amino-7-[ethoxy(propyl)carbamoyl]-6H-thieno[3,2-b]azepin-2-yl]methyl]azetidine-1-carboxylate, 183c To a mixture of 183b (0.2 g, 530 umol, 1 eq) and N-ethoxypropan-1-amine (96.2 mg, 689 umol, 1.3 eq, HCl) in DMA (3 mL) and DCM (3 mL) was added EDCI (406 mg, 2.12 mmol, 4 eq), and then stirred at 15° C. for 2 hr. The mixture was concentrated to give a residue. The residue was purified by Prep-HPLC (column: Phenomenex Synergi C18 150*25*10 um; mobile phase: [water(0.1% TFA)-ACN]; B %: 25%-55%, 8 min) to give 183c (130 mg, 273 umol, 51.6% yield, 97.2% purity) as light-yellow solid. $^1$H NMR (400 MHz, MeOD) δ7.47 (s, 1H), 6.93 (s, 1H), 4.07 (br t, J=8.4 Hz, 2H), 3.95 (q, J=7.2 Hz, 2H), 3.82-3.63 (m, 4H), 3.44 (s, 2H), 3.18 (d, J=7.6 Hz, 2H), 3.02-2.81 (m, 1H), 1.76 (sxt, J=7.2 Hz, 2H), 1.45 (s, 9H), 1.20 (t, J=7.2 Hz, 3H), 0.99 (t, J=7.2 Hz, 3H). LC/MS [M+H] 463.2 (calculated); LC/MS [M+H] 463.1 (observed).

Preparation of TAZ-183

To a mixture of 183c (0.11 g, 238 umol, 1 eq) in DCM (10 mL) was added TFA (1.54 g, 13.5 mmol, 1 mL, 56.8 eq). The mixture was stirred at 15° C. for 1 hr. The pH of the mixture was adjusted to ~7 with saturated aqueous solution of $NaHCO_3$, then extracted with DCM/i-PrOH (3:1, 10 mL*3). The organic layer was dried over $Na_2SO_4$, concentrated to give TAZ-183 (60 mg, 151 umol, 63.3% yield, 90.95% purity) as light yellow solid. $^1$H NMR (400 MHz, MeOD) δ7.20 (s, 1H), 6.63 (s, 1H), 4.04 (br t, J=9.6 Hz, 2H), 3.83-3.75 (m, 4H), 3.59 (t, J=7.2 Hz, 2H), 3.36-3.30 (m, 1H), 3.05 (d, J=7.6 Hz, 2H), 2.88 (s, 2H), 1.62 (sxt, J=7.2 Hz, 2H), 1.08-1.00 (m, 3H), 0.85 (t, J=7.2 Hz, 3H). LC/MS [M+H] 363.2 (calculated); LC/MS [M+H] 363.1 (observed).

Example 185 Synthesis of cyclobutyl N-[3-[[5-amino-2-(4-piperidylmethyl)-6H-thieno[3,2-b]azepine-7-carbonyl]-propyl-amino]propyl]carbamate, TAZ-185

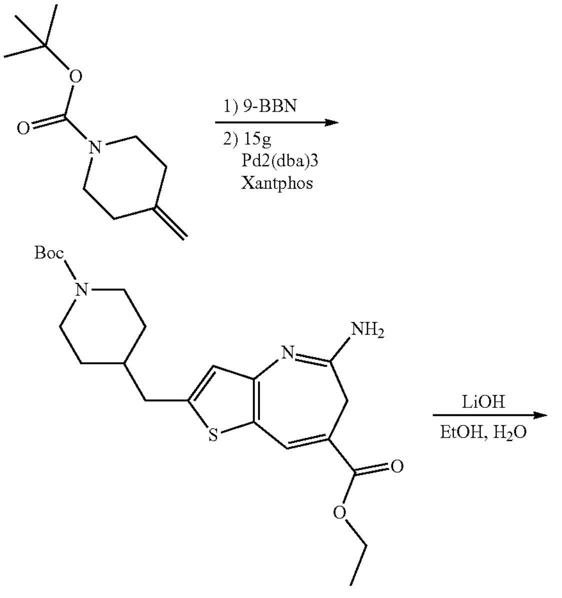

185a

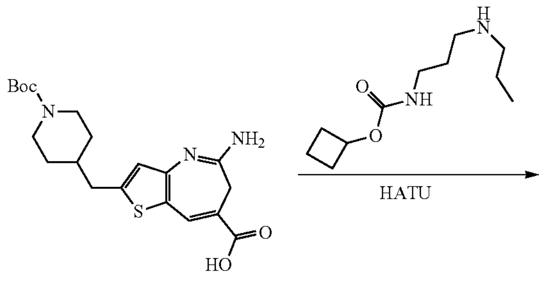

185b

-continued

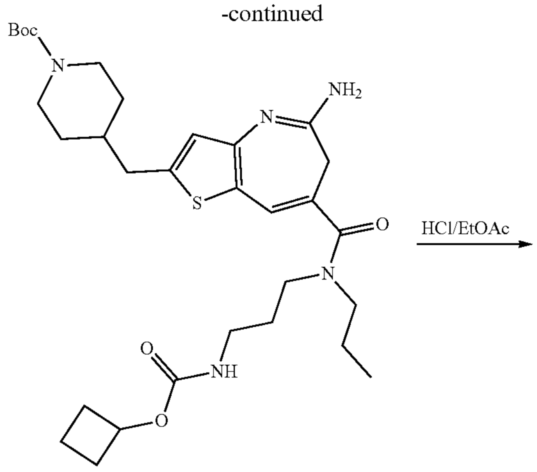

185c

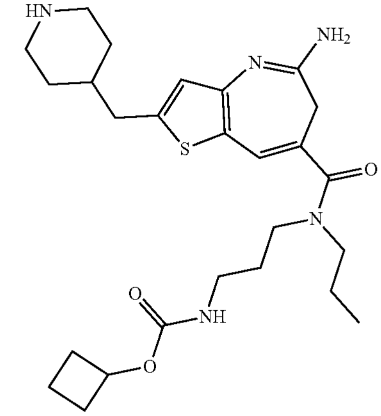

TAZ-185

Preparation of ethyl 5-amino-2-[(1-tert-butoxycarbonyl-4-piperidyl)methyl]-6H-thieno[3,2-b]azepine-7-carboxylate, 185a A mixture of tert-butyl 4-methylenepiperidine-1-carboxylate (4.51 g, 22.8 mmol, 2.0 eq) and 9-BBN (1 M, 57.1 mL, 5.0 eq) was heated to 70° C. and stirred at 70° C. for 2 hours, then ethyl 5-amino-2-bromo-6H-thieno[3,2-b]azepine-7-carboxylate, 15g (3.60 g, 11.4 mmol, 1.0 eq), Xantphos (1.59 g, 2.74 mmol, 0.24 eq), $Pd_2(dba)_3$ (836 mg, 913 umol, 0.08 eq), $K_2CO_3$ (4.74 g, 34.2 mmol, 3.0 eq), $H_2O$ (5 mL) and dioxane (50 mL) was added to this mixture after it was cooled to 20° C., then the mixture was stirred at 100° C. for 4 hours under N2. Water (200 mL) was added and the aqueous phase was extracted with ethyl acetate (50 mL*4), the combined organic phase was washed with brine (100 mL*1), dried with anhydrous $Na_2SO_4$, filtered and concentrated in vacuum. The residue was purified by silica gel chromatography (column height: 250 mm, diameter: 100 mm, 100-200 mesh silica gel, Petroleum ether/Ethyl acetate=10/1, 0/1) to afford 185a (1.8 g, 4.15 mmol, 36.35% yield) as brown oil.

Preparation of 5-amino-2-[(1-tert-butoxycarbonyl-4-piperidyl)methyl]-6H-thieno[3,2-b]azepine-7-carboxylic acid, 185b To a solution of L-185a (1.80 g, 4.15 mmol, 1.0 eq) in EtOH (3 mL) and $H_2O$ (5 mL) was added LiOH·$H_2O$ (696 mg, 16.6 mmol, 4.0 eq) in one portion at 20° C. under $N_2$, and then stirred at 20° C. for 4 hours. The reaction mixture was quenched with HCl (4 M) until pH=6, then EtOH was removed in vacuum. The precipitation was filtered and dried to afford 185b (1.20 g, 2.96 mmol, 71.2% yield) as yellow solid. $^1$H NMR (400 MHz, DMSO-$d_6$) δ7.61 (s, 1H), 6.58 (s, 1H), 3.86 (d, 2.0 Hz, 2H), 2.92 (s, 2H), 2.65 (d, J=6.4 Hz, 2H), 1.65-1.60 (m, 3H), 1.35 (s, 9H), 1.07-0.96 (m, 2H)

Preparation of tert-butyl 4-[[5-amino-7-[3-(cyclobutoxycarbonylamino) propyl-propyl-carbamoyl]-6H-thieno[3,2-b]azepin-2-yl]methyl]piperidine-1-carboxylate, 185c To a mixture of L-185b (200 mg, 493 umol, 1.0 eq) and cyclobutyl N-[3-(propylamino) propyl]carbamate (148 mg, 591 umol, 1.2 eq, HCl) in DMF (2 mL) was added HATU (187 mg, 493 umol, 1.0 eq) and DIEA (191 mg, 1.48 mmol, 257 μL, 3.0 eq) in one portion at 20° C. under $N_2$, the mixture was stirred at 20° C. for 1 hours. Water (10 mL) was added and the aqueous phase was extracted with ethyl acetate (10 mL*3), the combined organic phase was washed with brine (15 mL*2), dried with anhydrous $Na_2SO_4$, filtered and concentrated in vacuum. The residue was purified by silica gel chromatography (column height: 250 mm, diameter: 100 mm, 100-200 mesh silica gel, Petroleum ether/Ethyl acetate=5/1, 0/1 to Ethyl acetate/Methanol=10/1) to afford 185c (180 mg, 299 umol, 60.6% yield) as brown solid. $^1$H NMR (400 MHz, MeOD) δ6.88 (s, 1H), 6.68 (s, 1H), 4.88-4.80 (m, 1H), 4.08 (d, J=12.4 Hz, 2H), 3.49 (t, J=7.2 Hz, 2H), 3.41 (t, J=7.6 Hz, 2H), 3.11 (s, 2H), 2.75 (d, J=6.8 Hz, 3H), 2.36-2.23 (m, 2H), 1.86-1.59 (m, 10H), 1.47 (s, 9H), 1.22-1.09 (m, 2H), 0.90 (t, J=4.0, 3H)

Preparation of TAZ-185

To a solution of 185c (180 mg, 299 umol, 1.0 eq) in EtOAc (1 mL) was added HCl/EtOAc (4 M, 3.74 mL, 50 eq) in one portion at 20° C. under $N_2$, and then stirred at 20° C. for 1 hour. The reaction mixture was concentrated in vacuum to afford TAZ-185 (140 mg, 260 umol, 86.98% yield, HCl) as yellow oil.

Example 198 Synthesis of 5-amino-N-ethoxy-2-(4-piperidylmethyl)-N-propyl-6H-thieno[3,2-b]azepine-7-carboxamide, TAZ-198

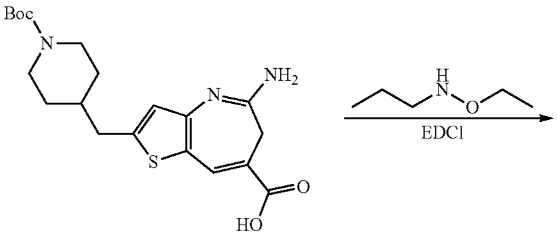

185b

-continued

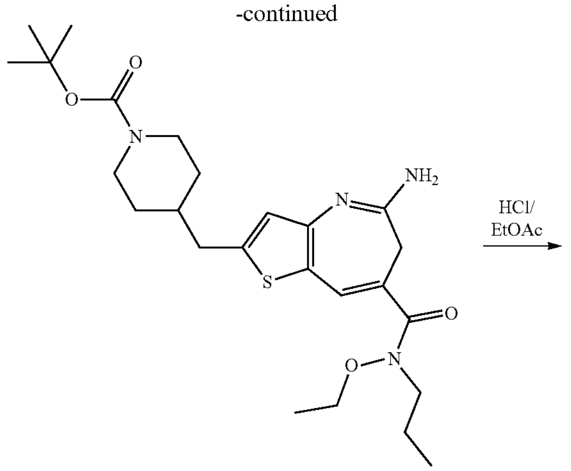

198a

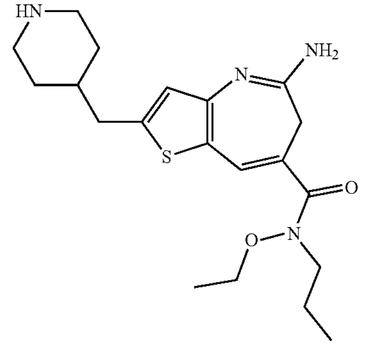

TAZ-198

Preparation of tert-butyl 4-[[5-amino-7-[ethoxy(propyl)carbamoyl]-6H-thieno[3,2-b]azepin-2-yl]methyl piperidine-1-carboxylate, 198a To a mixture of 5-amino-2-[(1-tert-butoxycarbonyl-4-piperidyl)methyl]-6H-thieno[3,2-b]azepine-7-carboxylic acid, 185b (200 mg, 493 umol, 1.0 eq) and N-ethoxypropan-1-amine (82.6 mg, 591 umol, 1.2 eq. HCl) in DMA (1 mL) and DCM (2 mL) was added EDCI (378 mg, 1.97 mmol, 4.0 eq) at 20° C. under $N_2$, and then stirred at 20° C. for 2 hours. DCM (2 mL) was removed in vacuum, then the aqueous phase was quenched with aq $NaHCO_3$ until pH=8, the water phase was extracted with EtOAc (15 mL*3), the combined organic phase was washed with brine (15 mL), dried with anhydrous $Na_2SO_4$, filtered and concentrated in vacuum. The residue was purified by silica gel chromatography (column height: 250 mm, diameter: 100 mm, 100-200 mesh silica gel, Petroleum ether/Ethyl acetate=5/1, 0.1 to Ethyl acetate/Methanol=10/1) to afford 198a (150 mg, 305 umol, 61.9% yield) as brown solid. $^1$H NMR (400 MHz, MeOD) δ7.35 (s, 1H), 6.68 (s, 1H), 4.08 (d, J=13.2 Hz, 2H), 3.90 (q, J=7.2 Hz, 2H), 3.71 (t, J=7.2 Hz, 2H), 3.33 (s, 2H), 3.08 (d, J=8.0 Hz 2H), 2.76 (d, J=6.8 Hz, 3H), 1.80-1.70 (m, 5H), 1.47 (s, 9H), 1.20-1.10 (m, 5H), 0.97 (t, J=7.2 Hz, 3H)

Preparation of TAZ-198

To a solution of 198a (150 mg, 305 umol, 1.0 eq) in EtOAc (1 mL) was added HCl/EtOAc (4 M, 3.82 mL, 50 eq) at 20° C. under $N_2$, the mixture was stirred at 20° C. for 1 hour. The reaction mixture was concentrated in vacuum to afford TAZ-198 (100 mg, 234 umol, 76.6% yield, HCl) as yellow oil.

Example 238 Synthesis of cyclobutyl N-[2-[[5-amino-2-(azetidin-3-ylmethyl)-6H-thieno[3,2-b]azepine-7-carbonyl]-propyl-amino]oxyethyl]carbamate, TAZ-238

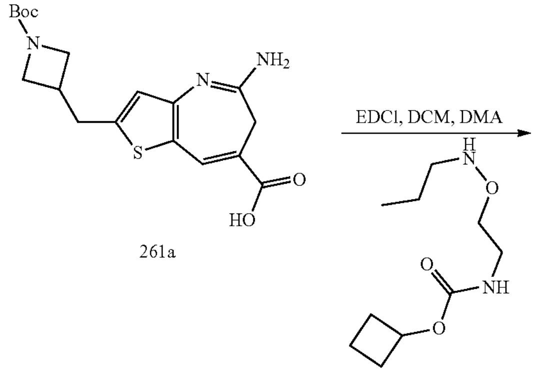

261a

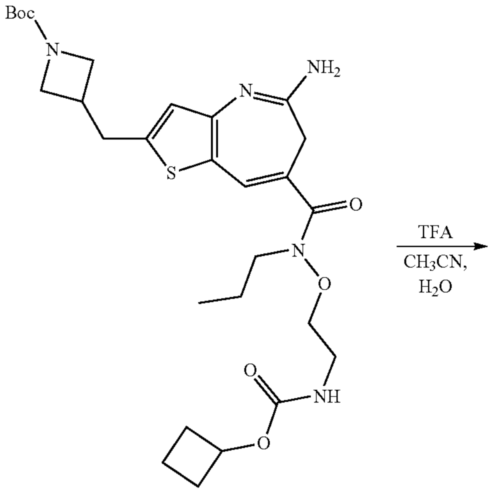

238a

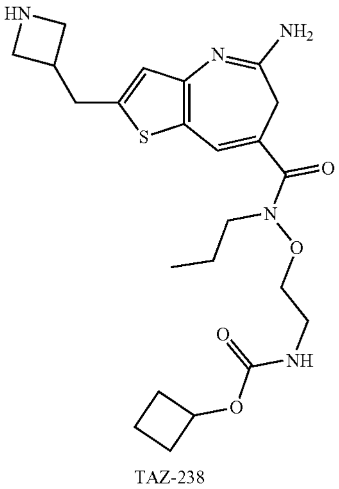

TAZ-238

Preparation of tert-butyl 3-[[5-amino-7-[2-(cyclobutoxycarbonylamino)ethoxy-propyl-carbamoyl]-6H-thieno[3,2-b]azepin-2-yl]methyl]azetidine-1-carboxylate, 238a To a solution of 5-amino-2-[(1-tert-butoxycarbonylazetidin-3-yl)methyl]-6H-thieno[3,2-b]azepine-7-carboxylic acid, 261a (200 mg, 529.86 umol, 1 eq) and cyclobutyl N-[2-(propylaminooxy)ethyl]carbamate (174.09 mg, 688.82 umol, 1.3 eq, HCl) in DCM (2 mL) and DMA (2 mL) was added EDCI (304.72 mg, 1.59 mmol, 3 eq) at 0° C., and then stirred at 25° C. for 1 hr. The reaction mixture was concentrated under reduced pressure to give a residue. The residue was diluted with $H_2O$ (10 mL) and the pH of the mixture was adjusted to ~9 with aq. $Na_2CO_3$ at 0° C. and it was extracted with EtOAc (10 mL*3). The combined organic layers were washed with brine (5 mL*3), dried over $Na_2SO_4$, filtered and concentrated under reduced pressure to give a residue. The residue was purified by column chromatography ($SiO_2$, Petroleum ether/Ethyl acetate=1/0 to 0/1) and then ($SiO_2$, EtOAc:MeOH=1:0 to 3:1) to give 238a (0.2 g, 347.39 umol, 65.56% yield) as a yellow solid. $^1H$ NMR (MeOD, 400 MHz) δ 7.32 (s, 1H), 6.69 (s, 1H), 4.81 (s, 1H), 4.08-3.99 (m, 2H), 3.89 (t, J=5.2 Hz, 2H), 3.72-3.62 (m, 4H), 3.29-3.25 (m, 2H), 3.09 (d, J=7.6 Hz, 2H), 3.02 (s, 2H), 2.95-2.83 (m, 1H), 2.32-2.21 (m, 2H), 2.05-1.94 (m, 2H), 1.77-1.54 (m, 4H), 1.45-1.40 (m, 9H), 0.94 (t, J=7.6 Hz, 3H). LC/MS [M+H] 576.3 (calculated); LC/MS [M+H] 576.3 (observed).

Preparation of TAZ-238

To a mixture of 238a (0.31 g, 538 umol, 1.0 eq) in DCM (6 mL) was added TFA (1.23 g, 10.8 mmol, 797 μL, 20.0 eq) in one portion at 25° C. and then stirred at 25° C. for 2 h. The mixture was concentrated to give a residue, the residue was diluted with $H_2O$ (15 mL), the mixture was extracted with MTBE (10 mL*2) to remove excess TFA, the aqueous phase was freeze-dried to afford TAZ-238 (0.38 g, 521 umol, 96.7% yield, 96.4% purity, TFA salt) as yellow solid. $^1H$ NMR (MeOD, 400 MHz) δ 7.47 (s, 1H), 6.96 (s, 1H), 4.81-4.74 (m, 1H), 4.22-4.13 (m, 2H), 3.96-3.86 (m, 4H), 3.71 (t, J=7.2 Hz, 2H), 3.41 (s, 2H), 3.29-3.22 (m, 5H), 2.25 (d, J=7.2 Hz, 2H), 2.03-1.89 (m, 2H), 1.80-1.55 (m, 4H), 0.96 (t, J=7.6 Hz, 3H). LC/MS [M+H] 476.2 (calculated); LC/MS [M+H] 476.1 (observed).

Example 253 Synthesis of 5-amino-2-(azetidin-3-ylmethyl)-N-isopropoxy-N-propyl-6H-thieno[3,2-b]azepine-7-carboxamide, TAZ-253

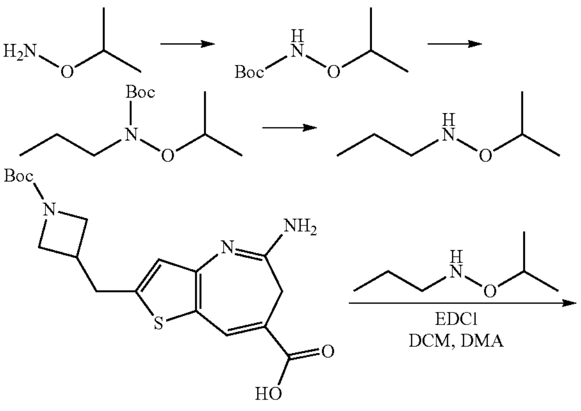

183b

-continued

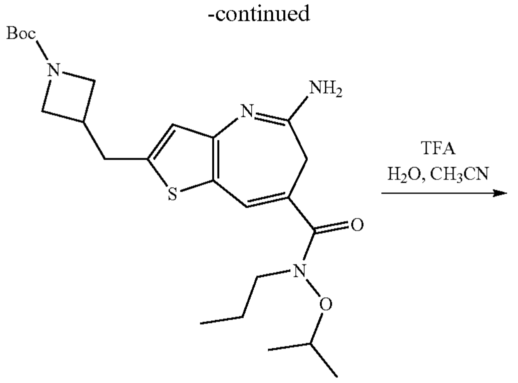

253a

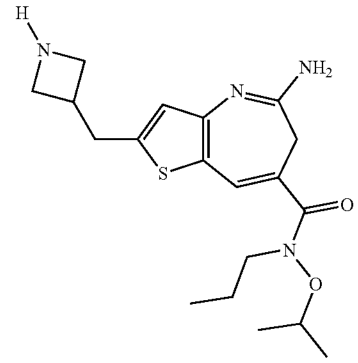

TAZ-253

Preparation of N-isopropoxypropan-1-amine

To a solution of O-isopropylhydroxylamine (2 g, 17.9 mmol, 1 eq, HCl) in THF (15 mL) was added a solution of $NaHCO_3$ (3.01 g, 35.8 mmol, 1.39 mL, 2 eq) in $H_2O$ (5 mL) and tert-butoxycarbonyl tert-butyl carbonate (5.87 g, 26.9 mmol, 6.18 mL, 1.5 eq), and then stirred at 20° C. for 2 h under N2 atmosphere. $H_2O$ (50 mL) was added to the mixture and then extracted with EtOAc (80 mL×3), the combined organic phase was washed with brine (50 mL×3), dried with anhydrous $Na_2SO_4$, filtered and concentrated in vacuum. The crude product was purified by silica gel chromatography eluted with (Petroleum ether:Ethyl acetate=1:0,1:1), tert-Butyl N-isopropoxycarbamate (2.81 g, 16.0 mmol, 89.46% yield) was obtained as light yellow oil. $^1$H NMR (MeOD, 400 MHz) δ7.00 (br s, 1H), 4.10-1.00 (m, 1H), 1.49 (s, 9H), 1.22 (d, J=6.4 Hz, 6H).

To a solution of tert-butyl N-isopropoxycarbamate (2.80 g, 15.9 mmol, 1 eq) in DMF (10 mL) was added NaH (959 mg, 23.9 mmol, 60% purity, 1.5 eq) at 0° C. under $N_2$ and it was stirred for 0.5 h, and then 1-iodopropane (5.43 g, 32.0 mmol, 3.12 mL, 2 eq) was added. The mixture was stirred at 25° C. for 2 h under $N_2$ atmosphere. The reaction mixture was quenched at 0° C. by the addition of (50 mL) sat. $NH_4Cl$ solution, then extracted with EtOAc (80 mL×3), the combined organic phase was washed with brine (30 mL×3), dried with anhydrous $Na_2SO_4$, filtered and concentrated in vacuum. The crude product was purified by silica gel chromatography eluted with Petroleum ether/Ethyl acetate=0:1-1:1. tert-butyl N-isopropoxy-N-propyl-carbamate (3.8 g, crude) was obtained as colorless oil. $^1$H NMR (MeOD, 400 MHz) δ4.12-4.02 (m, 1H), 3.39 (t, J=7.2 Hz, 2H), 1.70-1.61 (m, 2H), 1.49 (s, 9H), 1.21 (d, J=6.0 Hz, 6H), 0.90 (t, J=7.2 Hz, 3H).

To a solution of tert-butyl N-isopropoxy-N-propyl-carbamate (3.2 g, 14.7 mmol, 1 eq) in EtOAc (5 mL) was added HCl/EtOAc (4 M, 55.2 mL, 15 eq), and then stirred at 20° C. for 2 h. The reaction mixture was concentrated under reduced pressure to give a residue. N-isopropoxypropan-1-amine (1.61 g, 10.48 mmol, 71.16% yield, HCl) was obtained as colorless oil. $^1$H NMR (MeOD, 400 MHz) δ 4.76-4.67 (m, 1H), 3.23-3.16 (m, 2H), 2.00-1.89 (m, 2H), 1.41 (d, J=6.2 Hz, 6H), 1.03 (t, J=7.6 Hz, 3H).

Preparation of tert-butyl 3-[[5-amino-7-[isopropoxy (propyl)carbamoyl]-6H-thieno[3,2-b]azepin-2-yl] methyl]azetidine-1-carboxylate, 253a To a mixture of 5-amino-2-1(1-tert-butoxycarbonylazetidin-3-yl)methyl]-6H-thieno[3,2-b]azepine-7-carboxylic acid, 183b (400 mg, 1.06 mmol, 1 eq) and N-isopropoxypropan-1-amine (244 mg, 1.59 mmol, 1.50 eq, HCl) in DMA (2 mL) and DCM (2 mL) was added EDCI (610 mg, 3.18 mmol, 3 eq), and then stirred at 20° C. for 1 h. The reaction mixture was added $H_2O$ (20 mL) and then the pH of the mixture was adjusted to ~8 with aq $NaHCO_3$, extracted with EtOAc (30 mL×3), the combined organic phase was washed with brine (10 mL×3), dried with anhydrous $Na_2SO_4$, filtered and concentrated in vacuum. The crude product was purified by silica gel chromatography eluted with (Ethyl acetate, Methanol=1:0,5:1) to give 253a (410 mg, 860 umol, 81.17% yield) as a light yellow solid. $^1$H NMR (MeOD, 400 MHz) δ 7.34 (s, 1H), 6.73 (s, 1H), 4.20-4.15 (m, 1H), 4.09-4.00 (m, 2H), 3.74-3.63 (m, 4H), 3.06 (d, J=8.0 Hz, 2H), 2.95 (s, 2H), 2.90-2.84 (m, 1H), 1.76-1.67 (m, 2H), 1.43 (s, 9H), 1.17 (d, J=6.2 Hz, 6H), 0.94 (t, J=7.6 Hz, 3H).

Preparation of TAZ-253

To a solution of 253a (410 mg, 860 umol, 1 eq) in $CH_3CN$ (2 mL) and $H_2O$ (2 mL) was added TFA (785 mg, 6.88 mmol, 510 μL, 8 eq), and then stirred at 80° C. for 2 h under $N_2$ atmosphere. The reaction mixture was concentrated under reduced pressure to remove $CH_3CN$, the aqueous phase was extracted with and MTBE (15 mL×3) to remove excess TFA, the water phase was freeze-dried to give TAZ-253 (320 mg, 850 umol, 98.80% yield) as a light yellow solid. $^1$H NMR (MeOD, 400 MHz) δ 7.43 (s, 1H), 6.95 (s, 1H), 4.27-4.20 (m, 1H), 4.20-4.14 (m, 2H), 3.97-3.87 (m, 2H), 3.73 (br t, J=7.2 Hz, 2H), 3.40 (s, 2H), 3.30-3.25 (m, 3H), 1.81-1.69 (m, 2H), 1.18 (d, J=6.2 Hz, 6H), 0.96 (t, J=7.4 Hz, 3H). LC/MS [M+H] 377.2 (calculated); LC/MS [M+H] 377.1 (observed).

Example 260 Synthesis of isopropyl N-[2-[[5-amino-2-(azetidin-3-ylmethyl)-6H-thieno [3,2-b] azepine-7-carbonyl]-propyl-amino]oxyethyl]carbamate, TAZ-260

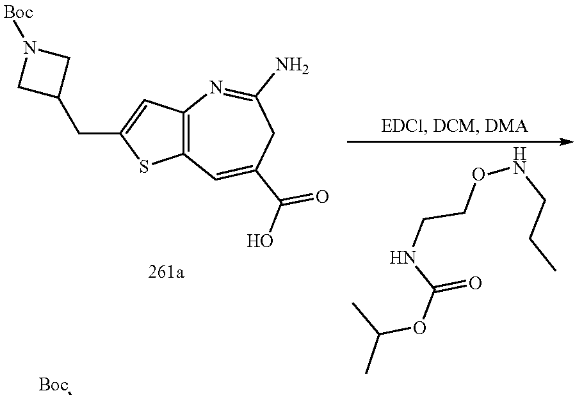

261a

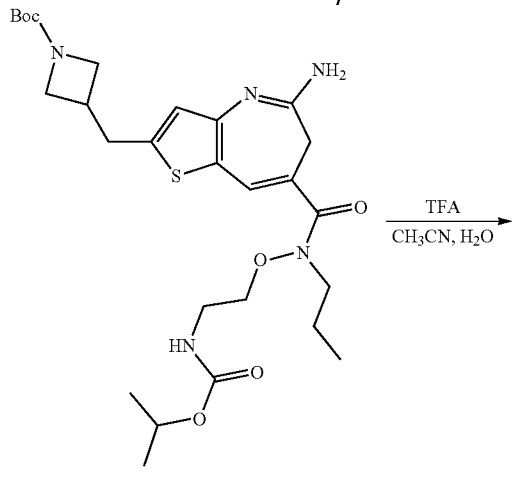

260a

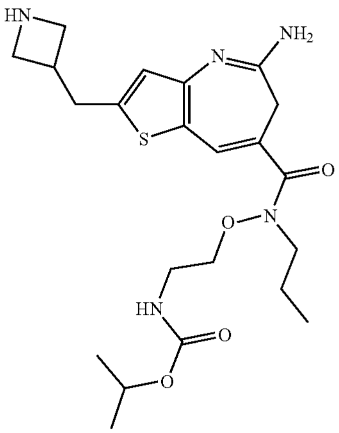

TAZ-260

Preparation of tert-butyl 3-[[5-amino-7-[2-(isopropoxycarbonylamino) ethoxy-propyl-carbamoyl]-6H-thieno[3,2-b]azepin-2-yl]methyl]azetidine-1-carboxylate, 260a To a mixture of isopropyl N-[2-(propylaminooxy)ethyl] carbamate (158 mg, 654 umol, 1.3 eq, HCl) and 5-amino-2-[(1-tert-butoxycarbonylazetidin-3-yl)methyl]-6H-thieno [3,2-b]azepine-7-carboxylic acid, 261a (0.19 g, 503 umol, 1.0 eq) in DCM (4 mL) and DMA (0.5 mL) was added EDCI (289 mg, 1.51 mmol, 3.0 eq) in one portion at 25° C. and then stirred at 25° C. for 0.5 h. The mixture was concentrated to remove DCM. Then the mixture was diluted with water (20 mL), the pH of the aqueous phase was adjusted to ~8 with sat. $NaHCO_3$ and then the mixture was extracted with EtOAc (20 mL×3). The organic layer was washed with brine, dried over $Na_2SO_4$, filtered and concentrated. The residue was purified by silica gel chromatography (column height: 250 mm, diameter: 100 mm, 100-200 mesh silica gel, Ethyl acetate/MeOH=1/0, 10/1) to afford 260a (0.18 g, 319 umol, 63.44% yield) as yellow oil. $^1$H NMR (MeOH, 400 MHz) δ 7.30 (s, 1H), 6.67 (s, 1H), 4.83-4.75 (m, 1H), 4.07-4.03 (m, 2H), 3.89 (t, J=5.4 Hz, 2H), 3.68 (t, J=7.0 Hz, 4H), 3.30-3.26 (m, 2H), 3.08 (d, J=7.6 Hz, 2H), 3.00 (s, 2H), 2.90-2.85 (m, 1H), 1.76-1.67 (m, 2H), 1.43 (s, 9H), 1.18 (d, J=6.0 Hz, 6H), 0.94 (t, J=7.2 Hz, 3H).

Preparation of TAZ-260

To a mixture of 260a (0.18 g, 319 umol, 1.0 eq) in $CH_3CN$ (2 mL) and $H_2O$ (2 mL) was added TFA (291 mg, 2.55 mmol, 189 μL, 8.0 eq) at 25° C. and it was stirred at 80° C. for 0.5 h. The mixture was concentrated to remove $CH_3CN$. Then the mixture was extracted with MTBE (10 mL×3) to remove excess TFA. The water phase was freeze-dried to give TAZ-260 (0.25 g, 310.30 umol, 97.18% yield, TFA salt) as a yellow solid. $^1$H NMR (MeOH, 400 MHz) δ7.47 (s, 1H), 6.96 (s, 1H), 4.81-4.76 (m, 1H), 4.23-4.09 (m, 2H), 3.98-3.86 (m, 4H), 3.71 (t, J=6.8 Hz, 2H), 3.41 (s, 2H), 3.29-3.18 (m, 5H), 1.83-1.64 (m, 2H), 1.25-1.12 (m, 6H), 0.96 (t, J=7.6 Hz, 3H). LC/MS [M+H] 464.2 (calculated); LC/MS [M+H] 464.1 (observed).

Example 261 Synthesis of 5-amino-2-(azetidin-3-ylmethyl)-N-[2-(ethylcarbamoylamino)ethoxy]-N-propyl-6H-thieno[3,2-b]azepine-7-carboxamide, TAZ-261

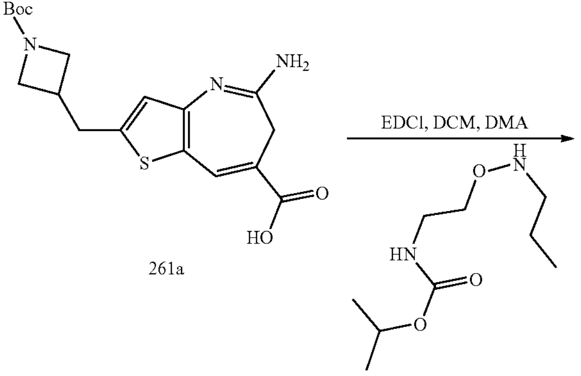

261a

-continued

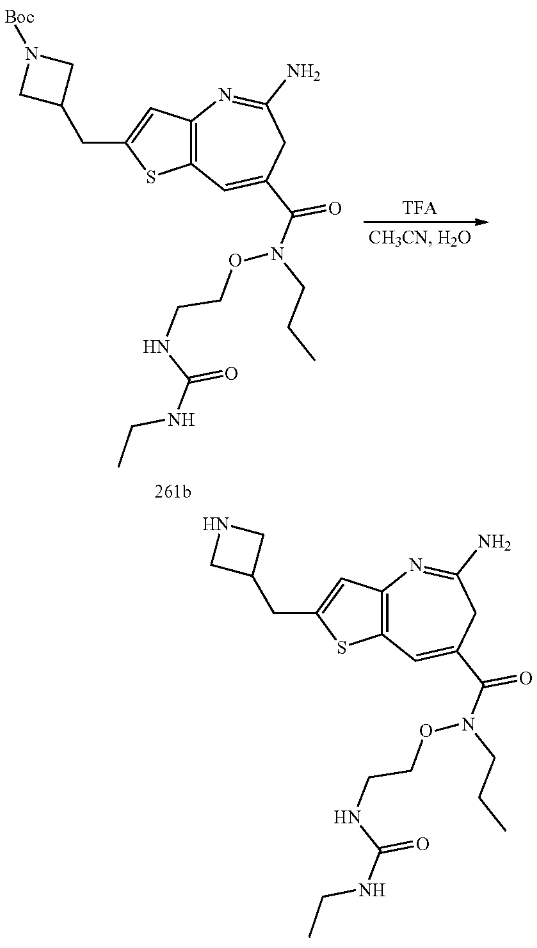

261b

TAZ-261

Preparation of tert-butyl 3-[[5-amino-7-[2-(ethylcarbamoylamino)ethoxy-propyl-carbamoyl]-6H-thieno[3,2-b]azepin-2-yl]methyl]azetidine-1-carboxylate, 261b To a solution of 2-|(1-tert-butoxycarbonylazetidin-3-yl)methyl]-5-amino-6H-thieno[3,2-b]azepine-7-carboxylic acid, 261a (230 mg, 607.76 umol, 1 eq) and 1-ethyl-3-[2-(propylaminooxy)ethyl]urea (192 mg, 851 umol, 1.4 eq, HCl) in DCM (3.00 mL) and DMA (3.00 mL) was added EDCI (350 mg, 1.82 mmol, 3 eq), and then stirred at 25° C. for 1 h. The mixture was concentrated to remove DCM and diluted with water (20 mL) and the pH of the mixture was adjusted about 9 by sat, $Na_2CO_3$ and extracted with EtOAc (20 mL×3). The organic layer was washed with brine (20 mL×3), dried over $Na_2SO_4$, filtered and concentrated. The residue was purified by flash silica gel chromatography (ISCO®; 0.5 g SepaFlash® Silica Flash Column, Eluent of 0-30% Ethyl acetate/MeOH (@; 35 mL/min) to give 261 b (270 mg, 492 umol, 80.97% yield) as light yellow solid. $^1H$ NMR (MeOD, 400 MHz) δ 7.29 (s, 1H), 6.68 (s, 1H), 4.10-4.00 (m, 2H), 3.88 (t, J=5.2 Hz, 2H), 3.74-3.61 (m, 4H), 3.29 (br s, 2H), 3.12-3.05 (m, 4H), 3.01 (s, 2H), 2.95-2.83 (m, 1H), 1.72 (sxt, J=7.2 Hz, 2H), 1.43 (s, 9H), 1.06 (t, J=7.2 Hz, 3H), 0.94 (t, J=7.6 Hz, 3H).

Preparation of TAZ-261

To a solution of 261b (270 mg, 492 umol, 1 eq) in $CH_3CN$ (3.00 mL) and $H_2O$ (3.00 mL) was added TFA (449 mg, 3.94 mmol, 291 μL, 8 eq), and then stirred at 80° C. for 1 h. The mixture was concentrated and diluted with water (20 mL) and extracted with MTBE (20 mL×2) to remove excess TFA and the aqueous phase was freeze-dried to give TAZ-261 (300 mg, 443.38 umol, 90.10% yield, 2TFA) as light yellow solid. IH NMR (MeOD, 400 MHz) δ 7.45 (s, 1H), 6.96 (s, 1H), 4.21-4.13 (m, 2H), 3.97-3.86 (m, 4H), 3.71 (t, J=7.2 Hz, 2H), 3.42 (s, 2H), 3.30-3.20 (m, 314), 3.06 (q, J=7.2 Hz, 2H), 1.80-1.68 (m, 2H), 1.05 (t, J=7.2 Hz, 3H), 0.96 (t, J=7.6 Hz, 3H). LC/MS [M+H] 449.2 (calculated); LC/MS [M+H] 449.1 (observed).

Example L-1 Synthesis of 2,3,5,6-tetrafluorophenyl (E)-40-(5-amino-6H-thieno[3,2-b]azepine-7-carbonyl)-35-((3-cyanophenyl)imino)-4,7,10,13,16,19,22,25,28,31-decaoxa-34,36,40-triazatritetracontanoate, TAZ-L-1

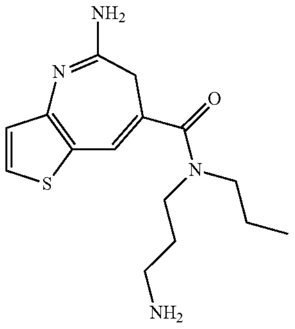

TAZ-11

+

-continued
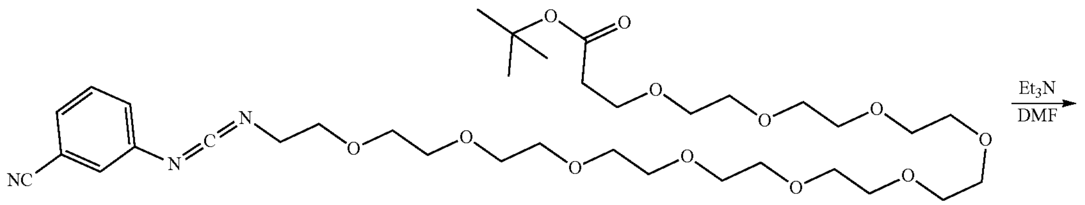
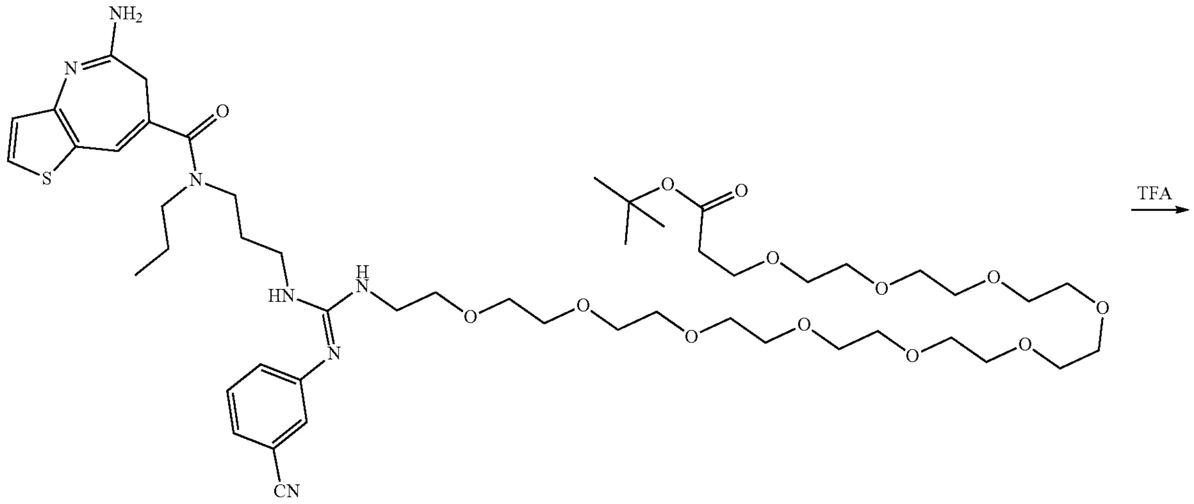
L-1a
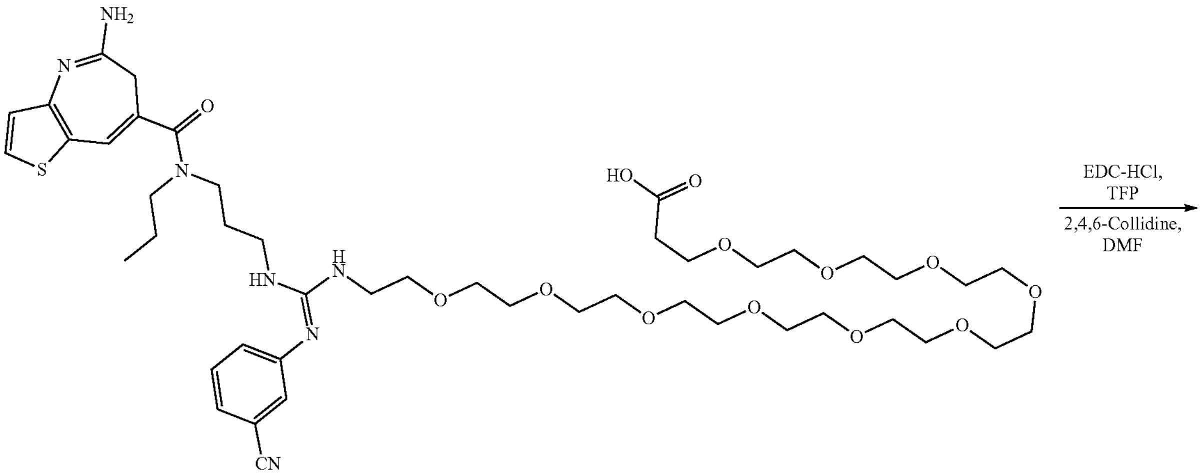
L-1b

-continued

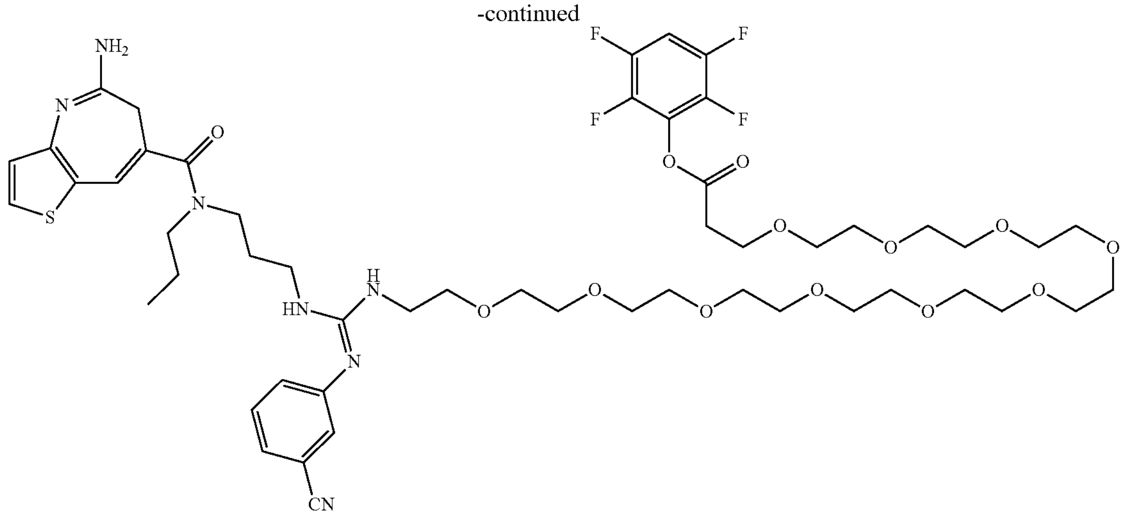

TAZ-L-1

Preparation of tert-butyl (E)-40-(5-amino-6H-thieno[3,2-b]azepine-7-carbonyl)-35-((3-cyanophenyl)imino)-4,7,10,13,16,19,22,2528,31-decaoxa-34,36,40-triazatritetracontanoate, L-1a TAZ-11 (0.05 g, 0.16 mmol, 1 eq.) and tert-butyl 1-((3-cyanophenyl)imino)-5,8,11,14,17,20,23,26,29,32-decaoxa-2-azapentatriacont-1-en-35-oate, PEG10-diimide (0.116 g, 0.16 mmol, 1 eq.) were dissolved in DMF. Triethylamine (0.068 ml, 0.49 mmol, 3 eq.) was added, and the reaction was stirred at ambient temperature. Upon consumption of amine starting material, the reaction was concentrated and purified by HPLC to give L-1a (0.102 g, 0.10 mmol, 62%). LC/MS [M+H] 1018.55 (calculated); LC/MS [M+H] 1018.91 (observed).

Preparation of (E)-40-(5-amino-6H-thieno[3,2-b]azepine-7-carbonyl)-35-((3-cyanophenyl)imino)-4,7,10,13,16,19,22,25,28,31-decaoxa-34,36,40-triazatritetracontanoic acid, L-1b L-1a (0.102 g, 0.10 mmol, 1 eq.) was dissolved in 100 μl TFA. After 15 minutes, the product was triturated with diethyl ether and then concentrated under vacuum to give L-1b (94.4 mg, 0.98 mmol, 98%). LC/MS [M+H] 962.49 (calculated); LC/MS [M+H] 962.85 (observed).

Preparation of TAZ-L-1

L-1b (0.094 g, 0.098 mmol, 1 eq.) and 2,3,5,6-tetrafluorophenol, TFP (0.033 g, 0.20 mmol, 2 eq.) were dissolved in DMF. Collidine (0.064 ml, 0.49 mmol, 5 eq.) was added, followed by 1-ethyl-3-(3-dimethylaminopropyl)carbodiimide hydrochloride, EDC-HCl (0.038 g, 0.20 mmol, 2 eq.). The reaction was stirred at room temperature until complete, then purified by HPLC to give TAZ-L-1 (0.057 g, 0.051 mmol, 52%). LC/MS [M+H] 1110.48 (calculated); LC/MS [M+H] 1110.87 (observed).

Example L-2 Synthesis of 2,3,5,6-tetrafluorophenyl (E)-41-(5-amino-6H-thieno[3,2-b]azepine-7-carbonyl)-35-((3-cyanophenyl)imino)-4,7,10,13,16,19,22,25,28,31-decaoxa-34,36,41-triazatetratetracont-38-ynoate, TAZ-L-2

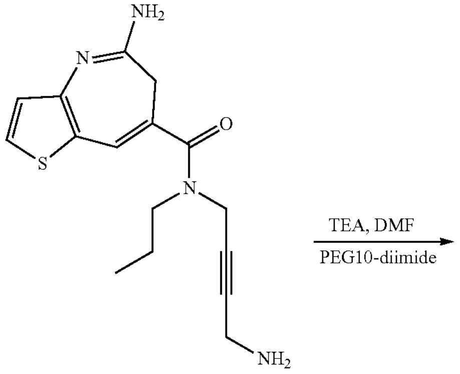

TAZ-17

-continued
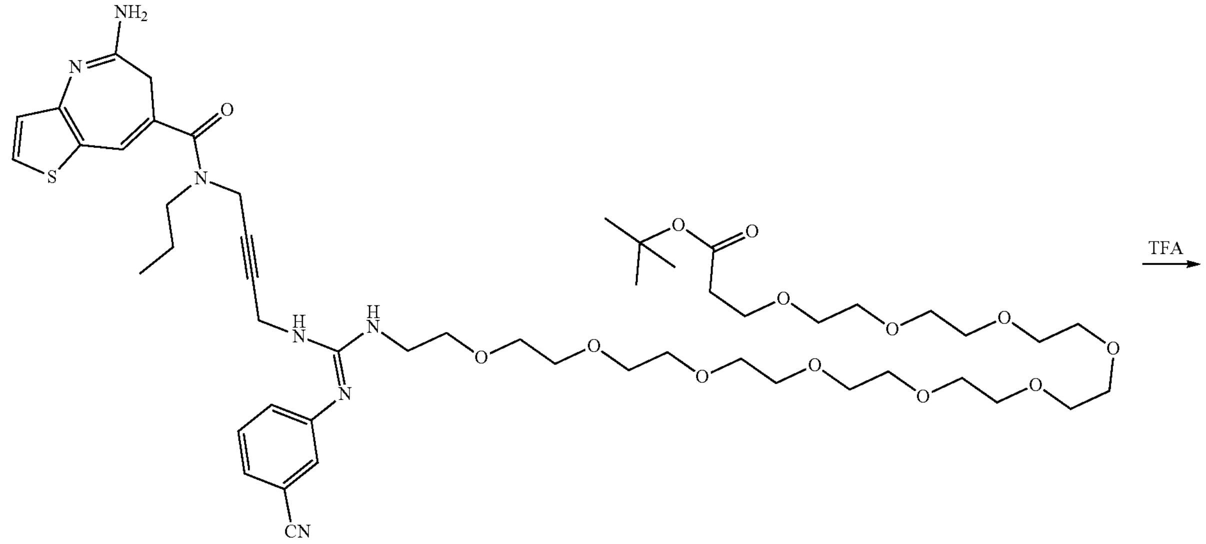
L-2a
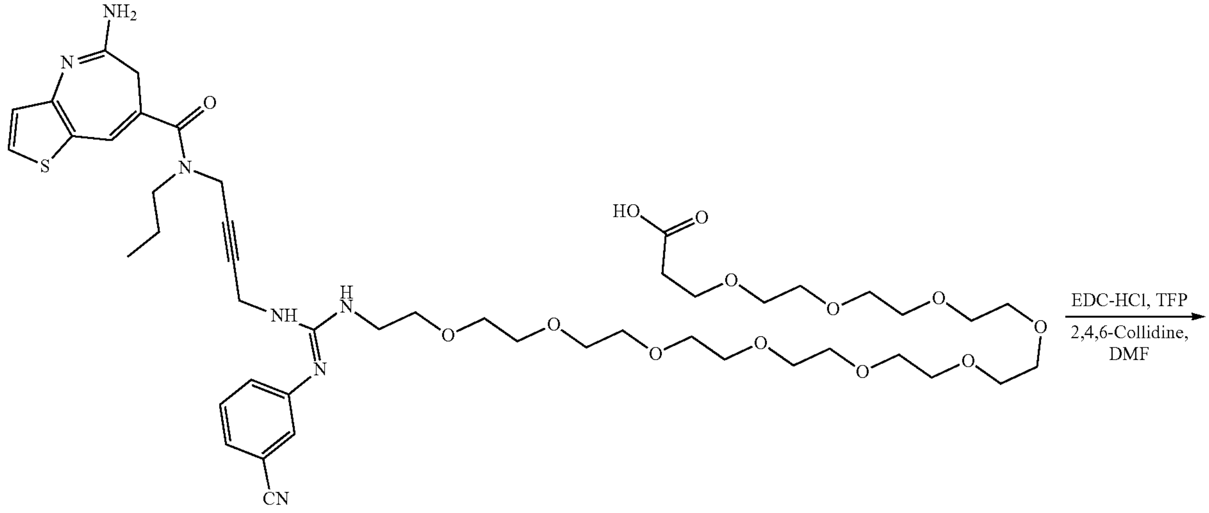
L-2b
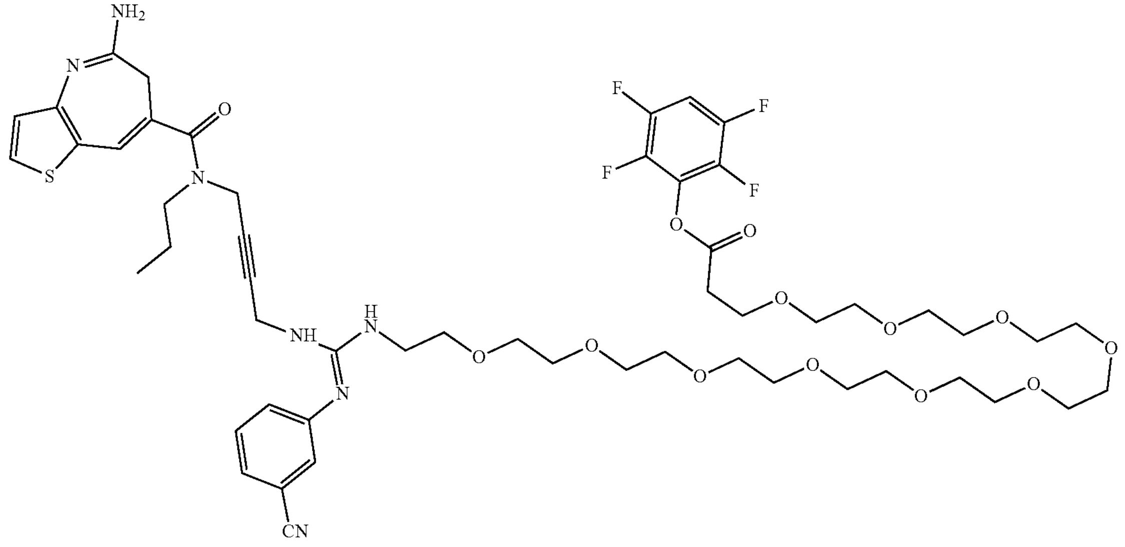
TAZ-L-2

Preparation of tert-butyl (E)-41-(5-amino-6H-thieno[3,2-b]azepine-7-carbonyl)-35-((3-cyanophenyl)imino)-4,7,10,13,16,19,22,25,28,31-decaoxa-34,36,41-triazatetratetracont-38-ynoate, L-2a TAZ-17 (0.05 g, 0.16 mmol, 1 eq.) and tert-butyl 1-((3-cyanophenyl)imino)-5,8,11,14,17,20,23,26,29,32-decaoxa-2-azapentatriacont-1-en-35-oate, PEG10-diimide (0.112 g, 0.16 mmol, 1 eq.) were dissolved in DMF. Triethylamine (0.066 ml, 0.47 mmol, 3 eq.) was added, and the reaction was stirred at ambient temperature. Upon consumption of amine starting material, the reaction was concentrated and purified by HPLC to give L-2a (0.120 g, 0.12 mmol, 74%). LC/MS [M+H] 1028.54 (calculated); LC/MS [M+H] 1028.92 (observed).

Preparation of (E)-41-(5-amino-6H-thieno[3,2-b]azepine-7-carbonyl)-35-((3-cyanophenyl)imino)-4,7,10,13,16,19,22,25,28,31-decaoxa-34,36,41-triazatetratetracont-38-ynoic acid, L-2b L-2a (0.120 g, 0.12 mmol, 1 eq.) was dissolved in 100 µl TFA. After 15 minutes, the product was concentrated and purified by HPLC to give L-2b (84.9 mg, 0.087 mmol, 75%). LC/MS [M+H] 972.47 (calculated); LC/MS [M+H] 972.83 (observed).

Preparation of TAZ-L-2

L-2b (0.085 g, 0.087 mmol, 1 eq.) and TFP (0.029 g, 0.17 mmol, 2 eq.) were dissolved in DMF. Collidine (0.058 ml, 0.44 mmol, 5 eq.) was added, followed by 1-ethyl-3-(3-dimethylaminopropyl)carbodiimide hydrochloride, EDC-HCl (0.033 g, 0.17 mmol, 2 eq.). The reaction was stirred at room temperature until complete, then purified by HPLC to give TAZ-L-2 (0.057 g, 0.055 mmol, 62%). LC/MS [M+H] 1120.47 (calculated); LC/MS [M+H] 1120.85 (observed).

Example L-3 Synthesis of 2,3,5,6-tetrafluorophenyl 39-(5-amino-7-(dipropylcarbamoyl)-6H-thieno[3,2-b]azepin-2-yl)-34-methyl-4,7,10,13,16,19,22,25,28,31-decaoxa-34-azanonatriacontanoate, TAZ-L-3

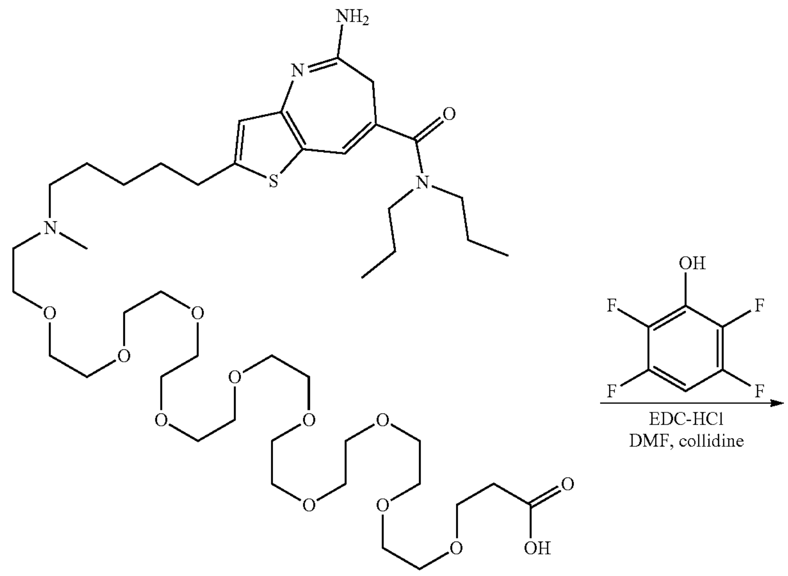

TAZ-25

-continued

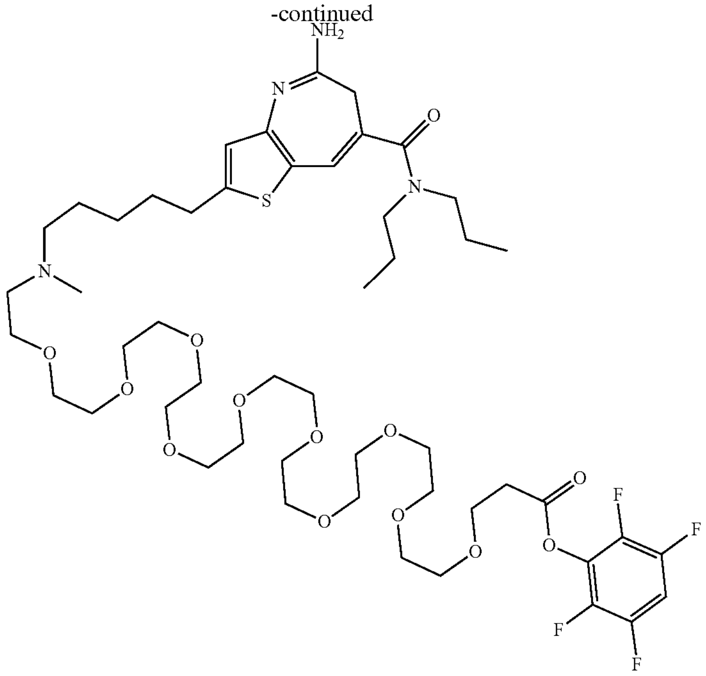

TAZ-L-3

TAZ-25 (0.18 g, 0.20 mmol, 1 eq.) and TFP (0.066 g, 0.40 mmol, 2 eq.) were dissolved in 1 ml DMF. Collidine (0.13 ml, 1.0 mmol, 5 eq.) was added, followed by 1-ethyl-3-(3-dimethylaminopropyl)carbodiimide hydrochloride. EDC-HCl (0.115 g, 0.60) mmol, 3 eq.). The reaction was stirred at room temperature until complete, then purified by HPLC to give TAZ-L-3 (0.103 g, 0.098 mmol, 49%). LC/MS [M+H] 1051.53 (calculated); LC/MS [M+H] 1051.74 (observed).

Example L-4 Synthesis of 2,3,5,6-tetrafluorophenyl 1-(4-((5-amino-N-propyl-6H-thieno[3,2-b]azepine-7-carboxamido)methyl)phenyl)-2-methyl-5,8,11,14,17,20,23,26,29,32-decaoxa-2-azapentatriacontan-35-oate, TAZ-L-4

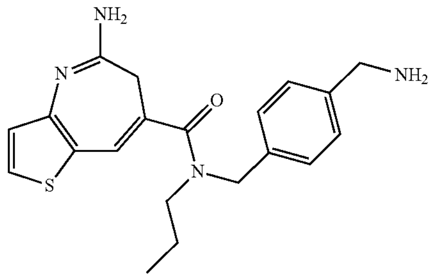

+

TAZ-30

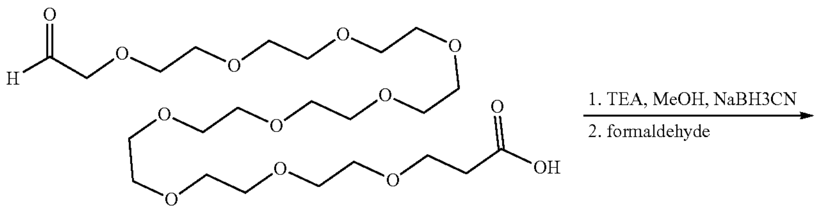

-continued

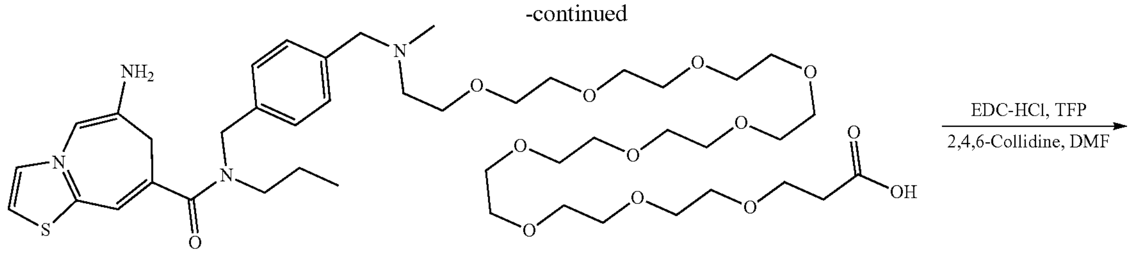

L-4a

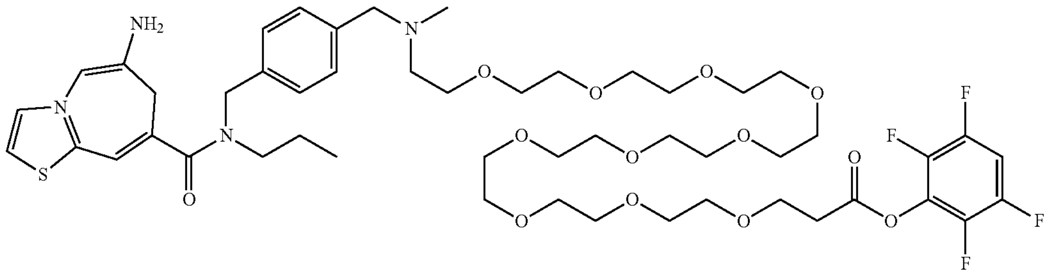

TAZ-L-4

Preparation of 1-(4-((5-amino-N-propyl-6H-thieno[3,2-b]azepine-7-carboxamido)methyl)phenyl)-2-methyl-5,8,11,14,17,20,23,26,29,32-decaoxa-2-aza-pentatriacontan-35-oic acid, L-4a 5-Amino-N-(4-(aminomethyl)benzyl)-N-propyl-6H-thieno[3,2-b]azepine-7-carboxamide, TAZ-30 (0.063 g, 0.17 mmol, 1 eq.) and 1-oxo-3,6,9,12,15,18,21,24,27,30-decaoxatritriacontan-33-oic acid (0.09 g, 0.17 mmol, 1 eq.) were dissolved in methanol. Triethylamine (0.14 ml, 1.0 mmol, 6 eq.) was added, followed by sodium cyanoborohydride (0.032 g, 0.51 mmol, 3 eq.). The reaction was monitored by LCMS. After 2 hours, formaldehyde (14 μl, 0.17 mmol, 37% w/w solution in water, 1 eq.) was added and the reaction stirred for an additional 30 minutes. Upon consumption of amine, the reaction was concentrated and purified by HPLC to give L-4a (0.045 g, 0.050 mmol, 29%). LC/MS [M+H] 895.47 (calculated); LC/MS [M+H] 895.80 (observed).

Preparation of TAZ-L-4

Intermediate L-4a (0.045 g, 0.05 mmol, 1 eq.) and TFP (0.017 g, 0.10 mmol, 2 eq.) were dissolved in 1 ml DMF. Collidine (0.033 ml, 0.25 mmol, 5 eq.) was added, followed by 1-ethyl-3-(3-dimethylaminopropyl)carbodiimide hydrochloride. EDC-HCl (0.029 g, 0.15 mmol, 3 eq.). The reaction was stirred at room temperature until complete, then purified by HPLC to give TAZ-L-4 (0.031 g, 0.030 mmol, 59%). LC/MS [M+H] 1043.47 (calculated); LC/MS [M+H] 1043.79 (observed).

Example L-10 Synthesis of (2,3,5,6-tetrafluorophenyl) 3-[2-[2-[2-[2-[2-[2-[2-[2-[2-[2-[[4-[[[5-amino-2-[5-(dimethylamino)pentyl]-6H-thieno[3,2-b]azepine-7-carbonyl]-propyl-amino]methyl]phenyl]methyl-methylamino]ethoxy]ethoxy]ethoxy]ethoxy]ethoxy]ethoxy]ethoxy]ethoxy]ethoxy]ethoxy]propanoate, TAZ-L-10

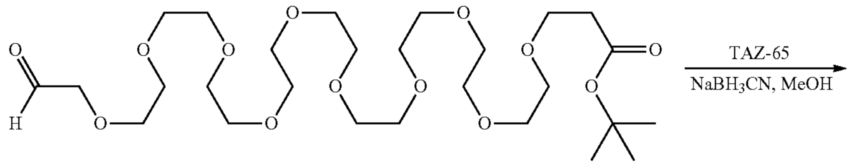

-continued

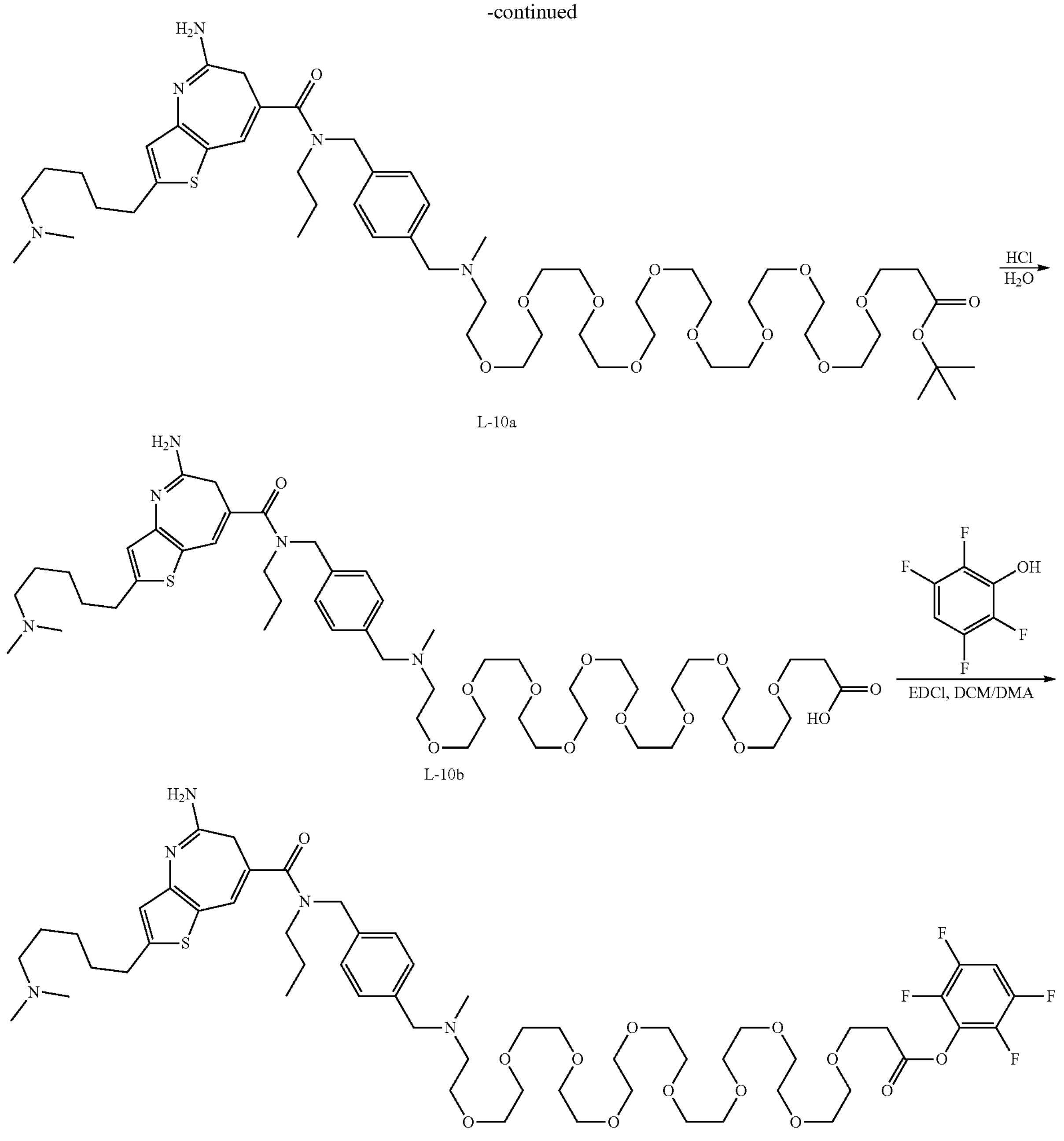

L-10a

L-10b

TAZ-L-10

Preparation of tert-butyl 3-[2-[2-[2-[2-[2-[2-[2-[2-[2-[2-[[4-[[[5-amino-2-[5-(dimethylamino)pentyl]-6H-thieno[3,2-b]azepine-7-carbonyl]-propyl-amino]methyl]phenyl]methyl-methylamino]ethoxy]ethoxy]ethoxy]ethoxy]ethoxy]ethoxy]ethoxy]ethoxy]ethoxy]ethoxy]propanoate, L-10a To a solution of 5-amino-2-[5-(dimethylamino)pentyl]-N-[[4-(methylaminomethyl)phenyl]methyl]-N-propyl-6H-thieno[3,2-b]azepine-7-carboxamide, TAZ-65 (300 mg, 527 umol, 1.0 eq, 2 HCl) in MeOH (10 mL) was added tert-butyl 3-[2-[2-[2-[2-[2-[2-[2-[2-[2-(2-oxoethoxy) ethoxy]ethoxy]ethoxy]ethoxy]ethoxy]ethoxy]ethoxy]ethoxy]ethoxy]propanoate (617 mg, 1.06 mmol, 2.0 eq), AcOH (3.1 mg, 52.7 umol, 0.10 eq) and $NaBH_3CN$ (66.3 mg, 1.06 mmol, 2.0 eq). The mixture was stirred for 12 hrs at 25° C. and then it was concentrated and purified by prep-HPLC (column: Nano-micro Kromasil C18 100*40 mm 10 um, mobile phase: [water (0.1% TFA)-ACN]; B %: 5/6-45%, 8 min) to give L-10a (350 mg, 328 umol, 62.33% yield) as colorless oil.

Preparation of 3-[2-[2-[2-[2-[2-[2-[2-[2-[2-[2-[[4-[[[5-amino-2-[5-(dimethylamino)pentyl]-6H-thieno[3,2-b]azepine-7-carbonyl]-propyl-amino]methyl]phenyl]methyl-methylamino]ethoxy]ethoxy]ethoxy]ethoxy]ethoxy]ethoxy]ethoxy]ethoxy]ethoxy]ethoxy]propanoic acid, L-10b To a mixture of L-10a (100 mg, 84.8 umol, 1.0 eq, TFA) in $H_2O$ (2 mL) was added HCl (12 M, 141 μL, 20.0 eq) at 25° C., and then stirred at 80° C. for 1 hr. The mixture was concentrated to afford L-10b (80.0 mg, 76.6 umol, 90.2% yield, HCl) as light yellow oil.

Preparation of TAZ-L-10

To a mixture of L-10b (50.0 mg, 49.6 umol, 1.0 eq) in DCM (2 mL) and DMA (0.1 mL) was added 1-ethyl-3-(3-dimethylaminopropyl)carbodiimide hydrochloride, EDCI (95.0 mg, 495 umol, 10.0 eq) at 15° C. and then stirred for 0.5 hr. The mixture was concentrated in vacuum to give a residue. The residue was purified by prep-HPLC (column: Phenomenex Synergi C18 150*25*10 um; mobile phase: [water (0.1% TFA)-ACN]; B %: 25%-50%, 8 min) to obtain TAZ-L-10 (21.0 mg, 16.5 umol, 34.5% yield, TFA) as light yellow oil. $^{1}$H NMR (MeOD, 400 MHz) S 7.57-7.50 (m, 2H), 7.48-7.43 (m, 3H), 7.12 (s, 1H), 6.92 (s, 1H), 4.80 (s, 2H), 4.50-4.32 (m, 2H), 3.90-3.87 (m, 4H), 3.70-3.59 (m, 38H), 3.38-3.40 (m, 6H), 3.01-2.99 (m, 2H), 2.90-2.98 (m, 2H), 2.90 (s, 9H), 1.79-1.78 (m, 4H), 1.70-1.65 (m, 2H), 1.52-1.49 (m, 2H), 0.93-0.87 (m, 3H). LC/MS [M+H] 1156.6 (calculated); LC/MS [M+H] 1156.6 (observed).

Example L-13 Synthesis of (2,3,5,6-tetrafluorophenyl) 3-[2-[2-[2-[2-[2-[2-[2-[2-[2-[2-[5-[5-amino-7-[[4-[(dimethylamino)methyl]phenyl]methyl-propyl-carbamoyl]-6H-thieno[3,2-b]azepin-2-yl]pentyl-methylamino]ethoxy]ethoxy]ethoxy]ethoxy]ethoxy]ethoxy]ethoxy]ethoxy]ethoxy]ethoxy]propanoate, TAZ-L-13

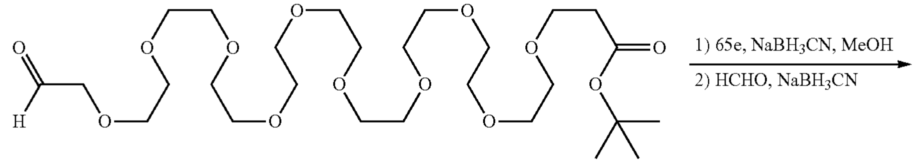

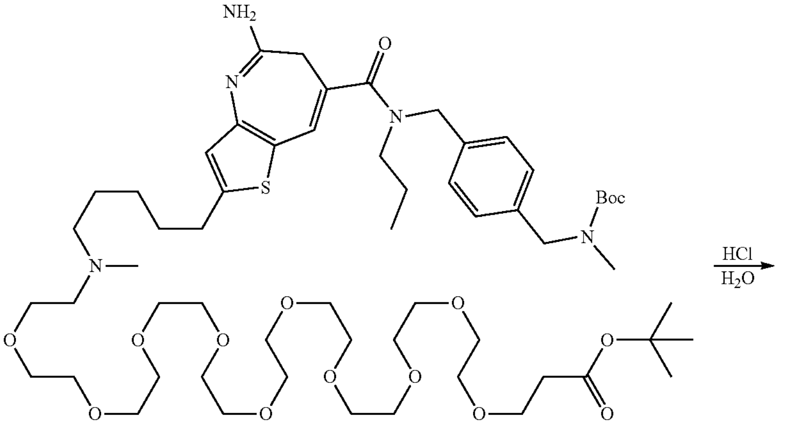

L-13a

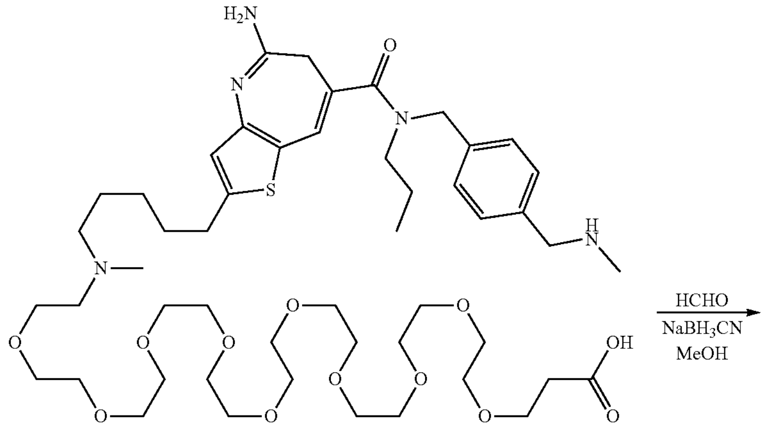

L-13b

-continued

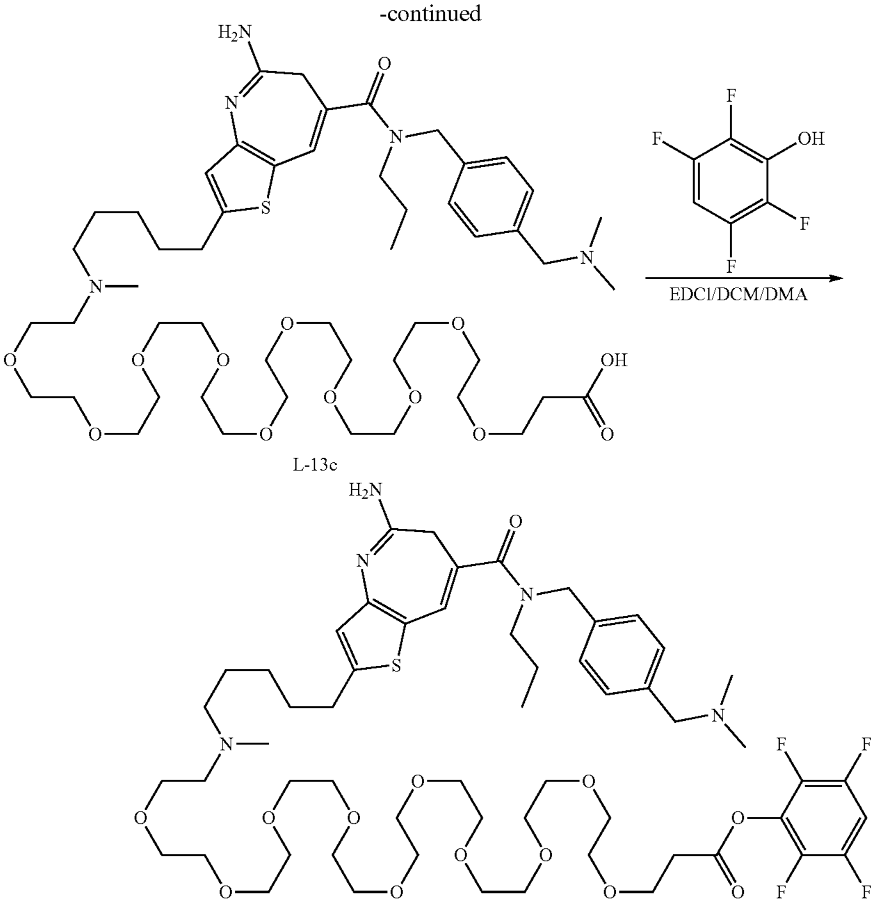

L-13c

TAZ-L-13

Preparation of tert-butyl 3-[2-[2-[2-[2-[2-[2-[2-[2-[2-[2-[5-[5-amino-7-[[4-[[tert- butoxycarbonyl (methyl)amino]methyl]phenyl]methyl-propyl-carbamoyl]-6H-thieno[3,2-b]azepin-2-yl]pentyl-methylamino]ethoxy]ethoxy]ethoxy]ethoxy]ethoxy]ethoxy]ethoxy]ethoxy]ethoxy]ethoxy]propanoate, L-13a To a solution of tert-butyl N-[[4-[[[5-amino-2-(5-amino-pentyl)-6H-thieno[3,2-b]azepine-7-carbonyl]-propyl-amino]methyl]phenyl]methyl]-N-methyl-carbamate, 65e (130 mg, 229 umol, 1.0 eq) in MeOH (50 mL) was added AcOH (13.7 mg, 228.96 umol, 13.0 uL, 1 eq) tert-butyl 3-[2-[2-[2-[2-[2-[2-[2-[2-[2-(2-oxoethoxy)ethoxy]ethoxy]ethoxy]ethoxy]ethoxy]ethoxy]ethoxy]ethoxy]ethoxy]propanoate (200 mg, 343 umol, 1.50 eq) and $NaBH_3CN$ (43.1 mg, 687 umol, 3.0 eq), and then stirred for 12 hrs at 25° C. Formaldehyde. HCHO (56 mg, 674 umol, 37% purity, 3.0 eq) and $NaBH_3CN$ (22.0 mg, 343 umol, 1.5 eq) were added to the mixture and then stirred for another 2 hrs at 25° C. The reaction mixture was quenched by addition $H_2O_2$ is mL and it was concentrated in vacuum to give a residue. The residue was purified by prep-HPLC (column: Phenomenex luna C18 250*50 mm*10 um; mobile phase: [water(0.1% TFA)-ACN]; B %: 30%-60%, 10 min) to give L-13a (100 mg, 86.92 umol, 38% yield) as colorless oil.

Preparation of 3-[2-[2-[2-[2-[2-[2-[2-[2-[2-[2-[5-[5-amino-7-[[4-(methylaminomethyl)phenyl]methyl-propyl-carbamoyl]-6H-thieno[3,2-b]azepin-2-yl]pentyl-methylamino]ethoxy]ethoxy]ethoxy]ethoxy]ethoxy]ethoxy]ethoxy]ethoxy]ethoxy]ethoxy]propanoic acid, L-13b To a solution of L-13a (100 mg, 86.9 umol, 1.0 eq) in $H_2O$ (0.5 mL) was added HCl (12 M, 145 μL, 20.0 eq) and then stirred for 0.5 h at 80° C. The reaction mixture was concentrated under pressure to give L-13b (92 mg, crude) as colorless oil.

Preparation of 3-[2-[2-[2-[2-[2-[2-[2-[2-[2-[2-[5-[5-amino-7-[[4-[(dimethylamino)methyl]phenyl]methyl-propyl-carbamoyl]-6H-thieno[3,2-b]azepin-2-yl]pentyl-methylamino]ethoxy]ethoxy]ethoxy]ethoxy]ethoxy]ethoxy]ethoxy]ethoxy]ethoxy]ethoxy]propanoic acid, L-13c To a mixture of HCHO, formaldehyde (30.4 mg, 375 umol, 37% purity, 5.0 eq) and L-13b (80 mg, 74.9 umol, 1.0 eq, 2HCl) in MeOH (I mL) was added $NaBH_3CN$ (9.4 mg, 150 umol, 2.0 eq) at 15° C. and then stirred at 15° C. for 1 hr. The mixture was filtered and the filtrate was purified by prep-HPLC (column: Phenomenex luna C18 80*40 mm*3 um; mobile phase: [water(0.04% HCl)-ACN]; B %: 5%-35%, 7 min) to obtain L-13c (55 mg, 50.87 umol, 67.86% yield, 2HCl) as colorless oil. $^{1}H$ NMR (MeOD, 400

MHz) S 7.56 (d, J=8.0 Hz, 2H), 7.48 (d, J=7.2 Hz, 2H), 7.13 (s, 1H), 6.95 (s, 1H), 4.83 (s, 2H), 4.35 (s, 2H), 3.76-3.70 (m, 2H), 3.70-3.62 (m, 40H), 3.50-3.47 (m, 6H), 3.35-3.28 (m, 2H), 2.94-2.91 (m, 5H), 2.88 (s, 6H), 2.56 (t, J=6.4 Hz, 2H), 1.82-1.81 (m, 3H), 1.69-1.65 (m, 2H), 1.53-1.49 (m, 2H), 0.91 (t, J=7.2 Hz, 3H)

Preparation of TAZ-L-13

To a mixture of L-13c (50 mg, 49.6 umol, 1.0 eq) in DCM (2 mL) and DMA (0.1 mL) was added 1-ethyl-3-(3-dimethylaminopropyl)carbodiimide hydrochloride, EDCI (95.0 mg, 496 umol, 10.0 eq) at 15° C. and then stirred at 15° C. for 0.5 hr. The mixture was concentrated under reduced pressure to give a residue. The residue was purified by prep-HPLC (column: Phenomenex Synergi C18 150*25*10 um; mobile phase: [water(0.1% TFA)-ACN]; B %: 20%-40%, 10 min) to afford TAZ-L-13 (23 mg, 19.89 umol, 40.11% yield) as light yellow oil. $^1$H NMR (MeOD, 400 MHz) S 7.53-7.51 (m, 2H), 7.46-7.40 (m, 3H), 7.11 (s, 1H), 6.92 (s, 1H), 4.80 (s, 2H), 4.33 (s, 2H), 3.89 (t, J=6.4 Hz, 2H), 3.89-3.85 (m, 2H), 3.70-3.63 (m, 38H), 3.54-3.42 (m, 4H), 3.39 (s, 2H), 2.99 (t, J=6.0 Hz, 2H), 2.94-2.91 (m, 5H), 2.87 (s, 6H), 1.80 (d, J=6.4 Hz, 4H), 1.69-1.64 (m, 2H), 1.52-1.50 (m, 2H), 0.90 (t, J=6.8 Hz, 3H). LC/MS [M+H] 1156.6 (calculated); LC/MS [M+H] 1156.6 (observed).

Example L-16 Synthesis of(2,3,5,6-tetrafluorophenyl) 3-[2-[2-[2-[2-[2-[2-[2-[2-[2-[2-[[4-[[(5-amino-6H-thieno [3,2-b]azepine-7-carbonyl)-propyl-amino] methyl]-2-(trifluoromethyl)phenyl]methyl-methylamino]ethoxy]ethoxy]ethoxy]ethoxy]ethoxy] ethoxy]ethoxy]ethoxy]ethoxy]ethoxy]propanoate, TAZ-L-16

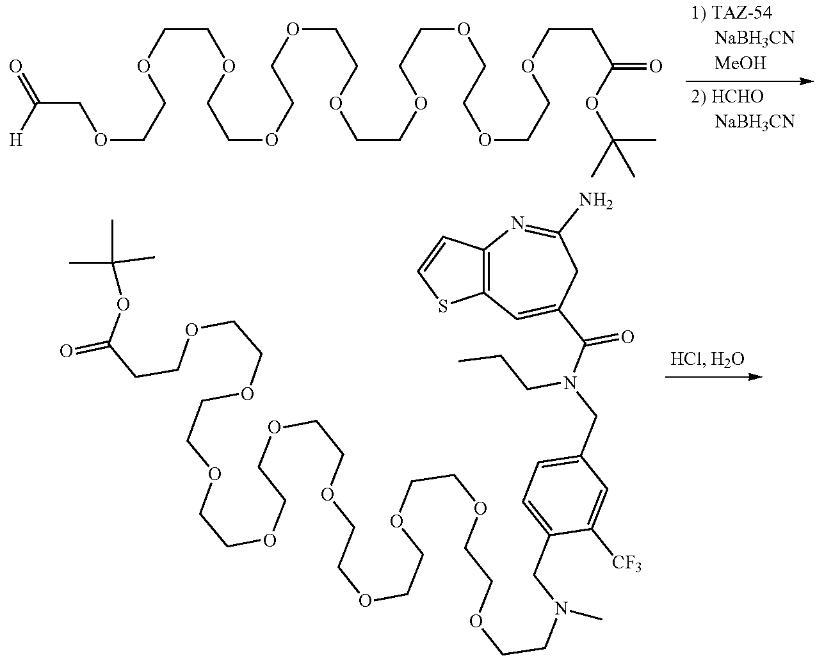

L-16a

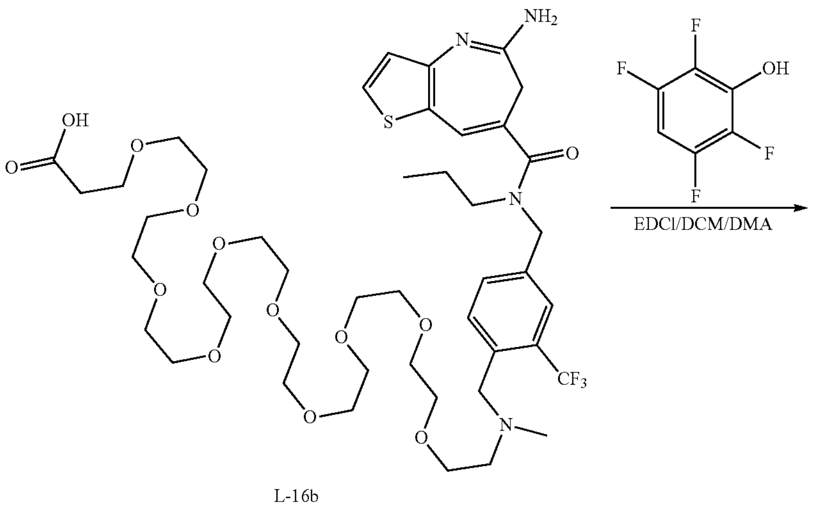

L-16b

-continued

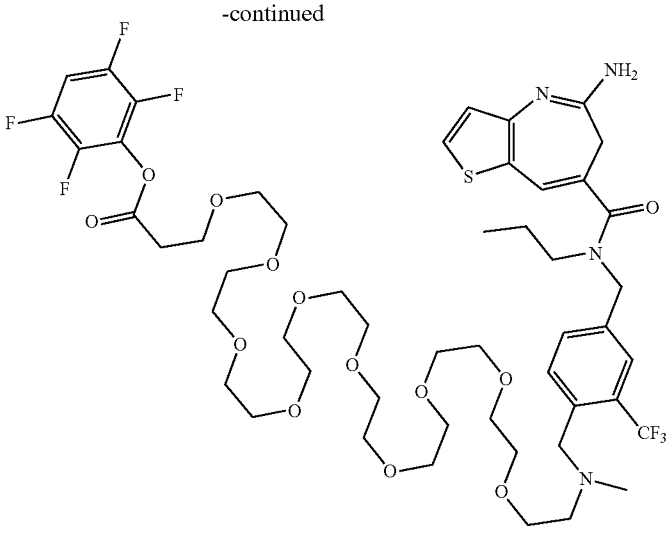

TAZ-L-16

Preparation of tert-butyl 3-[2-[2-[2-[2-[2-[2-[2-[2-[2-[2-[[4-[[(5-amino-6H-thieno[3,2-b]azepine-7-carbonyl)-propyl-amino]methyl]-2-(trifluoromethyl)phenyl]methyl-methylamino]ethoxy]ethoxy]ethoxy]ethoxy]ethoxy]ethoxy]ethoxy]ethoxy]ethoxy]ethoxy]propanoate, L-16a To a mixture of 5-amino-N-[[4-(aminomethyl)-3-(trifluoromethyl)phenyl]methyl]-N-propyl-6H-thieno[3,2-b]azepine-7-carboxamide, TAZ-54 (80.0 mg, 145 umol, 1.0 eq, TFA) and tert-butyl 3-[2-[2-[2-[2-[2-[2-[2-[2-[2-(2-oxoethoxy)ethoxy]ethoxy]ethoxy]ethoxy]ethoxy]ethoxy]ethoxy]ethoxy]ethoxy]propanoate (110 mg, 189 umol, 1.3 eq) in MeOH (20 mL) was added $NaBH_3CN$ (22.8 mg, 363 umol, 2.5 eq) at 20° C. and then stirred 20 hrs at this temperature. HCHO (70.7 mg, 872 umol, 64.9 uL, 37% purity, 6.0 eq) and $NaBH_3CN$ (22.8 mg, 363 umol, 2.5 eq) was added to the mixture, and it was stirred at 20° C. for another 1 hour. The reaction mixture was concentrated in vacuum and purified by prep-HPLC (column: Nano-micro Kromasil C18 100*40 mm 10 um; mobile phase: [water (0.1% TFA)-ACN]; B %: 3%-40%, 8 min) to afford L-16a (88.0 mg, 86.3 umol, 59.4% yield) as colorless oil. $^1H$ NMR (400 MHz, MeOD) δ7.90-7.83 (m, 2H), 7.83-7.78 (m, 1H), 7.76 (d, J=5.2 Hz, 1H), 7.22 (d, J=6.4 Hz, 1H), 7.16 (d, J=4.8 Hz, 1H), 4.73-4.55 (m, 2H), 3.93-3.84 (m, 2H), 3.71-3.70 (m, 4H), 3.68-3.57 (m, 38H), 3.49 (s, 2H), 3.41 (s, 2H), 2.95 (s, 3H), 2.48 (t, J=6.0 Hz, 2H), 1.75-1.67 (m, 2H), 1.47 (s, 9H), 0.93 (br t, J=7.6 Hz, 3H).

Preparation of 3-[2-[2-[2-[2-[2-[2-[2-[2-[2-[2-[[4-[(5-amino-6H-thieno[3,2-b]azepine-7-carbonyl)-propyl-amino]methyl]-2-(trifluoromethyl)phenyl]methyl-methylamino]ethoxy]ethoxy]ethoxy]ethoxy]ethoxy]ethoxy]ethoxy]ethoxy]ethoxy]ethoxy]propanoic acid, L-16b To a solution of L-16a (78.0 mg, 76.5 umol, 1.0 eq) in $H_2O$ (0.5 mL) and MeCN (0.1 mL) was added HCl (12 M, 191 μL, 30 eq) at 20° C. under $N_2$, the mixture was heated to 80° C. and then stirred for 1 hour. The reaction mixture was concentrated in vacuum to afford L-16b (70.0 mg, 72.6 umol, 94.9% yield) as colorless oil.

Preparation of TAZ-L-16

To a mixture of L-16b (60 mg, 62.3 umol, 1 eq) and 2,3,5,6-tetrafluorophenol (51.7 mg, 311 umol, 5.0 eq) in DCM (1 mL) and DMA (0.1 mL) was added EDCI (59.7 mg, 311 umol, 5.0 eq) at 20° C. under $N_2$, and then stirred at 20° C. for 1 hour. The reaction mixture was concentrated in vacuum. The residue was purified by prep-HPLC (column: Phenomenex Synergi C18 150*25*10 um; mobile phase: [water (0.1% TFA)-ACN]; B %: 25%-50%, 7 min) to afford TAZ-L-16 (15 mg, 13.5 umol, 21.67% yield) as colorless oil. $^1H$ NMR (400 MHz, MeOD) δ7.88-7.83 (m, 2H), 7.82-7.78 (m, 1H), 7.76 (d, J=5.6 Hz, 1H), 7.48-7.41 (m, 1H), 7.22 (s, 1H), 7.16 (d, J=5.6 Hz, 1H), 4.96 (s, 2H), 3.92-3.87 (m, 4H), 3.71-3.58 (m, 38H), 3.52-3.48 (m, 2H), 3.41 (s, 2H), 3.34 (s, 2H), 2.99 (t, J=6.0 Hz, 2H), 2.95 (s, 3H), 1.75-1.66 (m, 2H), 0.92 (t, J=7.2 Hz, 3H). LC/MS [M+H] 1111.5 (calculated); LC/MS [M+H] 1111.5 (observed).

Example L-22 Synthesis of (2,3,5,6-tetrafluorophenyl) 3-[2-[2-[2-[2-[2-[2-[2-[2-[2-[2-[[4-[[(5-amino-6H-thieno I3,2-b]azepine-7-carbonyl)-propyl-amino] methyl]-3-(trifluoromethyl)phenyl]methyl-methylamino]ethoxy]ethoxy]ethoxy]ethoxy]ethoxy] ethoxy]ethoxy]ethoxy]ethoxy]ethoxy]propanoate, TAZ-L-22
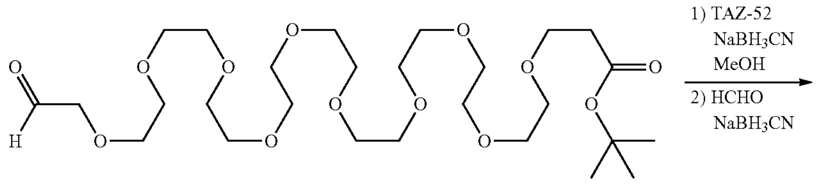
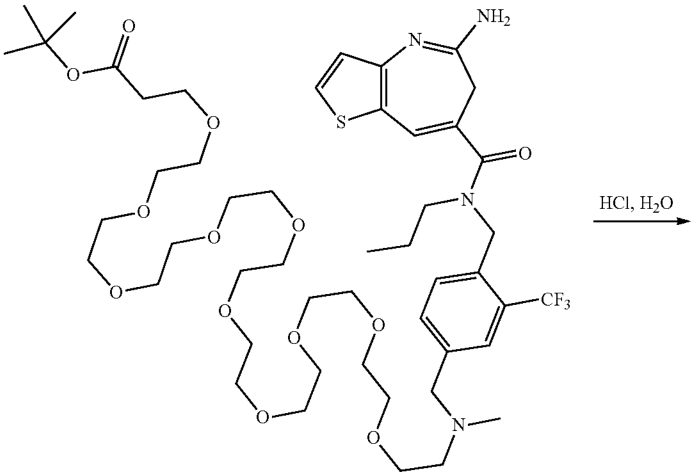
L-22a
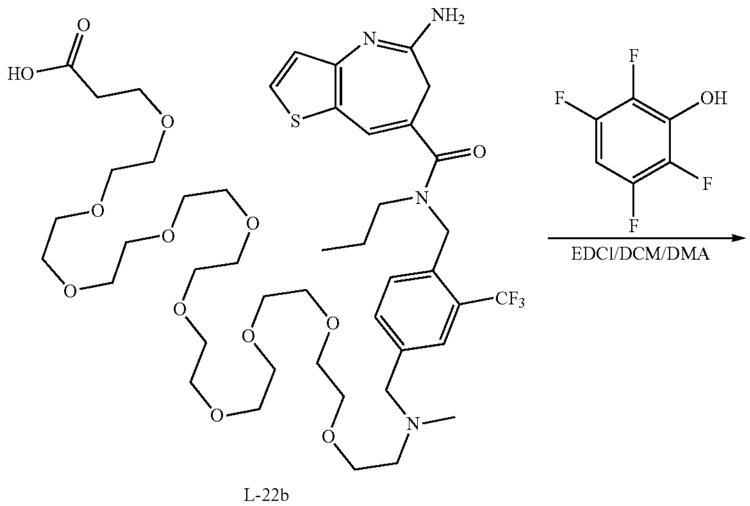
L-22b -continued

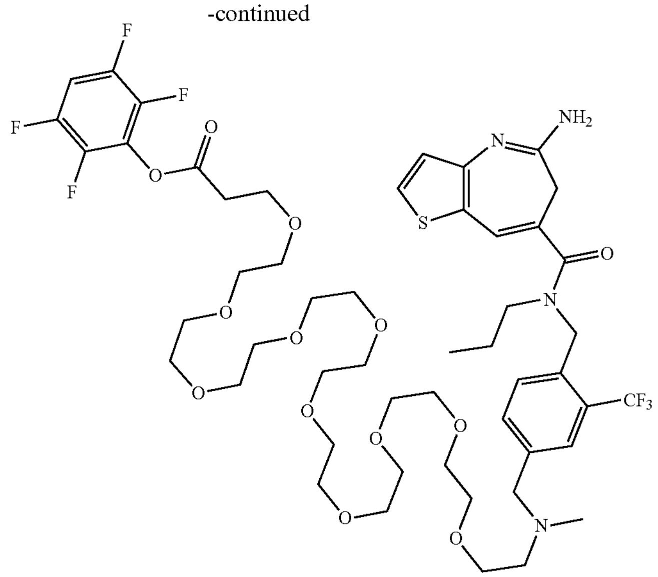

TAZ-L-22

Preparation of tert-butyl 3-[2-[2-[2-[2-12-[2-[2-[2-[2-[2-[[4-[[(5-amino-6H-thieno[3,2-b]azepine-7-carbonyl)-propyl-amino]methyl]-3-(trifluoromethyl)phenyl]methyl-methylamino]ethoxy]ethoxy]ethoxy]ethoxy]ethoxy]ethoxy]ethoxy]ethoxy]ethoxy]ethoxy]propanoate, L-22a To a mixture of tert-butyl 3-[2-[2-[2-[2-[2-[2-[2-[2-[2-(2-oxoethoxy)ethoxy]ethoxy]ethoxy]ethoxy]ethoxy]ethoxy]ethoxy]ethoxy]ethoxy]propanoate (51.9 mg, 89 umol, 1.4 eq) in MeOH (3 mL) was added 5-amino-N-[[4-(aminomethyl)-2-(trifluoromethyl)phenyl]methyl]-N-propyl-6H-thieno[3,2-b]azepine-7-carboxamide, TAZ-52 (30 mg, 63 umol, 1.0 eq. HCl) at 25° C. The mixture was stirred for 10 min. then $NaBH_3CN$ (7.97 mg, 126.86 umol, 2 eq) was added and it was stirred at 25° C. for 23 hours, then formaldehyde (15.44 mg, 190.29 umol, 14.17 uL, 3 eq) and $NaBH_3CN$ (7.97 mg, 126.86 umol, 2 eq) was added and the reaction was stirred for another 1 hour. Followed, the reaction mixture was concentrated and purified by prep-HPLC (column: Phenomenex Luna C18 150*30 mm*5 um; mobile phase: [water (0.1% TFA)-ACN]; B %: 25%-55%, 10 min) to give L-22a (60 mg, crude) as colorless oil.

Preparation of 3-[2-[2-[2-[2-[2-[2-[2-[2-[2-[2-[[4-[[(5-amino-6H-thieno[3,2-b]azepine-7-carbonyl)-propyl-amino]methyl]-3-(trifluoromethyl)phenyl]methyl-methylamino]ethoxy]ethoxy]ethoxy]ethoxy]ethoxy]ethoxy]ethoxy]ethoxy]ethoxy]ethoxy]propanoic acid, L-22b To a mixture of L-22a (60 mg, 58.87 umol, 1 eq) in $H_2O$ (0.5 mL) was added HCl (12 M, 150 μL, 30 eq) in one portion at 15° C. and then stirred at 80° C. for 2 hours. The mixture was concentrated in vacuum to obtain L-22b (45 mg, 45.02 umol, 76.47% yield, HCl) as light yellow oil.

Preparation of TAZ-L-22

To a mixture of L-22b (40 mg, 40 umol, 1.0 eq, HCl) in DCM (0.2 mL) and DMA (0.02 mL) was added 2,3,5,6-tetrafluorophenol (53.2 mg, 320 umol, 8.0 eq) and EDCI (76.7 mg, 400 umol, 10 eq) at 15° C., and then stirred for 30 min. The reaction was concentrated under reduced pressure at 30° C. and purified by prep-HPLC (column: Phenomenex Synergi C18 150*25*10 um; mobile phase: [water (0.1% TFA)-ACN]; B %: 20%-50/o, 8 min) to afford TAZ-L-22 (24.7 mg, 22.23 umol, 55.55% yield) as light yellow oil. $^1H$ NMR (MeOD, 400 MHz) δ 7.98 (s, 1H), 7.86-7.84 (m, 1H), 7.76-7.72 (m, 1H), 7.65 (d, J=8.0 Hz, 1H), 7.48-7.39 (m, 1H), 7.14 (d, J=5.2 Hz, 1H), 4.96 (s, 2H), 4.70-4.41 (m, 2H), 3.92-3.82 (m, 4H), 3.70-3.54 (m, 38H), 3.44-3.40 (m, 4H), 3.34 (s, 2H), 2.97 (t, J=6.0 Hz, 2H), 2.91 (s, 3H), 1.75-1.59 (m, 2H), 0.91 (t, J=6.8 Hz, 3H). LC/MS [M+H] 1111.5 (calculated); LC/MS [M+H] 1111.4 (observed).

Example L-32 Synthesis of 2,3,5,6-tetrafluorophenyl 40-(5-amino-7-((3-(3,3-dimethylbutanamido)propyl)(propyl)carbamoyl)-6H-thieno[3,2-b]azepin-2-yl)-34-oxo-4,7,10,13,16,19,22,25,28,31-decaoxa-35-azatetracontanoate, TAZ-L-32

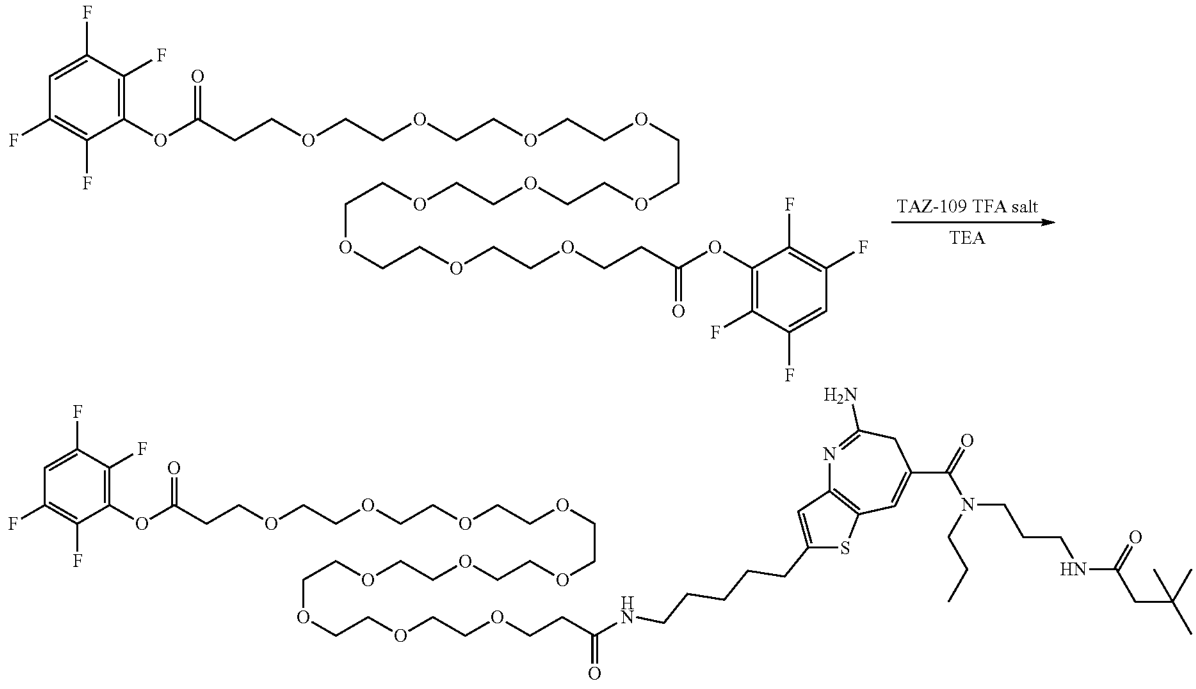

TAZ-L-32

Bis(2,3,5,6-tetrafluorophenyl) 4,7,10,13,16,19,22,25,28,31-decaoxatetratriacontanedioate (10 mg, 0.12 mmol, 1 eq.) was dissolved in 0.5 ml acetonitrile, ACN. To this solution was added dropwise a solution of the trifluoroacetate salt of 5-amino-2-(5-aminopentyl)-N-(3-(3,3-dimethylbutanamido)propyl)-N-propyl-6H-thieno[3,2-b]azepine-7-carboxamide, TAZ-109 (7.4 mg, 0.012 mmol, 1 eq.) and triethylamine, TEA (0.01 ml, 0.073 mmol, 6 eq.) in 1 ml ACN. Upon completion, the reaction was purified by HPLC to TAZ-L-32 as a colorless glass (4 mg, 0.03 mmol, 28%). LC/MS [M+H] 1178.59 (calculated). LC/MS [M+H] 1178.83 (observed).

Example L-34 Synthesis of 2,3,5,6-tetrafluorophenyl 39-(5-amino-7-((3-(3,3-dimethylbutanamido)propyl)(propyl)carbamoyl)-6H-thieno[3,2-b]azepin-2-yl)-34-methyl-4,7,10,13,16,19,22,25,28,31-decaoxa-34-azanonatriacontanoate, TAZ-L-34

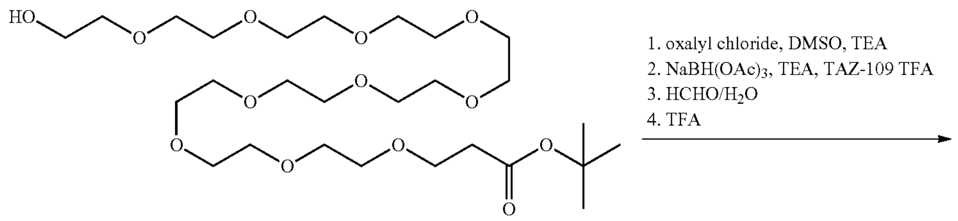

-continued

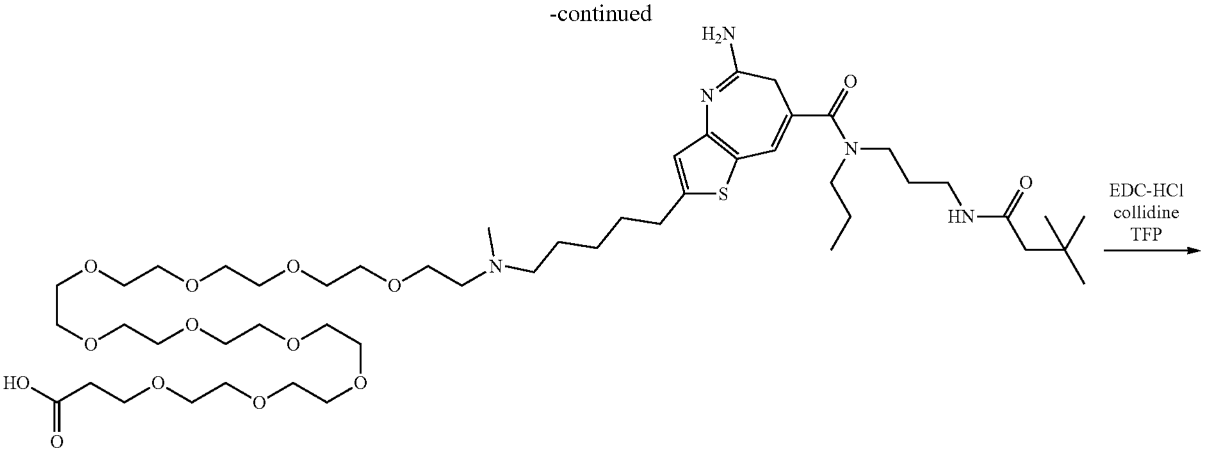

L-34a

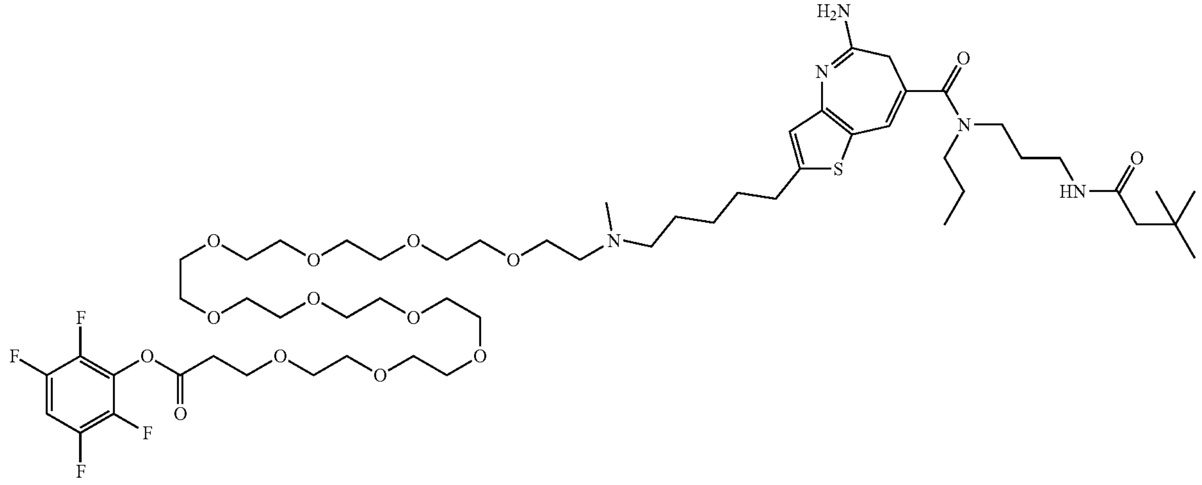

TAZ-L-34

Preparation of 39-(5-amino-7-((3-(3,3-dimethylbutanamido)propyl)(propyl)carbamoyl)-6H-thieno[3,2-b]azepin-2-yl)-34-methyl-4,7,10,13,16,19,22,25,28,31-decaoxa-34-azanonatriacontanoic acid, L-34a Oxalyl chloride (0.023 ml, 0.27 mmol, 3 eq.) was dissolved in 2.5 ml DCM at −78° C. dimethylsulfoxide, DMSO (0.038 ml, 0.54 mmol, 6 eq.) was added dropwise. The reaction was stirred at −78° C. for 15 minutes, then tert-butyl 1-hydroxy-3,6,9,12,15,18,21,24,27,30-decaoxatritriacontan-33-oate (0.052 g, 0.089 mmol, 1 eq.) was added dropwise as a solution in 0.5 ml DCM. The reaction was stirred 30 minutes at −78° C., and then triethylamine, TEA (0.112 ml, 0.80 mmol, 9 eq.) was added dropwise. The reaction was stirred 30 more minutes at −78° C., then removed from cooling and allowed to warm to ambient temperature over 30 minutes to form the crude aldehyde intermediate. The trifluoroacetate salt of 5-amino-2-(5-aminopentyl)-N-(3-(3,3-dimethylbutanamido)propyl)-N-propyl-6H-thieno[3,2-b]azepine-7-carboxamide, TAZ-109 (0.054 g, 0.089 mmol, 1 eq.) and sodium triacetoxyborohydride, STAB (0.186 g, 0.88 mmol, 9.8 eq.) were suspended in 2 ml DCM with an additional 0.05 ml TEA. The crude aldehyde solution was added to the stirring solution. The reaction was stirred at room temperature for 3 hours, and then formaldehyde (0.0073 g, 0.089 mmol, 1 eq., 37 wt. % in $H_2O$) added. After 15 minutes, the reaction was concentrated and purified by HPLC to give as a colorless residue, which was dissolved in minimal TFA and allowed to stand for 15 minutes. The solution was then concentrated and triturated with diethyl ether to give L-34a (0.042 g, 0.041 mmol, 46%). LC/MS [M+H] 1016.62 (calculated); LC/MS [M+H] 1016.95 (observed).

Preparation of TAZ-L-34

Intermediate L-34a (0.042 g, 0.041 mmol, 1 eq.) and 2,3,5,6-tetrafluorophenol, TFP (0.014 g, 0.082 mmol, 2 eq.) were dissolved in 3 ml ACN. Collidine (0.054 ml, 0.406 mmol, 9.83 eq.) was added, followed by 1-ethyl-3-(3-dimethylaminopropyl)carbodiimide hydrochloride. EDC-HCl (0.017 g, 0.088 mmol, 2.13 eq.). The reaction was stirred at room temperature and monitored by LCMS, then diluted with 2 ml $H_2O$ and purified by HPLC to give TAZ-L-34 (0.0198 g, 0.017 mmol, 41%). LC/MS [M+H] 1164.61 (calculated); LC/MS [M+H] 1164.81 (observed).

Example L-52 Synthesis of 2,3,5,6-tetrafluorophenyl 40-(5-amino-7-(propyl(3-(2-(trifluoromethoxy) acetamido)propyl)carbamoyl)-6H-thieno[3,2-b]azepin-2-yl)-34-oxo-4,7,10,13,16,19,22,25,28,31-decaoxa-35-azatetracontanoate, TAZ-L-52
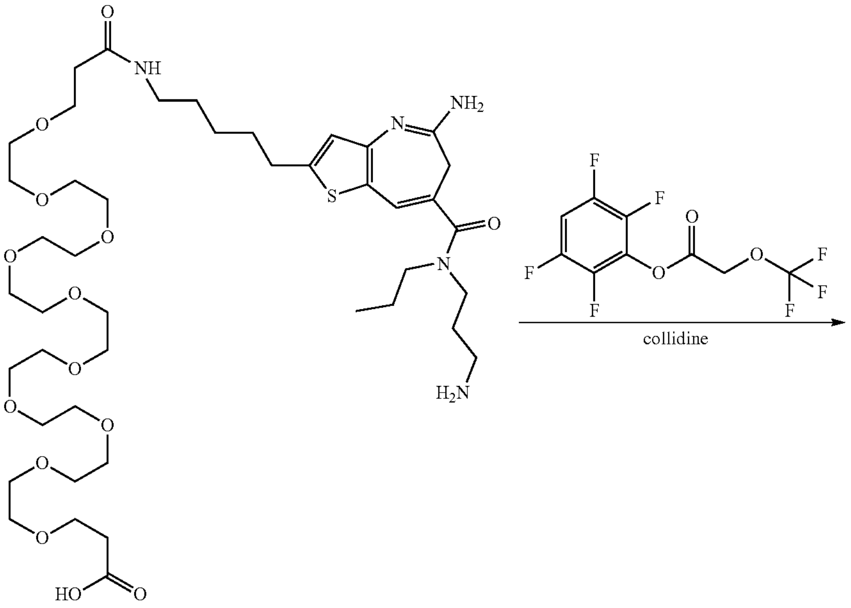
L-53b
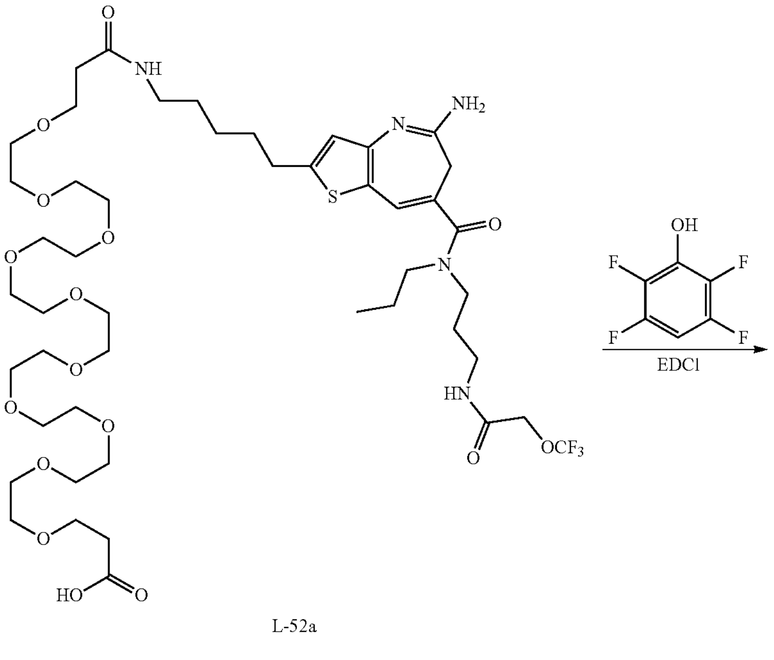
L-52a -continued

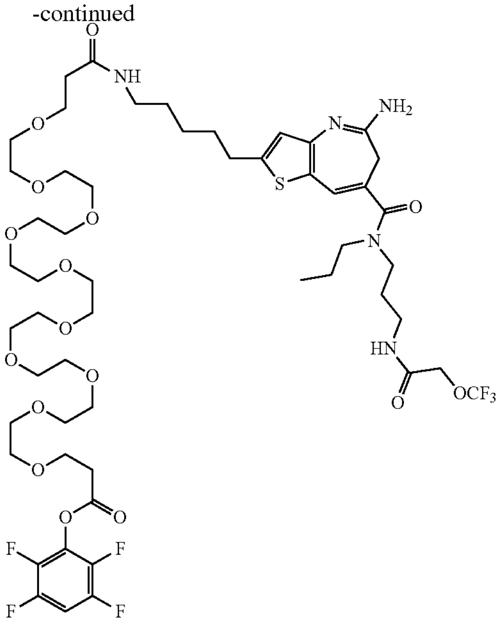

TAZ-L-52

Preparation of 40-(5-amino-7-(propyl(3-(2-(trifluoromethoxy)acetamido)propyl)carbamoyl)-6H-thieno[3,2-b]azepin-2-yl)-34-oxo-4,7,10,13,16,19,22,25,28,31-decaoxa-35-azatetracontanoic acid, L-52a 2,3,5,6-Tetrafluorophenyl 2-(trifluoromethoxy)acetate (0.012 g, 0.041 mmol, 1 equiv.) and 34(5-amino-2-(1-carboxy-33-oxo-3,6,9,12,15,18,21,24,27,30-decaoxa-34-azanonatriacontan-39-yl)-N-propyl-6H-thieno[3,2-b]azepine-7-carboxamido)propan-1-aminium trifluoroacetate, L-53b (0.038 g, 0.041 mmol, 1 equiv.) were combined in acetonitrile. Collidine (0.027 ml, 0.205 mmol, 5 equiv.) was added, and the reaction monitored by HPLC. Upon completion, the reaction was concentrated and purified by HPLC to give L-52a (0.07 g, 0.066 mmol, 160%) as a syrup containing a significant amount of residual collidine. The crude material was carried on to the next step without further purification. LC/MS [M+H] 1058.52 (calculated); LC/MS [M+H] 1058.84 (observed).

Preparation of TAZ-L-52

Intermediate L-52a (0.07 g, 0.066 mmol, 1 equiv.) and 2,3,5,6-tetrafluorophenol (0.011 g, 0.66 mmol, 1 equiv.) were dissolved in 1 ml acetonitrile. Collidine (0.017 ml, 0.16 mmol, 2 equiv.) was added, followed by EDC (0.013 g, 0.66 mmol, 1 equiv.). The reaction was stirred at room temperature and monitored by LCMS, then diluted with water and purified by reverse-phase HPLC to give TAZ-L-52 (0.095 g, 0.075 mmol, 49%). LC/MS [M+H) 1206.51 (calculated); LC/MS [M+H] 1206.51 (observed).

Example L-53 Synthesis of 2,3,5,6-tetrafluorophenyl 40-(5-amino-7-((3-((cyclobutoxycarbonyl)amino)propyl)(propyl)carbamoyl)-6H-thieno[3,2-b]azepin-2-yl)-34-oxo-4,7,10,13,16,19,22,25,28,31-decaoxa-35-azatetracontanoate. TAZ-L-53

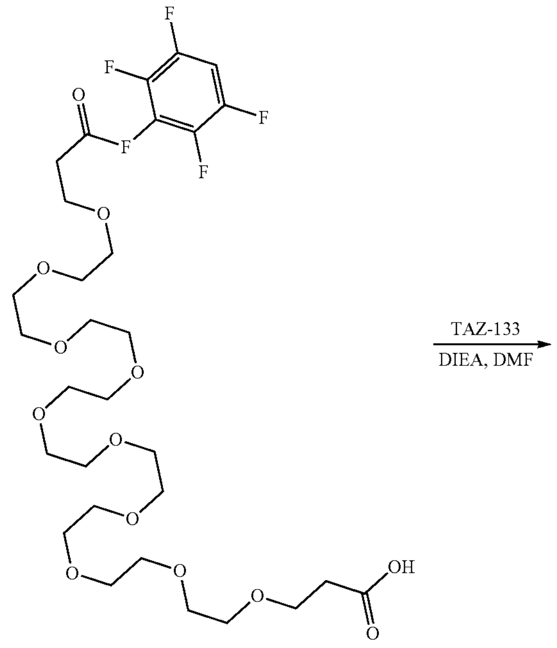

-continued

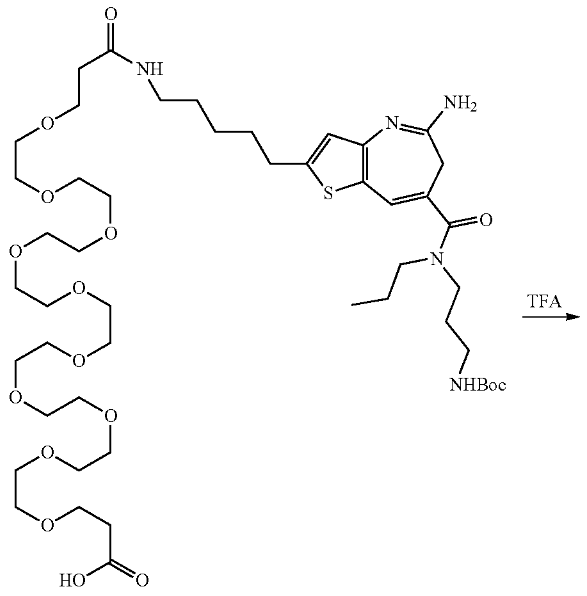

L-53a

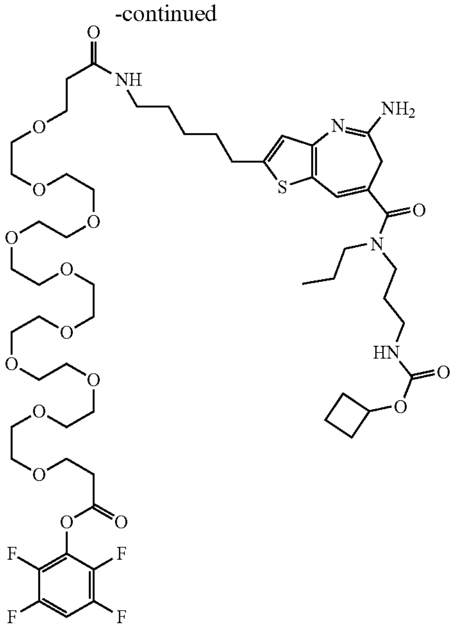

TAZ-L-53

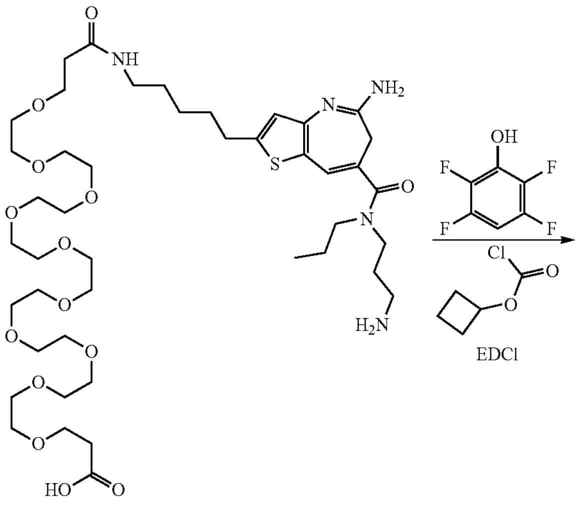

L-53b

Preparation of 40-(5-amino-74((3-((tert-butoxycarbonyl)amino)propyl)(propyl)carbamoyl)-6H-thieno[3,2-b]azepin-2-yl)-34-oxo-4,7,10,13,16,19,22,25,28,31-decaoxa-35-azatetracontanoic acid. L-53a Tert-butyl (3-(5-amino-2-(5-aminopentyl)-N-propyl-6H-thieno[3,2-b]azepine-7-carboxamido)propyl)carbamate, TAZ-133 (0.234 g, 0.48 mmol, 1 equiv.) and 34-oxo-34-(2,3,5,6-tetrafluorophenoxy)-4,7,10,13,16,19,22,25,28,31-decaoxatetratriacontanoic acid (0.34 g, 0.48 mmol, 1 equiv.) were dissolved in DMF. Triethylamine (0.33 g, 2.4 mmol, 5 equiv.) was added and the reaction stirred at room temperature. Upon consumption of amine starting material, the reaction was diluted with water and purified by reverse-phase HPLC to give L-53a (0.385 g, 0.40 mmol, 84%). LC/MS [M+H] 1032.58 (calculated); LC/MS [M+H] 1032.89 (observed).

Preparation of 3-(5-amino-2-(1-carboxy-33-oxo-3,6,9,12,15,18,21,24,27,30-decaoxa-34-azanonatriacontan-39-yl)-N-propyl-6H-thieno[3,2-b]azepine-7-carboxamido)propan-1-aminium trifluoroacetate, L-53b Intermediate L-53a (0.27 g, 0.26 mmol, 1 equiv.) was dissolved in minimal TFA and allowed to stand at room temperature. Upon complete consumption of starting material, the reaction was concentrated and triturated with diethyl ether to give L-53b (0.268 g, 0.256 mmol, 98%). LC/MS [M+H] 932.53 (calculated); LC/MS [M+H] 932.81 (observed).

Preparation of TAZ-L-53

Cyclobutyl chloroformate (0.1 ml, 0.094 mmol, 1.24 equiv.), 2,3,5,6-tetrafluorophenol (0.065 g, 0.39 mmol, 5 equiv.), and collidine (0.103 ml, 0.78 mmol, 10 equiv.) were dissolved in 1 ml acetonitrile and allowed to stand for one hour. Intermediate L-53b (0.073 g, 0.078 mmol, 1 equiv.)

was dissolved in this reaction mixture and the reaction monitored by LCMS. EDC (0.03 g, 0.157 mmol, 2 equiv.) was added to the solution upon consumption of the amine, and the reaction stirred at room temperature. Upon completion, the reaction was concentrated and purified by HPLC to give TAZ-L-53 (0.027 g, 0.023 mmol, 29%). LC/MS [M+H] 1178.56 (calculated); LC/MS [M+H] 1178.85 (observed).

Example L-59 Synthesis of (R)-2-((5-(5-amino-7-(3-(3,3-dimethylbutanamido)propyl)(propyl)carbamoyl)-6H-thieno[3,2-b]azepin-2-yl)pentyl)carbamoyl)-4,37-dioxo-37-(2,3,5,6-tetrafluorophenoxy)-7,10,13,16,19,22,25,28,31,34-decaoxa-3-azaheptatriacontane-1-sulfonic acid, TAZ-L-59

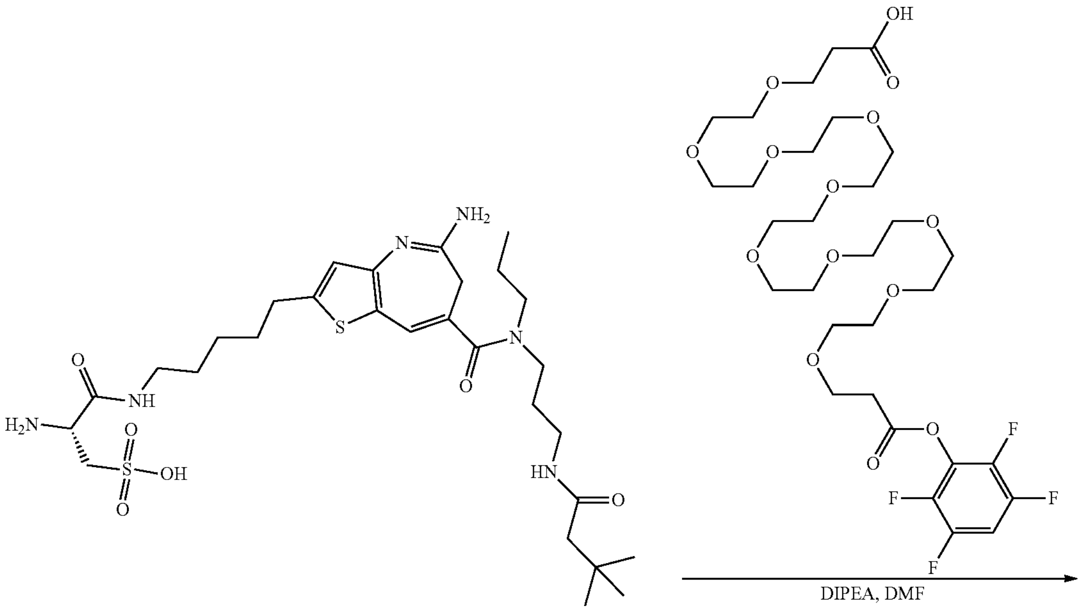

L-59a

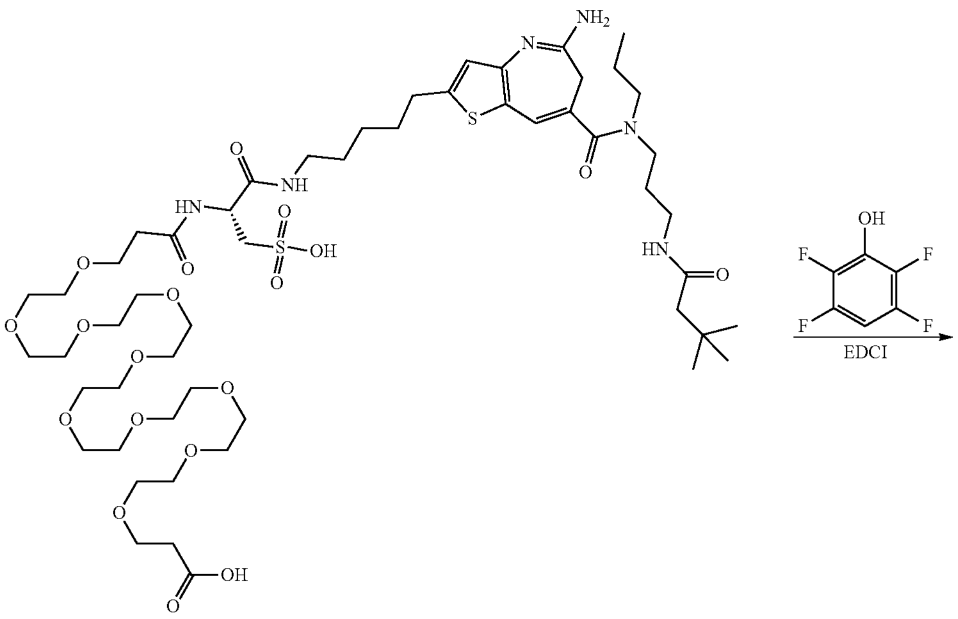

L-59b

-continued

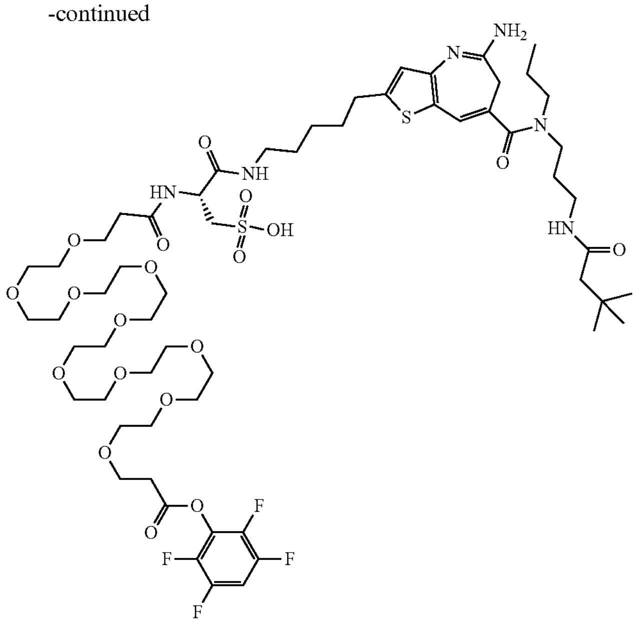

TAZ-L-59

Preparation of (R)-43-(5-amino-7-((3-(3,3-dimethylbutanamido)propyl)(propyl)carbamoyl)-6H-thieno[3,2-b]azepin-2-yl)-34,37-dioxo-36-(sulfomethyl)-4,7,10,13,16,19,22,25,28,31-decaoxa-35,38-diazatritetracontanoic acid, L-59b (R)-2-amino-3-((5-(5-amino-7-((3-(3,3-dimethylbutanamido)propyl)(propyl)carbamoyl)-6H-thieno[3,2-b]azepin-2-yl)pentyl)amino)-3-oxopropane-1-sulfonic acid, L-59a (0.034 g, 0.053 mmol, 1 equiv.) was dissolved in DMF (1.5 ml). To this solution were added DIPEA (0.046 ml, 0.265 mmol, 5 equiv.), followed by 34-oxo-34-(2,3,5,6-tetrafluorophenoxy)-4,7,10,13,16,19,22,25,28,31-decaoxatetratriacontanoic acid (0.037 g, 0.053 mmol, 1 equiv.). The reaction was heated to 40° C. for 20 minutes, then cooled to room temperature and purified by reverse-phase HPLC to give L-59b (0.036 g, 0.30 mmol, 58%) as a yellow film. LC/MS [M+H] 1181.59 (calculated); LC/MS [M+H] 1181.87 (observed).

Preparation of TAZ-L-59

Intermediate L-59b (0.036 g, 0.03 mmol, 1 equiv.) was dissolved in DMF. To this solution were added 2,3,5,6-tetrafluorophenol (0.02 g, 0.09 mmol, 3 equiv.), collidine (0.02 ml, 0.15 mmol, 5 equiv.), and EDCI (0.02 g, 0.09 mmol, 3 equiv.). The reaction was monitored by LCMS, and then concentrated and purified by HPLC to give TAZ-L-59 (0.034 g, 0.031 mmol, 84%). LC/MS [M+H] 1329.59 (calculated); LC/MS [M+H] 1329.88 (observed).

Example L-83 Synthesis of (2,3,5,6-tetrafluorophenyl)$_3$-[2-[2-[2-[2-[2-[2-[2-[2-[2-[2-[4-[[5-amino-7-[3-(cyclobutoxycarbonylamino)propyl-propyl-carbamoyl]-6H-thieno[3,2-b]azepin-2-yl]methyl]-1-piperidyl]ethoxy]ethoxy]ethoxy]ethoxy]ethoxy]ethoxy]ethoxy]ethoxy]ethoxy]ethoxy]propanoate, TAZ-L-83

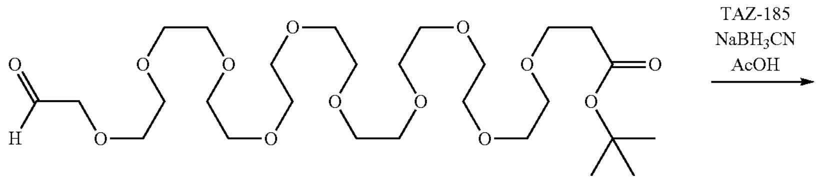

-continued
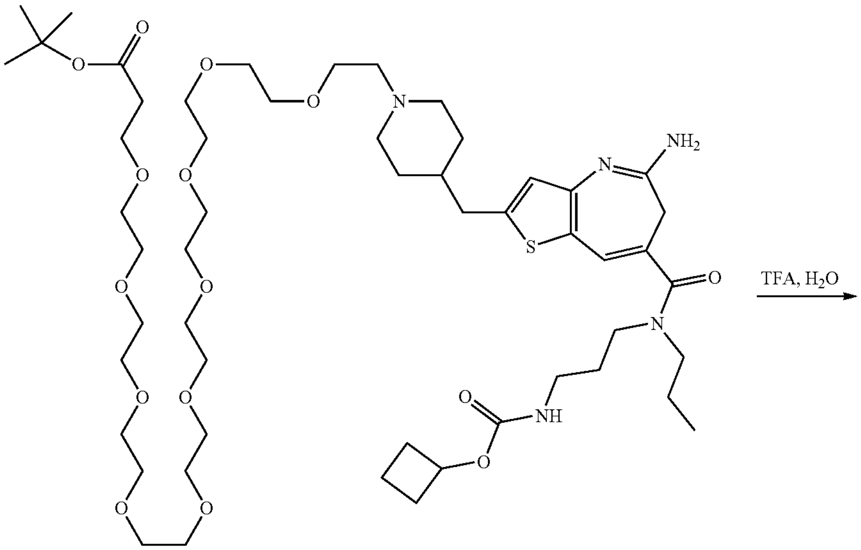
L-83a
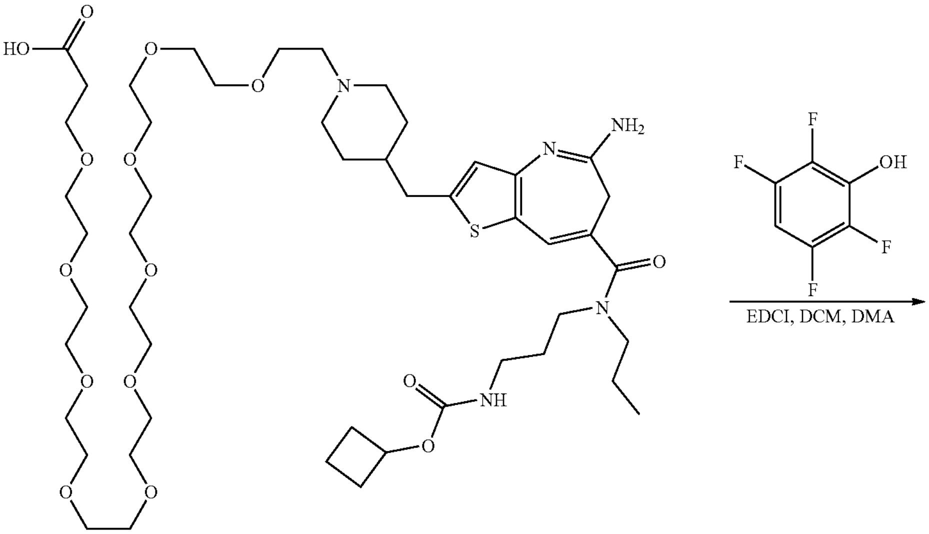
L-83b

-continued

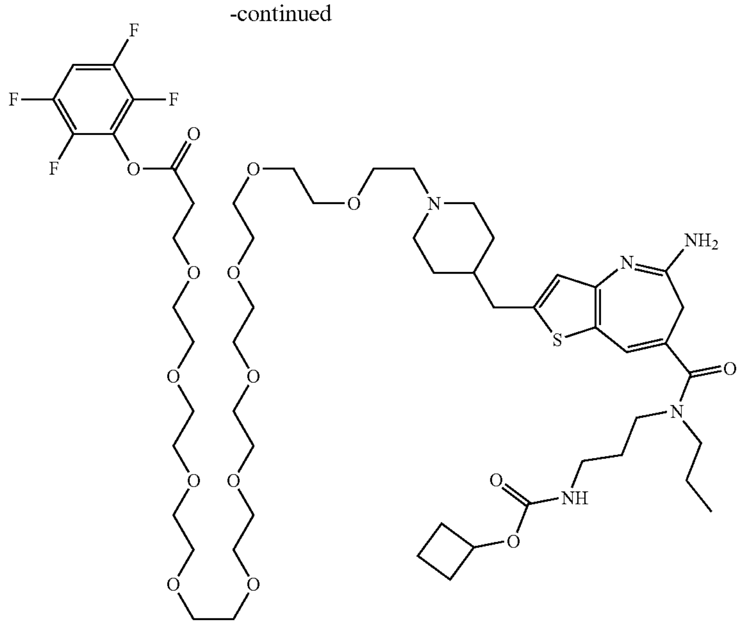

TAZ-L-83

Preparation of tert-butyl 3-[2-[2-[2-[2-[2-[2-[2-[2-[2-[2-[4-[[5-amino-7-[3-(cyclobutoxycarbonylamino) propyl-propyl-carbamoyl]-6H-thieno[3,2-b]azepin-2-yl]methyl]-1-piperidyl]ethoxy]ethoxy]ethoxy]ethoxy]ethoxy]ethoxy]ethoxy]ethoxy]ethoxy]ethoxy]propanoate, L-83a To a mixture of cyclobutyl N-[3-[[5-amino-2-(4-piperidylmethyl)-6H-thieno[3,2-b]azepine-7-carbonyl]-propyl-amino]propyl]carbamate, TAZ-185 (75.0 mg, 149 umol, 1.0 eq) and tert-butyl 3-[2-[2-[2-[2-[2-[2-[2-12-[2-(2-oxoethoxy)ethoxy]ethoxy]ethoxy]ethoxy]ethoxy]ethoxy]ethoxy]ethoxy]ethoxy]propanoate (437 mg, 747 umol, 5.0 eq) in MeOH (5 mL) was added $NaBH_3CN$ (37.5 mg, 598 umol, 4.0 eq) in one portion at 20° C. under $N_2$, and then stirred at 20° C. for 40 hours. The reaction mixture was concentrated in vacuum and the residue was purified by prep-HPLC (column: Phenomenex Synergi C18 150*30 mm*4 um; mobile phase: [water(0.1% TFA)-ACN]; B %: 20%-50%, 8 min) to afford L-83a (100 mg, 93.4 umol, 62.5% yield) as colorless oil. $^1$H NMR (400 MHz, MeOD) δ7.08 (s, 1H), 6.96 (s, 1H), 4.85-4.80 (m, 1H), 3.85 (d, J=4.8 Hz, 2H), 3.75-3.57 (m, 40H), 3.56-3.43 (m, 6H), 3.38 (s, 2H), 3.11 (dd, J=4.0, 5.4 Hz, 2H), 3.08-2.97 (m, 2H), 2.91 (d, J=6.4 Hz, 2H), 2.36-2.23 (m, 2H), 2.10-1.92 (m, 5H), 1.87-1.75 (m, 3H), 1.72-1.54 (m, 5H), 1.47 (s, 9H), 0.93 (s, 3H)

Preparation of 3-[2-[2-[2-[2-[2-[2-[2-[2-[2-[2-[4-[[5-amino-7-[3-(cyclobutoxycarbonylamino)propyl-propyl-carbamoyl]-6H-thieno[3,2-b]azepin-2-yl]methyl]-1-piperidyl]ethoxy]ethoxy]ethoxy]ethoxy]ethoxy]ethoxy]ethoxy]ethoxy]ethoxy]ethoxy]propanoic acid, L-83b To a solution of L-83a(100 mg, 93.4 umol, 1.0 eq) in MeCN (0.5 mL) and $H_2O$ (2 ML) was added HCl (12 M, 233 μL, 30 eq) in one portion at 20° C. under N2, and then stirred at 80° C. for 1 hour. The reaction mixture was concentrated in vacuum to afford L-83b (80.0 mg, 78.8 umol, 84.4% yield) as colorless oil.

Preparation of TAZ-L-83

To a mixture of L-83b (80.0 mg, 78.8 umol, 1.0 eq) and 2,3,5,6-tetrafluorophenol (131 mg, 788 umol, 10 eq) in DCM (2 mL) and DMA (0.5 mL) was added EDCI (151 mg, 788 umol, 10 eq) in one portion at 20° C. under N2, the mixture was stirred at 20° C. for 1 hour. DCM (2 mL) was removed in vacuum and the mixture was filtered, the filtrate was purified by prep-HPLC (column: Phenomenex Synergi C18 150*30 mm*4 um; mobile phase: [water(0.1% TFA)-ACN]; B %: 20%-50%, 8 min) to afford TAZ-L-83 (43.0 mg, 36.3 umol, 46.0% yield, 98.20% purity) as colorless oil. $^1$H NMR (400 MHz, MeOD) δ7.49-7.42 (m, 1H), 7.07 (s, 1H), 6.95 (s, 1H), 3.89 (t, J=6.0 Hz, 2H), 3.87-3.83 (m, 2H), 3.70-3.46 (m, 42H), 3.37 (s, 2H), 3.17-3.08 (m, 3H), 3.00 (t, J=6.0 Hz, 4H), 2.91 (d, J=6.8 Hz, 2H), 2.34-2.25 (m, 2H), 2.09-1.96 (m, 5H), 1.87-1.58 (m, 8H), 0.92 (t, J=4.0 Hz, 3H). LC/MS [M+H] 1162.6 (calculated); LC/MS [M+H] 1162.4 (observed).

Example L-84 Synthesis of (2,3,5,6-tetrafluorophenyl)3-[2-[2-[2-[2-[2-[2-[2-[2-[2-[2-[4-[[5-amino-7-[ethoxy(propyl)carbamoyl]-6H-thieno[3,2-b]azepin-2-yl]methyl]-1-piperidyl]ethoxy]ethoxy]ethoxy]ethoxy]ethoxy]ethoxy]ethoxy]ethoxy]ethoxy]ethoxy]propanoate, TAZ-L-84
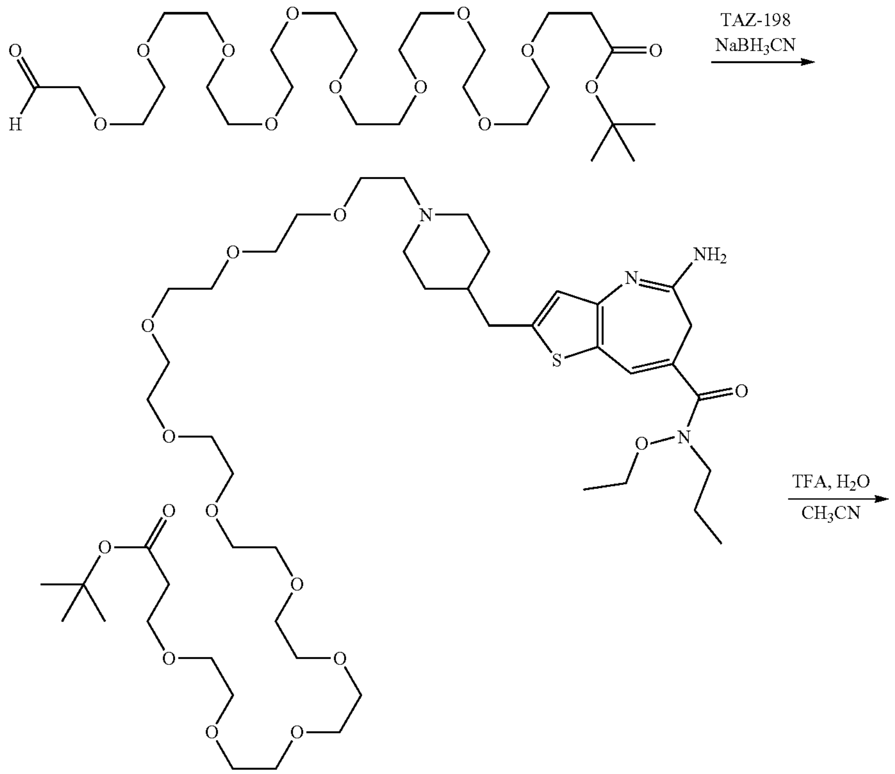
L-84a
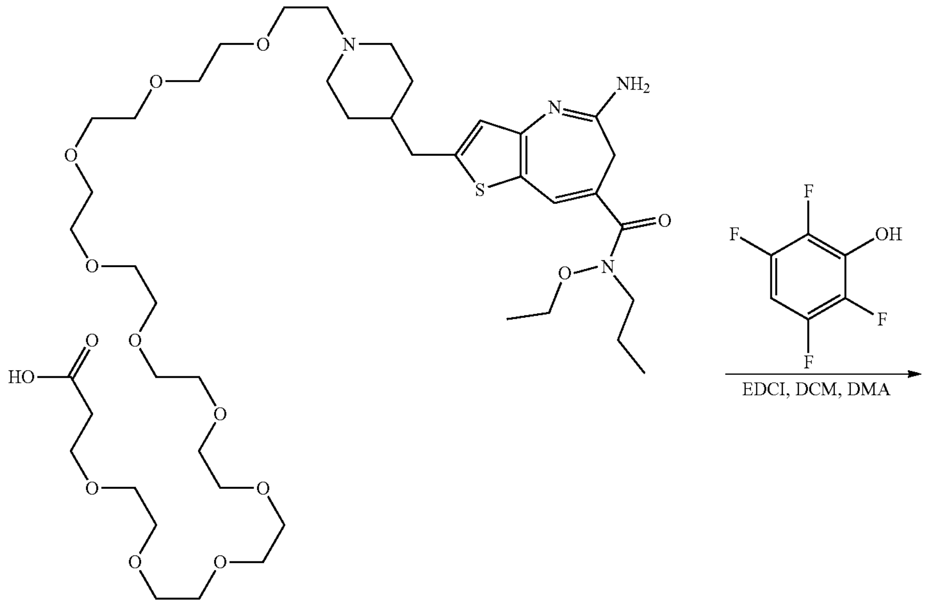
L-84b -continued

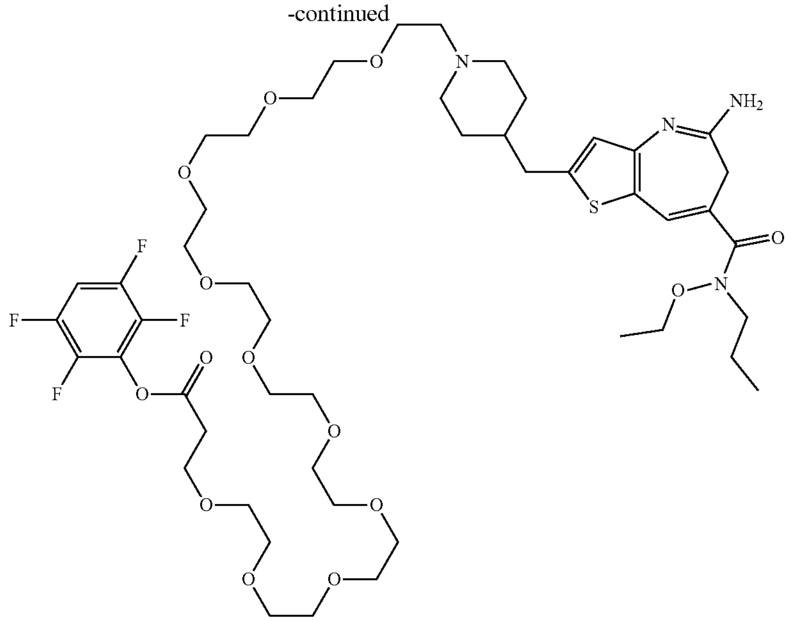

TAZ-L-84

Preparation of tert-butyl 3-[2-[2-[2-[2-[2-[2-[2-[2-[2-[2-[4-[[5-amino-7-[ethoxy(propyl)carbamoyl]-6H-thieno[3,2-b]azepin-2-yl]methyl]-1-piperidyl]ethoxy]ethoxy]ethoxy]ethoxy]ethoxy]ethoxy]ethoxy]ethoxy]ethoxy]ethoxy]propanoate, L-84a To a mixture of 5-amino-N-ethoxy-2-(4-piperidylmethyl)-N-propyl-6H-thieno[3,2-b]azepine-7-carboxamide, TAZ-198 (60.0 mg, 153 umol, 1.0 eq) and tert-butyl 3-[2-[2-[2-[2-[2-[2-[2-[2-[2-(2-oxoethoxy)ethoxy]ethoxy]ethoxy]ethoxy]ethoxy]ethoxy]ethoxy]ethoxy]ethoxy]propanoate (449 mg, 768 umol, 5.0 eq) in MeOH (5 mL) was added $NaBH_3CN$ (28.9 mg, 460 umol, 3.0 eq) in one portion at 20° C. under $N_2$, and then stirred at 20° C. for 40 hours. The reaction mixture was concentrated in vacuum and the residue was purified by prep-HPLC (column: Phenomenex Synergi C18 150*30 mm*4 um; mobile phase: [water(0.1% TFA)-ACN]; B %: 20%-45%, 8 min) to afford L-84a (100 mg, 104 umol, 67.8% yield) as colorless oil. $^1$H NMR (400 MHz, MeOD) δ7.48 (s, 1H), 6.97 (s, 1H), 3.95 (q, J=7.2 Hz, 2H), 3.85 (d, J=4.4 Hz, 2H), 3.77-3.65 (m, 40H), 3.45 (s, 2H), 3.01 (d, J=12.4 Hz, 2H), 2.92 (d, J=6.4 Hz, 2H), 2.49 (t, J=6.4 Hz, 2H), 2.05-2.00 (m, 3H), 1.82-1.72 (m, 2H), 1.66-1.54 (m, 2H), 1.47 (s, 9H), 1.20 (t, J=7.2 Hz, 3H), 1.00 (t, J=7.2 Hz, 3H).

Preparation of 3-[2-[2-[2-[2-[2-[2-[2-[2-[2-[2-[4-[[5-amino-7-[ethoxy(propyl)carbamoyl]-6H-thieno[3,2-b]azepin-2-yl]methyl]-1-piperidyl]ethoxy]ethoxy]ethoxy]ethoxy]ethoxy]ethoxy]ethoxy]ethoxy]ethoxy]ethoxy]propanoic acid, L-84b To a solution of L-84a (100 mg, 104 umol, 1.0 eq) in MeCN (0.5 mL) and $H_2O$ (2 mL) was added HCl (12 M, 260.62 uL, 30 eq) in one portion at 20° C. under $N_2$, and then stirred at 80° C. for 1 hour. The reaction mixture was concentrated in vacuum, to afford L-84b (80 mg, 88.58 umol, 84.97% yield) as colorless oil.

Preparation of TAZ-L-84

To a mixture of L-84b (80 mg, 88.5 umol, 1.0 eq) and 2,3,5,6-tetrafluorophenol (147 mg, 885 umol, 10 eq) in DCM (2 mL) and DMA (0.5 mL) was added EDCI (84.9 mg, 442 umol, 5.0 eq) in one portion at 20° C. under $N_2$, the mixture was stirred at 20° C. for 1 hour. DCM (2 mL) was removed in vacuum and the mixture was filtered, the residue was purified by prep-HPLC (column: Phenomenex Synergi C18 150*30 mm*4 um; mobile phase: [water(0.1% TFA)-ACN]; B %: 20%-50%, 8 min) to afford TAZ-L-84 (37 mg, 35.09 umol, 39.61% yield, 99.68% purity) as colorless oil. $^1$H NMR (400 MHz, MeOD) δ7.48 (s, 1H), 7.46-7.41 (m, 1H), 6.96 (s, 1H), 3.95 (q, J=6.8 Hz, 3H), 3.89 (t, J=6.0 Hz, 2H), 3.87-3.83 (m, 2H), 3.71-3.61 (m, 40H), 3.44 (s, 2H), 3.37-3.34 (m, 3H), 3.05-2.95 (m, 5H), 2.91 (d, J=6.4 Hz, 2H), 2.05-1.95 (m, 2H), 1.82-1.72 (m, 2H), 1.66-1.54 (m, 2H), 1.20 (t, J=7.2 Hz, 3H), 0.99 (t, J=7.2 Hz, 3H). LC/MS [M+H] 1151.5 (calculated); LC/MS [M+H] 1151.3 (observed).

Example L-87 Synthesis of (2,3,5,6-tetrafluorophenyl) 3-[2-[2-[2-[2-[2-[2-[2-[2-[2-[2-[4-[2-[5-amino-7-[ethoxy(propyl)carbamoyl]-6H-thieno[3,2-b]azepin-2-yl]ethyl]-1-piperidyl]ethoxy]ethoxy]ethoxy]ethoxy]ethoxy]ethoxy] ethoxy]ethoxy]ethoxy]ethoxy]propanoate, TAZ-L-87
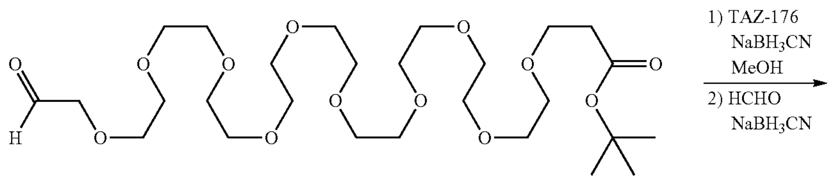
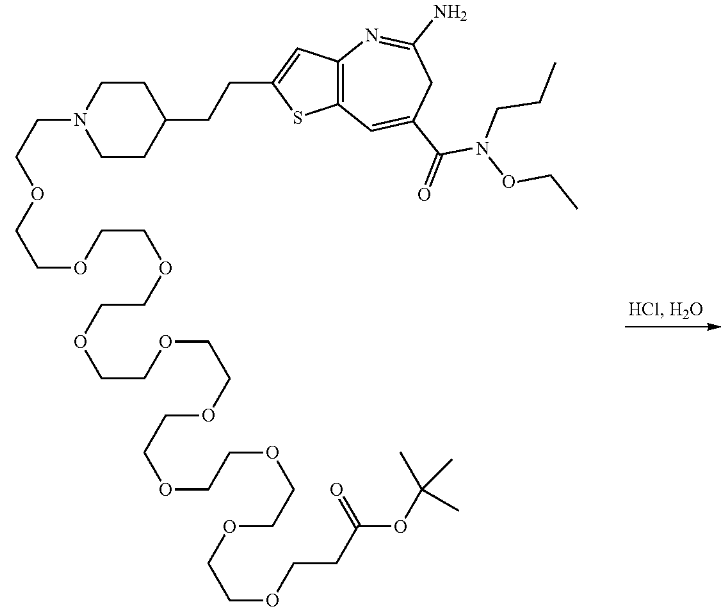
L-87a
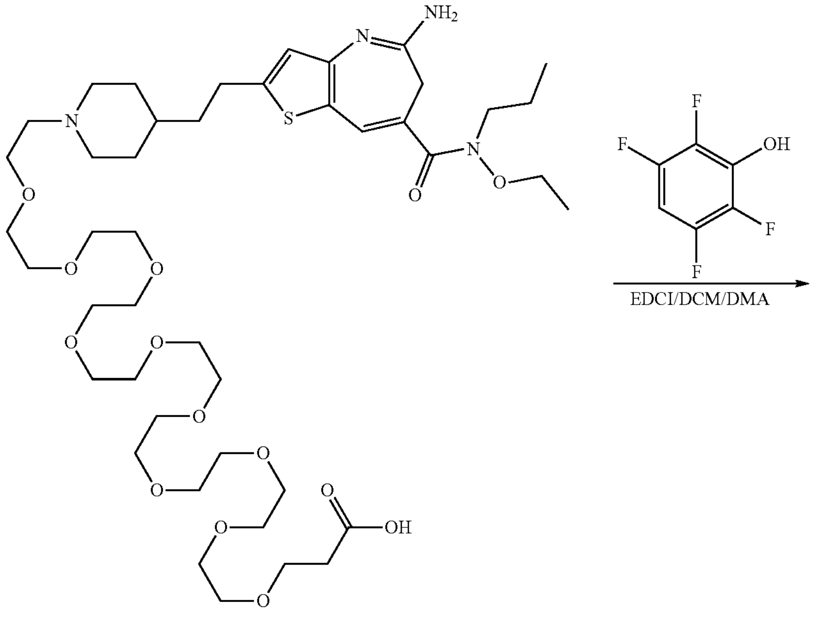
L-87b -continued

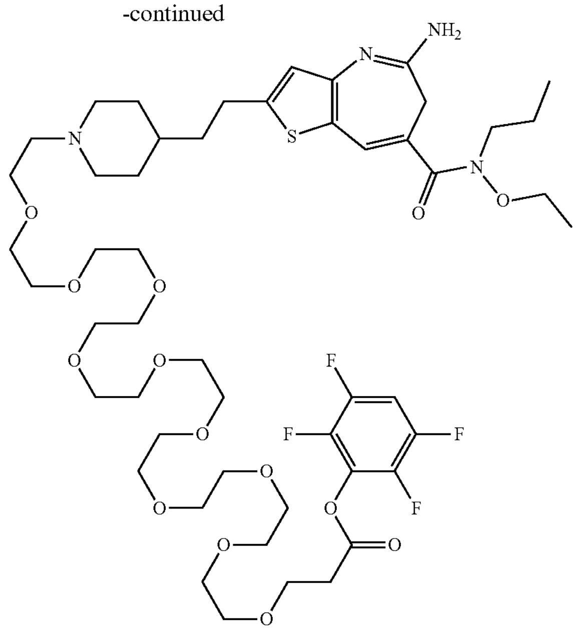

TAZ-L-87

Preparation of tert-butyl 3-[2-[2-[2-[2-12-[2-12-[2-[2-[2-[4-[2-15-amino-7-[ethoxy (propyl)carbamoyl]-6H-thieno[3,2-b]azepin-2-yl]ethyl]-1-piperidyl] ethoxy]ethoxy]ethoxy]ethoxy]ethoxy]ethoxy] ethoxy]ethoxy]ethoxy]ethoxy]propanoate, L-87a To a mixture of 5-amino-N-ethoxy-2-[2-(4-piperidyl) ethyl]-N-propyl-6H-thieno[3,2-b]azepine-7-carboxamide, TAZ-176 (0.15 g, 340 umol, 1.0 eq, HCl) in MeOH (3 mL) was added tert-butyl 3-[2-[2-[2-[2-[2-[2-[2-[2-[2-(2-oxoethoxy)ethoxy]ethoxy]ethoxy]ethoxy]ethoxy]ethoxy]ethoxy] ethoxy]ethoxy]propanoate (597 mg, 1.02 mmol, 3.0 eq) and $NaBH_3CN$ (42.8 mg, 680 umol, 2.0 eq) in one portion at 25° C. and it was stirred at 25° C. for 12 h. The mixture was concentrated to give a residue. The residue was purified by prep-HPLC(column: Phenomenex luna C18 100*40 mm*5 um; mobile phase: [water(0.1% TFA)-ACN]; B %: 12%-42%, 8 min) to give L-87a (0.18 g, 165.55 umol, 48.67% yield, TFA) as yellow oil. $^1$H NMR (MeOD, 400 MHz) δ 7.45 (s, 1H), 6.94 (s, 1H), 3.96-3.90 (m, 2H), 3.86-3.82 (m, 2H), 3.75-3.71 (m, 2H), 3.70-3.67 (m, 6H), 3.66-3.59 (m, 36H), 3.42 (s, 2H), 3.06-2.90 (m, 4H), 2.47 (t, J=6.2 Hz, 2H), 2.13-2.00 (m, 2H), 1.87-1.60 (m, 6H), 1.60-1.48 (m, 2H), 1.45 (s, 10H), 1.18 (t, J=7.2 Hz, 3H), 0.97 (t, J=7.6 Hz, 3H).

Preparation of 3-[2-[2-[2-[2-[2-12-[2-[2-[2-[2-[4-[2-[5-amino-7-[ethoxy(propyl)carbamoyl]-6H-thieno[3,2-b]azepin-2-yl]ethyl]-1-piperidyl]ethoxy]ethoxy] ethoxy]ethoxy]ethoxy]ethoxy]ethoxy]ethoxy] ethoxy]ethoxy]propanoic acid, L-87b To a mixture of L-87a (0.18 g, 166 umol, 1.0 eq, TFA) in $H_2O$ (2.5 mL) and $CH_3CN$ (0.3 mL) was added HCl (12 M, 345 μL, 25.0 eq) in one portion at 25° C. and it was stirred at 80° C. for 1 h. The mixture was concentrated to give L-87b (0.15 g, crude, HCl) as yellow oil.

Preparation of TAZ-L-87

To a mixture of L-87b (0.05 g, 52.4 umol, 1.0 eq. HCl) in DCM (1 mL) and DMA (0.2 mL) was added 2,3,5,6-tetrafluorophenol (69.7 mg, 419 umol, 8.0 eq) and EDCI (101 mg, 524 umol, 10.0 eq) in one portion at 25° C. and it was stirred at 25° C. for 0.5 h. The mixture was concentrated to give a residue. The residue was purified by prep-HPLC (column: Phenomenex Synergi C18 150*30 mm*4 um; mobile phase: [water(0.1% TFA)-ACN]; B %: 20%-50%, 8 min) to give TAZ-L-87 (14.5 mg, 12.30 umol, 23.45% yield, TFA) as yellow oil. $^1$H NMR (MeOD, 400 MHz) δ 7.49-7.38 (m, 2H), 6.92 (s, 1H), 3.93 (q, J=8 Hz, 2H), 3.87 (t, J=6.0 Hz, 2H), 3.85-3.81 (m, 2H), 3.74-3.70 (m, 2H), 3.69-3.61 (m, 40H), 3.42 (s, 2H), 3.03-2.91 (m, 6H), 2.07 (d, J=13.6 Hz, 2H), 1.79-1.66 (m, 5H), 1.58-1.43 (m, 2H), 1.18 (t, J=7.2 Hz, 3H), 0.97 (t, J=7.6 Hz, 3H). LC/MS [M+H] 1065.5 (calculated); LC/MS [M+H] 1065.4 (observed).

Example L-88 Synthesis of (2,3,5,6-tetrafluorophenyl) 3-[2-12-[2-[2-12-[2-12-[2-[2-[3-[4-[2-[5-amino-7-[ethoxy(propyl)carbamoyl]-6H-thieno[3,2-b]azepin-2-yl]ethyl]-1-piperidyl]-3-oxo-propoxy]ethoxy]ethoxy]ethoxy]ethoxy]ethoxy]ethoxy]ethoxy]ethoxy]ethoxy]propanoate, TAZ-L-88
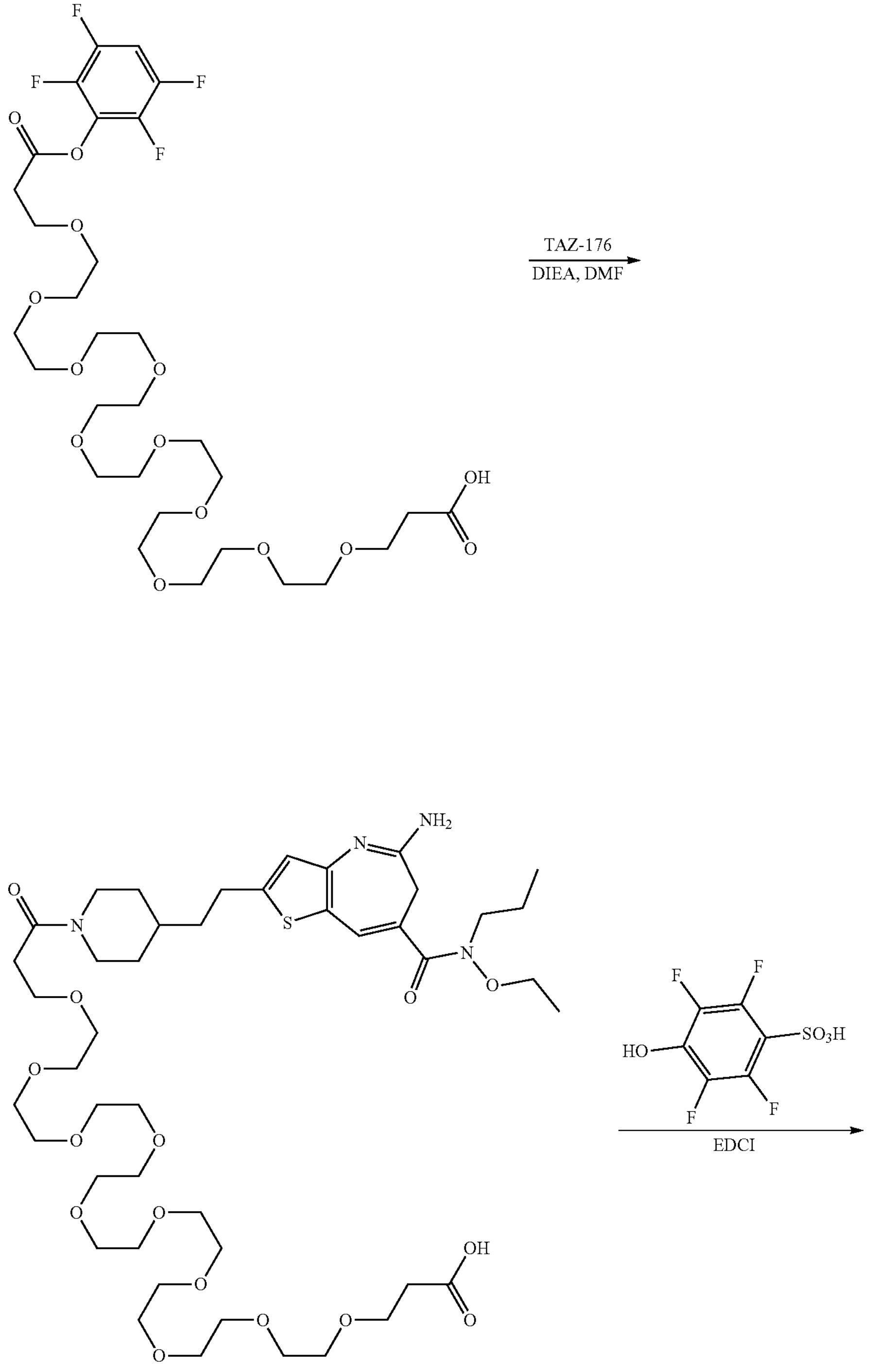
L-88a -continued

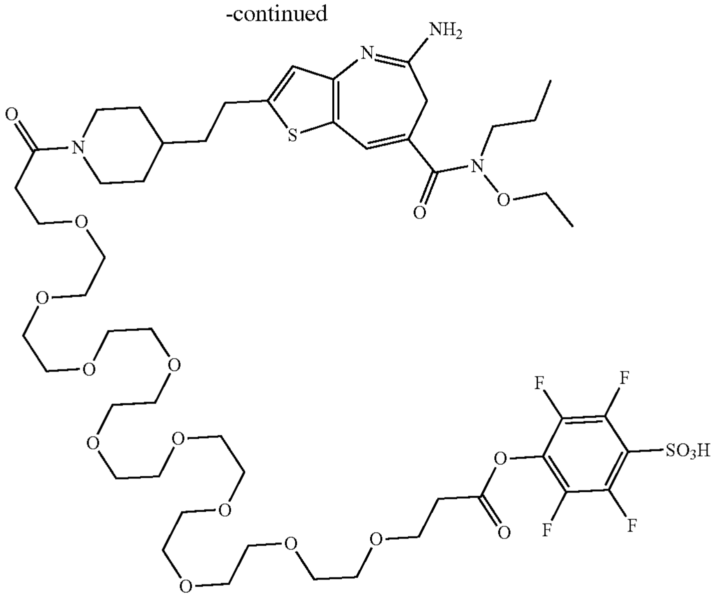

TAZ-L-88

Preparation of 3-[2-[2-[2-[2-[2-[2-[2-[2-[2-[3-[4-[2-[5-amino-7-[ethoxy(propyl) carbamoyl]-6H-thieno[3,2-b]azepin-2-yl]ethyl]-1-piperidyl]-3-oxo-propoxy]ethoxy]ethoxy]ethoxy]ethoxy]ethoxy]ethoxy]ethoxy]ethoxy]ethoxy]propanoic acid, L-88a To a mixture of 5-amino-N-ethoxy-2-[2-(4-piperidyl)ethyl]-N-propyl-6H-thieno[3,2-b]azepine-7-carboxamide, TAZ-176 (60.0 mg, 136 umol, 1.0 eq, HCl) and 3-[2-[2-[2-[2-[2-[2-[2-[2-[2-[3-oxo-3-(2,3,5,6-tetrafluorophenoxy)propoxy]ethoxy]ethoxy]ethoxy]ethoxy]ethoxy]ethoxy]ethoxy]ethoxy]ethox y]propanoic acid (106 mg, 150 umol, 1.1 eq) in DMF (0.5 mL) was added DIEA (52.8 mg, 408 umol, 71.1 uL, 3.0 eq) in one portion at 25° C. and it was stirred at 25° C. for 0.5 h. Then the mixture was filtered and purified by prep-HPLC (column: Welch Xtimate C18 150*25 mm*5 um; mobile phase: [water(0.04% HCl)-ACN]; B %: 20%-35%, 8 min) to give L-88a (40 mg, 42.32 umol, 31.11% yield) as yellow oil.

Preparation of TAZ-L-88

To a mixture of L-88a (40 mg, 40.8 umol, 1.0 eq) in DCM (1 mL) and DMA (0.2 mL) was added 2,3,5,6-tetrafluorophenol (54.1 mg, 326 umol, 8.0 eq) and EDCI (78.1 mg, 407 umol, 10.0 eq) in one portion at 25° C. and it was stirred at 25° C. for 0.5 h. The mixture was concentrated to give a residue, and the residue was purified by prep-HPLC(column: Phenomenex Synergi C18 150*30 mm*4 um; mobile phase: [water(0.1% TFA)-ACN]; B %: 30%-60%, 8 min) to give TAZ-L-88 (36.2 mg, 33.11 umol, 81.26% yield) as yellow oil. $^1$H NMR (MeOD, 400 MHz) δ 7.46 (s, 1H), 7.45-7.39 (m, 1H), 6.90 (s, 1H), 4.53 (d, J=13.2 Hz, 1H), 4.04 (d, J=13.6 Hz, 1H), 3.93 (q, J=7.2 Hz, 2H), 3.87 (t, J=6.0 Hz, 2H), 3.77-3.69 (m, 4H), 3.66-3.60 (m, 36H), 3.42 (s, 2H), 3.06 (t, J=12.0 Hz, 1H), 2.98 (t, J=6.0 Hz, 2H—), 2.93 (t, J=7.6 Hz, 2H), 2.78-2.51 (m, 3H), 1.89-1.63 (m, 7H), 1.30-1.07 (m, 5H), 0.97 (t, J=7.6 Hz, 3H). LC/MS [M+H] 1093.5 (calculated); LC/MS [M+H] 1093.4 (observed).

Example L-92 Synthesis of(2,3,5,6-tetrafluorophenyl) 3-[2-[2-[2-[2-[2-[2-[2-[2-[2-[2-[3-[5-amino-7-[ethoxy(propyl)carbamoyl]-6H-thieno[3,2-b]azepin-2-yl]methyl]azetidin-1-yl]ethoxy]ethoxy]ethoxy]ethoxy]ethoxy]ethoxy]ethoxy]ethoxy]ethoxy]ethoxy]propanoate, TAZ-L-92

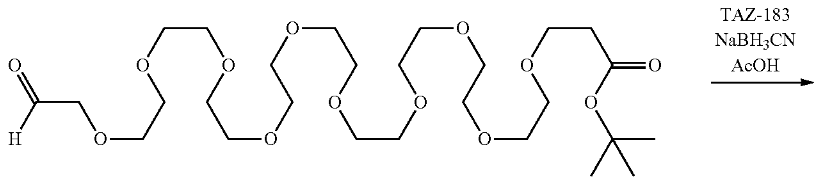

-continued
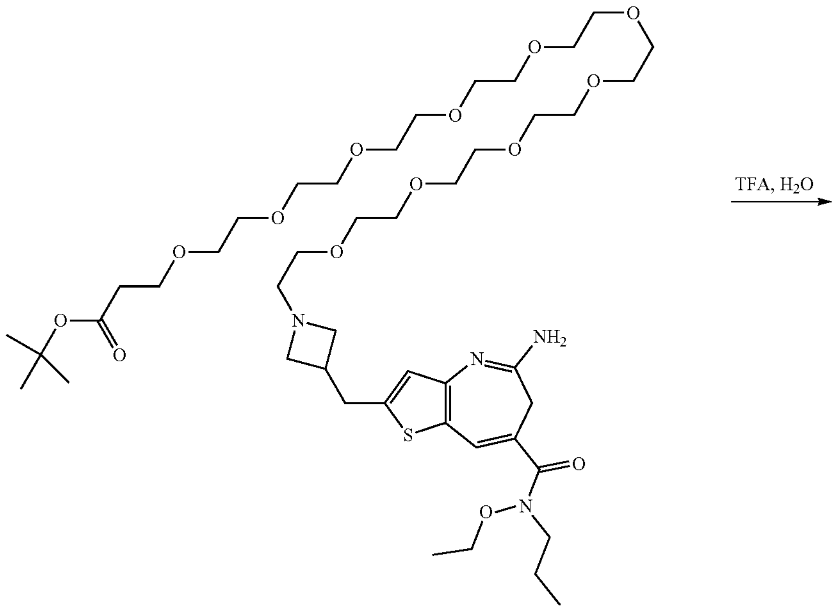
L-92a
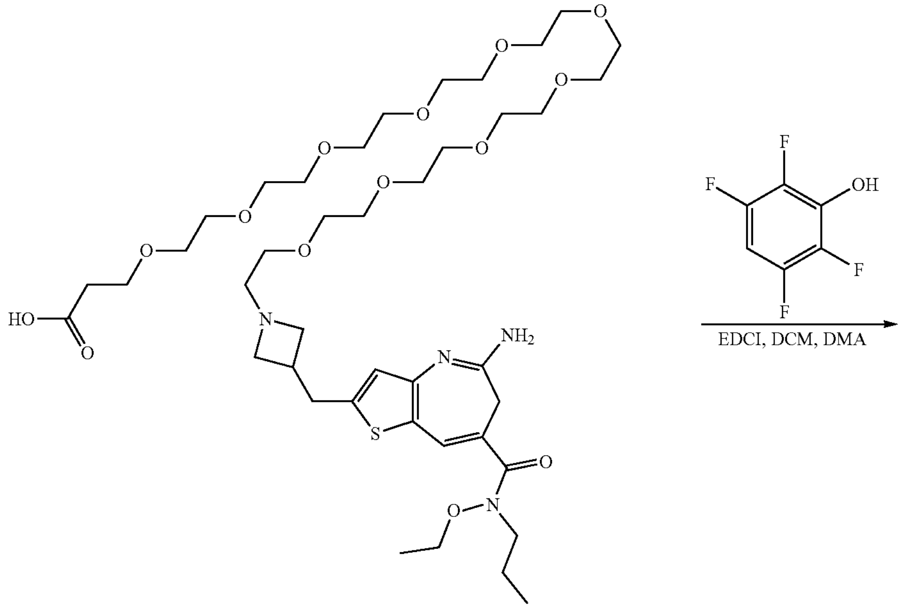
L-92b

-continued

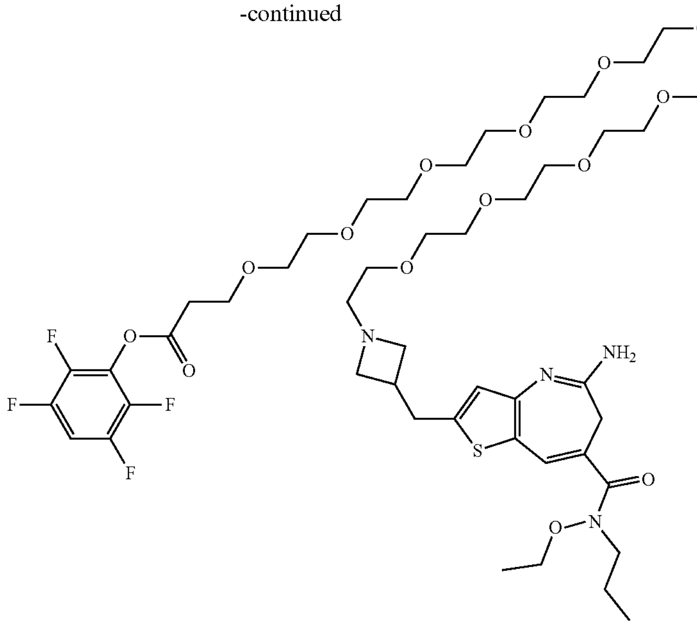

TAZ-L-92

Preparation of tert-butyl 3-[2-[2-[2-[2-[2-[2-[2-[2-[2-[3-[[5-amino-7-[ethoxy(propyl)carbamoyl]-6H-thieno[3,2-b]azepin-2-yl]methyl]azetidin-1-yl]ethoxy]ethoxy]ethoxy]ethoxy]ethoxy]ethoxy]ethoxy]ethoxy]ethoxy]ethoxy]propanoate, L-92a To a mixture of 5-amino-2-(azetidin-3-ylmethyl)-N-ethoxy-N-propyl-6H-thieno [3,2-b]azepine-7-carboxamide, TAZ-183 (0.006 g, 166 umol, 1 eq) and tert-butyl 3-[2-[2-[2-[2-[2-[2-[2-[2-[2-(2-oxoethoxy)ethoxy]ethoxy]ethoxy]ethoxy]ethoxy]ethoxy]ethoxy]ethoxy]ethoxy]propanoate (290 mg, 497 umol, 3 eq) in MeOH (5 mL) was added $NaBH_3CN$ (20.8 mg, 331 umol, 2 eq) and AcOH (9.94 mg, 166 umol, 1 eq), and then stirred at 15° C. for 10 hr. The mixture was concentrated to give a residue. The residue was purified prep-HPLC(TFA)(column: Phenomenex Synergi C18 150*30 mm*4 um; mobile phase: [water(0.1% TFA)-ACN]; B %: 20%-45%, 8 min) to give L-92a (20 mg, 19.1 umol, 11.6% yield, TFA) as yellow solid.

Preparation of 3-[2-[2-[2-[2-[2-[2-[2-[2-[2-[2-[3-[[5-amino-7-[ethoxy(propyl)carbamoyl]-6H-thieno[3,2-b]azepin-2-yl]methyl]azetidin-1-yl]ethoxy]ethoxy]ethoxy]ethoxy]ethoxy]ethoxy]ethoxy]ethoxy]ethoxy]ethoxy]propanoic acid, L-92b To a mixture of L-92a (20 mg, 19.1 umol, 1 eq, TFA) in $H_2O$ (0.5 mL) was add TFA (10.9 mg, 95.7 umol, 5 eq) at 25° C. and then stirred at 80° C. for 4 hr. The mixture was concentrated to give a residue. The residue was purified by prep-HPLC(column: Phenomenex Gemini-NX C18 75*30 mm*3 um; mobile phase; [water(10 mM $NH_4HCO_3$)-ACN]; B %: 25%-45%, 6 min) to give L-92b (13 mg, 14.9 umol, 77.6% yield) as colorless oil.

Preparation of TAZ-L-92

To a mixture of L-92b (12 mg, 13.7 umol, 1 eq) and 2,3,5,6-tetrafluorophenol (18.2 mg, 110 umol, 8 eq) in DCM (1 mL) and DMA (0.1 mL) was added EDCI (26.3 mg, 137 umol, 10 eq), and then stirred at 15° C. for 0.5 hr. The mixture was concentrated to give a residue. The residue was purified by prep-HPLC(column: Phenomenex Synergi C18 150*30 mm*4 um; mobile phase: [water(0.1% TFA)-ACN]; B %: 20%-50%, 8 min) to give TAZ-L-92 (6.3 mg, 5.54 umol, 40.4% yield, 100% purity. TFA) as colorless oil. IH NMR (400 MHz, MeOD) δ7.57-7.32 (m, 2H), 6.98 (br s, 1H), 4.43-3.79 (m, 8H), 3.77-3.52 (m, 40H), 3.44 (s, 2H), 3.33-3.26 (m, 4H), 3.18-3.11 (m, 1H), 3.00 (t, J=6.0 Hz, 2H), 1.83-1.68 (m, 2H), 1.20 (t, J=7.2 Hz, 3H), 0.99 (t, J=7.6 Hz, 3H). LC/MS [M+H] 1023.5 (calculated); LC/MS [M+H] 1023.3 (observed).

Example L-93 Synthesis of (2,3,5,6-tetrafluorophenyl) 3-[2-[2-[2-[2-[2-[2-[2-[2-[2-[3-[4-[[5-amino-7-[ethoxy(propyl)carbamoyl]-6H-thieno[3,2-b]azepin-2-yl]methyl]-1-piperidyl]-3-oxo-propoxy]ethoxy]ethoxy]ethoxy]ethoxy]ethoxy]ethoxy]ethoxy]ethoxy]ethoxy]propanoate, TAZ-L-93

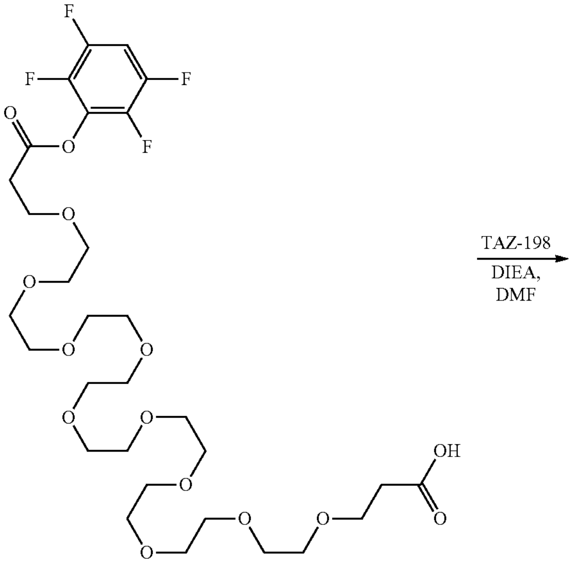

-continued

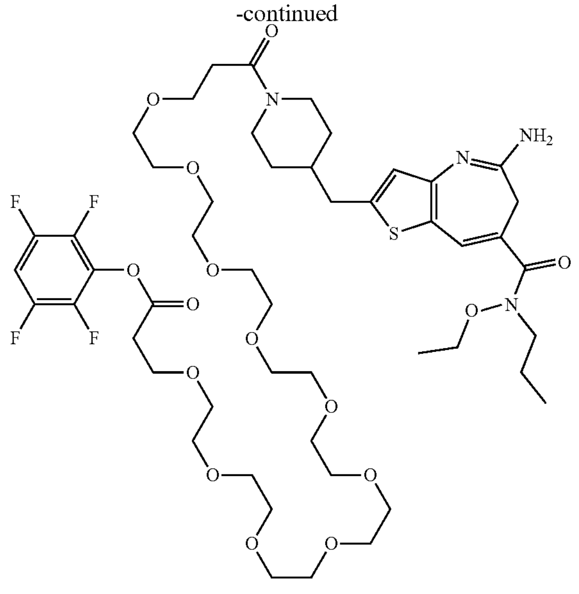

TAZ-L-93

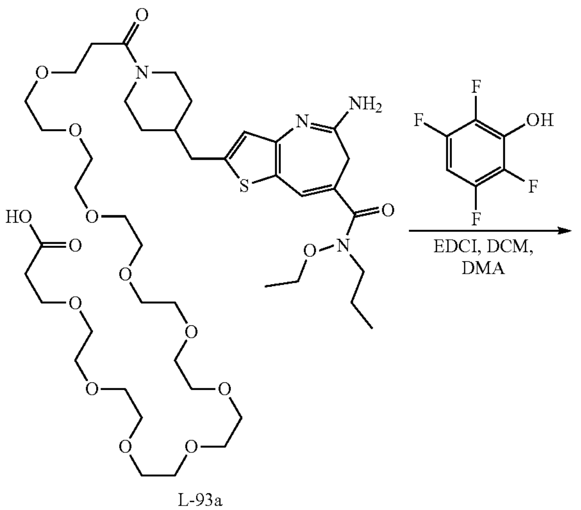

L-93a

Preparation of 3-[2-[2-[2-[2-[2-[2-[2-12-[2-13-[4-[[5-amino-7-[ethoxy(propyl) carbamoyl]-6H-thieno[3,2-b]azepin-2-yl]methyl]-1-piperidyl]-3-oxo-propoxy]ethoxy]ethoxy]ethoxy]ethoxy]ethoxy]ethoxy]ethoxy]ethoxy]ethoxy]propanoic acid, L-93a To a mixture of 5-amino-N-ethoxy-2-(4-piperidylmethyl)-N-propyl-6H-thieno[3,2-b]azepine-7-carboxamide, TAZ-198 (30.0 mg, 70.3 umol, 1.0 eq, HCl) and 3-[2-[2-12-[2-12-[2-[2-[2-[2-[3-oxo-3-(2,3,5,6-tetrafluorophenoxy)propoxy]ethoxy]ethoxy]ethoxy]ethoxy]ethoxy]ethoxy]ethoxy]ethoxy]ethoxy]propanoic acid (54.6 mg, 77.3 umol, 1.1 eq) in DMF (0.5 mL) was added DIEA (27.2 mg, 210 umol, 36.7 uL, 3.0 eq) in one portion at 20° C. under $N_2$, and then stirred at 20° C. for 1 hour. The reaction mixture was filtered and the filtrate was purified by prep-HPLC (column: Xtimate C18 100*30 mm*3 um; mobile phase: [water (0.04% HCl)-ACN]; B %: 22%-45%, 8 min) to afford L-93a (60.0 mg, 64.4 umol, 91.7% yield) as colorless oil.

Preparation of TAZ-L-93

To a mixture of L-93a (60.0 mg, 64.4 umol, 1.0 eq) and 2,3,5,6-tetrafluorophenol (107 mg, 644 umol, 10 eq) in DCM (2 mL) and DMA (0.5 mL) was added EDCI (123.53 mg, 644.37 umol, 10 eq) in one portion at 20° C. under $N_2$, and then stirred at 20° C. for 1 hour. The reaction mixture was filtered and the filtrate was purified by prep-HPLC (column: Phenomenex Synergi C18 150*30 mm*4 um; mobile phase: [water(0.1% TFA)-ACN]; B %: 30%-55%, 8 min) to afford TAZ-L-93 (44.2 mg, 40.2 umol, 62.4% yield, 98.2% purity) as colorless oil. $^{1}$H NMR (400 MHz, MeOD) δ7.49 (s, 1H), 7.47-7.41 (m, 1H), 6.92 (s, 1H), 4.56 (d, J=12.8 Hz, 1H), 4.06 (d, J=13.6 Hz, 1H), 3.95 (q. J=7.2 Hz, 2H), 3.89 (t, J=6.0 Hz, 2H), 3.80-3.71 (m, 4H), 3.70-3.58 (m, 36H), 3.45 (s, 2H), 3.10 (t, J=12.0 Hz, 1H), 3.00 (t, J=6.0 Hz, 2H), 2.86 (d, J=7.0 Hz, 2H), 2.77-2.57 (m, 3H), 1.95-1.90 (m, 1H), 1.80-1.75 (m, 4H), 1.35-1.20 (m, 5H), 0.99 (t, J=7.2 Hz, 3H). LC/MS [M+H] 1079.5 (calculated); LC/MS [M+H] 1079.4 (observed).

Example L-98 Synthesis of(2,3,5,6-tetrafluorophenyl)$_3$-[2-[2-[2-[2-[2-[2-[2-[2-[2-[3-[3-[[5-amino-7-[ethoxy(propyl)carbamoyl]-6H-thieno[3,2-b]azepin-2-yl]methyl]azetidin-1-yl]-3-oxo-propoxy]ethoxy]ethoxy]ethoxy]ethoxy]ethoxy]ethoxy]ethoxy]ethoxy]ethoxy]propanoate, TAZ-L-98
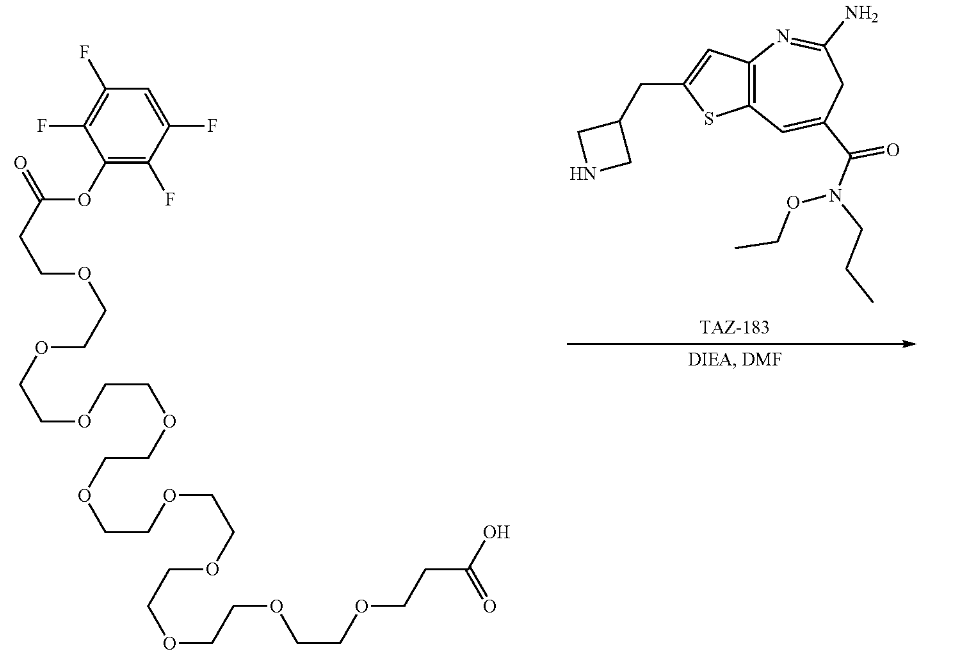
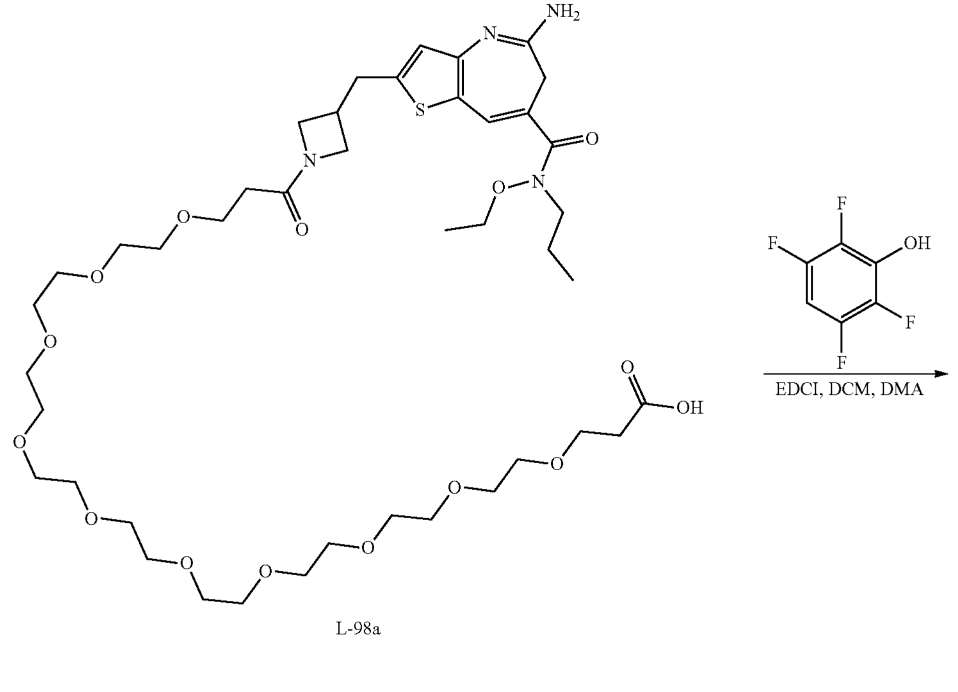
L-98a -continued

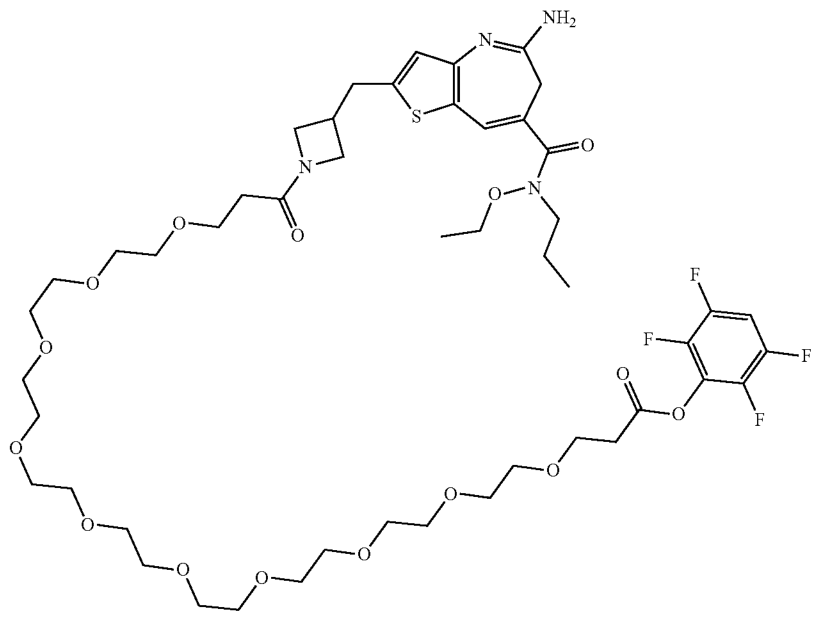

TAZ-L-98

Preparation of 3-[2-[2-[2-[2-[2-[2-12-[2-[2-[3-[3-[[5-amino-7-[ethoxy(propyl)carbamoyl]-6H-thienol[3,2-b]azepin-2-yl]methyl]azetidin-1-yl]-3-oxo-propoxy]ethoxy]ethoxy]ethoxy]ethoxy]ethoxy]ethoxy]ethoxy]ethoxy]ethoxy]propanoic acid, L-98a To a mixture of 5-amino-2-(azetidin-3-ylmethyl)-N-ethoxy-N-propyl-6H-thieno[3,2-b]azepine-7-carboxamide, TAZ-183 (150 mg, 315 umol, 1 eq, TFA) and DIEA (102 mg, 787 umol, 137 μL, 2.5 eq) in DMF (2 mL) was added 3-[2-[2-[2-[2-[2-[2-[2-[2-[2-[3-oxo-3-(2,3,5,6-tetrafluoro-phenoxy)propoxy]ethoxy]ethoxy]ethoxy]ethoxy]ethoxy]ethoxy]ethoxy]ethoxy]ethoxy]propanoic acid (223 mg, 315 umol, 1 eq), and then stirred at 20° C. for 0.5 hr. The mixture was concentrated to give a residue. The residue was purified by Prep-HPLC(column: Waters Xbridge Prep OBD C18 150*40 mm*I10 um; mobile phase: [water(10 mM $NH_4HCO_3$)-ACN]; B %: 5%-40%, 8 min) to give L-98a (0.08 g, 88.6 umol, 28.1% yield) as yellow oil.

Preparation of TAZ-L-98

To a mixture of L-98a (0.08 g, 88.6 umol, 1 eq) and 2,3,5,6-tetrafluorophenol (118 mg, 709 umol, 8 eq) in DCM (3 mL) and DMA (0.3 mL) was added EDCI (170 mg, 886 umol, 10 eq). The mixture was stirred at 15° C. for 0.5 hr. The mixture was concentrated to give a residue. The residue was purified by Prep-HPLC(column: Phenomenex Synergi C18 150*25*10 um; mobile phase: [water(0.1% TFA)-ACN]; B %: 25%-50%, 10 min and column: Phenomenex Synergi C18 150*25*10 um; mobile phase: [water(0.1% TFA)-ACN]; B %: 25%-50%, 8 min) to give TAZ-L-98 (34.3 mg, 31.9 umol, 36.0% yield, 97.7% purity) as colorless oil. $^1$H NMR (400 MHz, MeOD) δ7.49-7.38 (m, 2H), 6.92 (s, 1H), 4.42-4.35 (m, 1H), 4.10 (t, J=9.2 Hz, 1H), 4.06-3.97 (m, 1H), 3.93 (q, J=7.2 Hz, 2H), 3.89-3.85 (m, 2H), 3.73-3.69 (m, 4H), 3.66-3.51 (m, 37H), 3.40 (s, 2H), 3.19 (br d. J=7.6 Hz, 2H), 2.99-2.96 (m, 3H), 2.48-2.24 (m, 2H), 1.74 (q, J=7.2 Hz, 2H), 1.18 (t, J=7.2 Hz, 3H), 0.97 (t, J=7.2 Hz, 3H). LC/MS [M+H] 1051.5 (calculated); LC/MS [M+H] 1051.3 (observed).

Example L-128 Synthesis of 4-[3-[2-[2-[2-[2-[2-[2-[2-[2-[2-[3-[3-[5-amino-7-[2-(cyclobutoxycarbonylamino)ethoxy-propyl-carbamoyl]-6H-thieno[3,2-b]azepin-2-yl]methyl]azetidin-1-yl]-3-oxo-propoxy]ethoxy]ethoxy]ethoxy]ethoxy]ethoxy]ethoxy]ethoxy]ethoxy]ethoxy]propanoyloxy]-2,3,5,6-tetrafluoro-benzenesulfonic acid, TAZ-L-128
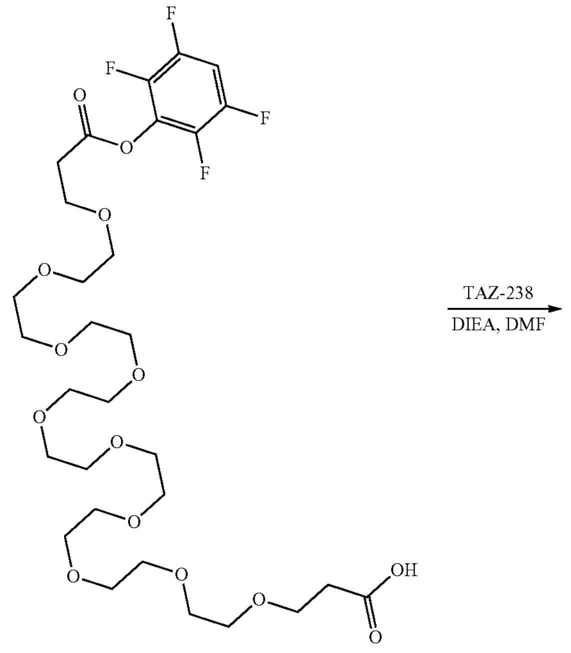
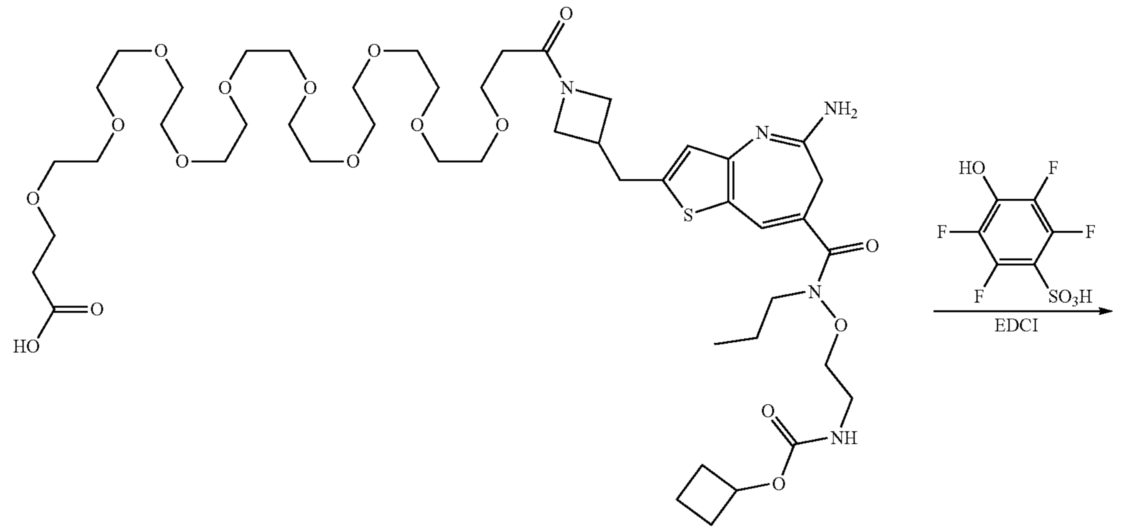
128a -continued

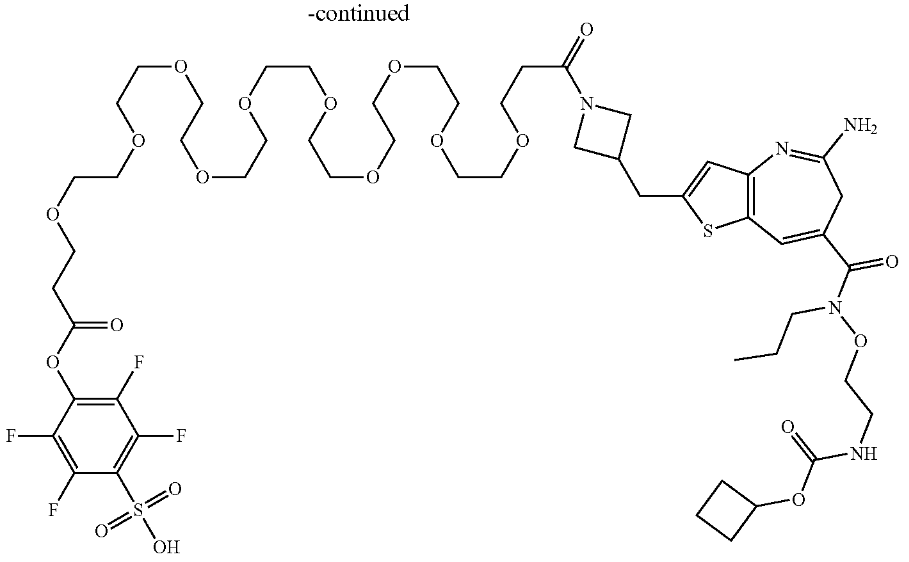

TAZ-128

Preparation of 3-[2-[2-[2-[2-[2-12-[2-[2-[2-[3-[3-[5-amino-7-[2-(cyclobutoxycarbonylamino)ethoxy-propyl-carbamoyl]-6H-thieno[3,2-b]azepin-2-yl]methyl]azetidin-1-yl]-3-oxo-propoxy]ethoxy]ethoxy]ethoxy]ethoxy]ethoxy]ethoxy]ethoxy]ethoxy]ethoxy]propanoic acid, 128a To a mixture of cyclobutyl N-[2-[5-amino-2-(azetidin-3-ylmethyl)-6H-thieno[3,2-b]azepine-7-carbonyl]-propyl-amino]oxyethyl]carbamate, TAZ-238 (0.12 g, 171 umol, 1.0 eq, TFA) in DMF (2 mL) was added DIEA (66.1 mg, 512 umol, 89.1 uL, 3.0 eq) and 3-[2-[2-[2-[2-[2-[2-12-[2-[2-[3-oxo-3-(2,3,5,6-tetrafluorophenoxy)propoxy]ethoxy]ethoxy]ethoxy]ethoxy]ethoxy]ethoxy]ethoxy]ethoxy]ethoxy]propanoic acid (121 mg, 171 umol, 1.0 eq) in one portion at 0° C. and then stirred at 0° C. for 0.5 h. The mixture was filtered and purified by prep-HPLC(column: Welch Xtimate C18 100*25 mm*3 um; mobile phase: [water(0.05% HCl)-ACN]; B %: 20%-40%, 8 min) to give 128a (45 mg, 42.8 umol, 25.1% yield, HCl) as yellow oil. $^1$H NMR (MeOD, 400 MHz) δ7.51 (s, 1H), 6.96 (s, 1H), 4.81-4.76 (m, 1H), 4.40 (t, J=8.4 Hz, 1H), 4.11 (t, J=9.2 Hz, 1H), 4.03 (dd, J=5.6, 8.8 Hz, 1H), 3.92 (t, J=5.2 Hz, 2H), 3.77-3.68 (m, 7H), 3.66-3.55 (m, 36H), 3.42 (s, 2H), 3.30-2.25 (m, 2H), 3.20 (d, J=8.0 Hz, 2H), 3.06-2.89 (m, 1H), 2.54 (t, J=6.4 Hz, 2H), 2.44-2.31 (m, 2H), 2.30-2.20 (m, 2H), 2.05-1.90 (m, 2H), 1.80-1.68 (m, 3H), 1.66-1.52 (m, 1H), 0.96 (t, J=7.6 Hz, 3H)

Preparation of TAZ-128

To a mixture of 128a (40 mg, 38.0 umol, 1.0 eq. HCl) and sodium 2,3,5,6-tetrafluoro-4-hydroxy-benzenesulfonate (50.9 mg, 190 umol, 5.0 eq) in DCM (1.5 mL) and DMA (0.2 mL) was added EDCI (51.0 mg, 266 umol, 7.0 eg) in one portion at 25° C. and then stirred at 25° C. for 0.5 h. Then the mixture was concentrated. The residue was purified by prep-HPLC(column: Phenomnenex Synergi C18 150*25*10 um; mobile phase: [water(0.1% TFA)-ACN]; B %: 15%-45%, 8 min) to give TAZ-128 (35.2 mg, 28.3 umol, 74.5% yield) as yellow solid. $^1$H NMR (MeOD, 400 MHz) δ 7.49 (s, 1H), 6.96 (s, 1H), 4.79-4.73 (mi, 1H), 4.43-4.35 (m, 1H), 4.16-3.98 (m, 2H), 3.97-3.83 (m, 4H), 3.77-3.67 (m, 5H), 3.66-3.57 (nm, 34H), 3.42 (s, 2H), 3.30-3.25 (m, 4H), 3.19 (d, J=8.0 Hz, 2H), 2.98 (t, J=5.6 Hz, 3H), 2.44-2.19 (m, 4H), 2.03-1.89 (m, 2H), 1.80-1.54 (m, 4H), 0.96 (t, J=7.6 Hz, 3H). LC/MS [M+H] 1244.5 (calculated); LC/MS [M+H] 1244.2 (observed).

Example L-131 Synthesis of 4-[3-[2-[2-[3-[4-[2-[5-amino-7-[ethoxy(propyl)carbamoyl]-6H-thieno [3,2-b]azepin-2-yl]ethyl]-piperidyl]-3-oxo-propoxy]ethoxy]ethoxy]propanoyloxy]-2,3,5,6-tetrafluoro-benzenesulfonic acid, TAZ-L-131

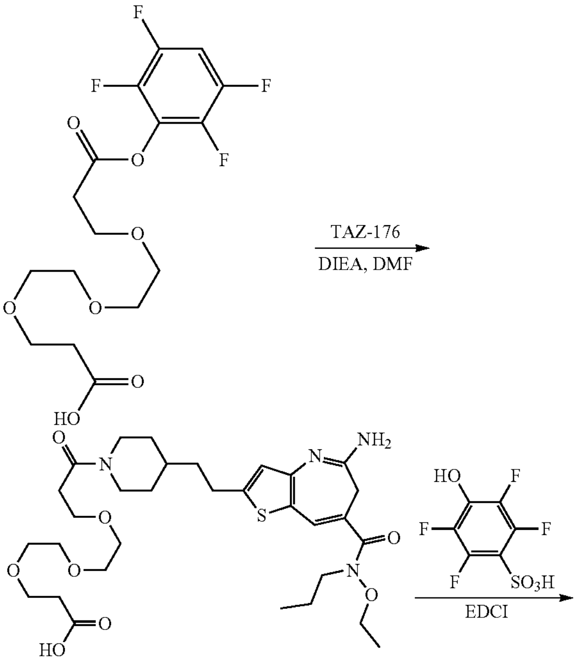

L-131a

-continued

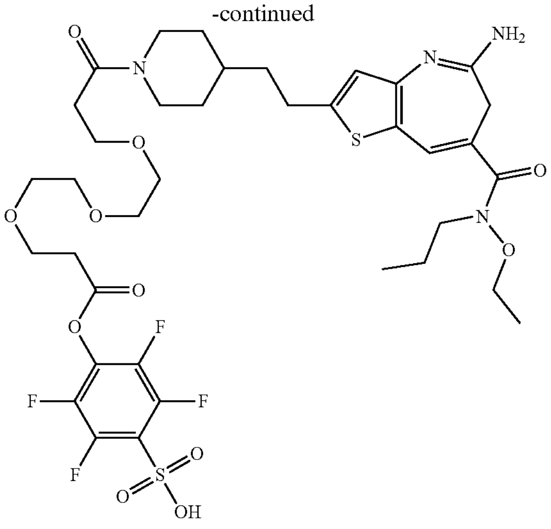

TAZ-131

Preparation of 3-[2-[2-[3-[4-[2-[5-amino-7-[ethoxy (propyl)carbamoyl]-6H-thieno [3,2-b]azepin-2-yl] ethyl]-1-piperidyl]-3-oxo-propoxy]ethoxy]ethoxy] propanoic acid, L-131a To a mixture of 5-amino-N-ethoxy-2-[2-(4-piperidyl) ethyl]-N-propyl-6H-thieno[3,2-b]azepine-7-carboxamide, TAZ-176 (0.1 g, 227 umol, 1.0 eq, HCl) in DMF (2 mL) was added DIEA (87.9 mg, 680 umol, 118 μL, 3.0 eq) and 3-[2-[2-[3-oxo-3-(2,3,5,6-tetrafluorophenoxy)propoxy] ethoxy]ethoxy]propanoic acid (90.3 mg, 227 umol, 1.0 eq) in one portion at 0° C. and it was stirred at 0° C. for 0.5 h. The mixture was purified by prep-HPLC(column: Welch Xtimate C18 100*25 mm*3 um; mobile phase: [water (0.05% HCl)-ACN]; B %: 15%-35%, 8 min) to give L-131a (0.06 g, 94.22 umol, 41.55% yield) as yellow oil. $^{1}$H NMR (MeOD, 400 MHz) δ7.46 (s, 1H), 6.89 (s, 1H), 4.54 (d, J=13.6 Hz, 1H), 4.04 (d, J=13.6 Hz, 1H), 3.93 (q, J=7.2 Hz, 2H), 3.77-3.69 (m, 6H), 3.63-3.58 (m, 8H), 3.42 (s, 2H), 3.15-3.01 (m, 1H), 2.94 (t, J=7.6 Hz, 2H), 2.75-2.51 (m, 5H), 1.88-1.78 (m, 2H), 1.78-1.71 (m, 2H), 1.70-1.65 (m, 2H), 1.29-1.07 (m, 5H), 0.97 (t, J=7.6 Hz, 3H).

Preparation of TAZ-L-131

To a mixture of L-131a (0.06 g, 89.1 umol, 1.0 eq, HCl) and sodium 2,3,5,6-tetrafluoro-4-hydroxy-benzenesulfonate (95.6 mg, 356 umol, 4.0 eq) in DCM (1.5 mL) and DMA (0.3 mL) was added EDCI (103 mg, 535 umol, 6.0 eq) in one portion at 25° C. and it was stirred at 25° C. for 0.5 h. The mixture was concentrated to give a residue, and the residue was purified by prep-HPLC(column: Phenomenex Synergi C18 150*25*10 um; mobile phase: [water(0.2% FA)-ACN]; B %: 20%-45%, 8 min) to give TAZ-L-131 (31.7 mg, 36.65 umol, 41.13% yield) as white solid. $^{1}$H NMR (MeOD, 400 MHz) δ7.43 (s, 1H), 6.88 (s, 1H), 4.51 (d, J=13.2 Hz, 1H), 4.01 (d, J=13.6 Hz, 1H), 3.96-3.84 (m, 4H), 3.78-3.69 (m, 4H), 3.68-3.54 (m, 8H), 3.42 (s, 2H), 3.07-3.01 (m, 1H), 2.98 (t, J=5.6 Hz, 2H), 2.88 (t, J=7.2 Hz, 2H), 2.74-2.53 (m, 3H), 1.84-1.68 (m, 4H), 1.68-1.55 (m, 3H), 1.25-1.03 (m, 5H), 0.97 (t, J=7.6 Hz, 3H). LC/MS [M+H] 865.3 (calculated); LC/MS [M+H] 865.3 (observed).

Example L-133 Synthesis of 4-[3-[2-[2-[2-[2-[2-[2-[2-[2-[2-[2-[3-[[5-amino-7-[2-(cyclobutoxycarbonylamino)ethoxy-propyl-carbamoyl]-6H-thieno[3,2-b]azepin-2-yl]methyl]azetidin-1-yl]ethoxy]ethoxy]ethoxy]ethoxy]ethoxy]ethoxy]ethoxy]ethoxy]ethoxy]ethoxy]propanoyloxy]-2,3,5,6-tetrafluoro-benzenesulfonic acid, TAZ-L-133

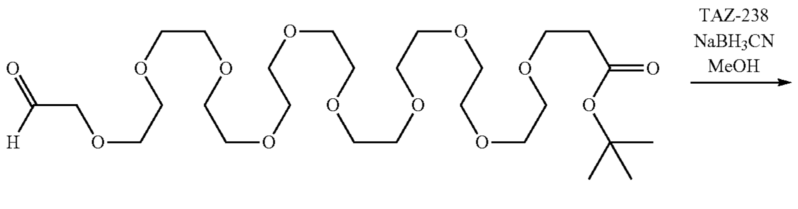

-continued
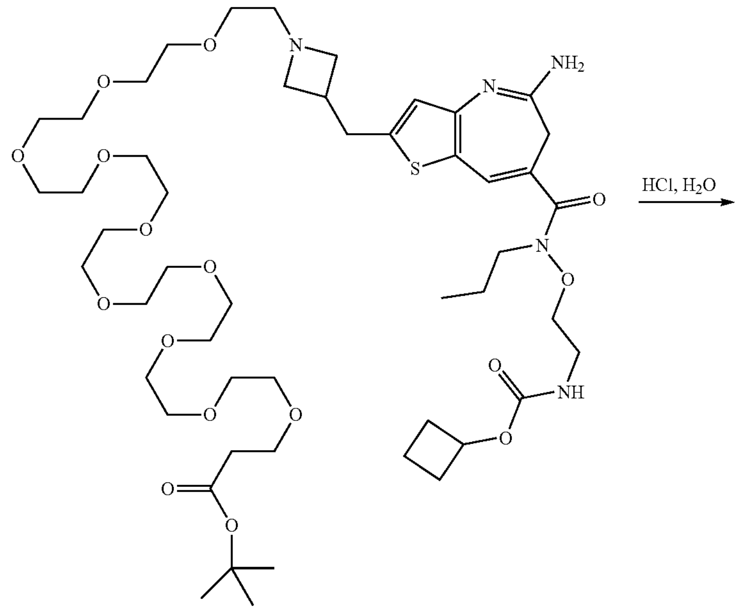
L-133a
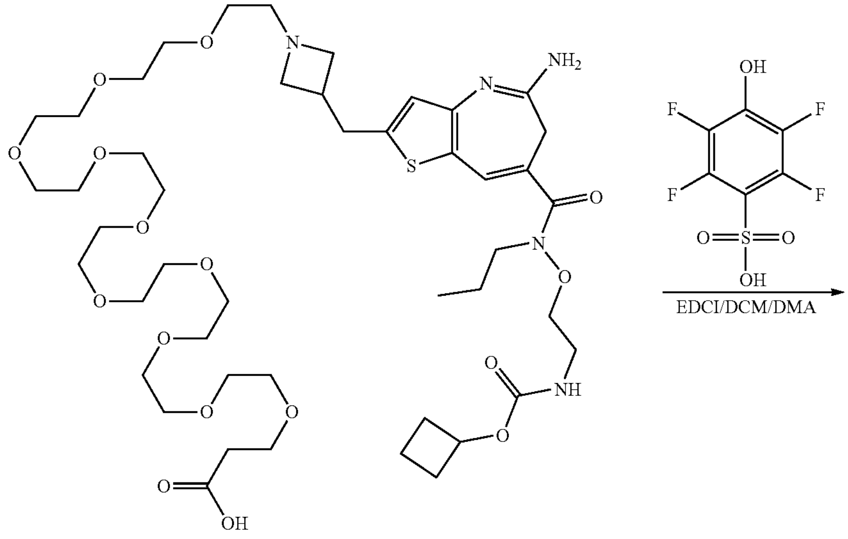
L-133b

-continued

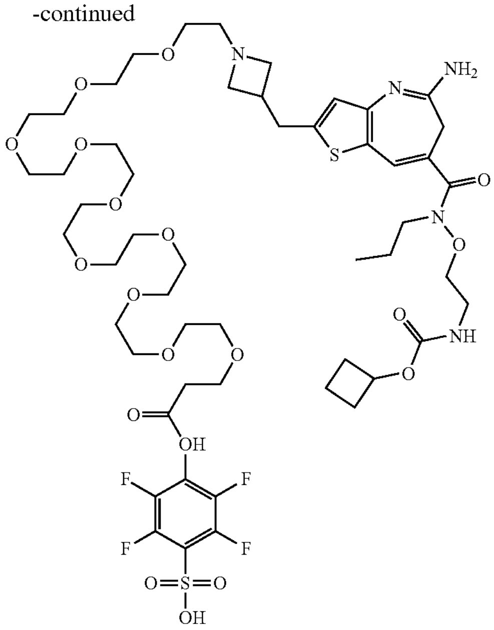

TAZ-L-133

Preparation of tert-butyl 3-[2-[2-[2-[2-[2-[2-[2-[2-[2-[2-[3-[[5-amino-7-[2-(cyclobutoxycarbonylamino)ethoxy-propyl-carbamoyl]-6H-thieno[3,2-b]azepin-2-yl]methyl]azetidin-1-yl]ethoxy]ethoxy]ethoxy]ethoxy]ethoxy]ethoxy]ethoxy]ethoxy]ethoxy]ethoxy]propanoate, L-133a To a mixture of cyclobutyl N-[2-[[5-amino-2-(azetidin-3-ylmethyl)-6H-thieno[3,2-b]azepine-7-carbonyl]-propyl-amino]oxyethyl]carbamate, TAZ-238 (0.14 g, 199 umol, 1.0 eq, TFA) and tert-butyl 3-[2-[2-[2-[2-[2-[2-[2-[2-[2-(2-oxo-ethoxy)ethoxy]ethoxy]ethoxy]ethoxy]ethoxy]ethoxy]ethoxy]ethoxy]ethoxy]propanoate (151 mg, 259 umol, 1.3 eq) in MeOH (3 mL) was added $NaBH_3CN$ (25.0 mg, 398 umol, 2.0 eq) in one portion at 25° C. and then stirred at 25° C. for 12 h. The mixture was concentrated. The residue was purified by prep-HPLC(column: Phenomenex Synergi C18 150*25*10 um; mobile phase: [water(0.1% TFA)-ACN]; B %: 20%-50%, 8 min) to give L-133a (0.2 g, 173 umol, 86.8% yield, TFA) as yellow oil. $^1H$ NMR (MeOD, 400 MHz) δ 7.49 (s, 1H), 6.98 (s, 1H), 4.85-4.80 (m, 1H), 4.44-4.25 (m, 2H), 4.18-3.97 (m, 2H), 3.92 (t, J=5.2 Hz, 2H), 3.74-3.67 (m, 6H), 3.66-3.61 (m, 40H), 3.42 (s, 2H), 3.28-3.23 (m, 3H), 2.47 (td, J=1.6, 6.4 Hz, 2H), 2.31-2.19 (m, 2H), 2.02-1.91 (m, 2H), 1.76-1.71 (m, 3H), 1.67-1.54 (m, 1H), 1.45 (s, 9H), 0.96 (t, J=7.6 Hz, 3H).

Preparation of 3-[2-[2-[2-[2-[2-[2-[2-[2-[2-[2-13-115-amino-7-[2-(cyclobutoxycarbonylamino)ethoxy-propyl-carbamoyl]-6H-thieno[3,2-b]azepin-2-yl]methyl]azetidin-1-yl]ethoxy]ethoxy]ethoxy]ethoxy]ethoxy]ethoxy]ethoxy]ethoxy]ethoxy]ethoxy]propanoic acid, L-133b To a mixture of L-133a (0.2 g, 173 umol, 1.0 eq, TFA) in $H_2O$ (3 mL) and $CH_3CN$ (0.5 mL) was added HCl (12 M, 216 µL, 15.0 eq) in one portion at 25° C. and then stirred at 80° C. for 0.5 h. The mixture was concentrated. The residue was purified by prep-HPLC(column: Welch Xtimate C18 100*25 mm*3 um; mobile phase: [water(0.05% HCl)-ACN]; B %: 10%-30%, 8 min) to give L-133b (40 mg, 39.0 umol, 22.6% yield, HCl) as yellow oil.

Preparation of TAZ-L-133

To a mixture of L-133b (40 mg, 39.0 umol, 1.0 eq, HCl) and sodium 2,3,5,6-tetrafluoro-4-hydroxy-benzenesulfonate (41.9 mg, 156 umol, 4.0 eq) in DCM (1 mL) and DMA (0.1 mL) was added EDCI (52.4 mg, 273 umol, 7.0 eq) in one portion at 25° C. and then stirred at 25° C. for 0.5 h. The mixture was filtered and concentrated. The residue was purified by prep-HPLC(column: Phenomenex Synergi C18 150*25*10 um; mobile phase: [water(0.1% TFA)-ACN]; B %: 10%-30%, 8 min) to give TAZ-L-133 (14.7 mg, 12.1 umol, 30.9% yield) as yellow oil. $^1H$ NMR (MeOD, 400 MHz) δ7.48 (s, 1H), 7.02-6.96 (m, 1H), 4.84-4.84 (m, 1H), 4.41-4.25 (m, 2H), 4.15-4.14 (m, 1H), 4.19-3.97 (m, 2H), 3.95-3.84 (m, 4H), 3.76-3.68 (m, 4H), 3.68-3.58 (m, 38H), 3.52-3.44 (m, 2H), 3.42 (s, 2H), 3.28-3.21 (m, 3H), 2.99 (t, J=5.6 Hz, 2H), 2.25 (q. J=8.4 Hz, 2H), 2.04-1.90 (m, 2H), 1.80-1.54 (m, 4H), 0.96 (t, J=7.6 Hz, 3H). LCMS [M+H] 1216.5 (calculated); LC/MS [M+H] 1216.6 (observed).

Example L-139 Synthesis of 4-[3-[2-[2-[2-[2-[2-[2-[2-[2-[2-[3-[3-[[5-amino-7-[isopropoxy(propyl)carbamoyl]-6H-thieno[3,2-b]azepin-2-yl]methyl]azetidin-1-yl]-3-oxo-propoxy]ethoxy]ethoxy]ethoxy]ethoxy]ethoxy]ethoxy]ethoxy]ethoxy]ethoxy]propanoyloxy]-2,3,5,6-tetrafluoro-benzenesulfonic acid, TAZ-L-139
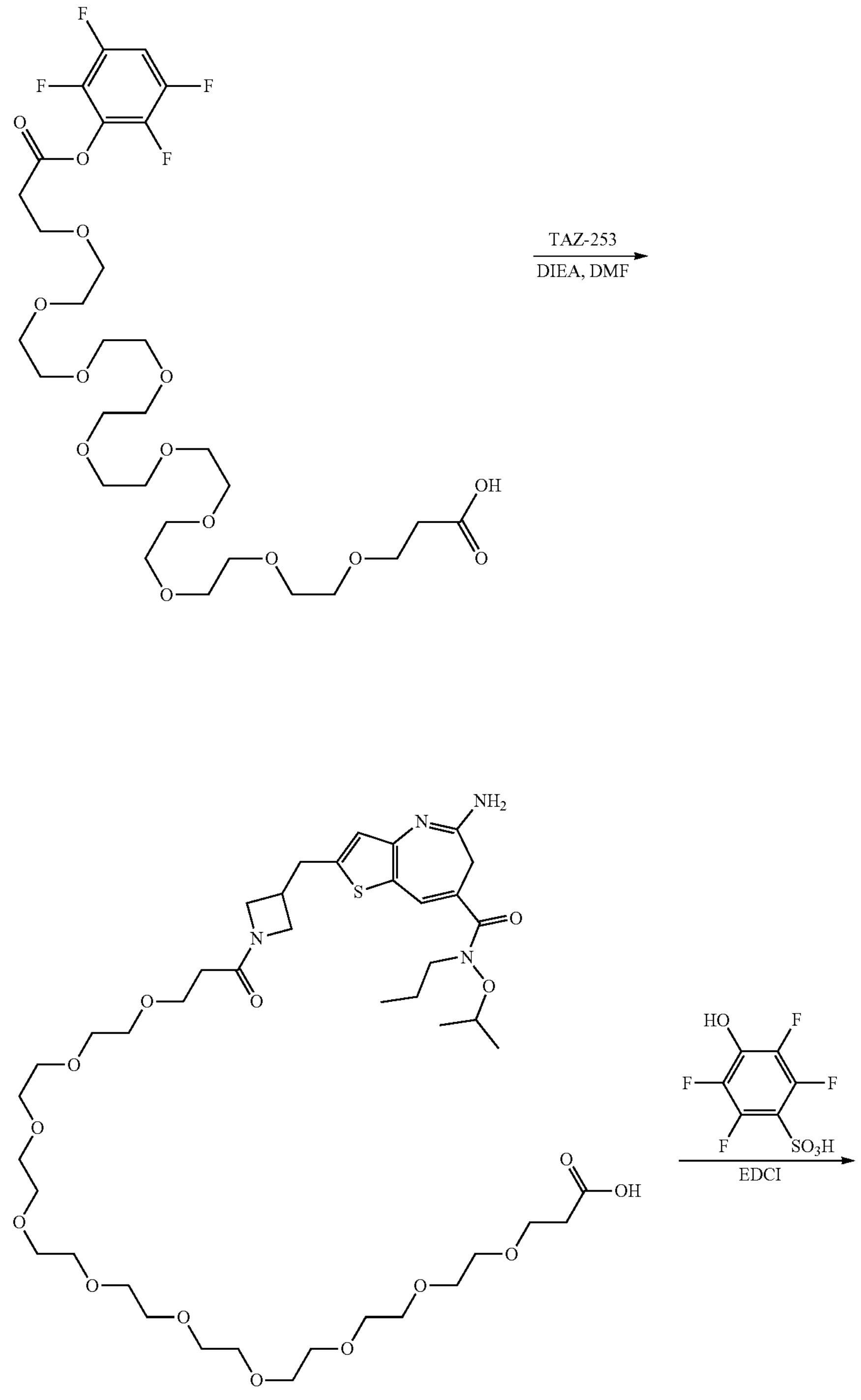
L-139a -continued

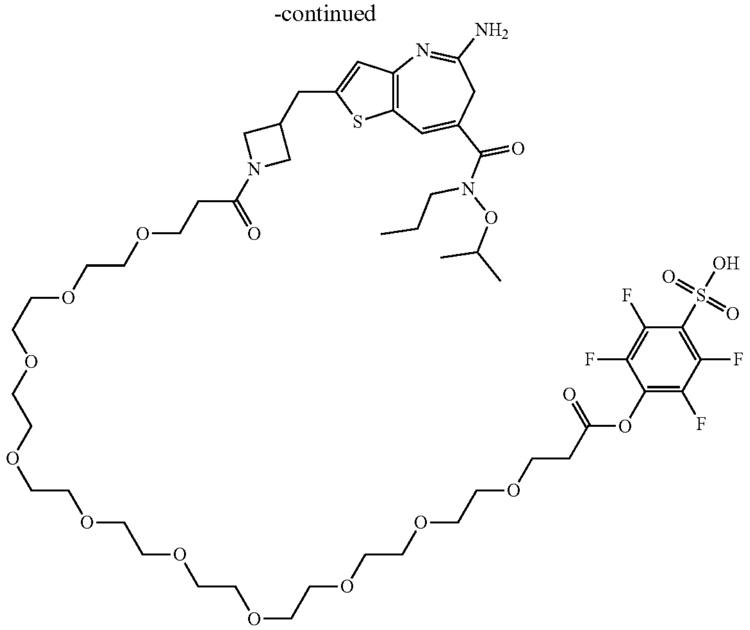

TAZ-L-139

Preparation of 3-[2-[2-[2-[2-[2-[2-[2-[2-[2-[3-[3-[[5-amino-7-[isopropoxy(propyl) carbamoyl]-6H-thieno [3,2-b]azepin-2-yl]methyl]azetidin-11-yl]-3-oxo-propoxy]ethoxy]ethoxy]ethoxy]ethoxy]ethoxy] ethoxy]ethoxy]ethoxy]ethoxy]propanoic acid, L-139a To a mixture of 5-amino-2-(azetidin-3-ylmethyl)-N-isopropoxy-N-propyl-6H-thieno[3,2-b]azepine-7-carboxamide, TAZ-253 (100 mg, 204 umol, 1 eq, TFA) and 3-[2-[2-[2-[2-[[2-[2-[2-[2-[2-[3-oxo-3-(2,3,5,6-tetrafliuorophenoxy)propoxy]ethoxy]ethoxy]ethoxy] ethoxy]ethoxy]ethoxy]ethoxy]ethoxy]ethoxy]propanoic acid (158 mg, 224 umol, 1.1 eq) in THE (3 mL) was added $Et_3N$ (61.9 mg, 612 umol, 85.1 uL, 3 eq), and then stirred at 20° C. for 1 h. The residue was poured into water (5 mL) and the pH of the mixture was adjusted to about 6 with 1M HCl. The aqueous phase was extracted with ethyl acetate (8 mL×1)-discarded, the aqueous phase was further extracted with dichloromethane/isopropyl alcohol=3:1 (8 mL×3), the combined organic phase was dried with anhydrous $Na_2SO_4$, filtered and concentrated in vacuum to give L-139a (150 mg, 164 umol, 80.23% yield) as a light yellow oil.

Preparation of TAZ-L-139

To a solution of L-139a (100 mg, 109 umol, 1 eq) in DCM (1.5 mL) and DMA (0.5 mL) was added sodium 2,3,5,6-tetrafluoro-4-hydroxy-benzenesulfonate (117 mg, 436 umol, 4 eq) and EDCI (83.6 mg, 436 umol, 4 eq), and then stirred at 20° C. for 2 h. The reaction mixture was filtered and concentrated under residue pressure. The residue was purified by prep-HPLC (column: Phenomenex Synergi C18 150*25*10 um; mobile phase: [water(0.1% TFA)-ACN]; B %: 15%-35%, 8 min) to give TAZ-L-139 (69.7 mg, 55.3 umol, 50.76% yield, TFA) as a light yellow solid. $^1H$ NMR (MeOD, 400 MHz) δ7.45 (s, 1H), 6.96 (s, 1H), 4.85-4.80 (m, 1H), 4.39 (t, J=8.6 Hz, 1H), 4.26-4.20 (m, 1H), 4.11 (t, J=9.2 Hz, 1H), 4.02 (dd, J=5.2, 8.5 Hz, 1H), 3.87 (t, J=5.8 Hz, 2H), 3.82-3.67 (m, 6H), 3.66-3.58 (m, 34H), 3.42 (s, 2H), 3.18 (d, J=7.8 Hz, 2H), 3.05-2.95 (m, 3H), 2.42-2.31 (m, 2H), 1.79-1.69 (m, 2H), 1.18 (d, J=6.2 Hz, 6H), 0.95 (t, J=7.4 Hz, 3H). LC/MS [M+H] 1145.4 (calculated); LC/MS [M+H] 1145.4 (observed).

Example L-144 Synthesis of 4-[3-[2-[2-[2-[2-[2-[2-[2-[2-[2-[3-[3-[5-amino-7-[2-(isopropoxycarbonylamino)ethoxy-propyl-carbamoyl]-6H-thieno[3,2-b]azepin-2-yl]methyl]azetidin-1-yl]-3-oxo-propoxy] ethoxy]ethoxy]ethoxy]ethoxy]ethoxy]ethoxy] ethoxy]ethoxy]ethoxy]propanoyloxy]-2,3,5,6-tetrafluoro-benzenesulfonic acid, TAZ-L-144

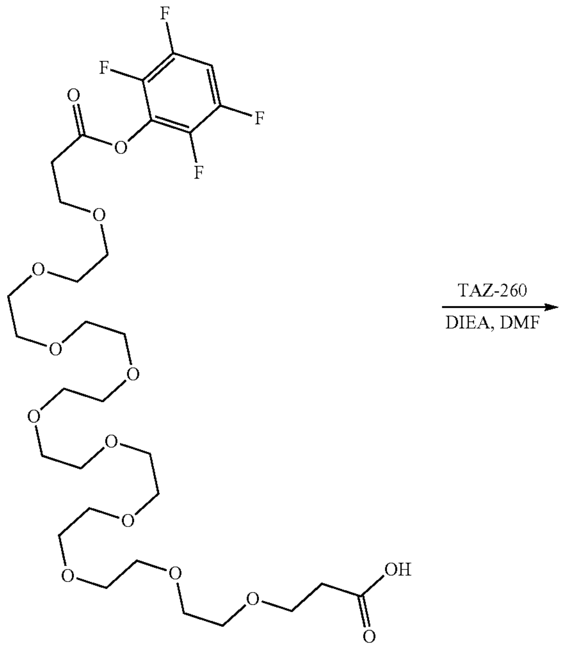

-continued

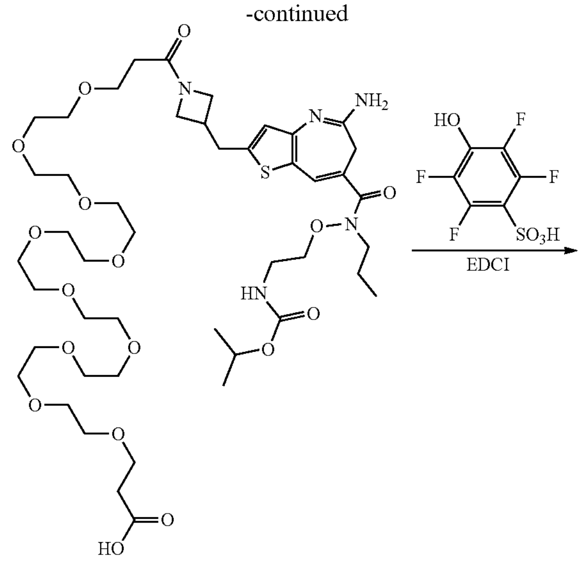

L-144a

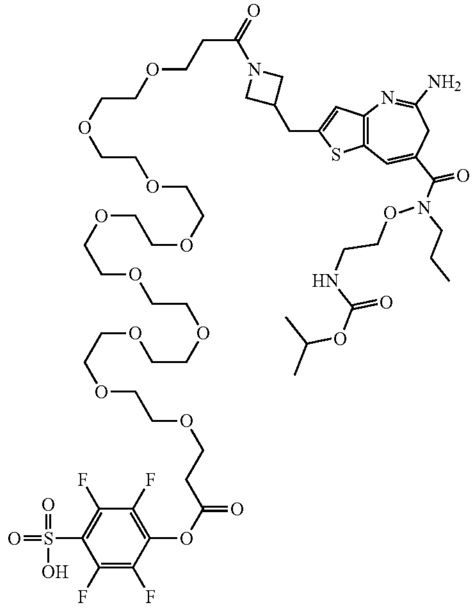

TAZ-L-144

Preparation of 3-[2-[2-[2-[2-[2-[2-[2-[2-[2-[3-[3-[[5-amino-7-12-(isopropoxycarbonylamino)ethoxy-propyl-carbamoyl]-6H-thieno[3,2-b]azepin-2-yl]methyl]azetidin-1-yl]-3-oxo-propoxy]ethoxy]ethoxy]ethoxy]ethoxy]ethoxy]ethoxy]ethoxy]ethoxy]ethoxy]propanoic acid, L-144a To a mixture of isopropyl N-[2-[[5-amino-2-(azetidin-3-ylmethyl)-6H-thieno[3,2-b]azepine-7-carbonyl]-propyl-amino]oxyethyl]carbamate, TAZ-260 (0.13 g, 161 umol, 1.0 eq, TFA salt) in THF (4 mL) was added $Et_3N$ (49.0 mg, 484 umol, 67.4 uL, 3.0 eq) and 3-[2-[2-[2-[2-[2-[2-[2-[2-[2-[3-oxo-3-(2,3,5,6-tetrafluorophenoxy)propoxy]ethoxy]ethoxy]ethoxy]ethoxy]ethoxy]ethoxy]ethoxy]ethoxy]ethoxy]propanoic acid (114 mg, 161 umol, 1.0 eq) in one portion at 0° C. and then stirred at 0° C. for 0.5 h. The mixture was diluted with water (5 mL) and the pH of the mixture was adjusted to ~6 with TFA. Then it was extracted with EtOAc (10 mL)-discarded. The water phase was further extracted with DCM:i-PrOH=3:1(10 mL×3). The organic layer was dried over $Na_2SO_4$, filtered and concentrated to give L-144a (0.21 g, crude, 3TFA) as yellow oil.

Preparation of TAZ-L-144

To a mixture of L-144a (0.2 g, 199 umol, 1.0 eq) in DCM (3 mL) and DMA (0.3 mL) was added sodium; 2,3,5,6-tetrafluoro-4-hydroxy-benzenesulfonate (267 mg, 9% umol, 5.0 eq) and EDCI (267 mg, 1.39 mmol, 7.0 eq) in one portion at 25° C. and then stirred at 25° C. for 0.5 h. The mixture was concentrated to give a residue. The residue was purified by prep-HPLC(column: Phenomenex Synergi C18 150*25*10 um; mobile phase; [water(0.1% TFA)-ACN]; B %: 15%-40%, 8 min) to give TAZ-L-144 (98.2 mg, 79.69 umol, 40.01% yield) as light yellow oil. $^1H$ NMR (MeOH, 400 MHz) δ 7.49 (s, 1H), 6.96 (s, 1H), 4.82-4.74 (m, 1H), 4.39 (t, J=8.8 Hz, 1H), 4.11 (t, J=9.2 Hz, 1H), 4.03 (dd, J=5.6, 9.2 Hz, 1H), 3.93 (t, J=5.2 Hz, 2H), 3.87 (t, J=6.0 Hz, 2H), 3.76-3.69 (m, 5H), 3.68-3.52 (m, 38H), 3.43 (s, 2H), 3.18 (d, J=7.6 Hz, 2H), 2.98 (t, J=6.0 Hz, 3H), 2.43-2.30 (m, 2H), 1.79-1.68 (m, 2H), 1.17 (d, J=6.4 Hz, 6H), 0.95 (t, J=7.6 Hz, 3H). LC/MS [M+H] 1232.5 (calculated); LC/MS [M+H] 1232.7 (observed).

Example L-145 Synthesis of 4-[3-[2-[2-[2-[2-[2-[2-[2-[2-[2-[3-[3-[5-amino-7-[2-(ethylcarbamoylamino)ethoxy-propyl-carbamoyl]-6H-thieno[3,2-b]azepin-2-yl]methyl]azetidin-1-yl]-3-oxo-propoxy]ethoxy]ethoxy]ethoxy]ethoxy]ethoxy]ethoxy]ethoxy]ethoxy]ethoxy]propanoyloxy]-2,3,5,6-tetrafluoro-benzenesulfonic acid, TAZ-L-145

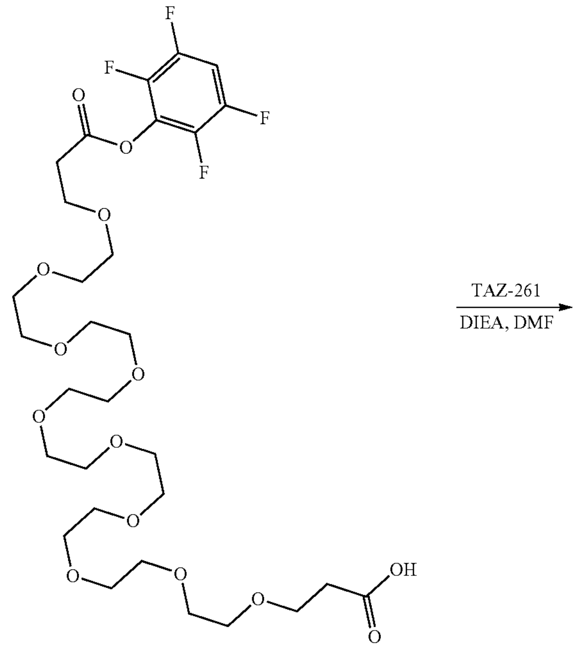

-continued

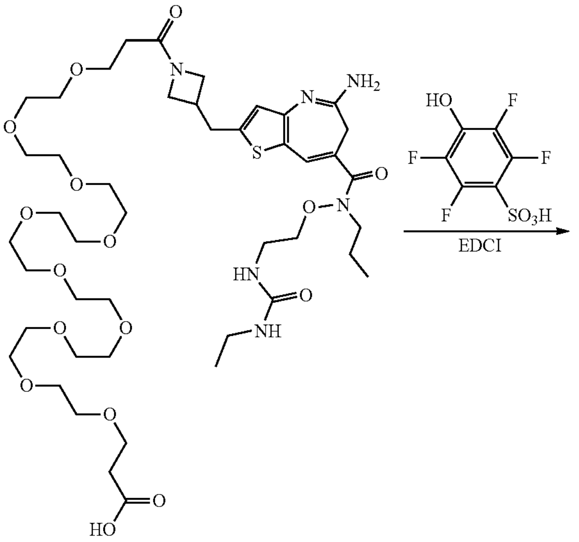

L-145a

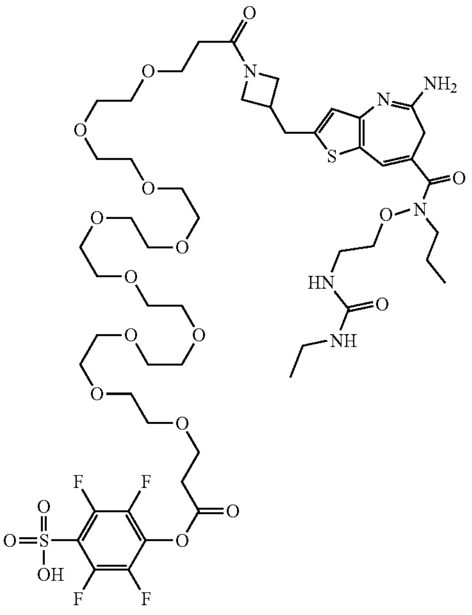

TAZ-L-145

Preparation of 3-[2-[2-[2-[2-[2-[2-[2-[2-[2-[3-[3-[[5-amino-7-[2-(ethylcarbamoylamino)ethoxy-propyl-carbamoyl]-6H-thieno[3,2-b]azepin-2-yl]methyl] azetidin-1-yl]-3-oxo-propoxy]ethoxy]ethoxy]ethoxy] ethoxy]ethoxy]ethoxy]ethoxy]ethoxy]ethoxy] propanoic acid, L-145a To a solution of 5-amino-2-(azetidin-3-ylmethyl)-N-[2-(ethylcarbamoylamino) ethoxy]-N-propyl-6H-thieno[3,2-b] azepine-7-carboxamide, TAZ-261 (120 mg, 177 umol, 1 eq, TFA) in THF (3.00 mL) was added $Et_3N$ (54.0 mg, 532 umol, 3 eq) and 3-[2-[2-[2-[2-[2-[2-[2-[2-[2-[3-oxo-3-(2,3,5,6-tetrafluorophenoxy)propoxy]ethoxy]ethoxy]ethoxy] ethoxy]ethoxy]ethoxy]ethoxy]ethoxy]ethoxy]propanoic acid (125 mg, 177 umol, 1 eq), and then stirred at 0° C. for 1 h. The mixture was diluted with water (10 mL) and the pH of the mixture was adjusted to about pH 6 by TFA and extracted with MTBE (10 mL)-discarded and the water phase was further extracted with DCM:i-PrOH=3:1 (20 mL×3). The organic layer was washed with brine (30 mL×3), dried over $Na_2SO_4$, filtered and concentrated to give L-145a (170 mg, 172 umol, 96.90% yield) as light yellow oil.

Preparation of TAZ-L-145

To a solution of L-145a (170 mg, 172 umol, 1 eq) and sodium 2,3,5,6-tetrafluoro-4-hydroxybenzenesulfonate (184 mg, 687 umol, 4 eq) in DCM (3.00 mL) and DMA (0.15 mL) was added EDCI (132 mg, 687 umol, 4 eq), and then stirred at 25° C. for 1 h. The mixture was concentrated to give a residue. The residue was purified by prep-HPLC (column: Phenomenex Synergi C18 150*25*10 um; mobile phase: [water(0.1% TFA)-ACN]; B %: 20%-40%, 8 min) to give TAZ-L-145 (103 mg, 77.37 umol, 45.02% yield, TFA) as light yellow oil. $^1H$ NMR (MeOD, 400 MHz) δ 7.47 (s, 1H), 6.95 (s, 1H), 4.39 (t, J=8.5 Hz, 1H), 4.11 (t, J=9.0 Hz, 1H), 4.02 (dd, J=5.3, 8.8 Hz, 1H), 3.89 (td, J=5.6, 13.9 Hz, 4H), 3.76-3.68 (m, 6H), 3.67-3.56 (m, 36H), 3.44 (s, 2H), 3.18 (d, J=7.5 Hz, 2H), 3.07 (q, J=7.3 Hz, 3H), 2.98 (t, J=5.9 Hz, 2H), 2.44-2.30 (m, 2H), 1.79-1.69 (m, 2H), 1.05 (t, J=7.2 Hz, 3H), 0.96 (t, J=7.4 Hz, 3H). LC/MS [M+H] 1217.5 (calculated); LC/MS [M+H] 1217.6 (observed).

Example L-147 Synthesis of 4-((40-(5-amino-7-((2-((cyclobutoxycarbonyl)amino)ethoxy)(propyl)carbamoyl)-6H-thieno[3,2-b]azepin-2-yl)-34-oxo-4,7,10,13,16,19,22,25,28,31-decaoxa-35-azatetracontanoyl)oxy)-2,3,5,6-tetrafluorobenzenesulfonic acid, TAZ-L-147

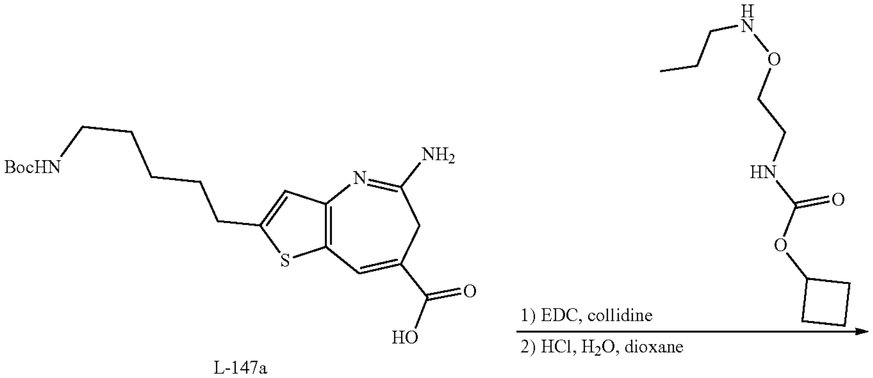

L-147a

-continued
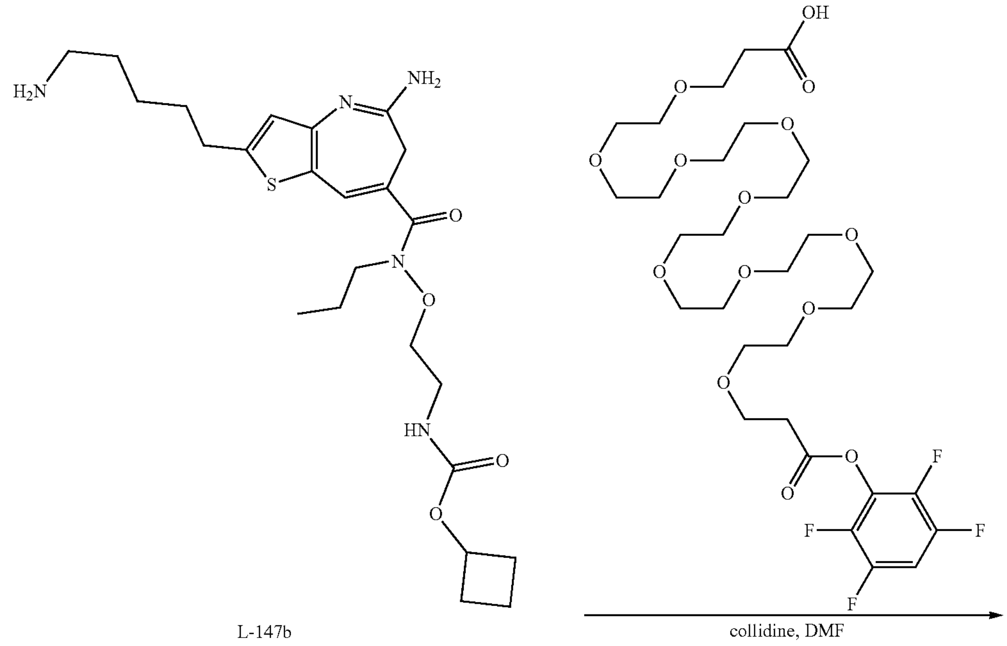
L-147b
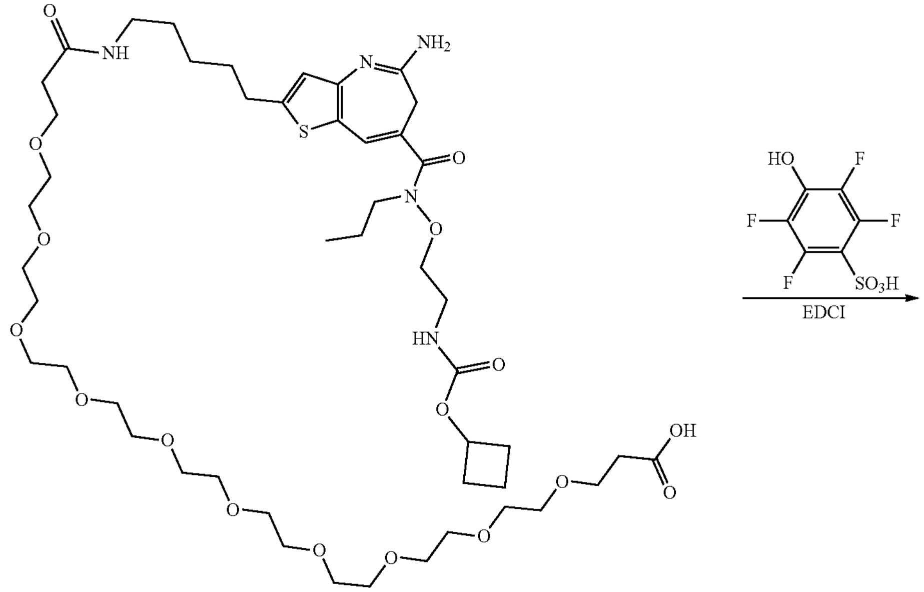
L-147c

-continued

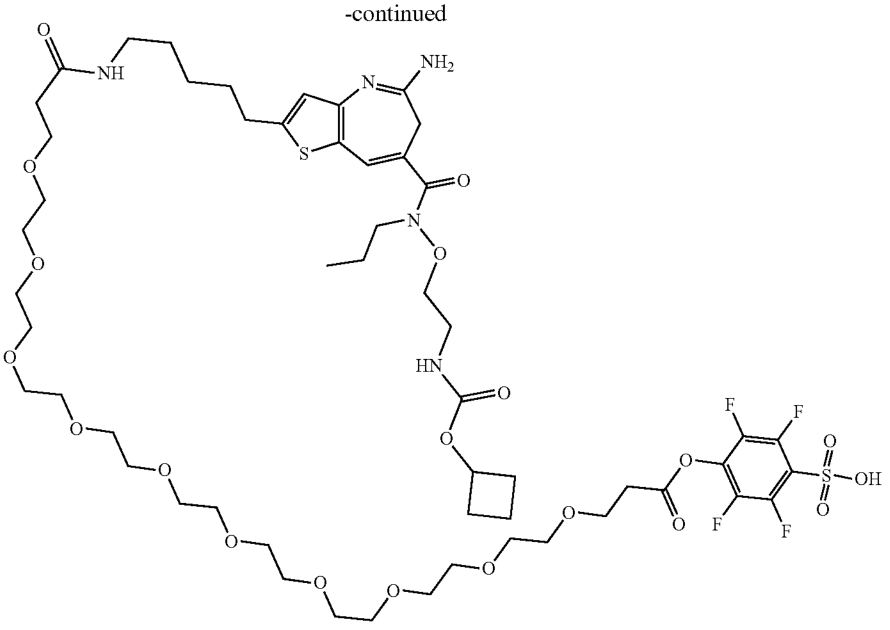

TAZ-L-147

Preparation of 5-(5-amino-7-((2-((cyclobutoxycarbonyl)amino)ethoxy)(propyl)carbamoyl)-6H-thieno[3,2-b]azepin-2-yl)pentan-1-aminium chloride, L-147b 5-Amino-2-(5-((tert-butoxycarbonyl)amino)pentyl)-6H-thieno[3,2-b]azepine-7-carboxylic acid, L-147a (0.78 g, 1.98 mmol, 1 equiv.) and cyclobutyl (2-((propylamino)oxy)ethyl)carbamate (0.5 g, 1.98 mmol, 1 equiv.) were combined in DMF. Collidine (0.52 ml, 3.9 mmol, 1.98 equiv.) was added, followed by EDCI, also known as EDC, 1-ethyl-3-(3-dimethylaminopropyl)carbodiimide, CAS Reg. No 1892-57-5 (0.38 g, 1.98 mmol, 1 equiv.). The reaction monitored by LCMS, then concentrated and purified by reverse-phase flash chromatography. Combined fractions were lyophilized, then taken up in 4 N HCl/dioxane. The deprotected product was purified by reverse-phase flash chromatography to give L-147b (0.8 g, 1.51 mmol, 82%). LC/MS [M+H] 492.26 (calculated); LC/MS [M+H] 492.45 (observed).

Preparation of 40-(5-amino-7-((2-((cyclobutoxycarbonyl)amino)ethoxy)(propyl)carbamoyl)-6H-thieno[3,2-b]azepin-2-yl)-34-oxo-4,7,10,13,16,19,22,25,28,31-decaoxa-35-azatetracontanoic acid, L-147c Intermediate L-147b (0.148 g, 0.3 mmol, 1 equiv.) and 34-oxo-34-(2,3,5,6-tetrafluorophenoxy)-4,7,10,13,16,19,22,25,28,31-decaoxatetratriacontanoic acid (0.23 g, 0.32 mmol, 1.07 equiv.) were dissolved in 3 ml DMF. Collidine (0.2 ml, 1.5 mmol, 5 equiv.) was added, and the reaction stirred at ambient temperature. The reaction was purified by reverse-phase HPLC to give L-147c (0.16 g, 0.16 mmol, 52%). LC/MS [M+H] 1032.54 (calculated); LC/MS [M+H] 1032.81 (observed).

Preparation of TAZ-L-147

Intermediate L-147c (0.16 g, 0.155 mmol, 1 equiv.) and 2,3,5,6-tetrafluoro-4-hydroxybenzenesulfonic acid (0.083 g, 0.31 mmol, 2 equiv.) were dissolved in 2 ml DMF. Collidine (0.1 ml, 0.78 mmol, 5 equiv.) was added, followed by EDC (0.045 g, 0.23 mmol, 1.5 equiv.). The reaction was stirred at room temperature and monitored by LCMS, then diluted with water and purified by reverse-phase HPLC to give TAZ-L-147 (0.095 g, 0.075 mmol, 49%). LC/MS [M+H] 1260.49 (calculated); LC/MS [M+H] 1260.70 (observed).

Example 201 Preparation of Immunoconjugates (IC)

In an exemplary procedure, an antibody is buffer exchanged into a conjugation buffer containing 100 mM boric acid, 50 mM sodium chloride, 1 mM ethylenediaminetetraacetic acid at pH 8 3, using G-25 SEPHADEX™ desalting columns (Sigma-Aldrich. St Louis. MO). The eluates are then each adjusted to a concentration of about 1-10 mg/ml using the buffer and then sterile filtered. The antibody is pre-warmed to 20-30° C. and rapidly mixed with 2-20 (e.g., 7-10) molar equivalents of thienoazepine-linker (TAZ-L) compound of Formula II. The reaction is allowed to proceed for about 16 hours at 30° C. and the immunoconjugate (IC) is separated from reactants by running over two successive G-25 desalting columns equilibrated in phosphate buffered saline (PBS) at pH 7.2 to provide the Immunoconjugate (IC) of Table 3. Adjuvant-antibody ratio (DAR) is determined by liquid chromatography mass spectrometry analysis using a C4 reverse phase column on an ACQUITY™ UPLC H-class (Waters Corporation, Milford, MA) connected to a XEVO™ G2-XS TOF mass spectrometer (Waters Corporation).

For conjugation, the antibody may be dissolved in a aqueous buffer system known in the art that will not adversely impact the stability or antigen-binding specificity of the antibody. Phosphate buffered saline may be used. The thienoazepine-linker (TAZ-L) intermediate compound is dissolved in a solvent system comprising at least one polar aprotic solvent as described elsewhere herein. In some such aspects, thienoazepine-linker (TAZ-L) intermediate is dissolved to a concentration of about 5 mM, about 10 mM, about 20 mM, about 30 mM, about 40 mM or about 50 mM, and ranges thereof such as from about 5 mM to about 50 mM or from about 10 mM to about 30 mM in pH 8 Tris buffer (e.g., 50 mM Tris). In some aspects, the thienoazepine-linker intermediate is dissolved in DMSO (dimethylsulfoxide), DMA (dimethylacetamide) or acetonitrile, or another suitable dipolar aprotic solvent.

Alternatively in the conjugation reaction, an equivalent excess of thienoazepine-linker (TAZ-L) intermediate solution may be diluted and combined with antibody solution. The thienoazepine-linker intermediate solution may suitably be diluted with at least one polar aprotic solvent and at least one polar protic solvent, examples of which include water, methanol, ethanol, n-propanol, and acetic acid. The molar equivalents of thienoazepine-linker intermediate to antibody may be about 1.5:1, about 3:1, about 5:1, about 10:1, about 15:1, or about 20:1, and ranges thereof, such as from about 1.5:1 to about 20:1 from about 1.5:1 to about 15:1, from about 1.5:1 to about 10:1, from about 3:1 to about 15:1, from about 3:1 to about 10:1, from about 5:1 to about 15:1 or from about 5:1 to about 10:1. The reaction may suitably be monitored for completion by methods known in the art, such as LC-MS. The conjugation reaction is typically complete in a range from about 1 hour to about 16 hours. After the reaction is complete, a reagent may be added to the reaction mixture to quench the reaction. If antibody thiol groups are reacting with a thiol-reactive group such as maleimide of the thienoazepine-linker intermediate, unreacted antibody thiol groups may be reacted with a capping reagent. An example of a suitable capping reagent is ethylmaleimide.

Following conjugation, the immunoconjugates may be purified and separated from unconjugated reactants and/or conjugate aggregates by purification methods known in the art such as, for example and not limited to, size exclusion chromatography, hydrophobic interaction chromatography, ion exchange chromatography, chromatofocusing, ultrafiltration, centrifugal ultrafiltration, tangential flow filtration, and combinations thereof. For instance, purification may be preceded by diluting the immunoconjugate, such in 20 mM sodium succinate, pH 5. The diluted solution is applied to a cation exchange column followed by washing with, e.g., at least 10 column volumes of 20 mM sodium succinate, pH 5. The conjugate may be suitably eluted with a buffer such as PBS.

Example 202 HEK Reporter Assay

HEK293 reporter cells expressing human TLR7 or human TLR8 were purchased from Invivogen and vendor protocols were followed for cellular propagation and experimentation. Briefly, cells were grown to 80-85% confluence at 5% $CO_2$ in DMEM supplemented with 10% FBS, Zeocin, and Blasticidin. Cells were then seeded in 96-well flat plates at $4\times10^4$ cells/well with substrate containing HEK detection medium and immunostimulatory molecules. Activity was measured using a plate reader at 620-655 nm wavelength.

Example 203 Assessment of Immunoconjugate Activity In Vitro

This example shows that Immunoconjugates of the invention are effective at eliciting myeloid activation, and therefore are useful for the treatment of cancer.

Isolation of Human Antigen Presenting Cells: Human myeloid antigen presenting cells (APCs) were negatively selected from human peripheral blood obtained from healthy blood donors (Stanford Blood Center, Palo Alto, California) by density gradient centrifugation using a ROSETTESEP™ Human Monocyte Enrichment Cocktail (Stem Cell Technologies, Vancouver, Canada) containing monoclonal antibodies against CD14, CD16, CD40, CD86, CD123, and HLA-DR. Immature APCs were subsequently purified to >90% purity via negative selection using an EASYSEP™ Human Monocyte Enrichment Kit (Stem Cell Technologies) without CD16 depletion containing monoclonal antibodies against CD14, CD16, CD40, CD86, CD123, and HLA-DR.

Myeloid APC Activation Assay: $2\times10^5$ APCs were incubated in 96-well plates (Corning, Corning, NY) containing iscove's modified dulbecco's medium, IMDM (Lonza) supplemented with 10% FBS, 100 U/mL penicillin, 100 μg/mL (micrograms per milliliter) streptomycin, 2 mM L-glutamine, sodium pyruvate, non-essential amino acids, and where indicated, various concentrations of unconjugated (naked) PD-L1 or HER2 antibodies and immunoconjugates of the invention (as prepared according to the Example above). Trastuzumab and avelumab were used as the antibody constructs. Cell-free supernatants were analyzed after 18 hours via ELISA to measure TNFα secretion as a readout of a proinflammatory response.

All references, including publications, patent applications, and patents, cited herein are hereby incorporated by reference to the same extent as if each reference were individually and specifically indicated to be incorporated by reference and were set forth in its entirety herein.

The invention claimed is:

1. An immunoconjugate comprising an antibody covalently attached to one or more 5-aminothienoazepine moieties by a linker, and having Formula I:

$$Ab—[L—TAZ]_p \qquad I$$

or a pharmaceutically acceptable salt thereof, wherein:

Ab is the antibody;

p is an integer from 1 to 8;

TAZ is the 5-aminothienoazepine moiety having the formula:

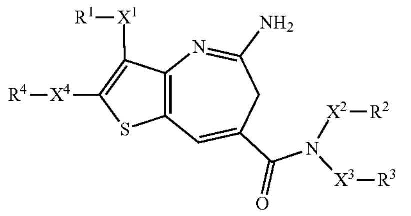

$R^1$, $R^2$, $R^3$, and $R^4$ are independently selected from the group consisting of H, $C_1$-$C_{12}$ alkyl, $C_2$-$C_6$ alkenyl, $C_2$-$C_6$ alkynyl, $C_3$-$C_{12}$ carbocyclyl, $C_6$-$C_{20}$ aryl, $C_2$-$C_9$ heterocyclyl, and $C_1$-$C_{20}$ heteroaryl, where alkyl, alkenyl, alkynyl, carbocyclyl, aryl, heterocyclyl, and heteroaryl are independently and optionally substituted with one or more groups selected from;

—($C_1$-$C_{12}$ alkyldiyl)-N($R^5$)—*;

—($C_1$-$C_{12}$ alkyldiyl)-N($R^5$)$_2$;

—($C_1$-$C_{12}$ alkyldiyl)-O$R^5$;

—($C_3$-$C_{12}$ carbocyclyl);

—($C_3$-$C_{12}$ carbocyclyl)-*;

—($C_3$-$C_{12}$ carbocyclyl)-($C_1$-$C_{12}$ alkyldiyl)-N$R^5$—*;

—($C_3$-$C_{12}$ carbocyclyl)-($C_1$-$C_{12}$ alkyldiyl)-N($R^5$)$_2$;

—($C_3$-$C_{12}$ carbocyclyl)-N$R^3$—C(═N$R^5$)N$R^5$—*;

—($C_6$-$C_{20}$ aryl);

—($C_6$-$C_{20}$ aryl)-*;

—($C_6$-$C_{20}$ aryldiyl)-N($R^5$)—*;

—($C_6$-$C_{20}$ aryldiyl)-($C_1$-$C_{12}$ alkyldiyl)-N($R^5$)—*;

—($C_6$-$C_{20}$ aryldiyl)-($C_1$-$C_{12}$ alkyldiyl)-($C_2$-$C_{20}$ heterocyclyldiyl)-*;

—($C_6$-$C_{20}$ aryldiyl)-($C_1$-$C_{12}$ alkyldiyl)-N($R^5$)$_2$;

—($C_6$-$C_{20}$ aryldiyl)-($C_1$-$C_{12}$ alkyldiyl)-N$R^5$—C(═N$R^{5a}$)N($R^5$)—*;

—($C_2$-$C_{20}$ heterocyclyl);

—($C_2$-$C_{20}$ heterocyclyl)-*;

—($C_2$-$C_9$ heterocyclyl)-($C_1$-$C_{12}$ alkyldiyl)-N$R^5$—*;

—($C_2$-$C_9$ heterocyclyl)-($C_1$-$C_{12}$ alkyldiyl)-N($R^5$)$_2$;

—($C_2$-$C_9$ heterocyclyl)-C(═O)—($C_1$-$C_{12}$ alkyldiyl)-N($R^5$)—*;

—($C_2$-$C_9$ heterocyclyl)-N$R^5$—C(═N$R^{5a}$)N$R^{5a}$—*;

—($C_2$-$C_9$ heterocyclyl)-N$R^5$—($C_6$-$C_{20}$ aryldiyl)-($C_1$-$C_{12}$ alkyldiyl)-N($R^5$)—*;

—($C_2$-$C_9$ heterocyclyl)-($C_6$-$C_{20}$ aryldiyl)-*;

—($C_1$-$C_{20}$ heteroaryl);

—($C_1$-$C_{20}$ heteroaryl)-*;

—($C_1$-$C_{20}$ heteroaryl)-($C_1$-$C_{12}$ alkyldiyl)-N($R^5$)—*;

—($C_1$-$C_{20}$ heteroaryl)-($C_1$-$C_{12}$ alkyldiyl)-N($R^5$)$_2$;

—($C_1$-$C_{20}$ heteroaryl)-N$R^5$—C(═N$R^{5a}$)N($R^5$)—*;

—($C_1$-$C_{20}$ heteroaryl)-N($R^5$)C(═O)—($C_1$-$C_{12}$ alkyldiyl)-N($R^5$)—*;

—C(═O)—*;

—C(═O)—($C_1$-$C_{12}$ alkyldiyl)-N($R^5$)—*;

—C(═O)—($C_2$-$C_{20}$ heterocyclyldiyl)-*;

—C(═O)N($R^5$)$_2$;

—C(═O)N($R^5$)—*;

—C(═O)N($R^5$)—($C_1$-$C_{12}$ alkyldiyl)-N($R^5$)C(═O)$R^5$;

—C(═O)N($R^5$)—($C_1$-$C_{12}$ alkyldiyl)-N($R^5$)C(═O)N($R^5$)$_2$;

—C(═O)N$R^5$—($C_1$-$C_{12}$ alkyldiyl)-N($R^5$)$CO_2R^3$;

—C(═O)N$R^5$—($C_1$-$C_{12}$ alkyldiyl)-N($R^5$)C(═N$R^{5a}$)N($R^5$)$_2$;

—C(═O)N$R^5$—($C_1$-$C_{12}$ alkyldiyl)-N$R^5$C(═N$R^{5a}$)$R^5$;

—C(═O)N$R^5$—($C_1$-$C_8$ alkyldiyl)-N$R^5$($C_2$-$C_8$ heteroaryl);

—C(═O)N$R^5$—($C_1$-$C_{20}$ heteroaryldiyl)-N($R^5$)—*;

—C(═O)N$R^5$—($C_1$-$C_{20}$ heteroaryldiyl)-*;

—C(═O)N$R^5$—($C_1$-$C_{20}$ heteroaryldiyl)-($C_1$-$C_{12}$ alkyldiyl)-N($R^5$)$_2$;

—C(═O)N$R^5$—($C_1$-$C_{20}$ heteroaryldiyl)-($C_2$-$C_{20}$ heterocyclyldiyl)-C(═O)N$R^5$—($C_1$-$C_{12}$ alkyldiyl)-N$R^5$—*;

—N($R^5$)$_2$;

—N($R^5$)—*;

—N($R^5$)C(═O)$R^5$;

—N($R^5$)C(═O)—*;

—N($R^5$)C(═O)N($R^5$)$_2$;

—N($R^5$)C(═O)N($R^5$)—*;

—N($R^5$)$CO_2R^5$;

—N$R^5$C(═N$R^{5a}$)N($R^5$)$_2$;

—N$R^5$C(═N$R^{5a}$)N($R^5$)—*;

—N$R^5$C(═N$R^{5a}$)$R^5$;

—N($R^5$)C(═O)—($C_1$-$C_{12}$ alkyldiyl)-N($R^5$)—*;

—N($R^5$)—($C_2$-$C_5$ heteroaryl);

—N($R^5$)—S(═O)—($C_1$-$C_{12}$ alkyl);

—O—($C_1$-$C_{12}$ alkyl);

—O—($C_1$-$C_{12}$ alkyldiyl)-N($R^5$)$_2$;

—O—($C_1$-$C_{12}$ alkyldiyl)-N($R^5$)—*;

—S(═O)$_2$—($C_2$-$C_{20}$ heterocyclyldiyl)-*;

—S(═O)$_2$—($C_2$-$C_{20}$ heterocyclyldiyl)-($C_1$-$C_{12}$ alkyldiyl)-N($R^5$)$_2$;

—S(═O)$_2$—($C_2$-$C_{20}$ heterocyclyldiyl)-($C_1$-$C_{12}$ alkyldiyl)-N$R^5$—*; and —S(═O)$_2$—($C_2$-$C_{20}$ heterocyclyldiyl)-($C_1$-$C_{12}$ alkyldiyl)-OH;

or $R^2$ and $R^3$ together form a 5- or 6-membered heterocyclyl ring;

$X^1$, $X^2$, $X^3$, and $X^4$ are independently selected from the group consisting of a bond, C(═O), C(═O)N($R^5$), O, N($R^5$), S, S(O)$_2$, and S(O)$_2$N($R^5$);

$R^5$ is selected from the group consisting of H, $C_6$-$C_{20}$ aryl, $C_3$-$C_{12}$ carbocyclyl, $C_6$-$C_{20}$ aryldiyl, $C_1$-$C_{12}$ alkyl, and $C_1$-$C_{12}$ alkyldiyl, or two $R^5$ groups together form a 5- or 6-membered heterocyclyl ring;

$R^{5a}$ is selected from the group consisting of $C_6$-$C_{20}$ aryl and $C_1$-$C_{20}$ heteroaryl;

where the asterisk * indicates the attachment site of L, and where one of $R^1$, $R^2$, $R^3$ and $R^4$ is attached to L;

L is the linker selected from the group consisting of:

—C(═O)—(PEG)-;

—C(═O(PEG)-C(═O)—;

—C(═O)—(PEG)-O—;

—C(═O(PEG)-C(═O)—(PEP)-;

—C(═O(PEG)-C(═O)N($R^5$)—($C_1$-$C_{12}$ alkyldiyl)-;

—C(═O(PEG)-C(═O)N($R^5$)—($C_1$-$C_{12}$ alkyldiyl)-N($R^5$)C(═O)—($C_2$-$C_5$ monoheterocyclyldiyl)-;

—C(═O(PEG)-C(═O)N($R^5$)—($C_1$-$C_{12}$ alkyldiyl)-(MCgluc)-;

—C(═O(PEG)-C(═O)-(MCgluc)-;

—C(═O(PEG)-C(═O)—(PEP)—N($R^5$)—($C_1$-$C_{12}$ alkyldiyl)-;

—C(═O(PEG)-C(═O)—(PEP)—N($R^5$)—($C_1$-$C_{12}$ alkyldiyl)-N($R^5$)C(═O)—($C_2$-$C_5$ monoheterocyclyldiyl)-;

—C(═O)—(PEG)-N($R^5$)—;

—C(═O(PEG)-N($R^5$)C(═O)—;

—C(═O(PEG)-N($R^5$)—(PEG)-C(═O)—(PEP)-;

—C(═O)—(PEG)-N*($R^5$)$_2$(EG)-C(═O)—(PEP)-;

—C(═O(PEG)-C(═O)—N($R^5$)CH($AA_1$)C(═O)-(PEG)-C(═O)—(PEP)-;

—C(═O(PEG)-C(═O)—N($R^5$)CH($AA_1$)C(═O)—N($R^5$)—($C_1$-$C_{12}$ alkyldiyl)-;

—C(═O(PEG)-SS—($C_1$-$C_{12}$ alkyldiyl)-OC(═O)—;

—C(═O(PEG)-SS—($C_1$-$C_{12}$ alkyldiyl)-C(═O)—;

—C(═O)—($C_1$-$C_{12}$ alkyldiyl)-C(═O)—(PEP)-;

—C(═O)$C_1$-$C_{12}$ alkyldiyl)-C(═O)—(PEP)—N($R^5$)—($C_1$-$C_{12}$ alkyldiyl)-;

—C(═O)—($C_1$-$C_{12}$ alkyldiyl)-C(═O)—(PEP)—N($R^5$)—($C_1$-$C_{12}$ alkyldiyl)-N($R^5$)—C(═O);

—C(═O)—($C_1$-$C_{12}$ alkyldiyl)-C(═O)—(PEP)—N($R^5$)—($C_1$-$C_{12}$ alkyldiyl)-N($R^5$)C(═O)—($C_2$-$C_5$ monoheterocyclyldiyl)-;

—C(═O)—$CH_2CH_2OCH_2CH_2$—($C_1$-$C_{20}$ heteroaryldiyl)-$CH_2O$—(PEG)-C(═O)-(MCgluc)-;

—C(═O)—$CH_2CH_2OCH_2CH_2$—($C_1$-$C_{20}$ heteroaryldiyl)-$CH_2O$—(PEG)-C(═O)-(MCgluc)-N($R^5$)—($C_1$-$C_{12}$ alkyldiyl)-N($R^5$)C(═O)—($C_2$-$C_5$ monoheterocyclyldiyl)-; and -(succinimidyl)-$(CH_2)_m$—C(═O)—(PEP)—N($R^5$)—($C_1$-$C_{12}$ alkyldiyl)-N($R^5$)C(═O)—($C_2$-$C_5$ monoheterocyclyldiyl)-;

PEG has the formula: —$(CH_2CH_2O)_n$—$(CH_2)_m$—; m is an integer from 1 to 5, and n is an integer from 2 to 50;

PEP has the formula:

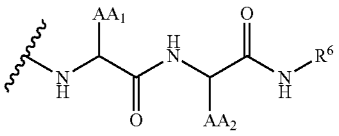

where $AA_1$ and $AA_2$ are independently selected from an amino acid side chain, or $AA_1$ or $AA_2$ and an adjacent nitrogen atom form a 5-membered ring proline amino acid, and the wavy line indicates a point of attachment;

$R^6$ is selected from the group consisting of $C_6$-$C_{20}$ aryldiyl and $C_1$-$C_{20}$ heteroaryldiyl, substituted with —$CH_2O$—C(═O)— and optionally with:

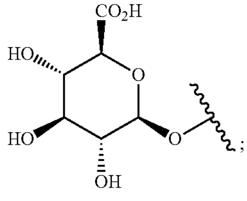 [SMILES: *O[C@@H]1O[C@H](C(=O)O)[C@@H](O)[C@H](O)[C@H]1O]
;

and

MCgluc is selected from the groups:

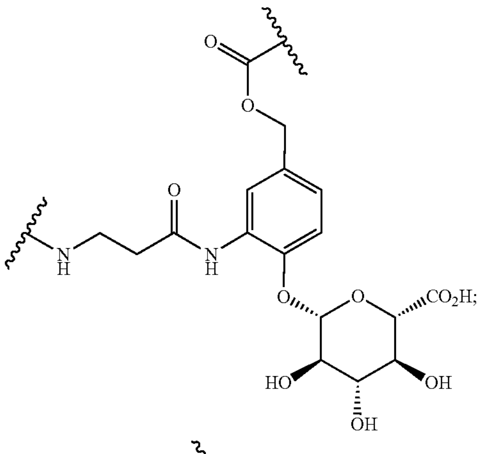
;

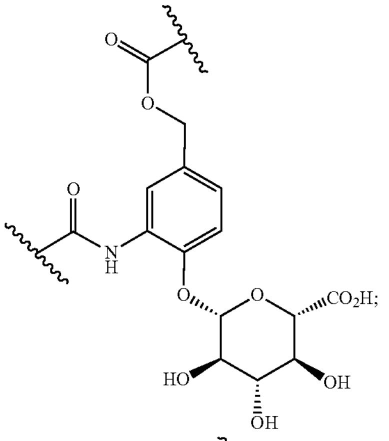
; and

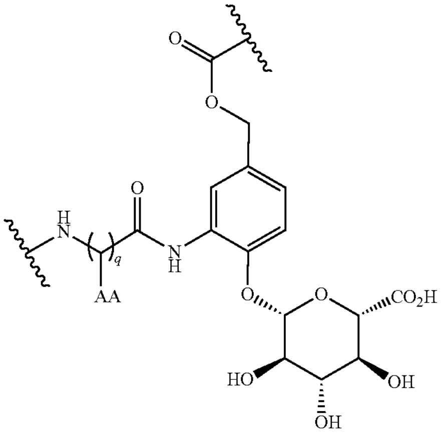

where q is 1 to 8, and AA is an amino acid side chain; and alkyl, alkyldiyl, alkenyl, alkenyldiyl, alkynyl, alkynyldiyl, aryl, aryldiyl, carbocyclyl, carbocyclyldiyl, heterocyclyl, heterocyclyldiyl, heteroaryl, and heteroaryldiyl are independently and optionally substituted with one or more groups independently selected from F, Cl, Br, I, —CN, —$CH_3$, —$CH_2CH_3$, —CH═$CH_2$, —C≡CH, —C≡$CCH_3$, —$CH_2CH_2CH_3$, —CH($CH_3$), —$CH_2$CH($CH_3$), —$CH_2OH$, —$CH_2OCH_3$, —$CH_2CH_2OH$, —C($CH_3$)OH, —CH(OH)CH($CH_3$), —C($CH_3$)$CH_2OH$, —$CH_2CH_2SO_2CH_3$, —$CH_2OP(O)(OH)_2$, —$CH_2F$, —$CHF_2$, —$CF_3$, —$CH_2CF_3$, —$CH_2CHF_2$, —CH $(CH_3)CN$, $—C(CH_3)CN$, $—CH_2CN$, $—CH_2NH_2$, $—CH_2NHSO_2CH_3$, $—CH_2NHCH_3$, $—CH_2N(CH_3)$, $—CO_2K$, $—COCH_3$, $—CO_2CH_3$, $—CO_2C(CH_3)$, $—COCH(OH)CH_3$, $—CONH_2$, $—CONHCH_3$, $—CON(CH_3)$, $—C(CH_3)CONH_2$, $—NH_2$, $—NHCH_3$, $—N(CH_3)$, $—NHCOCH_3$, $—N(CH_3)COCH_3$, $—NHS(O)_2CH_3$, $—N(CH_3)C(CH_3)CONH_2$, $—N(CH_3)CH_2CH_2S(O)_2CH_3$, $—NHC(═NH)H$, $—NHC(═NH)CH_3$, $—NHC(═NH)NH_2$, $—NHC(═O)NH_2$, $—NO_2$, $═O$, $—OH$, $—OCH_3$, $—OCH_2CH_3$, $—CH_2CH_2OCH_3$, $—OCH_2CH_2OH$, $—CH_2CH_2N(CH_3)$, $—O(CH_2CH_2O)$, $—(CH_2)\text{~}CO_2H$, $—O(CH_2CH_2O)_nH$, $—OCH_2F$, $—OCHF_2$, $OCF_3$, $—OP(OXOH)_2$, $—S(O)_2N(CH_3)$, $—SCH_3$, $—S(O)_2CH_3$, and $—S(O)_3H$.

2. The immunoconjugate of claim 1 wherein the antibody is an antibody construct that has an antigen binding domain that binds to a target selected from PD-L1, HER2, and CEA.

3. The immunoconjugate of claim 2 wherein the antibody is selected from the group consisting of atezolizumab, durvalumab, avelumab, trastuzumab, pertuzumab, and labetuzumab.

4. The immunoconjugate of claim 1 wherein PEP has the formula:

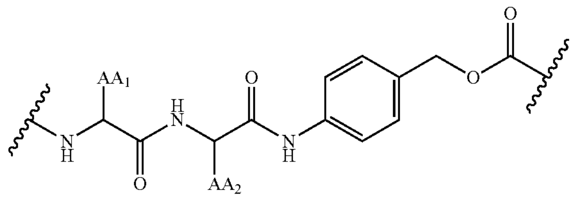

wherein $AA_1$ and $AA_2$ are independently selected from a side chain of a naturally-occurring amino acid.

5. The immunoconjugate of claim 1 wherein $AA_1$ or $AA_2$ with an adjacent nitrogen atom form a 5-membered ring proline amino acid.

6. The immunoconjugate of claim 1 wherein PEP has the formula:

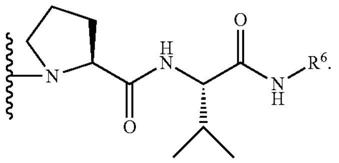

7. The immunoconjugate of claim 1 wherein MCgluc has the formula:

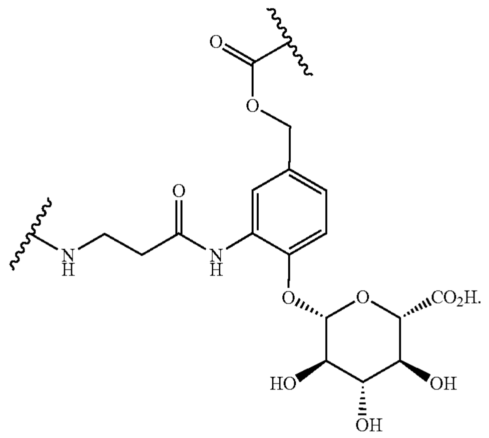 [SMILES: *NCCC(=O)Nc1cc(COC(*)=O)ccc1O[C@@H]1O[C@H](C(=O)O)[C@@H](O)[C@H](O)[C@H]1O]

8. The immunoconjugate of claim 1 wherein $AA_1$ and $AA_2$ are independently selected from H, $—CH_3$, $—CH(CH_3)_2$, $—CH_2(C_6H_5)$, $—CH_2CH_2CH_2CH_2NH_2$, $—CH_2CH_2CH_2NHC(NH)NH_2$, $—CHCH(CH_3)CH_3$, $—CH_2SO_3H$, and $—CH_2CH_2CH_2NHC(O)NH_2$.

9. The immunoconjugate of claim 8 wherein $AA_1$ is $—CH(CH_3)_2$, and $AA_2$ is $—CH_2CH_2CH_2NHC(O)NH_2$.

10. The immunoconjugate of claim 1 wherein $AA_1$ and $AA_2$ are independently selected from GlcNAc aspartic acid, $—CH_2SO_3H$, and $—CH_2OPO_3H$.

11. The immunoconjugate of claim 1 wherein $X^1$ is a bond, and $R^1$ is H.

12. The immunoconjugate of claim 1 wherein $X^2$ is a bond, and $R^2$ is $C_1$-$C_8$ alkyl.

13. The immunoconjugate of claim 1 wherein $X^2$ and $X^3$ are each a bond, and $R^2$ and $R^3$ are independently selected from $C_1$-$C_8$ alkyl, $—O—(C_1$-$C_{12}$ alkyl), $—(C_1$-$C_{12}$ alkyldiyl)-$OR^5$, $—(C_1$-$C_8$ alkyldiyl)-$N(R^5)CO_2R^3$, and $—O—(—C_{12}$ alkyl)-$N(R^5)CO_2R^3$.

14. The immunoconjugate of claim 13 wherein $R^2$ and $R^3$ are each independently selected from $—CH_2CH_2CH_3$, $—OCH_2CH_3$, $—CH_2CH_2CF_3$, and $—CH_2CH_2CH_2OH$.

15. The immunoconjugate of claim 13 wherein $R^2$ is $C_1$-$C_8$ alkyl and $R^3$ is $—(C_1$-$C_8$ alkyldiyl)-$N(R^5)CO_2R^4$.

16. The immunoconjugate of claim 13 wherein $R^2$ is $—CH_2CH_2CH_3$ and $R^3$ is $—CH_2CH_2CH_2NHCO_2$(t-Bu).

17. The immunoconjugate of claim 13 wherein $R^2$ and $R^3$ are each $—CH_2CH_2CH_3$.

18. The immunoconjugate of claim 1 wherein $X^3—R^3$ is selected from the group consisting of:

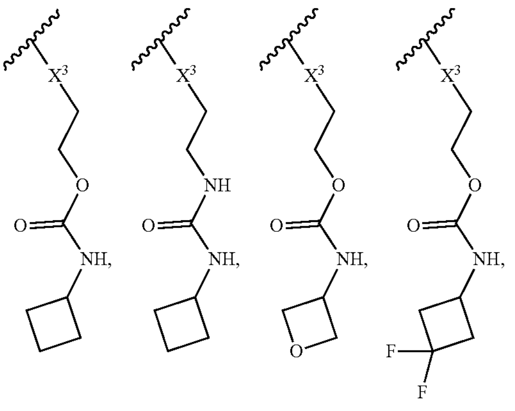

-continued

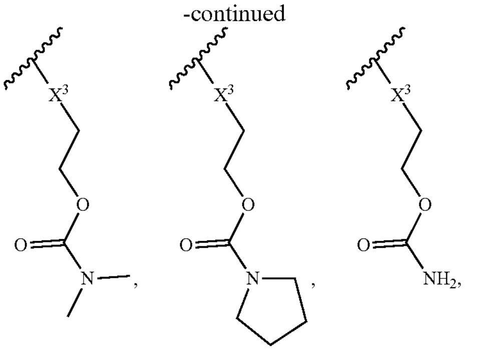

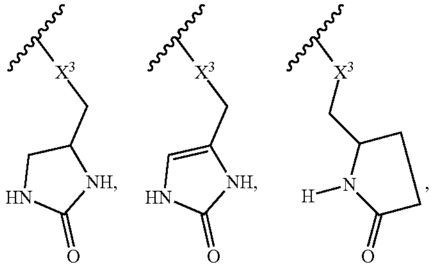

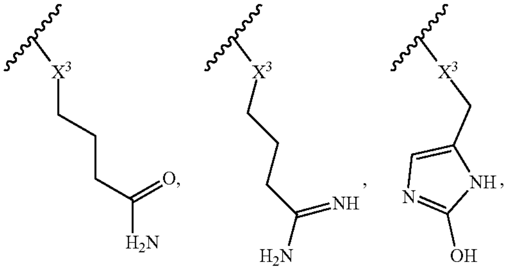

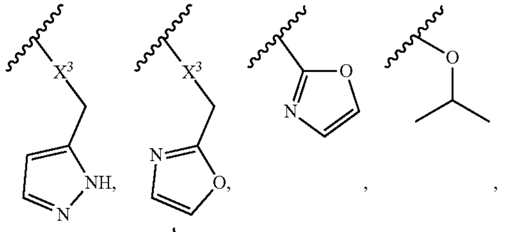

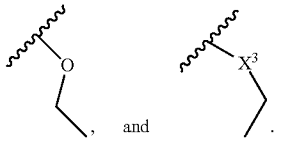

19. The immunoconjugate of claim 1 wherein one of $R^2$ and $R^3$ is selected from:

—($C_1$-$C_{12}$ alkyldiyl)-N($R^5$)—*;

—($C_1$-$C_{12}$ alkyldiyl)-O—($C_1$-$C_{12}$ alkyldiyl)-N($R^5$)—*;

—($C_1$-$C_{12}$ alkyldiyl)-N($R^5$)C(═N$R^5$)—N($R^5$)—*;

—($C_1$-$C_{12}$ alkyldiyl)-($C_6$-$C_{20}$ aryldiyl)-($C_1$-$C_{12}$ alkyldiyl)-N($R^5$)—*;

—($C_1$-$C_{12}$ alkyldiyl)-($C_6$-$C_{20}$ aryldiyl)-($C_1$-$C_{12}$ alkyldiyl)-N($R^5$)—C(═N$R^5$)N($R^5$)—*;

—($C_2$-$C_6$ alkynyldiyl)-N($R^5$)—*; and

—($C_2$-$C_6$ alkynyldiyl)-N($R^5$)C(═N$R^5$)N($R^5$)—*;

$X^2$ and $X^3$ are a bond, and where the asterisk * indicates the attachment site of L.

20. The immunoconjugate of claim 1 wherein L is selected from the group consisting of:

—C(═O)—(PEG)-;

—C(═O)—(PEG)-C(═O)—;

—C(═O)—(PEG)-O—;

—C(═O)—(PEG)-N($R^5$)—; and

—C(═O)—(PEG)-N($R^5$)C(═O)—.

21. The immunoconjugate of claim 1 selected from Formulae Ia-Ic:

Ia

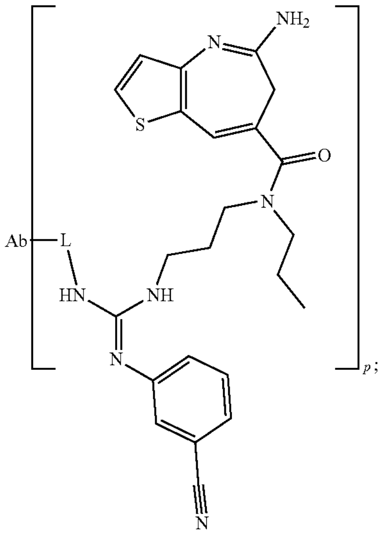

Ib

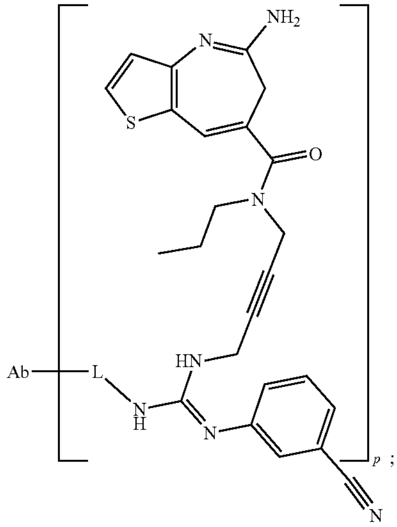

Ic

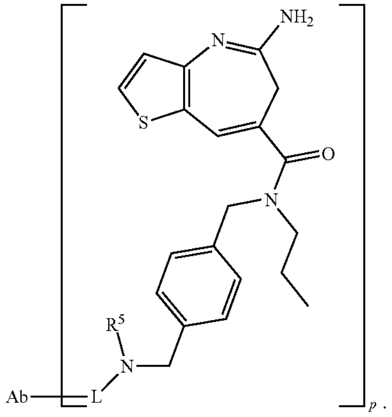

22. The immunoconjugate of claim 1 selected from Formulae Id-Ih:

Id

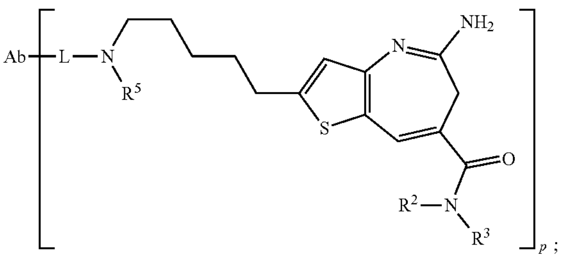

Ie

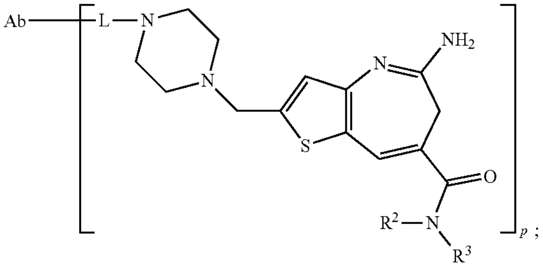

If

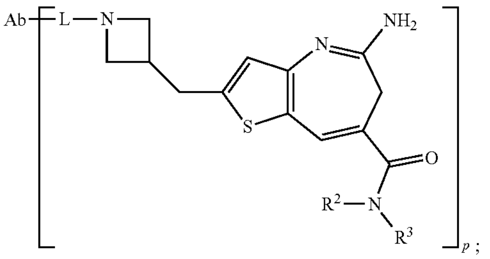

-continued

Ig

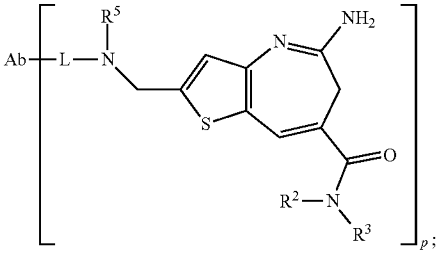

and

Ih

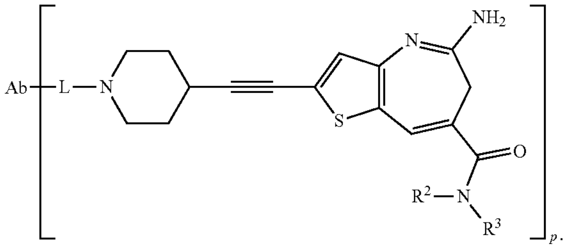

23. The immunoconjugate of claim 22 wherein $R^2$ and $R^3$ are independently selected from $C_1$-$C_8$ alkyl, —O—($C_1$-$C_{12}$ alkyl), —($C_1$-$C_{12}$ alkyldiyl)-$OR^5$, —($C_1$-$C_8$ alkyldiyl)-N($R^5$)$CO_2R^5$, and —O—($C_1$-$C_{12}$ alkyl)-N(RV)$CO_2R^5$.

24. The immunoconjugate of claim 23 wherein $R^2$ and $R^3$ are each independently selected from —$CH_2CH_2CH_3$, —$OCH_2CH_3$, —$CH_2CH_2CF_3$, and —$CH_2CH_2CH_2OH$.

25. An immunoconjugate prepared by conjugation of an antibody with a 5-amino-thienoazepine-linker compound selected from the group consisting of:

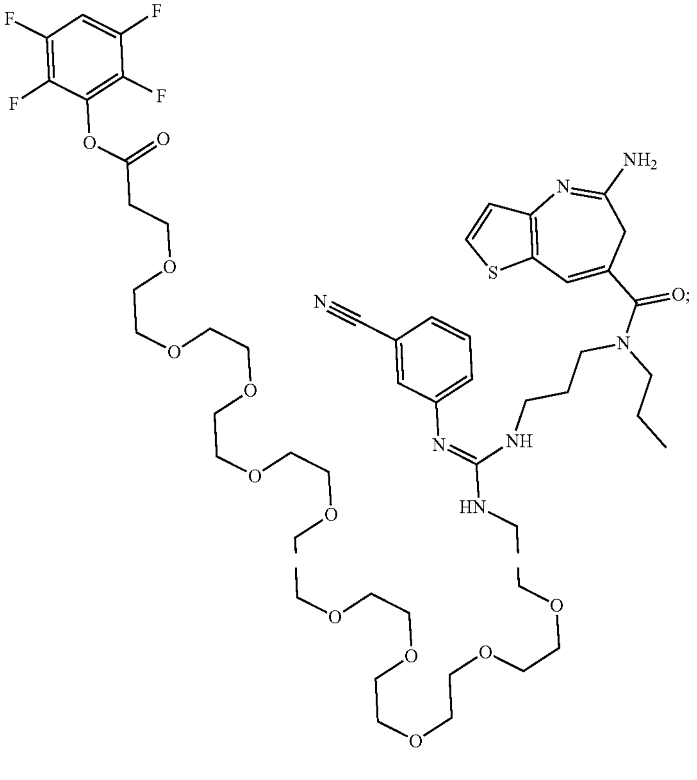

-continued
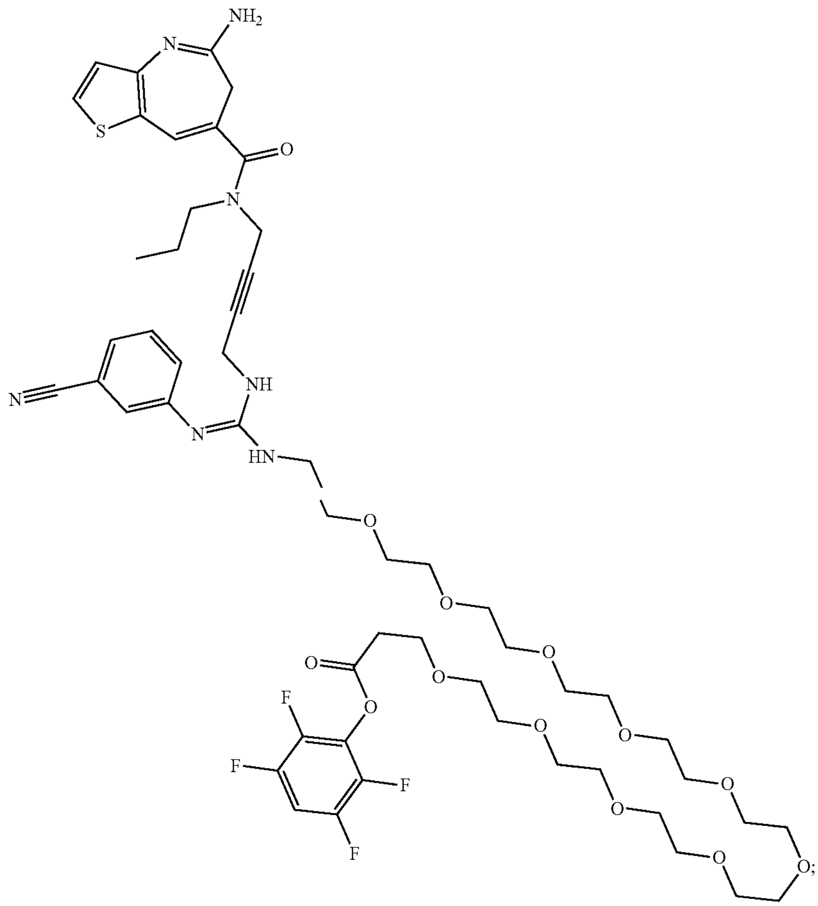
;
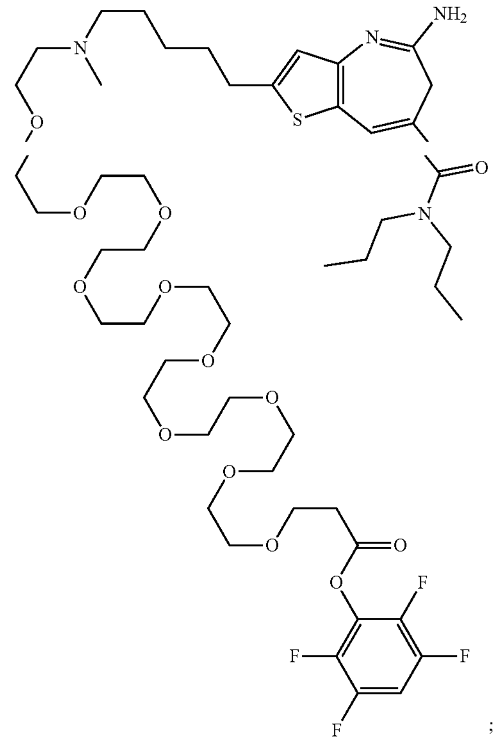
;
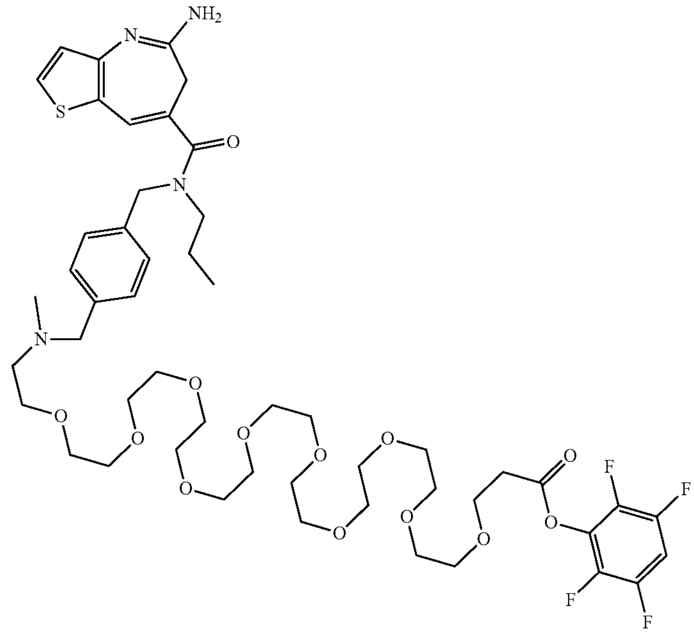
;

-continued
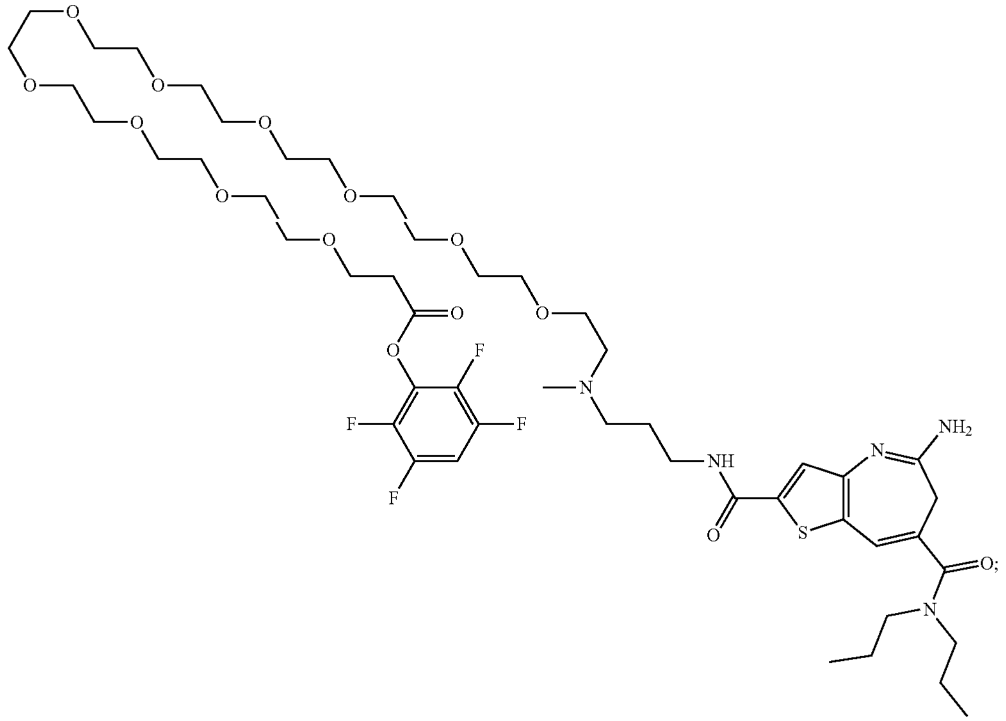
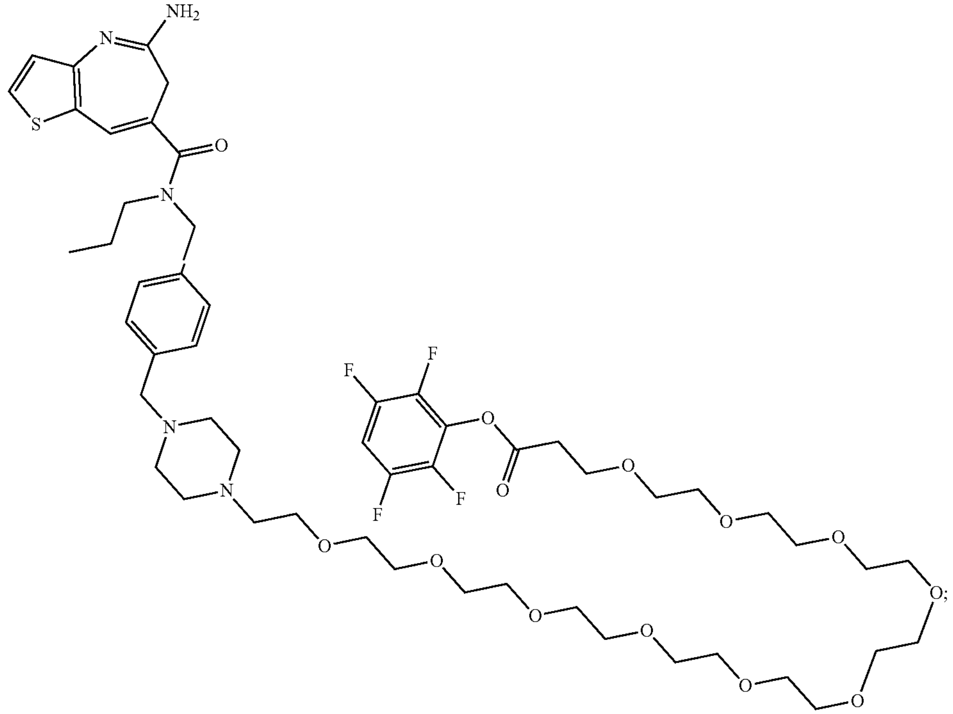
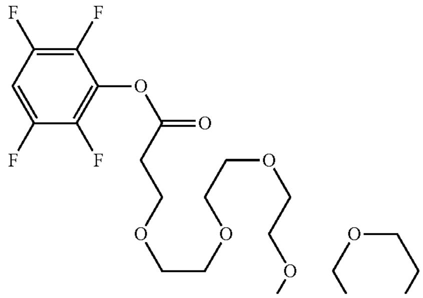

-continued
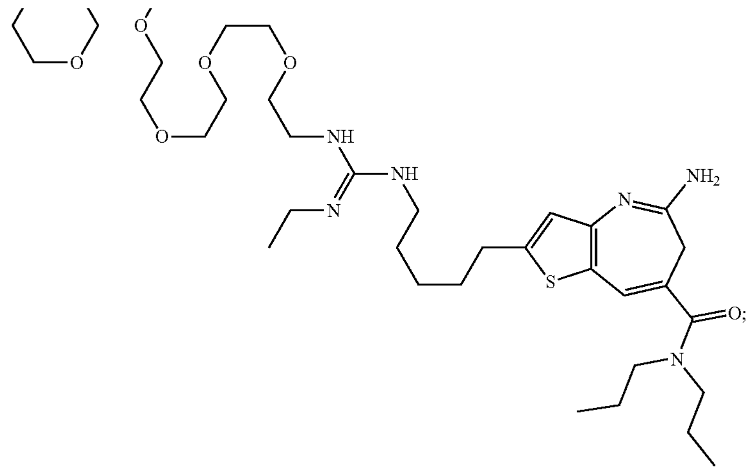
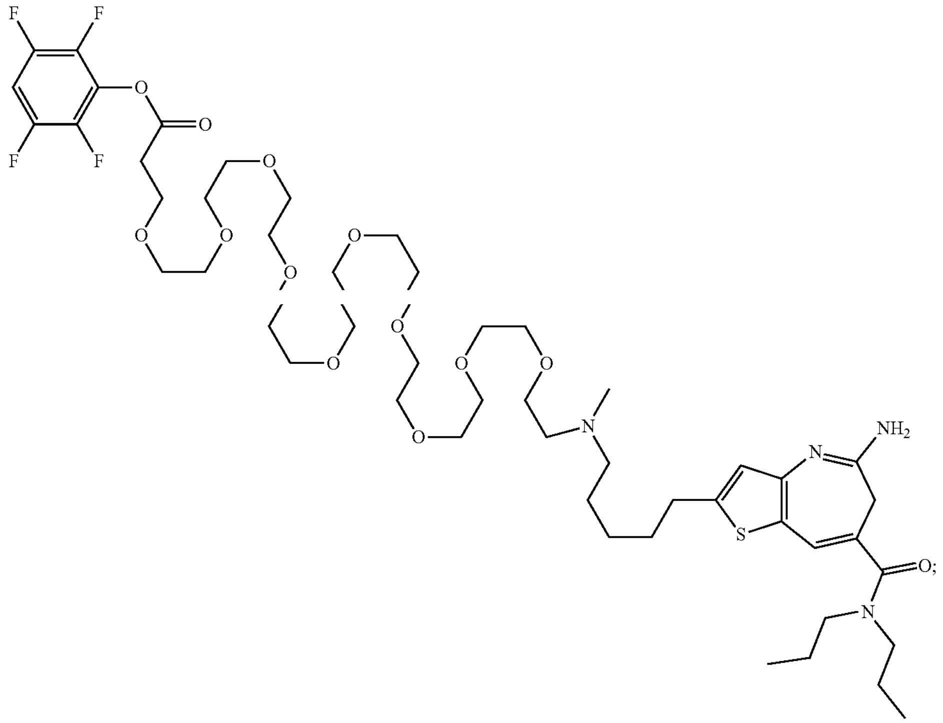
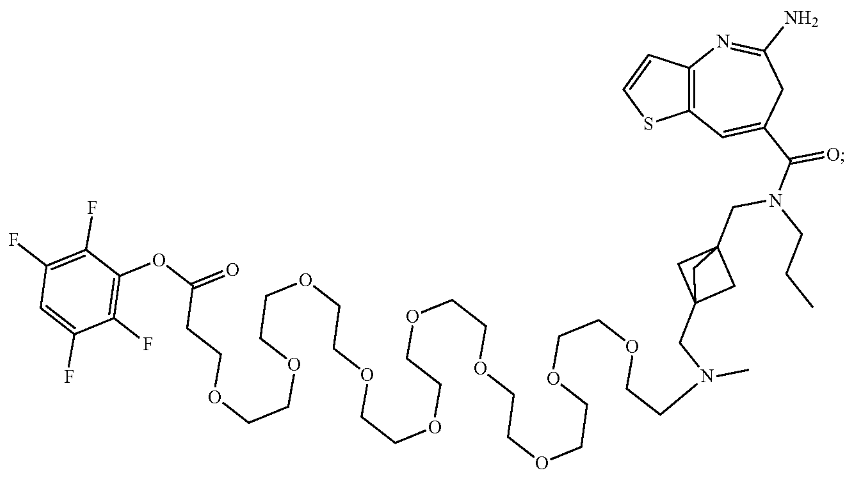

-continued
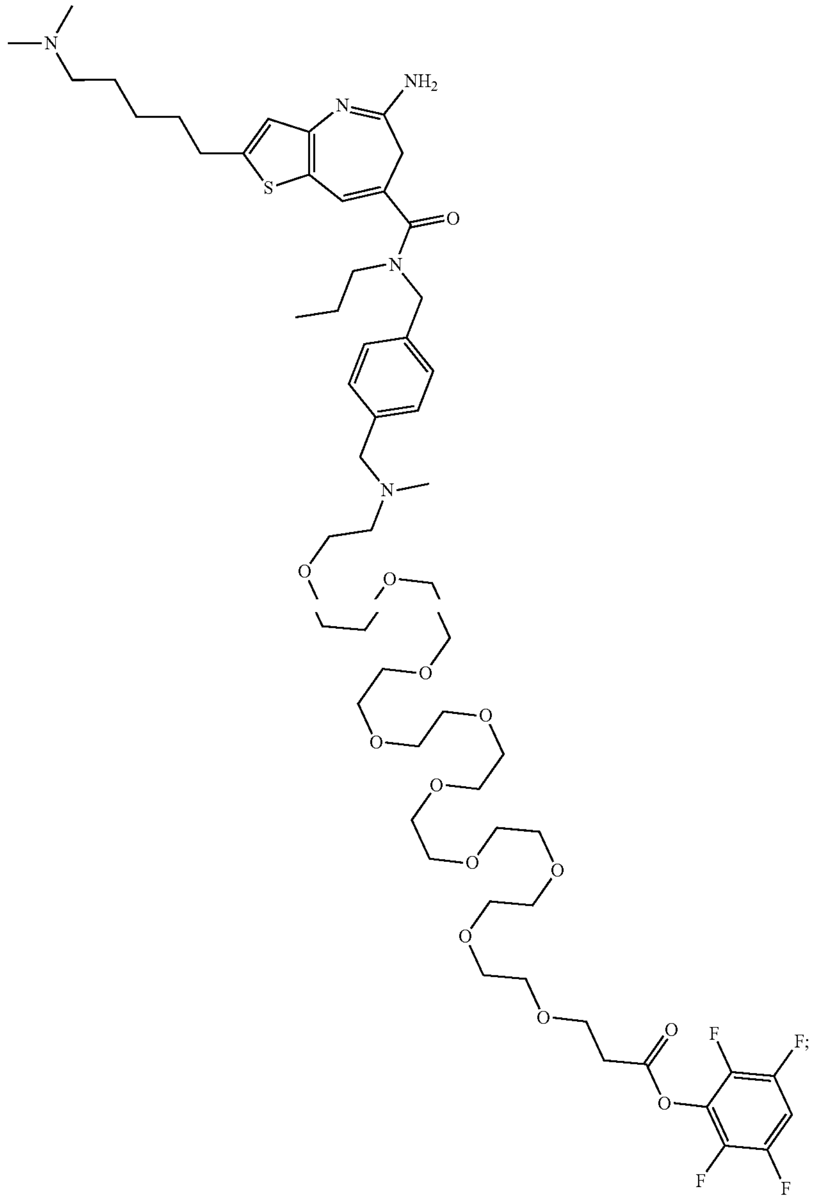
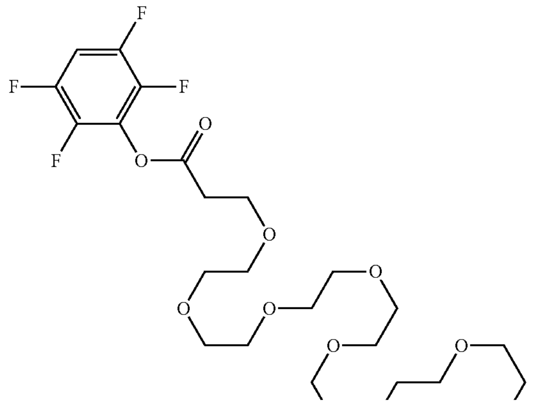

-continued
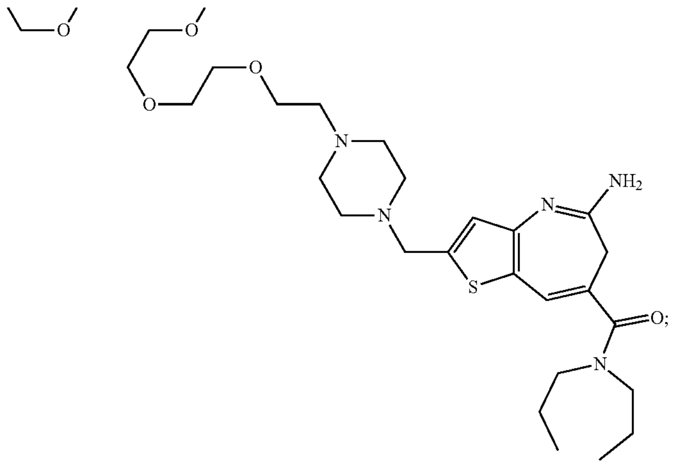
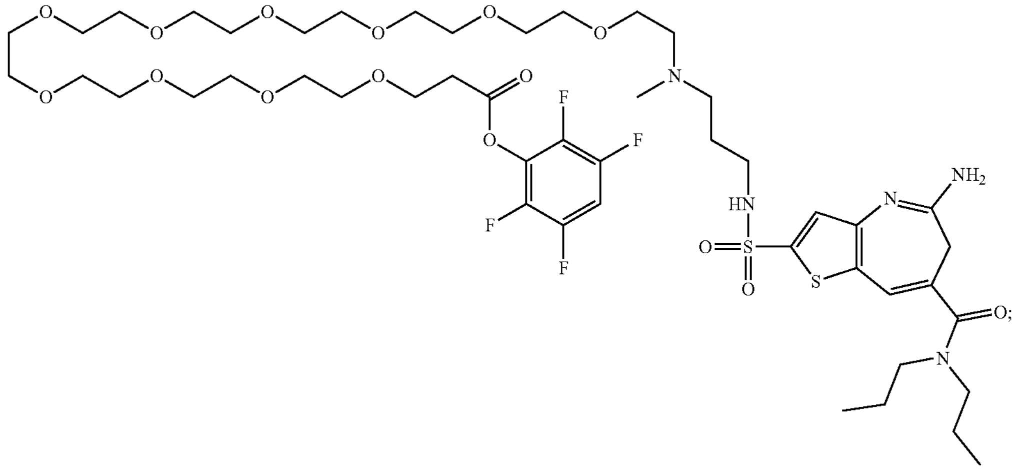
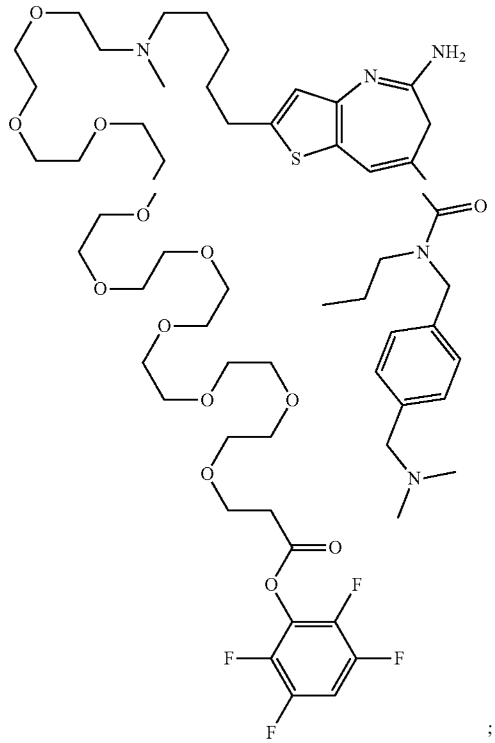
;
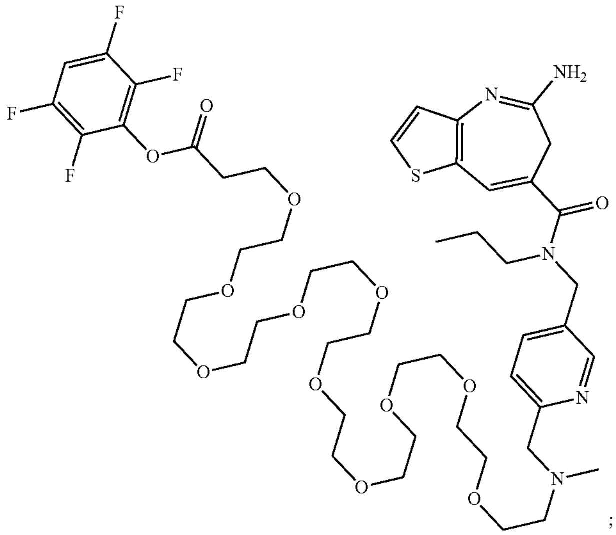
;

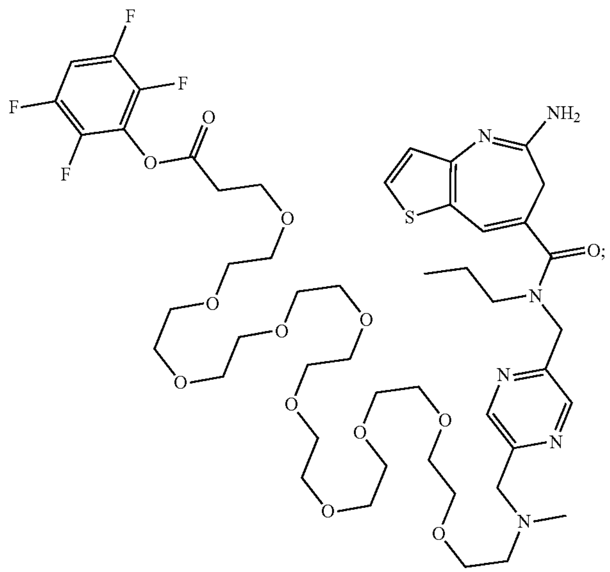
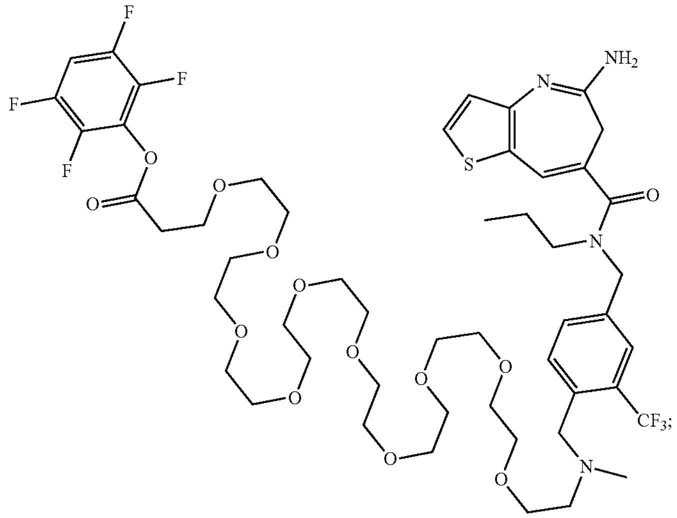
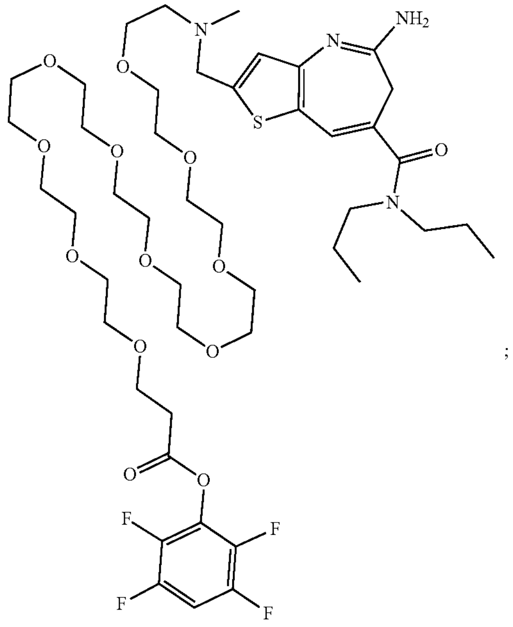
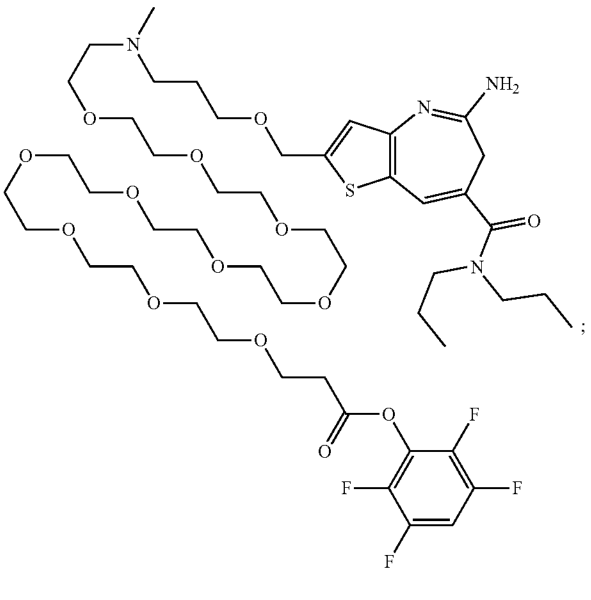

-continued
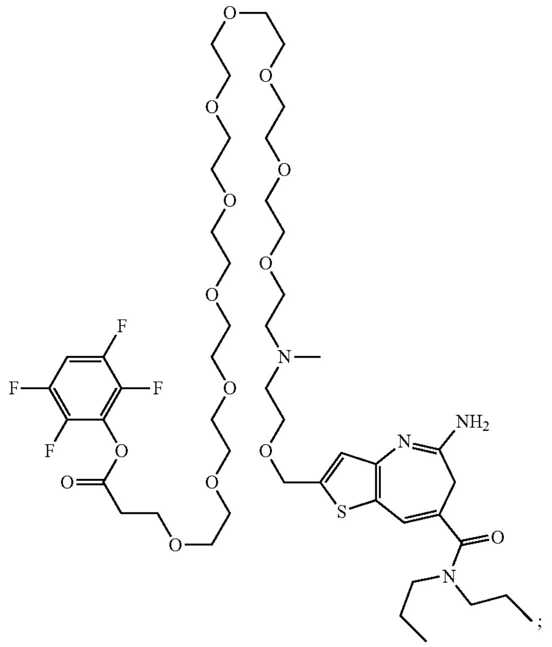
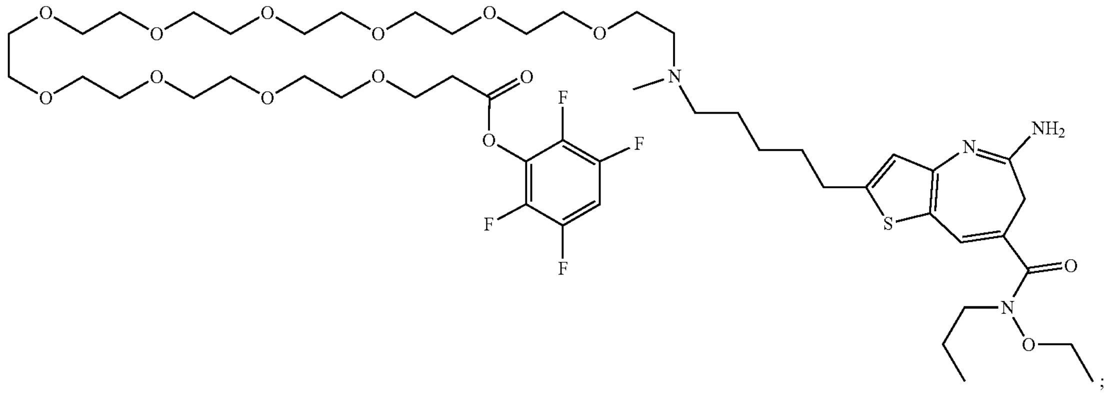
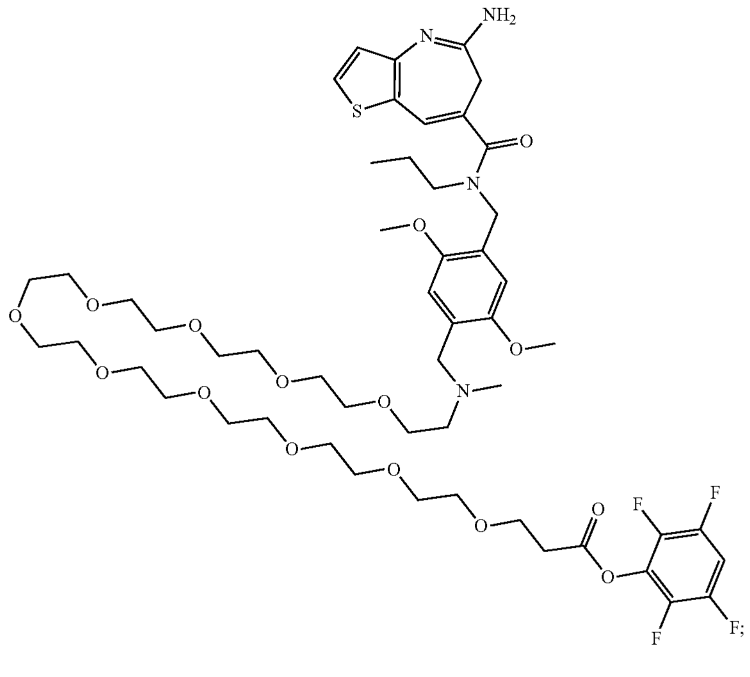

-continued
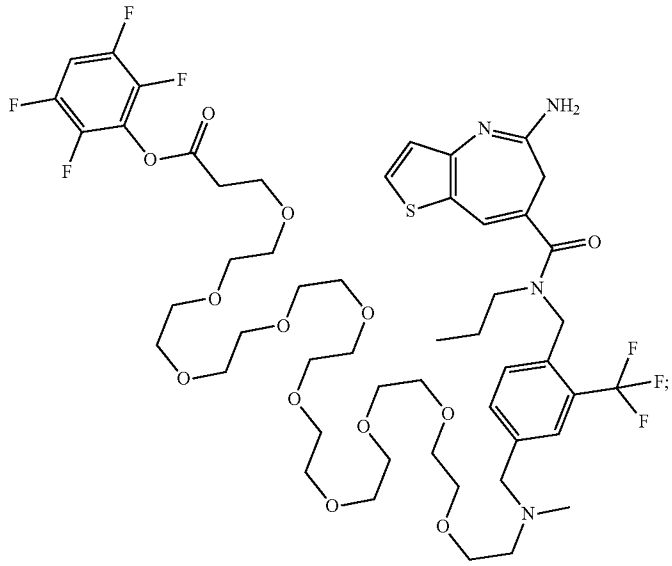
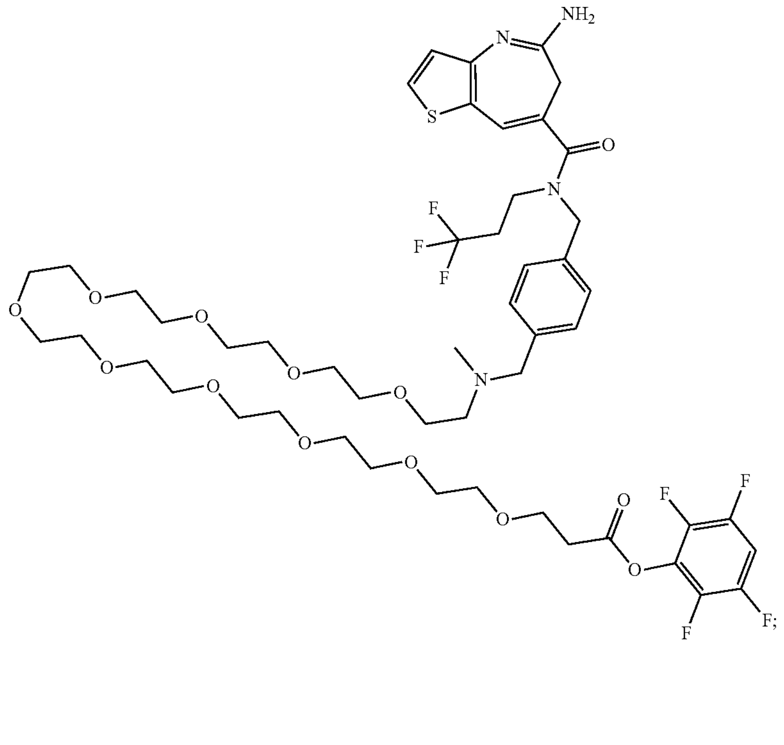

-continued
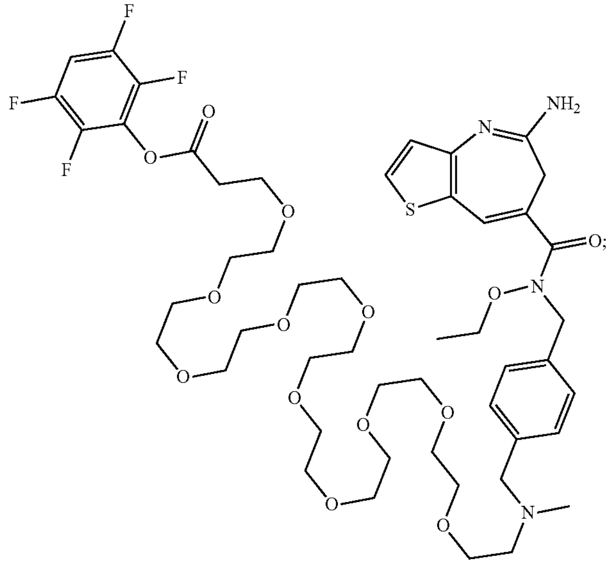
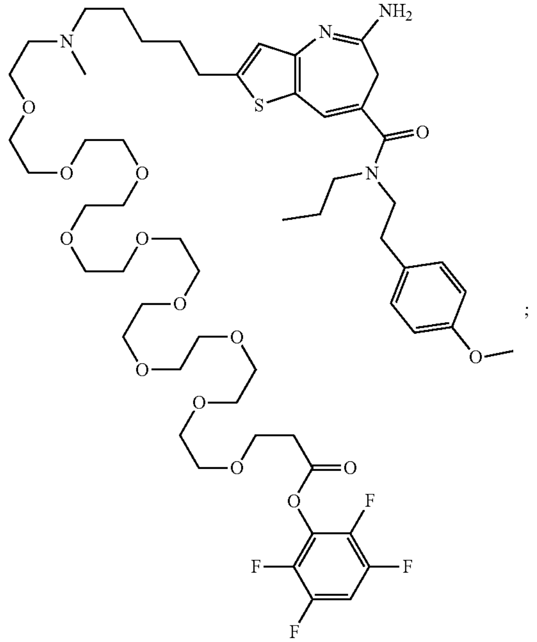
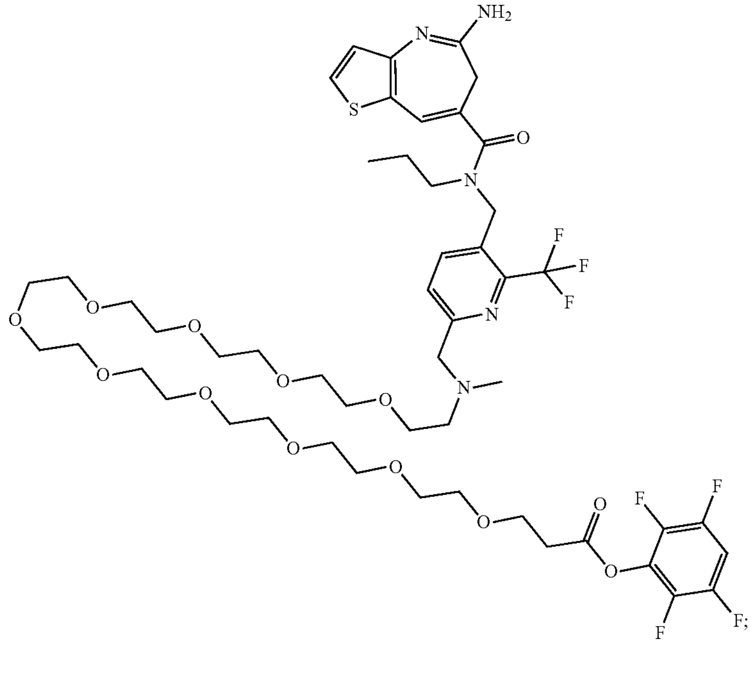

-continued
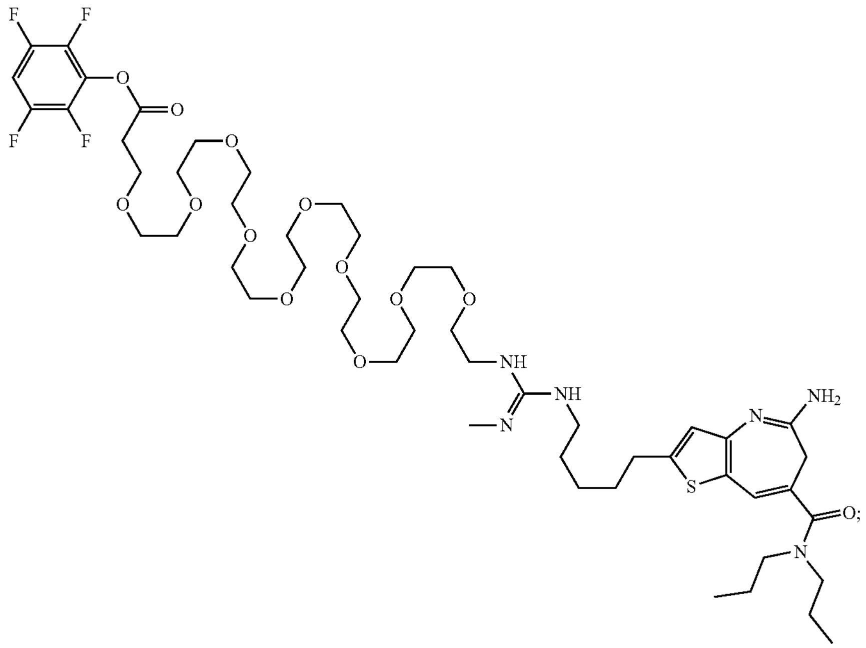
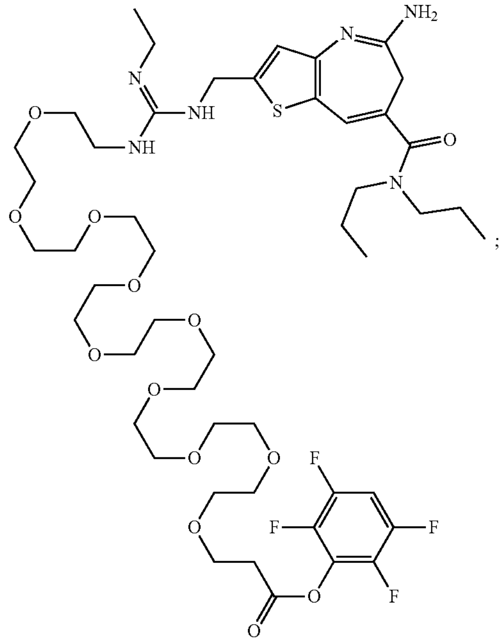
;

-continued
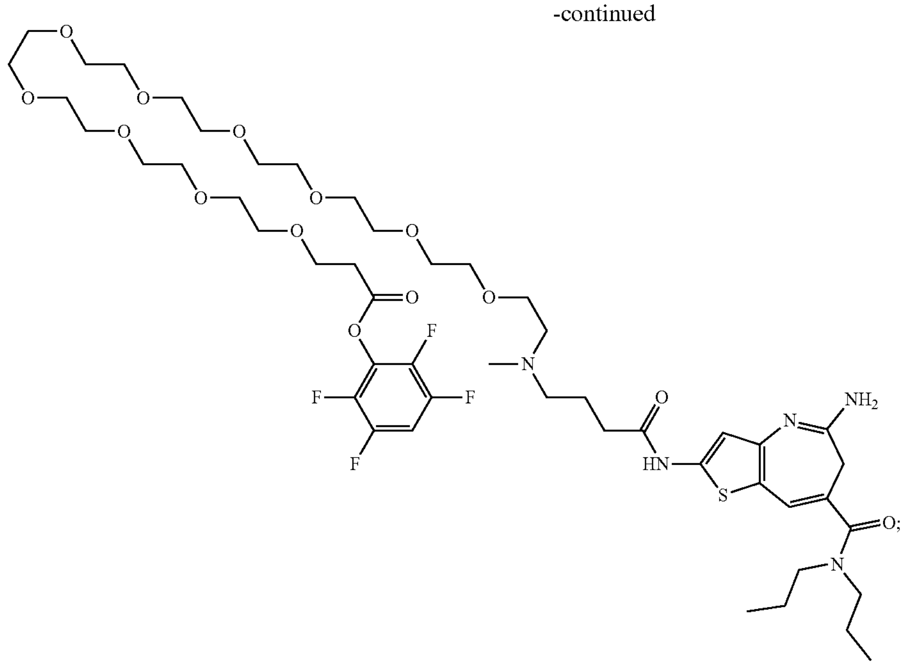
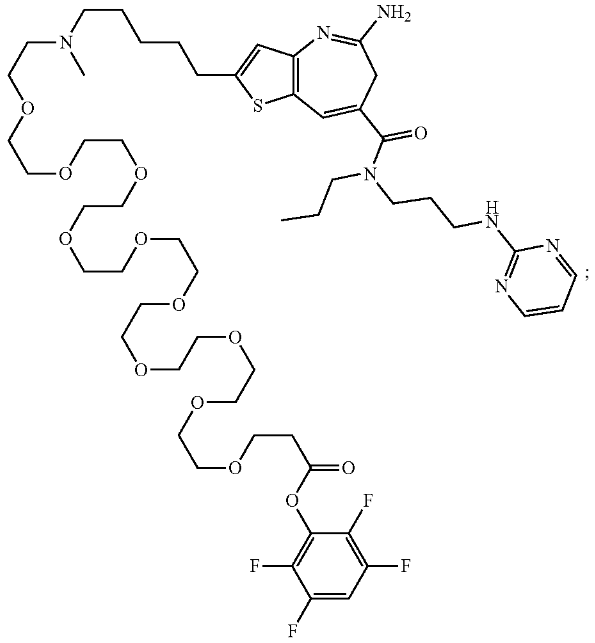
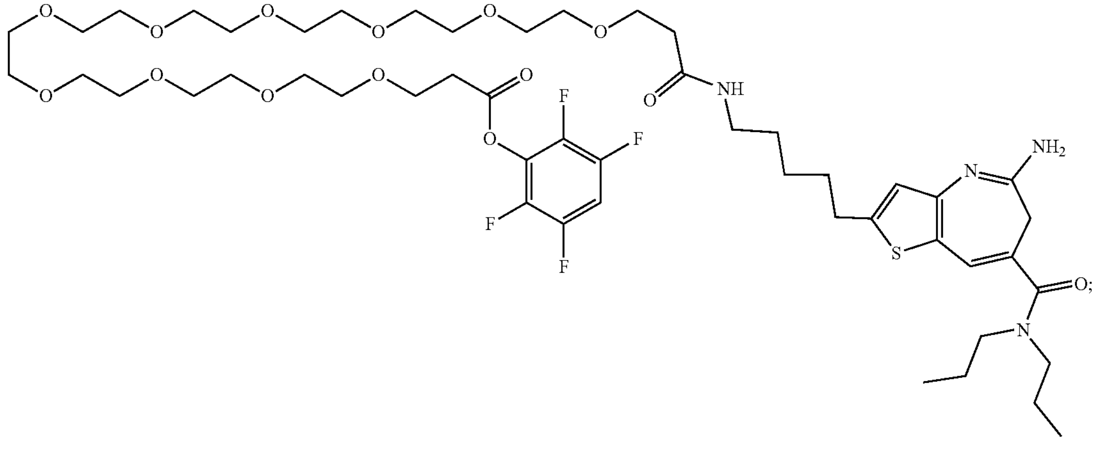

-continued
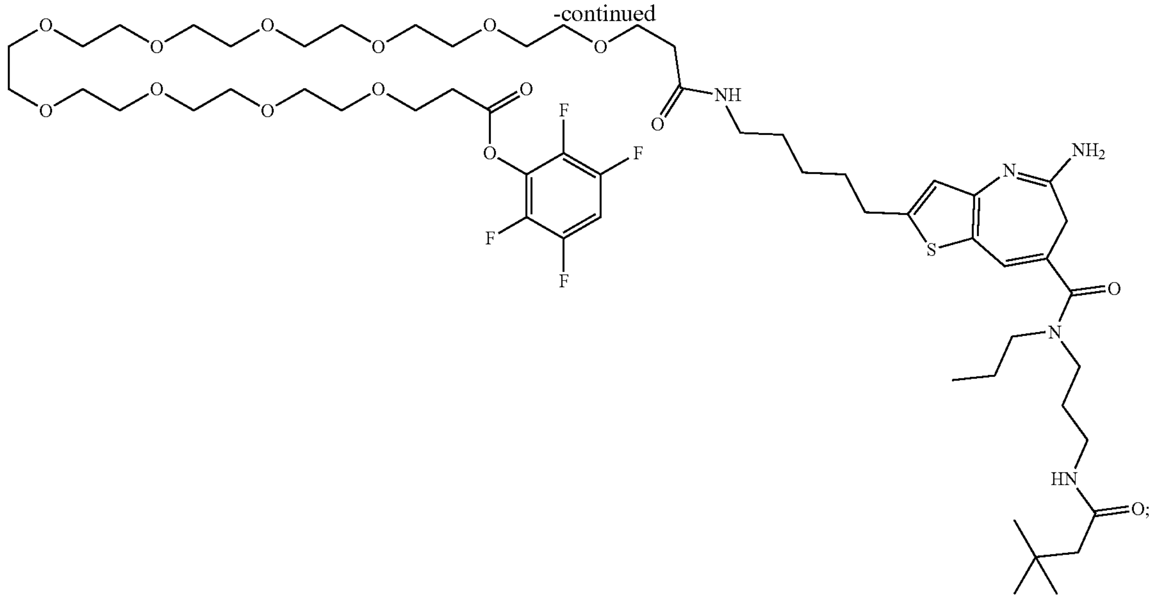
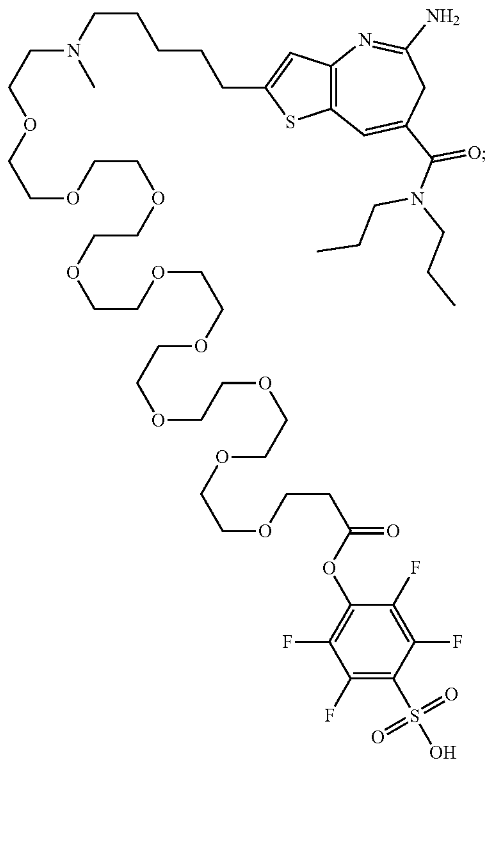

-continued
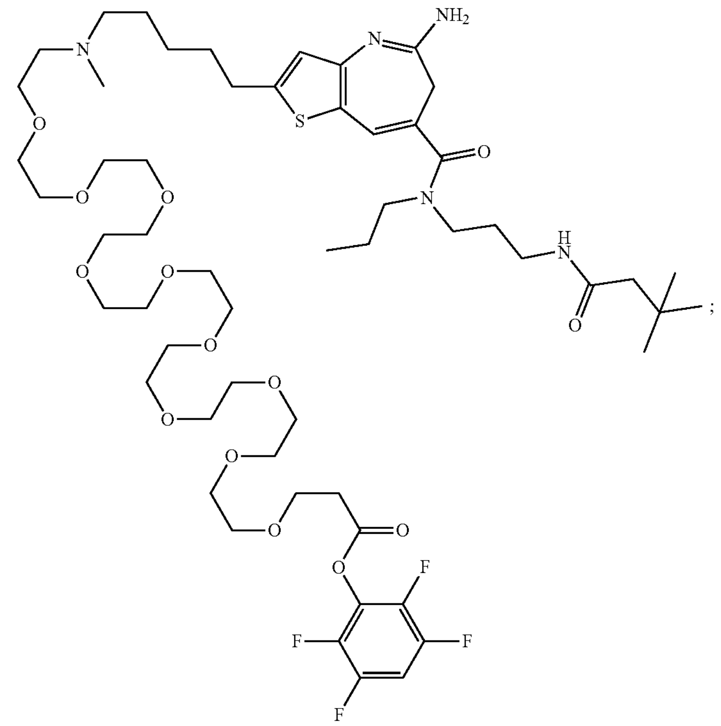
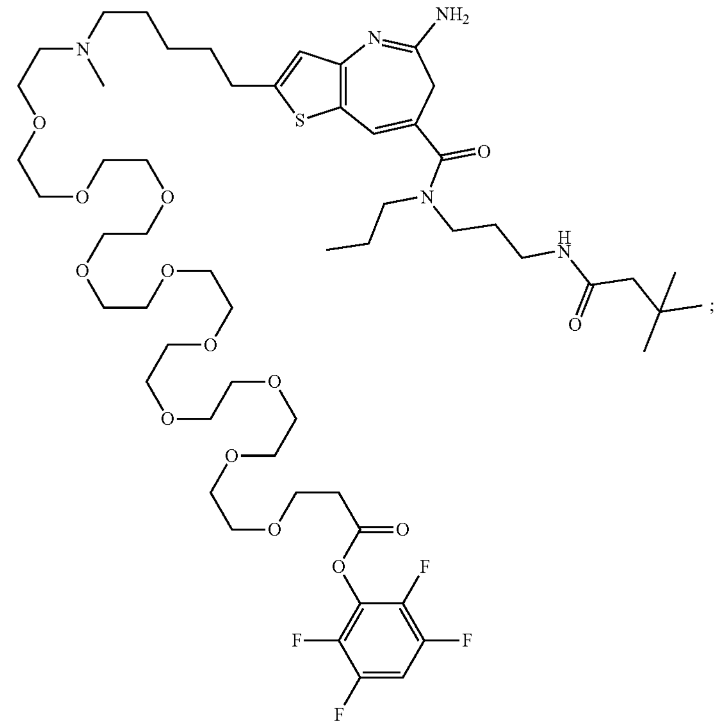

-continued
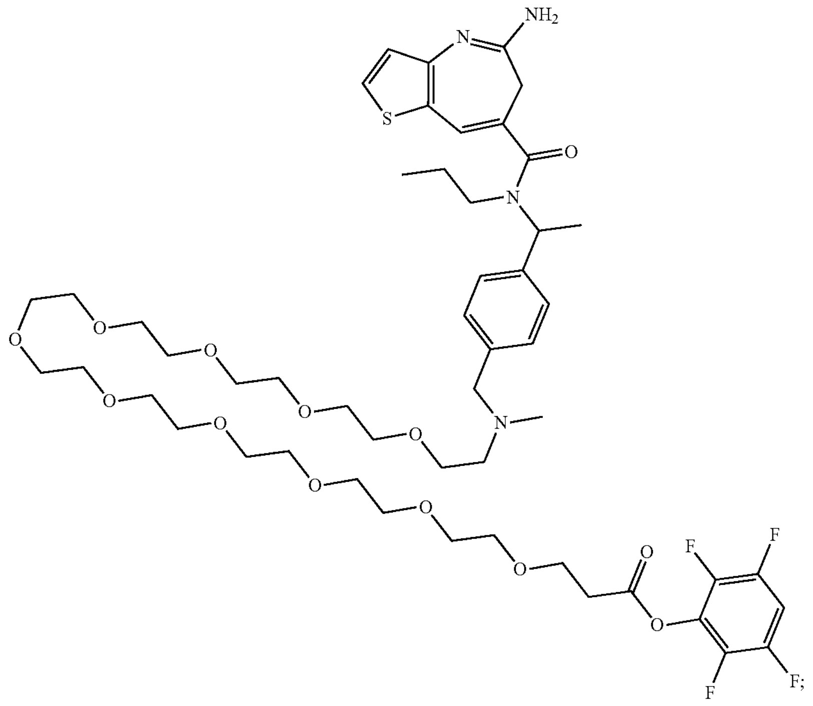
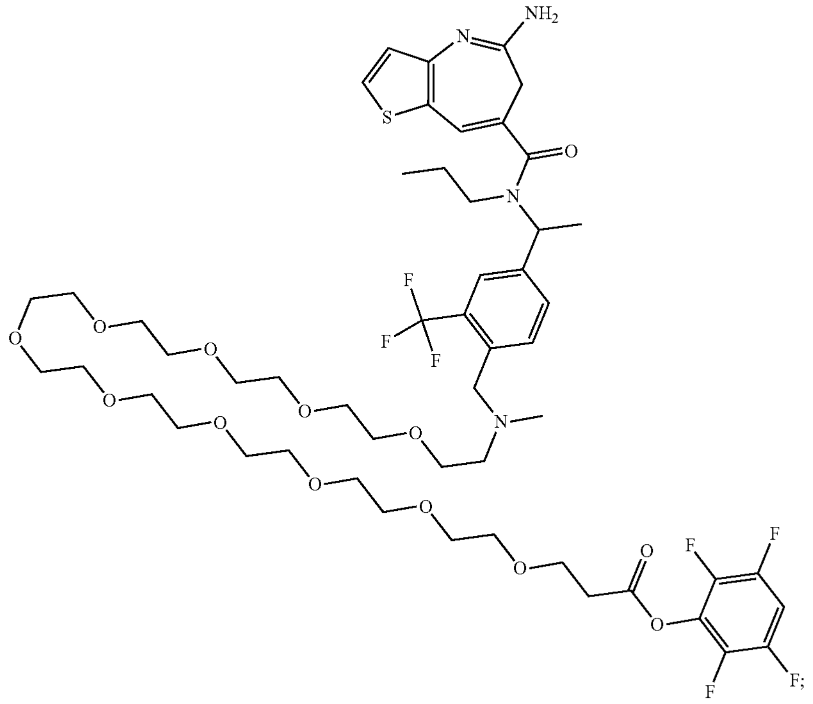

-continued
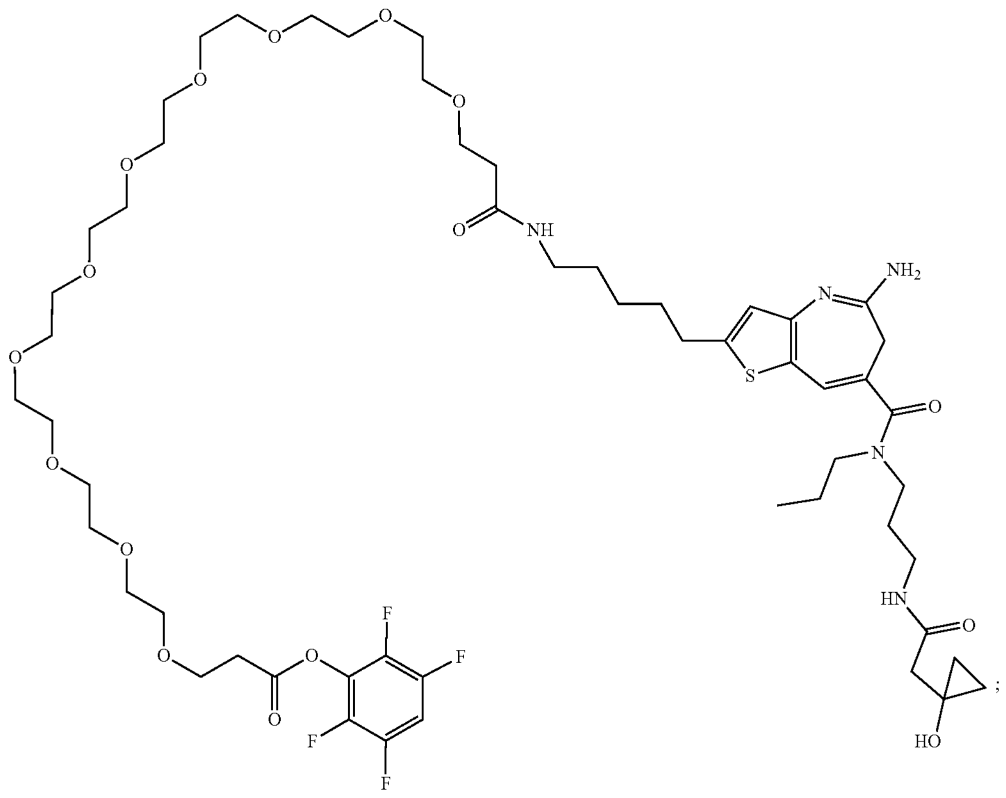
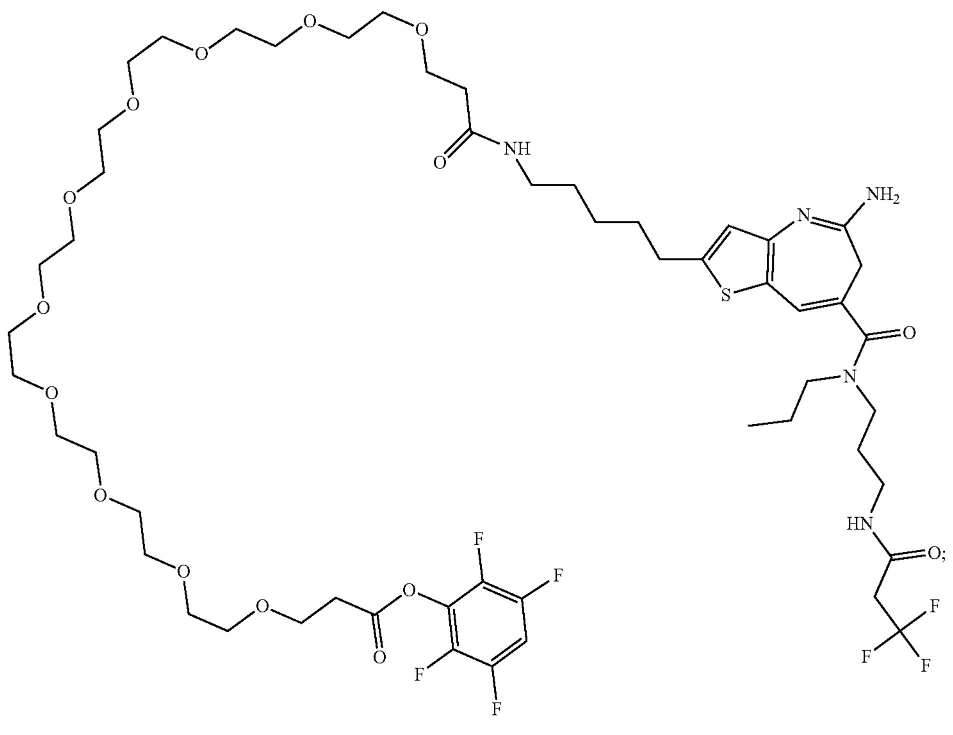

-continued
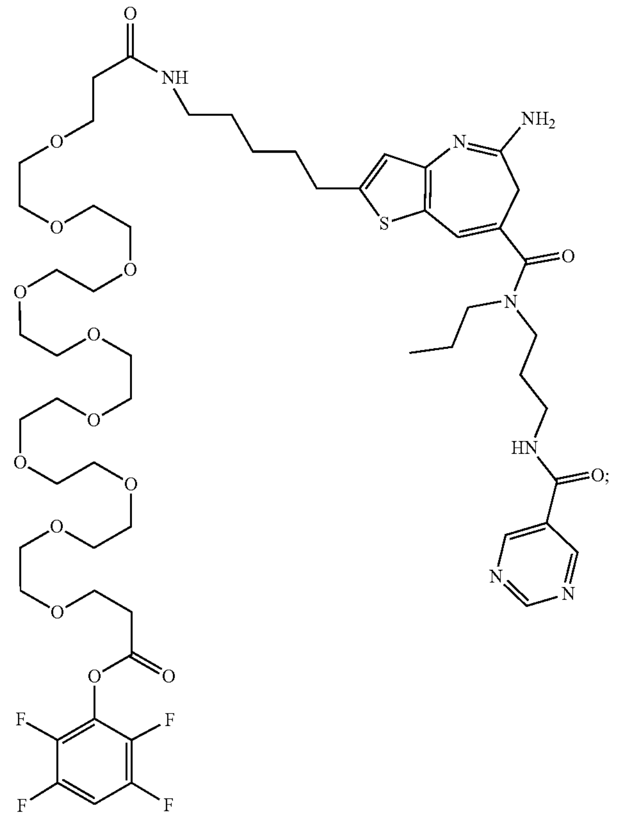
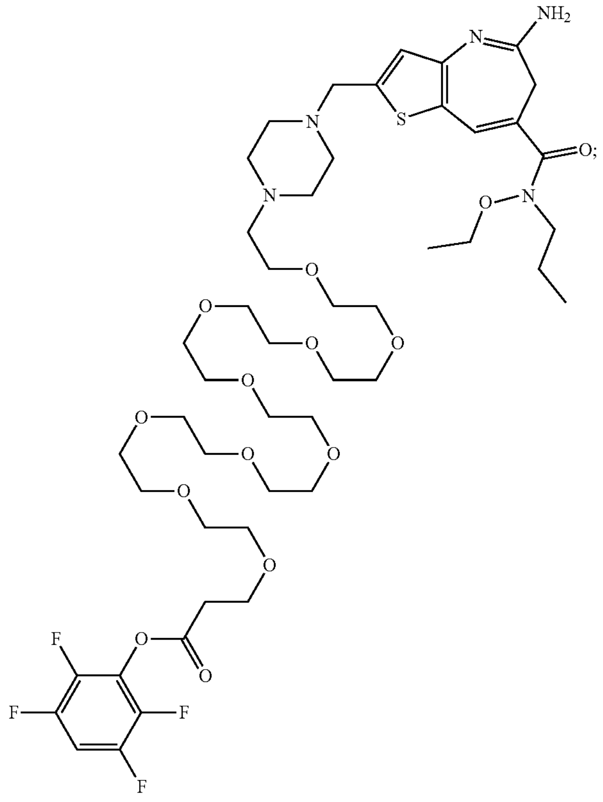

-continued
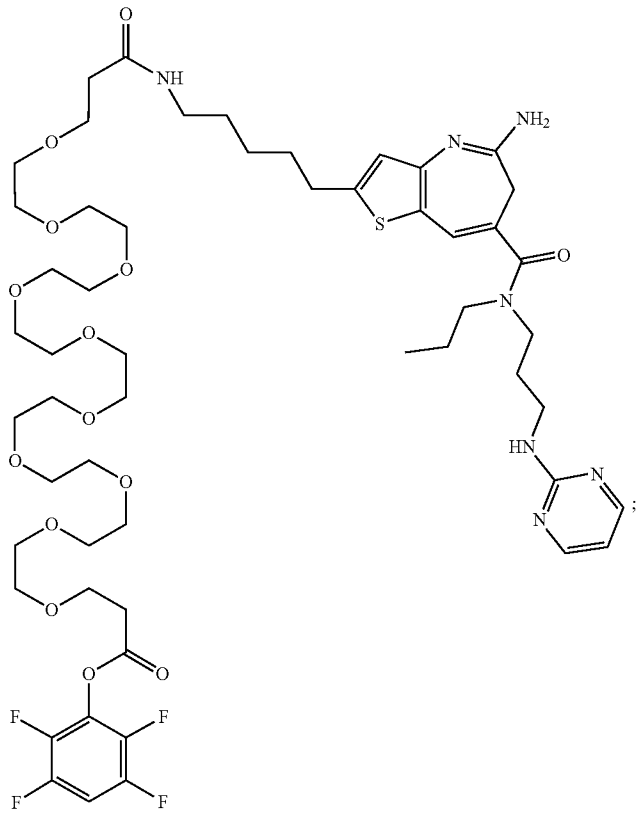
;
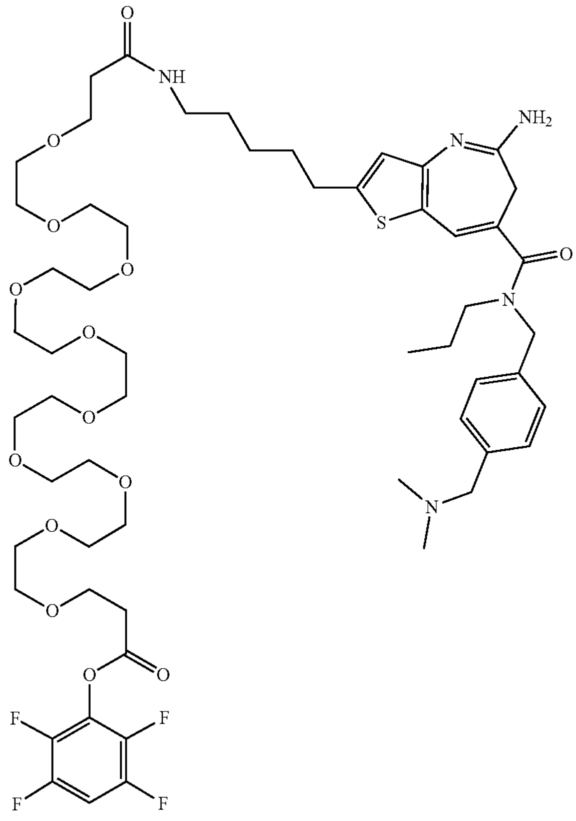

-continued
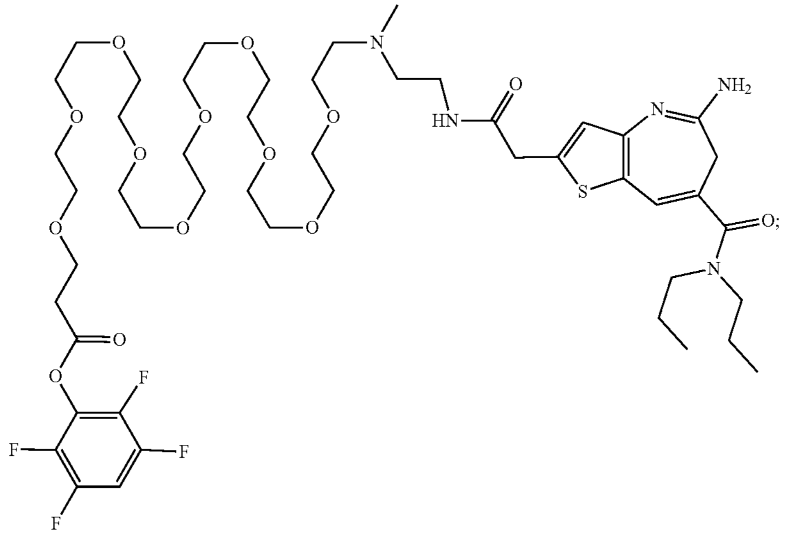
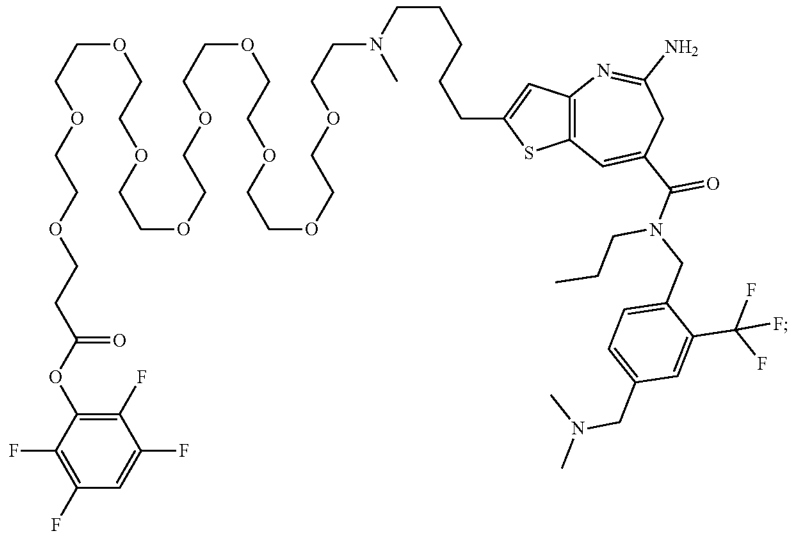
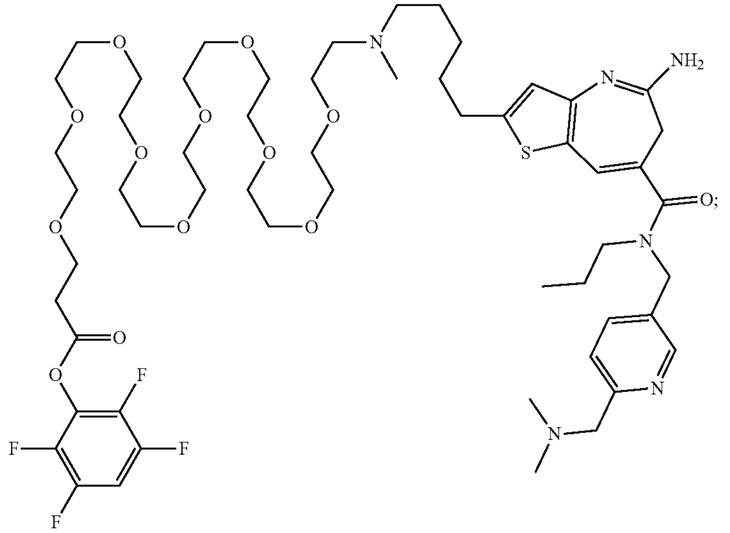

-continued
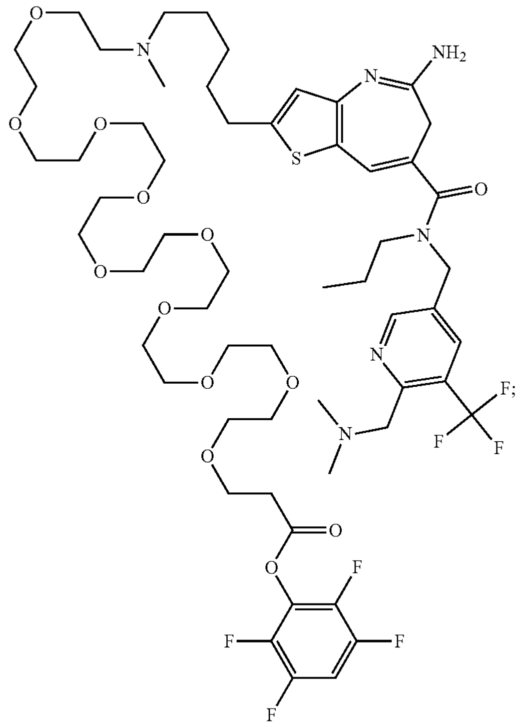
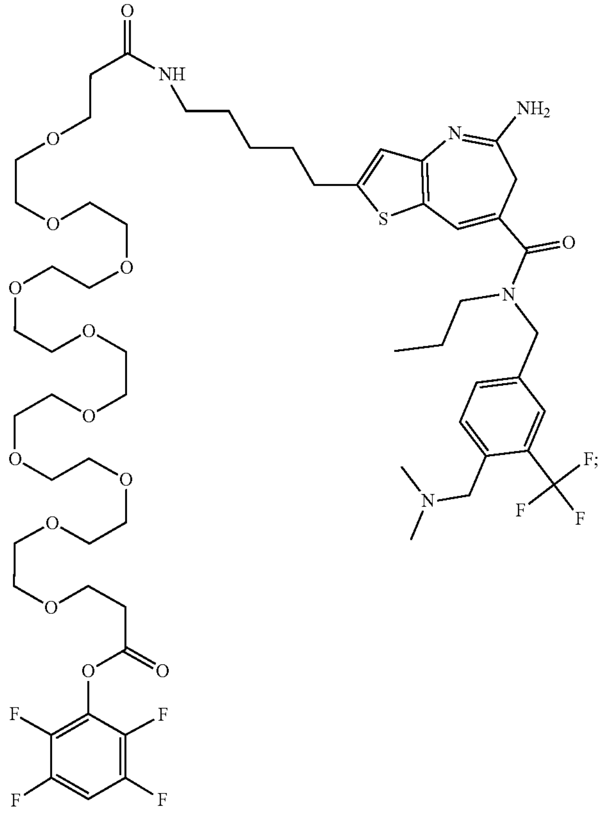

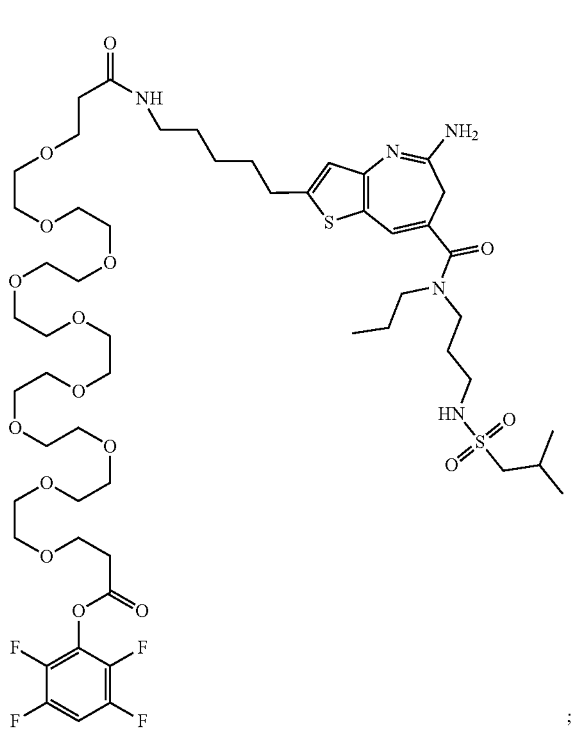
;
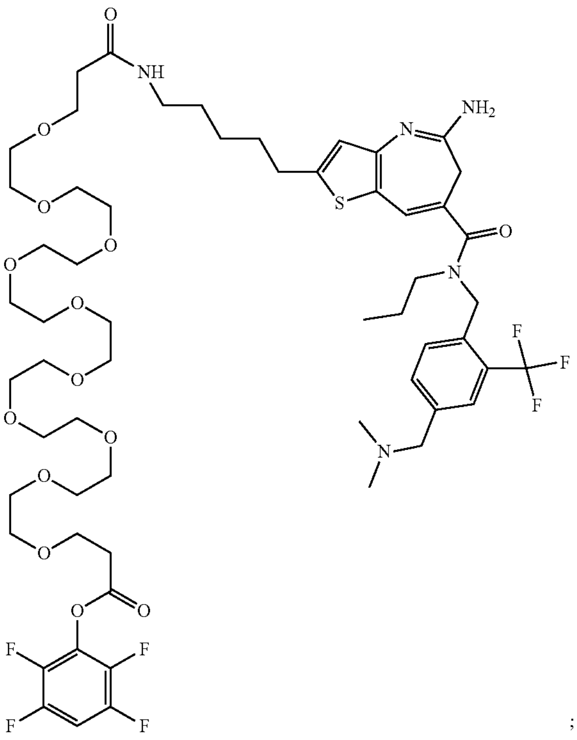
;
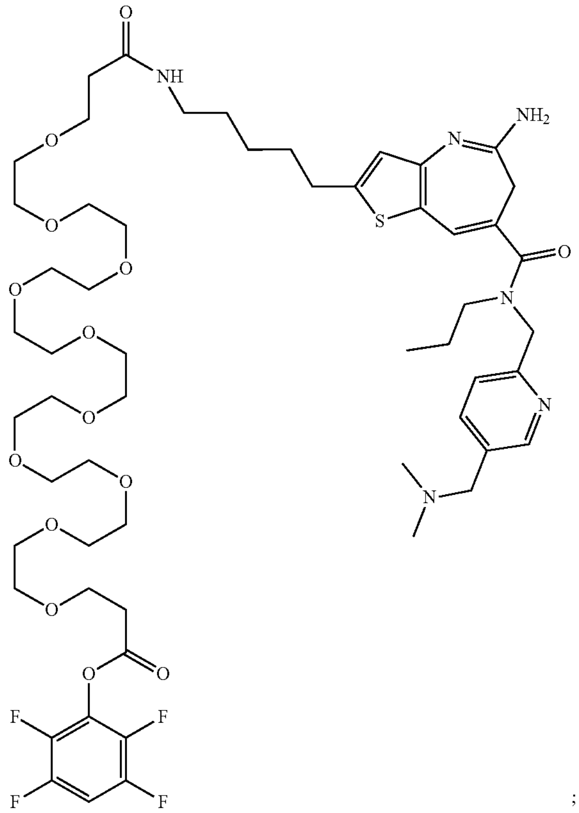
;
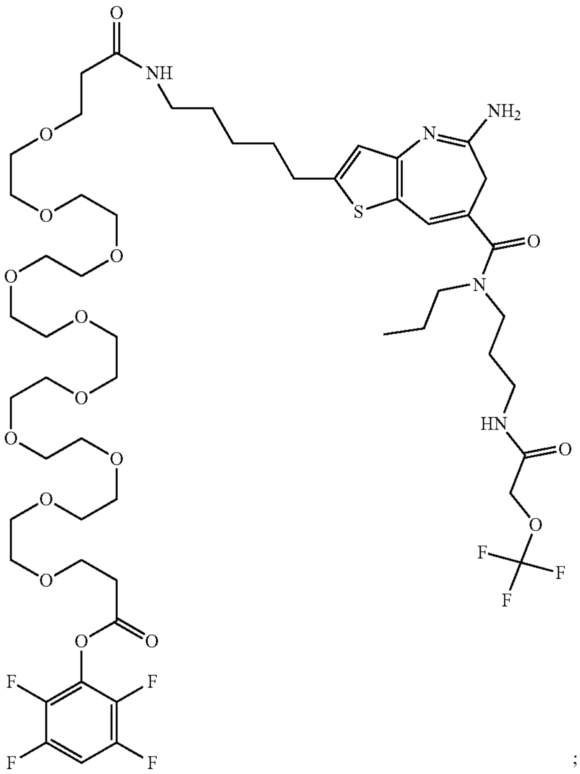
;

-continued
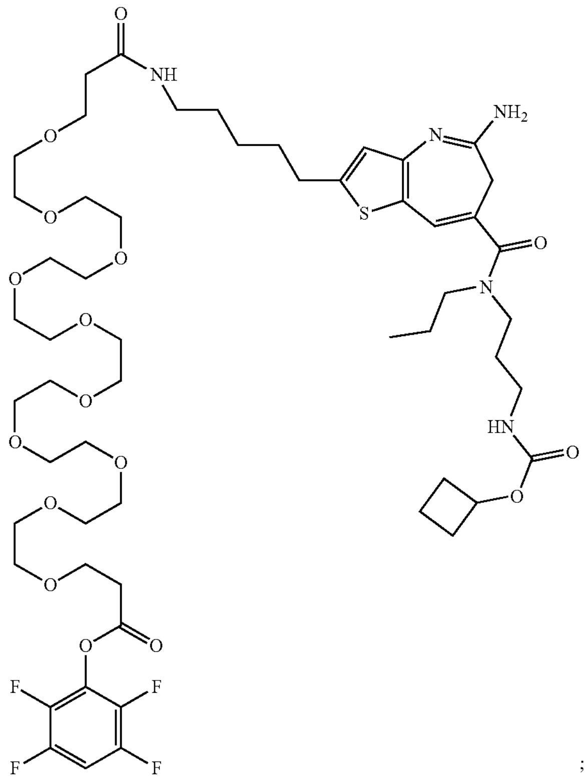
;
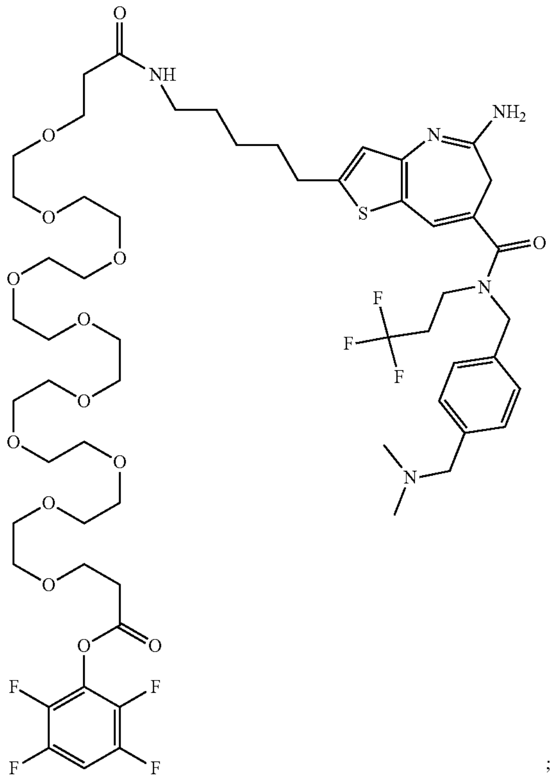
;
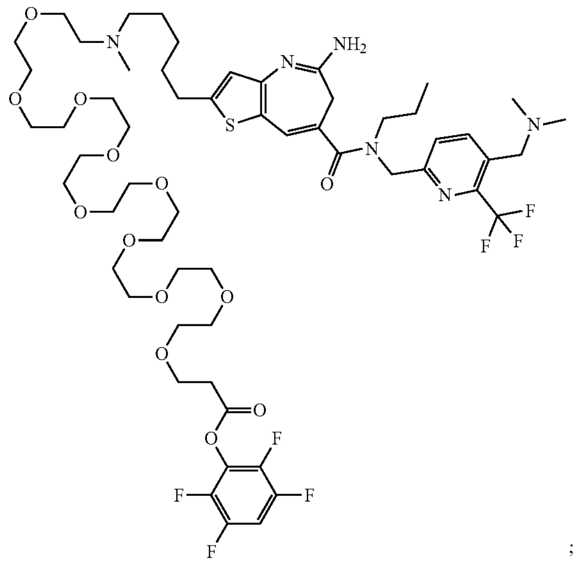
;
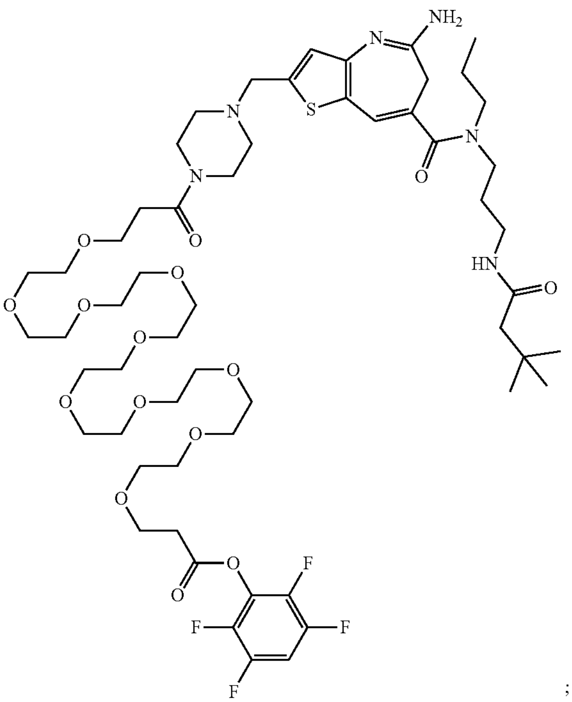
;

-continued
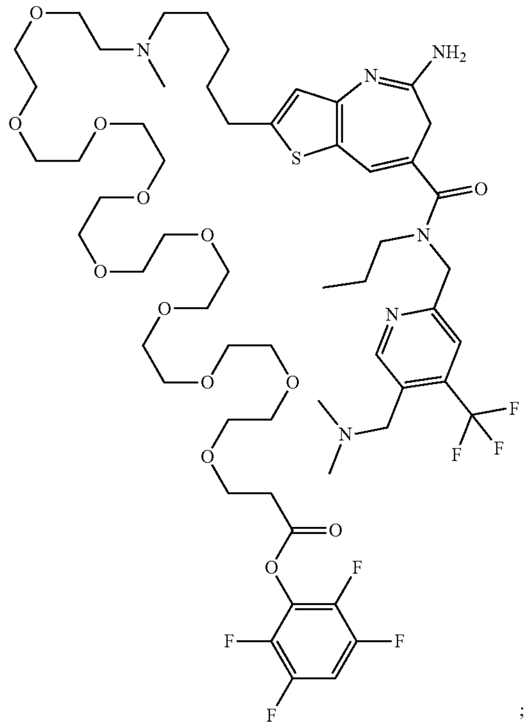
;
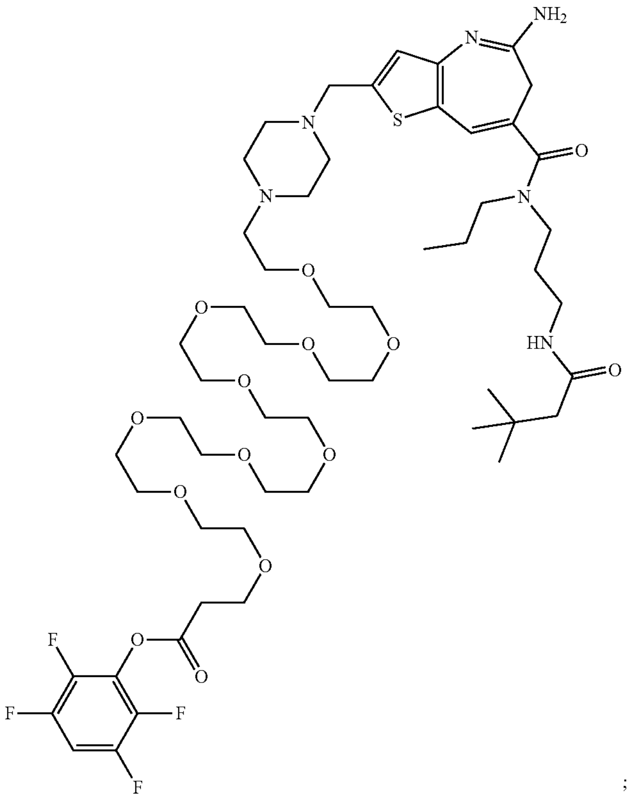
;
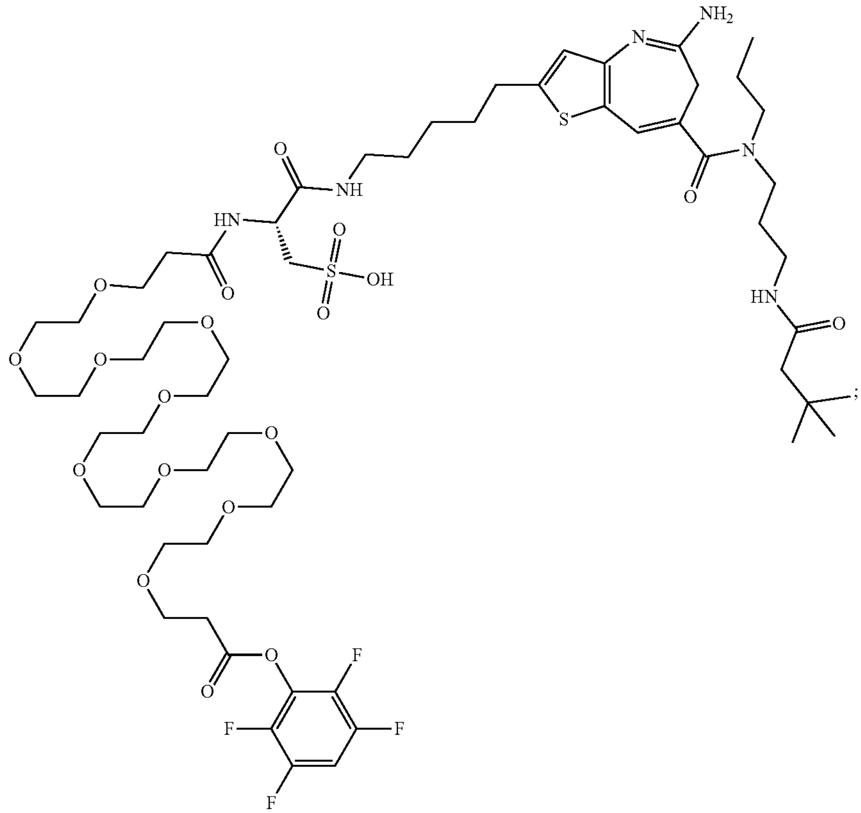
;

-continued
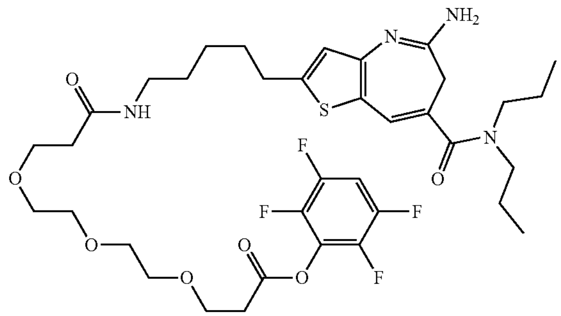
;
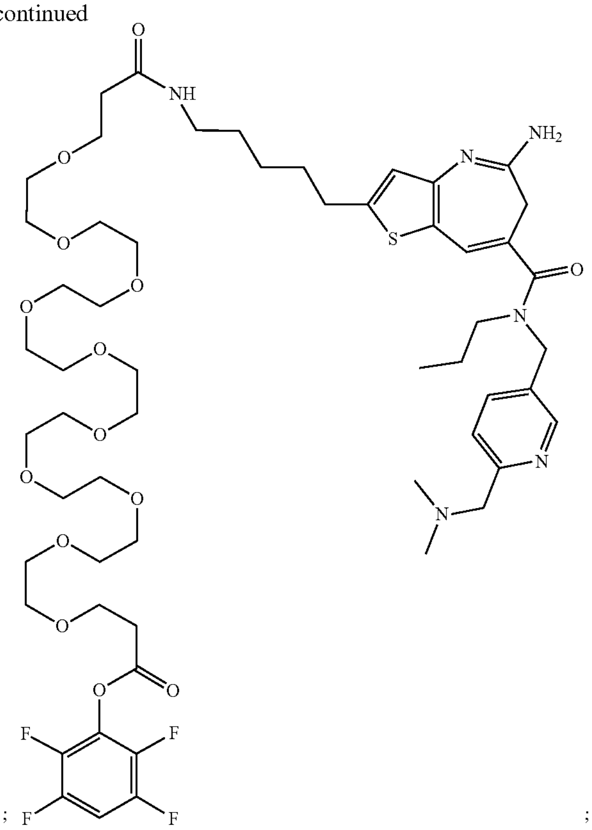
;
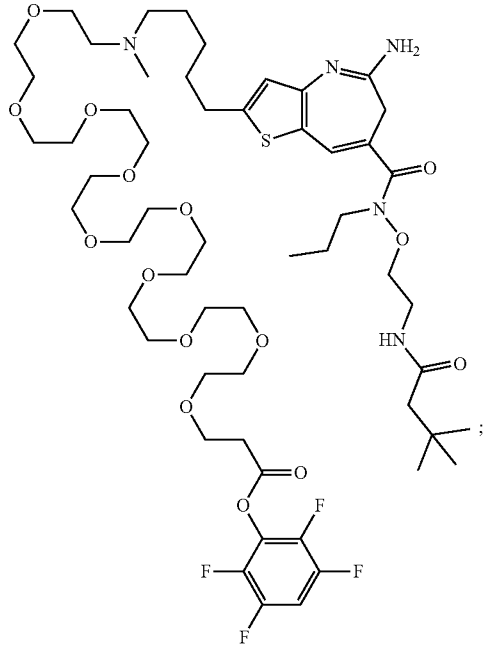
;
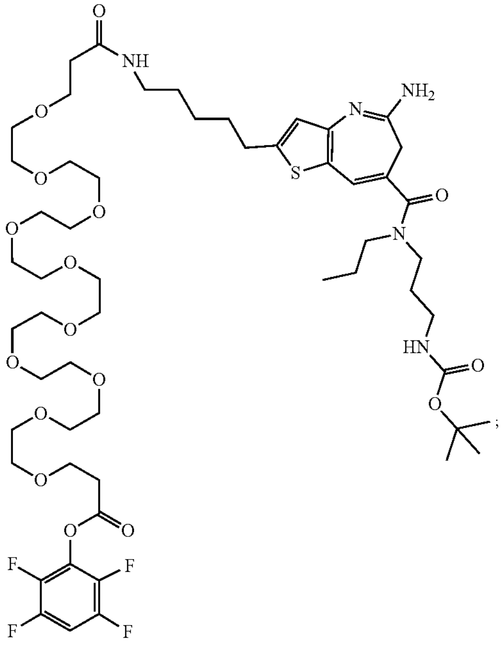
;

-continued
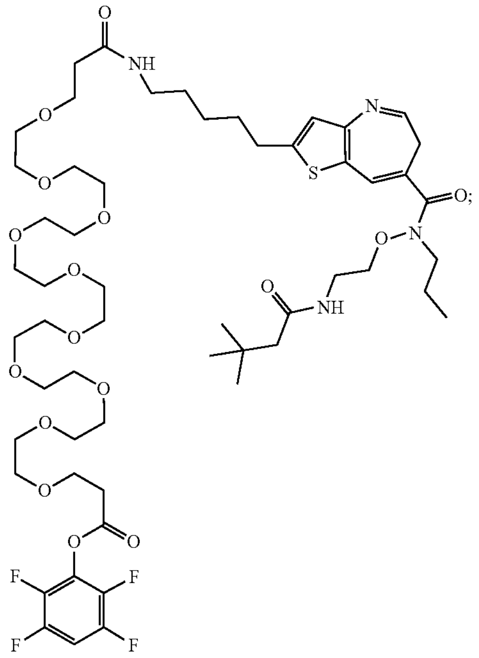
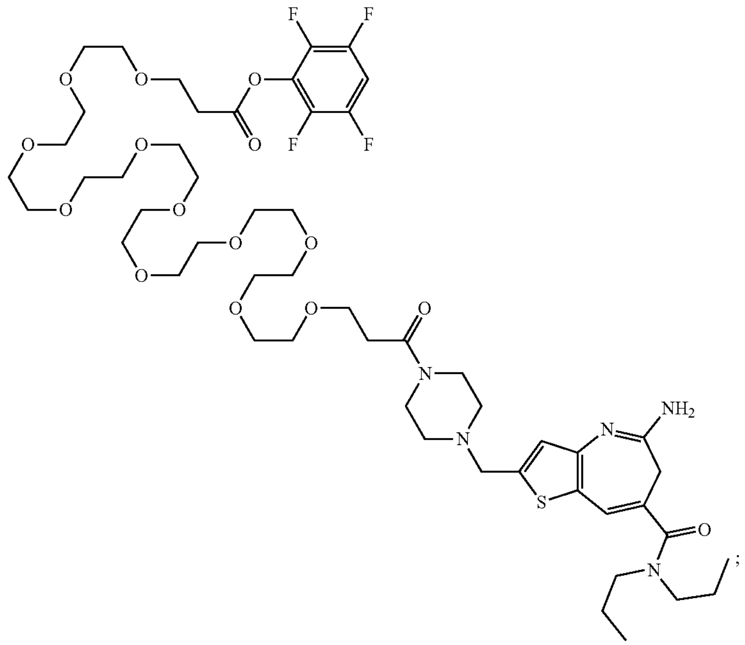

-continued
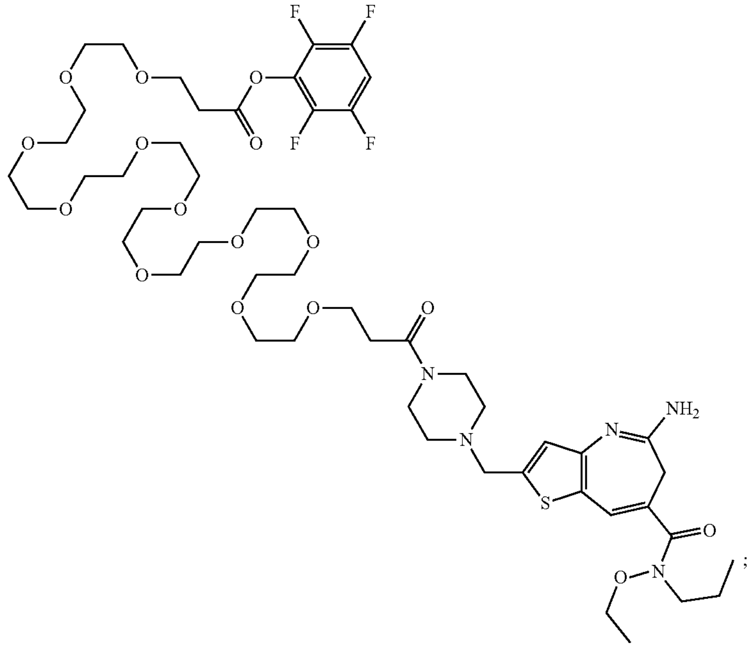
;
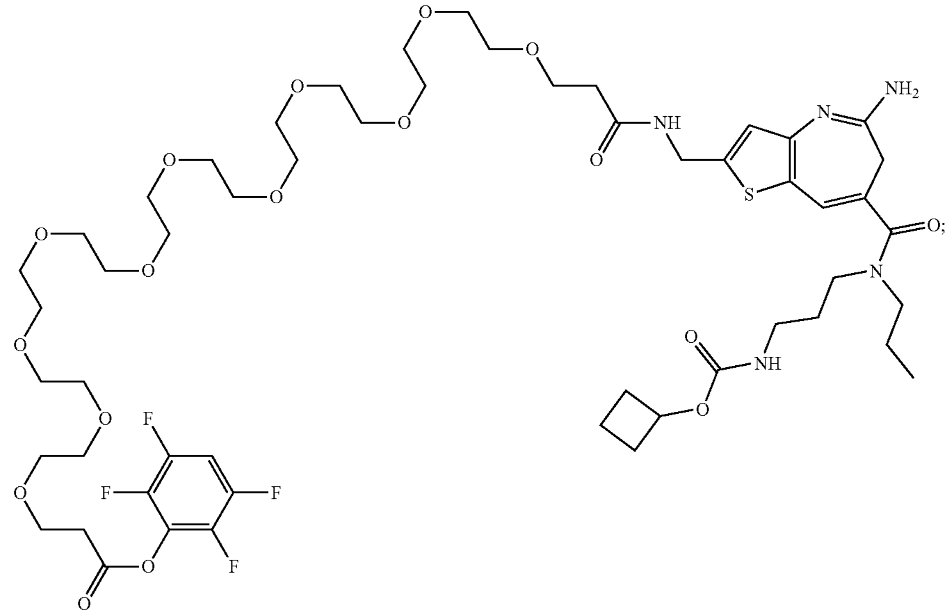
;
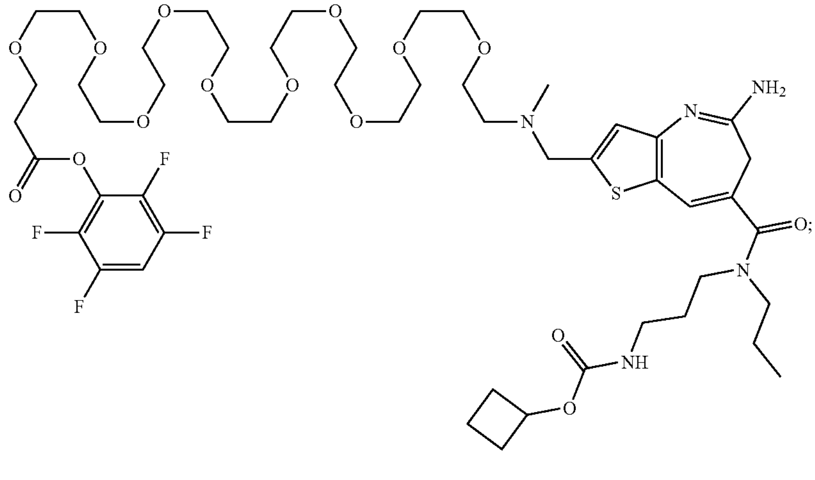
;

-continued
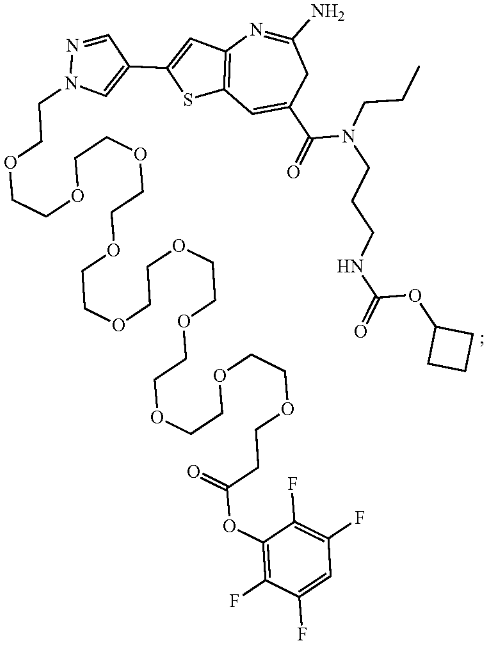
;
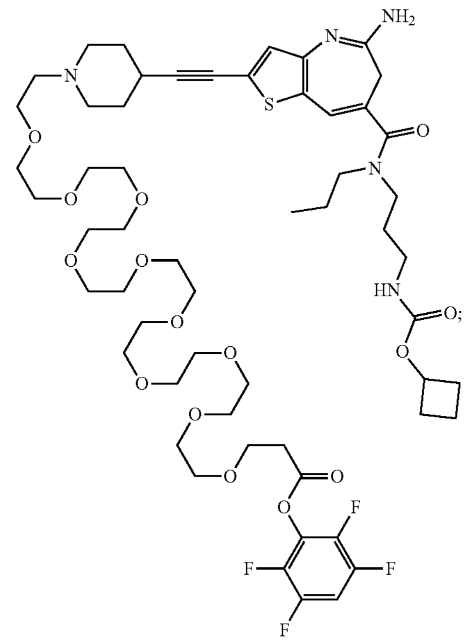
;
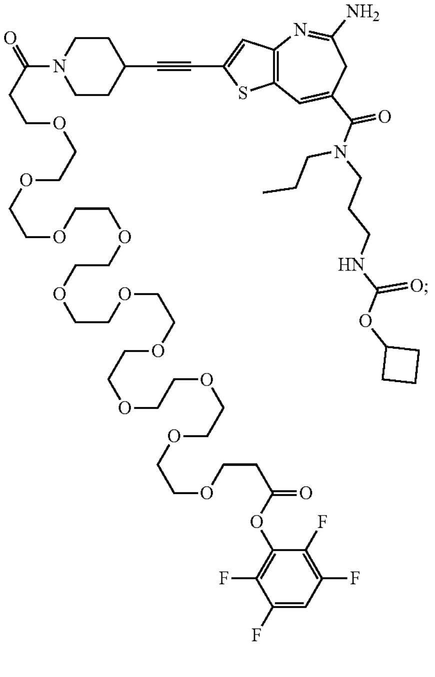
;
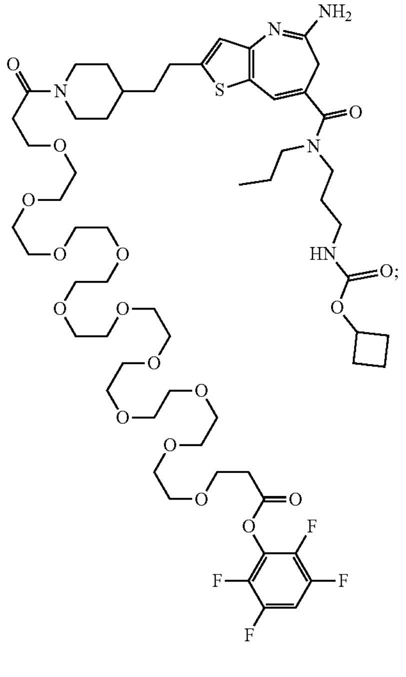
;

-continued
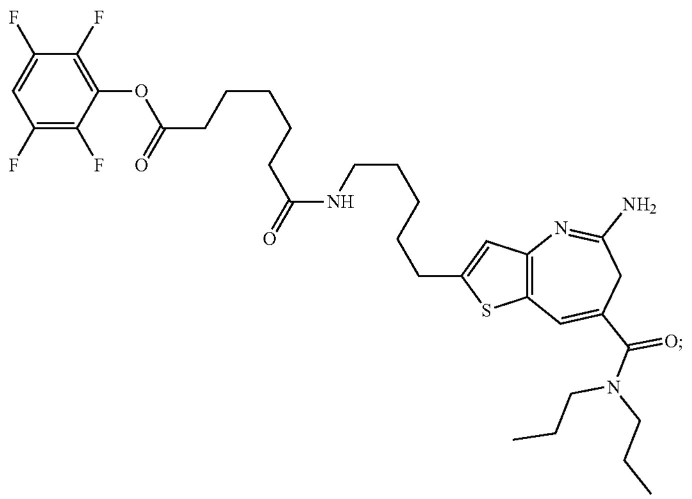
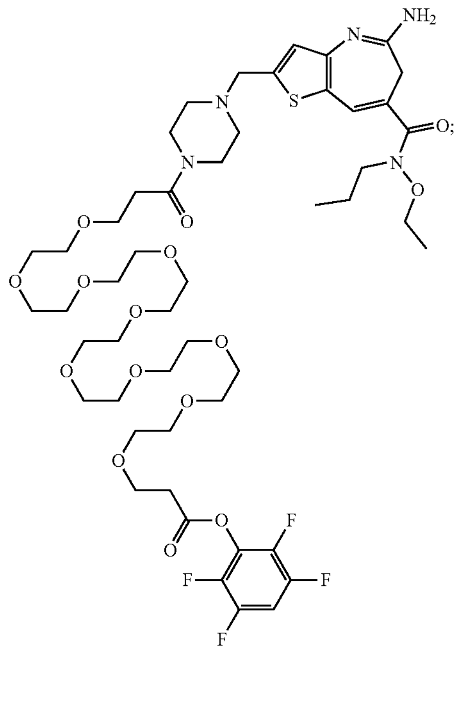
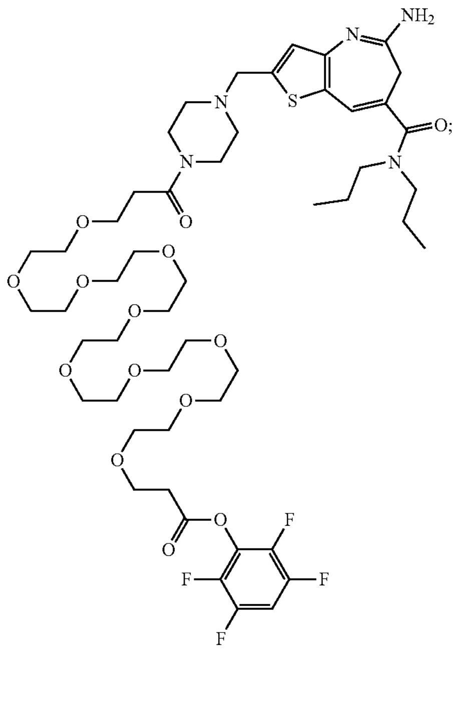

-continued
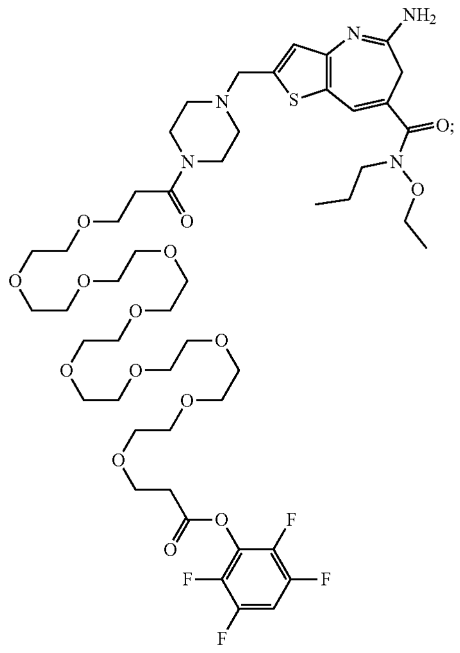
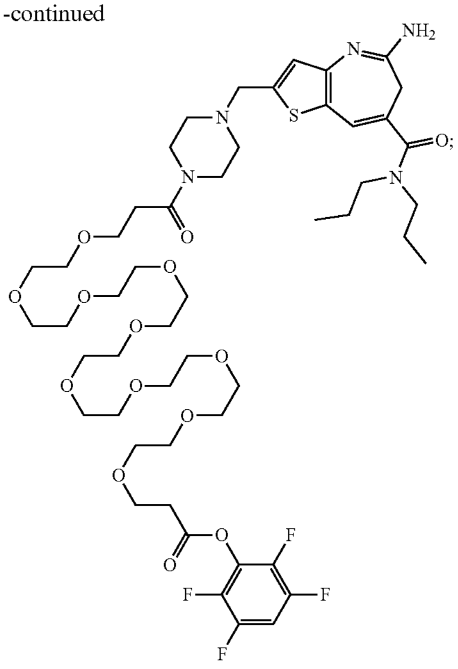
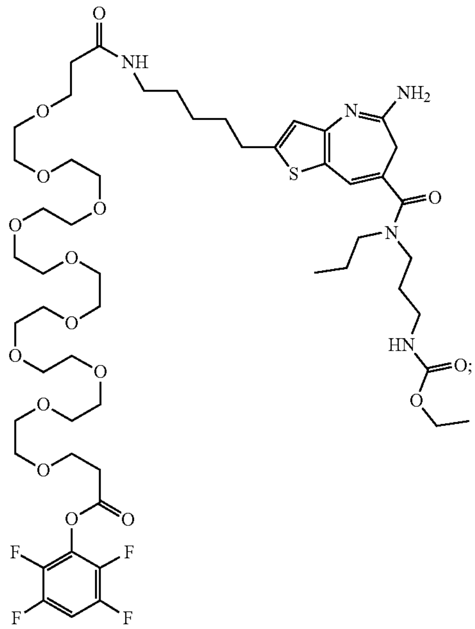

-continued
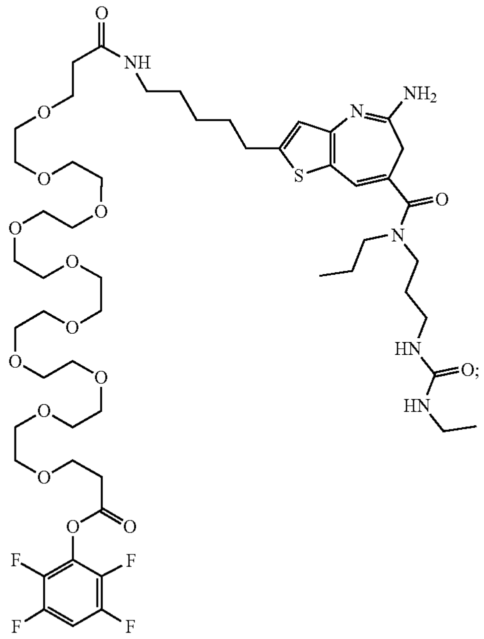
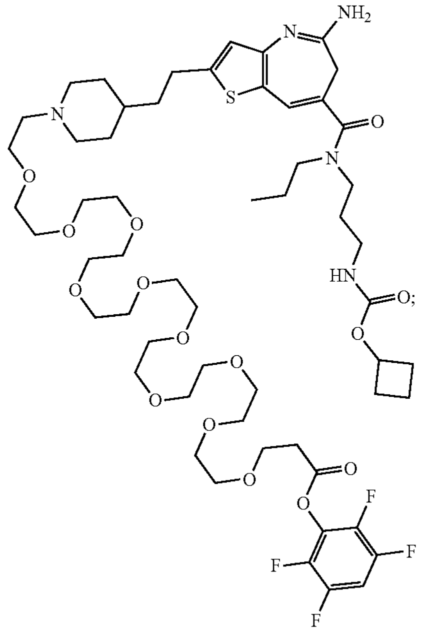

-continued
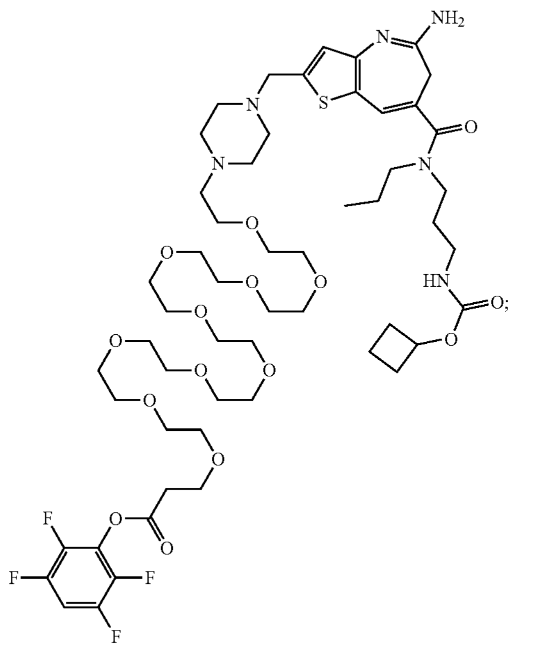
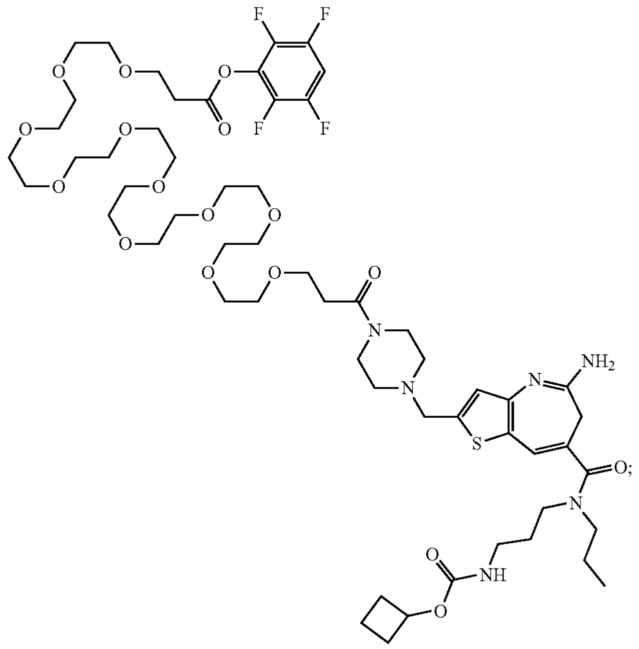

-continued
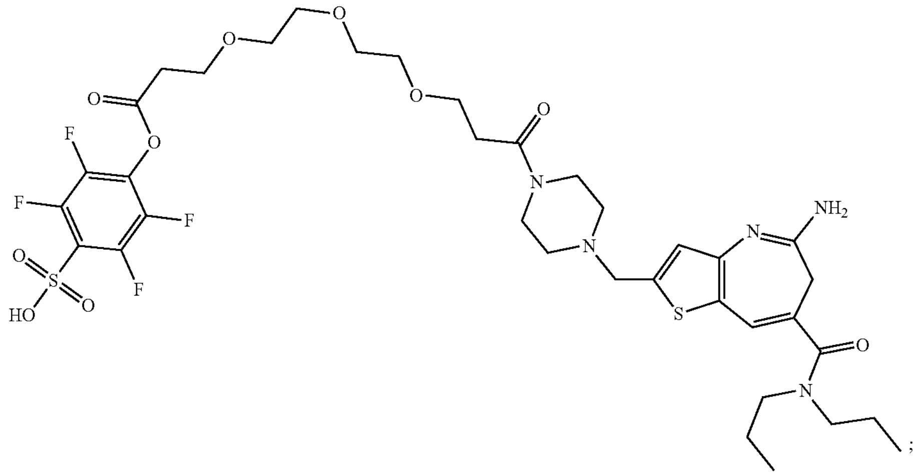
;
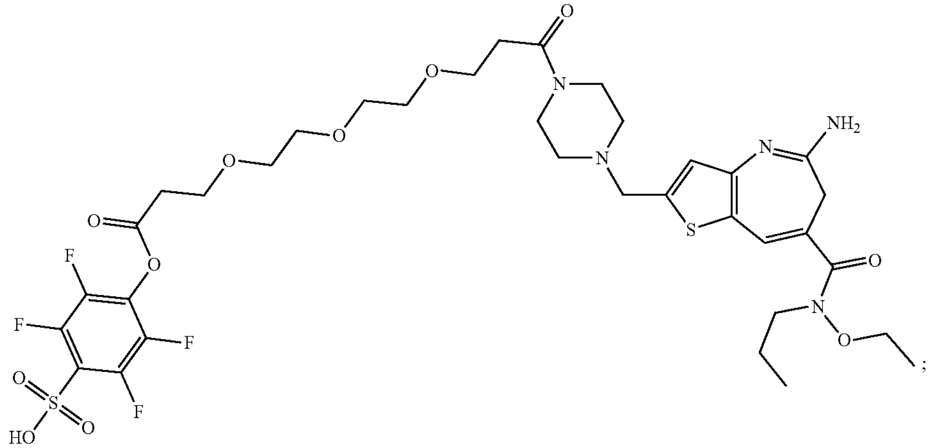
;
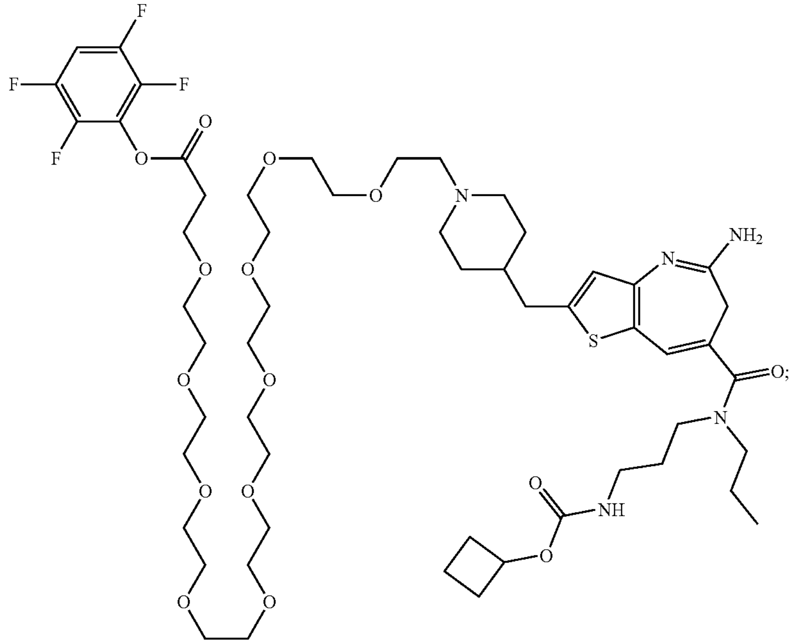
;

-continued
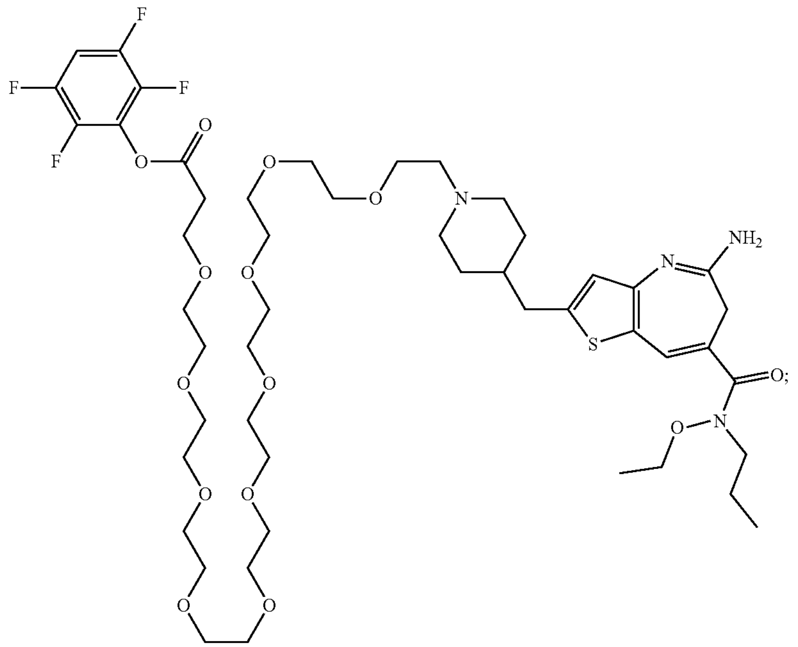
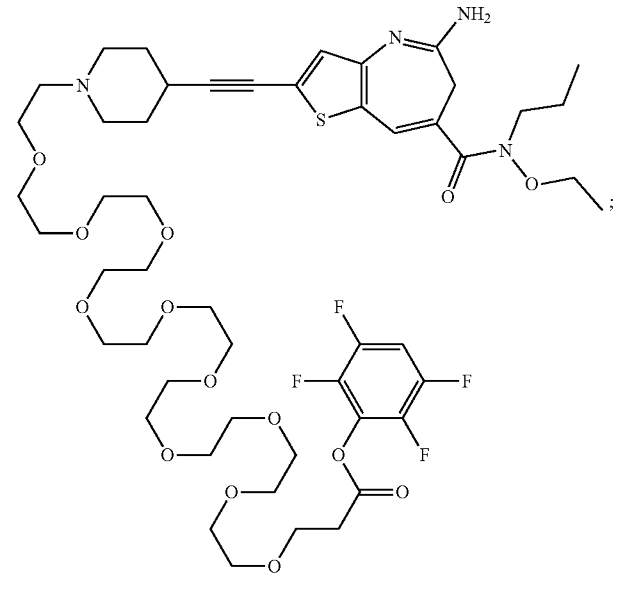

-continued
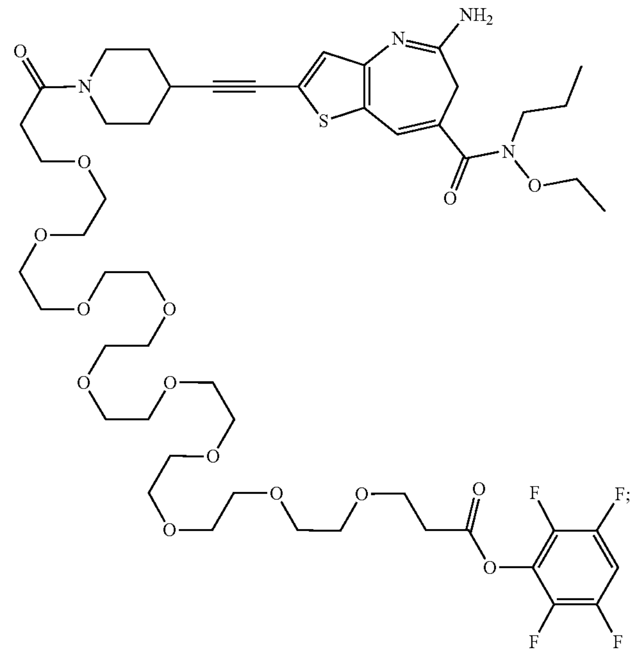
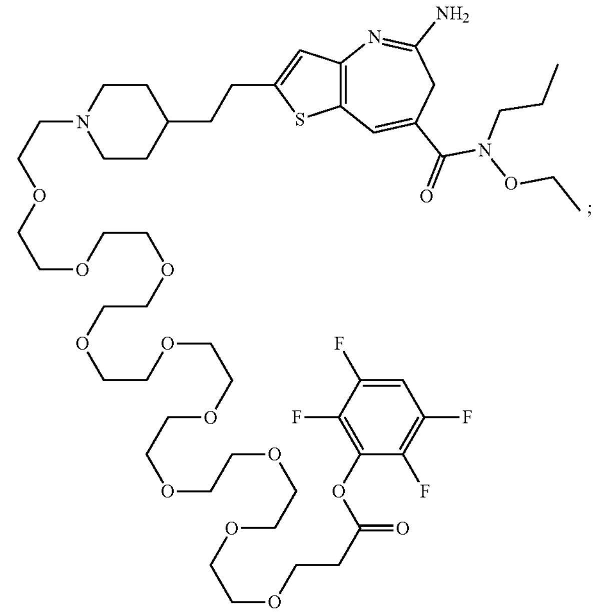

-continued
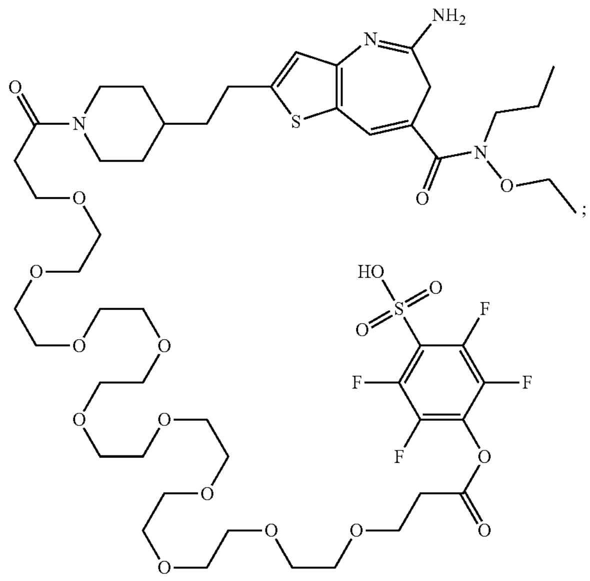
;
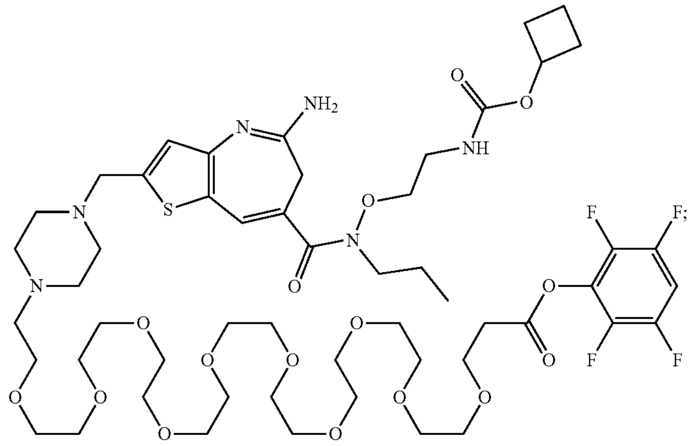
;
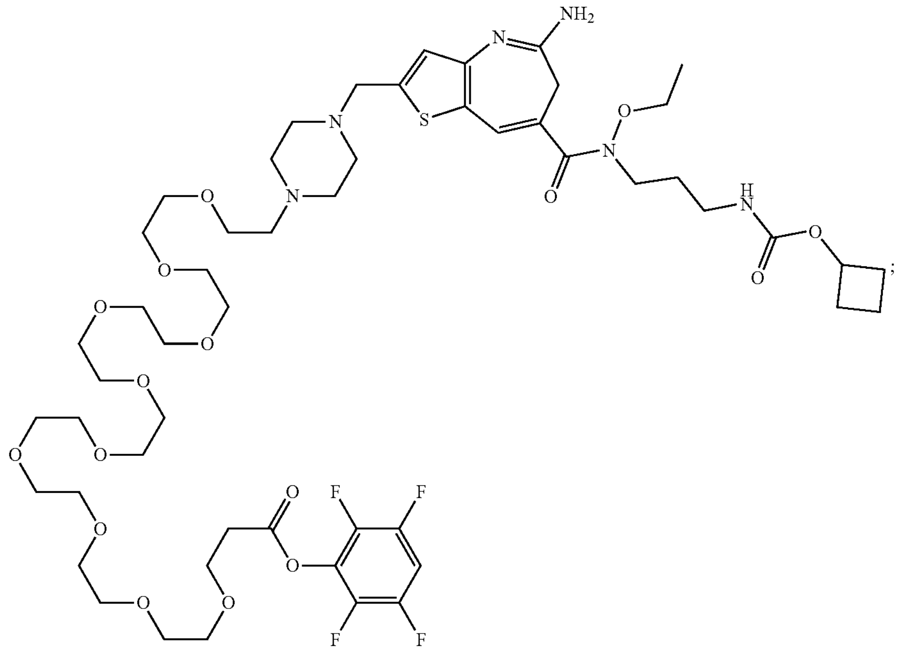
;

-continued
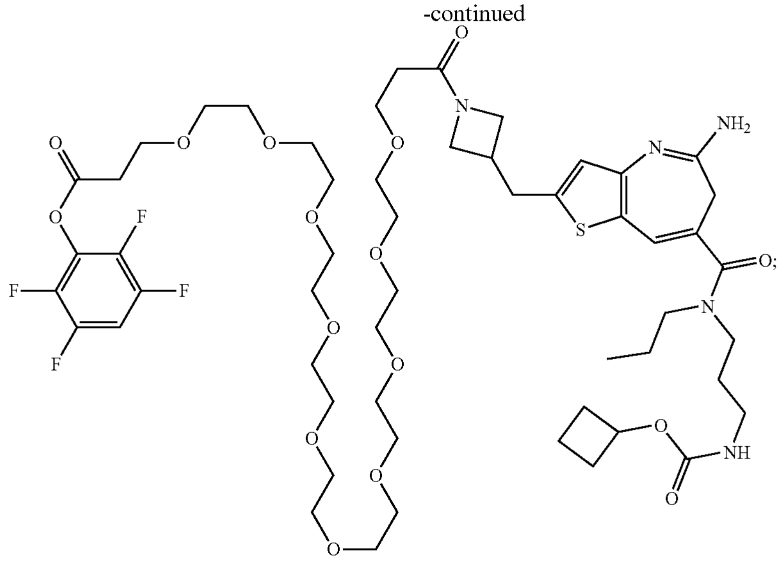
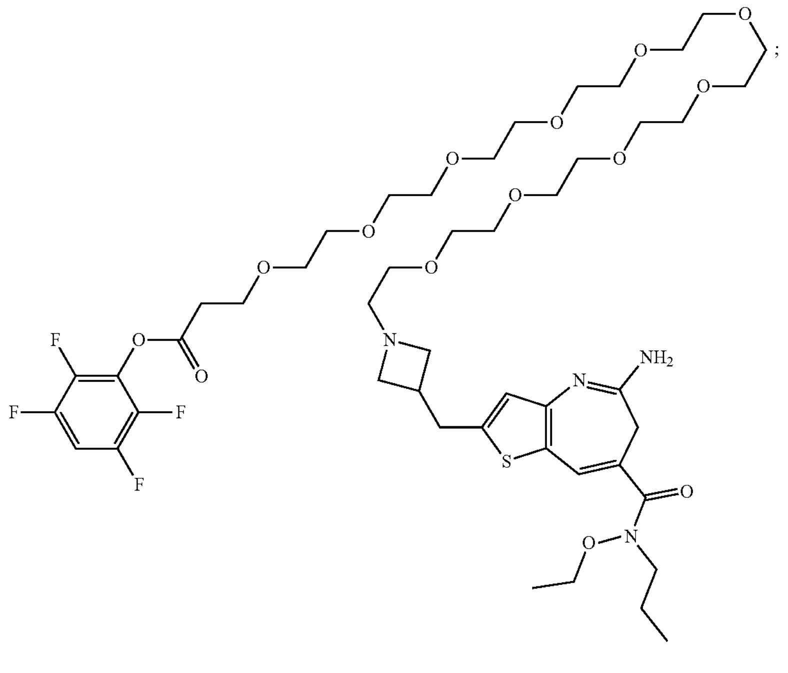

-continued
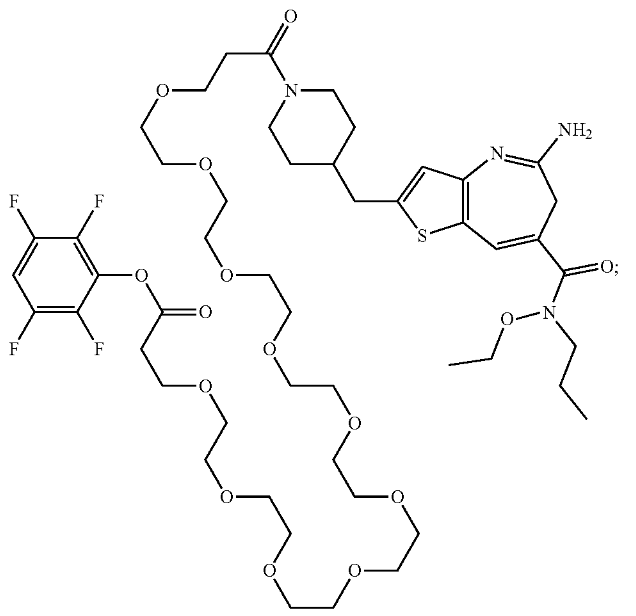
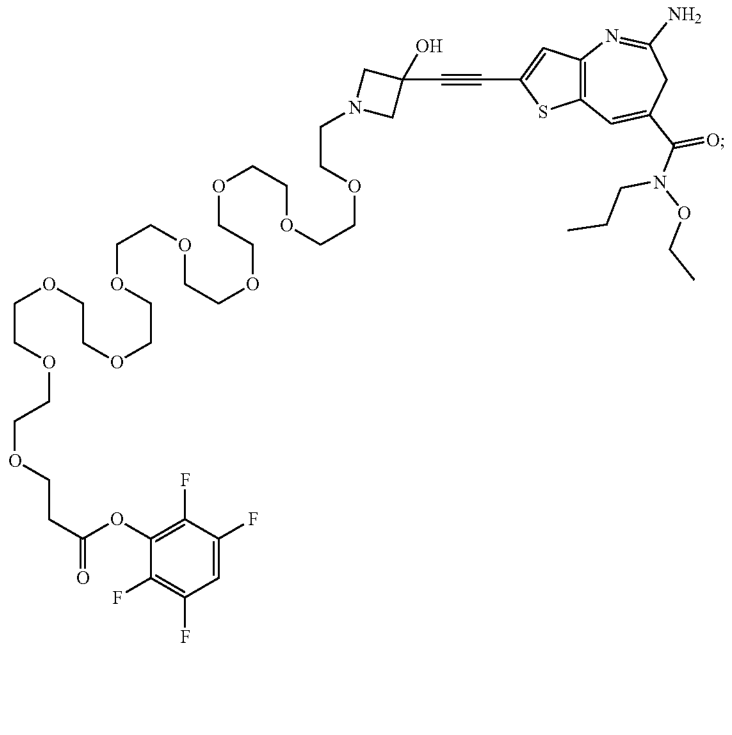

-continued
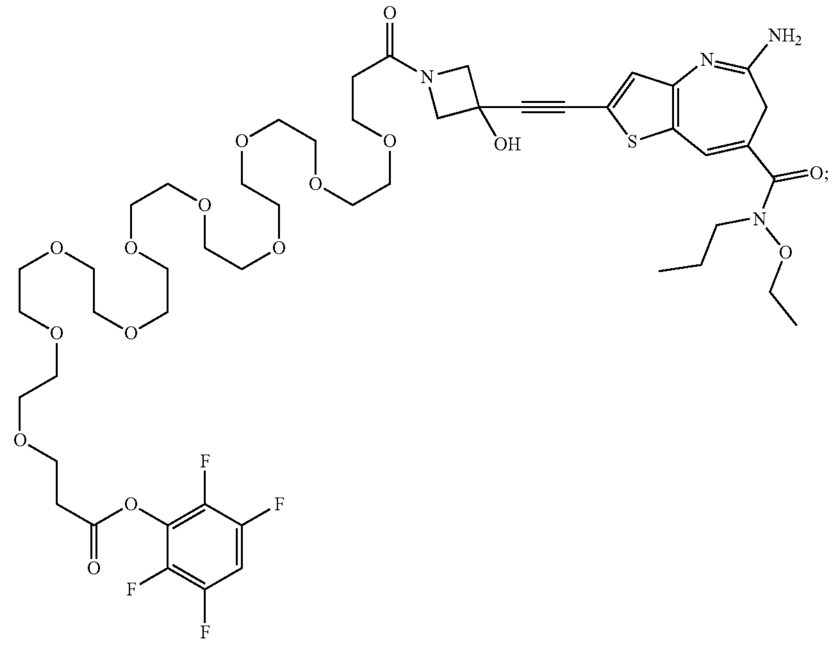
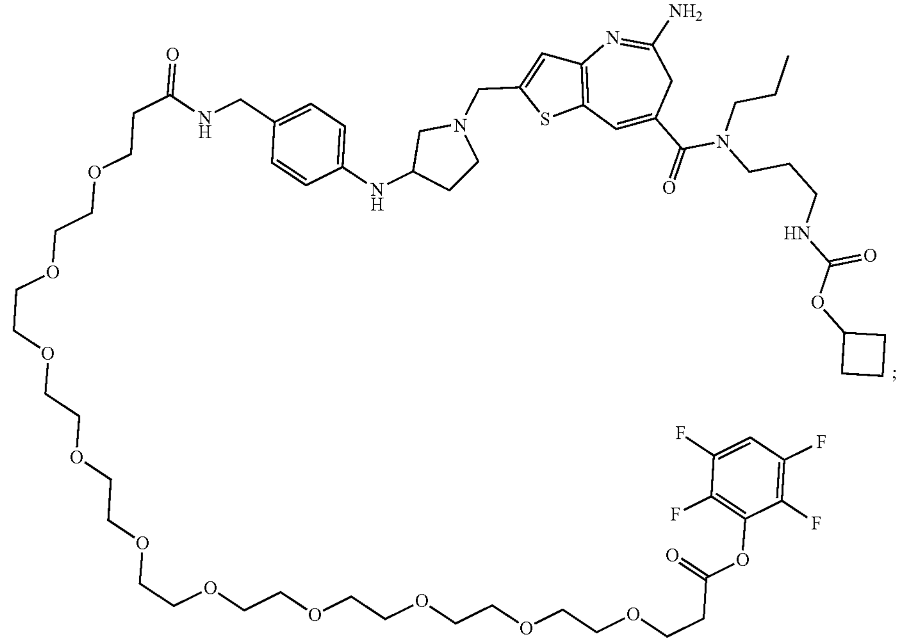

-continued
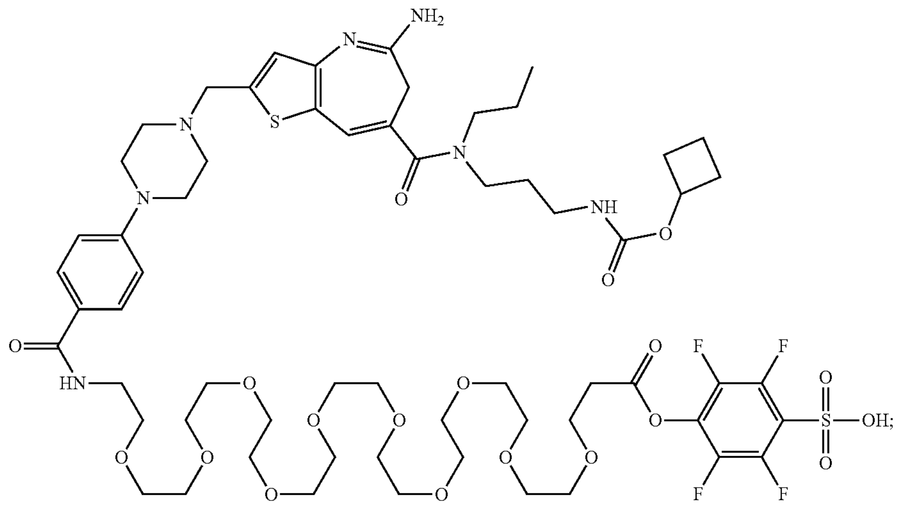
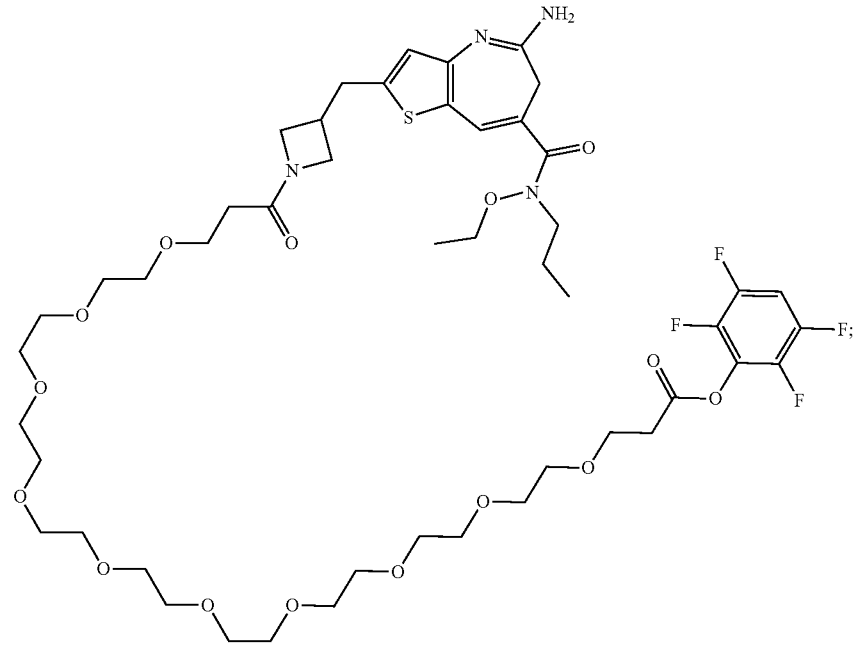
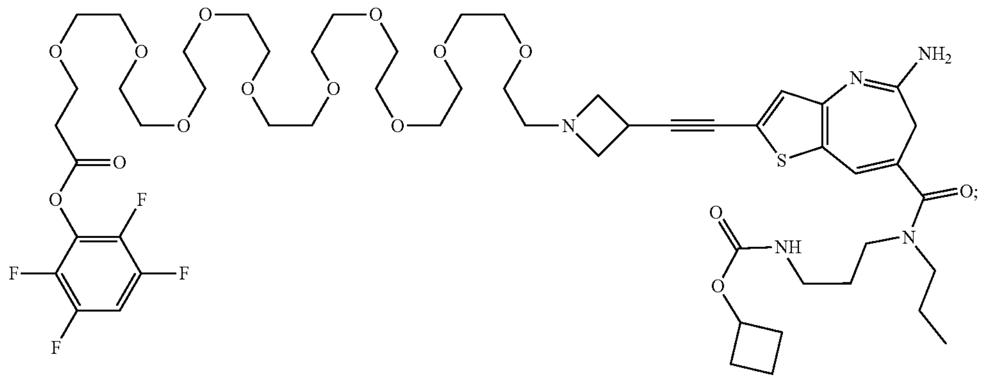

-continued
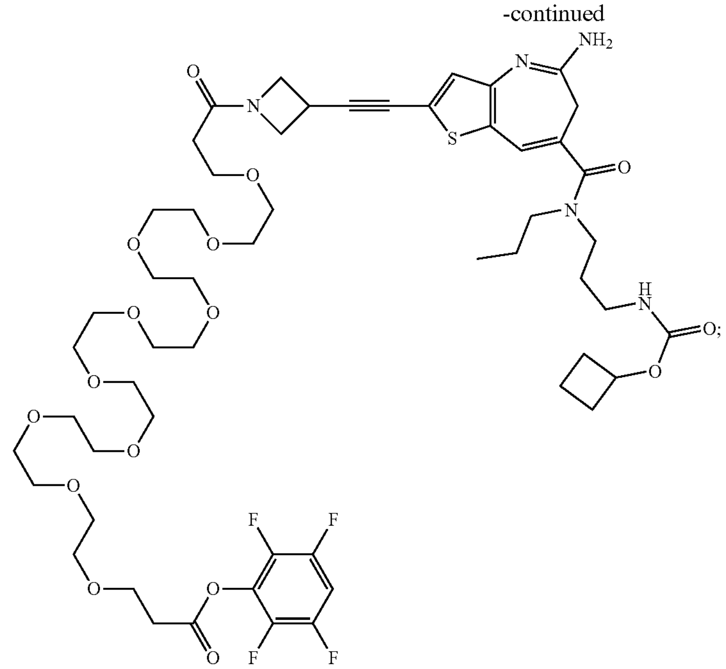
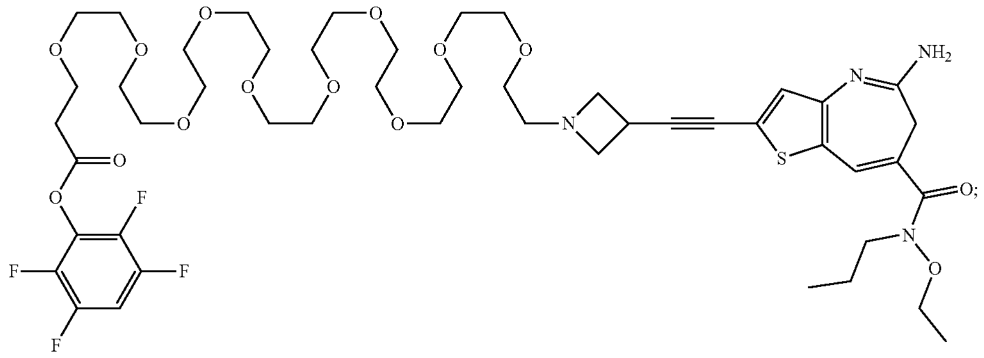
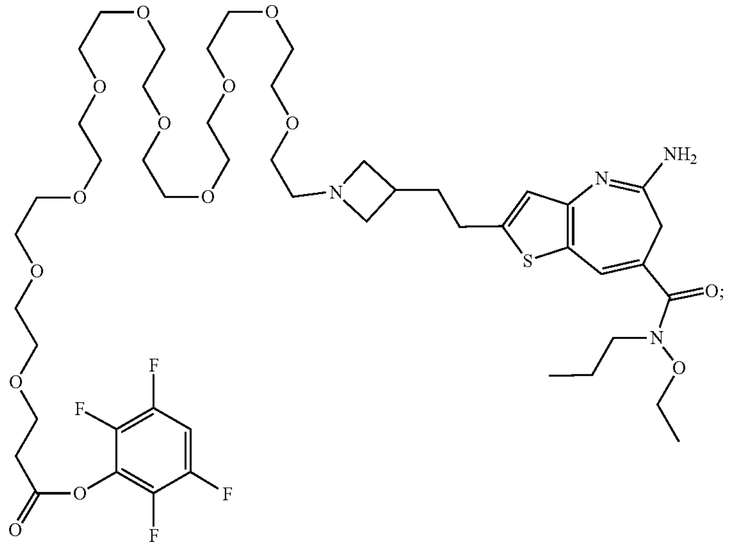

-continued
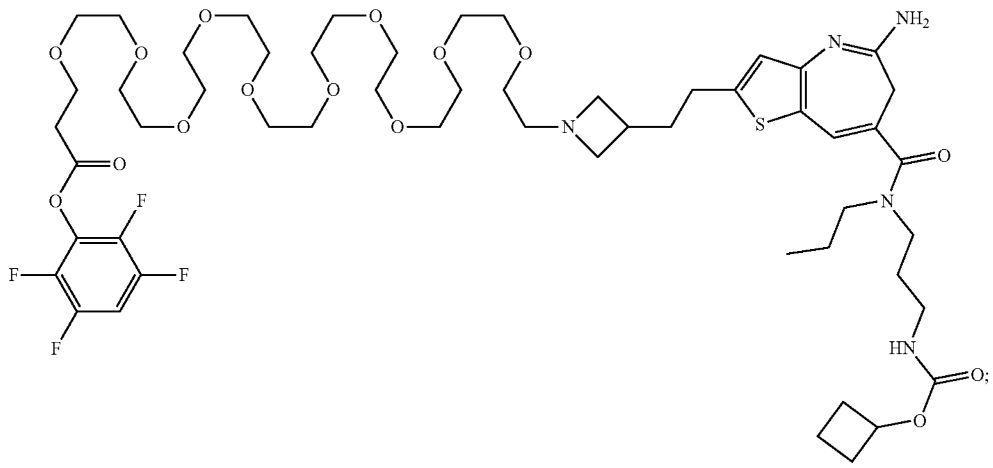
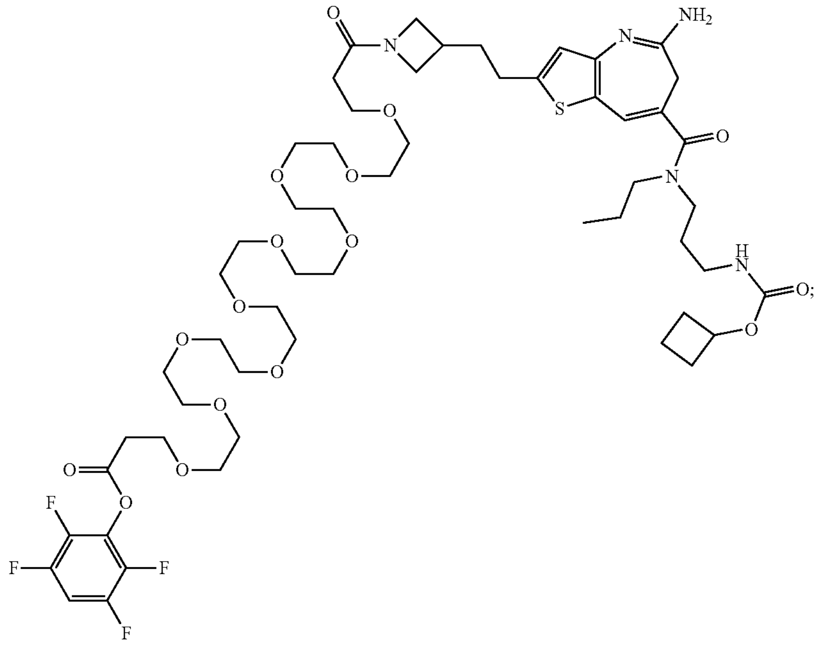
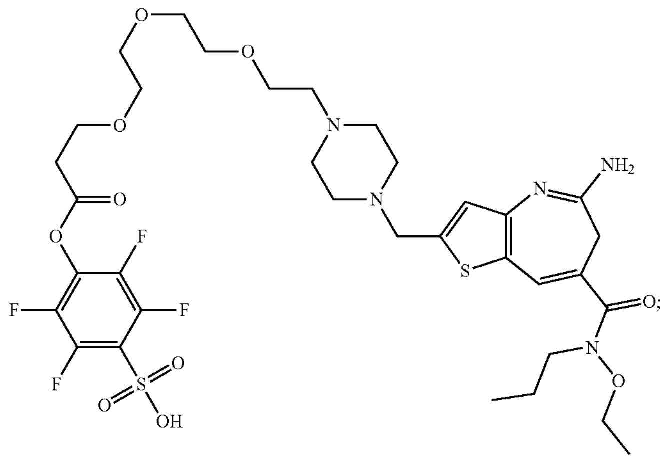

-continued
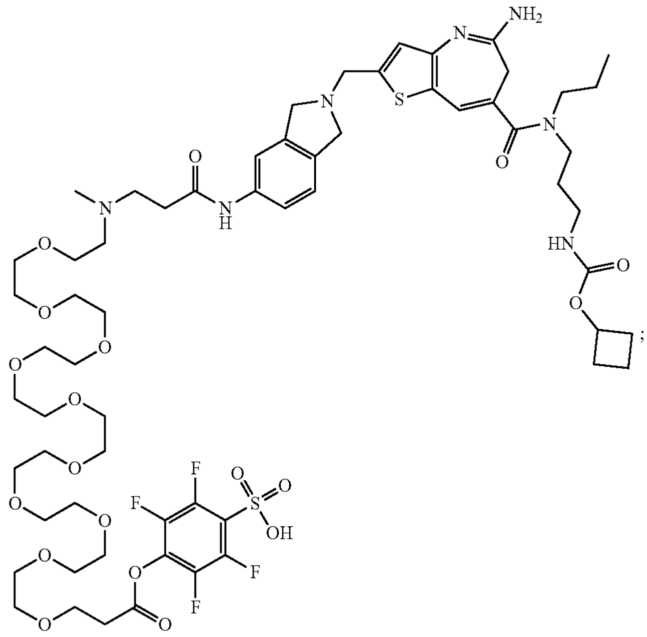
;
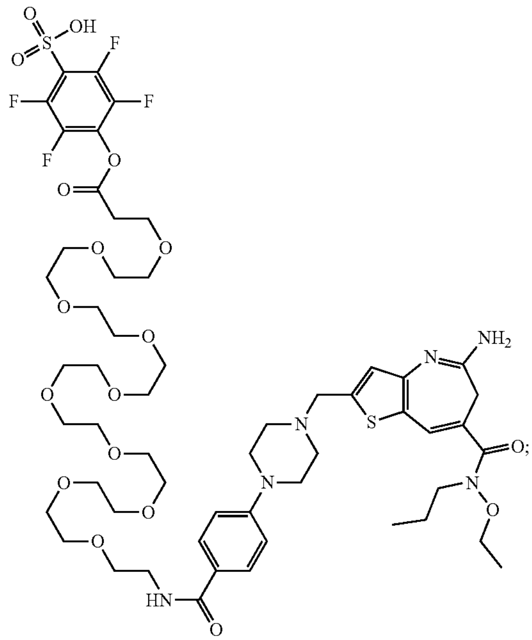
;

-continued
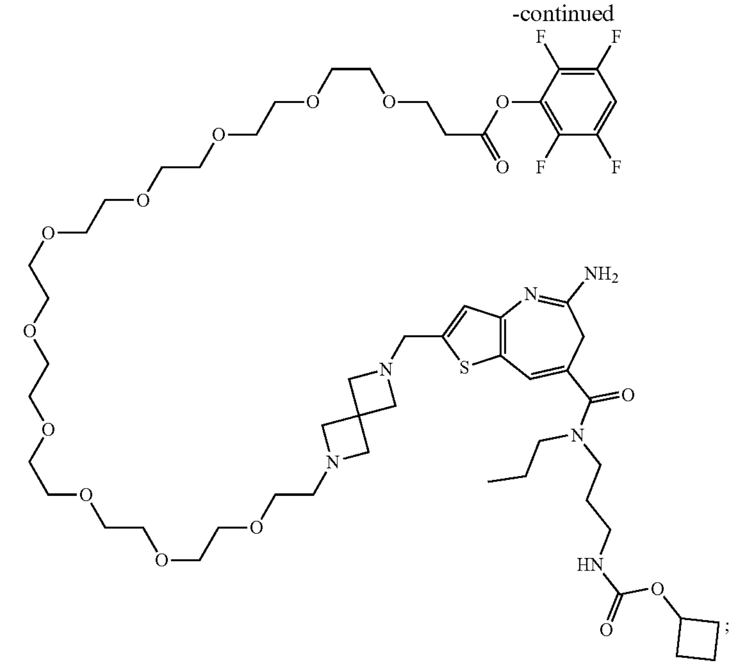
;
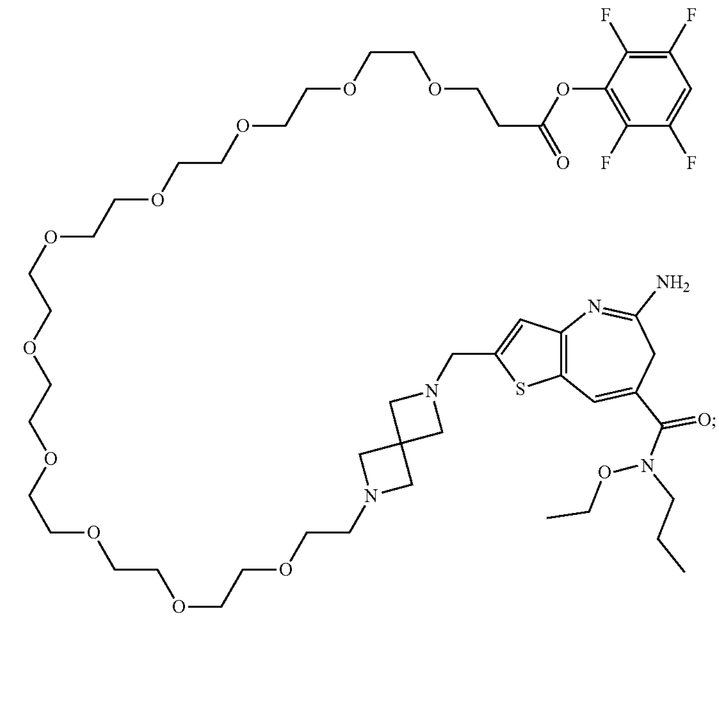
;

-continued
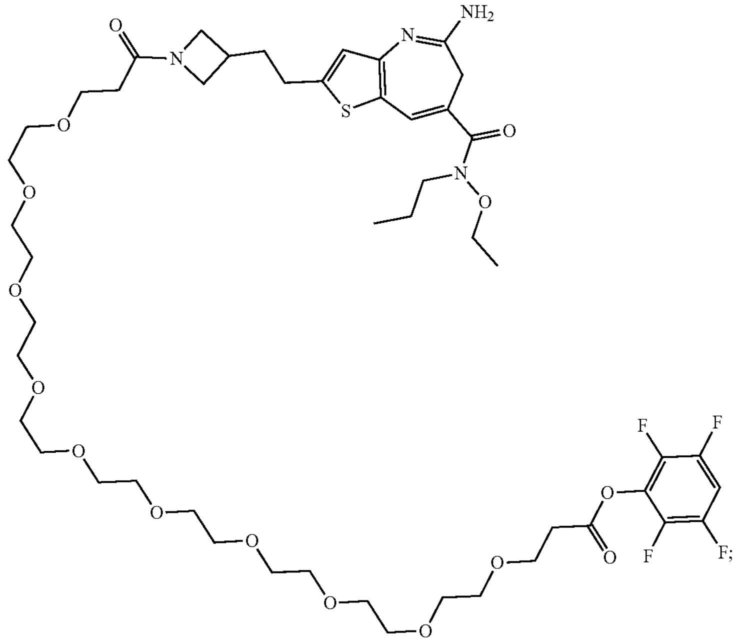
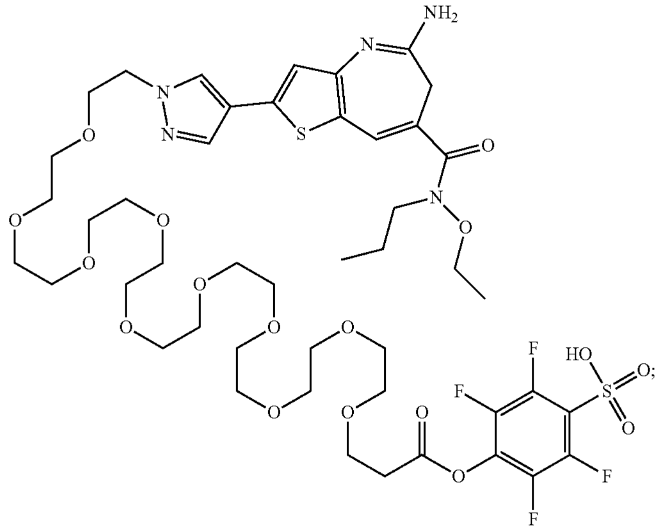

-continued
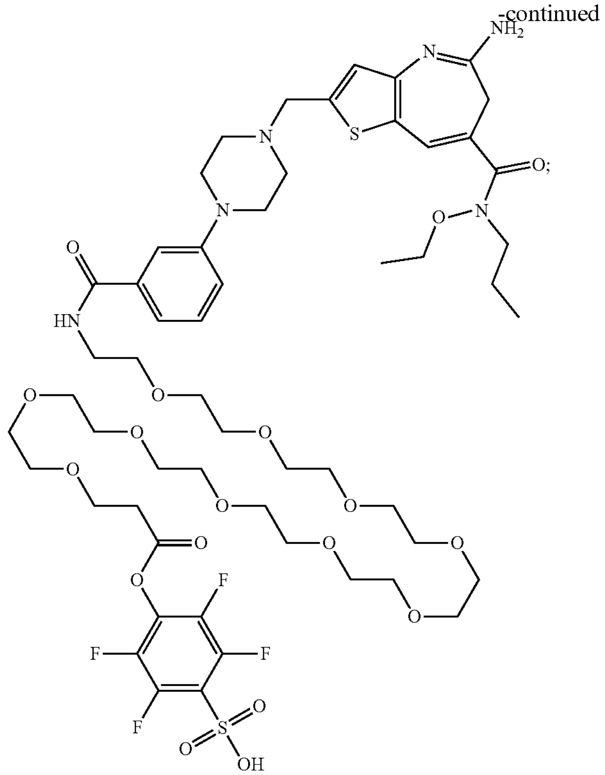
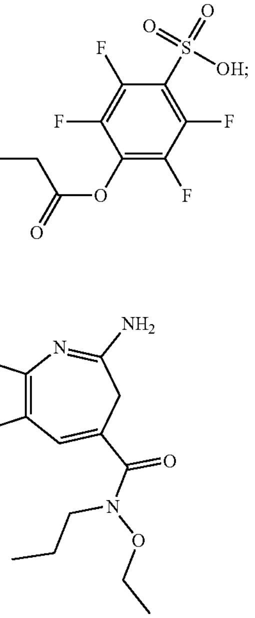
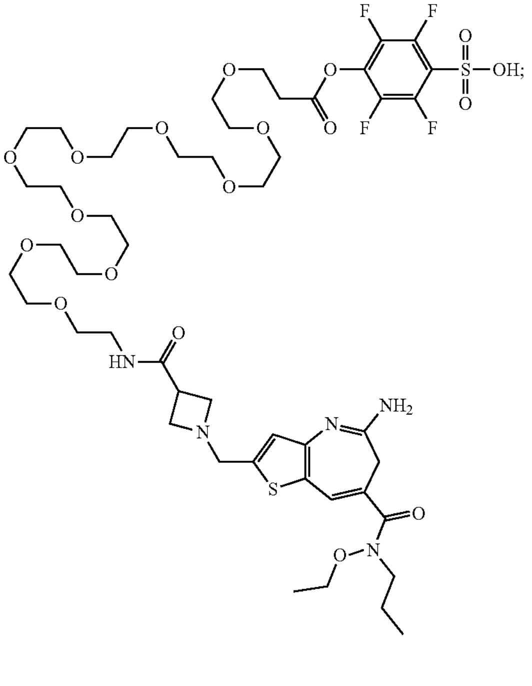

-continued
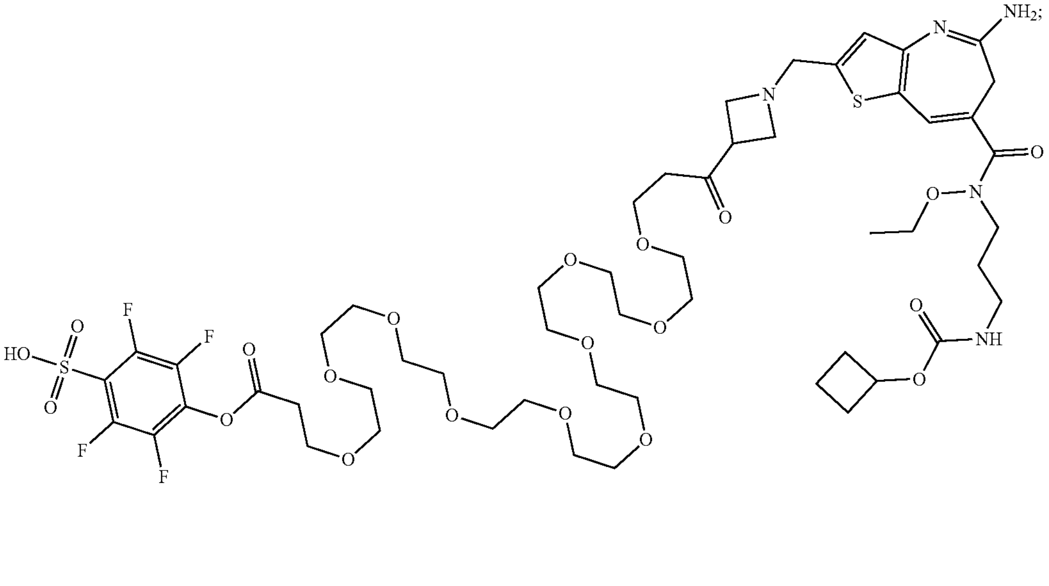
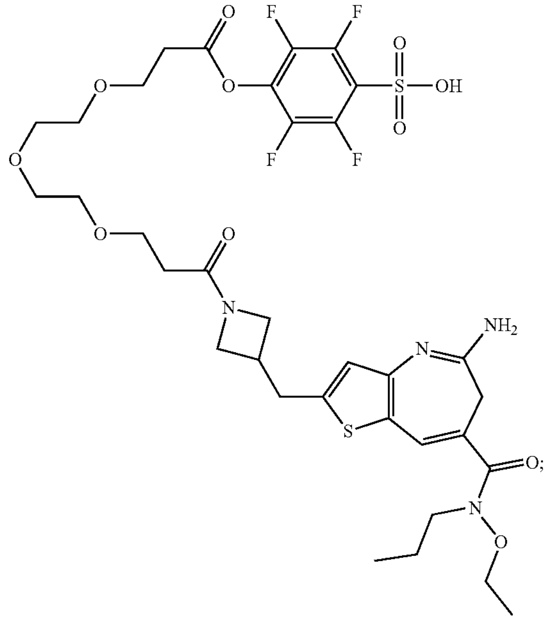

-continued
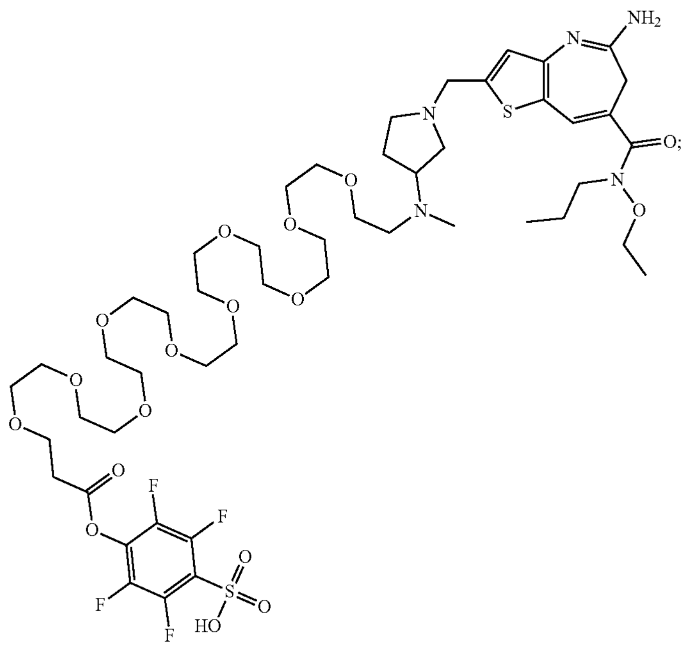
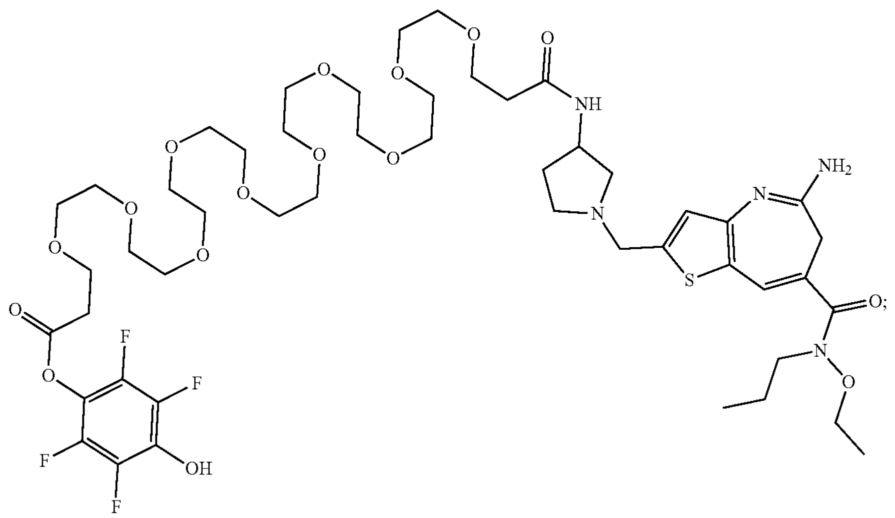

-continued
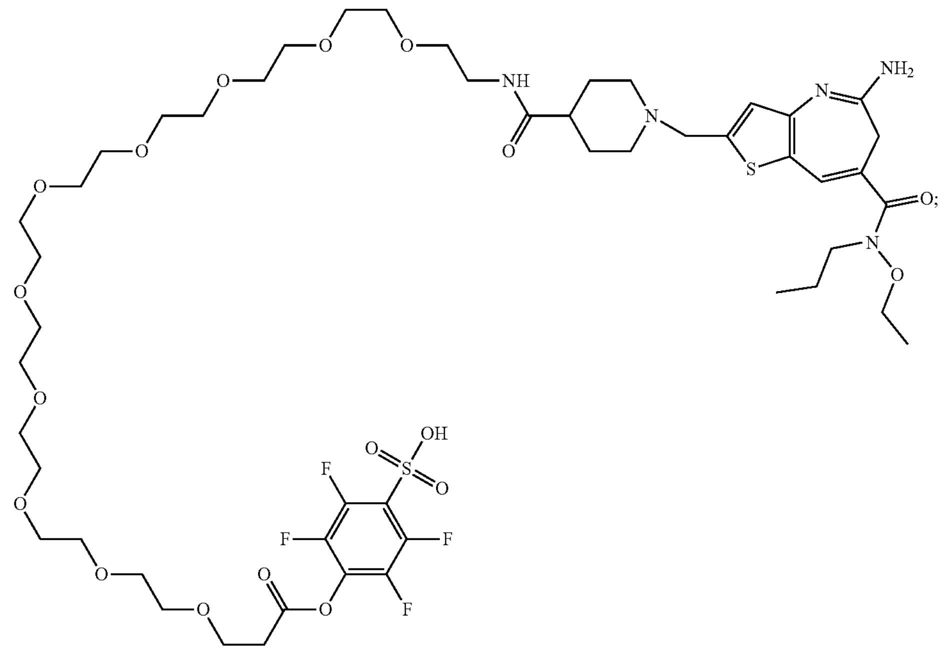
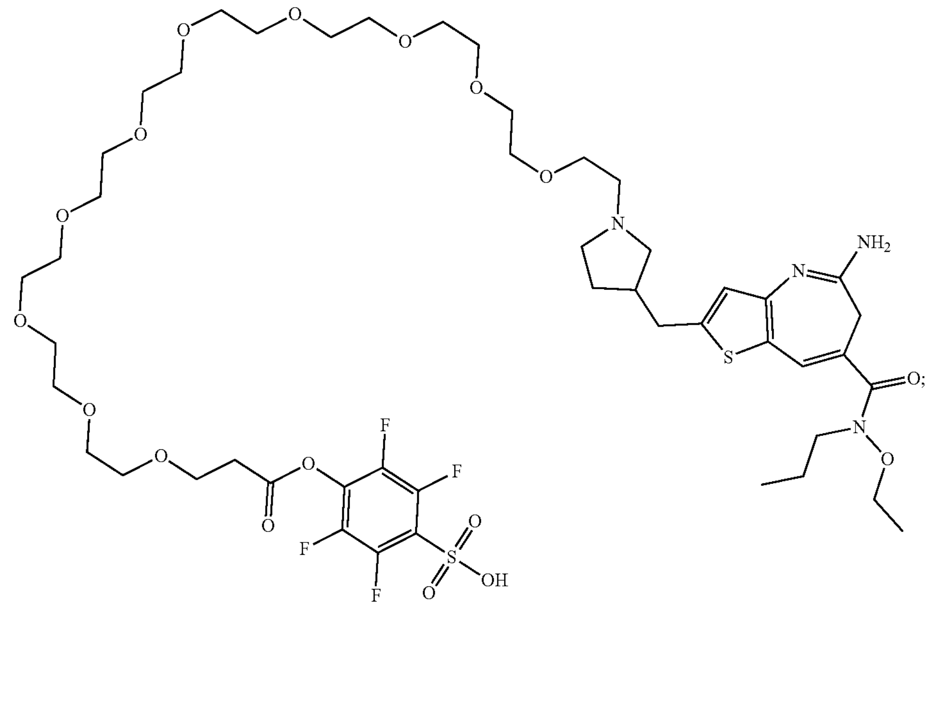

-continued
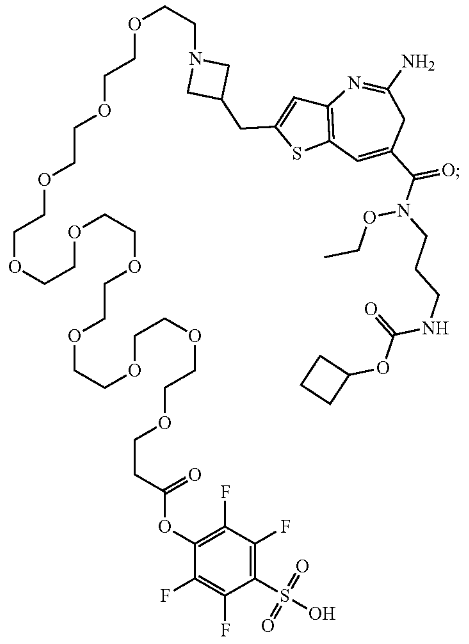
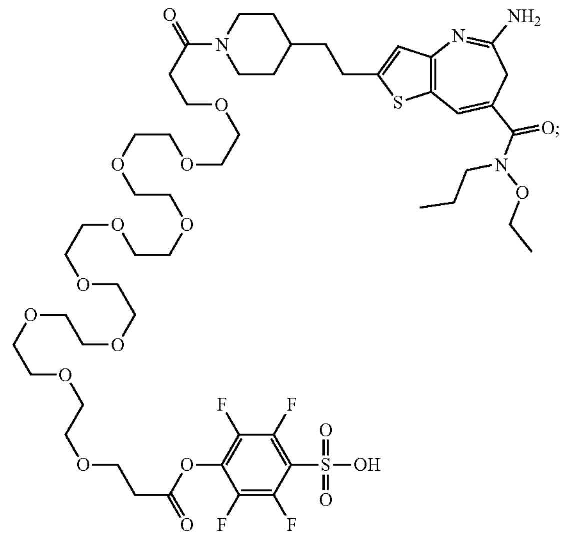
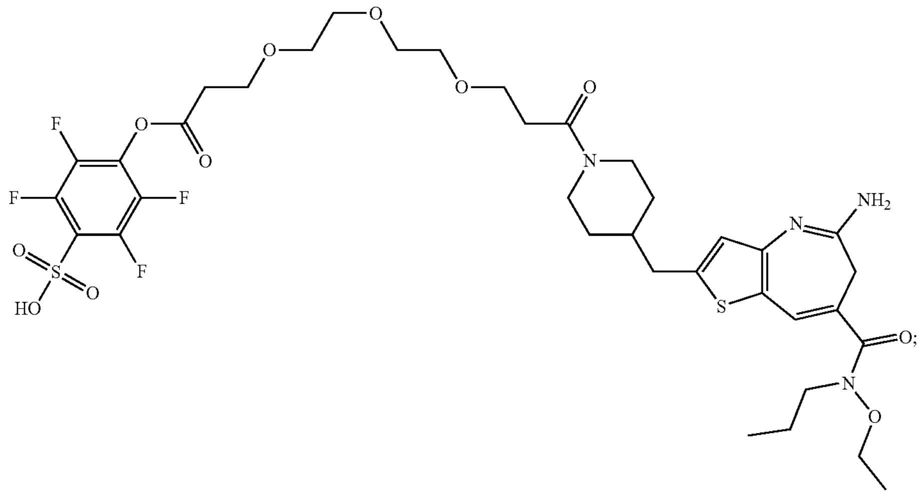

-continued
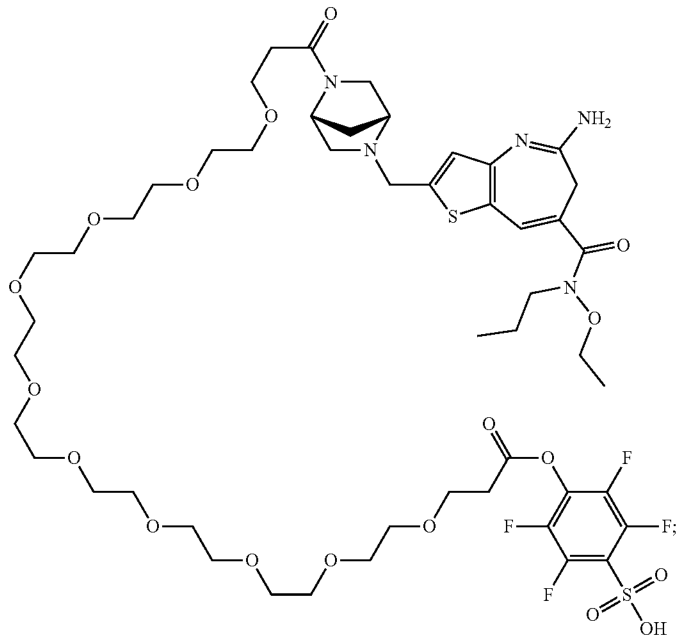
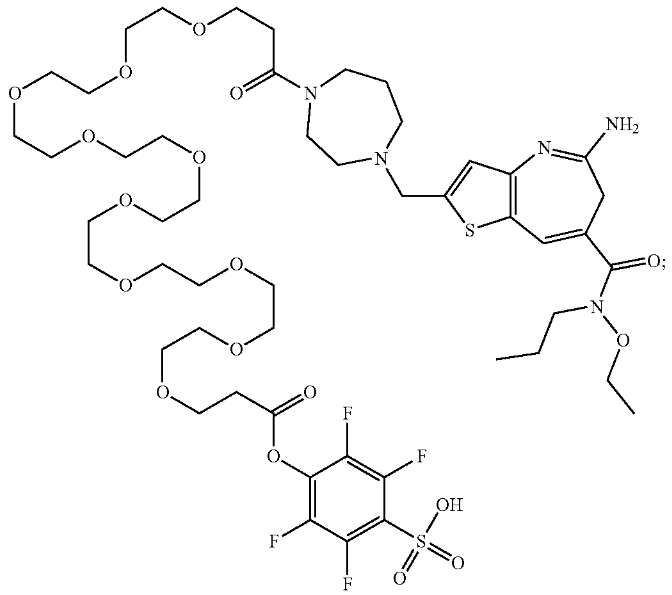

-continued
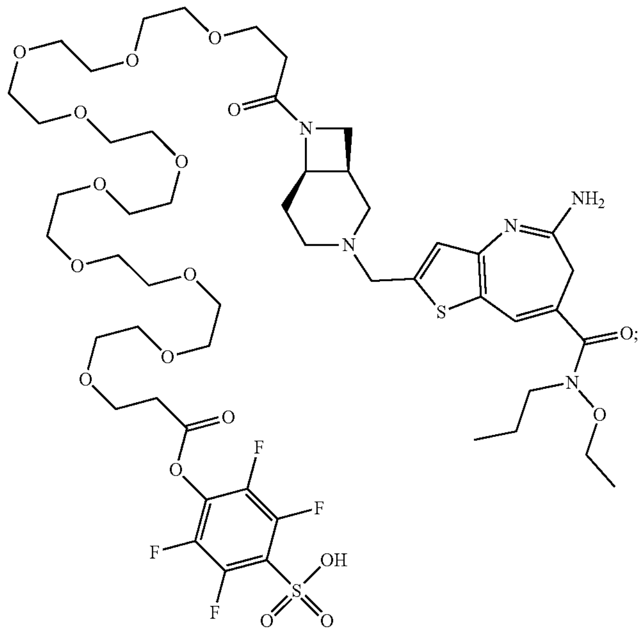
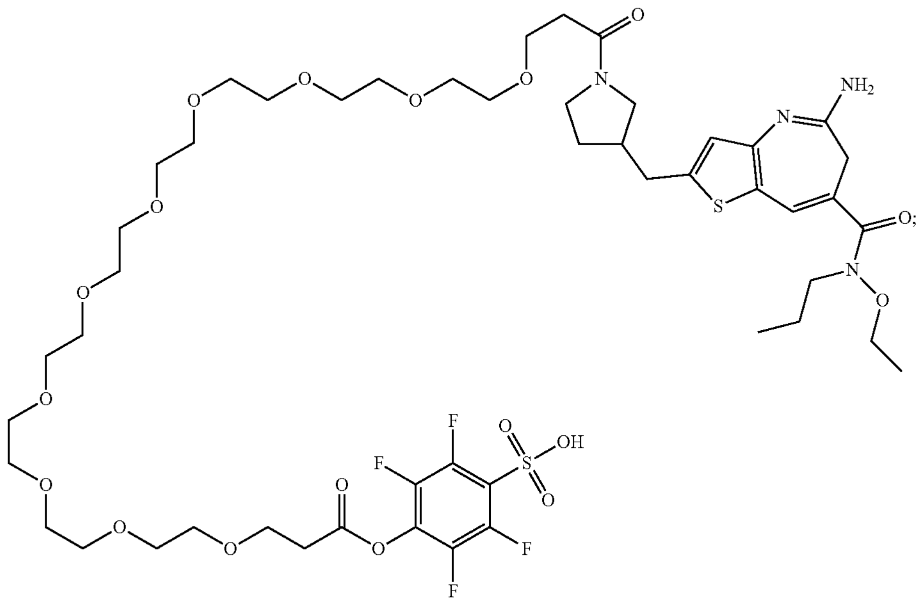

-continued
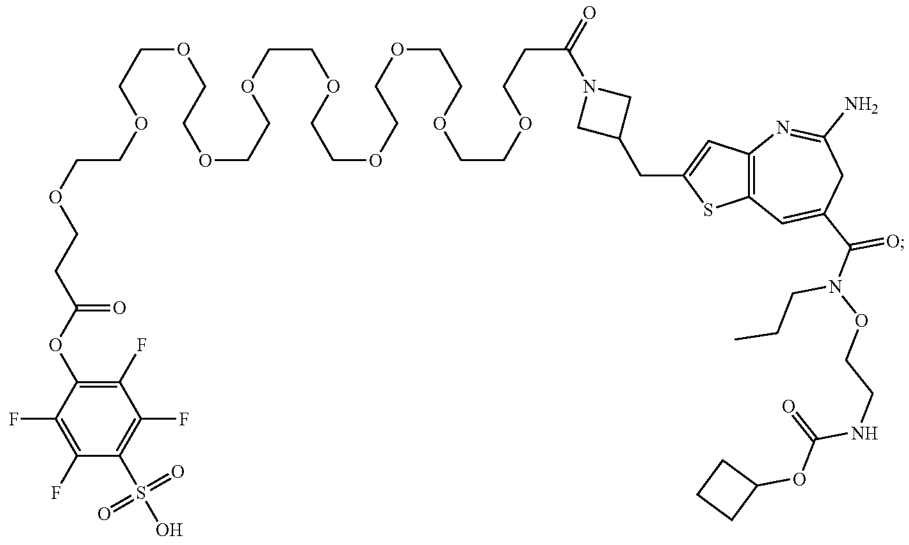
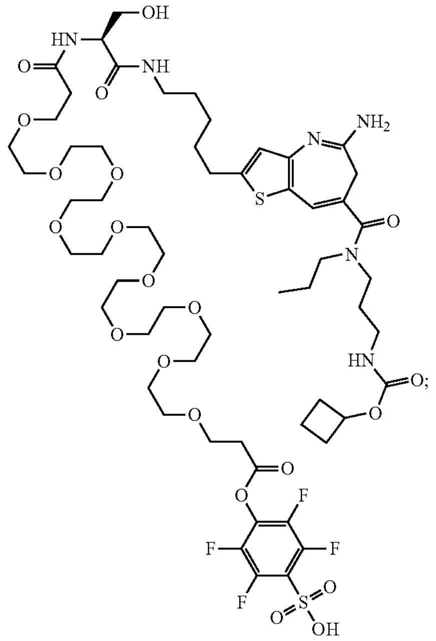
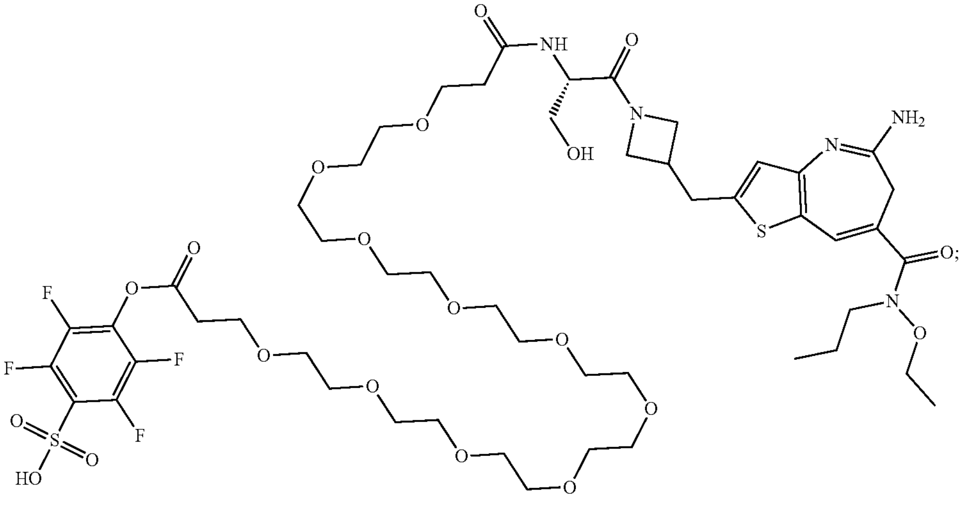

-continued
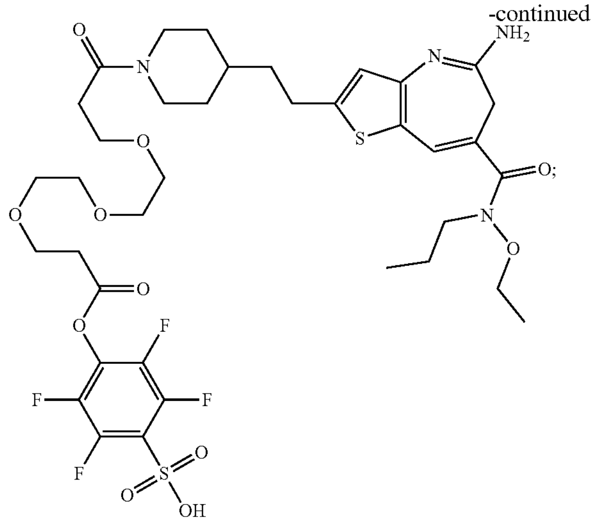
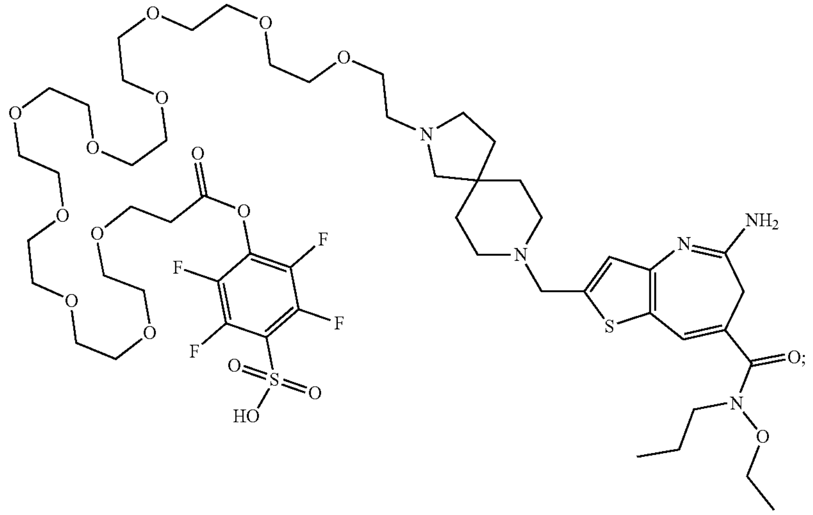

-continued
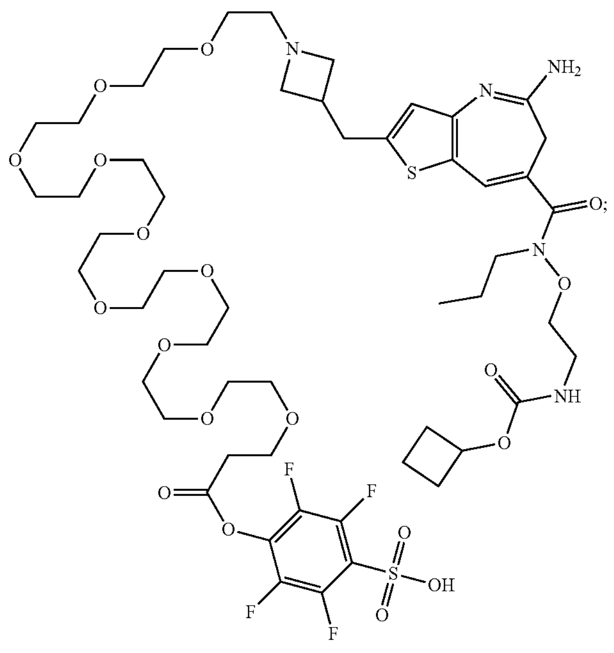
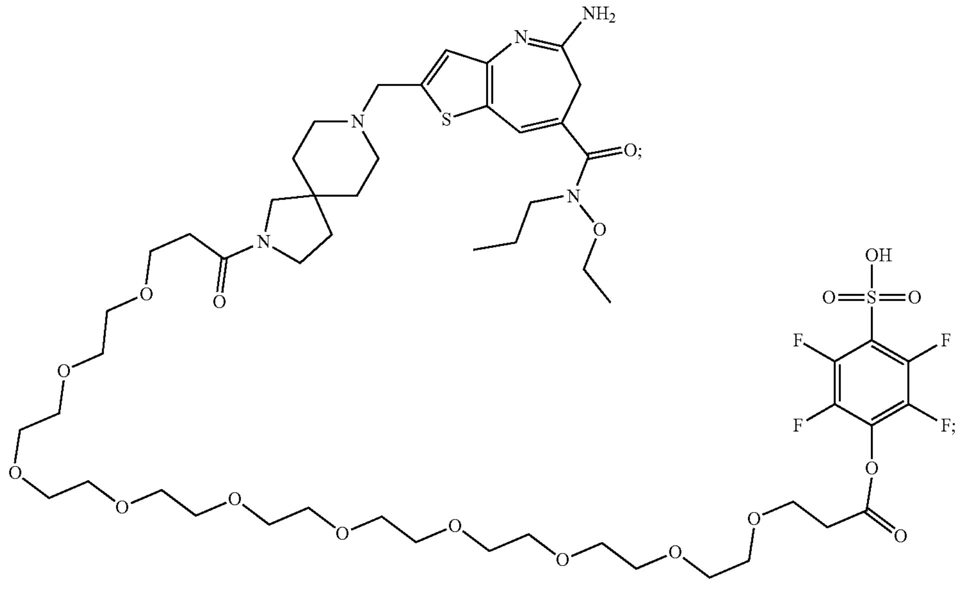

-continued
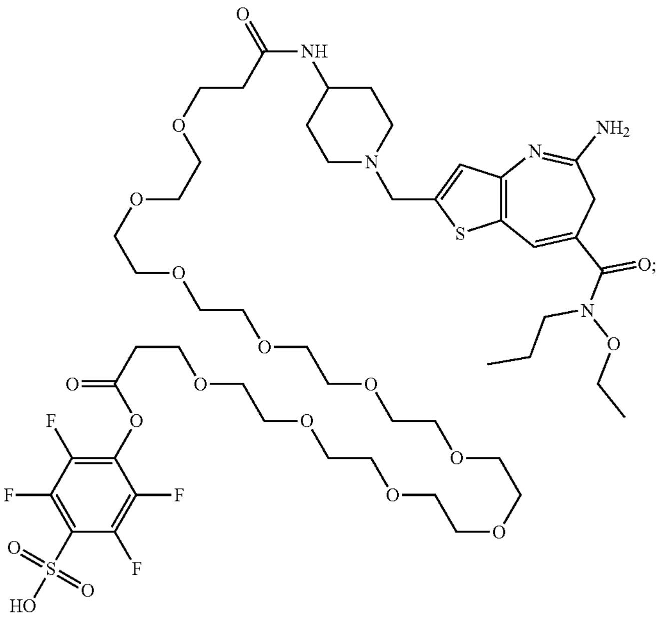
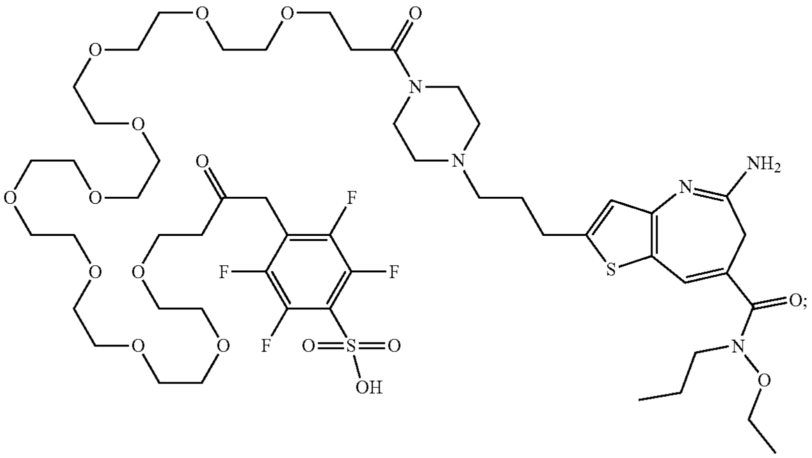
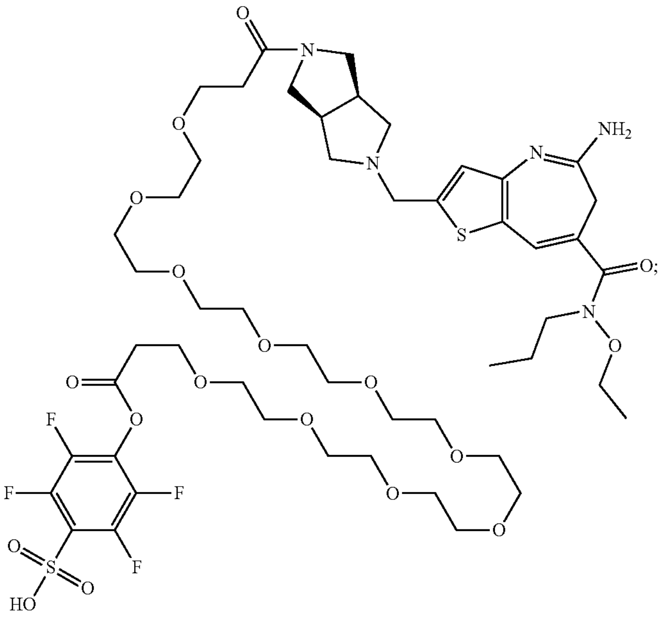

-continued
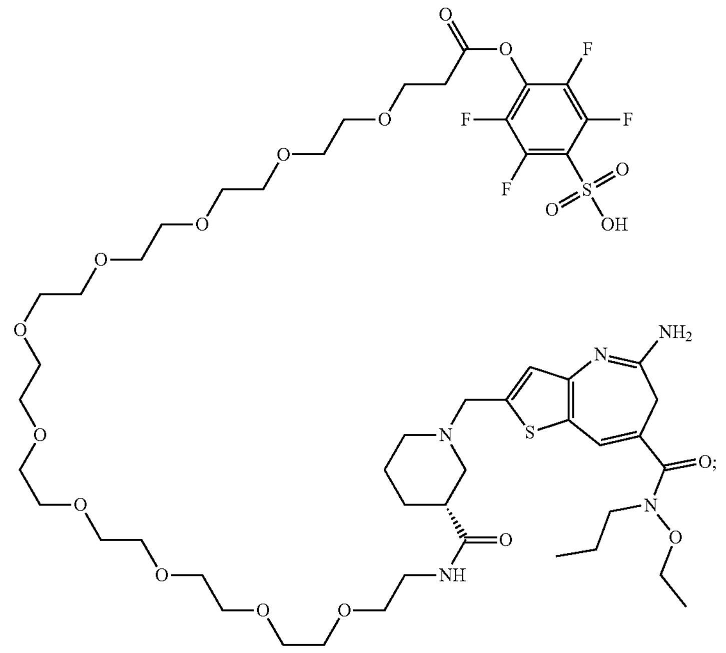
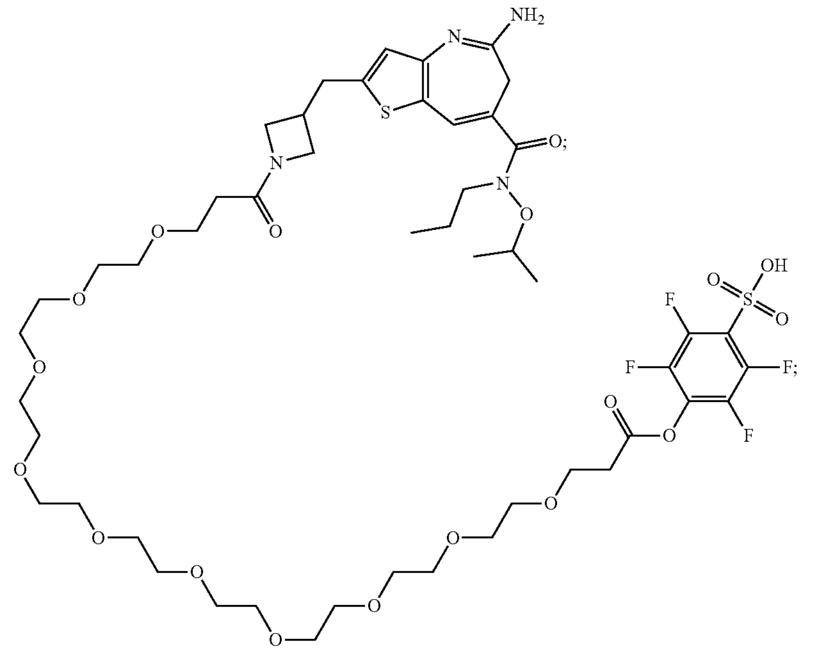

-continued
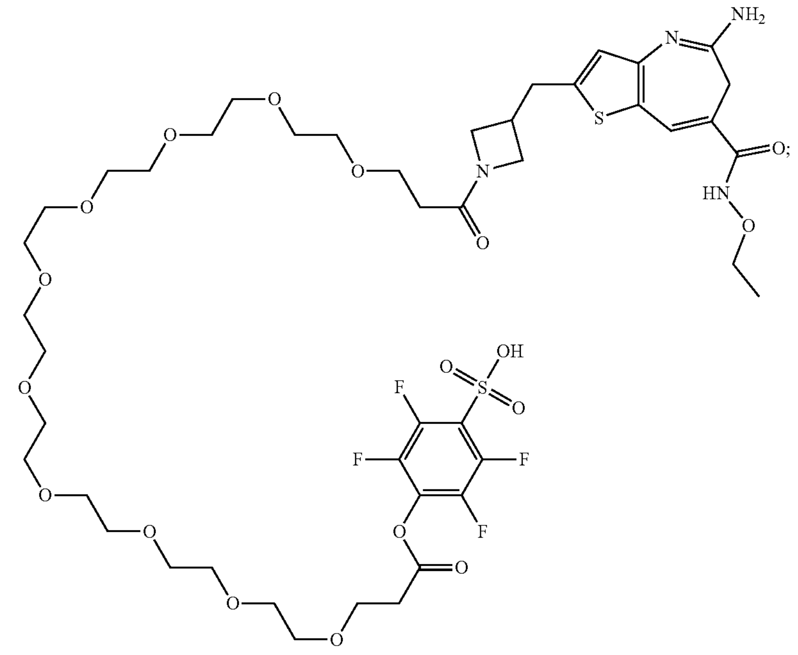
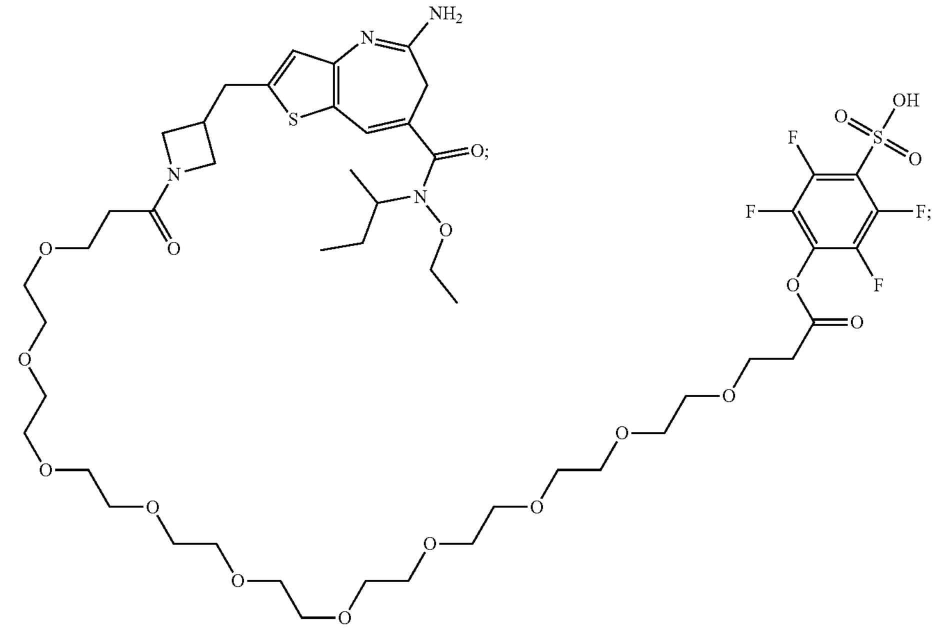

-continued
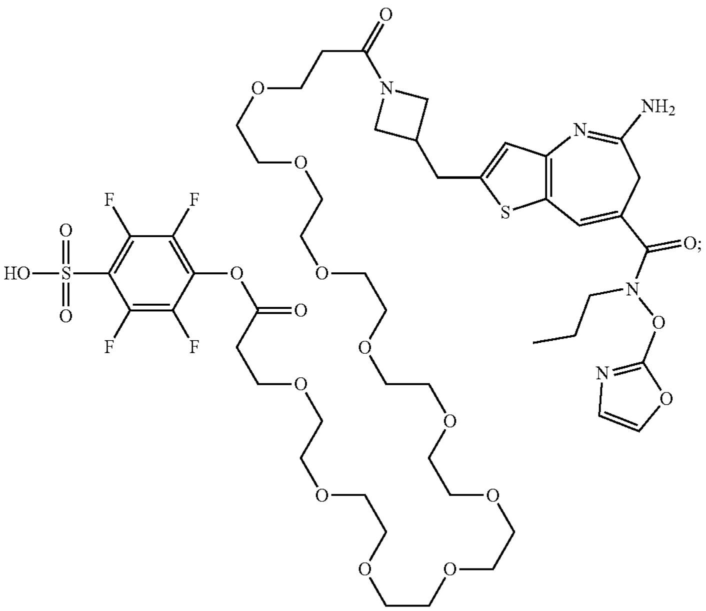
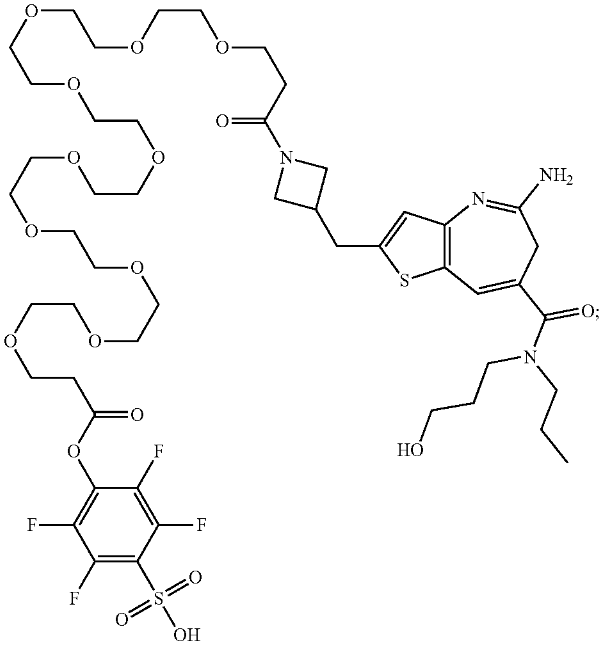

-continued
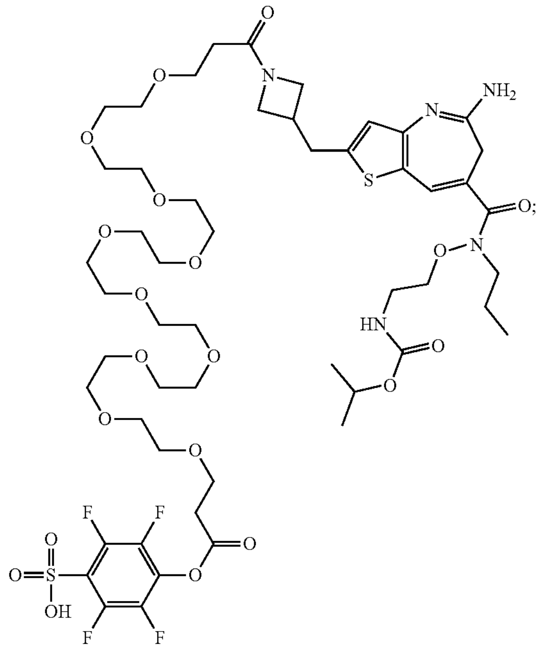
;
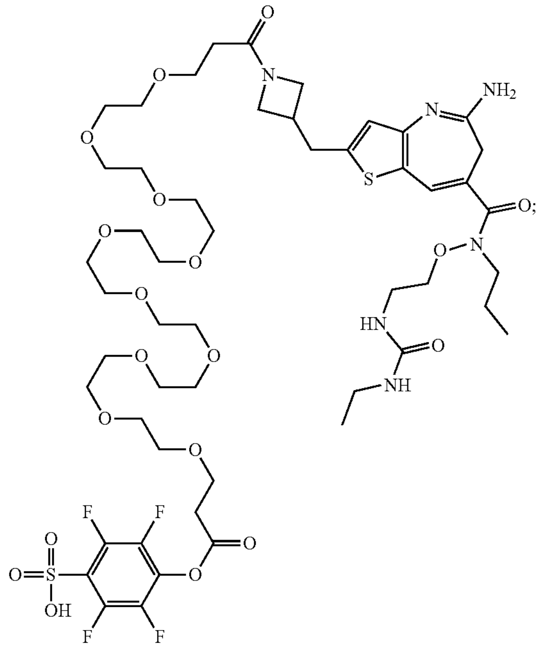
;

-continued
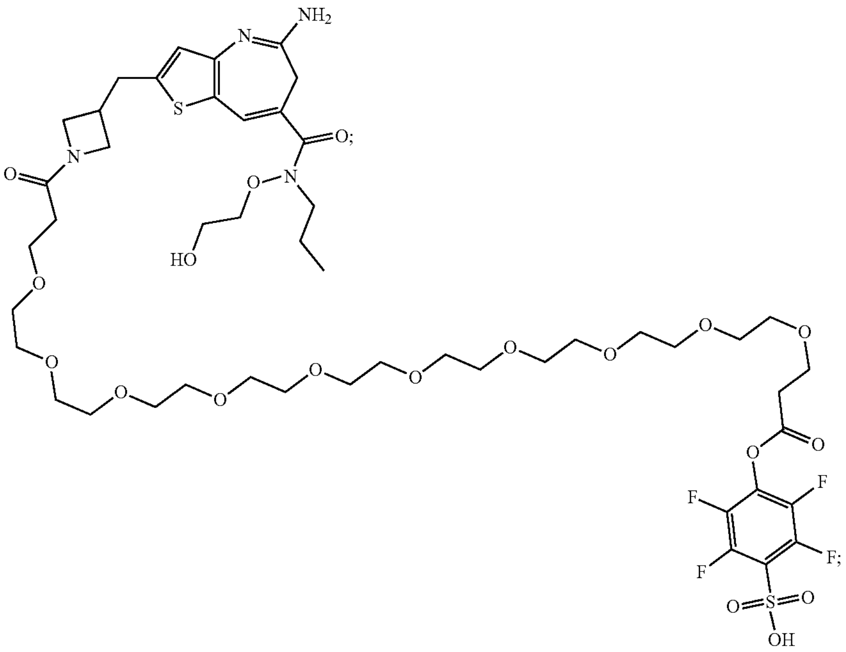
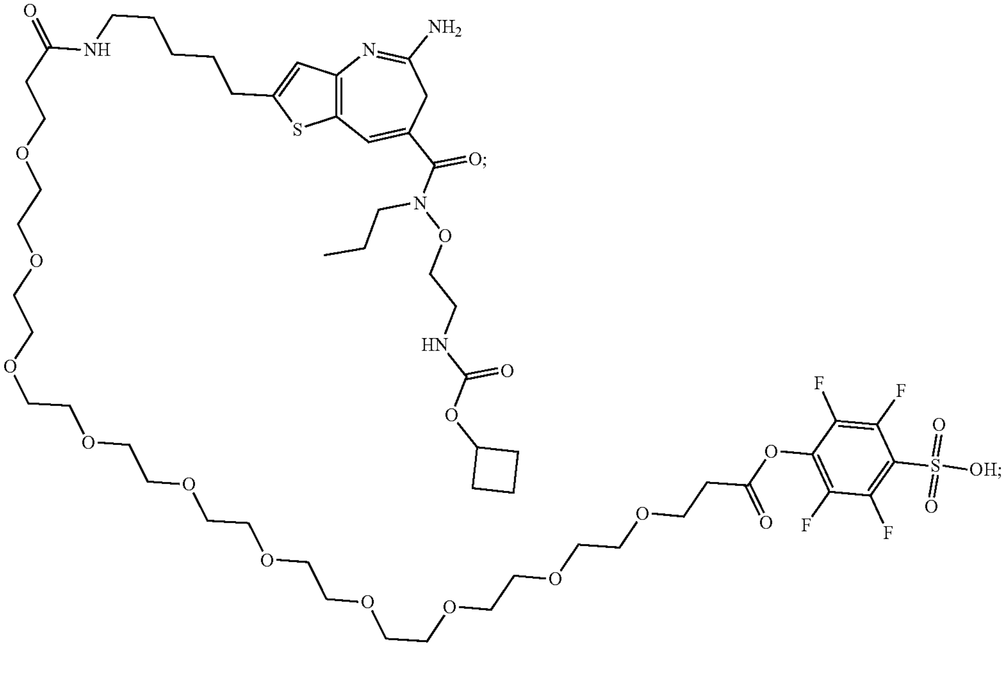

-continued
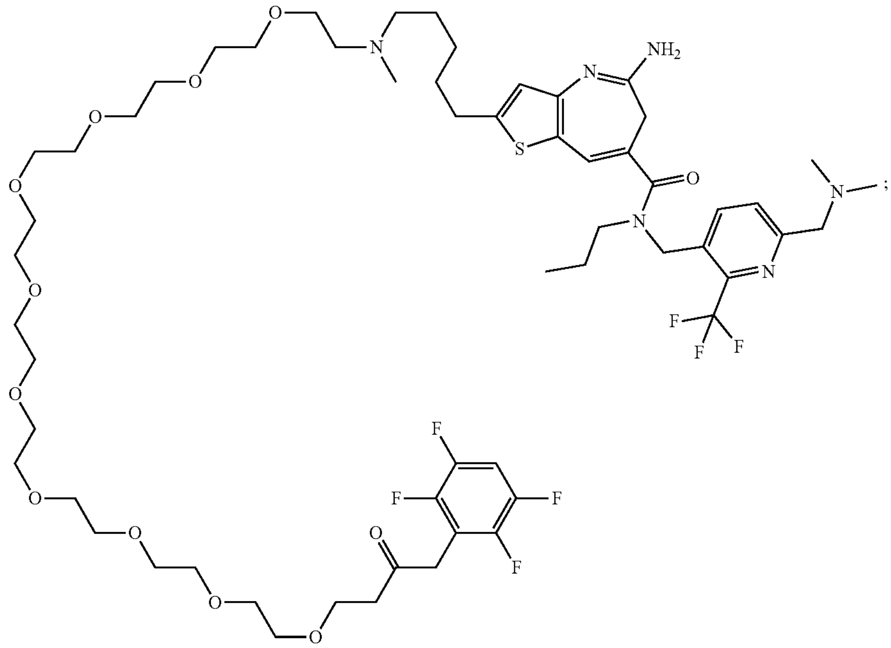
;
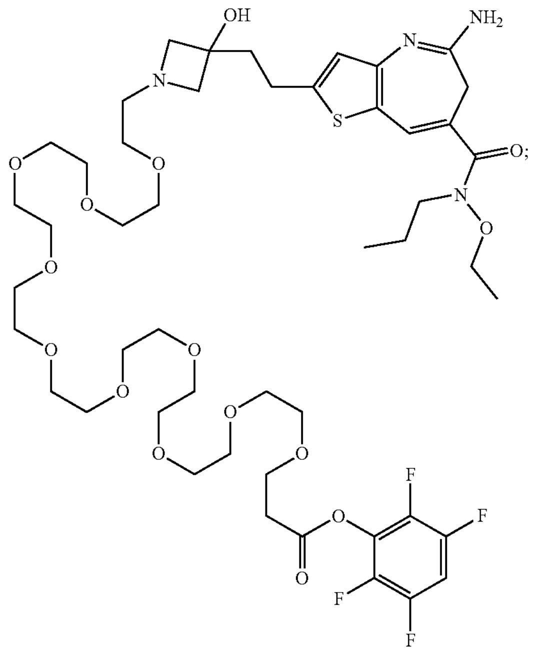
; and

-continued

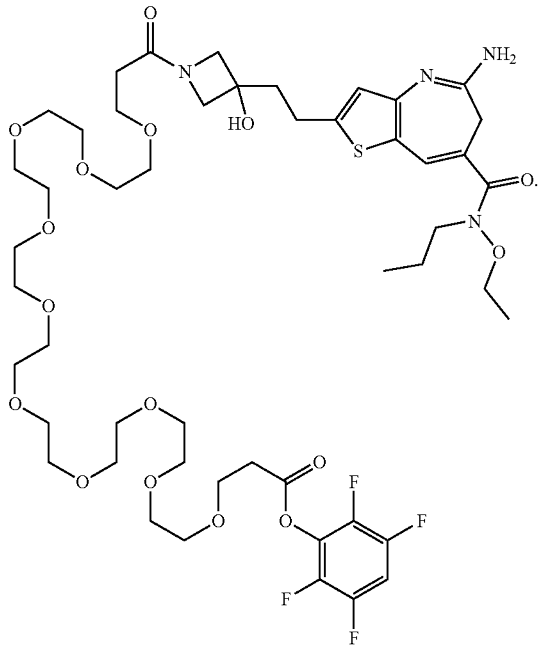 [SMILES: CCCN(OCC)C(=O)C1=Cc2sc(CCC3(O)CN(C(=O)CCOCCOCCOCCOCCOCCOCCOCCOCCOCCOCCC(=O)Oc4c(F)c(F)cc(F)c4F)C3)cc2N=C(N)C1]

26. A pharmaceutical composition comprising a therapeutically effective amount of an immunoconjugate according to claim 1 and one or more pharmaceutically acceptable diluent, vehicle, carrier or excipient.

27. A method for treating cancer comprising administering a therapeutically effective amount of a pharmaceutical composition according to claim 26, to a patient in need thereof, wherein the cancer is selected from bladder cancer, urinary tract cancer, urothelial carcinoma, lung cancer, non-small cell lung cancer, Merkel cell carcinoma, colon cancer, colorectal cancer, gastric cancer, and breast cancer.

28. The method of claim 27, wherein the cancer is susceptible to a pro-inflammatory response induced by TLR7 and/or TLR8 agonism.

29. The method of claim 27, wherein the cancer is selected from a PD-L1-expressing cancer, a HER2-expressing cancer, and a CEA-expressing cancer.

30. The method of claim 27, wherein the cancer is selected from triple-negative breast cancer, metastatic Merkel cell carcinoma, HER2 overexpressing gastric cancer, and gastroesophageal junction adenocarcinoma.

* * * * *

SEQUENCE LISTING

```
Sequence total quantity: 607
SEQ ID NO: 1            moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 1
SYAIS                                                              5

SEQ ID NO: 2            moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
```

```
SEQUENCE: 2
SYYMH                                                                 5

SEQ ID NO: 3             moltype = AA  length = 5
FEATURE                  Location/Qualifiers
REGION                   1..5
                         note = Description of Artificial Sequence: Synthetic peptide
source                   1..5
                         mol_type = protein
                         organism = synthetic construct
SEQUENCE: 3
RHLLH                                                                 5

SEQ ID NO: 4             moltype = AA  length = 5
FEATURE                  Location/Qualifiers
REGION                   1..5
                         note = Description of Artificial Sequence: Synthetic peptide
source                   1..5
                         mol_type = protein
                         organism = synthetic construct
SEQUENCE: 4
SHHMH                                                                 5

SEQ ID NO: 5             moltype = AA  length = 4
FEATURE                  Location/Qualifiers
REGION                   1..4
                         note = Description of Artificial Sequence: Synthetic peptide
source                   1..4
                         mol_type = protein
                         organism = synthetic construct
SEQUENCE: 5
RFMH                                                                  4

SEQ ID NO: 6             moltype = AA  length = 5
FEATURE                  Location/Qualifiers
REGION                   1..5
                         note = Description of Artificial Sequence: Synthetic peptide
source                   1..5
                         mol_type = protein
                         organism = synthetic construct
SEQUENCE: 6
SYYIH                                                                 5

SEQ ID NO: 7             moltype = AA  length = 5
FEATURE                  Location/Qualifiers
REGION                   1..5
                         note = Description of Artificial Sequence: Synthetic peptide
source                   1..5
                         mol_type = protein
                         organism = synthetic construct
SEQUENCE: 7
NYYIH                                                                 5

SEQ ID NO: 8             moltype = AA  length = 5
FEATURE                  Location/Qualifiers
REGION                   1..5
                         note = Description of Artificial Sequence: Synthetic peptide
source                   1..5
                         mol_type = protein
                         organism = synthetic construct
SEQUENCE: 8
HYYMH                                                                 5

SEQ ID NO: 9             moltype = AA  length = 5
FEATURE                  Location/Qualifiers
REGION                   1..5
                         note = Description of Artificial Sequence: Synthetic peptide
source                   1..5
                         mol_type = protein
                         organism = synthetic construct
SEQUENCE: 9
GYYMH                                                                 5

SEQ ID NO: 10            moltype = AA  length = 5
FEATURE                  Location/Qualifiers
REGION                   1..5
                         note = Description of Artificial Sequence: Synthetic peptide
source                   1..5
                         mol_type = protein
```

```
                        organism = synthetic construct
SEQUENCE: 10
NYMYH                                                                       5

SEQ ID NO: 11           moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 11
TYYVH                                                                       5

SEQ ID NO: 12           moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 12
SYALS                                                                       5

SEQ ID NO: 13           moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 13
RHYVH                                                                       5

SEQ ID NO: 14           moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 14
SHYMH                                                                       5

SEQ ID NO: 15           moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 15
DYYMH                                                                       5

SEQ ID NO: 16           moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 16
GYTLH                                                                       5

SEQ ID NO: 17           moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 17
NHYMH                                                                       5

SEQ ID NO: 18           moltype = AA  length = 5
FEATURE                 Location/Qualifiers
REGION                  1..5
                        note = Description of Artificial Sequence: Synthetic peptide
source                  1..5
```

```
                        mol_type = protein
                        organism = synthetic construct
SEQUENCE: 18
NSYMH                                                          5

SEQ ID NO: 19           moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 19
TYYMH                                                          5

SEQ ID NO: 20           moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 20
RHFIH                                                          5

SEQ ID NO: 21           moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 21
TFGIS                                                          5

SEQ ID NO: 22           moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 22
SYGIN                                                          5

SEQ ID NO: 23           moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 23
NHYVH                                                          5

SEQ ID NO: 24           moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 24
VINPSAGSTD YAQKFQG                                             17

SEQ ID NO: 25           moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 25
WMNPNSDIAG YAQKFQG                                             17

SEQ ID NO: 26           moltype = AA  length = 17
FEATURE                 Location/Qualifiers
REGION                  1..17
                        note = Description of Artificial Sequence: Synthetic peptide
```

```
source                  1..17
                        mol_type = protein
                        organism = synthetic construct
SEQUENCE: 26
WISPQHGVRN YAQKFQG                                          17

SEQ ID NO: 27           moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 27
WVSPSHGLTG YAQKFQG                                          17

SEQ ID NO: 28           moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 28
WMSLNSGLTG YAQKFQG                                          17

SEQ ID NO: 29           moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 29
WMKPSSGTTG YAQKFQG                                          17

SEQ ID NO: 30           moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 30
WMNPNGDVAG YAQKFQG                                          17

SEQ ID NO: 31           moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 31
GIDPNSGGTN YAQKFQG                                          17

SEQ ID NO: 32           moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 32
WMNPDSGSTG YAQKFQG                                          17

SEQ ID NO: 33           moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 33
WMSLNSGLTG YAQKFQG                                          17

SEQ ID NO: 34           moltype = AA  length = 17
FEATURE                 Location/Qualifiers
REGION                  1..17
```

-continued

```
                      note = Description of Artificial Sequence: Synthetic peptide
source                1..17
                      mol_type = protein
                      organism = synthetic construct
SEQUENCE: 34
WMNPNGDVAG YADSFQG                                                  17

SEQ ID NO: 35         moltype = AA  length = 17
FEATURE               Location/Qualifiers
REGION                1..17
                      note = Description of Artificial Sequence: Synthetic peptide
source                1..17
                      mol_type = protein
                      organism = synthetic construct
SEQUENCE: 35
WISTYHGSTN YAQKFQG                                                  17

SEQ ID NO: 36         moltype = AA  length = 17
FEATURE               Location/Qualifiers
REGION                1..17
                      note = Description of Artificial Sequence: Synthetic peptide
source                1..17
                      mol_type = protein
                      organism = synthetic construct
SEQUENCE: 36
WMNPNTVYTG SAQKFQG                                                  17

SEQ ID NO: 37         moltype = AA  length = 17
FEATURE               Location/Qualifiers
REGION                1..17
                      note = Description of Artificial Sequence: Synthetic peptide
source                1..17
                      mol_type = protein
                      organism = synthetic construct
SEQUENCE: 37
RIIPAVGSVT YAQKFQG                                                  17

SEQ ID NO: 38         moltype = AA  length = 17
FEATURE               Location/Qualifiers
REGION                1..17
                      note = Description of Artificial Sequence: Synthetic peptide
source                1..17
                      mol_type = protein
                      organism = synthetic construct
SEQUENCE: 38
GIIPIFGTAN YAQKFQG                                                  17

SEQ ID NO: 39         moltype = AA  length = 17
FEATURE               Location/Qualifiers
REGION                1..17
                      note = Description of Artificial Sequence: Synthetic peptide
source                1..17
                      mol_type = protein
                      organism = synthetic construct
SEQUENCE: 39
WMSPSSGITG YAQKFQG                                                  17

SEQ ID NO: 40         moltype = AA  length = 17
FEATURE               Location/Qualifiers
REGION                1..17
                      note = Description of Artificial Sequence: Synthetic peptide
source                1..17
                      mol_type = protein
                      organism = synthetic construct
SEQUENCE: 40
WMTPSTGNAG YAQKFQG                                                  17

SEQ ID NO: 41         moltype = AA  length = 17
FEATURE               Location/Qualifiers
REGION                1..17
                      note = Description of Artificial Sequence: Synthetic peptide
source                1..17
                      mol_type = protein
                      organism = synthetic construct
SEQUENCE: 41
WMNPNSGNTG YAQKFQG                                                  17

SEQ ID NO: 42         moltype = AA  length = 17
FEATURE               Location/Qualifiers
```

```
REGION                  1..17
                        note = Description of Artificial Sequence: Synthetic peptide
source                  1..17
                        mol_type = protein
                        organism = synthetic construct
SEQUENCE: 42
WMHPNSGHTG YAQKFQG                                                   17

SEQ ID NO: 43           moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 43
WMNPNSGHTG NAQKFQG                                                   17

SEQ ID NO: 44           moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 44
WIDPNSGVTS SAQKFQG                                                   17

SEQ ID NO: 45           moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 45
WISPNSGVTD FTQKFQG                                                   17

SEQ ID NO: 46           moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 46
WMNPNSGHTG YAQRFQG                                                   17

SEQ ID NO: 47           moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 47
WMSPNGGNTG YAQKFQG                                                   17

SEQ ID NO: 48           moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 48
WMDPSSGYTG SAHKFQG                                                   17

SEQ ID NO: 49           moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 49
WMNPHSADTG YAEKFQG                                                   17

SEQ ID NO: 50           moltype = AA  length = 17
```

-continued

```
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 50
WLTPSTGHAG YAQKFQG                                              17

SEQ ID NO: 51           moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 51
WMNPNSGHTG YAQKFQG                                              17

SEQ ID NO: 52           moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 52
WISPQHGVRN YAHKFQG                                              17

SEQ ID NO: 53           moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 53
MINPSGGSTS YAQKFQG                                              17

SEQ ID NO: 54           moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 54
WISPRSGVTS YAQKFQG                                              17

SEQ ID NO: 55           moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 55
WMDPNSGNTG YAQKFQG                                              17

SEQ ID NO: 56           moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 56
WMNPTGGITG YAQKFQG                                              17

SEQ ID NO: 57           moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 57
WVSPIHGLTG YAPRFQG                                              17
```

```
SEQ ID NO: 58           moltype = AA  length = 18
FEATURE                 Location/Qualifiers
REGION                  1..18
                        note = Description of Artificial Sequence: Synthetic peptide
source                  1..18
                        mol_type = protein
                        organism = synthetic construct
SEQUENCE: 58
DLYPYVVVVA AGSYGMDV                                          18

SEQ ID NO: 59           moltype = AA  length = 12
FEATURE                 Location/Qualifiers
REGION                  1..12
                        note = Description of Artificial Sequence: Synthetic peptide
source                  1..12
                        mol_type = protein
                        organism = synthetic construct
SEQUENCE: 59
PSIVGAYDAF DI                                                12

SEQ ID NO: 60           moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 60
ESVEGYFDL                                                    9

SEQ ID NO: 61           moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 61
DNWNVHDAFD I                                                 11

SEQ ID NO: 62           moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 62
GTYNDAFDI                                                    9

SEQ ID NO: 63           moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 63
EQWLVNDAFD I                                                 11

SEQ ID NO: 64           moltype = AA  length = 13
FEATURE                 Location/Qualifiers
REGION                  1..13
                        note = Description of Artificial Sequence: Synthetic peptide
source                  1..13
                        mol_type = protein
                        organism = synthetic construct
SEQUENCE: 64
DSSGWMRNDA FDI                                               13

SEQ ID NO: 65           moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 65
SMFPTIFGDN AFDI                                              14
```

| | |
|---|---|
| SEQ ID NO: 66 | moltype = AA length = 14 |
| FEATURE | Location/Qualifiers |
| REGION | 1..14 |
| | note = Description of Artificial Sequence: Synthetic peptide |
| source | 1..14 |
| | mol_type = protein |
| | organism = synthetic construct |
| SEQUENCE: 66 | |
| ALFPYPFYYY YMDV | 14 |
| SEQ ID NO: 67 | moltype = AA length = 7 |
| FEATURE | Location/Qualifiers |
| REGION | 1..7 |
| | note = Description of Artificial Sequence: Synthetic peptide |
| source | 1..7 |
| | mol_type = protein |
| | organism = synthetic construct |
| SEQUENCE: 67 | |
| DRGWFDP | 7 |
| SEQ ID NO: 68 | moltype = AA length = 10 |
| FEATURE | Location/Qualifiers |
| REGION | 1..10 |
| | note = Description of Artificial Sequence: Synthetic peptide |
| source | 1..10 |
| | mol_type = protein |
| | organism = synthetic construct |
| SEQUENCE: 68 | |
| DARGYSGYDL | 10 |
| SEQ ID NO: 69 | moltype = AA length = 9 |
| FEATURE | Location/Qualifiers |
| REGION | 1..9 |
| | note = Description of Artificial Sequence: Synthetic peptide |
| source | 1..9 |
| | mol_type = protein |
| | organism = synthetic construct |
| SEQUENCE: 69 | |
| EGRHGEYLY | 9 |
| SEQ ID NO: 70 | moltype = AA length = 11 |
| FEATURE | Location/Qualifiers |
| REGION | 1..11 |
| | note = Description of Artificial Sequence: Synthetic peptide |
| source | 1..11 |
| | mol_type = protein |
| | organism = synthetic construct |
| SEQUENCE: 70 | |
| EGWGSSGYFD Y | 11 |
| SEQ ID NO: 71 | moltype = AA length = 15 |
| FEATURE | Location/Qualifiers |
| REGION | 1..15 |
| | note = Description of Artificial Sequence: Synthetic peptide |
| source | 1..15 |
| | mol_type = protein |
| | organism = synthetic construct |
| SEQUENCE: 71 | |
| HLFPTVFDDY YGMDV | 15 |
| SEQ ID NO: 72 | moltype = AA length = 10 |
| FEATURE | Location/Qualifiers |
| REGION | 1..10 |
| | note = Description of Artificial Sequence: Synthetic peptide |
| source | 1..10 |
| | mol_type = protein |
| | organism = synthetic construct |
| SEQUENCE: 72 | |
| GGYSYGSFQH | 10 |
| SEQ ID NO: 73 | moltype = AA length = 10 |
| FEATURE | Location/Qualifiers |
| REGION | 1..10 |
| | note = Description of Artificial Sequence: Synthetic peptide |
| source | 1..10 |
| | mol_type = protein |
| | organism = synthetic construct |
| SEQUENCE: 73 | |

```
VRWSSDAFDI                                                        10

SEQ ID NO: 74          moltype = AA  length = 9
FEATURE                Location/Qualifiers
REGION                 1..9
                       note = Description of Artificial Sequence: Synthetic peptide
source                 1..9
                       mol_type = protein
                       organism = synthetic construct
SEQUENCE: 74
EEWLGHFQH                                                         9

SEQ ID NO: 75          moltype = AA  length = 9
FEATURE                Location/Qualifiers
REGION                 1..9
                       note = Description of Artificial Sequence: Synthetic peptide
source                 1..9
                       mol_type = protein
                       organism = synthetic construct
SEQUENCE: 75
ERFLGGMDV                                                         9

SEQ ID NO: 76          moltype = AA  length = 9
FEATURE                Location/Qualifiers
REGION                 1..9
                       note = Description of Artificial Sequence: Synthetic peptide
source                 1..9
                       mol_type = protein
                       organism = synthetic construct
SEQUENCE: 76
GNWVDAFDI                                                         9

SEQ ID NO: 77          moltype = AA  length = 11
FEATURE                Location/Qualifiers
REGION                 1..11
                       note = Description of Artificial Sequence: Synthetic peptide
source                 1..11
                       mol_type = protein
                       organism = synthetic construct
SEQUENCE: 77
ESEVMMAYFQ H                                                      11

SEQ ID NO: 78          moltype = AA  length = 9
FEATURE                Location/Qualifiers
REGION                 1..9
                       note = Description of Artificial Sequence: Synthetic peptide
source                 1..9
                       mol_type = protein
                       organism = synthetic construct
SEQUENCE: 78
ESWSGEFDY                                                         9

SEQ ID NO: 79          moltype = AA  length = 9
FEATURE                Location/Qualifiers
REGION                 1..9
                       note = Description of Artificial Sequence: Synthetic peptide
source                 1..9
                       mol_type = protein
                       organism = synthetic construct
SEQUENCE: 79
EAVAGPMDV                                                         9

SEQ ID NO: 80          moltype = AA  length = 10
FEATURE                Location/Qualifiers
REGION                 1..10
                       note = Description of Artificial Sequence: Synthetic peptide
source                 1..10
                       mol_type = protein
                       organism = synthetic construct
SEQUENCE: 80
DAWELLAFDI                                                        10

SEQ ID NO: 81          moltype = AA  length = 10
FEATURE                Location/Qualifiers
REGION                 1..10
                       note = Description of Artificial Sequence: Synthetic peptide
source                 1..10
                       mol_type = protein
                       organism = synthetic construct
```

```
SEQUENCE: 81
DRWDGDYYSA                                                    10

SEQ ID NO: 82          moltype = AA  length = 10
FEATURE                Location/Qualifiers
REGION                 1..10
                       note = Description of Artificial Sequence: Synthetic peptide
source                 1..10
                       mol_type = protein
                       organism = synthetic construct
SEQUENCE: 82
ESWELTGFDY                                                    10

SEQ ID NO: 83          moltype = AA  length = 9
FEATURE                Location/Qualifiers
REGION                 1..9
                       note = Description of Artificial Sequence: Synthetic peptide
source                 1..9
                       mol_type = protein
                       organism = synthetic construct
SEQUENCE: 83
ERFAGGMDA                                                     9

SEQ ID NO: 84          moltype = AA  length = 8
FEATURE                Location/Qualifiers
REGION                 1..8
                       note = Description of Artificial Sequence: Synthetic peptide
source                 1..8
                       mol_type = protein
                       organism = synthetic construct
SEQUENCE: 84
DSGGAFDI                                                      8

SEQ ID NO: 85          moltype = AA  length = 9
FEATURE                Location/Qualifiers
REGION                 1..9
                       note = Description of Artificial Sequence: Synthetic peptide
source                 1..9
                       mol_type = protein
                       organism = synthetic construct
SEQUENCE: 85
EVFEGGMDV                                                     9

SEQ ID NO: 86          moltype = AA  length = 9
FEATURE                Location/Qualifiers
REGION                 1..9
                       note = Description of Artificial Sequence: Synthetic peptide
source                 1..9
                       mol_type = protein
                       organism = synthetic construct
SEQUENCE: 86
EGYGGNYGN                                                     9

SEQ ID NO: 87          moltype = AA  length = 9
FEATURE                Location/Qualifiers
REGION                 1..9
                       note = Description of Artificial Sequence: Synthetic peptide
source                 1..9
                       mol_type = protein
                       organism = synthetic construct
SEQUENCE: 87
EDFYGDFDY                                                     9

SEQ ID NO: 88          moltype = AA  length = 9
FEATURE                Location/Qualifiers
REGION                 1..9
                       note = Description of Artificial Sequence: Synthetic peptide
source                 1..9
                       mol_type = protein
                       organism = synthetic construct
SEQUENCE: 88
ELSRWGFDY                                                     9

SEQ ID NO: 89          moltype = AA  length = 14
FEATURE                Location/Qualifiers
REGION                 1..14
                       note = Description of Artificial Sequence: Synthetic peptide
source                 1..14
                       mol_type = protein
```

```
                        organism = synthetic construct
SEQUENCE: 89
DIFPTMIAGG GFDL                                                        14

SEQ ID NO: 90           moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 90
GGYSYGSFDY                                                             10

SEQ ID NO: 91           moltype = AA  length = 15
FEATURE                 Location/Qualifiers
REGION                  1..15
                        note = Description of Artificial Sequence: Synthetic peptide
source                  1..15
                        mol_type = protein
                        organism = synthetic construct
SEQUENCE: 91
GSFPLVFTIF GVGDV                                                       15

SEQ ID NO: 92           moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 92
DLDYVRAFDI                                                             10

SEQ ID NO: 93           moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 93
ESWGGYFDL                                                              9

SEQ ID NO: 94           moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 94
DRTTYAFDI                                                              9

SEQ ID NO: 95           moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 95
VHGSGSDGMD V                                                           11

SEQ ID NO: 96           moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 96
RASQGIDSYL A                                                           11

SEQ ID NO: 97           moltype = AA  length = 11
FEATURE                 Location/Qualifiers
REGION                  1..11
                        note = Description of Artificial Sequence: Synthetic peptide
source                  1..11
```

```
                        mol_type = protein
                        organism = synthetic construct
SEQUENCE: 97
RASQSISSWL A                                                        11

SEQ ID NO: 98           moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 98
RASQSISSYL N                                                        11

SEQ ID NO: 99           moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 99
RASQGISSYL A                                                        11

SEQ ID NO: 100          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 100
RASQTISNYL N                                                        11

SEQ ID NO: 101          moltype = AA  length = 12
FEATURE                 Location/Qualifiers
REGION                  1..12
                        note = Description of Artificial Sequence: Synthetic peptide
source                  1..12
                        mol_type = protein
                        organism = synthetic construct
SEQUENCE: 101
RASQSVDRNY VT                                                       12

SEQ ID NO: 102          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 102
RASQGISQYL A                                                        11

SEQ ID NO: 103          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 103
QASQDIGNYL N                                                        11

SEQ ID NO: 104          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 104
RASQGIRNDL G                                                        11

SEQ ID NO: 105          moltype = AA  length = 11
FEATURE                 Location/Qualifiers
REGION                  1..11
                        note = Description of Artificial Sequence: Synthetic peptide
```

```
source                  1..11
                        mol_type = protein
                        organism = synthetic construct
SEQUENCE: 105
RASQIIGNYL A                                                       11

SEQ ID NO: 106          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 106
RASQIISSYL N                                                       11

SEQ ID NO: 107          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 107
QASQDISNYL N                                                       11

SEQ ID NO: 108          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 108
RASQGISNYL A                                                       11

SEQ ID NO: 109          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 109
RASQGISNNL N                                                       11

SEQ ID NO: 110          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 110
RASQGISNGL S                                                       11

SEQ ID NO: 111          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 111
RASQSITGWL A                                                       11

SEQ ID NO: 112          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 112
RASQGIRNDL A                                                       11

SEQ ID NO: 113          moltype = AA  length = 11
FEATURE                 Location/Qualifiers
REGION                  1..11
```

```
                        note = Description of Artificial Sequence: Synthetic peptide
source                  1..11
                        mol_type = protein
                        organism = synthetic construct
SEQUENCE: 113
QASQDISSYL N                                                        11

SEQ ID NO: 114          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 114
RASQSITTYL N                                                        11

SEQ ID NO: 115          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 115
RASQSVSTWL A                                                        11

SEQ ID NO: 116          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 116
RASQSISNWL A                                                        11

SEQ ID NO: 117          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 117
QASQGISNYL A                                                        11

SEQ ID NO: 118          moltype = AA  length = 12
FEATURE                 Location/Qualifiers
REGION                  1..12
                        note = Description of Artificial Sequence: Synthetic peptide
source                  1..12
                        mol_type = protein
                        organism = synthetic construct
SEQUENCE: 118
RASQSLSSSS LA                                                       12

SEQ ID NO: 119          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 119
RASEHIANWL A                                                        11

SEQ ID NO: 120          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 120
RASQSVGSWV A                                                        11

SEQ ID NO: 121          moltype = AA  length = 11
FEATURE                 Location/Qualifiers
```

-continued

```
REGION                1..11
                      note = Description of Artificial Sequence: Synthetic peptide
source                1..11
                      mol_type = protein
                      organism = synthetic construct
SEQUENCE: 121
RASQSISPWL A                                                  11

SEQ ID NO: 122        moltype = AA  length = 11
FEATURE               Location/Qualifiers
REGION                1..11
                      note = Description of Artificial Sequence: Synthetic peptide
source                1..11
                      mol_type = protein
                      organism = synthetic construct
SEQUENCE: 122
RASQGISRYL A                                                  11

SEQ ID NO: 123        moltype = AA  length = 12
FEATURE               Location/Qualifiers
REGION                1..12
                      note = Description of Artificial Sequence: Synthetic peptide
source                1..12
                      mol_type = protein
                      organism = synthetic construct
SEQUENCE: 123
RASQTVSSNY LA                                                 12

SEQ ID NO: 124        moltype = AA  length = 11
FEATURE               Location/Qualifiers
REGION                1..11
                      note = Description of Artificial Sequence: Synthetic peptide
source                1..11
                      mol_type = protein
                      organism = synthetic construct
SEQUENCE: 124
RSSQGIRNDL S                                                  11

SEQ ID NO: 125        moltype = AA  length = 11
FEATURE               Location/Qualifiers
REGION                1..11
                      note = Description of Artificial Sequence: Synthetic peptide
source                1..11
                      mol_type = protein
                      organism = synthetic construct
SEQUENCE: 125
RDSHSITTWL A                                                  11

SEQ ID NO: 126        moltype = AA  length = 11
FEATURE               Location/Qualifiers
REGION                1..11
                      note = Description of Artificial Sequence: Synthetic peptide
source                1..11
                      mol_type = protein
                      organism = synthetic construct
SEQUENCE: 126
RASQSISRWL A                                                  11

SEQ ID NO: 127        moltype = AA  length = 11
FEATURE               Location/Qualifiers
REGION                1..11
                      note = Description of Artificial Sequence: Synthetic peptide
source                1..11
                      mol_type = protein
                      organism = synthetic construct
SEQUENCE: 127
RASQVIRNDL A                                                  11

SEQ ID NO: 128        moltype =   length =
SEQUENCE: 128
000

SEQ ID NO: 129        moltype = AA  length = 7
FEATURE               Location/Qualifiers
REGION                1..7
                      note = Description of Artificial Sequence: Synthetic peptide
source                1..7
                      mol_type = protein
                      organism = synthetic construct
```

```
SEQUENCE: 129
AASSLQS                                                    7

SEQ ID NO: 130          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 130
GASNLQS                                                    7

SEQ ID NO: 131          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 131
GASTRAT                                                    7

SEQ ID NO: 132          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 132
GASNLHS                                                    7

SEQ ID NO: 133          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 133
AASSLES                                                    7

SEQ ID NO: 134          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 134
SASNLQS                                                    7

SEQ ID NO: 135          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 135
AASTLES                                                    7

SEQ ID NO: 136          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 136
HASILET                                                    7

SEQ ID NO: 137          moltype = AA  length = 7
FEATURE                 Location/Qualifiers
REGION                  1..7
                        note = Description of Artificial Sequence: Synthetic peptide
source                  1..7
                        mol_type = protein
```

```
                        organism = synthetic construct
SEQUENCE: 137
AASTLQS                                                                      7

SEQ ID NO: 138          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 138
AATTLQS                                                                      7

SEQ ID NO: 139          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 139
DATHLET                                                                      7

SEQ ID NO: 140          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 140
AASSLQT                                                                      7

SEQ ID NO: 141          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 141
AASSLQG                                                                      7

SEQ ID NO: 142          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 142
AASNLES                                                                      7

SEQ ID NO: 143          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 143
DVSHLES                                                                      7

SEQ ID NO: 144          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 144
DASSLQS                                                                      7

SEQ ID NO: 145          moltype = AA  length = 7
FEATURE                 Location/Qualifiers
REGION                  1..7
                        note = Description of Artificial Sequence: Synthetic peptide
source                  1..7
```

```
                        mol_type = protein
                        organism = synthetic construct
SEQUENCE: 145
GVSSLES                                                7

SEQ ID NO: 146          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 146
PASTLQS                                                7

SEQ ID NO: 147          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 147
DASNLET                                                7

SEQ ID NO: 148          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 148
GASTRAS                                                7

SEQ ID NO: 149          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 149
DSSSLQT                                                7

SEQ ID NO: 150          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 150
ATSTLQS                                                7

SEQ ID NO: 151          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 151
LASNSHS                                                7

SEQ ID NO: 152          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 152
QQSYSTPIT                                              9

SEQ ID NO: 153          moltype = AA  length = 9
FEATURE                 Location/Qualifiers
REGION                  1..9
                        note = Description of Artificial Sequence: Synthetic peptide
```

```
source                  1..9
                        mol_type = protein
                        organism = synthetic construct
SEQUENCE: 153
QQSYTTPIT                                                                  9

SEQ ID NO: 154          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 154
QQIFSTPLT                                                                  9

SEQ ID NO: 155          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 155
QQSYSTPLT                                                                  9

SEQ ID NO: 156          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 156
QQSYTTPYT                                                                  9

SEQ ID NO: 157          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 157
QQTFTTPLT                                                                  9

SEQ ID NO: 158          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 158
QQANSFPFT                                                                  9

SEQ ID NO: 159          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 159
QQSYTTPYS                                                                  9

SEQ ID NO: 160          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 160
QQTFITPLT                                                                  9

SEQ ID NO: 161          moltype = AA  length = 8
FEATURE                 Location/Qualifiers
REGION                  1..8
```

```
                        note = Description of Artificial Sequence: Synthetic peptide
source                  1..8
                        mol_type = protein
                        organism = synthetic construct
SEQUENCE: 161
QQSYSTPT                                                          8

SEQ ID NO: 162          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 162
QQGFSTPFT                                                         9

SEQ ID NO: 163          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 163
QQSFTNPVT                                                         9

SEQ ID NO: 164          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 164
QQSYSAPYT                                                         9

SEQ ID NO: 165          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 165
QQSYSTPYT                                                         9

SEQ ID NO: 166          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 166
QQSHSTPLT                                                         9

SEQ ID NO: 167          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 167
QQSYSTPFT                                                         9

SEQ ID NO: 168          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 168
QQYGSSPFT                                                         9

SEQ ID NO: 169          moltype = AA  length = 9
FEATURE                 Location/Qualifiers
```

```
REGION                 1..9
                       note = Description of Artificial Sequence: Synthetic peptide
source                 1..9
                       mol_type = protein
                       organism = synthetic construct
SEQUENCE: 169
QQTYSTPIT                                                    9

SEQ ID NO: 170         moltype = AA  length = 9
FEATURE                Location/Qualifiers
REGION                 1..9
                       note = Description of Artificial Sequence: Synthetic peptide
source                 1..9
                       mol_type = protein
                       organism = synthetic construct
SEQUENCE: 170
QQYYTTPLT                                                    9

SEQ ID NO: 171         moltype = AA  length = 9
FEATURE                Location/Qualifiers
REGION                 1..9
                       note = Description of Artificial Sequence: Synthetic peptide
source                 1..9
                       mol_type = protein
                       organism = synthetic construct
SEQUENCE: 171
QQSFSTPLT                                                    9

SEQ ID NO: 172         moltype = AA  length = 9
FEATURE                Location/Qualifiers
REGION                 1..9
                       note = Description of Artificial Sequence: Synthetic peptide
source                 1..9
                       mol_type = protein
                       organism = synthetic construct
SEQUENCE: 172
QQSYSTPPT                                                    9

SEQ ID NO: 173         moltype = AA  length = 9
FEATURE                Location/Qualifiers
REGION                 1..9
                       note = Description of Artificial Sequence: Synthetic peptide
source                 1..9
                       mol_type = protein
                       organism = synthetic construct
SEQUENCE: 173
LQHNSYPLT                                                    9

SEQ ID NO: 174         moltype = AA  length = 9
FEATURE                Location/Qualifiers
REGION                 1..9
                       note = Description of Artificial Sequence: Synthetic peptide
source                 1..9
                       mol_type = protein
                       organism = synthetic construct
SEQUENCE: 174
QQSYSTPVT                                                    9

SEQ ID NO: 175         moltype = AA  length = 9
FEATURE                Location/Qualifiers
REGION                 1..9
                       note = Description of Artificial Sequence: Synthetic peptide
source                 1..9
                       mol_type = protein
                       organism = synthetic construct
SEQUENCE: 175
QHFYNTQYT                                                    9

SEQ ID NO: 176         moltype = AA  length = 10
FEATURE                Location/Qualifiers
REGION                 1..10
                       note = Description of Artificial Sequence: Synthetic peptide
source                 1..10
                       mol_type = protein
                       organism = synthetic construct
SEQUENCE: 176
QQSLQYPSHF                                                   10

SEQ ID NO: 177         moltype = AA  length = 30
```

-continued

```
FEATURE                 Location/Qualifiers
REGION                  1..30
                        note = Description of Artificial Sequence: Synthetic
                         polypeptide
source                  1..30
                        mol_type = protein
                        organism = synthetic construct
SEQUENCE: 177
QVQLVQSGAE VKKPGASVKV SCKASGGTFS                                   30

SEQ ID NO: 178          moltype = AA  length = 30
FEATURE                 Location/Qualifiers
REGION                  1..30
                        note = Description of Artificial Sequence: Synthetic
                         polypeptide
source                  1..30
                        mol_type = protein
                        organism = synthetic construct
SEQUENCE: 178
QVQLVQSGAE VKKPGASVKV SCKASGYTFT                                   30

SEQ ID NO: 179          moltype = AA  length = 30
FEATURE                 Location/Qualifiers
REGION                  1..30
                        note = Description of Artificial Sequence: Synthetic
                         polypeptide
source                  1..30
                        mol_type = protein
                        organism = synthetic construct
SEQUENCE: 179
QVQLVQSGAE VKKPGASVKV SCKASGYTFN                                   30

SEQ ID NO: 180          moltype = AA  length = 30
FEATURE                 Location/Qualifiers
REGION                  1..30
                        note = Description of Artificial Sequence: Synthetic
                         polypeptide
source                  1..30
                        mol_type = protein
                        organism = synthetic construct
SEQUENCE: 180
QVQLVQSGAE VKKPGASVKV SCKASGNTFT                                   30

SEQ ID NO: 181          moltype = AA  length = 30
FEATURE                 Location/Qualifiers
REGION                  1..30
                        note = Description of Artificial Sequence: Synthetic
                         polypeptide
source                  1..30
                        mol_type = protein
                        organism = synthetic construct
SEQUENCE: 181
QVQLVQSGAE VKKPGASVKV SCKASGHSFT                                   30

SEQ ID NO: 182          moltype = AA  length = 30
FEATURE                 Location/Qualifiers
REGION                  1..30
                        note = Description of Artificial Sequence: Synthetic
                         polypeptide
source                  1..30
                        mol_type = protein
                        organism = synthetic construct
SEQUENCE: 182
QVQLVQSGAE VKKPGASVKV SCKASGYPFT                                   30

SEQ ID NO: 183          moltype = AA  length = 30
FEATURE                 Location/Qualifiers
REGION                  1..30
                        note = Description of Artificial Sequence: Synthetic
                         polypeptide
source                  1..30
                        mol_type = protein
                        organism = synthetic construct
SEQUENCE: 183
QVQLVQSGAE VKKPGASVKV SCKASGYRFT                                   30

SEQ ID NO: 184          moltype = AA  length = 30
FEATURE                 Location/Qualifiers
REGION                  1..30
```

```
                         note = Description of Artificial Sequence: Synthetic
                          polypeptide
source                   1..30
                         mol_type = protein
                         organism = synthetic construct
SEQUENCE: 184
QVQLVQSGAE VKKPGSSVKV SCKASGGTFS                                    30

SEQ ID NO: 185           moltype = AA  length = 30
FEATURE                  Location/Qualifiers
REGION                   1..30
                         note = Description of Artificial Sequence: Synthetic
                          polypeptide
source                   1..30
                         mol_type = protein
                         organism = synthetic construct
SEQUENCE: 185
QVQLVQSGAE VKKPGASVKV SCKASGDTFT                                    30

SEQ ID NO: 186           moltype = AA  length = 30
FEATURE                  Location/Qualifiers
REGION                   1..30
                         note = Description of Artificial Sequence: Synthetic
                          polypeptide
source                   1..30
                         mol_type = protein
                         organism = synthetic construct
SEQUENCE: 186
QVQLAQSGAE VKKPGASVKV SCKASGYTFT                                    30

SEQ ID NO: 187           moltype = AA  length = 30
FEATURE                  Location/Qualifiers
REGION                   1..30
                         note = Description of Artificial Sequence: Synthetic
                          polypeptide
source                   1..30
                         mol_type = protein
                         organism = synthetic construct
SEQUENCE: 187
QVQLVQSGAE VKKPGASVKV SCKASGYTFS                                    30

SEQ ID NO: 188           moltype = AA  length = 30
FEATURE                  Location/Qualifiers
REGION                   1..30
                         note = Description of Artificial Sequence: Synthetic
                          polypeptide
source                   1..30
                         mol_type = protein
                         organism = synthetic construct
SEQUENCE: 188
QVQLVQSGAE VKKPGASVKV SCKASGYPFS                                    30

SEQ ID NO: 189           moltype = AA  length = 30
FEATURE                  Location/Qualifiers
REGION                   1..30
                         note = Description of Artificial Sequence: Synthetic
                          polypeptide
source                   1..30
                         mol_type = protein
                         organism = synthetic construct
SEQUENCE: 189
QVQLVQSGAE VKKPGASVKV SCKASGYSFT                                    30

SEQ ID NO: 190           moltype = AA  length = 30
FEATURE                  Location/Qualifiers
REGION                   1..30
                         note = Description of Artificial Sequence: Synthetic
                          polypeptide
source                   1..30
                         mol_type = protein
                         organism = synthetic construct
SEQUENCE: 190
QVQLVQSGAE VKKPGASVKV SCKASGYTFI                                    30

SEQ ID NO: 191           moltype = AA  length = 30
FEATURE                  Location/Qualifiers
REGION                   1..30
                         note = Description of Artificial Sequence: Synthetic
                          polypeptide
```

-continued

```
source                  1..30
                        mol_type = protein
                        organism = synthetic construct
SEQUENCE: 191
QVQLVQSGAE VKKPGSSVKV SCKASGYTFT                                        30

SEQ ID NO: 192          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 192
WVRQAPGQGL EWMG                                                         14

SEQ ID NO: 193          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 193
WVRQAPGQGL EWLG                                                         14

SEQ ID NO: 194          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 194
WVRQAPGQGL EWIG                                                         14

SEQ ID NO: 195          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 195
WVRQAPGQGL EWVG                                                         14

SEQ ID NO: 196          moltype = AA  length = 32
FEATURE                 Location/Qualifiers
REGION                  1..32
                        note = Description of Artificial Sequence: Synthetic
                         polypeptide
source                  1..32
                        mol_type = protein
                        organism = synthetic construct
SEQUENCE: 196
RVTMTRDTST STVYMELSSL RSEDTAVYYC AR                                     32

SEQ ID NO: 197          moltype = AA  length = 32
FEATURE                 Location/Qualifiers
REGION                  1..32
                        note = Description of Artificial Sequence: Synthetic
                         polypeptide
source                  1..32
                        mol_type = protein
                        organism = synthetic construct
SEQUENCE: 197
RVTMTRDTST STVYMELSSL RSEDTAVYYC AI                                     32

SEQ ID NO: 198          moltype = AA  length = 32
FEATURE                 Location/Qualifiers
REGION                  1..32
                        note = Description of Artificial Sequence: Synthetic
                         polypeptide
source                  1..32
                        mol_type = protein
                        organism = synthetic construct
SEQUENCE: 198
RVTMTRDTST STVYMELSSL RSEDTAVYYC TR                                     32
```

```
SEQ ID NO: 199          moltype = AA  length = 32
FEATURE                 Location/Qualifiers
REGION                  1..32
                        note = Description of Artificial Sequence: Synthetic
                         polypeptide
source                  1..32
                        mol_type = protein
                        organism = synthetic construct
SEQUENCE: 199
RVTITADEST STAYMELSSL RSEDTAVYYC AR                                32

SEQ ID NO: 200          moltype = AA  length = 32
FEATURE                 Location/Qualifiers
REGION                  1..32
                        note = Description of Artificial Sequence: Synthetic
                         polypeptide
source                  1..32
                        mol_type = protein
                        organism = synthetic construct
SEQUENCE: 200
RVTMTRDTST STVNMELSSL RSEDTAVYYC AR                                32

SEQ ID NO: 201          moltype = AA  length = 32
FEATURE                 Location/Qualifiers
REGION                  1..32
                        note = Description of Artificial Sequence: Synthetic
                         polypeptide
source                  1..32
                        mol_type = protein
                        organism = synthetic construct
SEQUENCE: 201
RVTMTRDTST STVYMELSSL RSEDTAVYYC AE                                32

SEQ ID NO: 202          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 202
WGQGTLVTVS S                                                       11

SEQ ID NO: 203          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 203
WGQGTTVTVS S                                                       11

SEQ ID NO: 204          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 204
WGQGTMVTVS S                                                       11

SEQ ID NO: 205          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 205
WGPGTMVTVS S                                                       11

SEQ ID NO: 206          moltype = AA  length = 11
FEATURE                 Location/Qualifiers
REGION                  1..11
                        note = Description of Artificial Sequence: Synthetic peptide
source                  1..11
                        mol_type = protein
```

```
                        organism = synthetic construct
SEQUENCE: 206
WGRGTLVTVS S                                                  11

SEQ ID NO: 207          moltype = AA  length = 23
FEATURE                 Location/Qualifiers
REGION                  1..23
                        note = Description of Artificial Sequence: Synthetic peptide
source                  1..23
                        mol_type = protein
                        organism = synthetic construct
SEQUENCE: 207
DIQMTQSPSS LSASVGDRVT ITC                                     23

SEQ ID NO: 208          moltype = AA  length = 23
FEATURE                 Location/Qualifiers
REGION                  1..23
                        note = Description of Artificial Sequence: Synthetic peptide
source                  1..23
                        mol_type = protein
                        organism = synthetic construct
SEQUENCE: 208
EIVMTQSPAT LSVSPGERAT LSC                                     23

SEQ ID NO: 209          moltype = AA  length = 23
FEATURE                 Location/Qualifiers
REGION                  1..23
                        note = Description of Artificial Sequence: Synthetic peptide
source                  1..23
                        mol_type = protein
                        organism = synthetic construct
SEQUENCE: 209
DIQITHSPSS LSASVGYRLT ITC                                     23

SEQ ID NO: 210          moltype = AA  length = 15
FEATURE                 Location/Qualifiers
REGION                  1..15
                        note = Description of Artificial Sequence: Synthetic peptide
source                  1..15
                        mol_type = protein
                        organism = synthetic construct
SEQUENCE: 210
WYQQKPGKAP KLLIY                                              15

SEQ ID NO: 211          moltype = AA  length = 15
FEATURE                 Location/Qualifiers
REGION                  1..15
                        note = Description of Artificial Sequence: Synthetic peptide
source                  1..15
                        mol_type = protein
                        organism = synthetic construct
SEQUENCE: 211
WYQQKPGQAP RLLIY                                              15

SEQ ID NO: 212          moltype = AA  length = 15
FEATURE                 Location/Qualifiers
REGION                  1..15
                        note = Description of Artificial Sequence: Synthetic peptide
source                  1..15
                        mol_type = protein
                        organism = synthetic construct
SEQUENCE: 212
WYHQKPWNAP KLMIY                                              15

SEQ ID NO: 213          moltype = AA  length = 32
FEATURE                 Location/Qualifiers
REGION                  1..32
                        note = Description of Artificial Sequence: Synthetic
                         polypeptide
source                  1..32
                        mol_type = protein
                        organism = synthetic construct
SEQUENCE: 213
GVPSRFSGSG SGTDFTLTIS SLQPEDFATY YC                           32

SEQ ID NO: 214          moltype = AA  length = 32
FEATURE                 Location/Qualifiers
REGION                  1..32
                        note = Description of Artificial Sequence: Synthetic
```

```
                          polypeptide
source                    1..32
                          mol_type = protein
                          organism = synthetic construct
SEQUENCE: 214
GIPARFSGSG SGTEFTLTIS SLQSEDFAVY YC                              32

SEQ ID NO: 215            moltype = AA  length = 32
FEATURE                   Location/Qualifiers
REGION                    1..32
                          note = Description of Artificial Sequence: Synthetic
                           polypeptide
source                    1..32
                          mol_type = protein
                          organism = synthetic construct
SEQUENCE: 215
GVPSRFSGSG SGTYFTLTIS SLQPEDFATY YC                              32

SEQ ID NO: 216            moltype = AA  length = 32
FEATURE                   Location/Qualifiers
REGION                    1..32
                          note = Description of Artificial Sequence: Synthetic
                           polypeptide
source                    1..32
                          mol_type = protein
                          organism = synthetic construct
SEQUENCE: 216
GVPSRFSGSG SGTDFTLTIS SLQPEDFAPY YC                              32

SEQ ID NO: 217            moltype = AA  length = 10
FEATURE                   Location/Qualifiers
REGION                    1..10
                          note = Description of Artificial Sequence: Synthetic peptide
source                    1..10
                          mol_type = protein
                          organism = synthetic construct
SEQUENCE: 217
FGGGTKVEIK                                                       10

SEQ ID NO: 218            moltype = AA  length = 10
FEATURE                   Location/Qualifiers
REGION                    1..10
                          note = Description of Artificial Sequence: Synthetic peptide
source                    1..10
                          mol_type = protein
                          organism = synthetic construct
SEQUENCE: 218
FGQGTKVEIK                                                       10

SEQ ID NO: 219            moltype = AA  length = 10
FEATURE                   Location/Qualifiers
REGION                    1..10
                          note = Description of Artificial Sequence: Synthetic peptide
source                    1..10
                          mol_type = protein
                          organism = synthetic construct
SEQUENCE: 219
FGQGTRLEIK                                                       10

SEQ ID NO: 220            moltype = AA  length = 10
FEATURE                   Location/Qualifiers
REGION                    1..10
                          note = Description of Artificial Sequence: Synthetic peptide
source                    1..10
                          mol_type = protein
                          organism = synthetic construct
SEQUENCE: 220
FGGGTKLEIK                                                       10

SEQ ID NO: 221            moltype = AA  length = 10
FEATURE                   Location/Qualifiers
REGION                    1..10
                          note = Description of Artificial Sequence: Synthetic peptide
source                    1..10
                          mol_type = protein
                          organism = synthetic construct
SEQUENCE: 221
FGQGTKLEIK                                                       10
```

```
SEQ ID NO: 222         moltype = AA  length = 10
FEATURE                Location/Qualifiers
REGION                 1..10
                       note = Description of Artificial Sequence: Synthetic peptide
source                 1..10
                       mol_type = protein
                       organism = synthetic construct
SEQUENCE: 222
FGPGTKVDIK                                                             10

SEQ ID NO: 223         moltype = AA  length = 127
FEATURE                Location/Qualifiers
REGION                 1..127
                       note = Description of Artificial Sequence: Synthetic
                        polypeptide
source                 1..127
                       mol_type = protein
                       organism = synthetic construct
SEQUENCE: 223
QVQLVQSGAE VKKPGASVKV SCKASGGTFS SYAISWVRQA PGQGLEWMGV INPSAGSTDY  60
AQKFQGRVTM TRDTSTSTVY MELSSLRSED TAVYYCARDL YPYVVVVAAG SYGMDVWGQG  120
TLVTVSS                                                            127

SEQ ID NO: 224         moltype = AA  length = 121
FEATURE                Location/Qualifiers
REGION                 1..121
                       note = Description of Artificial Sequence: Synthetic
                        polypeptide
source                 1..121
                       mol_type = protein
                       organism = synthetic construct
SEQUENCE: 224
QVQLVQSGAE VKKPGASVKV SCKASGYTFT SYYMHWVRQA PGQGLEWMGW MNPNSDIAGY  60
AQKFQGRVTM TRDTSTSTVY MELSSLRSED TAVYYCAIPS IVGAYDAFDI WGQGTLVTVS  120
S                                                                  121

SEQ ID NO: 225         moltype = AA  length = 118
FEATURE                Location/Qualifiers
REGION                 1..118
                       note = Description of Artificial Sequence: Synthetic
                        polypeptide
source                 1..118
                       mol_type = protein
                       organism = synthetic construct
SEQUENCE: 225
QVQLVQSGAE VKKPGASVKV SCKASGYTFT RHLLHWVRQA PGQGLEWMGW ISPQHGVRNY  60
AQKFQGRVTM TRDTSTSTVY MELSSLRSED TAVYYCARES VEGYFDLWGQ GTLVTVSS    118

SEQ ID NO: 226         moltype = AA  length = 120
FEATURE                Location/Qualifiers
REGION                 1..120
                       note = Description of Artificial Sequence: Synthetic
                        polypeptide
source                 1..120
                       mol_type = protein
                       organism = synthetic construct
SEQUENCE: 226
QVQLVQSGAE VKKPGASVKV SCKASGYTFT SHHMHWVRQA PGQGLEWMGW VSPSHGLTGY  60
AQKFQGRVTM TRDTSTSTVY MELSSLRSED TAVYYCARDN WNVHDAFDIW GQGTLVTVSS  120

SEQ ID NO: 227         moltype = AA  length = 117
FEATURE                Location/Qualifiers
REGION                 1..117
                       note = Description of Artificial Sequence: Synthetic
                        polypeptide
source                 1..117
                       mol_type = protein
                       organism = synthetic construct
SEQUENCE: 227
QVQLVQSGAE VKKPGASVKV SCKASGYTFN RFMHWVRQAP GQGLEWMGWM SLNSGLTGYA  60
QKFQGRVTMT RDTSTSTVYM ELSSLRSEDT AVYYCTRGTY NDAFDIWGQG TLVTVSS     117

SEQ ID NO: 228         moltype = AA  length = 120
FEATURE                Location/Qualifiers
REGION                 1..120
                       note = Description of Artificial Sequence: Synthetic
                        polypeptide
source                 1..120
                       mol_type = protein
```

```
                      organism = synthetic construct
SEQUENCE: 228
QVQLVQSGAE VKKPGASVKV SCKASGYTFT SYYIHWVRQA PGQGLEWMGW MKPSSGTTGY  60
AQKFQGRVTM TRDTSTSTVY MELSSLRSED TAVYYCAREQ WLVNDAFDIW GQGTLVTVSS  120

SEQ ID NO: 229        moltype = AA  length = 120
FEATURE               Location/Qualifiers
REGION                1..120
                      note = Description of Artificial Sequence: Synthetic
                       polypeptide
source                1..120
                      mol_type = protein
                      organism = synthetic construct
SEQUENCE: 229
QVQLVQSGAE VKKPGASVKV SCKASGYTFT SYYIHWVRQA PGQGLEWMGW MKPSSGTTGY  60
AQKFQGRVTM TRDTSTSTVY MELSSLRSED TAVYYCAREQ WLVNDAFDIW GQGTLVTVSS  120

SEQ ID NO: 230        moltype = AA  length = 123
FEATURE               Location/Qualifiers
REGION                1..123
                      note = Description of Artificial Sequence: Synthetic
                       polypeptide
source                1..123
                      mol_type = protein
                      organism = synthetic construct
SEQUENCE: 230
QVQLVQSGAE VKKPGASVKV SCKASGNTFT SYYMHWVRQA PGQGLEWMGG IDPNSGGTNY  60
AQKFQGRVTM TRDTSTSTVY MELSSLRSED TAVYYCARSM FPTIFGDNAF DIWGQGTLVT  120
VSS                                                                123

SEQ ID NO: 231        moltype = AA  length = 123
FEATURE               Location/Qualifiers
REGION                1..123
                      note = Description of Artificial Sequence: Synthetic
                       polypeptide
source                1..123
                      mol_type = protein
                      organism = synthetic construct
SEQUENCE: 231
QVQLVQSGAE VKKPGASVKV SCKASGHSFT HYYMHWVRQA PGQGLEWMGW MNPDSGSTGY  60
AQKFQGRVTM TRDTSTSTVY MELSSLRSED TAVYYCARAL FPYPFYYYYM DVWGQGTLVT  120
VSS                                                                123

SEQ ID NO: 232        moltype = AA  length = 116
FEATURE               Location/Qualifiers
REGION                1..116
                      note = Description of Artificial Sequence: Synthetic
                       polypeptide
source                1..116
                      mol_type = protein
                      organism = synthetic construct
SEQUENCE: 232
QVQLVQSGAE VKKPGASVKV SCKASGYTFT GYYMHWVRQA PGQGLEWIGW MSLNSGLTGY  60
AQKFQGRVTM TRDTSTSTVY MELSSLRSED TAVYYCARDR GWFDPWGQGT LVTVSS      116

SEQ ID NO: 233        moltype = AA  length = 122
FEATURE               Location/Qualifiers
REGION                1..122
                      note = Description of Artificial Sequence: Synthetic
                       polypeptide
source                1..122
                      mol_type = protein
                      organism = synthetic construct
SEQUENCE: 233
QVQLVQSGAE VKKPGASVKV SCKASGYTFT NYYIHWVRQA PGQGLEWLGW MNPNGDVAGY  60
ADSFQGRVTM TRDTSTSTVY MELSSLRSED TAVYYCAIDS SGWMRNDAFD IWGQGTLVTV  120
SS                                                                 122

SEQ ID NO: 234        moltype = AA  length = 119
FEATURE               Location/Qualifiers
REGION                1..119
                      note = Description of Artificial Sequence: Synthetic
                       polypeptide
source                1..119
                      mol_type = protein
                      organism = synthetic construct
SEQUENCE: 234
QVQLVQSGAE VKKPGASVKV SCKASGGTFS NYMYHWVRQA PGQGLEWMGW ISTYHGSTNY  60
AQKFQGRVTM TRDTSTSTVY MELSSLRSED TAVYYCARDA RGYSGYDLWG QGTLVTVSS   119
```

```
SEQ ID NO: 235         moltype = AA  length = 118
FEATURE                Location/Qualifiers
REGION                 1..118
                       note = Description of Artificial Sequence: Synthetic
                        polypeptide
source                 1..118
                       mol_type = protein
                       organism = synthetic construct
SEQUENCE: 235
QVQLVQSGAE VKKPGASVKV SCKASGYPFT SYYMHWVRQA PGQGLEWMGW MNPNSDIAGY  60
AQKFQGRVTM TRDTSTSTVY MELSSLRSED TAVYYCAREG RHGEYLYWGQ GTLVTVSS    118

SEQ ID NO: 236         moltype = AA  length = 120
FEATURE                Location/Qualifiers
REGION                 1..120
                       note = Description of Artificial Sequence: Synthetic
                        polypeptide
source                 1..120
                       mol_type = protein
                       organism = synthetic construct
SEQUENCE: 236
QVQLVQSGAE VKKPGASVKV SCKASGYRFT TYYVHWVRQA PGQGLEWMGW MNPNTVYTGS  60
AQKFQGRVTM TRDTSTSTVY MELSSLRSED TAVYYCAREG WGSSGYFDYW GQGTLVTVSS  120

SEQ ID NO: 237         moltype = AA  length = 124
FEATURE                Location/Qualifiers
REGION                 1..124
                       note = Description of Artificial Sequence: Synthetic
                        polypeptide
source                 1..124
                       mol_type = protein
                       organism = synthetic construct
SEQUENCE: 237
QVQLVQSGAE VKKPGSSVKV SCKASGGTFS SYALSWVRQA PGQGLEWMGR IIPAVGSVTY  60
AQKFQGRVTI TADESTSTAY MELSSLRSED TAVYYCARHL FPTVFDDYYG MDVWGQGTLV  120
TVSS                                                               124

SEQ ID NO: 238         moltype = AA  length = 119
FEATURE                Location/Qualifiers
REGION                 1..119
                       note = Description of Artificial Sequence: Synthetic
                        polypeptide
source                 1..119
                       mol_type = protein
                       organism = synthetic construct
SEQUENCE: 238
QVQLVQSGAE VKKPGSSVKV SCKASGGTFS SYAISWVRQA PGQGLEWMGG IIPIFGTANY  60
AQKFQGRVTI TADESTSTAY MELSSLRSED TAVYYCARGG YSYGSFQHWG QGTLVTVSS   119

SEQ ID NO: 239         moltype = AA  length = 119
FEATURE                Location/Qualifiers
REGION                 1..119
                       note = Description of Artificial Sequence: Synthetic
                        polypeptide
source                 1..119
                       mol_type = protein
                       organism = synthetic construct
SEQUENCE: 239
QVQLVQSGAE VKKPGASVKV SCKASGDTFT RHYVHWVRQA PGQGLEWMGW MSPSSGITGY  60
AQKFQGRVTM TRDTSTSTVY MELSSLRSED TAVYYCARVR WSSDAFDIWG QGTLVTVSS   119

SEQ ID NO: 240         moltype = AA  length = 118
FEATURE                Location/Qualifiers
REGION                 1..118
                       note = Description of Artificial Sequence: Synthetic
                        polypeptide
source                 1..118
                       mol_type = protein
                       organism = synthetic construct
SEQUENCE: 240
QVQLVQSGAE VKKPGASVKV SCKASGYTFT SYYMHWVRQA PGQGLEWVGW MTPSTGNAGY  60
AQKFQGRVTM TRDTSTSTVY MELSSLRSED TAVYYCAREE WLGHFQHWGQ GTLVTVSS    118

SEQ ID NO: 241         moltype = AA  length = 118
FEATURE                Location/Qualifiers
REGION                 1..118
                       note = Description of Artificial Sequence: Synthetic
                        polypeptide
```

-continued

```
source                  1..118
                        mol_type = protein
                        organism = synthetic construct
SEQUENCE: 241
QVQLVQSGAE VKKPGASVKV SCKASGYTFT SHYMHWVRQA PGQGLEWMGW MNPNSGNTGY  60
AQKFQGRVTM TRDTSTSTVY MELSSLRSED TAVYYCARER FLGGMDVWGQ GTTVTVSS    118

SEQ ID NO: 242          moltype = AA  length = 118
FEATURE                 Location/Qualifiers
REGION                  1..118
                        note = Description of Artificial Sequence: Synthetic
                         polypeptide
source                  1..118
                        mol_type = protein
                        organism = synthetic construct
SEQUENCE: 242
QVQLVQSGAE VKKPGASVKV SCKASGYTFT DYYMHWVRQA PGQGLEWMGW MHPNSGHTGY  60
AQKFQGRVTM TRDTSTSTVN MELSSLRSED TAVYYCAREE WLGHFQHWGQ GTLVTVSS    118

SEQ ID NO: 243          moltype = AA  length = 118
FEATURE                 Location/Qualifiers
REGION                  1..118
                        note = Description of Artificial Sequence: Synthetic
                         polypeptide
source                  1..118
                        mol_type = protein
                        organism = synthetic construct
SEQUENCE: 243
QVQLVQSGAE VKKPGASVKV SCKASGYTFT SHYMHWVRQA PGQGLEWMGW MNPNSGHTGN  60
AQKFQGRVTM TRDTSTSTVY MELSSLRSED TAVYYCARGN WVDAFDIWGQ GTMVTVSS    118

SEQ ID NO: 244          moltype = AA  length = 120
FEATURE                 Location/Qualifiers
REGION                  1..120
                        note = Description of Artificial Sequence: Synthetic
                         polypeptide
source                  1..120
                        mol_type = protein
                        organism = synthetic construct
SEQUENCE: 244
QVQLVQSGAE VKKPGASVKV SCKASGYTFT GYTLHWVRQA PGQGLEWMGW IDPNSGVTSS  60
AQKFQGRVTM TRDTSTSTVY MELSSLRSED TAVYYCARES EVMMAYFQHW GQGTLVTVSS  120

SEQ ID NO: 245          moltype = AA  length = 118
FEATURE                 Location/Qualifiers
REGION                  1..118
                        note = Description of Artificial Sequence: Synthetic
                         polypeptide
source                  1..118
                        mol_type = protein
                        organism = synthetic construct
SEQUENCE: 245
QVQLVQSGAE VKKPGASVKV SCKASGYTFT GYYMHWVRQA PGQGLEWMGW ISPNSGVTDF  60
TQKFQGRVTM TRDTSTSTVY MELSSLRSED TAVYYCARES WSGEFDYWGQ GTLVTVSS    118

SEQ ID NO: 246          moltype = AA  length = 118
FEATURE                 Location/Qualifiers
REGION                  1..118
                        note = Description of Artificial Sequence: Synthetic
                         polypeptide
source                  1..118
                        mol_type = protein
                        organism = synthetic construct
SEQUENCE: 246
QVQLVQSGAE VKKPGASVKV SCKASGDTFT NHYMHWVRQA PGQGLEWMGW MNPNSGHTGY  60
AQRFQGRVTM TRDTSTSTVY MELSSLRSED TAVYYCAREA VAGPMDVWGQ GTTVTVSS    118

SEQ ID NO: 247          moltype = AA  length = 119
FEATURE                 Location/Qualifiers
REGION                  1..119
                        note = Description of Artificial Sequence: Synthetic
                         polypeptide
source                  1..119
                        mol_type = protein
                        organism = synthetic construct
SEQUENCE: 247
QVQLVQSGAE VKKPGASVKV SCKASGYTFT GYYMHWVRQA PGQGLEWMGW MNPNSDIAGY  60
AQKFQGRVTM TRDTSTSTVY MELSSLRSED TAVYYCARDA WELLAFDIWG QGTLVTVSS   119
```

```
SEQ ID NO: 248          moltype = AA  length = 119
FEATURE                 Location/Qualifiers
REGION                  1..119
                        note = Description of Artificial Sequence: Synthetic
                         polypeptide
source                  1..119
                        mol_type = protein
                        organism = synthetic construct
SEQUENCE: 248
QVQLAQSGAE VKKPGASVKV SCKASGYTFT NHYMHWVRQA PGQGLEWMGW MNPNSGNTGY  60
AQKFQGRVTM TRDTSTSTVY MELSSLRSED TAVYYCARDR WDGDYYSAWG QGTLVTVSS   119

SEQ ID NO: 249          moltype = AA  length = 119
FEATURE                 Location/Qualifiers
REGION                  1..119
                        note = Description of Artificial Sequence: Synthetic
                         polypeptide
source                  1..119
                        mol_type = protein
                        organism = synthetic construct
SEQUENCE: 249
QVQLVQSGAE VKKPGASVKV SCKASGYTFT NYYIHWVRQA PGQGLEWMGW MSPNGGNTGY  60
AQKFQGRVTM TRDTSTSTVY MELSSLRSED TAVYYCARES WELTGFDYWG QGTLVTVSS   119

SEQ ID NO: 250          moltype = AA  length = 118
FEATURE                 Location/Qualifiers
REGION                  1..118
                        note = Description of Artificial Sequence: Synthetic
                         polypeptide
source                  1..118
                        mol_type = protein
                        organism = synthetic construct
SEQUENCE: 250
QVQLVQSGAE VKKPGASVKV SCKASGYTFT SYYMHWVRQA PGQGLEWMGW MNPNSGNTGY  60
AQKFQGRVTM TRDTSTSTVY MELSSLRSED TAVYYCARER FAGGMDAWGQ GTTVTVSS    118

SEQ ID NO: 251          moltype = AA  length = 117
FEATURE                 Location/Qualifiers
REGION                  1..117
                        note = Description of Artificial Sequence: Synthetic
                         polypeptide
source                  1..117
                        mol_type = protein
                        organism = synthetic construct
SEQUENCE: 251
QVQLVQSGAE VKKPGASVKV SCKASGYTFS NSYMHWVRQA PGQGLEWMGW MDPSSGYTGS  60
AHKFQGRVTM TRDTSTSTVY MELSSLRSED TAVYYCAEDS GGAFDIWGQG TMVTVSS     117

SEQ ID NO: 252          moltype = AA  length = 118
FEATURE                 Location/Qualifiers
REGION                  1..118
                        note = Description of Artificial Sequence: Synthetic
                         polypeptide
source                  1..118
                        mol_type = protein
                        organism = synthetic construct
SEQUENCE: 252
QVQLVQSGAE VKKPGASVKV SCKASGYPFS TYYMHWVRQA PGQGLEWMGW MNPHSADTGY  60
AEKFQGRVTM TRDTSTSTVY MELSSLRSED TAVYYCAREV FEGGMDVWGQ GTTVTVSS    118

SEQ ID NO: 253          moltype = AA  length = 118
FEATURE                 Location/Qualifiers
REGION                  1..118
                        note = Description of Artificial Sequence: Synthetic
                         polypeptide
source                  1..118
                        mol_type = protein
                        organism = synthetic construct
SEQUENCE: 253
QVQLVQSGAE VKKPGASVKV SCKASGYTFT SYYMHWVRQA PGQGLEWMGW LTPSTGHAGY  60
AQKFQGRVTM TRDTSTSTVY MELSSLRSED TAVYYCAREG YGGNYGNWGQ GTLVTVSS    118

SEQ ID NO: 254          moltype = AA  length = 118
FEATURE                 Location/Qualifiers
REGION                  1..118
                        note = Description of Artificial Sequence: Synthetic
                         polypeptide
source                  1..118
                        mol_type = protein
```

```
                          organism = synthetic construct
SEQUENCE: 254
QVQLVQSGAE VKKPGASVKV SCKASGYTFT SYYMHWVRQA PGQGLEWMGW MNPNSGHTGY  60
AQKFQGRVTM TRDTSTSTVY MELSSLRSED TAVYYCARED FYGDFDYWGQ GTLVTVSS    118

SEQ ID NO: 255            moltype = AA  length = 118
FEATURE                   Location/Qualifiers
REGION                    1..118
                          note = Description of Artificial Sequence: Synthetic
                           polypeptide
source                    1..118
                          mol_type = protein
                          organism = synthetic construct
SEQUENCE: 255
QVQLVQSGAE VKKPGASVKV SCKASGYTFT RHFIHWVRQA PGQGLEWMGW IDPNSGVTSS  60
AQKFQGRVTM TRDTSTSTVY MELSSLRSED TAVYYCAREL SRWGFDYWGP GTMVTVSS    118

SEQ ID NO: 256            moltype = AA  length = 118
FEATURE                   Location/Qualifiers
REGION                    1..118
                          note = Description of Artificial Sequence: Synthetic
                           polypeptide
source                    1..118
                          mol_type = protein
                          organism = synthetic construct
SEQUENCE: 256
QVQLVQSGAE VKKPGASVKV SCKASGYTFT RHLLHWVRQA PGQGLEWMGW ISPQHGVRNY  60
AHKFQGRVTM TRDTSTSTVY MELSSLRSED TAVYYCARES VEGYFDLWGR GTLVTVSS    118

SEQ ID NO: 257            moltype = AA  length = 123
FEATURE                   Location/Qualifiers
REGION                    1..123
                          note = Description of Artificial Sequence: Synthetic
                           polypeptide
source                    1..123
                          mol_type = protein
                          organism = synthetic construct
SEQUENCE: 257
QVQLVQSGAE VKKPGASVKV SCKASGYPFS SYYMHWVRQA PGQGLEWMGM INPSGGSTSY  60
AQKFQGRVTM TRDTSTSTVY MELSSLRSED TAVYYCARDI FPTMIAGGGF DLWGRGTLVT  120
VSS                                                                123

SEQ ID NO: 258            moltype = AA  length = 119
FEATURE                   Location/Qualifiers
REGION                    1..119
                          note = Description of Artificial Sequence: Synthetic
                           polypeptide
source                    1..119
                          mol_type = protein
                          organism = synthetic construct
SEQUENCE: 258
QVQLVQSGAE VKKPGSSVKV SCKASGGTFS TFGISWVRQA PGQGLEWMGG IIPIFGTANY  60
AQKFQGRVTI TADESTSTAY MELSSLRSED TAVYYCARGG YSYGSFDYWG QGTLVTVSS   119

SEQ ID NO: 259            moltype = AA  length = 124
FEATURE                   Location/Qualifiers
REGION                    1..124
                          note = Description of Artificial Sequence: Synthetic
                           polypeptide
source                    1..124
                          mol_type = protein
                          organism = synthetic construct
SEQUENCE: 259
QVQLVQSGAE VKKPGASVKV SCKASGYTFT SYGINWVRQA PGQGLEWMGW MNPNSGNTGY  60
AQKFQGRVTM TRDTSTSTVY MELSSLRSED TAVYYCARGS FPLVFTIFGV GDVWGQGTMV  120
TVSS                                                               124

SEQ ID NO: 260            moltype = AA  length = 119
FEATURE                   Location/Qualifiers
REGION                    1..119
                          note = Description of Artificial Sequence: Synthetic
                           polypeptide
source                    1..119
                          mol_type = protein
                          organism = synthetic construct
SEQUENCE: 260
QVQLVQSGAE VKKPGASVKV SCKASGYTFT SYYMHWVRQA PGQGLEWMGW ISPRSGVTSY  60
AQKFQGRVTM TRDTSTSTVY MELSSLRSED TAVYYCARDL DYVRAFDIWG QGTTVTVSS   119
```

-continued

```
SEQ ID NO: 261         moltype = AA  length = 118
FEATURE                Location/Qualifiers
REGION                 1..118
                       note = Description of Artificial Sequence: Synthetic
                        polypeptide
source                 1..118
                       mol_type = protein
                       organism = synthetic construct
SEQUENCE: 261
QVQLVQSGAE VKKPGASVKV SCKASGYSFT SYYMHWVRQA PGQGLEWMGW MDPNSGNTGY  60
AQKFQGRVTM TRDTSTSTVY MELSSLRSED TAVYYCARES WGGYFDLWGR GTLVTVSS    118

SEQ ID NO: 262         moltype = AA  length = 118
FEATURE                Location/Qualifiers
REGION                 1..118
                       note = Description of Artificial Sequence: Synthetic
                        polypeptide
source                 1..118
                       mol_type = protein
                       organism = synthetic construct
SEQUENCE: 262
QVQLVQSGAE VKKPGASVKV SCKASGYTFI NHYVHWVRQA PGQGLEWMGW MNPTGGITGY  60
AQKFQGRVTM TRDTSTSTVY MELSSLRSED TAVYYCARDR TTYAFDIWGQ GTMVTVSS    118

SEQ ID NO: 263         moltype = AA  length = 118
FEATURE                Location/Qualifiers
REGION                 1..118
                       note = Description of Artificial Sequence: Synthetic
                        polypeptide
source                 1..118
                       mol_type = protein
                       organism = synthetic construct
SEQUENCE: 263
QVQLVQSGAE VKKPGASVKV SCKASGYTFT SHYMHWVRQA PGQGLEWMGW MNPNSGHTGN  60
AQKFQGRVTM TRDTSTSTVY MELSSLRSED TAVYYCARGN WVDAFDIWGQ GTMVTVSS    118

SEQ ID NO: 264         moltype = AA  length = 120
FEATURE                Location/Qualifiers
REGION                 1..120
                       note = Description of Artificial Sequence: Synthetic
                        polypeptide
source                 1..120
                       mol_type = protein
                       organism = synthetic construct
SEQUENCE: 264
QVQLVQSGAE VKKPGSSVKV SCKASGYTFT RHLLHWVRQA PGQGLEWMGW VSPIHGLTGY  60
APRFQGRVTI TADESTSTAY MELSSLRSED TAVYYCARVH GSGSDGMDVW GQGTTVTVSS  120

SEQ ID NO: 265         moltype = AA  length = 107
FEATURE                Location/Qualifiers
REGION                 1..107
                       note = Description of Artificial Sequence: Synthetic
                        polypeptide
source                 1..107
                       mol_type = protein
                       organism = synthetic construct
SEQUENCE: 265
DIQMTQSPSS LSASVGDRVT ITCRASQGID SYLAWYQQKP GKAPKLLIYA ASSLQSGVPS  60
RFSGSGSGTD FTLTISSLQP EDFATYYCQQ SYSTPITFGG GTKVEIK                107

SEQ ID NO: 266         moltype = AA  length = 107
FEATURE                Location/Qualifiers
REGION                 1..107
                       note = Description of Artificial Sequence: Synthetic
                        polypeptide
source                 1..107
                       mol_type = protein
                       organism = synthetic construct
SEQUENCE: 266
DIQMTQSPSS LSASVGDRVT ITCRASQSIS SWLAWYQQKP GKAPKLLIYA ASSLQSGVPS  60
RFSGSGSGTD FTLTISSLQP EDFATYYCQQ SYTTPITFGG GTKVEIK                107

SEQ ID NO: 267         moltype = AA  length = 107
FEATURE                Location/Qualifiers
REGION                 1..107
                       note = Description of Artificial Sequence: Synthetic
                        polypeptide
source                 1..107
                       mol_type = protein
```

-continued

```
                         organism = synthetic construct
SEQUENCE: 267
DIQMTQSPSS LSASVGDRVT ITCRASQSIS SYLNWYQQKP GKAPKLLIYA ASSLQSGVPS  60
RFSGSGSGTD FTLTISSLQP EDFATYYCQQ IFSTPLTFGG GTKVEIK                107

SEQ ID NO: 268           moltype = AA  length = 107
FEATURE                  Location/Qualifiers
REGION                   1..107
                         note = Description of Artificial Sequence: Synthetic
                          polypeptide
source                   1..107
                         mol_type = protein
                         organism = synthetic construct
SEQUENCE: 268
DIQMTQSPSS LSASVGDRVT ITCRASQGIS SYLAWYQQKP GKAPKLLIYG ASNLQSGVPS  60
RFSGSGSGTD FTLTISSLQP EDFATYYCQQ SYSTPLTFGG GTKVEIK                107

SEQ ID NO: 269           moltype = AA  length = 107
FEATURE                  Location/Qualifiers
REGION                   1..107
                         note = Description of Artificial Sequence: Synthetic
                          polypeptide
source                   1..107
                         mol_type = protein
                         organism = synthetic construct
SEQUENCE: 269
DIQMTQSPSS LSASVGDRVT ITCRASQTIS NYLNWYQQKP GKAPKLLIYA ASSLQSGVPS  60
RFSGSGSGTD FTLTISSLQP EDFATYYCQQ SYTTPITFGG GTKVEIK                107

SEQ ID NO: 270           moltype = AA  length = 108
FEATURE                  Location/Qualifiers
REGION                   1..108
                         note = Description of Artificial Sequence: Synthetic
                          polypeptide
source                   1..108
                         mol_type = protein
                         organism = synthetic construct
SEQUENCE: 270
EIVMTQSPAT LSVSPGERAT LSCRASQSVD RNYVTWYQQK PGQAPRLLIY GASTRATGIP  60
ARFSGSGSGT EFTLTISSLQ SEDFAVYYCQ QSYTTPYTFG QGTKVEIK               108

SEQ ID NO: 271           moltype = AA  length = 107
FEATURE                  Location/Qualifiers
REGION                   1..107
                         note = Description of Artificial Sequence: Synthetic
                          polypeptide
source                   1..107
                         mol_type = protein
                         organism = synthetic construct
SEQUENCE: 271
DIQMTQSPSS LSASVGDRVT ITCRASQGIS QYLAWYQQKP GKAPKLLIYG ASNLHSGVPS  60
RFSGSGSGTD FTLTISSLQP EDFATYYCQQ TFTTPLTFGG GTKVEIK                107

SEQ ID NO: 272           moltype = AA  length = 107
FEATURE                  Location/Qualifiers
REGION                   1..107
                         note = Description of Artificial Sequence: Synthetic
                          polypeptide
source                   1..107
                         mol_type = protein
                         organism = synthetic construct
SEQUENCE: 272
DIQMTQSPSS LSASVGDRVT ITCQASQDIG NYLNWYQQKP GKAPKLLIYA ASSLESGVPS  60
RFSGSGSGTD FTLTISSLQP EDFATYYCQQ SYSTPLTFGG GTKVEIK                107

SEQ ID NO: 273           moltype = AA  length = 107
FEATURE                  Location/Qualifiers
REGION                   1..107
                         note = Description of Artificial Sequence: Synthetic
                          polypeptide
source                   1..107
                         mol_type = protein
                         organism = synthetic construct
SEQUENCE: 273
DIQMTQSPSS LSASVGDRVT ITCRASQGIR NDLGWYQQKP GKAPKLLIYS ASNLQSGVPS  60
RFSGSGSGTD FTLTISSLQP EDFATYYCQQ ANSFPFTFGG GTKVEIK                107

SEQ ID NO: 274           moltype = AA  length = 107
FEATURE                  Location/Qualifiers
```

```
REGION                  1..107
                        note = Description of Artificial Sequence: Synthetic
                         polypeptide
source                  1..107
                        mol_type = protein
                        organism = synthetic construct
SEQUENCE: 274
DIQMTQSPSS LSASVGDRVT ITCRASQSIS SWLAWYQQKP GKAPKLLIYA ASTLESGVPS  60
RFSGSGSGTD FTLTISSLQP EDFATYYCQQ SYTTPYSFGG GTKVEIK                107

SEQ ID NO: 275          moltype = AA  length = 107
FEATURE                 Location/Qualifiers
REGION                  1..107
                        note = Description of Artificial Sequence: Synthetic
                         polypeptide
source                  1..107
                        mol_type = protein
                        organism = synthetic construct
SEQUENCE: 275
DIQMTQSPSS LSASVGDRVT ITCRASQGIS QYLAWYQQKP GKAPKLLIYG ASNLHSGVPS  60
RFSGSGSGTD FTLTISSLQP EDFATYYCQQ TFITPLTFGG GTKVEIK                107

SEQ ID NO: 276          moltype = AA  length = 106
FEATURE                 Location/Qualifiers
REGION                  1..106
                        note = Description of Artificial Sequence: Synthetic
                         polypeptide
source                  1..106
                        mol_type = protein
                        organism = synthetic construct
SEQUENCE: 276
DIQMTQSPSS LSASVGDRVT ITCRASQIIG NYLAWYQQKP GKAPKLLIYH ASILETGVPS  60
RFSGSGSGTD FTLTISSLQP EDFATYYCQQ SYSTPTFGGG TKVEIK                 106

SEQ ID NO: 277          moltype = AA  length = 107
FEATURE                 Location/Qualifiers
REGION                  1..107
                        note = Description of Artificial Sequence: Synthetic
                         polypeptide
source                  1..107
                        mol_type = protein
                        organism = synthetic construct
SEQUENCE: 277
DIQMTQSPSS LSASVGDRVT ITCRASQIIS SYLNWYQQKP GKAPKLLIYA ASSLQSGVPS  60
RFSGSGSGTD FTLTISSLQP EDFATYYCQQ GFSTPFTFGG GTKVEIK                107

SEQ ID NO: 278          moltype = AA  length = 107
FEATURE                 Location/Qualifiers
REGION                  1..107
                        note = Description of Artificial Sequence: Synthetic
                         polypeptide
source                  1..107
                        mol_type = protein
                        organism = synthetic construct
SEQUENCE: 278
DIQMTQSPSS LSASVGDRVT ITCQASQDIS NYLNWYQQKP GKAPKLLIYA ASSLQSGVPS  60
RFSGSGSGTD FTLTISSLQP EDFATYYCQQ SFTNPVTFGG GTKVEIK                107

SEQ ID NO: 279          moltype = AA  length = 107
FEATURE                 Location/Qualifiers
REGION                  1..107
                        note = Description of Artificial Sequence: Synthetic
                         polypeptide
source                  1..107
                        mol_type = protein
                        organism = synthetic construct
SEQUENCE: 279
DIQMTQSPSS LSASVGDRVT ITCRASQGIS NYLAWYQQKP GKAPKLLIYA ASTLQSGVPS  60
RFSGSGSGTD FTLTISSLQP EDFATYYCQQ SYSAPYTFGG GTKVEIK                107

SEQ ID NO: 280          moltype = AA  length = 107
FEATURE                 Location/Qualifiers
REGION                  1..107
                        note = Description of Artificial Sequence: Synthetic
                         polypeptide
source                  1..107
                        mol_type = protein
                        organism = synthetic construct
SEQUENCE: 280
```

-continued

```
DIQMTQSPSS LSASVGDRVT ITCRASQGIS NNLNWYQQKP GKAPKLLIYA ATTLQSGVPS  60
RFSGSGSGTD FTLTISSLQP EDFATYYCQQ SYSTPYTFGG GTKVEIK               107

SEQ ID NO: 281          moltype = AA  length = 107
FEATURE                 Location/Qualifiers
REGION                  1..107
                        note = Description of Artificial Sequence: Synthetic
                         polypeptide
source                  1..107
                        mol_type = protein
                        organism = synthetic construct
SEQUENCE: 281
DIQMTQSPSS LSASVGDRVT ITCRASQSIS SYLNWYQQKP GKAPKLLIYA ASSLQSGVPS  60
RFSGSGSGTD FTLTISSLQP EDFATYYCQQ SYSTPLTFGG GTKVEIK               107

SEQ ID NO: 282          moltype = AA  length = 107
FEATURE                 Location/Qualifiers
REGION                  1..107
                        note = Description of Artificial Sequence: Synthetic
                         polypeptide
source                  1..107
                        mol_type = protein
                        organism = synthetic construct
SEQUENCE: 282
DIQMTQSPSS LSASVGDRVT ITCRASQGIS NGLSWYQQKP GKAPKLLIYA ASTLQSGVPS  60
RFSGSGSGTD FTLTISSLQP EDFATYYCQQ SHSTPLTFGG GTKVEIK               107

SEQ ID NO: 283          moltype = AA  length = 107
FEATURE                 Location/Qualifiers
REGION                  1..107
                        note = Description of Artificial Sequence: Synthetic
                         polypeptide
source                  1..107
                        mol_type = protein
                        organism = synthetic construct
SEQUENCE: 283
DIQMTQSPSS LSASVGDRVT ITCRASQSIT GWLAWYQQKP GKAPKLLIYA ASSLQSGVPS  60
RFSGSGSGTD FTLTISSLQP EDFATYYCQQ SYSTPYTFGQ GTKVEIK               107

SEQ ID NO: 284          moltype = AA  length = 107
FEATURE                 Location/Qualifiers
REGION                  1..107
                        note = Description of Artificial Sequence: Synthetic
                         polypeptide
source                  1..107
                        mol_type = protein
                        organism = synthetic construct
SEQUENCE: 284
DIQMTQSPSS LSASVGDRVT ITCRASQSIS SWLAWYQQKP GKAPKLLIYD ATHLETGVPS  60
RFSGSGSGTD FTLTISSLQP EDFATYYCQQ SYSTPITFGQ GTRLEIK               107

SEQ ID NO: 285          moltype = AA  length = 107
FEATURE                 Location/Qualifiers
REGION                  1..107
                        note = Description of Artificial Sequence: Synthetic
                         polypeptide
source                  1..107
                        mol_type = protein
                        organism = synthetic construct
SEQUENCE: 285
DIQMTQSPSS LSASVGDRVT ITCRASQGIR NDLAWYQQKP GKAPKLLIYA ASTLQSGVPS  60
RFSGSGSGTD FTLTISSLQP EDFATYYCQQ SYSTPLTFGG GTKVEIK               107

SEQ ID NO: 286          moltype = AA  length = 107
FEATURE                 Location/Qualifiers
REGION                  1..107
                        note = Description of Artificial Sequence: Synthetic
                         polypeptide
source                  1..107
                        mol_type = protein
                        organism = synthetic construct
SEQUENCE: 286
DIQMTQSPSS LSASVGDRVT ITCQASQDIS SYLNWYQQKP GKAPKLLIYA ASSLQTGVPS  60
RFSGSGSGTD FTLTISSLQP EDFATYYCQQ SYSTPYTFGQ GTKLEIK               107

SEQ ID NO: 287          moltype = AA  length = 107
FEATURE                 Location/Qualifiers
REGION                  1..107
                        note = Description of Artificial Sequence: Synthetic
```

```
                          polypeptide
source                   1..107
                         mol_type = protein
                         organism = synthetic construct
SEQUENCE: 287
DIQMTQSPSS LSASVGDRVT ITCRASQSIT TYLNWYQQKP GKAPKLLIYA ASSLQGGVPS  60
RFSGSGSGTD FTLTISSLQP EDFATYYCQQ SYSTPYTFGQ GTKVEIK                107

SEQ ID NO: 288           moltype = AA  length = 107
FEATURE                  Location/Qualifiers
REGION                   1..107
                         note = Description of Artificial Sequence: Synthetic
                          polypeptide
source                   1..107
                         mol_type = protein
                         organism = synthetic construct
SEQUENCE: 288
DIQMTQSPSS LSASVGDRVT ITCRASQSIS SYLNWYQQKP GKAPKLLIYA ASSLQSGVPS  60
RFSGSGSGTD FTLTISSLQP EDFATYYCQQ SYSTPLTFGG GTKLEIK                107

SEQ ID NO: 289           moltype = AA  length = 107
FEATURE                  Location/Qualifiers
REGION                   1..107
                         note = Description of Artificial Sequence: Synthetic
                          polypeptide
source                   1..107
                         mol_type = protein
                         organism = synthetic construct
SEQUENCE: 289
DIQMTQSPSS LSASVGDRVT ITCRASQSVS TWLAWYQQKP GKAPKLLIYA ASNLESGVPS  60
RFSGSGSGTD FTLTISSLQP EDFATYYCQQ SYSTPYTFGQ GTKLEIK                107

SEQ ID NO: 290           moltype = AA  length = 107
FEATURE                  Location/Qualifiers
REGION                   1..107
                         note = Description of Artificial Sequence: Synthetic
                          polypeptide
source                   1..107
                         mol_type = protein
                         organism = synthetic construct
SEQUENCE: 290
DIQMTQSPSS LSASVGDRVT ITCRASQSIS NWLAWYQQKP GKAPKLLIYD VSHLESGVPS  60
RFSGSGSGTD FTLTISSLQP EDFATYYCQQ SYSTPFTFGP GTKVDIK                107

SEQ ID NO: 291           moltype = AA  length = 107
FEATURE                  Location/Qualifiers
REGION                   1..107
                         note = Description of Artificial Sequence: Synthetic
                          polypeptide
source                   1..107
                         mol_type = protein
                         organism = synthetic construct
SEQUENCE: 291
DIQMTQSPSS LSASVGDRVT ITCQASQGIS NYLAWYQQKP GKAPKLLIYD ASSLQSGVPS  60
RFSGSGSGTD FTLTISSLQP EDFATYYCQQ SYSTPLTFGG GTKVEIK                107

SEQ ID NO: 292           moltype = AA  length = 108
FEATURE                  Location/Qualifiers
REGION                   1..108
                         note = Description of Artificial Sequence: Synthetic
                          polypeptide
source                   1..108
                         mol_type = protein
                         organism = synthetic construct
SEQUENCE: 292
EIVMTQSPAT LSVSPGERAT LSCRASQSLS SSSLAWYQQK PGQAPRLLIY GASTRATGIP  60
ARFSGSGSGT EFTLTISSLQ SEDFAVYYCQ QYGSSPFTFG PGTKVDIK               108

SEQ ID NO: 293           moltype = AA  length = 107
FEATURE                  Location/Qualifiers
REGION                   1..107
                         note = Description of Artificial Sequence: Synthetic
                          polypeptide
source                   1..107
                         mol_type = protein
                         organism = synthetic construct
SEQUENCE: 293
DIQMTQSPSS LSASVGDRVT ITCRASEHIA NWLAWYQQKP GKAPKLLIYG VSSLESGVPS  60
RFSGSGSGTD FTLTISSLQP EDFATYYCQQ SYSTPYTFGQ GTKLEIK                107
```

```
SEQ ID NO: 294          moltype = AA  length = 107
FEATURE                 Location/Qualifiers
REGION                  1..107
                        note = Description of Artificial Sequence: Synthetic
                         polypeptide
source                  1..107
                        mol_type = protein
                        organism = synthetic construct
SEQUENCE: 294
DIQMTQSPSS LSASVGDRVT ITCRASQSVG SWVAWYQQKP GKAPKLLIYP ASTLQSGVPS  60
RFSGSGSGTD FTLTISSLQP EDFATYYCQQ SYSTPLTFGG GTKVEIK                107

SEQ ID NO: 295          moltype = AA  length = 107
FEATURE                 Location/Qualifiers
REGION                  1..107
                        note = Description of Artificial Sequence: Synthetic
                         polypeptide
source                  1..107
                        mol_type = protein
                        organism = synthetic construct
SEQUENCE: 295
DIQMTQSPSS LSASVGDRVT ITCRASQSIS PWLAWYQQKP GKAPKLLIYD ASNLETGVPS  60
RFSGSGSGTD FTLTISSLQP EDFATYYCQQ TYSTPITFGQ GTRLEIK                107

SEQ ID NO: 296          moltype = AA  length = 107
FEATURE                 Location/Qualifiers
REGION                  1..107
                        note = Description of Artificial Sequence: Synthetic
                         polypeptide
source                  1..107
                        mol_type = protein
                        organism = synthetic construct
SEQUENCE: 296
DIQMTQSPSS LSASVGDRVT ITCRASQGIS RYLAWYQQKP GKAPKLLIYA ASTLQSGVPS  60
RFSGSGSGTD FTLTISSLQP EDFATYYCQQ SYSTPLTFGQ GTKVEIK                107

SEQ ID NO: 297          moltype = AA  length = 108
FEATURE                 Location/Qualifiers
REGION                  1..108
                        note = Description of Artificial Sequence: Synthetic
                         polypeptide
source                  1..108
                        mol_type = protein
                        organism = synthetic construct
SEQUENCE: 297
EIVMTQSPAT LSVSPGERAT LSCRASQTVS SNYLAWYQQK PGQAPRLLIY GASTRASGIP  60
ARFSGSGSGT EFTLTISSLQ SEDFAVYYCQ QYYTTPLTFG GGTKVEIK               108

SEQ ID NO: 298          moltype = AA  length = 107
FEATURE                 Location/Qualifiers
REGION                  1..107
                        note = Description of Artificial Sequence: Synthetic
                         polypeptide
source                  1..107
                        mol_type = protein
                        organism = synthetic construct
SEQUENCE: 298
DIQMTQSPSS LSASVGDRVT ITCRASQSIS SYLNWYQQKP GKAPKLLIYA ASSLQSGVPS  60
RFSGSGSGTD FTLTISSLQP EDFATYYCQQ SFSTPLTFGQ GTRLEIK                107

SEQ ID NO: 299          moltype = AA  length = 107
FEATURE                 Location/Qualifiers
REGION                  1..107
                        note = Description of Artificial Sequence: Synthetic
                         polypeptide
source                  1..107
                        mol_type = protein
                        organism = synthetic construct
SEQUENCE: 299
DIQMTQSPSS LSASVGDRVT ITCRASQSIS SWLAWYQQKP GKAPKLLIYD ASNLETGVPS  60
RFSGSGSGTD FTLTISSLQP EDFATYYCQQ SYSTPPTFGQ GTKVEIK                107

SEQ ID NO: 300          moltype = AA  length = 107
FEATURE                 Location/Qualifiers
REGION                  1..107
                        note = Description of Artificial Sequence: Synthetic
                         polypeptide
source                  1..107
```

```
                         mol_type = protein
                         organism = synthetic construct
SEQUENCE: 300
DIQMTQSPSS LSASVGDRVT ITCRASQGIS NNLNWYQQKP GKAPKLLIYA TSTLQSGVPS  60
RFSGSGSGTD FTLTISSLQP EDFATYYCQQ SYSTPYTFGQ GTKVEIK                107

SEQ ID NO: 301           moltype = AA  length = 107
FEATURE                  Location/Qualifiers
REGION                   1..107
                         note = Description of Artificial Sequence: Synthetic
                          polypeptide
source                   1..107
                         mol_type = protein
                         organism = synthetic construct
SEQUENCE: 301
DIQMTQSPSS LSASVGDRVT ITCRSSQGIR NDLSWYQQKP GKAPKLLIYL ASNSHSGVPS  60
RFSGSGSGTD FTLTISSLQP EDFATYYCLQ HNSYPLTFGG GTKVEIK                107

SEQ ID NO: 302           moltype = AA  length = 107
FEATURE                  Location/Qualifiers
REGION                   1..107
                         note = Description of Artificial Sequence: Synthetic
                          polypeptide
source                   1..107
                         mol_type = protein
                         organism = synthetic construct
SEQUENCE: 302
DIQMTQSPSS LSASVGDRVT ITCRASQSIS RWLAWYQQKP GKAPKLLIYA ASSLQSGVPS  60
RFSGSGSGTD FTLTISSLQP EDFATYYCQQ SYSTPYTFGQ GTKLEIK                107

SEQ ID NO: 303           moltype = AA  length = 107
FEATURE                  Location/Qualifiers
REGION                   1..107
                         note = Description of Artificial Sequence: Synthetic
                          polypeptide
source                   1..107
                         mol_type = protein
                         organism = synthetic construct
SEQUENCE: 303
DIQMTQSPSS LSASVGDRVT ITCRASQSIS SWLAWYQQKP GKAPKLLIYD SSSLQTGVPS  60
RFSGSGSGTD FTLTISSLQP EDFATYYCQQ SYSTPVTFGQ GTKVEIK                107

SEQ ID NO: 304           moltype = AA  length = 107
FEATURE                  Location/Qualifiers
REGION                   1..107
                         note = Description of Artificial Sequence: Synthetic
                          polypeptide
source                   1..107
                         mol_type = protein
                         organism = synthetic construct
SEQUENCE: 304
DIQITHSPSS LSASVGYRLT ITCRDSHSIT TWLAWYHQKP WNAPKLMIYA ASNLESGVPS  60
RFSGSGSGTY FTLTISSLQP EDFATYYCQH FYNTQYTFGQ GTKVEIK                107

SEQ ID NO: 305           moltype = AA  length = 108
FEATURE                  Location/Qualifiers
REGION                   1..108
                         note = Description of Artificial Sequence: Synthetic
                          polypeptide
source                   1..108
                         mol_type = protein
                         organism = synthetic construct
SEQUENCE: 305
DIQMTQSPSS LSASVGDRVT ITCRASQVIR NDLAWYQQKP GKAPKLLIYA ASTLQSGVPS  60
RFSGSGSGTD FTLTISSLQP EDFATYYCQQ SLQYPSHFFG QGTKVEIK               108

SEQ ID NO: 306           moltype = AA  length = 107
FEATURE                  Location/Qualifiers
REGION                   1..107
                         note = Description of Artificial Sequence: Synthetic
                          polypeptide
source                   1..107
                         mol_type = protein
                         organism = synthetic construct
SEQUENCE: 306
DIQMTQSPSS LSASVGDRVT ITCRASQSIS RYLNWYQQKP GKAPKLLIYA ASTLQSGVPS  60
RFSGSGSGTD FTLTISSLQP EDFAPYYCQQ SYSTPLTFGP GTKVDIK                107

SEQ ID NO: 307           moltype = AA  length = 290
```

-continued

```
FEATURE                Location/Qualifiers
REGION                 1..290
                       note = Description of Artificial Sequence: Synthetic
                        polypeptide
source                 1..290
                       mol_type = protein
                       organism = synthetic construct
SEQUENCE: 307
MRIFAVFIFM TYWHLLNAFT VTVPKDLYVV EYGSNMTIEC KFPVEKQLDL AALIVYWEME  60
DKNIIQFVHG EEDLKVQHSS YRQRARLLKD QLSLGNAALQ ITDVKLQDAG VYRCMISYGG  120
ADYKRITVKV NAPYNKINQR ILVVDPVTSE HELTCQAEGY PKAEVIWTSS DHQVLSGKTT  180
TTNSKREEKL FNVTSTLRIN TTTNEIFYCT FRRLDPEENH TAELVIPELP LAHPPNERTH  240
LVILGAILLC LGVALTFIFR LRKGRMMDVK KCGIQDTNSK KQSDTHLEET            290

SEQ ID NO: 308         moltype = AA  length = 5
FEATURE                Location/Qualifiers
REGION                 1..5
                       note = Description of Artificial Sequence: Synthetic peptide
source                 1..5
                       mol_type = protein
                       organism = synthetic construct
SEQUENCE: 308
SDYMH                                                                5

SEQ ID NO: 309         moltype = AA  length = 5
FEATURE                Location/Qualifiers
REGION                 1..5
                       note = Description of Artificial Sequence: Synthetic peptide
source                 1..5
                       mol_type = protein
                       organism = synthetic construct
SEQUENCE: 309
GYYMH                                                                5

SEQ ID NO: 310         moltype = AA  length = 5
FEATURE                Location/Qualifiers
REGION                 1..5
                       note = Description of Artificial Sequence: Synthetic peptide
source                 1..5
                       mol_type = protein
                       organism = synthetic construct
SEQUENCE: 310
SYYMH                                                                5

SEQ ID NO: 311         moltype = AA  length = 5
FEATURE                Location/Qualifiers
REGION                 1..5
                       note = Description of Artificial Sequence: Synthetic peptide
source                 1..5
                       mol_type = protein
                       organism = synthetic construct
SEQUENCE: 311
GYYIH                                                                5

SEQ ID NO: 312         moltype = AA  length = 5
FEATURE                Location/Qualifiers
REGION                 1..5
                       note = Description of Artificial Sequence: Synthetic peptide
source                 1..5
                       mol_type = protein
                       organism = synthetic construct
SEQUENCE: 312
THYMH                                                                5

SEQ ID NO: 313         moltype = AA  length = 5
FEATURE                Location/Qualifiers
REGION                 1..5
                       note = Description of Artificial Sequence: Synthetic peptide
source                 1..5
                       mol_type = protein
                       organism = synthetic construct
SEQUENCE: 313
SHDIN                                                                5

SEQ ID NO: 314         moltype = AA  length = 5
FEATURE                Location/Qualifiers
REGION                 1..5
                       note = Description of Artificial Sequence: Synthetic peptide
source                 1..5
```

```
                        mol_type = protein
                        organism = synthetic construct
SEQUENCE: 314
DHYLH                                                                       5

SEQ ID NO: 315          moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 315
NYYMH                                                                       5

SEQ ID NO: 316          moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 316
AYYVH                                                                       5

SEQ ID NO: 317          moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 317
RHYVH                                                                       5

SEQ ID NO: 318          moltype = AA  length = 4
FEATURE                 Location/Qualifiers
REGION                  1..4
                        note = Description of Artificial Sequence: Synthetic peptide
source                  1..4
                        mol_type = protein
                        organism = synthetic construct
SEQUENCE: 318
NYIH                                                                        4

SEQ ID NO: 319          moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 319
NHYVH                                                                       5

SEQ ID NO: 320          moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 320
SHYMH                                                                       5

SEQ ID NO: 321          moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 321
RHLLH                                                                       5

SEQ ID NO: 322          moltype = AA  length = 17
FEATURE                 Location/Qualifiers
REGION                  1..17
                        note = Description of Artificial Sequence: Synthetic peptide
```

```
source                 1..17
                       mol_type = protein
                       organism = synthetic construct
SEQUENCE: 322
WMSPYNGITG YAQKFQG                                                17

SEQ ID NO: 323         moltype = AA  length = 17
FEATURE                Location/Qualifiers
REGION                 1..17
                       note = Description of Artificial Sequence: Synthetic peptide
source                 1..17
                       mol_type = protein
                       organism = synthetic construct
SEQUENCE: 323
WMSPSSGITG YAQKFQG                                                17

SEQ ID NO: 324         moltype = AA  length = 17
FEATURE                Location/Qualifiers
REGION                 1..17
                       note = Description of Artificial Sequence: Synthetic peptide
source                 1..17
                       mol_type = protein
                       organism = synthetic construct
SEQUENCE: 324
WMTTNSGITG YAQKFQG                                                17

SEQ ID NO: 325         moltype = AA  length = 17
FEATURE                Location/Qualifiers
REGION                 1..17
                       note = Description of Artificial Sequence: Synthetic peptide
source                 1..17
                       mol_type = protein
                       organism = synthetic construct
SEQUENCE: 325
GIIPIFGTAS YAQKFQG                                                17

SEQ ID NO: 326         moltype = AA  length = 17
FEATURE                Location/Qualifiers
REGION                 1..17
                       note = Description of Artificial Sequence: Synthetic peptide
source                 1..17
                       mol_type = protein
                       organism = synthetic construct
SEQUENCE: 326
WMNPNSGHAG SAQKFQG                                                17

SEQ ID NO: 327         moltype = AA  length = 17
FEATURE                Location/Qualifiers
REGION                 1..17
                       note = Description of Artificial Sequence: Synthetic peptide
source                 1..17
                       mol_type = protein
                       organism = synthetic construct
SEQUENCE: 327
WMNPNSGNTG YAQKFQG                                                17

SEQ ID NO: 328         moltype = AA  length = 17
FEATURE                Location/Qualifiers
REGION                 1..17
                       note = Description of Artificial Sequence: Synthetic peptide
source                 1..17
                       mol_type = protein
                       organism = synthetic construct
SEQUENCE: 328
WMNPNSGNTG YSQKFQG                                                17

SEQ ID NO: 329         moltype = AA  length = 17
FEATURE                Location/Qualifiers
REGION                 1..17
                       note = Description of Artificial Sequence: Synthetic peptide
source                 1..17
                       mol_type = protein
                       organism = synthetic construct
SEQUENCE: 329
WMNPNIGNTG YAQKFQG                                                17

SEQ ID NO: 330         moltype = AA  length = 17
FEATURE                Location/Qualifiers
REGION                 1..17
```

-continued

```
                        note = Description of Artificial Sequence: Synthetic peptide
source                  1..17
                        mol_type = protein
                        organism = synthetic construct
SEQUENCE: 330
WMNPNGGTTG YAQNFQG                                                  17

SEQ ID NO: 331          moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 331
WMNPNRGITD SAQKFQG                                                  17

SEQ ID NO: 332          moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 332
WMNPNSGSAG YAQKFQG                                                  17

SEQ ID NO: 333          moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 333
WIHPRSGATG YAPKFQG                                                  17

SEQ ID NO: 334          moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 334
WISPRSGVTS YAQKFQG                                                  17

SEQ ID NO: 335          moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 335
WMDPNSGNTG YAQKFQG                                                  17

SEQ ID NO: 336          moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 336
WMNPTGGITG YAQKFQG                                                  17

SEQ ID NO: 337          moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 337
WMNPNSGHTG NAQKFQG                                                  17

SEQ ID NO: 338          moltype = AA  length = 17
FEATURE                 Location/Qualifiers
```

-continued

```
REGION                  1..17
                        note = Description of Artificial Sequence: Synthetic peptide
source                  1..17
                        mol_type = protein
                        organism = synthetic construct
SEQUENCE: 338
WVSPIHGLTG YAPRFQG                                                      17

SEQ ID NO: 339          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 339
DRFSGSYDY                                                               9

SEQ ID NO: 340          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 340
DRGWFDP                                                                 7

SEQ ID NO: 341          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 341
EGYSSGLDY                                                               9

SEQ ID NO: 342          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 342
DGRFWSGYPD Y                                                            11

SEQ ID NO: 343          moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 343
ESIAVAGYDY                                                              10

SEQ ID NO: 344          moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 344
DRWYMGSADY                                                              10

SEQ ID NO: 345          moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 345
DDWGGDWFDP                                                              10

SEQ ID NO: 346          moltype = AA  length = 10
```

```
FEATURE                Location/Qualifiers
REGION                 1..10
                       note = Description of Artificial Sequence: Synthetic peptide
source                 1..10
                       mol_type = protein
                       organism = synthetic construct
SEQUENCE: 346
ERLSVAGFDY                                                 10

SEQ ID NO: 347         moltype = AA  length = 10
FEATURE                Location/Qualifiers
REGION                 1..10
                       note = Description of Artificial Sequence: Synthetic peptide
source                 1..10
                       mol_type = protein
                       organism = synthetic construct
SEQUENCE: 347
EPLQLGGFDY                                                 10

SEQ ID NO: 348         moltype = AA  length = 10
FEATURE                Location/Qualifiers
REGION                 1..10
                       note = Description of Artificial Sequence: Synthetic peptide
source                 1..10
                       mol_type = protein
                       organism = synthetic construct
SEQUENCE: 348
EGFGPNAFDI                                                 10

SEQ ID NO: 349         moltype = AA  length = 10
FEATURE                Location/Qualifiers
REGION                 1..10
                       note = Description of Artificial Sequence: Synthetic peptide
source                 1..10
                       mol_type = protein
                       organism = synthetic construct
SEQUENCE: 349
DSWYGDWFDP                                                 10

SEQ ID NO: 350         moltype = AA  length = 9
FEATURE                Location/Qualifiers
REGION                 1..9
                       note = Description of Artificial Sequence: Synthetic peptide
source                 1..9
                       mol_type = protein
                       organism = synthetic construct
SEQUENCE: 350
EVIEVGMDV                                                  9

SEQ ID NO: 351         moltype = AA  length = 9
FEATURE                Location/Qualifiers
REGION                 1..9
                       note = Description of Artificial Sequence: Synthetic peptide
source                 1..9
                       mol_type = protein
                       organism = synthetic construct
SEQUENCE: 351
EAWFGELST                                                  9

SEQ ID NO: 352         moltype = AA  length = 9
FEATURE                Location/Qualifiers
REGION                 1..9
                       note = Description of Artificial Sequence: Synthetic peptide
source                 1..9
                       mol_type = protein
                       organism = synthetic construct
SEQUENCE: 352
EAYVAAFDI                                                  9

SEQ ID NO: 353         moltype = AA  length = 9
FEATURE                Location/Qualifiers
REGION                 1..9
                       note = Description of Artificial Sequence: Synthetic peptide
source                 1..9
                       mol_type = protein
                       organism = synthetic construct
SEQUENCE: 353
ERGYNAFDY                                                  9
```

```
SEQ ID NO: 354          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 354
DSVFGLDY                                                          8

SEQ ID NO: 355          moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 355
DLDYVRAFDI                                                        10

SEQ ID NO: 356          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 356
ESWGGYFDL                                                         9

SEQ ID NO: 357          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 357
DRTTYAFDI                                                         9

SEQ ID NO: 358          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 358
GNWVDAFDI                                                         9

SEQ ID NO: 359          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 359
VHGSGSDGMD V                                                      11

SEQ ID NO: 360          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 360
RASQSISSWL A                                                      11

SEQ ID NO: 361          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 361
RASQSVGTWL A                                                      11
```

```
SEQ ID NO: 362          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 362
RASQGISNYL A                                                       11

SEQ ID NO: 363          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 363
RASQSISTWL A                                                       11

SEQ ID NO: 364          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 364
QASQDISNHL N                                                       11

SEQ ID NO: 365          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 365
RASQGISSWL A                                                       11

SEQ ID NO: 366          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 366
RASESISSWL A                                                       11

SEQ ID NO: 367          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 367
RASQSVGSWL A                                                       11

SEQ ID NO: 368          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 368
RASQNISNFL N                                                       11

SEQ ID NO: 369          moltype = AA  length = 12
FEATURE                 Location/Qualifiers
REGION                  1..12
                        note = Description of Artificial Sequence: Synthetic peptide
source                  1..12
                        mol_type = protein
                        organism = synthetic construct
SEQUENCE: 369
```

-continued

```
RASQSLSSSY LA                                                   12

SEQ ID NO: 370          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 370
RASQSISSYL N                                                    11

SEQ ID NO: 371          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 371
RASQSISRWL A                                                    11

SEQ ID NO: 372          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 372
RDSHSITTWL A                                                    11

SEQ ID NO: 373          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 373
RASQVIRNDL A                                                    11

SEQ ID NO: 374          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 374
RASQSISRYL N                                                    11

SEQ ID NO: 375          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 375
AASSLQS                                                         7

SEQ ID NO: 376          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 376
AASTLEN                                                         7

SEQ ID NO: 377          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
```

```
SEQUENCE: 377
RASNLES                                                      7

SEQ ID NO: 378          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 378
AASTLQR                                                      7

SEQ ID NO: 379          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 379
AASTLQS                                                      7

SEQ ID NO: 380          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 380
GASNLQR                                                      7

SEQ ID NO: 381          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 381
AASNLQS                                                      7

SEQ ID NO: 382          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 382
GASSLQS                                                      7

SEQ ID NO: 383          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 383
AASHLQS                                                      7

SEQ ID NO: 384          moltype =   length =
SEQUENCE: 384
000

SEQ ID NO: 385          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 385
DSSSLQT                                                      7

SEQ ID NO: 386          moltype = AA  length = 7
FEATURE                 Location/Qualifiers
```

-continued

```
REGION                1..7
                      note = Description of Artificial Sequence: Synthetic peptide
source                1..7
                      mol_type = protein
                      organism = synthetic construct
SEQUENCE: 386
AASNLES                                                                   7

SEQ ID NO: 387        moltype = AA  length = 9
FEATURE               Location/Qualifiers
REGION                1..9
                      note = Description of Artificial Sequence: Synthetic peptide
source                1..9
                      mol_type = protein
                      organism = synthetic construct
SEQUENCE: 387
QQSYSTPYT                                                                 9

SEQ ID NO: 388        moltype = AA  length = 9
FEATURE               Location/Qualifiers
REGION                1..9
                      note = Description of Artificial Sequence: Synthetic peptide
source                1..9
                      mol_type = protein
                      organism = synthetic construct
SEQUENCE: 388
QQSFSTPYT                                                                 9

SEQ ID NO: 389        moltype = AA  length = 9
FEATURE               Location/Qualifiers
REGION                1..9
                      note = Description of Artificial Sequence: Synthetic peptide
source                1..9
                      mol_type = protein
                      organism = synthetic construct
SEQUENCE: 389
QQSYSTPLT                                                                 9

SEQ ID NO: 390        moltype = AA  length = 9
FEATURE               Location/Qualifiers
REGION                1..9
                      note = Description of Artificial Sequence: Synthetic peptide
source                1..9
                      mol_type = protein
                      organism = synthetic construct
SEQUENCE: 390
QQSYSTPFT                                                                 9

SEQ ID NO: 391        moltype = AA  length = 9
FEATURE               Location/Qualifiers
REGION                1..9
                      note = Description of Artificial Sequence: Synthetic peptide
source                1..9
                      mol_type = protein
                      organism = synthetic construct
SEQUENCE: 391
QQSYSTPIT                                                                 9

SEQ ID NO: 392        moltype = AA  length = 9
FEATURE               Location/Qualifiers
REGION                1..9
                      note = Description of Artificial Sequence: Synthetic peptide
source                1..9
                      mol_type = protein
                      organism = synthetic construct
SEQUENCE: 392
QQYYSTPYT                                                                 9

SEQ ID NO: 393        moltype = AA  length = 9
FEATURE               Location/Qualifiers
REGION                1..9
                      note = Description of Artificial Sequence: Synthetic peptide
source                1..9
                      mol_type = protein
                      organism = synthetic construct
SEQUENCE: 393
QQSYSLPYT                                                                 9

SEQ ID NO: 394        moltype = AA  length = 9
```

-continued

```
FEATURE                Location/Qualifiers
REGION                 1..9
                       note = Description of Artificial Sequence: Synthetic peptide
source                 1..9
                       mol_type = protein
                       organism = synthetic construct
SEQUENCE: 394
HQYFTTPLT                                                                    9

SEQ ID NO: 395         moltype = AA  length = 9
FEATURE                Location/Qualifiers
REGION                 1..9
                       note = Description of Artificial Sequence: Synthetic peptide
source                 1..9
                       mol_type = protein
                       organism = synthetic construct
SEQUENCE: 395
QQSYSMPYT                                                                    9

SEQ ID NO: 396         moltype = AA  length = 9
FEATURE                Location/Qualifiers
REGION                 1..9
                       note = Description of Artificial Sequence: Synthetic peptide
source                 1..9
                       mol_type = protein
                       organism = synthetic construct
SEQUENCE: 396
QQSYSTPVT                                                                    9

SEQ ID NO: 397         moltype = AA  length = 9
FEATURE                Location/Qualifiers
REGION                 1..9
                       note = Description of Artificial Sequence: Synthetic peptide
source                 1..9
                       mol_type = protein
                       organism = synthetic construct
SEQUENCE: 397
QHFYNTQYT                                                                    9

SEQ ID NO: 398         moltype = AA  length = 10
FEATURE                Location/Qualifiers
REGION                 1..10
                       note = Description of Artificial Sequence: Synthetic peptide
source                 1..10
                       mol_type = protein
                       organism = synthetic construct
SEQUENCE: 398
QQSLQYPSHF                                                                   10

SEQ ID NO: 399         moltype = AA  length = 30
FEATURE                Location/Qualifiers
REGION                 1..30
                       note = Description of Artificial Sequence: Synthetic
                        polypeptide
source                 1..30
                       mol_type = protein
                       organism = synthetic construct
SEQUENCE: 399
QVQLVQSGAE VKKPGASVKV SCKASGYTFS                                             30

SEQ ID NO: 400         moltype = AA  length = 30
FEATURE                Location/Qualifiers
REGION                 1..30
                       note = Description of Artificial Sequence: Synthetic
                        polypeptide
source                 1..30
                       mol_type = protein
                       organism = synthetic construct
SEQUENCE: 400
QVQLVQSGAE VKKPGASVKV SCKASGYTFT                                             30

SEQ ID NO: 401         moltype = AA  length = 30
FEATURE                Location/Qualifiers
REGION                 1..30
                       note = Description of Artificial Sequence: Synthetic
                        polypeptide
source                 1..30
                       mol_type = protein
                       organism = synthetic construct
```

-continued

```
SEQUENCE: 401
QVQLVQSGAE VKKPGSSVKV SCKASGYTFT                                    30

SEQ ID NO: 402          moltype = AA  length = 30
FEATURE                 Location/Qualifiers
REGION                  1..30
                        note = Description of Artificial Sequence: Synthetic
                         polypeptide
source                  1..30
                        mol_type = protein
                        organism = synthetic construct
SEQUENCE: 402
QVQLVQSGAE VKEPGASVKV SCKASGYTFT                                    30

SEQ ID NO: 403          moltype = AA  length = 30
FEATURE                 Location/Qualifiers
REGION                  1..30
                        note = Description of Artificial Sequence: Synthetic
                         polypeptide
source                  1..30
                        mol_type = protein
                        organism = synthetic construct
SEQUENCE: 403
QVQLVQSGAE VKKPGASVKV SCKASGYNFS                                    30

SEQ ID NO: 404          moltype =   length =
SEQUENCE: 404
000

SEQ ID NO: 405          moltype = AA  length = 30
FEATURE                 Location/Qualifiers
REGION                  1..30
                        note = Description of Artificial Sequence: Synthetic
                         polypeptide
source                  1..30
                        mol_type = protein
                        organism = synthetic construct
SEQUENCE: 405
QVQLVQSGAE VKKPGASVKV SCKASGYSFT                                    30

SEQ ID NO: 406          moltype = AA  length = 30
FEATURE                 Location/Qualifiers
REGION                  1..30
                        note = Description of Artificial Sequence: Synthetic
                         polypeptide
source                  1..30
                        mol_type = protein
                        organism = synthetic construct
SEQUENCE: 406
QVQLVQSGAE VKKPGASVKV SCKASGYTFI                                    30

SEQ ID NO: 407          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 407
WVRQAPGQGL EWMG                                                     14

SEQ ID NO: 408          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 408
WMRQAPGQGL EWIG                                                     14

SEQ ID NO: 409          moltype = AA  length = 32
FEATURE                 Location/Qualifiers
REGION                  1..32
                        note = Description of Artificial Sequence: Synthetic
                         polypeptide
source                  1..32
                        mol_type = protein
                        organism = synthetic construct
```

-continued

```
SEQUENCE: 409
RVTMTRDTST STVYMELSSL RSEDTAVYYC AR                            32

SEQ ID NO: 410          moltype = AA  length = 32
FEATURE                 Location/Qualifiers
REGION                  1..32
                        note = Description of Artificial Sequence: Synthetic
                         polypeptide
source                  1..32
                        mol_type = protein
                        organism = synthetic construct
SEQUENCE: 410
RVTITADEST STAYMELSSL RSEDTAVYYC AR                            32

SEQ ID NO: 411          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 411
WGQGTLVTVS S                                                   11

SEQ ID NO: 412          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 412
WGQGTTVTVS S                                                   11

SEQ ID NO: 413          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 413
WGRGTLVTVS S                                                   11

SEQ ID NO: 414          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 414
WGQGTMVTVS S                                                   11

SEQ ID NO: 415          moltype = AA  length = 23
FEATURE                 Location/Qualifiers
REGION                  1..23
                        note = Description of Artificial Sequence: Synthetic peptide
source                  1..23
                        mol_type = protein
                        organism = synthetic construct
SEQUENCE: 415
DIQMTQSPSS LSASVGDRVT ITC                                      23

SEQ ID NO: 416          moltype = AA  length = 23
FEATURE                 Location/Qualifiers
REGION                  1..23
                        note = Description of Artificial Sequence: Synthetic peptide
source                  1..23
                        mol_type = protein
                        organism = synthetic construct
SEQUENCE: 416
EIVMTQSPAT LSVSPGERAT LSC                                      23

SEQ ID NO: 417          moltype = AA  length = 23
FEATURE                 Location/Qualifiers
REGION                  1..23
                        note = Description of Artificial Sequence: Synthetic peptide
source                  1..23
```

```
                        mol_type = protein
                        organism = synthetic construct
SEQUENCE: 417
DIQITHSPSS LSASVGYRLT ITC                                              23

SEQ ID NO: 418          moltype = AA  length = 15
FEATURE                 Location/Qualifiers
REGION                  1..15
                        note = Description of Artificial Sequence: Synthetic peptide
source                  1..15
                        mol_type = protein
                        organism = synthetic construct
SEQUENCE: 418
WYQQKPGKAP KLLIY                                                       15

SEQ ID NO: 419          moltype = AA  length = 15
FEATURE                 Location/Qualifiers
REGION                  1..15
                        note = Description of Artificial Sequence: Synthetic peptide
source                  1..15
                        mol_type = protein
                        organism = synthetic construct
SEQUENCE: 419
WYQQKPGQAP RLLIY                                                       15

SEQ ID NO: 420          moltype = AA  length = 15
FEATURE                 Location/Qualifiers
REGION                  1..15
                        note = Description of Artificial Sequence: Synthetic peptide
source                  1..15
                        mol_type = protein
                        organism = synthetic construct
SEQUENCE: 420
WYHQKPWNAP KLMIY                                                       15

SEQ ID NO: 421          moltype = AA  length = 32
FEATURE                 Location/Qualifiers
REGION                  1..32
                        note = Description of Artificial Sequence: Synthetic
                         polypeptide
source                  1..32
                        mol_type = protein
                        organism = synthetic construct
SEQUENCE: 421
GVPSRFSGSG SGTDFTLTIS SLQPEDFATY YC                                    32

SEQ ID NO: 422          moltype = AA  length = 32
FEATURE                 Location/Qualifiers
REGION                  1..32
                        note = Description of Artificial Sequence: Synthetic
                         polypeptide
source                  1..32
                        mol_type = protein
                        organism = synthetic construct
SEQUENCE: 422
GIPARFSGSG SGTEFTLTIS SLQSEDFAVY YC                                    32

SEQ ID NO: 423          moltype = AA  length = 32
FEATURE                 Location/Qualifiers
REGION                  1..32
                        note = Description of Artificial Sequence: Synthetic
                         polypeptide
source                  1..32
                        mol_type = protein
                        organism = synthetic construct
SEQUENCE: 423
GVPSRFSGSG SGTYFTLTIS SLQPEDFATY YC                                    32

SEQ ID NO: 424          moltype = AA  length = 32
FEATURE                 Location/Qualifiers
REGION                  1..32
                        note = Description of Artificial Sequence: Synthetic
                         polypeptide
source                  1..32
                        mol_type = protein
                        organism = synthetic construct
SEQUENCE: 424
GVPSRFSGSG SGTDFTLTIS SLQPEDFAPY YC                                    32
```

```
SEQ ID NO: 425          moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 425
FGGGTKVEIK                                                        10

SEQ ID NO: 426          moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 426
FGQGTKLEIK                                                        10

SEQ ID NO: 427          moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 427
FGQGTKVEIK                                                        10

SEQ ID NO: 428          moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 428
FGQGTRLEIK                                                        10

SEQ ID NO: 429          moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 429
FGPGTKVDIK                                                        10

SEQ ID NO: 430          moltype = AA  length = 118
FEATURE                 Location/Qualifiers
REGION                  1..118
                        note = Description of Artificial Sequence: Synthetic
                         polypeptide
source                  1..118
                        mol_type = protein
                        organism = synthetic construct
SEQUENCE: 430
QVQLVQSGAE VKKPGASVKV SCKASGYTFS SDYMHWVRQA PGQGLEWMGW MSPYNGITGY  60
AQKFQGRVTM TRDTSTSTVY MELSSLRSED TAVYYCARDR FSGSYDYWGQ GTLVTVSS    118

SEQ ID NO: 431          moltype = AA  length = 116
FEATURE                 Location/Qualifiers
REGION                  1..116
                        note = Description of Artificial Sequence: Synthetic
                         polypeptide
source                  1..116
                        mol_type = protein
                        organism = synthetic construct
SEQUENCE: 431
QVQLVQSGAE VKKPGASVKV SCKASGYTFT GYYMHWVRQA PGQGLEWMGW MSPSSGITGY  60
AQKFQGRVTM TRDTSTSTVY MELSSLRSED TAVYYCARDR GWFDPWGQGT LVTVSS      116

SEQ ID NO: 432          moltype = AA  length = 118
FEATURE                 Location/Qualifiers
REGION                  1..118
                        note = Description of Artificial Sequence: Synthetic
                         polypeptide
```

```
source                  1..118
                        mol_type = protein
                        organism = synthetic construct
SEQUENCE: 432
QVQLVQSGAE VKKPGASVKV SCKASGYTFS SYYMHWVRQA PGQGLEWMGW MTTNSGITGY  60
AQKFQGRVTM TRDTSTSTVY MELSSLRSED TAVYYCAREG YSSGLDYWGQ GTLVTVSS    118

SEQ ID NO: 433          moltype = AA  length = 120
FEATURE                 Location/Qualifiers
REGION                  1..120
                        note = Description of Artificial Sequence: Synthetic
                         polypeptide
source                  1..120
                        mol_type = protein
                        organism = synthetic construct
SEQUENCE: 433
QVQLVQSGAE VKKPGSSVKV SCKASGYTFT GYYIHWVRQA PGQGLEWMGG IIPIFGTASY  60
AQKFQGRVTI TADESTSTAY MELSSLRSED TAVYYCARDG RFWSGYPDYW GQGTLVTVSS  120

SEQ ID NO: 434          moltype = AA  length = 119
FEATURE                 Location/Qualifiers
REGION                  1..119
                        note = Description of Artificial Sequence: Synthetic
                         polypeptide
source                  1..119
                        mol_type = protein
                        organism = synthetic construct
SEQUENCE: 434
QVQLVQSGAE VKKPGASVKV SCKASGYTFS THYMHWVRQA PGQGLEWMGW MNPNSGHAGS  60
AQKFQGRVTM TRDTSTSTVY MELSSLRSED TAVYYCARES IAVAGYDYWG QGTLVTVSS   119

SEQ ID NO: 435          moltype = AA  length = 119
FEATURE                 Location/Qualifiers
REGION                  1..119
                        note = Description of Artificial Sequence: Synthetic
                         polypeptide
source                  1..119
                        mol_type = protein
                        organism = synthetic construct
SEQUENCE: 435
QVQLVQSGAE VKKPGASVKV SCKASGYTFT SHDINWVRQA PGQGLEWMGW MNPNSGNTGY  60
AQKFQGRVTM TRDTSTSTVY MELSSLRSED TAVYYCARDR WYMGSADYWG QGTLVTVSS   119

SEQ ID NO: 436          moltype = AA  length = 119
FEATURE                 Location/Qualifiers
REGION                  1..119
                        note = Description of Artificial Sequence: Synthetic
                         polypeptide
source                  1..119
                        mol_type = protein
                        organism = synthetic construct
SEQUENCE: 436
QVQLVQSGAE VKKPGASVKV SCKASGYTFT SYYMHWVRQA PGQGLEWMGW MNPNSGNTGY  60
AQKFQGRVTM TRDTSTSTVY MELSSLRSED TAVYYCARDD WGGDWFDPWG QGTLVTVSS   119

SEQ ID NO: 437          moltype = AA  length = 119
FEATURE                 Location/Qualifiers
REGION                  1..119
                        note = Description of Artificial Sequence: Synthetic
                         polypeptide
source                  1..119
                        mol_type = protein
                        organism = synthetic construct
SEQUENCE: 437
QVQLVQSGAE VKKPGASVKV SCKASGYTFS THYMHWVRQA PGQGLEWMGW MNPNSGNTGY  60
SQKFQGRVTM TRDTSTSTVY MELSSLRSED TAVYYCARER LSVAGFDYWG QGTLVTVSS   119

SEQ ID NO: 438          moltype = AA  length = 119
FEATURE                 Location/Qualifiers
REGION                  1..119
                        note = Description of Artificial Sequence: Synthetic
                         polypeptide
source                  1..119
                        mol_type = protein
                        organism = synthetic construct
SEQUENCE: 438
QVQLVQSGAE VKEPGASVKV SCKASGYTFT DHYLHWVRQA PGQGLEWMGW MNPNIGNTGY  60
AQKFQGRVTM TRDTSTSTVY MELSSLRSED TAVYYCAREP LQLGGFDYWG QGTLVTVSS   119
```

-continued

```
SEQ ID NO: 439         moltype = AA  length = 119
FEATURE                Location/Qualifiers
REGION                 1..119
                       note = Description of Artificial Sequence: Synthetic
                        polypeptide
source                 1..119
                       mol_type = protein
                       organism = synthetic construct
SEQUENCE: 439
QVQLVQSGAE VKKPGASVKV SCKASGYTFT GYYMHWVRQA PGQGLEWMGW MNPNGGTTGY  60
AQNFQGRVTM TRDTSTSTVY MELSSLRSED TAVYYCAREG FGPNAFDIWG QGTTVTVSS   119

SEQ ID NO: 440         moltype = AA  length = 119
FEATURE                Location/Qualifiers
REGION                 1..119
                       note = Description of Artificial Sequence: Synthetic
                        polypeptide
source                 1..119
                       mol_type = protein
                       organism = synthetic construct
SEQUENCE: 440
QVQLVQSGAE VKKPGASVKV SCKASGYTFT GYYMHWVRQA PGQGLEWMGW MNPNSGNTGY  60
AQKFQGRVTM TRDTSTSTVY MELSSLRSED TAVYYCARDS WYGDWFDPWG QGTLVTVSS   119

SEQ ID NO: 441         moltype = AA  length = 118
FEATURE                Location/Qualifiers
REGION                 1..118
                       note = Description of Artificial Sequence: Synthetic
                        polypeptide
source                 1..118
                       mol_type = protein
                       organism = synthetic construct
SEQUENCE: 441
QVQLVQSGAE VKKPGASVKV SCKASGYTFT GYYMHWMRQA PGQGLEWIGW MSPYNGITGY  60
AQKFQGRVTM TRDTSTSTVY MELSSLRSED TAVYYCAREV IEVGMDVWGQ GTTVTVSS    118

SEQ ID NO: 442         moltype = AA  length = 118
FEATURE                Location/Qualifiers
REGION                 1..118
                       note = Description of Artificial Sequence: Synthetic
                        polypeptide
source                 1..118
                       mol_type = protein
                       organism = synthetic construct
SEQUENCE: 442
QVQLVQSGAE VKKPGASVKV SCKASGYTFT NYYMHWVRQA PGQGLEWMGW MSPSSGITGY  60
AQKFQGRVTM TRDTSTSTVY MELSSLRSED TAVYYCAREA WFGELSTWGQ GTLVTVSS    118

SEQ ID NO: 443         moltype = AA  length = 118
FEATURE                Location/Qualifiers
REGION                 1..118
                       note = Description of Artificial Sequence: Synthetic
                        polypeptide
source                 1..118
                       mol_type = protein
                       organism = synthetic construct
SEQUENCE: 443
QVQLVQSGAE VKKPGASVKV SCKASGYNFS AYYVHWVRQA PGQGLEWMGW MNPNRGITDS  60
AQKFQGRVTM TRDTSTSTVY MELSSLRSED TAVYYCAREA YVAAFDIWGQ GTTVTVSS    118

SEQ ID NO: 444         moltype = AA  length = 118
FEATURE                Location/Qualifiers
REGION                 1..118
                       note = Description of Artificial Sequence: Synthetic
                        polypeptide
source                 1..118
                       mol_type = protein
                       organism = synthetic construct
SEQUENCE: 444
QVQLVQSGAE VKKPGASVKV SCKASGYTFT RHYVHWVRQA PGQGLEWMGW MNPNSGSAGY  60
AQKFQGRVTM TRDTSTSTVY MELSSLRSED TAVYYCARER GYNAFDYWGQ GTLVTVSS    118

SEQ ID NO: 445         moltype = AA  length = 116
FEATURE                Location/Qualifiers
REGION                 1..116
                       note = Description of Artificial Sequence: Synthetic
                        polypeptide
source                 1..116
                       mol_type = protein
```

```
                         organism = synthetic construct
SEQUENCE: 445
QVQLVQSGAE VKKPGASVKV SCKASGYTLP NYIHWVRQAP GQGLEWMGWI HPRSGATGYA  60
PKFQGRVTMT RDTSTSTVYM ELSSLRSEDT AVYYCARDSV FGLDYWGQGT LVTVSS      116

SEQ ID NO: 446           moltype = AA  length = 119
FEATURE                  Location/Qualifiers
REGION                   1..119
                         note = Description of Artificial Sequence: Synthetic
                          polypeptide
source                   1..119
                         mol_type = protein
                         organism = synthetic construct
SEQUENCE: 446
QVQLVQSGAE VKKPGASVKV SCKASGYTFT SYYMHWVRQA PGQGLEWMGW ISPRSGVTSY  60
AQKFQGRVTM TRDTSTSTVY MELSSLRSED TAVYYCARDL DYVRAFDIWG QGTTVTVSS   119

SEQ ID NO: 447           moltype = AA  length = 118
FEATURE                  Location/Qualifiers
REGION                   1..118
                         note = Description of Artificial Sequence: Synthetic
                          polypeptide
source                   1..118
                         mol_type = protein
                         organism = synthetic construct
SEQUENCE: 447
QVQLVQSGAE VKKPGASVKV SCKASGYSFT SYYMHWVRQA PGQGLEWMGW MDPNSGNTGY  60
AQKFQGRVTM TRDTSTSTVY MELSSLRSED TAVYYCARES WGGYFDLWGR GTLVTVSS    118

SEQ ID NO: 448           moltype = AA  length = 118
FEATURE                  Location/Qualifiers
REGION                   1..118
                         note = Description of Artificial Sequence: Synthetic
                          polypeptide
source                   1..118
                         mol_type = protein
                         organism = synthetic construct
SEQUENCE: 448
QVQLVQSGAE VKKPGASVKV SCKASGYTFI NHYVHWVRQA PGQGLEWMGW MNPTGGITGY  60
AQKFQGRVTM TRDTSTSTVY MELSSLRSED TAVYYCARDR TTYAFDIWGQ GTMVTVSS    118

SEQ ID NO: 449           moltype = AA  length = 118
FEATURE                  Location/Qualifiers
REGION                   1..118
                         note = Description of Artificial Sequence: Synthetic
                          polypeptide
source                   1..118
                         mol_type = protein
                         organism = synthetic construct
SEQUENCE: 449
QVQLVQSGAE VKKPGASVKV SCKASGYTFT SHYMHWVRQA PGQGLEWMGW MNPNSGHTGN  60
AQKFQGRVTM TRDTSTSTVY MELSSLRSED TAVYYCARGN WVDAFDIWGQ GTMVTVSS    118

SEQ ID NO: 450           moltype = AA  length = 120
FEATURE                  Location/Qualifiers
REGION                   1..120
                         note = Description of Artificial Sequence: Synthetic
                          polypeptide
source                   1..120
                         mol_type = protein
                         organism = synthetic construct
SEQUENCE: 450
QVQLVQSGAE VKKPGSSVKV SCKASGYTFT RHLLHWVRQA PGQGLEWMGW VSPIHGLTGY  60
APRFQGRVTI TADESTSTAY MELSSLRSED TAVYYCARVH GSGSDGMDVW GQGTTVTVSS  120

SEQ ID NO: 451           moltype = AA  length = 107
FEATURE                  Location/Qualifiers
REGION                   1..107
                         note = Description of Artificial Sequence: Synthetic
                          polypeptide
source                   1..107
                         mol_type = protein
                         organism = synthetic construct
SEQUENCE: 451
DIQMTQSPSS LSASVGDRVT ITCRASQSIS SWLAWYQQKP GKAPKLLIYA ASSLQSGVPS  60
RFSGSGSGTD FTLTISSLQP EDFATYYCQQ SYSTPYTFGG GTKVEIK                107

SEQ ID NO: 452           moltype = AA  length = 107
FEATURE                  Location/Qualifiers
```

-continued

```
REGION                  1..107
                        note = Description of Artificial Sequence: Synthetic
                         polypeptide
source                  1..107
                        mol_type = protein
                        organism = synthetic construct
SEQUENCE: 452
DIQMTQSPSS LSASVGDRVT ITCRASQSVG TWLAWYQQKP GKAPKLLIYA ASTLENGVPS  60
RFSGSGSGTD FTLTISSLQP EDFATYYCQQ SFSTPYTFGG GTKVEIK                107

SEQ ID NO: 453          moltype = AA  length = 107
FEATURE                 Location/Qualifiers
REGION                  1..107
                        note = Description of Artificial Sequence: Synthetic
                         polypeptide
source                  1..107
                        mol_type = protein
                        organism = synthetic construct
SEQUENCE: 453
DIQMTQSPSS LSASVGDRVT ITCRASQSIS SWLAWYQQKP GKAPKLLIYA ASSLQSGVPS  60
RFSGSGSGTD FTLTISSLQP EDFATYYCQQ SYSTPYTFGG GTKVEIK                107

SEQ ID NO: 454          moltype = AA  length = 107
FEATURE                 Location/Qualifiers
REGION                  1..107
                        note = Description of Artificial Sequence: Synthetic
                         polypeptide
source                  1..107
                        mol_type = protein
                        organism = synthetic construct
SEQUENCE: 454
DIQMTQSPSS LSASVGDRVT ITCRASQGIS NYLAWYQQKP GKAPKLLIYR ASNLESGVPS  60
RFSGSGSGTD FTLTISSLQP EDFATYYCQQ SYSTPLTFGG GTKVEIK                107

SEQ ID NO: 455          moltype = AA  length = 107
FEATURE                 Location/Qualifiers
REGION                  1..107
                        note = Description of Artificial Sequence: Synthetic
                         polypeptide
source                  1..107
                        mol_type = protein
                        organism = synthetic construct
SEQUENCE: 455
DIQMTQSPSS LSASVGDRVT ITCRASQSIS SWLAWYQQKP GKAPKLLIYA ASTLQRGVPS  60
RFSGSGSGTD FTLTISSLQP EDFATYYCQQ SYSTPYTFGQ GTKLEIK                107

SEQ ID NO: 456          moltype = AA  length = 107
FEATURE                 Location/Qualifiers
REGION                  1..107
                        note = Description of Artificial Sequence: Synthetic
                         polypeptide
source                  1..107
                        mol_type = protein
                        organism = synthetic construct
SEQUENCE: 456
DIQMTQSPSS LSASVGDRVT ITCRASQSIS TWLAWYQQKP GKAPKLLIYA ASTLQSGVPS  60
RFSGSGSGTD FTLTISSLQP EDFATYYCQQ SYSTPFTFGQ GTKVEIK                107

SEQ ID NO: 457          moltype = AA  length = 107
FEATURE                 Location/Qualifiers
REGION                  1..107
                        note = Description of Artificial Sequence: Synthetic
                         polypeptide
source                  1..107
                        mol_type = protein
                        organism = synthetic construct
SEQUENCE: 457
DIQMTQSPSS LSASVGDRVT ITCQASQDIS NHLNWYQQKP GKAPKLLIYG ASNLQRGVPS  60
RFSGSGSGTD FTLTISSLQP EDFATYYCQQ SYSTPITFGQ GTRLEIK                107

SEQ ID NO: 458          moltype = AA  length = 107
FEATURE                 Location/Qualifiers
REGION                  1..107
                        note = Description of Artificial Sequence: Synthetic
                         polypeptide
source                  1..107
                        mol_type = protein
                        organism = synthetic construct
SEQUENCE: 458
```

-continued

```
DIQMTQSPSS LSASVGDRVT ITCRASQGIS SWLAWYQQKP GKAPKLLIYA ASSLQSGVPS  60
RFSGSGSGTD FTLTISSLQP EDFATYYCQQ SYSTPYTFGQ GTKVEIK                107

SEQ ID NO: 459         moltype = AA  length = 107
FEATURE                Location/Qualifiers
REGION                 1..107
                       note = Description of Artificial Sequence: Synthetic
                        polypeptide
source                 1..107
                       mol_type = protein
                       organism = synthetic construct
SEQUENCE: 459
DIQMTQSPSS LSASVGDRVT ITCRASESIS SWLAWYQQKP GKAPKLLIYA ASSLQSGVPS  60
RFSGSGSGTD FTLTISSLQP EDFATYYCQQ SYSTPLTFGQ GTKLEIK                107

SEQ ID NO: 460         moltype = AA  length = 107
FEATURE                Location/Qualifiers
REGION                 1..107
                       note = Description of Artificial Sequence: Synthetic
                        polypeptide
source                 1..107
                       mol_type = protein
                       organism = synthetic construct
SEQUENCE: 460
DIQMTQSPSS LSASVGDRVT ITCRASQSIS SWLAWYQQKP GKAPKLLIYA ASNLQSGVPS  60
RFSGSGSGTD FTLTISSLQP EDFATYYCQQ YYSTPYTFGQ GTKVEIK                107

SEQ ID NO: 461         moltype = AA  length = 107
FEATURE                Location/Qualifiers
REGION                 1..107
                       note = Description of Artificial Sequence: Synthetic
                        polypeptide
source                 1..107
                       mol_type = protein
                       organism = synthetic construct
SEQUENCE: 461
DIQMTQSPSS LSASVGDRVT ITCRASQSVG SWLAWYQQKP GKAPKLLIYG ASSLQSGVPS  60
RFSGSGSGTD FTLTISSLQP EDFATYYCQQ SYSTPLTFGG GTKVEIK                107

SEQ ID NO: 462         moltype = AA  length = 107
FEATURE                Location/Qualifiers
REGION                 1..107
                       note = Description of Artificial Sequence: Synthetic
                        polypeptide
source                 1..107
                       mol_type = protein
                       organism = synthetic construct
SEQUENCE: 462
DIQMTQSPSS LSASVGDRVT ITCRASQSIS SWLAWYQQKP GKAPKLLIYA ASHLQSGVPS  60
RFSGSGSGTD FTLTISSLQP EDFATYYCQQ SYSTPYTFGQ GTRLEIK                107

SEQ ID NO: 463         moltype = AA  length = 107
FEATURE                Location/Qualifiers
REGION                 1..107
                       note = Description of Artificial Sequence: Synthetic
                        polypeptide
source                 1..107
                       mol_type = protein
                       organism = synthetic construct
SEQUENCE: 463
DIQMTQSPSS LSASVGDRVT ITCRASQNIS NFLNWYQQKP GKAPKLLIYA ASSLQSGVPS  60
RFSGSGSGTD FTLTISSLQP EDFATYYCQQ SYSLPYTFGQ GTKVEIK                107

SEQ ID NO: 464         moltype = AA  length = 107
FEATURE                Location/Qualifiers
REGION                 1..107
                       note = Description of Artificial Sequence: Synthetic
                        polypeptide
source                 1..107
                       mol_type = protein
                       organism = synthetic construct
SEQUENCE: 464
DIQMTQSPSS LSASVGDRVT ITCRASQGIS SWLAWYQQKP GKAPKLLIYA ASSLQSGVPS  60
RFSGSGSGTD FTLTISSLQP EDFATYYCQQ SYSTPLTFGG GTKVEIK                107

SEQ ID NO: 465         moltype = AA  length = 108
FEATURE                Location/Qualifiers
REGION                 1..108
                       note = Description of Artificial Sequence: Synthetic
```

```
                         polypeptide
source                   1..108
                         mol_type = protein
                         organism = synthetic construct
SEQUENCE: 465
EIVMTQSPAT LSVSPGERAT LSCRASQSLS SSYLAWYQQK PGQAPRLLIY GASTRATGIP  60
ARFSGSGSGT EFTLTISSLQ SEDFAVYYCH QYFTTPLTFG QGTRLEIK               108

SEQ ID NO: 466           moltype = AA  length = 107
FEATURE                  Location/Qualifiers
REGION                   1..107
                         note = Description of Artificial Sequence: Synthetic
                          polypeptide
source                   1..107
                         mol_type = protein
                         organism = synthetic construct
SEQUENCE: 466
DIQMTQSPSS LSASVGDRVT ITCRASQSIS SYLNWYQQKP GKAPKLLIYA ASTLQSGVPS  60
RFSGSGSGTD FTLTISSLQP EDFATYYCQQ SYSMPYTFGQ GTKLEIK                107

SEQ ID NO: 467           moltype = AA  length = 107
FEATURE                  Location/Qualifiers
REGION                   1..107
                         note = Description of Artificial Sequence: Synthetic
                          polypeptide
source                   1..107
                         mol_type = protein
                         organism = synthetic construct
SEQUENCE: 467
DIQMTQSPSS LSASVGDRVT ITCRASQSIS RWLAWYQQKP GKAPKLLIYA ASSLQSGVPS  60
RFSGSGSGTD FTLTISSLQP EDFATYYCQQ SYSTPYTFGQ GTKLEIK                107

SEQ ID NO: 468           moltype = AA  length = 107
FEATURE                  Location/Qualifiers
REGION                   1..107
                         note = Description of Artificial Sequence: Synthetic
                          polypeptide
source                   1..107
                         mol_type = protein
                         organism = synthetic construct
SEQUENCE: 468
DIQMTQSPSS LSASVGDRVT ITCRASQSIS SWLAWYQQKP GKAPKLLIYD SSSLQTGVPS  60
RFSGSGSGTD FTLTISSLQP EDFATYYCQQ SYSTPVTFGQ GTKVEIK                107

SEQ ID NO: 469           moltype = AA  length = 107
FEATURE                  Location/Qualifiers
REGION                   1..107
                         note = Description of Artificial Sequence: Synthetic
                          polypeptide
source                   1..107
                         mol_type = protein
                         organism = synthetic construct
SEQUENCE: 469
DIQITHSPSS LSASVGYRLT ITCRDSHSIT TWLAWYHQKP WNAPKLMIYA ASNLESGVPS  60
RFSGSGSGTY FTLTISSLQP EDFATYYCQH FYNTQYTFGQ GTKVEIK                107

SEQ ID NO: 470           moltype = AA  length = 108
FEATURE                  Location/Qualifiers
REGION                   1..108
                         note = Description of Artificial Sequence: Synthetic
                          polypeptide
source                   1..108
                         mol_type = protein
                         organism = synthetic construct
SEQUENCE: 470
DIQMTQSPSS LSASVGDRVT ITCRASQVIR NDLAWYQQKP GKAPKLLIYA ASTLQSGVPS  60
RFSGSGSGTD FTLTISSLQP EDFATYYCQQ SLQYPSHFFG QGTKVEIK               108

SEQ ID NO: 471           moltype = AA  length = 107
FEATURE                  Location/Qualifiers
REGION                   1..107
                         note = Description of Artificial Sequence: Synthetic
                          polypeptide
source                   1..107
                         mol_type = protein
                         organism = synthetic construct
SEQUENCE: 471
DIQMTQSPSS LSASVGDRVT ITCRASQSIS RYLNWYQQKP GKAPKLLIYA ASTLQSGVPS  60
RFSGSGSGTD FTLTISSLQP EDFAPYYCQQ SYSTPLTFGP GTKVDIK                107
```

```
SEQ ID NO: 472          moltype = AA  length = 106
FEATURE                 Location/Qualifiers
REGION                  1..106
                        note = Description of Artificial Sequence: Synthetic
                         polypeptide
source                  1..106
                        mol_type = protein
                        organism = synthetic construct
SEQUENCE: 472
DIQLTQSPSS LSASVGDRVT ITCKASQDVG TSVAWYQQKP GKAPKLLIYW TSTRHTGVPS  60
RFSGSGSGTD FTFTISSLQP EDIATYYCQQ YSLYRSFGQG TKVEIK                106

SEQ ID NO: 473          moltype = AA  length = 23
FEATURE                 Location/Qualifiers
REGION                  1..23
                        note = Description of Artificial Sequence: Synthetic peptide
source                  1..23
                        mol_type = protein
                        organism = synthetic construct
SEQUENCE: 473
DIQLTQSPSS LSASVGDRVT ITC                                         23

SEQ ID NO: 474          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 474
KASQDVGTSV A                                                      11

SEQ ID NO: 475          moltype = AA  length = 15
FEATURE                 Location/Qualifiers
REGION                  1..15
                        note = Description of Artificial Sequence: Synthetic peptide
source                  1..15
                        mol_type = protein
                        organism = synthetic construct
SEQUENCE: 475
WYQQKPGKAP KLLIY                                                  15

SEQ ID NO: 476          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 476
WTSTRHT                                                           7

SEQ ID NO: 477          moltype = AA  length = 32
FEATURE                 Location/Qualifiers
REGION                  1..32
                        note = Description of Artificial Sequence: Synthetic
                         polypeptide
source                  1..32
                        mol_type = protein
                        organism = synthetic construct
SEQUENCE: 477
GVPSRFSGSG SGTDFTFTIS SLQPEDIATY YC                               32

SEQ ID NO: 478          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 478
QQYSLYRS                                                          8

SEQ ID NO: 479          moltype = AA  length = 10
FEATURE                 Location/Qualifiers
REGION                  1..10
                        note = Description of Artificial Sequence: Synthetic peptide
source                  1..10
```

```
                      mol_type = protein
                      organism = synthetic construct
SEQUENCE: 479
FGQGTKVEIK                                                        10

SEQ ID NO: 480        moltype = AA  length = 119
FEATURE               Location/Qualifiers
REGION                1..119
                      note = Description of Artificial Sequence: Synthetic
                       polypeptide
source                1..119
                      mol_type = protein
                      organism = synthetic construct
SEQUENCE: 480
EVQLVESGGG VVQPGRSLRL SCSSSGFDFT TYWMSWVRQA PGKGLEWVAE IHPDSSTINY  60
APSLKDRFTI SRDNSKNTLF LQMDSLRPED TGVYFCASLY FGFPWFAYWG QGTPVTVSS   119

SEQ ID NO: 481        moltype = AA  length = 30
FEATURE               Location/Qualifiers
REGION                1..30
                      note = Description of Artificial Sequence: Synthetic
                       polypeptide
source                1..30
                      mol_type = protein
                      organism = synthetic construct
SEQUENCE: 481
EVQLVESGGG VVQPGRSLRL SCSSSGFDFT                                  30

SEQ ID NO: 482        moltype = AA  length = 5
FEATURE               Location/Qualifiers
REGION                1..5
                      note = Description of Artificial Sequence: Synthetic peptide
source                1..5
                      mol_type = protein
                      organism = synthetic construct
SEQUENCE: 482
TYWMS                                                             5

SEQ ID NO: 483        moltype = AA  length = 14
FEATURE               Location/Qualifiers
REGION                1..14
                      note = Description of Artificial Sequence: Synthetic peptide
source                1..14
                      mol_type = protein
                      organism = synthetic construct
SEQUENCE: 483
WVRQAPGKGL EWVA                                                   14

SEQ ID NO: 484        moltype = AA  length = 17
FEATURE               Location/Qualifiers
REGION                1..17
                      note = Description of Artificial Sequence: Synthetic peptide
source                1..17
                      mol_type = protein
                      organism = synthetic construct
SEQUENCE: 484
EIHPDSSTIN YAPSLKD                                                17

SEQ ID NO: 485        moltype = AA  length = 32
FEATURE               Location/Qualifiers
REGION                1..32
                      note = Description of Artificial Sequence: Synthetic
                       polypeptide
source                1..32
                      mol_type = protein
                      organism = synthetic construct
SEQUENCE: 485
RFTISRDNSK NTLFLQMDSL RPEDTGVYFC AS                               32

SEQ ID NO: 486        moltype = AA  length = 10
FEATURE               Location/Qualifiers
REGION                1..10
                      note = Description of Artificial Sequence: Synthetic peptide
source                1..10
                      mol_type = protein
                      organism = synthetic construct
SEQUENCE: 486
LYFGFPWFAY                                                        10
```

```
SEQ ID NO: 487          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 487
WGQGTPVTVS S                                                          11

SEQ ID NO: 488          moltype = AA  length = 108
FEATURE                 Location/Qualifiers
REGION                  1..108
                        note = Description of Artificial Sequence: Synthetic
                         polypeptide
source                  1..108
                        mol_type = protein
                        organism = synthetic construct
SEQUENCE: 488
DIQMTQSPSS LSASVGDRVT ITCKASAAVG TYVAWYQQKP GKAPKLLIYS ASYRKRGVPS  60
RFSGSGSGTD FTLTISSLQP EDFATYYCHQ YYTYPLFTFG QGTKLEIK               108

SEQ ID NO: 489          moltype = AA  length = 23
FEATURE                 Location/Qualifiers
REGION                  1..23
                        note = Description of Artificial Sequence: Synthetic peptide
source                  1..23
                        mol_type = protein
                        organism = synthetic construct
SEQUENCE: 489
DIQMTQSPSS LSASVGDRVT ITC                                             23

SEQ ID NO: 490          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 490
KASAAVGTYV A                                                          11

SEQ ID NO: 491          moltype = AA  length = 15
FEATURE                 Location/Qualifiers
REGION                  1..15
                        note = Description of Artificial Sequence: Synthetic peptide
source                  1..15
                        mol_type = protein
                        organism = synthetic construct
SEQUENCE: 491
WYQQKPGKAP KLLIY                                                      15

SEQ ID NO: 492          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 492
SASYRKR                                                               7

SEQ ID NO: 493          moltype = AA  length = 32
FEATURE                 Location/Qualifiers
REGION                  1..32
                        note = Description of Artificial Sequence: Synthetic
                         polypeptide
source                  1..32
                        mol_type = protein
                        organism = synthetic construct
SEQUENCE: 493
GVPSRFSGSG SGTDFTLTIS SLQPEDFATY YC                                   32

SEQ ID NO: 494          moltype = AA  length = 10
FEATURE                 Location/Qualifiers
REGION                  1..10
                        note = Description of Artificial Sequence: Synthetic peptide
source                  1..10
                        mol_type = protein
```

-continued

```
                        organism = synthetic construct
SEQUENCE: 494
HQYYTYPLFT                                                     10

SEQ ID NO: 495          moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 495
FGQGTKLEIK                                                     10

SEQ ID NO: 496          moltype = AA  length = 30
FEATURE                 Location/Qualifiers
REGION                  1..30
                        note = Description of Artificial Sequence: Synthetic
                         polypeptide
source                  1..30
                        mol_type = protein
                        organism = synthetic construct
SEQUENCE: 496
QVQLVQSGAE VKKPGASVKV SCKASGYTFT                               30

SEQ ID NO: 497          moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 497
EFGMN                                                          5

SEQ ID NO: 498          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 498
WVRQAPGQGL EWMG                                                14

SEQ ID NO: 499          moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 499
WINTKTGEAT YVEEFKG                                             17

SEQ ID NO: 500          moltype = AA  length = 32
FEATURE                 Location/Qualifiers
REGION                  1..32
                        note = Description of Artificial Sequence: Synthetic
                         polypeptide
source                  1..32
                        mol_type = protein
                        organism = synthetic construct
SEQUENCE: 500
RVTFTTDTST STAYMELRSL RSDDTAVYYC AR                            32

SEQ ID NO: 501          moltype = AA  length = 12
FEATURE                 Location/Qualifiers
REGION                  1..12
                        note = Description of Artificial Sequence: Synthetic peptide
source                  1..12
                        mol_type = protein
                        organism = synthetic construct
SEQUENCE: 501
WDFAYYVEAM DY                                                  12

SEQ ID NO: 502          moltype = AA  length = 11
FEATURE                 Location/Qualifiers
REGION                  1..11
```

```
                        note = Description of Artificial Sequence: Synthetic peptide
source                  1..11
                        mol_type = protein
                        organism = synthetic construct
SEQUENCE: 502
WGQGTTVTVS S                                                       11

SEQ ID NO: 503          moltype = AA  length = 106
FEATURE                 Location/Qualifiers
REGION                  1..106
                        note = Description of Artificial Sequence: Synthetic
                         polypeptide
source                  1..106
                        mol_type = protein
                        organism = synthetic construct
SEQUENCE: 503
ENVLTQSPSS MSASVGDRVN IACSASSSVS YMHWFQQKPG KSPKLWIYST SNLASGVPSR  60
FSGSGSGTDY SLTISSMQPE DAATYYCQQR SSYPLTFGGG TKLEIK                 106

SEQ ID NO: 504          moltype = AA  length = 23
FEATURE                 Location/Qualifiers
REGION                  1..23
                        note = Description of Artificial Sequence: Synthetic peptide
source                  1..23
                        mol_type = protein
                        organism = synthetic construct
SEQUENCE: 504
ENVLTQSPSS MSASVGDRVN IAC                                          23

SEQ ID NO: 505          moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 505
SASSSVSYMH                                                         10

SEQ ID NO: 506          moltype = AA  length = 15
FEATURE                 Location/Qualifiers
REGION                  1..15
                        note = Description of Artificial Sequence: Synthetic peptide
source                  1..15
                        mol_type = protein
                        organism = synthetic construct
SEQUENCE: 506
WFQQKPGKSP KLWIY                                                   15

SEQ ID NO: 507          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 507
STSNLAS                                                            7

SEQ ID NO: 508          moltype = AA  length = 32
FEATURE                 Location/Qualifiers
REGION                  1..32
                        note = Description of Artificial Sequence: Synthetic
                         polypeptide
source                  1..32
                        mol_type = protein
                        organism = synthetic construct
SEQUENCE: 508
GVPSRFSGSG SGTDYSLTIS SMQPEDAATY YC                                32

SEQ ID NO: 509          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 509
QQRSSYPLT                                                          9
```

```
SEQ ID NO: 510          moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 510
FGGGTKLEIK                                                            10

SEQ ID NO: 511          moltype = AA  length = 120
FEATURE                 Location/Qualifiers
REGION                  1..120
                        note = Description of Artificial Sequence: Synthetic
                         polypeptide
source                  1..120
                        mol_type = protein
                        organism = synthetic construct
SEQUENCE: 511
QVKLEQSGAE VVKPGASVKL SCKASGFNIK DSYMHWLRQG PGQRLEWIGW IDPENGDTEY  60
APKFQGKATF TTDTSANTAY LGLSSLRPED TAVYYCNEGT PTGPYYFDYW GQGTLVTVSS  120

SEQ ID NO: 512          moltype = AA  length = 30
FEATURE                 Location/Qualifiers
REGION                  1..30
                        note = Description of Artificial Sequence: Synthetic
                         polypeptide
source                  1..30
                        mol_type = protein
                        organism = synthetic construct
SEQUENCE: 512
QVKLEQSGAE VVKPGASVKL SCKASGFNIK                                      30

SEQ ID NO: 513          moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 513
DSYMH                                                                 5

SEQ ID NO: 514          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 514
WLRQGPGQRL EWIG                                                       14

SEQ ID NO: 515          moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 515
WIDPENGDTE YAPKFQG                                                    17

SEQ ID NO: 516          moltype = AA  length = 32
FEATURE                 Location/Qualifiers
REGION                  1..32
                        note = Description of Artificial Sequence: Synthetic
                         polypeptide
source                  1..32
                        mol_type = protein
                        organism = synthetic construct
SEQUENCE: 516
KATFTTDTSA NTAYLGLSSL RPEDTAVYYC NE                                   32

SEQ ID NO: 517          moltype = AA  length = 11
FEATURE                 Location/Qualifiers
REGION                  1..11
                        note = Description of Artificial Sequence: Synthetic peptide
```

```
source                  1..11
                        mol_type = protein
                        organism = synthetic construct
SEQUENCE: 517
GTPTGPYYFD Y                                                  11

SEQ ID NO: 518          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 518
WGQGTLVTVS S                                                  11

SEQ ID NO: 519          moltype = AA  length = 106
FEATURE                 Location/Qualifiers
REGION                  1..106
                        note = Description of Artificial Sequence: Synthetic
                         polypeptide
source                  1..106
                        mol_type = protein
                        organism = synthetic construct
SEQUENCE: 519
ENVLTQSPSS MSVSVGDRVT IACSASSSVP YMHWLQQKPG KSPKLLIYLT SNLASGVPSR  60
FSGSGSGTDY SLTISSVQPE DAATYYCQQR SSYPLTFGGG TKLEIK                106

SEQ ID NO: 520          moltype = AA  length = 23
FEATURE                 Location/Qualifiers
REGION                  1..23
                        note = Description of Artificial Sequence: Synthetic peptide
source                  1..23
                        mol_type = protein
                        organism = synthetic construct
SEQUENCE: 520
ENVLTQSPSS MSVSVGDRVT IAC                                     23

SEQ ID NO: 521          moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 521
SASSSVPYMH                                                    10

SEQ ID NO: 522          moltype = AA  length = 15
FEATURE                 Location/Qualifiers
REGION                  1..15
                        note = Description of Artificial Sequence: Synthetic peptide
source                  1..15
                        mol_type = protein
                        organism = synthetic construct
SEQUENCE: 522
WLQQKPGKSP KLLIY                                              15

SEQ ID NO: 523          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 523
LTSNLAS                                                       7

SEQ ID NO: 524          moltype = AA  length = 32
FEATURE                 Location/Qualifiers
REGION                  1..32
                        note = Description of Artificial Sequence: Synthetic
                         polypeptide
source                  1..32
                        mol_type = protein
                        organism = synthetic construct
SEQUENCE: 524
GVPSRFSGSG SGTDYSLTIS SVQPEDAATY YC                           32
```

-continued

```
SEQ ID NO: 525          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 525
QQRSSYPLT                                                            9

SEQ ID NO: 526          moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 526
FGGGTKLEIK                                                           10

SEQ ID NO: 527          moltype = AA  length = 120
FEATURE                 Location/Qualifiers
REGION                  1..120
                        note = Description of Artificial Sequence: Synthetic
                         polypeptide
source                  1..120
                        mol_type = protein
                        organism = synthetic construct
SEQUENCE: 527
QVKLEQSGAE VVKPGASVKL SCKASGFNIK DSYMHWLRQG PGQRLEWIGW IDPENGDTEY  60
APKFQGKATF TTDTSANTAY LGLSSLRPED TAVYYCNEGT PTGPYYFDYW GQGTLVTVSS  120

SEQ ID NO: 528          moltype = AA  length = 30
FEATURE                 Location/Qualifiers
REGION                  1..30
                        note = Description of Artificial Sequence: Synthetic
                         polypeptide
source                  1..30
                        mol_type = protein
                        organism = synthetic construct
SEQUENCE: 528
QVKLEQSGAE VVKPGASVKL SCKASGFNIK                                     30

SEQ ID NO: 529          moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 529
DSYMH                                                                5

SEQ ID NO: 530          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 530
WLRQGPGQRL EWIG                                                      14

SEQ ID NO: 531          moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 531
WIDPENGDTE YAPKFQG                                                   17

SEQ ID NO: 532          moltype = AA  length = 32
FEATURE                 Location/Qualifiers
REGION                  1..32
                        note = Description of Artificial Sequence: Synthetic
                         polypeptide
source                  1..32
```

```
                        mol_type = protein
                        organism = synthetic construct
SEQUENCE: 532
KATFTTDTSA NTAYLGLSSL RPEDTAVYYC NE                                  32

SEQ ID NO: 533          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 533
GTPTGPYYFD Y                                                         11

SEQ ID NO: 534          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 534
WGQGTLVTVS S                                                         11

SEQ ID NO: 535          moltype = AA  length = 23
FEATURE                 Location/Qualifiers
REGION                  1..23
                        note = Description of Artificial Sequence: Synthetic peptide
source                  1..23
                        mol_type = protein
                        organism = synthetic construct
SEQUENCE: 535
QTVLSQSPAI LSASPGEKVT MTC                                            23

SEQ ID NO: 536          moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 536
RASSSVTYIH                                                           10

SEQ ID NO: 537          moltype = AA  length = 15
FEATURE                 Location/Qualifiers
REGION                  1..15
                        note = Description of Artificial Sequence: Synthetic peptide
source                  1..15
                        mol_type = protein
                        organism = synthetic construct
SEQUENCE: 537
WYQQKPGSSP KSWIY                                                     15

SEQ ID NO: 538          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 538
ATSNLAS                                                              7

SEQ ID NO: 539          moltype = AA  length = 32
FEATURE                 Location/Qualifiers
REGION                  1..32
                        note = Description of Artificial Sequence: Synthetic
                         polypeptide
source                  1..32
                        mol_type = protein
                        organism = synthetic construct
SEQUENCE: 539
GVPARFSGSG SGTSYSLTIS RVEAEDAATY YC                                  32

SEQ ID NO: 540          moltype = AA  length = 9
FEATURE                 Location/Qualifiers
REGION                  1..9
```

```
                        note = Description of Artificial Sequence: Synthetic peptide
source                  1..9
                        mol_type = protein
                        organism = synthetic construct
SEQUENCE: 540
QHWSSKPPT                                                     9

SEQ ID NO: 541          moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 541
FGGGTKLEIK                                                    10

SEQ ID NO: 542          moltype = AA  length = 121
FEATURE                 Location/Qualifiers
REGION                  1..121
                        note = Description of Artificial Sequence: Synthetic
                         polypeptide
source                  1..121
                        mol_type = protein
                        organism = synthetic construct
SEQUENCE: 542
EVKLVESGGG LVQPGGSLRL SCATSGFTFT DYYMNWVRQP PGKALEWLGF IGNKANGYTT  60
EYSASVKGRF TISRDKSQSI LYLQMNTLRA EDSATYYCTR DRGLRFYFDY WGQGTTLTVS  120
S                                                             121

SEQ ID NO: 543          moltype = AA  length = 30
FEATURE                 Location/Qualifiers
REGION                  1..30
                        note = Description of Artificial Sequence: Synthetic
                         polypeptide
source                  1..30
                        mol_type = protein
                        organism = synthetic construct
SEQUENCE: 543
EVKLVESGGG LVQPGGSLRL SCATSGFTFT                              30

SEQ ID NO: 544          moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 544
DYYMN                                                         5

SEQ ID NO: 545          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 545
WVRQPPGKAL EWLG                                               14

SEQ ID NO: 546          moltype = AA  length = 19
FEATURE                 Location/Qualifiers
REGION                  1..19
                        note = Description of Artificial Sequence: Synthetic peptide
source                  1..19
                        mol_type = protein
                        organism = synthetic construct
SEQUENCE: 546
FIGNKANGYT TEYSASVKG                                          19

SEQ ID NO: 547          moltype = AA  length = 32
FEATURE                 Location/Qualifiers
REGION                  1..32
                        note = Description of Artificial Sequence: Synthetic
                         polypeptide
source                  1..32
                        mol_type = protein
                        organism = synthetic construct
```

```
SEQUENCE: 547
RFTISRDKSQ SILYLQMNTL RAEDSATYYC TR                          32

SEQ ID NO: 548         moltype = AA  length = 10
FEATURE                Location/Qualifiers
REGION                 1..10
                       note = Description of Artificial Sequence: Synthetic peptide
source                 1..10
                       mol_type = protein
                       organism = synthetic construct
SEQUENCE: 548
DRGLRFYFDY                                                   10

SEQ ID NO: 549         moltype = AA  length = 11
FEATURE                Location/Qualifiers
REGION                 1..11
                       note = Description of Artificial Sequence: Synthetic peptide
source                 1..11
                       mol_type = protein
                       organism = synthetic construct
SEQUENCE: 549
WGQGTTLTVS S                                                 11

SEQ ID NO: 550         moltype = AA  length = 111
FEATURE                Location/Qualifiers
REGION                 1..111
                       note = Description of Artificial Sequence: Synthetic
                        polypeptide
source                 1..111
                       mol_type = protein
                       organism = synthetic construct
SEQUENCE: 550
DIQLTQSPSS LSASVGDRVT ITCRAGESVD IFGVGFLHWY QQKPGKAPKL LIYRASNLES  60
GVPSRFSGSG SRTDFTLTIS SLQPEDFATY YCQQTNEDPY TFGQGTKVEI K          111

SEQ ID NO: 551         moltype = AA  length = 23
FEATURE                Location/Qualifiers
REGION                 1..23
                       note = Description of Artificial Sequence: Synthetic peptide
source                 1..23
                       mol_type = protein
                       organism = synthetic construct
SEQUENCE: 551
DIQLTQSPSS LSASVGDRVT ITC                                    23

SEQ ID NO: 552         moltype = AA  length = 15
FEATURE                Location/Qualifiers
REGION                 1..15
                       note = Description of Artificial Sequence: Synthetic peptide
source                 1..15
                       mol_type = protein
                       organism = synthetic construct
SEQUENCE: 552
RAGESVDIFG VGFLH                                             15

SEQ ID NO: 553         moltype = AA  length = 15
FEATURE                Location/Qualifiers
REGION                 1..15
                       note = Description of Artificial Sequence: Synthetic peptide
source                 1..15
                       mol_type = protein
                       organism = synthetic construct
SEQUENCE: 553
WYQQKPGKAP KLLIY                                             15

SEQ ID NO: 554         moltype = AA  length = 7
FEATURE                Location/Qualifiers
REGION                 1..7
                       note = Description of Artificial Sequence: Synthetic peptide
source                 1..7
                       mol_type = protein
                       organism = synthetic construct
SEQUENCE: 554
RASNLES                                                      7

SEQ ID NO: 555         moltype = AA  length = 32
FEATURE                Location/Qualifiers
REGION                 1..32
                       note = Description of Artificial Sequence: Synthetic
```

```
                          polypeptide
source                   1..32
                         mol_type = protein
                         organism = synthetic construct
SEQUENCE: 555
GVPSRFSGSG SRTDFTLTIS SLQPEDFATY YC                              32

SEQ ID NO: 556           moltype = AA  length = 9
FEATURE                  Location/Qualifiers
REGION                   1..9
                         note = Description of Artificial Sequence: Synthetic peptide
source                   1..9
                         mol_type = protein
                         organism = synthetic construct
SEQUENCE: 556
QQTNEDPYT                                                        9

SEQ ID NO: 557           moltype = AA  length = 10
FEATURE                  Location/Qualifiers
REGION                   1..10
                         note = Description of Artificial Sequence: Synthetic peptide
source                   1..10
                         mol_type = protein
                         organism = synthetic construct
SEQUENCE: 557
FGQGTKVEIK                                                       10

SEQ ID NO: 558           moltype = AA  length = 121
FEATURE                  Location/Qualifiers
REGION                   1..121
                         note = Description of Artificial Sequence: Synthetic
                          polypeptide
source                   1..121
                         mol_type = protein
                         organism = synthetic construct
SEQUENCE: 558
EVQLVESGGG LVQPGGSLRL SCAASGFNIK DTYMHWVRQA PGKGLEWVAR IDPANGNSKY  60
ADSVKGRFTI SADTSKNTAY LQMNSLRAED TAVYYCAPFG YYVSDYAMAY WGQGTLVTVS  120
S                                                                121

SEQ ID NO: 559           moltype = AA  length = 30
FEATURE                  Location/Qualifiers
REGION                   1..30
                         note = Description of Artificial Sequence: Synthetic
                          polypeptide
source                   1..30
                         mol_type = protein
                         organism = synthetic construct
SEQUENCE: 559
EVQLVESGGG LVQPGGSLRL SCAASGFNIK                                 30

SEQ ID NO: 560           moltype = AA  length = 5
FEATURE                  Location/Qualifiers
REGION                   1..5
                         note = Description of Artificial Sequence: Synthetic peptide
source                   1..5
                         mol_type = protein
                         organism = synthetic construct
SEQUENCE: 560
DTYMH                                                            5

SEQ ID NO: 561           moltype = AA  length = 14
FEATURE                  Location/Qualifiers
REGION                   1..14
                         note = Description of Artificial Sequence: Synthetic peptide
source                   1..14
                         mol_type = protein
                         organism = synthetic construct
SEQUENCE: 561
WVRQAPGKGL EWVA                                                  14

SEQ ID NO: 562           moltype = AA  length = 17
FEATURE                  Location/Qualifiers
REGION                   1..17
                         note = Description of Artificial Sequence: Synthetic peptide
source                   1..17
                         mol_type = protein
                         organism = synthetic construct
SEQUENCE: 562
```

```
RIDPANGNSK YADSVKG                                          17

SEQ ID NO: 563          moltype = AA  length = 32
FEATURE                 Location/Qualifiers
REGION                  1..32
                        note = Description of Artificial Sequence: Synthetic
                         polypeptide
source                  1..32
                        mol_type = protein
                        organism = synthetic construct
SEQUENCE: 563
RFTISADTSK NTAYLQMNSL RAEDTAVYYC AP                         32

SEQ ID NO: 564          moltype = AA  length = 12
FEATURE                 Location/Qualifiers
REGION                  1..12
                        note = Description of Artificial Sequence: Synthetic peptide
source                  1..12
                        mol_type = protein
                        organism = synthetic construct
SEQUENCE: 564
FGYYVSDYAM AY                                               12

SEQ ID NO: 565          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 565
WGQGTLVTVS S                                                11

SEQ ID NO: 566          moltype = AA  length = 107
FEATURE                 Location/Qualifiers
REGION                  1..107
                        note = Description of Artificial Sequence: Synthetic
                         polypeptide
source                  1..107
                        mol_type = protein
                        organism = synthetic construct
SEQUENCE: 566
DIQMTQSPAS LSASVGDRVT ITCRASENIF SYLAWYQQKP GKSPKLLVYN TRTLAEGVPS  60
RFSGSGSGTD FSLTISSLQP EDFATYYCQH HYGTPFTFGS GTKLEIK               107

SEQ ID NO: 567          moltype = AA  length = 23
FEATURE                 Location/Qualifiers
REGION                  1..23
                        note = Description of Artificial Sequence: Synthetic peptide
source                  1..23
                        mol_type = protein
                        organism = synthetic construct
SEQUENCE: 567
DIQMTQSPAS LSASVGDRVT ITC                                   23

SEQ ID NO: 568          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 568
RASENIFSYL A                                                11

SEQ ID NO: 569          moltype = AA  length = 15
FEATURE                 Location/Qualifiers
REGION                  1..15
                        note = Description of Artificial Sequence: Synthetic peptide
source                  1..15
                        mol_type = protein
                        organism = synthetic construct
SEQUENCE: 569
WYQQKPGKSP KLLVY                                            15

SEQ ID NO: 570          moltype = AA  length = 7
FEATURE                 Location/Qualifiers
REGION                  1..7
                        note = Description of Artificial Sequence: Synthetic peptide
```

```
source                  1..7
                        mol_type = protein
                        organism = synthetic construct
SEQUENCE: 570
NTRTLAE                                                                7

SEQ ID NO: 571          moltype = AA  length = 32
FEATURE                 Location/Qualifiers
REGION                  1..32
                        note = Description of Artificial Sequence: Synthetic
                         polypeptide
source                  1..32
                        mol_type = protein
                        organism = synthetic construct
SEQUENCE: 571
GVPSRFSGSG SGTDFSLTIS SLQPEDFATY YC                                    32

SEQ ID NO: 572          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 572
QHHYGTPFT                                                              9

SEQ ID NO: 573          moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 573
FGSGTKLEIK                                                             10

SEQ ID NO: 574          moltype = AA  length = 120
FEATURE                 Location/Qualifiers
REGION                  1..120
                        note = Description of Artificial Sequence: Synthetic
                         polypeptide
source                  1..120
                        mol_type = protein
                        organism = synthetic construct
SEQUENCE: 574
EVQLQESGPG LVKPGGSLSL SCAASGFVFS SYDMSWVRQT PERGLEWVAY ISSGGGITYA  60
PSTVKGRFTV SRDNAKNTLY LQMNSLTSED TAVYYCAAHY FGSSGPFAYW GQGTLVTVSS  120

SEQ ID NO: 575          moltype = AA  length = 30
FEATURE                 Location/Qualifiers
REGION                  1..30
                        note = Description of Artificial Sequence: Synthetic
                         polypeptide
source                  1..30
                        mol_type = protein
                        organism = synthetic construct
SEQUENCE: 575
EVQLQESGPG LVKPGGSLSL SCAASGFVFS                                       30

SEQ ID NO: 576          moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 576
SYDMS                                                                  5

SEQ ID NO: 577          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 577
WVRQTPERGL EWVA                                                        14
```

```
SEQ ID NO: 578          moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 578
YISSGGGITY APSTVKG                                                17

SEQ ID NO: 579          moltype = AA  length = 32
FEATURE                 Location/Qualifiers
REGION                  1..32
                        note = Description of Artificial Sequence: Synthetic
                         polypeptide
source                  1..32
                        mol_type = protein
                        organism = synthetic construct
SEQUENCE: 579
RFTVSRDNAK NTLYLQMNSL TSEDTAVYYC AA                               32

SEQ ID NO: 580          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 580
HYFGSSGPFA Y                                                      11

SEQ ID NO: 581          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 581
WGQGTLVTVS S                                                      11

SEQ ID NO: 582          moltype = AA  length = 116
FEATURE                 Location/Qualifiers
REGION                  1..116
                        note = Description of Artificial Sequence: Synthetic
                         polypeptide
source                  1..116
                        mol_type = protein
                        organism = synthetic construct
SEQUENCE: 582
QAVLTQPASL SASPGASASL TCTLRRGINV GAYSIYWYQQ KPGSPPQYLL RYKSDSDKQQ  60
GSGVSSRFSA SKDASANAGI LLISGLQSED EADYYCMIWH SGASAVFGGG TKLTVL      116

SEQ ID NO: 583          moltype = AA  length = 22
FEATURE                 Location/Qualifiers
REGION                  1..22
                        note = Description of Artificial Sequence: Synthetic peptide
source                  1..22
                        mol_type = protein
                        organism = synthetic construct
SEQUENCE: 583
QAVLTQPASL SASPGASASL TC                                          22

SEQ ID NO: 584          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 584
TLRRGINVGA YSIY                                                   14

SEQ ID NO: 585          moltype = AA  length = 15
FEATURE                 Location/Qualifiers
REGION                  1..15
                        note = Description of Artificial Sequence: Synthetic peptide
source                  1..15
```

```
                        mol_type = protein
                        organism = synthetic construct
SEQUENCE: 585
WYQQKPGSPP QYLLR                                             15

SEQ ID NO: 586          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 586
YKSDSDKQQG S                                                 11

SEQ ID NO: 587          moltype = AA  length = 34
FEATURE                 Location/Qualifiers
REGION                  1..34
                        note = Description of Artificial Sequence: Synthetic
                         polypeptide
source                  1..34
                        mol_type = protein
                        organism = synthetic construct
SEQUENCE: 587
GVSSRFSASK DASANAGILL ISGLQSEDEA DYYC                        34

SEQ ID NO: 588          moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 588
MIWHSGASAV                                                   10

SEQ ID NO: 589          moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 589
FGGGTKLTVL                                                   10

SEQ ID NO: 590          moltype = AA  length = 121
FEATURE                 Location/Qualifiers
REGION                  1..121
                        note = Description of Artificial Sequence: Synthetic
                         polypeptide
source                  1..121
                        mol_type = protein
                        organism = synthetic construct
SEQUENCE: 590
EVQLVESGGG LVQPGRSLRL SCAASGFTVS SYWMHWVRQA PGKGLEWVGF IRNKANGGTT  60
EYAASVKGRF TISRDDSKNT LYLQMNSLRA EDTAVYYCAR DRGLRFYFDY WGQGTTVTVS  120
S                                                            121

SEQ ID NO: 591          moltype = AA  length = 30
FEATURE                 Location/Qualifiers
REGION                  1..30
                        note = Description of Artificial Sequence: Synthetic
                         polypeptide
source                  1..30
                        mol_type = protein
                        organism = synthetic construct
SEQUENCE: 591
EVQLVESGGG LVQPGRSLRL SCAASGFTVS                             30

SEQ ID NO: 592          moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 592
SYWMH                                                        5
```

```
SEQ ID NO: 593          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 593
WVRQAPGKGL EWVG                                                   14

SEQ ID NO: 594          moltype = AA  length = 19
FEATURE                 Location/Qualifiers
REGION                  1..19
                        note = Description of Artificial Sequence: Synthetic peptide
source                  1..19
                        mol_type = protein
                        organism = synthetic construct
SEQUENCE: 594
FIRNKANGGT TEYAASVKG                                              19

SEQ ID NO: 595          moltype = AA  length = 19
FEATURE                 Location/Qualifiers
REGION                  1..19
                        note = Description of Artificial Sequence: Synthetic peptide
source                  1..19
                        mol_type = protein
                        organism = synthetic construct
SEQUENCE: 595
FIRNKANSGT TEYAASVKG                                              19

SEQ ID NO: 596          moltype = AA  length = 32
FEATURE                 Location/Qualifiers
REGION                  1..32
                        note = Description of Artificial Sequence: Synthetic
                         polypeptide
source                  1..32
                        mol_type = protein
                        organism = synthetic construct
SEQUENCE: 596
RFTISRDDSK NTLYLQMNSL RAEDTAVYYC AR                               32

SEQ ID NO: 597          moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 597
DRGLRFYFDY                                                        10

SEQ ID NO: 598          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 598
WGQGTTVTVS S                                                      11

SEQ ID NO: 599          moltype = AA  length = 121
FEATURE                 Location/Qualifiers
REGION                  1..121
                        note = Description of Artificial Sequence: Synthetic
                         polypeptide
source                  1..121
                        mol_type = protein
                        organism = synthetic construct
SEQUENCE: 599
EVQLVESGGG LVQPGRSLRL SCAASGFTVS SYWMHWVRQA PGKGLEWVGF ILNKANGGTT  60
EYAASVKGRF TISRDDSKNT LYLQMNSLRA EDTAVYYCAR DRGLRFYFDY WGQGTTVTVS  120
S                                                                 121

SEQ ID NO: 600          moltype = AA  length = 30
FEATURE                 Location/Qualifiers
REGION                  1..30
                        note = Description of Artificial Sequence: Synthetic
```

```
                         polypeptide
source                   1..30
                         mol_type = protein
                         organism = synthetic construct
SEQUENCE: 600
EVQLVESGGG LVQPGRSLRL SCAASGFTVS                                    30

SEQ ID NO: 601           moltype = AA  length = 5
FEATURE                  Location/Qualifiers
REGION                   1..5
                         note = Description of Artificial Sequence: Synthetic peptide
source                   1..5
                         mol_type = protein
                         organism = synthetic construct
SEQUENCE: 601
SYWMH                                                               5

SEQ ID NO: 602           moltype = AA  length = 14
FEATURE                  Location/Qualifiers
REGION                   1..14
                         note = Description of Artificial Sequence: Synthetic peptide
source                   1..14
                         mol_type = protein
                         organism = synthetic construct
SEQUENCE: 602
WVRQAPGKGL EWVG                                                     14

SEQ ID NO: 603           moltype = AA  length = 19
FEATURE                  Location/Qualifiers
REGION                   1..19
                         note = Description of Artificial Sequence: Synthetic peptide
source                   1..19
                         mol_type = protein
                         organism = synthetic construct
SEQUENCE: 603
FILNKANGGT TEYAASVKG                                                19

SEQ ID NO: 604           moltype = AA  length = 32
FEATURE                  Location/Qualifiers
REGION                   1..32
                         note = Description of Artificial Sequence: Synthetic
                          polypeptide
source                   1..32
                         mol_type = protein
                         organism = synthetic construct
SEQUENCE: 604
RFTISRDDSK NTLYLQMNSL RAEDTAVYYC AR                                 32

SEQ ID NO: 605           moltype = AA  length = 10
FEATURE                  Location/Qualifiers
REGION                   1..10
                         note = Description of Artificial Sequence: Synthetic peptide
source                   1..10
                         mol_type = protein
                         organism = synthetic construct
SEQUENCE: 605
DRGLRFYFDY                                                          10

SEQ ID NO: 606           moltype = AA  length = 11
FEATURE                  Location/Qualifiers
REGION                   1..11
                         note = Description of Artificial Sequence: Synthetic peptide
source                   1..11
                         mol_type = protein
                         organism = synthetic construct
SEQUENCE: 606
WGQGTTVTVS S                                                        11

SEQ ID NO: 607           moltype = AA  length = 30
FEATURE                  Location/Qualifiers
REGION                   1..30
                         note = Description of Artificial Sequence: Synthetic
                          polypeptide
source                   1..30
                         mol_type = protein
                         organism = synthetic construct
SEQUENCE: 607
QVQLVQSGAE VKKPGASVKV SCKASGYTLP                                    30
```